(12) United States Patent
Ma et al.

(10) Patent No.: US 11,905,528 B2
(45) Date of Patent: *Feb. 20, 2024

(54) COMPOUND CHIMERIC ANTIGEN RECEPTOR (CCAR) TARGETING MULTIPLE ANTIGENS, COMPOSITIONS AND METHODS OF USE THEREOF

(71) Applicant: ICELL GENE THERAPEUTICS, LLC, Stony Brook, NY (US)

(72) Inventors: Yupo Ma, Stony Brook, NY (US); Kevin Pinz, Stony Brook, NY (US); Xun Jiang, Stony Brook, NY (US); Masayuki Wada, Stony Brook, NY (US); Kevin Chen, Stony Brook, NY (US)

(73) Assignee: ICell Gene Therapeutics Inc., Stony Brook, NY (US)

(*) Notice: Subject to any disclaimer, the term of this patent is extended or adjusted under 35 U.S.C. 154(b) by 462 days.

This patent is subject to a terminal disclaimer.

(21) Appl. No.: 16/753,951

(22) PCT Filed: Oct. 12, 2018

(86) PCT No.: PCT/US2018/055705
§ 371 (c)(1),
(2) Date: Apr. 6, 2020

(87) PCT Pub. No.: WO2019/075395
PCT Pub. Date: Apr. 18, 2019

(65) Prior Publication Data
US 2020/0308541 A1    Oct. 1, 2020

Related U.S. Application Data

(60) Provisional application No. 62/628,973, filed on Feb. 10, 2018, provisional application No. 62/571,608, filed on Oct. 12, 2017.

(51) Int. Cl.
| | | |
|---|---|---|
| C12N 5/0783 | (2010.01) |
| A61P 35/00 | (2006.01) |
| A61K 35/17 | (2015.01) |
| C07K 14/435 | (2006.01) |
| C07K 14/54 | (2006.01) |
| C07K 14/705 | (2006.01) |
| C07K 14/725 | (2006.01) |
| C07K 14/73 | (2006.01) |
| C07K 14/715 | (2006.01) |
| C12N 9/10 | (2006.01) |

(52) U.S. Cl.
CPC ............ *C12N 5/0636* (2013.01); *A61K 35/17* (2013.01); *A61P 35/00* (2018.01); *C07K 14/435* (2013.01); *C07K 14/54* (2013.01); *C07K 14/5443* (2013.01); *C07K 14/705* (2013.01); *C07K 14/7051* (2013.01); *C07K 14/70503* (2013.01); *C07K 14/70514* (2013.01); *C07K 14/70575* (2013.01); *C07K 14/70589* (2013.01); *C07K 14/7155* (2013.01); *C12N 5/0646* (2013.01); *C12N 9/1081* (2013.01); *C07K 2319/03* (2013.01); *C12N 2510/00* (2013.01)

(58) Field of Classification Search
None
See application file for complete search history.

(56) References Cited

U.S. PATENT DOCUMENTS

2016/0296562 A1 * 10/2016 Pulé .................. A61P 37/02
2017/0224798 A1    8/2017 Cooper et al.

FOREIGN PATENT DOCUMENTS

WO    WO2016210293 A1    12/2016

OTHER PUBLICATIONS

International Search Report for International Appl. No. PCT/US2018/55705, 1-5 pgs, dated Feb. 22, 2019.

* cited by examiner

*Primary Examiner* — Peter J Reddig
(74) *Attorney, Agent, or Firm* — Hoffmann & Baron, LLP

(57) ABSTRACT

In one embodiment, the present disclosure provides an engineered cell having a first chimeric antigen receptor polypeptide including a first antigen recognition domain, a first signal peptide, a first hinge region, a first transmembrane domain, a first costimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain; wherein the first antigen recognition domain is different than the second antigen recognition domain.

7 Claims, 173 Drawing Sheets
Specification includes a Sequence Listing.

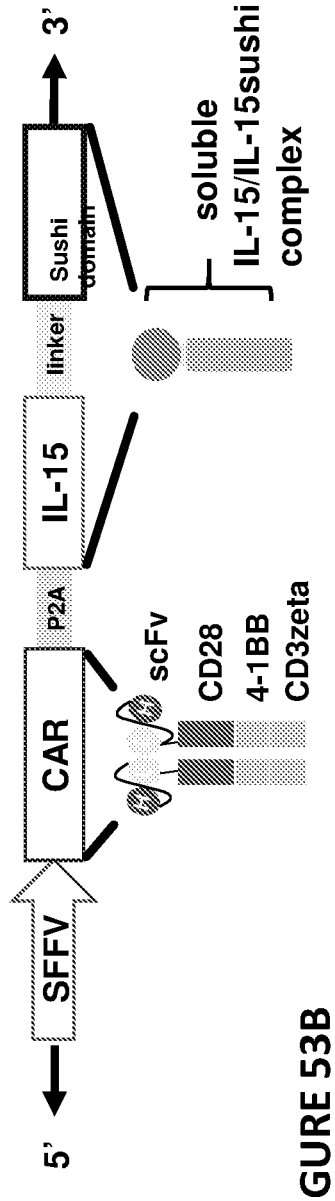
FIGURE 53A
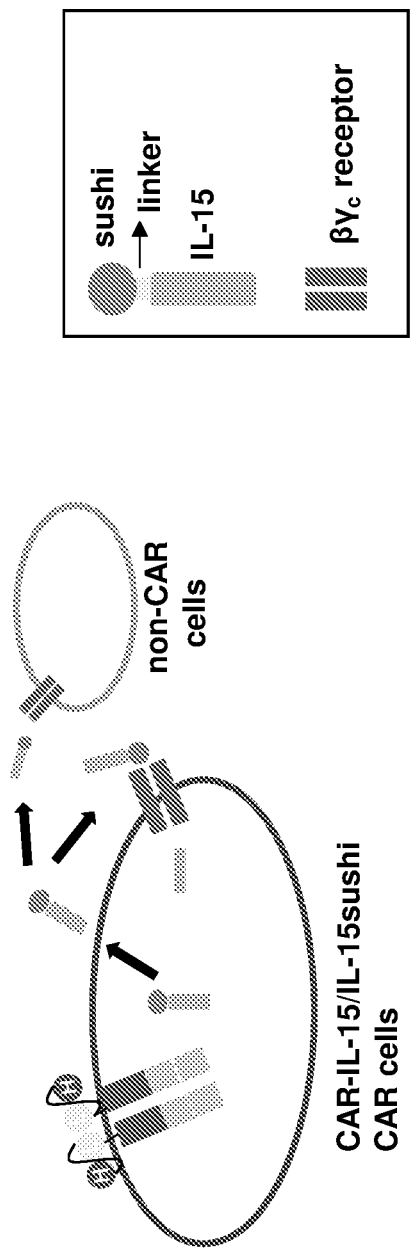
FIGURE 53B
FIGURE 53

COMPOUND CHIMERIC ANTIGEN RECEPTOR (CCAR) TARGETING MULTIPLE ANTIGENS, COMPOSITIONS AND METHODS OF USE THEREOF

CROSS-REFERENCE TO RELATED APPLICATIONS

This application is a National Stage Application that claims a benefit of priority from Application No. PCT/US2018/055705 filed Oct. 12, 2018, which claims priority to Application No. 62/571,608, filed Oct. 12, 2017, and Application No. 62/628,973 filed Feb. 10, 2018, the disclosures of which are herein incorporated in their entirety.

BACKGROUND

T cells, a type of lymphocyte, play a central role in cell-mediated immunity. They are distinguished from other lymphocytes, such as B cells and natural killer cells (NK cells), by the presence of a T-cell receptor (TCR) on the cell surface. T helper cells, also called CD4+T or CD4 T cells, express CD4 glycoprotein on their surface. Helper T cells are activated when exposed to peptide antigens presented by MHC (major histocompatibility complex) class II molecules. Once activated, these cells proliferate rapidly and secrete cytokines that regulate immune response. Cytotoxic T cells, also known as CD8+ T cells or CD8 T cells, express CD8 glycoprotein on the cell surface. The CD8+ T cells are activated when exposed to peptide antigens presented by MHC class I molecules. Memory T cells, a subset of T cells, persist long term and respond to their cognate antigen, thus providing the immune system with "memory" against past infections and/or tumor cells.

T cells can be genetically engineered to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CAR T cells is then infused into the patient.

Clinical trials to date have shown chimeric antigen receptor (CAR) T cells to have great promise in hematologic malignancies resistant to standard chemotherapies. Most notably, CD19-specific CAR (CD19CAR) T-cell therapies have had remarkable results including long-term remissions in B-cell malignancies (Kochenderfer, Wilson et al. 2010, Kalos, Levine et al. 2011, Porter, Levine et al. 2011, Davila, Riviere et al. 2013, Grupp, Frey et al. 2013, Grupp, Kalos et al. 2013, Kalos, Nazimuddin et al. 2013, Kochenderfer, Dudley et al. 2013, Kochenderfer, Dudley et al. 2013, Lee, Shah et al. 2013, Park, Riviere et al. 2013, Maude, Frey et al. 2014).

Despite the success of CAR therapy in B-cell leukemia and lymphoma, the application of CAR therapy to soft tissue tumors has not yet been well established. Given that malignant soft tissue tumor are associated with dramatically poorer outcomes compared to those of B-cell malignancies (Abramson, Feldman et al. 2014), CAR therapy in this respect has the potential to further address a great clinical need.

There are some roadblocks that hinder the broader adoption of CAR therapeutic approach. Among the most general challenges are: (1) selection of antigen target and chimeric antigen receptor(s); (2) CAR design; (3) tumor heterogeneity, particularly the variance in the surface expression of tumor antigens. Targeting single antigen carries the risk of immune escape and this could be overcome by targeting multiple desired antigens.

Most CAR chimeric antigen receptors are scFvs derived from monoclonal antibodies and some of these monoclonal antibodies have been used in the clinical trials or treatment for diseases. However, they have limited efficacy, which suggests that alternative and more potent targeting approaches, such as CARs are required.

Target discovery and selection are the initial step as there are no general rules to ensure or guide CAR design that are efficacious.

scFvs are the most commonly used chimeric antigen receptor for CARs. However, CAR affinity binding and locations of the recognized epitope on the antigen could affect the function. Additionally the level of the surface CAR expression on the T cells or NK cells is affected by an appropriate leader sequence and promoter. However, overexpressed CAR proteins could be toxic to cells.

Therefore, there remains a need for improved chimeric antigen receptor-based therapies that allow for more effective, safe, and efficient targeting of T-cell associated malignancies Furthermore, CAR targeting neuroblastoma is quite challenging because of the presence of heterogeneous tumor populations as well the presence of tumor micro-environment suppression. Antigen-specific immunotherapies for neuroblastoma have long been pursued to improve the patient treatment outcomes but success thus far has been limited as many these therapies have either been ineffective in the clinic or have an uncertain impact on patient outcomes. The ideal target(s) in neuroblastoma or other soft tissue tumors (such as sarcomas), diseases of great antigenic diversity, has not been established. The identification of appropriate target (s) is an important step for the CAR design and the CAR design is required to address tumor heterogeneity, CAR persistency and tumor microenvironment suppression. There is no general rule that CAR design is efficacious and safe.

Therefore, there remains a need for improved chimeric antigen receptor-based therapies that allow for more effective, safe, and efficient targeting of soft tissue tumors.

SUMMARY OF THE INVENTION

In one embodiment, the present disclosure provides an engineered cell having a first chimeric antigen receptor polypeptide including a first antigen recognition domain, a first signal peptide, a first hinge region, a first transmembrane domain, a first co-stimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain;

wherein the first antigen recognition domain is different than the second antigen recognition domain, and the first antigen recognition domain and second antigen rejection domain are selected from the group consisting of interleukin 6 receptor, NY-ESO-1, alpha fetoprotein (AFP), glypican-3 (GPC3), BAFF-R, BAFF, APRIL, BCMA, TACI, LeY, CD5, CD4, CD3, CD2, CD52, GD2, CD13, CD14, CD15 CD19, CD20, CD22, CD33, CD30, CD41, CD45, CD61, CD64, CD68, CD117, CD123, CD138, CD267, CD269, CD38, Flt3 receptor, CD4, CLL-1 and CS1(SLAMF7).

In another embodiment, the present disclosure provides an engineered polypeptide including a chimeric antigen receptor and an enhancer.

In another embodiment, the present disclosure provides a method of reducing the number of target cells including the steps of (i.) contacting said target cells with an effective amount of an engineered cell having at least one chimeric antigen receptor polypeptide, for engineered cells having multiple chimeric antigen receptor polypeptides, each chimeric antigen receptor polypeptide is independent; and (ii.) optionally, assaying for the reduction in the number of said cells. The target cells include at least one cell surface antigen selected from the group consisting of GD2, GD3, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD19, CD20, CD22, CD38, BCMA, CS1, NKG2D receptor, April receptor, BAFF receptor, TACI, CD3, CD4, CD8, CD5, CD7, CD2, and CD138. The target antigens can also include viral or fungal antigens, such as E6 and E7 from the human papillomavirus (HPV) or EBV (Epstein Barr virus) antigens.

In another embodiment, the present disclosure provides methods for treating B-cell lymphoma, T-cell lymphoma, multiple myeloma, chronic myeloid leukemia, acute myeloma leukemia, myelodysplastic syndromes, chronic myeloproliferative neoplasms, B-cell acute lymphoblastic leukemia (B-ALL), blastic plasmacytoid dendritic cell neoplasm, lung cancer, liver cancer, brain cancer, osteosarcoma, breast cancer, prostate cancer and cell proliferative diseases by administering any of the engineered cells described above to a patient in need thereof.

In another embodiment, the present disclosure provides a method of treating an autoimmune disease, said method including administering an engineered cell according to claim 1 to a patient in need thereof; wherein said autoimmune disease comprises systemic lupus erythematosus (SLE), multiple sclerosis (MS), Inflammatory bowel disease (IBD), Rheumatoid arthritis, Sjögren syndrome, dermatomyositis, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis), or eosinophilic granulomatosis with polyangiitis (EGPA, Churg-Strauss syndrome) and TTP (thrombotic thrombocytopenic purpura)

The present disclosure provides chimeric antigen receptors (CARS) targeting non-hematologic malignancies, compositions and methods of use thereof.

In one embodiment, the present disclosure provides an engineered cell having a first chimeric antigen receptor polypeptide including a first antigen recognition domain, a first signal peptide, a first hinge region, a first transmembrane domain, a first co-stimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain; wherein the first antigen recognition domain is different than the second antigen recognition domain.

In another embodiment, the present disclosure provides an engineered polypeptide including a chimeric antigen receptor and an enhancer (s). In a further embodiment, an enhancer can be selected from at least one of the group including, but not limited, IL-2, IL-7, IL-12, IL-15, IL-15/IL-15sush, IL-15/IL-15sushi anchor, IL-15/IL-15RA, IL-21, IL-21 anchor, PD-1, PD-L1, CSF1R, CTAL-4, TIM-3, cytoplasmic domain of IL-15 receptor alpha, 4-1BBL, IL-21, IL-21 anchor and TGFR beta, receptors.

In some embodiments, CAR having an antigen recognition domain (s) is part of an expression cassette. In a preferred embodiment, the expressing gene or the cassette may include an accessory gene or a tag or a part thereof. The accessory gene may be an inducible suicide gene or a part thereof, including, but not limited to, caspase 9 gene. The "suicide gene" ablation approach improves safety of the gene therapy and kills cells only when activated by a specific compound or a molecule. In some embodiments, the epitope tag is a c-myc tag, CD52, streptavidin-binding peptide (SBP), truncated EGFR gene (EGFRt) or a part or a combination thereof.

In some embodiments, CAR cells can be ablated by administrating an anti-CD52 monoclonal antibody (CAMPATH) to a subject.

In another embodiment, the present disclosure provides methods for treating soft tissue tumors, carcinoma, sarcomas, leukemia, and cell proliferative diseases by administering any of the engineered cells described above to a patient in need thereof.

(7A) MM1S model tumor generated by injection of 1.0×10⁶ luciferase⁺ cells per mouse. Mice treated with either BC1cCAR T-cells (right) or control T-cells (left) and IVIS image acquisition.

(7B) Average light intensity measured for BC1cCAR T-cell treated mice compared to control T-cell treated mice. (7C) Survival outcomes for BC1cCAR and control groups.

Figure 8A:
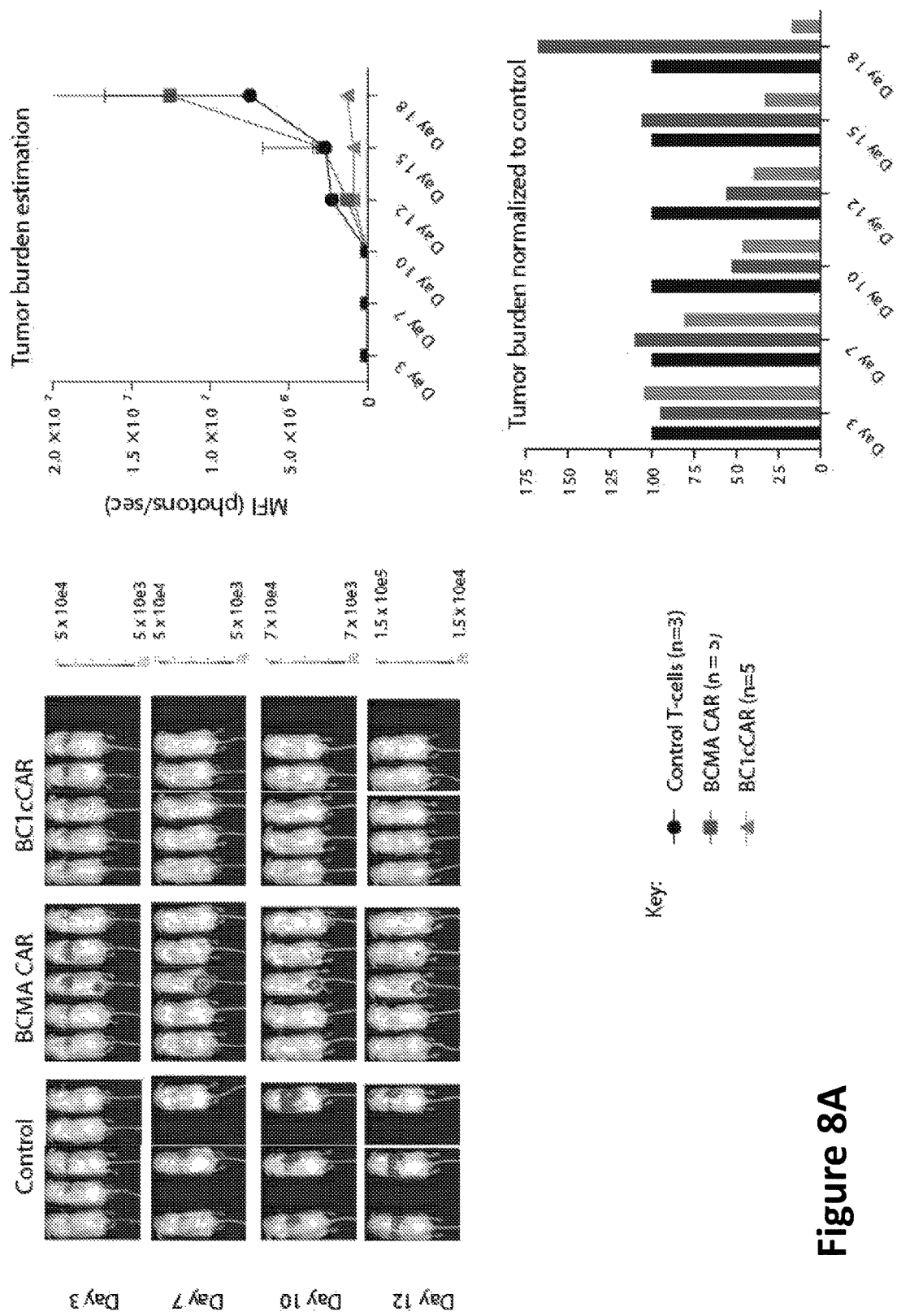
Figure 8B:
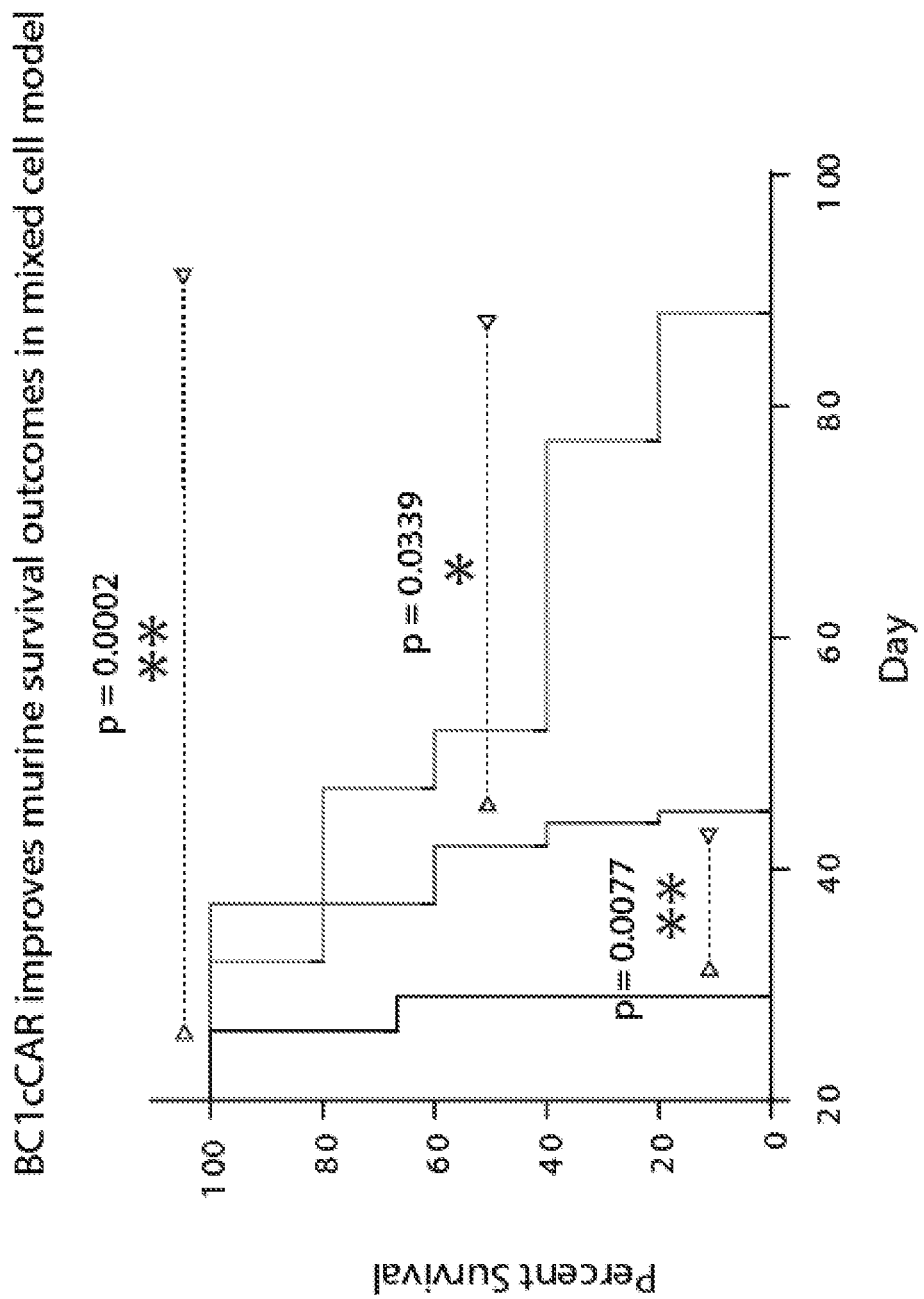

FIGS. 8A-8B: BC1cCAR T-cells exhibit improved cytotoxic effect in a mixed antigen xenogeneic mouse model (8A) Mouse model injected with BCMA and CS1 expressing K562 cells in a ratio of 4:1 BCMA:CS1 K562 cells (n=5 for each group). Mice were treated with either BC1cCAR T-cells, control T-cells, or a BCMA-specific CAR. Tumor burden was visualized by IVIS and plotted as a function of fluorescence intensity (right) for all groups. (8B) Survival outcomes for control treated, BCMA-CAR treated, and BC1cCAR treated mice.

Figure 9A:
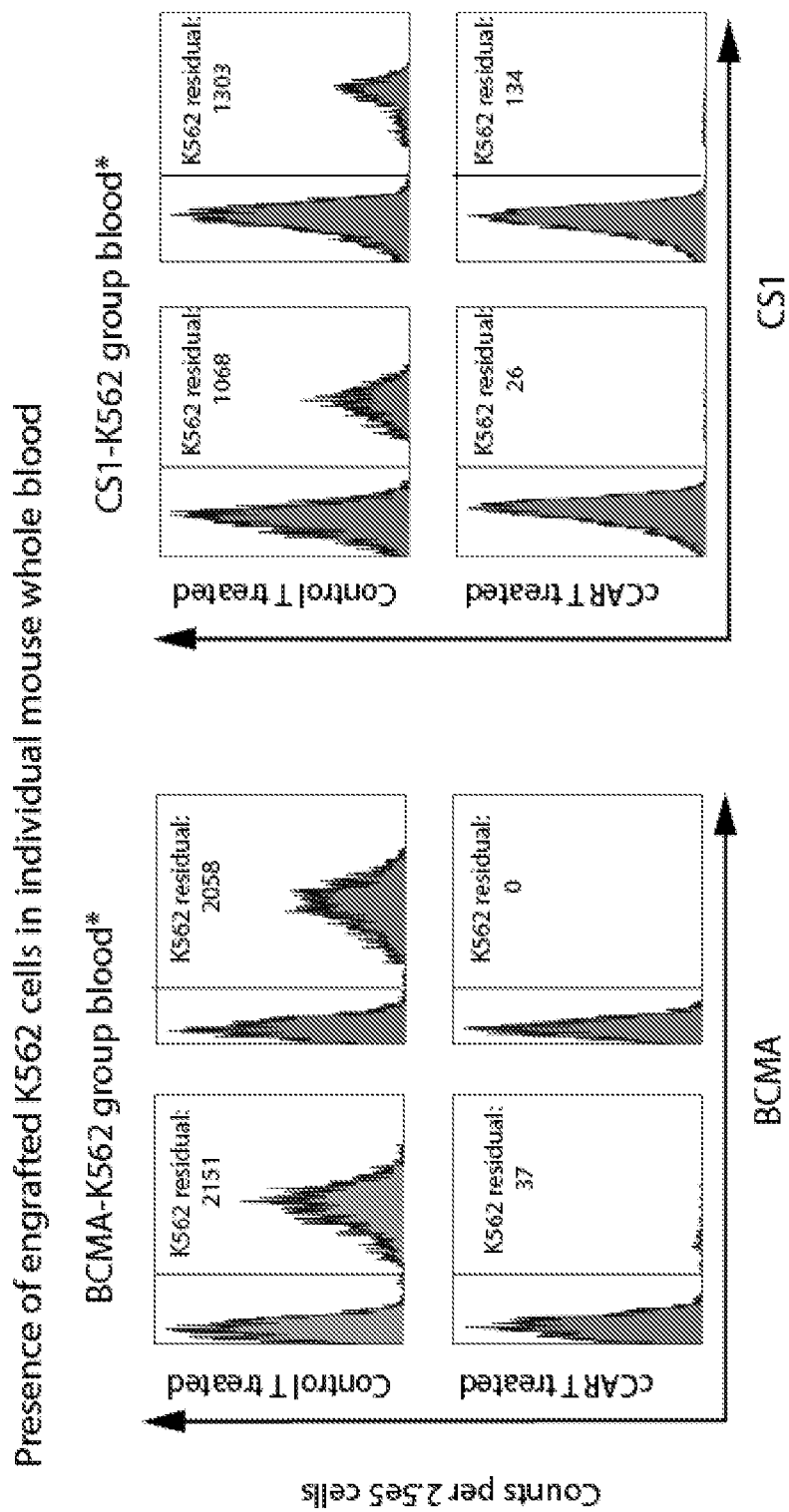
Figure 9B:
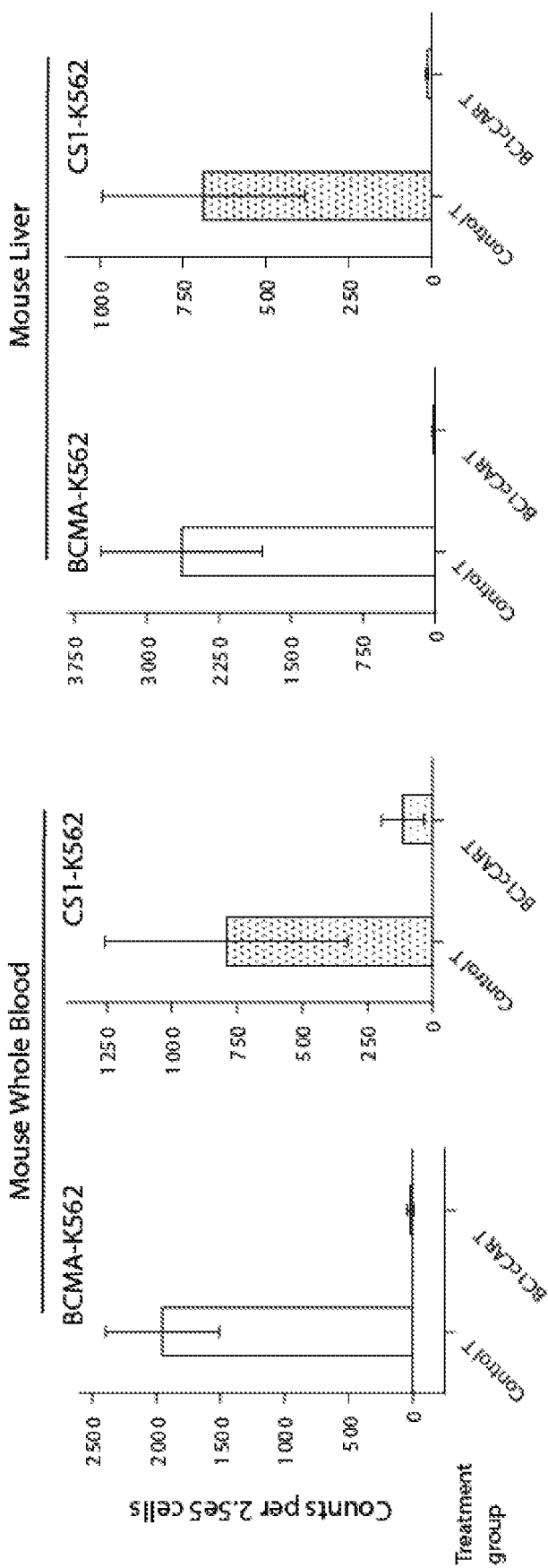
Figure 9C:
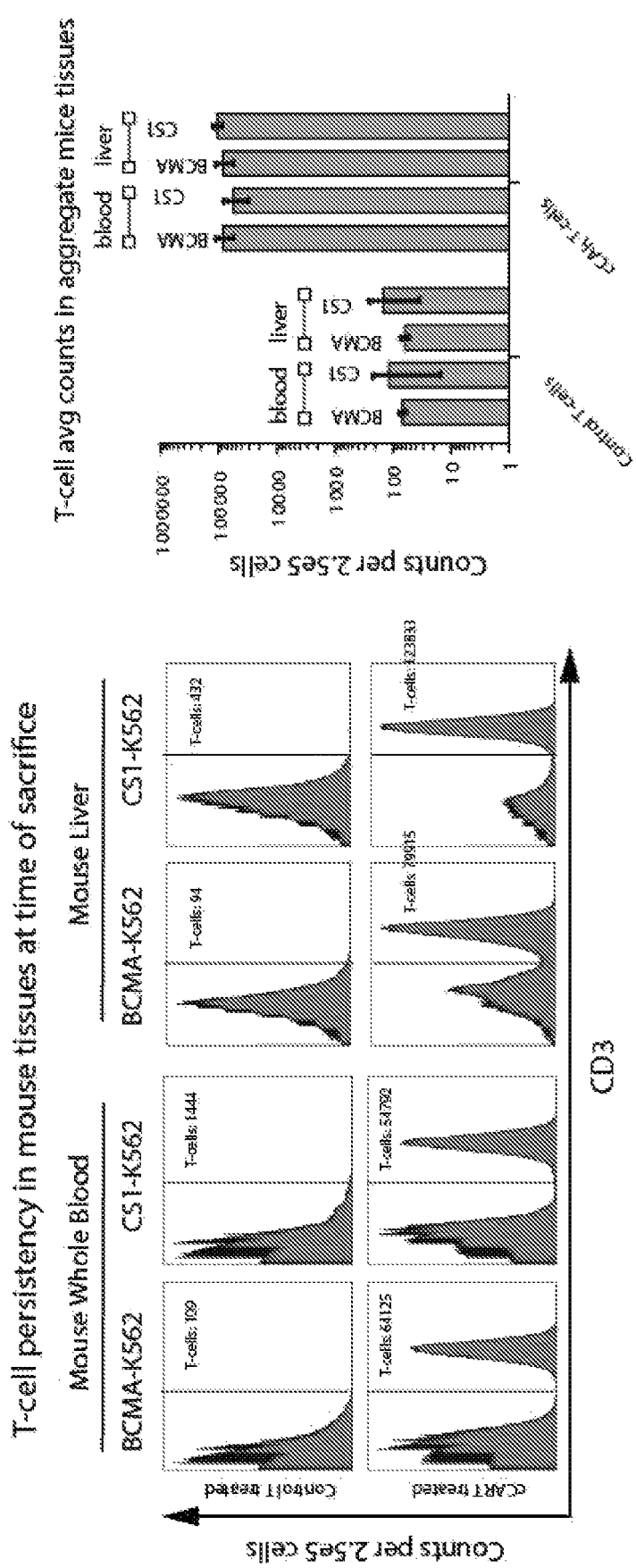

FIGS. 9A-9C: Improved BC1cCAR T-cell persistency and maintenance of tumor suppression in separate antigen models (9A) Whole blood samples from mice injected with either BCMA-K562 or CS1-K562 tumor cells (n=5 per group) were taken at time of sacrifice. Histogram population of BCMA or CS1 positive peaks represent tumor presence. (9B) Aggregate tissue analysis of both whole blood and liver samples across sacrificed mice are summarized. Mice tumor cell counts were established by FACS of antigen positive cells per 250000 cells collected per sample and averaged across all mice per treatment group. (9C) Whole blood and liver tissues were also analyzed for T-cell persistency by CD3 expression at time of sacrifice, summarized across all sacrificed mice (right).

Figure 10A:
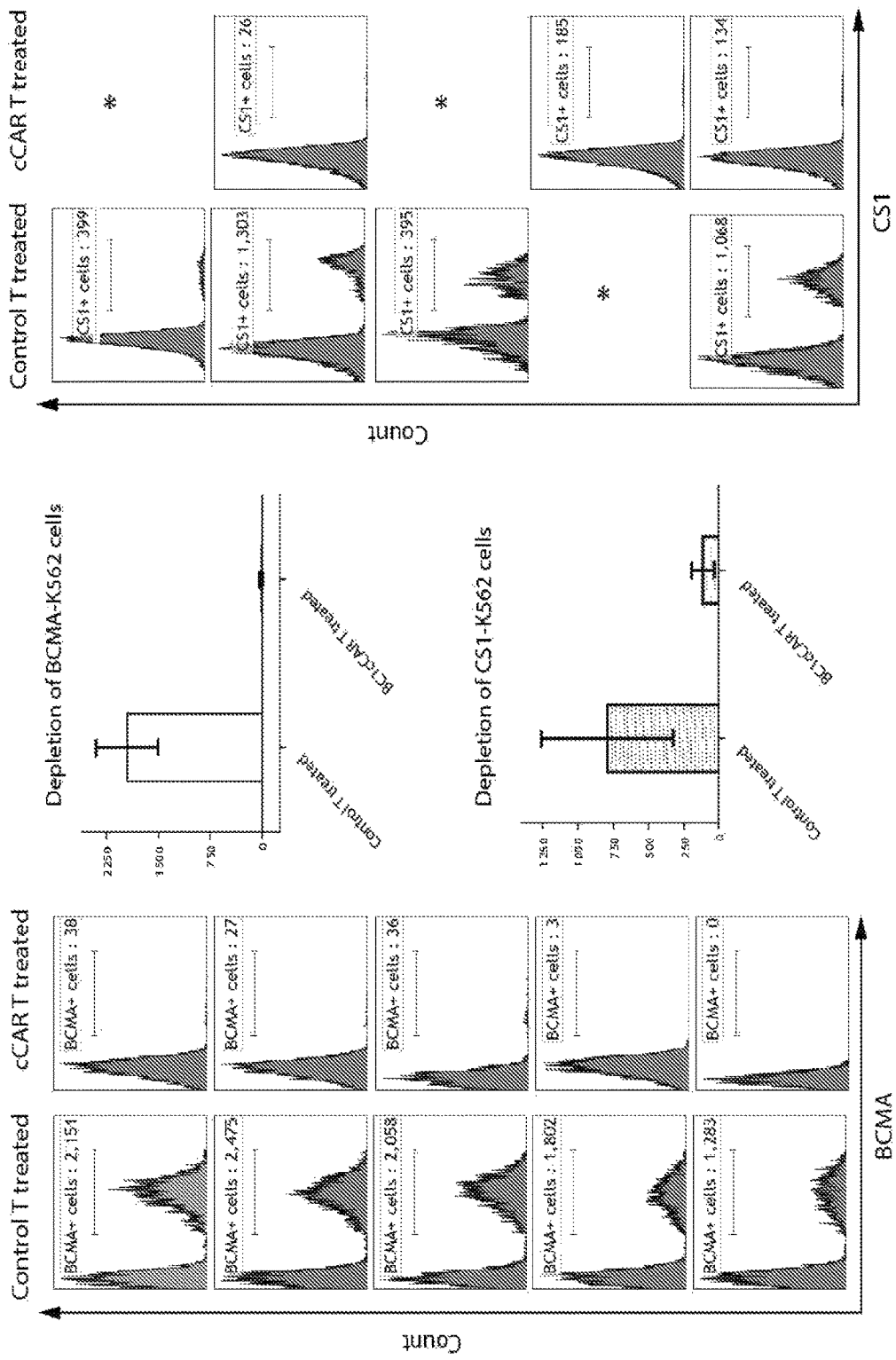

FIG. 10A: Analysis of mouse whole blood from separately injected BCMA-K562 or CS1-K562 injected mice At times of sacrifice (various), mice whole blood was collected and labeled with antibodies against CD3, CD45, BCMA, and CS1. Histograms were constructed to visualize presence of tumor and counts were averaged across 250 000 events to generate graphical summaries. Some mice died before sacrifice, and were unusable for sample collection.

Figure 10B:
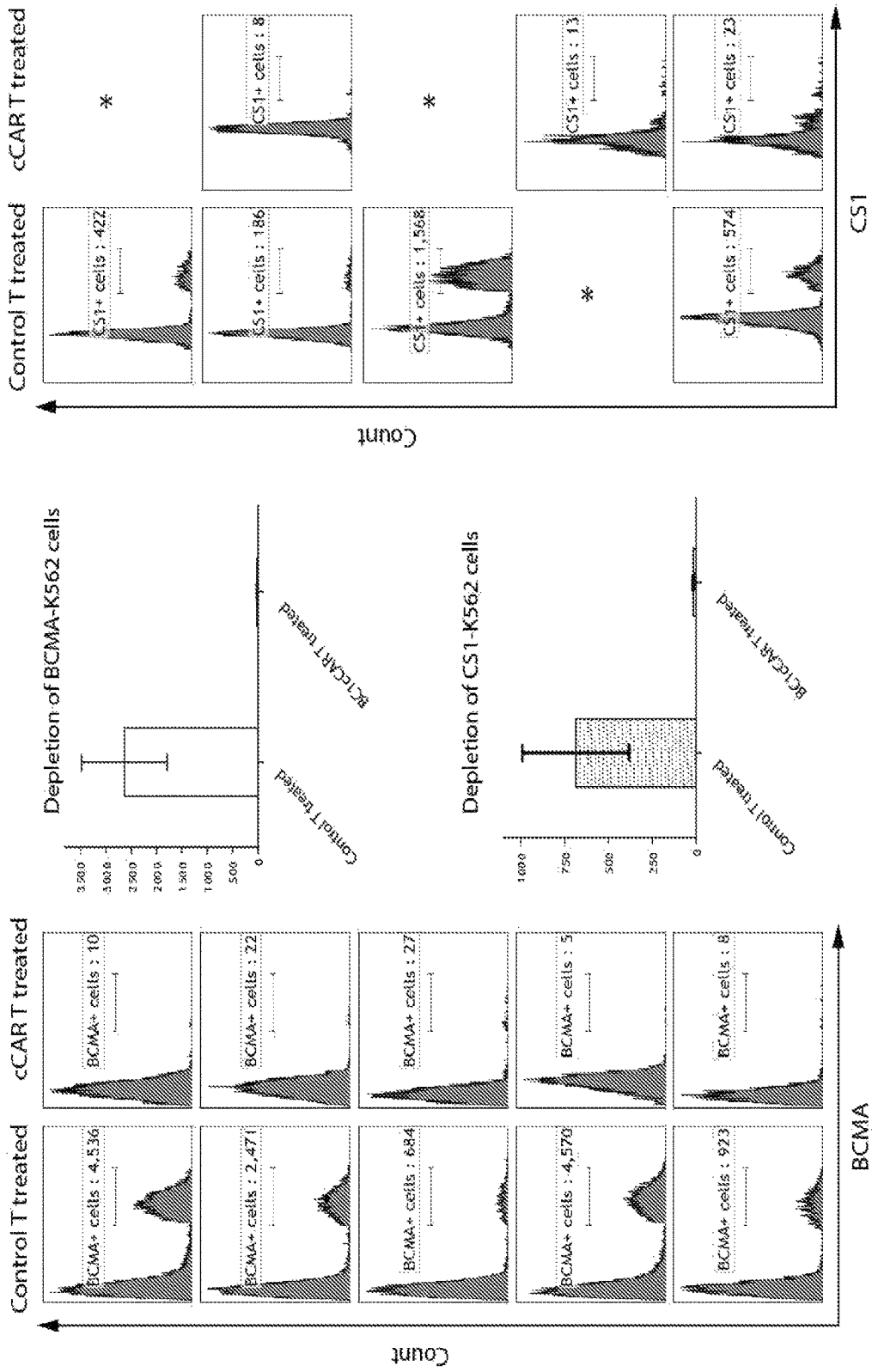

FIG. 10B: Analysis of mouse liver from separately injected BCMA-K562 or CS1-K562 injected mice At times of sacrifice (various), mice liver samples were collected and labeled with antibodies against CD3, CD45, BCMA, and CS1. Histograms were constructed to visualize presence of tumor and counts were averaged across 250 000 events to generate graphical summaries. Some mice died before sacrifice, and were unusable for sample collection.

Figure 11A:
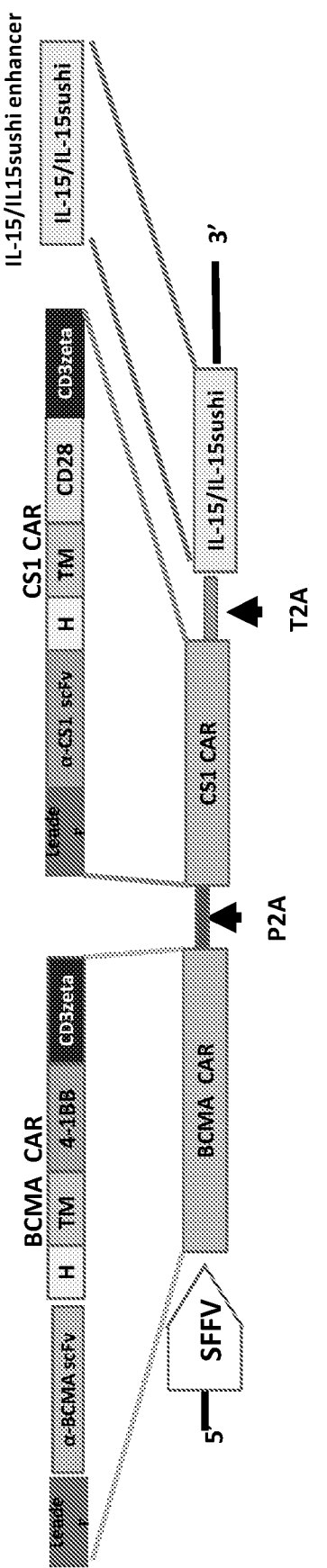

FIG. 11A. A schematic representation of cCAR-T with IL-15/IL-5sushi enhancer construct. The construct comprises a SFFV promoter driving the expression of multiple modular units of CARs, and IL-15/IL-15sushi linked by P2A and T2A peptide respectively. Upon cleavage of the linker, the cCARs split and engage upon targets expressing BCMA and/or CS1 and a secreting enhancer fusion of IL-15/IL-15sushi. As a novel cCAR construct, the activation domains of the construct may include, but is not limited to, 4-1BB or CD28 on the BCMA CAR segment and a CD28 or 4-1BB on the CS1 CAR segment. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7, IL-21, and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion can also enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Figure 11B:
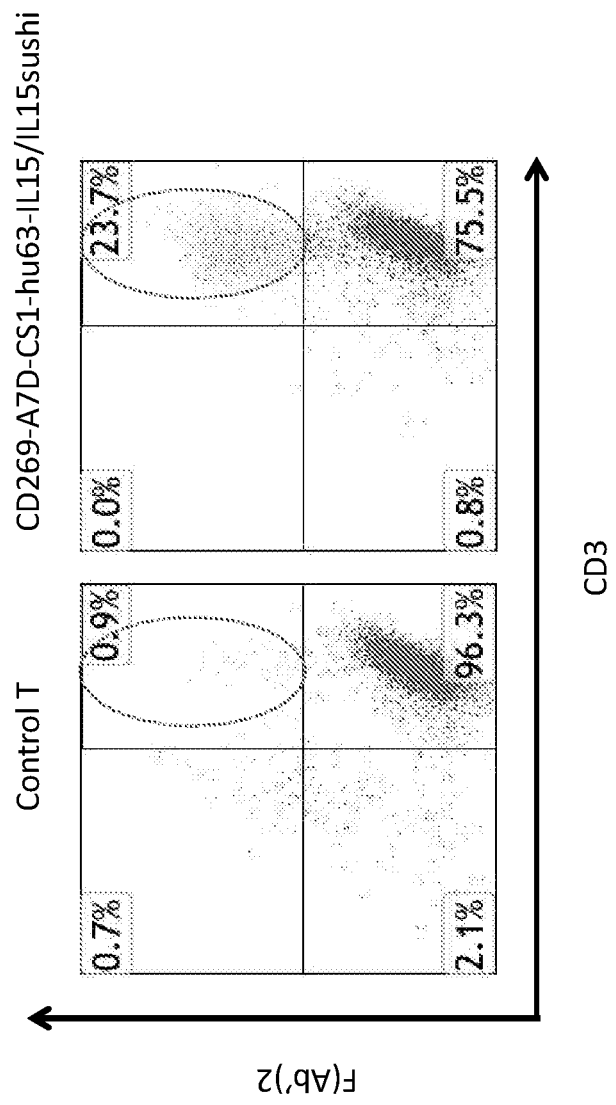

FIG. 11B. Expression of CAR T cells. Buffy coat cells were activated 3 days with anti-human CD3 antibody. Cells were transduced with either control vector (left) and CD269-A7D-hu63-IL15/IL-15sushi (right). After 3 days of incubation, cells were harvested and labeled for flow cytometry. CAR T cells are dots circled.

Figure 11C:
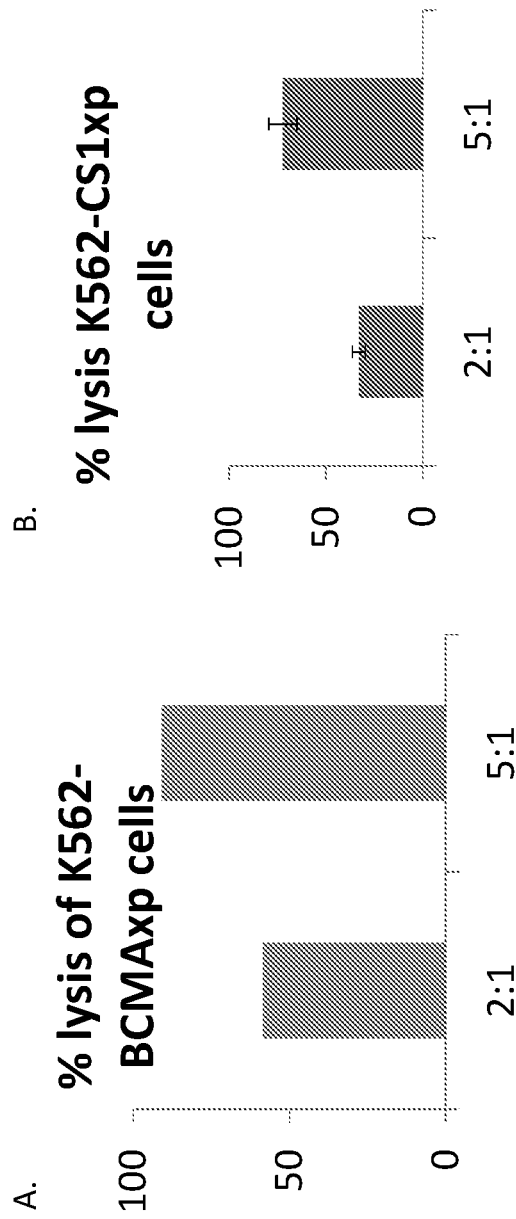

FIG. 11C. CD269-A7D-CS1-hu63-IL15/IL15sushi CAR T cells specifically lyse the K562 tumor cell line, which is synthetically expressing either BCMA (left) or CS1 (right) surface antigen, in co-culture assays. Co-culture experiments were performed at an effector to target ratio of 2:1 or 5:1 for 48 hours and were directly analyzed by flow cytometry for anti-human CS1 (CD319) and CD3.

Figure 11D:
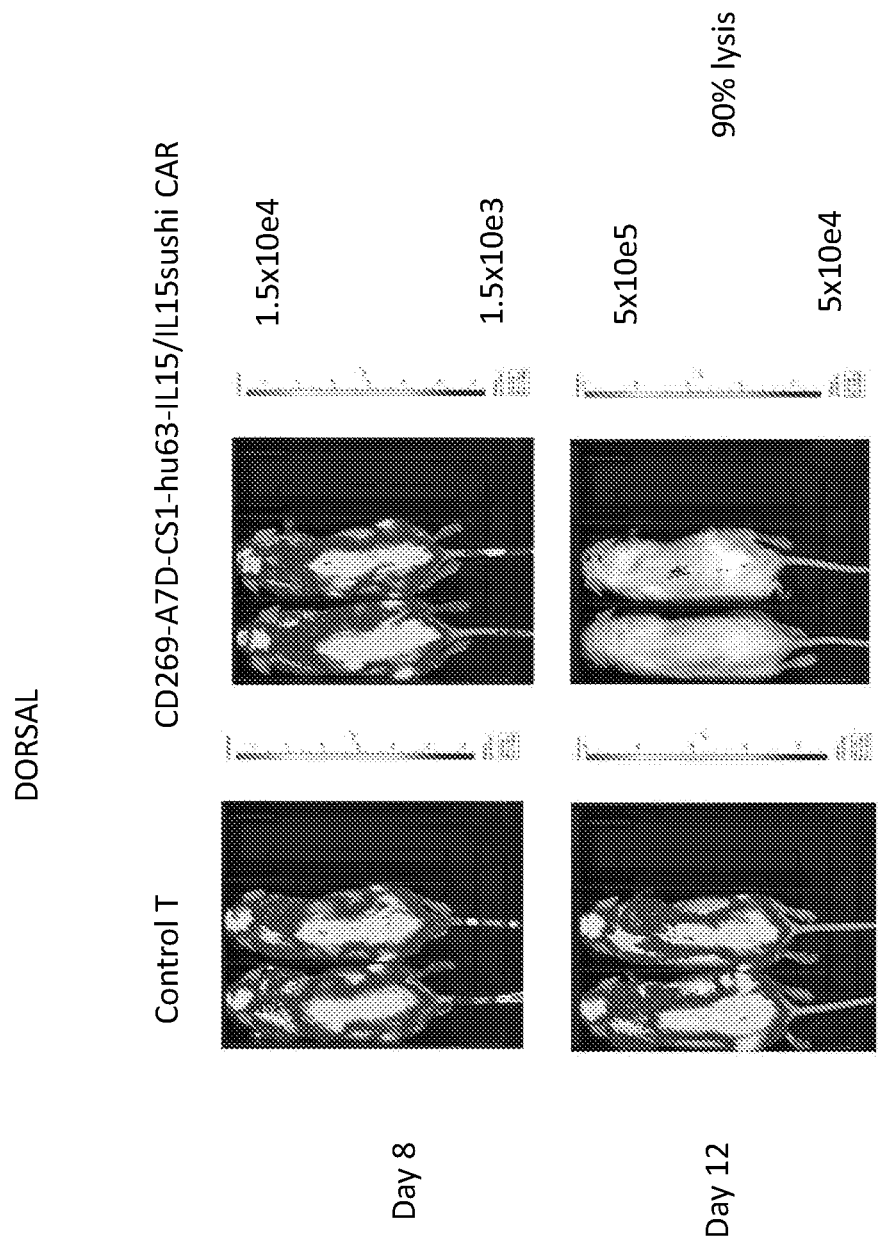

FIG. 11D. CD269-A7D-CS1-IL15/IL15sushi CAR T cells demonstrate strong anti-tumor effects in vivo against MM.1S tumor cell line (a myeloma cell line). NSG mice were sublethally irradiated and intravenously injected with 4.0×10⁶ luciferase-expressing MM.1S cells (Day 0) to induce measurable tumor formation. Starting 8 days after injection of tumor cells, mice were intravenously injected with a course of 15×10⁶ either CD269-A7D-CS1-IL15/ IL15sushi CAR T or vector control T cells. On days 8 (before T cell injection) and 12 (72 hours after T cell injection), mice were injected subcutaneously with RediJect D-Luciferin and subjected to IVIS imaging.

Figure 11E:
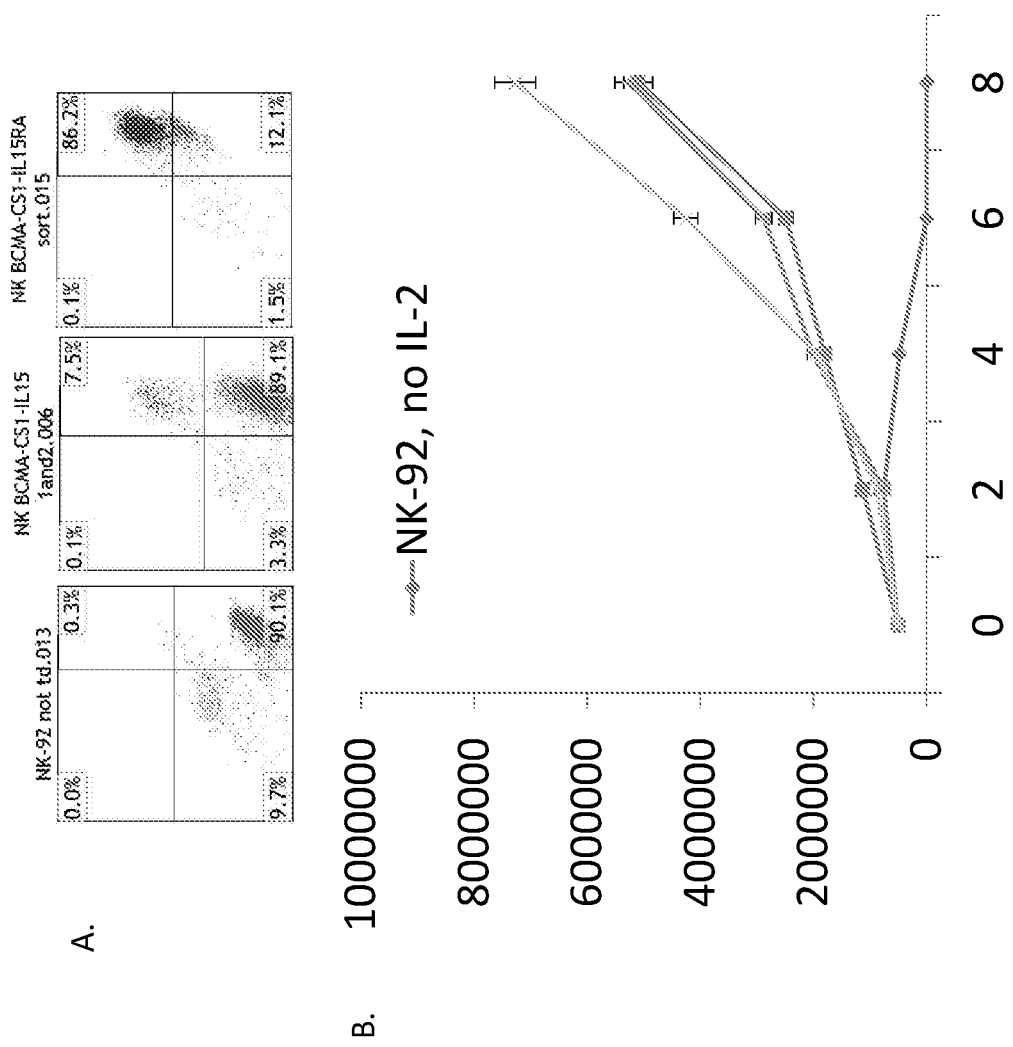

FIG. 11E. CD269-A7D-CS1-hu63-IL15/IL15sushi NK cells express functional IL15. NK-92 cell line was transduced with lentiviral vector containing CD269-A7D-CS1-hu63-IL15/IL15sushi CAR. (A) Cells were sorted on BD FACS Aria to select NK cells positive for the F(Ab')2 phenotype. (B) CD269-A7D-CS1-hu63-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted (B), and the volume increased to yield a concentration of approximately 0.5×10e6 cells/mL. This process was repeated on Days 4, 6 and 8.

Figure 11F:
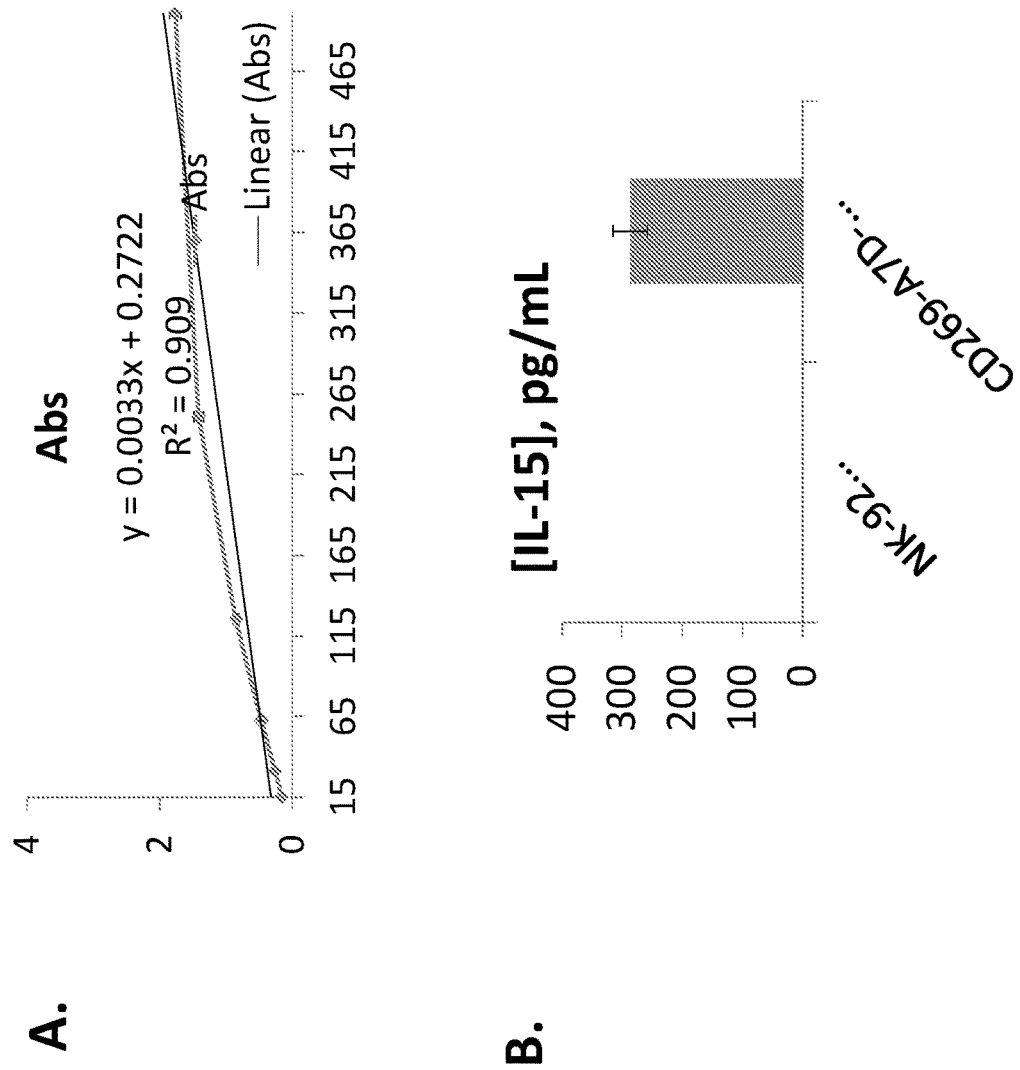

FIG. 11F. Sorted CD269-A7D-CS1-hu63-IL15/IL15sushi NK cells and wild-type control NK-92 cells were cultured in separate wells for 72 hours. Supernatant was collected and subjected to ELISA on 96-well plates precoated with IL-15 antibody. Following manufacturer's (Boster) directions, colorimetric results obtained on a plate reader were compared to a standard curve (A) generated with human IL-15 to determine concentration of IL-15 in the supernatants (B).

Figure 12A:
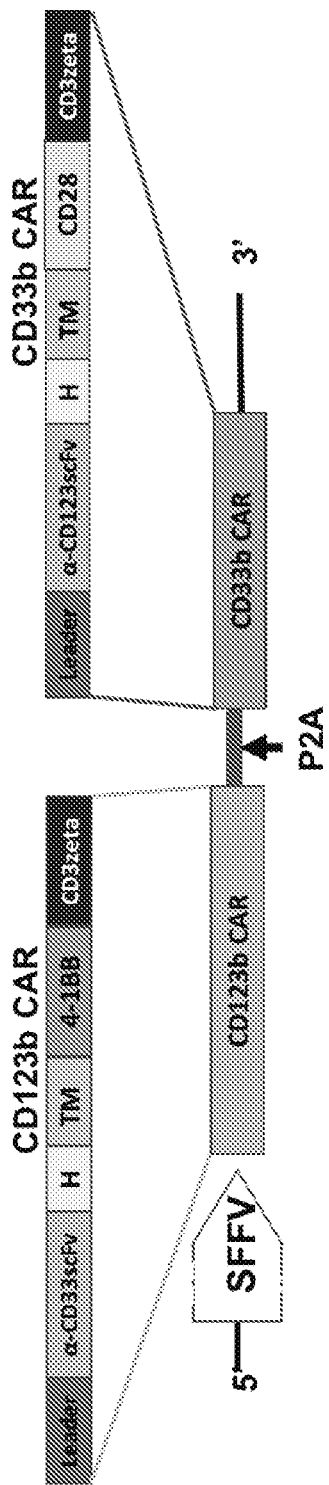
Figure 12B:
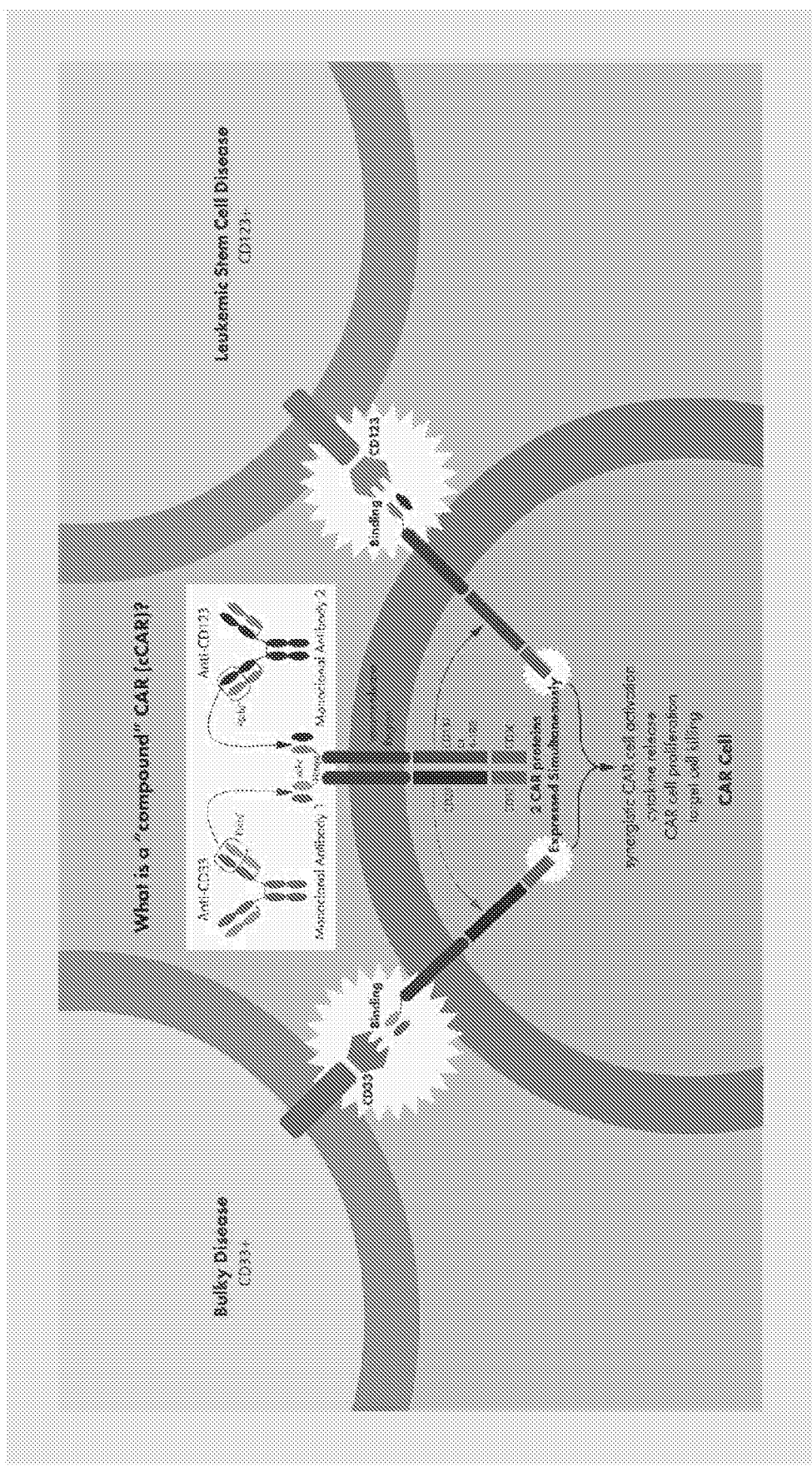

FIGS. 12A-12B: Genetic structure and function of CD123b–CD33b cCAR (A) Representation of CD123-CD33cCAR. (B) CD123b–CD33b cCAR T-cells are created by the viral transduction of patient donor T-cells with the CD123b–CD33b cCAR gene construct. The translated CD123 and CD33 CAR proteins are then expressed on the surface of the CAR T-cells, where they can recognize and bind the CD123 and CD33 target proteins on the surface of leukemic cells. The pharmacologic effect and mechanism of CD123b–CD33b cCAR T-cells is mediated by CD123b–CD33b cCAR recognition of the antigen, which triggers CD3zeta/Zap70 canonical cytotoxic T-cell activity further enhanced by the incorporation of CD28 or 4-1BB co-activation domains in the construct, creating a "second generation" CAR.

Figure 13:
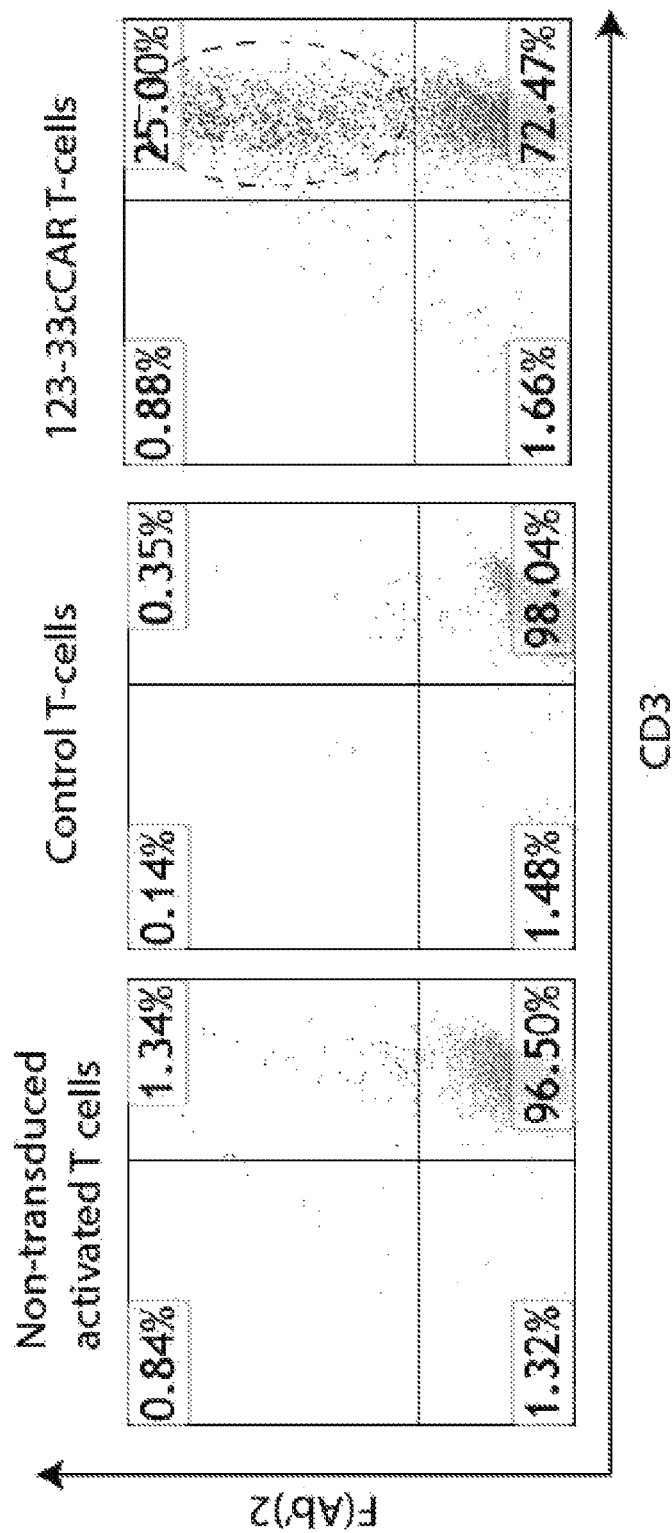

FIG. 13: CD123b–CD33b cCAR Transduction Efficiency Flow cytometry was used to determine CD123b–CD33b cCAR expression levels on the T-cell surface after transduction.

FIGS. 14A-D: CD123b–CD33b cCAR T-cells demonstrate targeted lysis of MOLM13 and U937 tumor cells lines. (14A) Flow cytometry analysis of control T-cells and CD123b–CD33b cCAR T-cells against MOLM13 (an AML cell line) tumor target cells at 2:1 and 5:1 E:T ratios. The target cell population is encircled. (14B) Flow cytometry analysis of control T-cells and CD123b–CD33b cCAR T-cells against U937 tumor target cells at 2:1 and 5:1 E:T ratios. The target cell population is encircled. 14(C) MOLM13 tumor cells (CD123+CD33+) and U937 cells (CD123-CD33+) alone stained for markers and their percent lysis summary at both E:T ratios. (14D) Dose-dependent cultures performed with HL60 (CD123dimCD33+) and KG1a (CD123dimCD33+) cells display high cCAR killing efficiency at E:T ratios ranging from 0.25:1 to 10:1.

FIGS. 15A-15E: CD123b–CD33b cCAR T-cells demonstrate targeted lysis of primary patient tumor cells. (15A) Flow cytometry analysis of control T-cells and CD123b–CD33b cCAR T-cells against PT1 tumor target cells at 2:1 and 5:1 E:T ratios. The target cell population is encircled. (15B) Flow cytometry analysis of control T-cells and CD123b–CD33b cCAR T-cells against PT2 tumor target cells at 2:1 and 5:1 E:T ratios. The target cell population is encircled. (15C) Flow cytometry analysis of control T-cells and CD123b–CD33b cCAR T-cells against PT3 tumor target cells at 2:1 and 5:1 E:T ratios. The target cell population (CD123+CD34+) is encircled and further broken down by CD38 expression to display LSC (CD123+CD34+CD38−) elimination. (15D) Flow cytometry analysis of control T-cells and CD123b–CD33b cCAR T-cells against PT4 tumor target cells at 2:1 and 5:1 E:T ratios. The target cell population (CD33+ bulk disease) is encircled. (15E) Percent lysis summary of CD123b–CD33b cCAR T-cells against all four patient samples at both 2:1 and 5:1 E:T ratios.

Figure 16A:
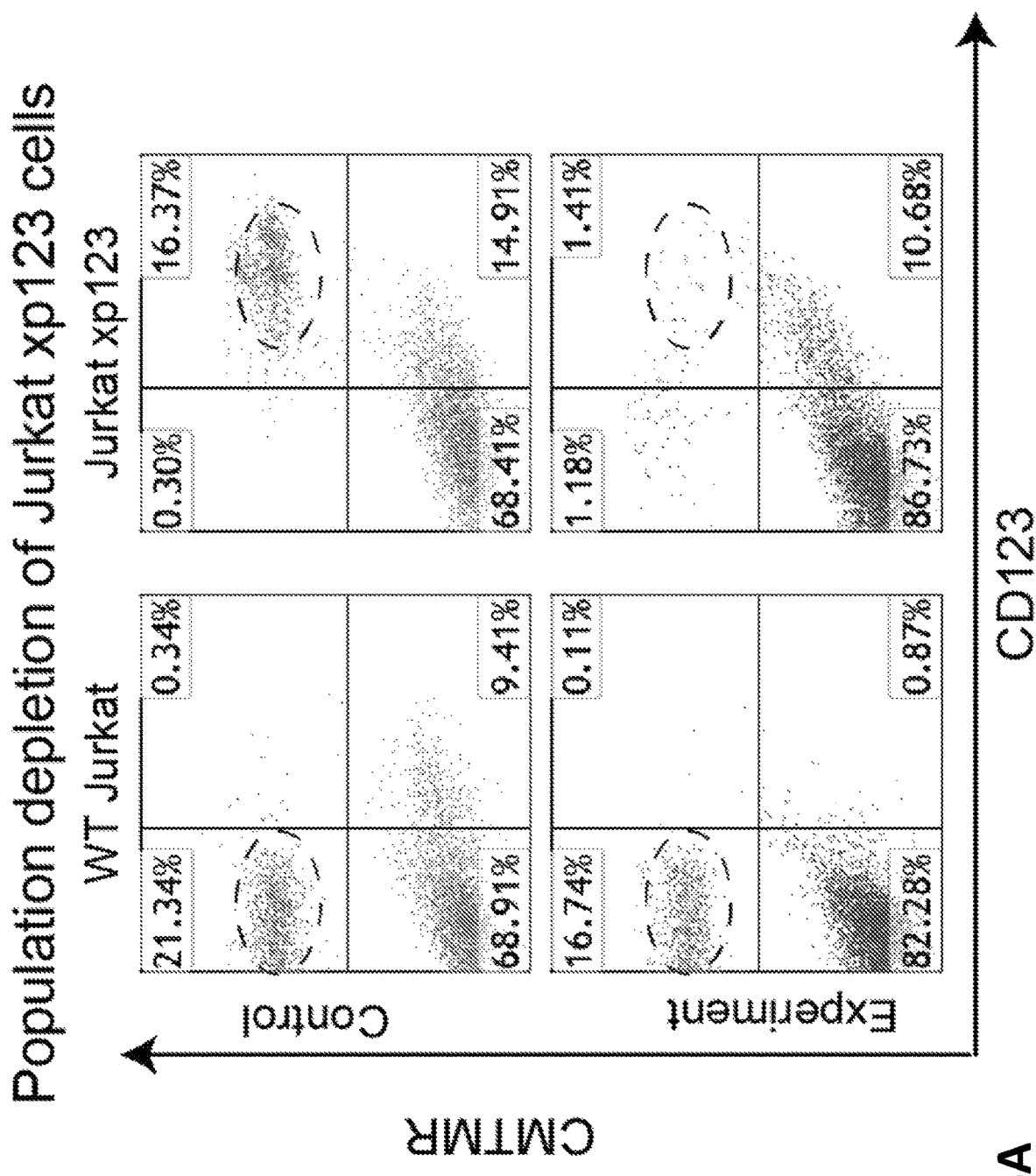
Figure 16B:
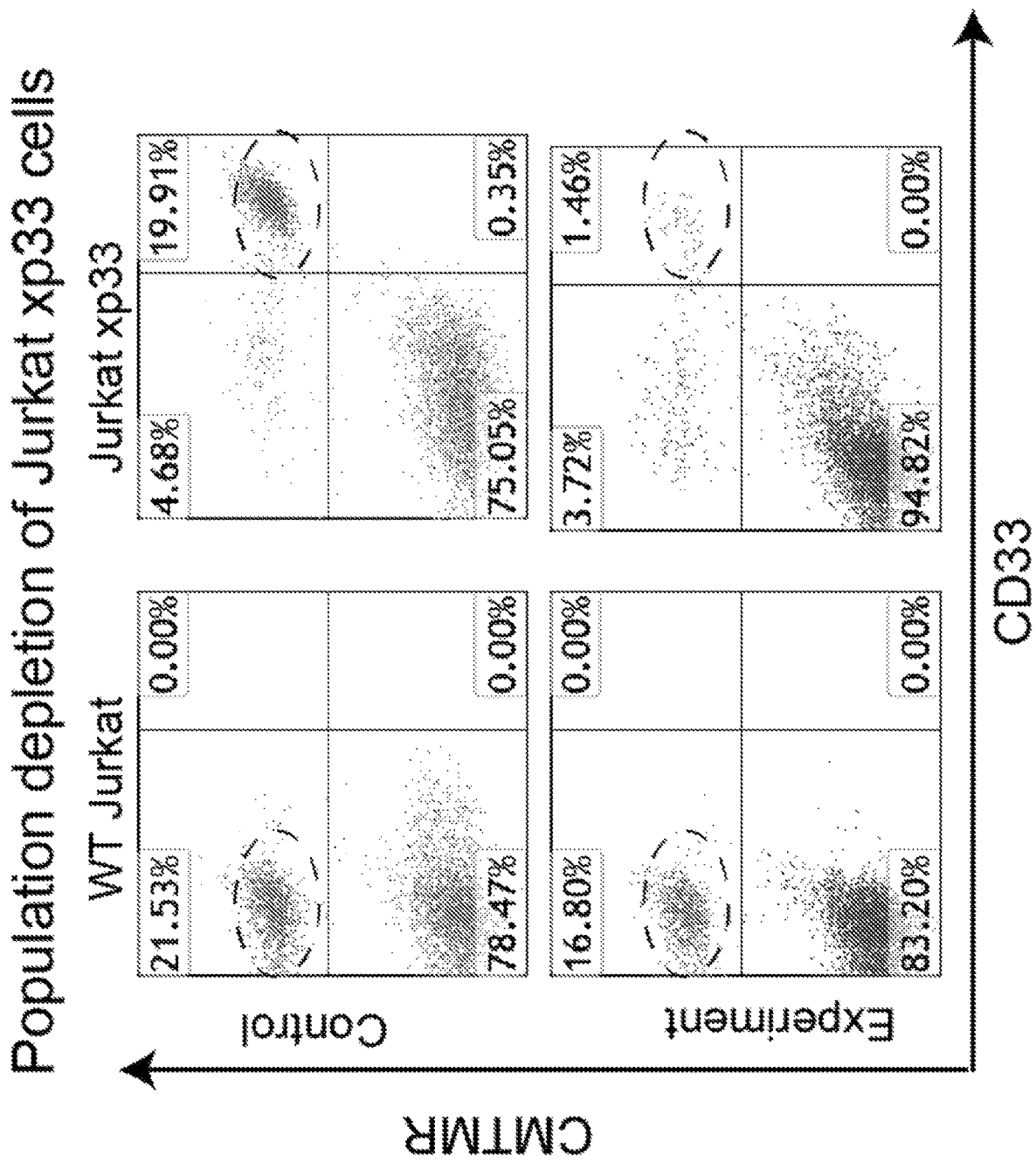
Figure 16C:
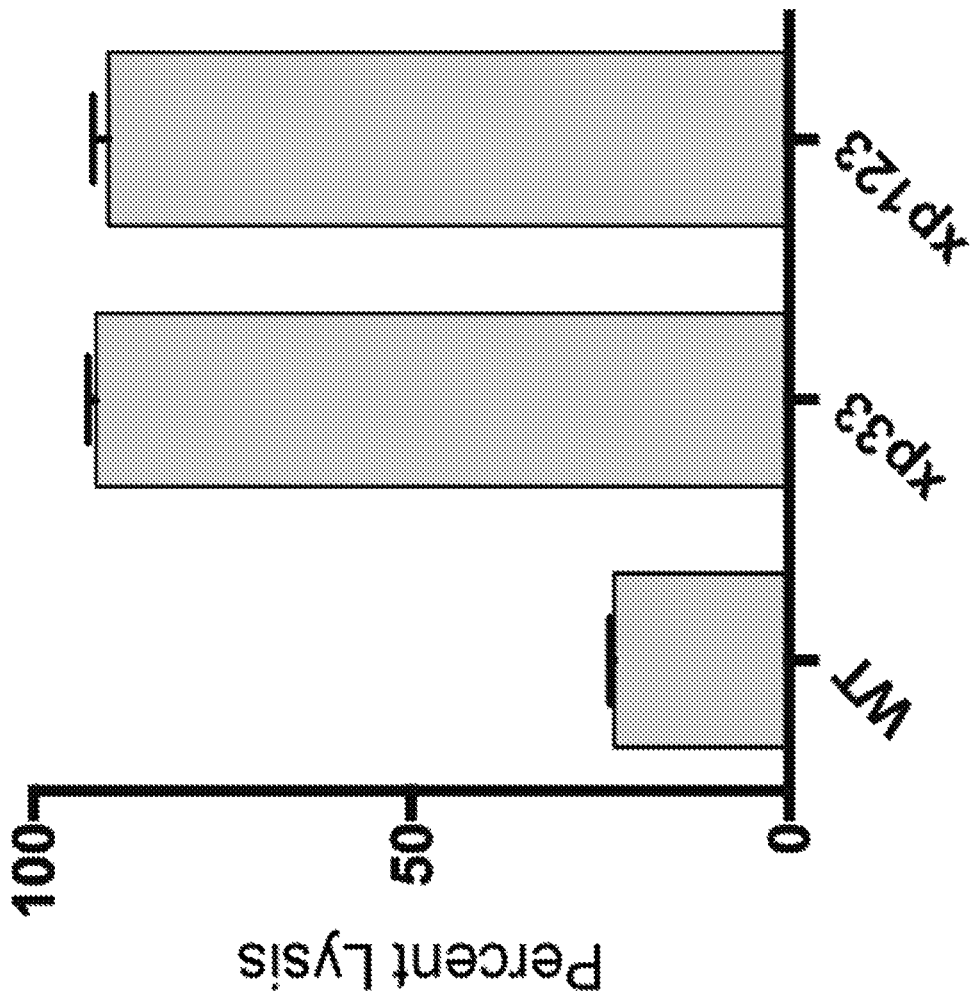

FIGS. 16A-16C: CD123b–CD33b cCAR T-cells ablate cells expressing either the CD33 or CD123 antigen with high efficacy.

(16A) Flow cytometry analysis of control T-cells and CD123b–CD33b cCAR T-cells against wild-type (WT) Jurkat tumor cells and Jurkat cells expressing CD123 (Jurkatxp123) at a 2:1 E:T ratio. The target cell population is encircled. (16B) Flow cytometry analysis of control T-cells and CD123b–CD33b cCAR T-cells against wild-type (WT) Jurkat tumor cells and Jurkat cells expressing CD33 (Jurkatxp33) at a 2:1 E:T ratio. The target cell population is encircled. (16C) Percent lysis summary of CD123b–CD33b cCAR T-cells against WT Jurkat cells, Jurkat xp33, and Jurkat xp123 cells ata 2:1 E:T ratio.

Figure 17A:
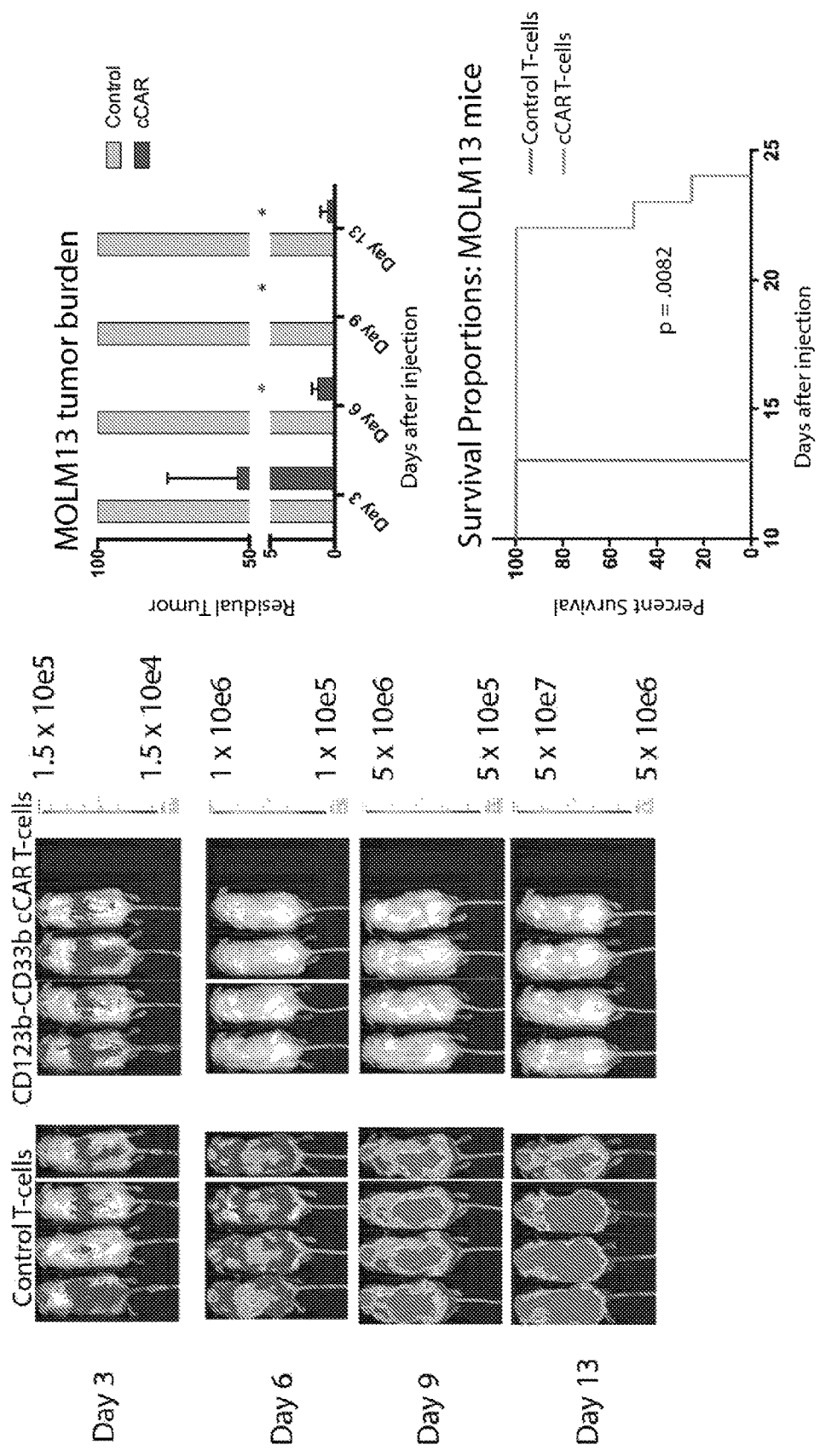
Figure 17B:
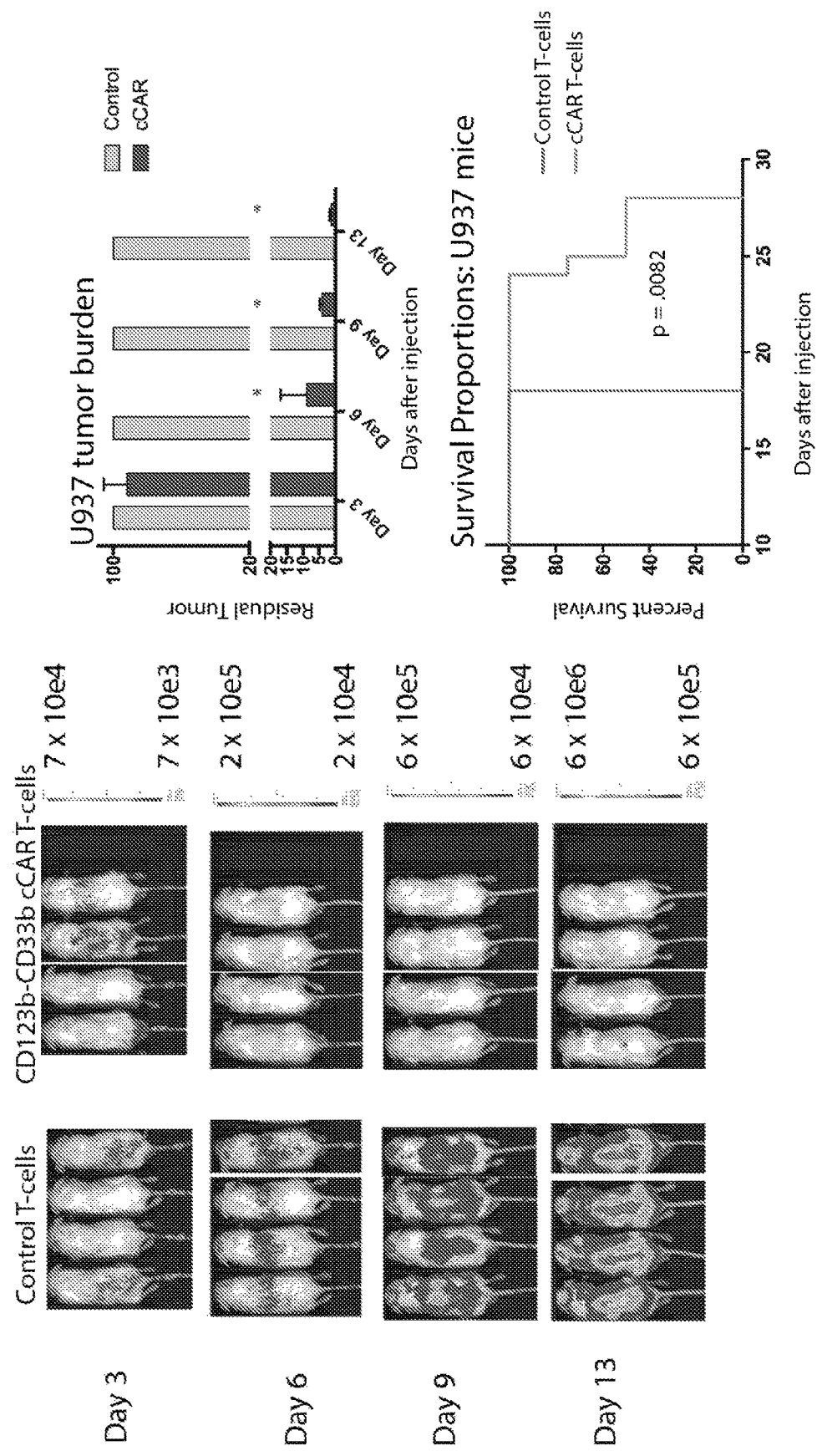
Figure 17C:
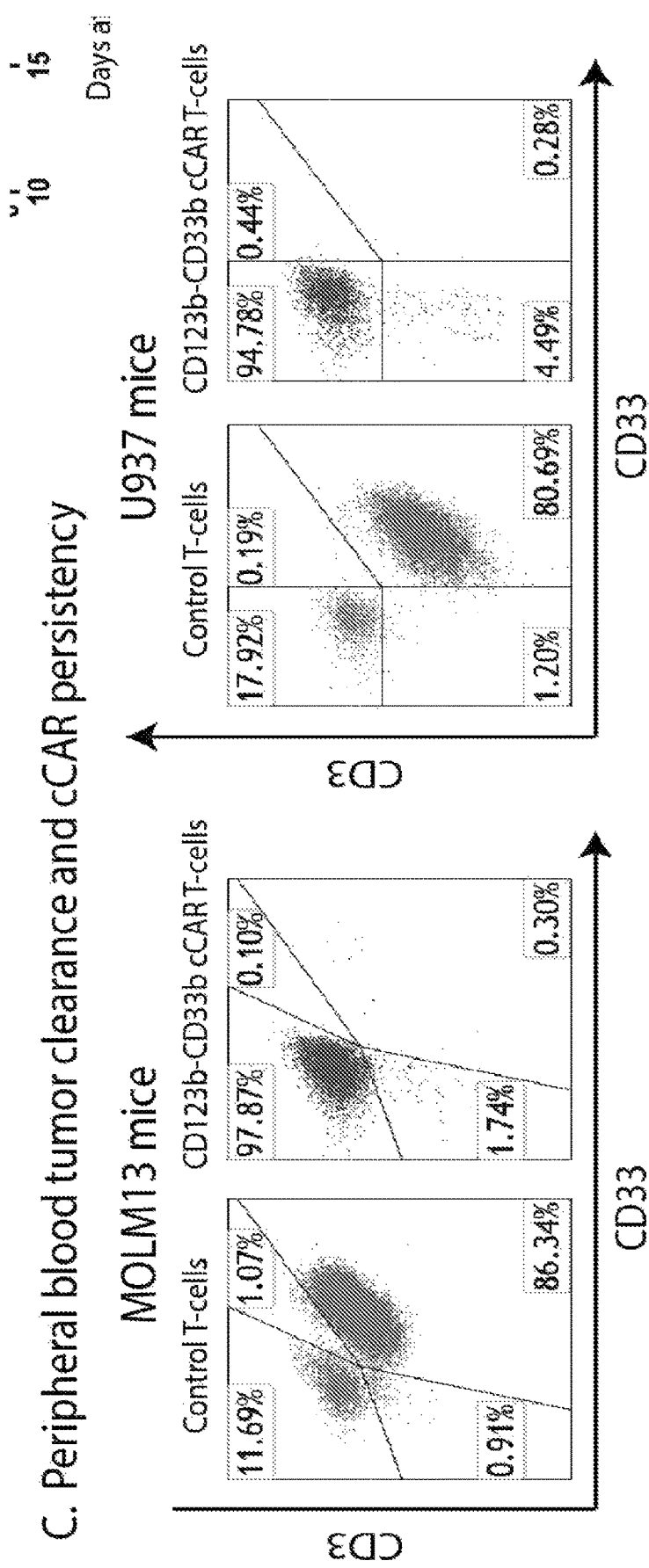

FIGS. 17A-17C: CD123b–CD33b cCAR T-cells demonstrate a profound anti-leukemic effect against MOLM13 and U937 cell lines in two in vivo xenograft mouse models.

(17A) IVIS imaging of luciferase-expressing MOLM13 cells on days 3, 6, 9, and 13 allowing tumor burden visualization (n=8 for each group). Graphical representation of tumor burden comparison between CD123b–CD33b cCAR T-cell and control T-cell treated mice over time. Tumor reduction is statistically significant from day 6 onward. Kaplan-Meier survival analysis curve represents survival outcomes (Mantel-Cox log-rank test p=0.0082). (17B) IVIS imaging of luciferase-expressing U937 cells on days 3, 6, 9, and 13 allowing tumor burden visualization (n=8 for each group). Graphical representation of tumor burden comparison between CD123b-CD33b cCAR T-cell and control T-cell treated mice over time. Tumor reduction is statistically significant from day 6 onward. Kaplan-Meier survival analysis curve represents survival outcomes (Mantel-Cox log-rank test p=0.0082). (17C) Peripheral blood of MOLM13 and U937 mice tumor models. Flow cytometry allowed visualization of CD45+CD3+ T-cells and CD45+CD33+ tumor cells.

Figure 18A:
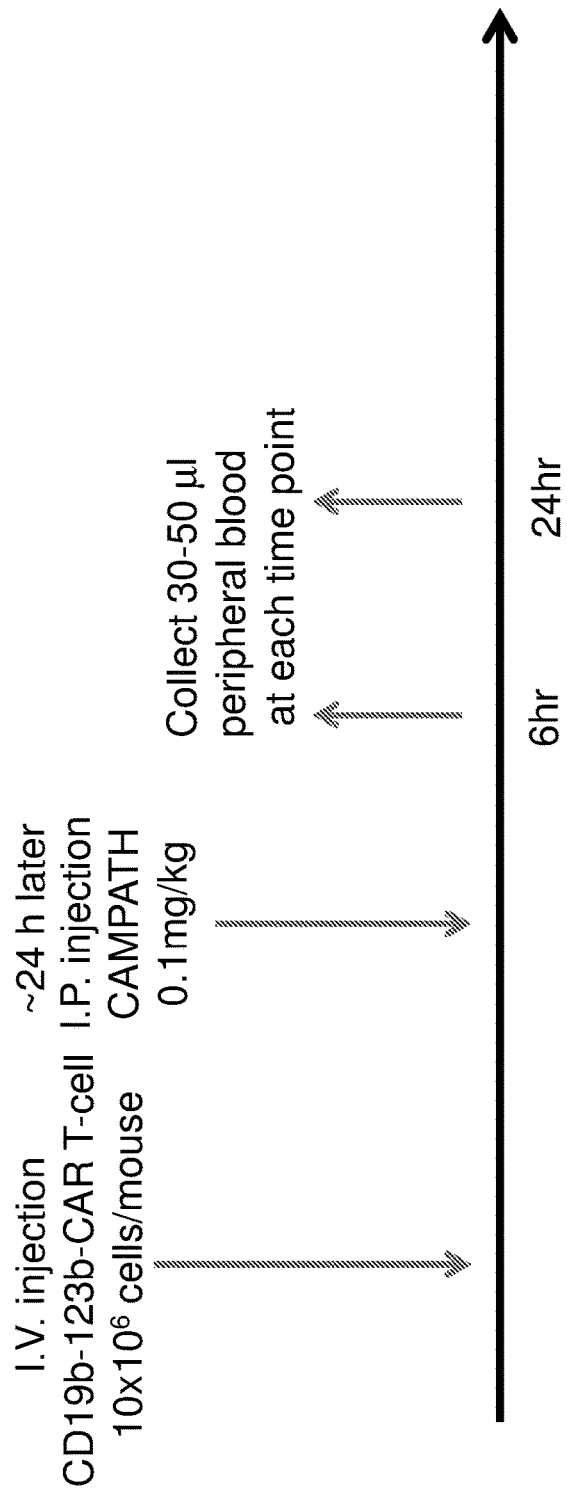
Figure 18B:
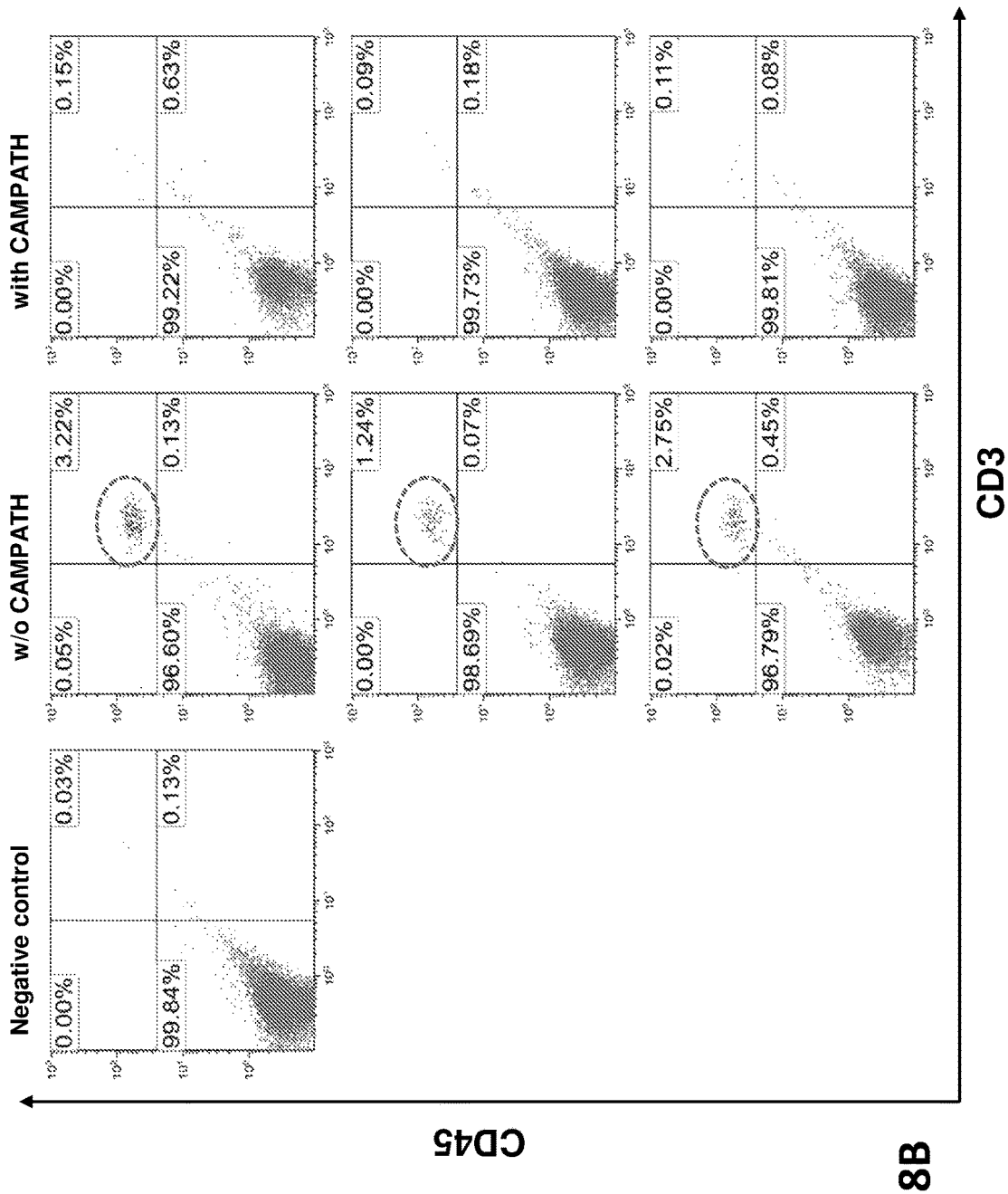
Figure 18C:
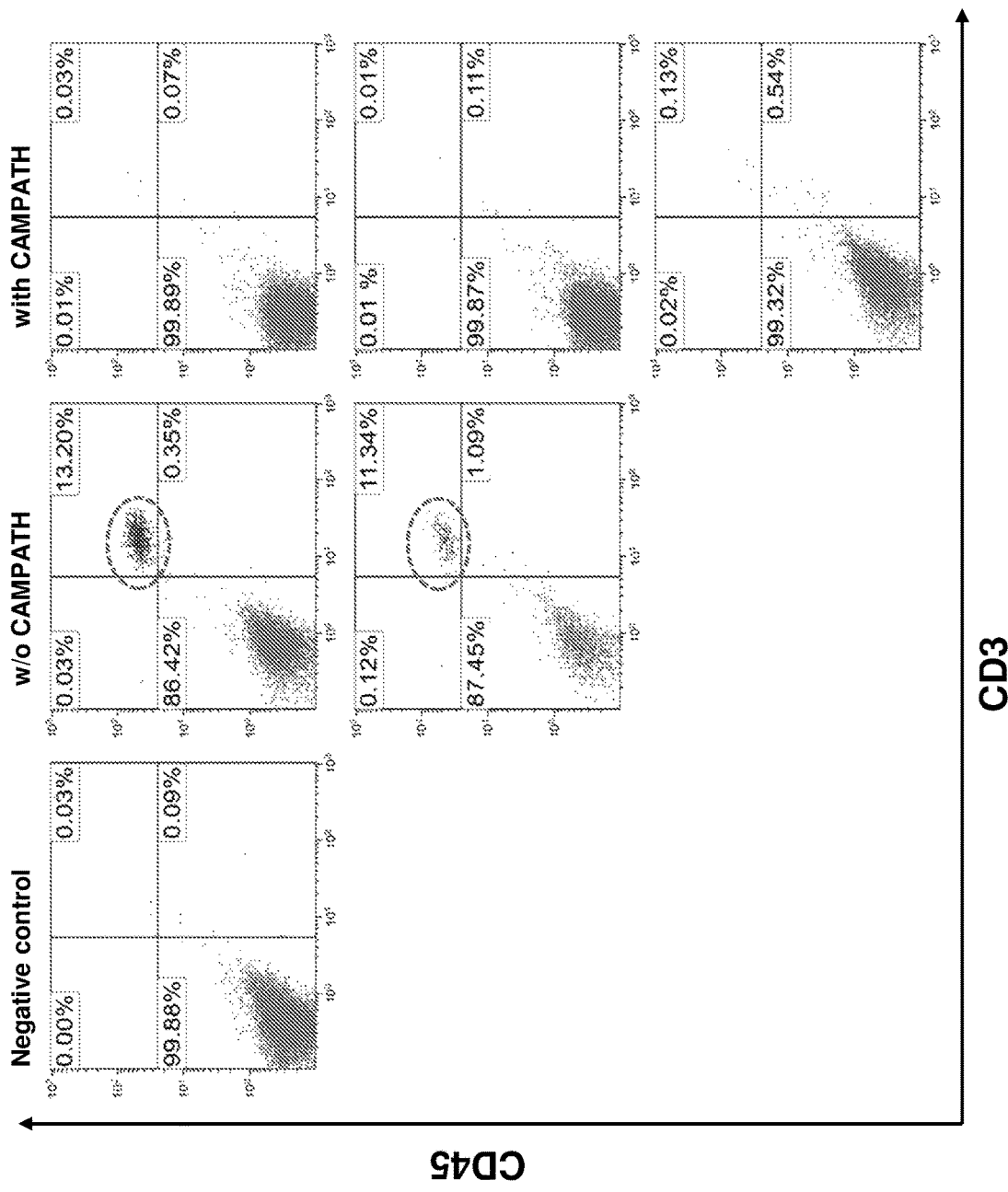

FIGS. 18A-18C: Depletion of infused CD123b–CD33b cCAR T-cells following treatment with CAMPATH.

(18A) Experimental schema to evaluate the effect of CAMPATH administration after CD19b-CD123 cCAR T-cell infusion into NGS mice. 10×10⁶ CD19b–CD123 cCAR T-cells were injected intravenously into sublethally irradiated mice (n=6) and −24 hours later, CAMPATH (0.1 mg/kg) or PBS were intraperitoneally injected (n=3 of each, except for hour 6 where n=2 for control group). 6 and 24 hour later, peripheral blood was collected to determine the persistence of CAR T-cells. (18B) Representation of persistence of infused CD19b–CD123 cCART-cells in peripheral blood 6 hours later with or without CAMPATH treatment. Presence of CD19b–CD123 cCART-cells was detected by flow cytometry. (18C) Representation of persistence of infused CD19b–CD123 cCART-cells in peripheral blood 24 hours later with or without CAMPATH treatment. Presence of CD19b–CD123 cCAR T-cells was detected by flow cytometry.

Figure 19:
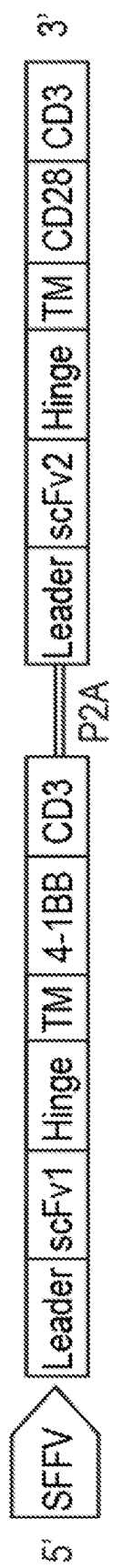

FIG. 19: Structure organization of CD19b–CD123 cCAR
A schematic representation of cCAR-T construct (CD19b–CD123cCAR). The construct comprises a SFFV promoter driving the expression of-multiple modular units of CARs linked by a P2A peptide. Upon cleavage of the linker, the cCARs split and engage upon targets expressing CD19b CAR and CD123 CAR targeting CD19 and CD123 antigen respectively. As a novel cCAR construct, the activation domains of the construct may include, but is not limited to, 4-1BB on the CD19b CAR segment and a CD28 region on the CD123 CAR. A hinge domain (H), a transmembrane domain (TM), a co-stimulatory domain (CD28 or 4-1BB) and the intracellular signaling domain CD3 zeta (CD3).

Figure 20:
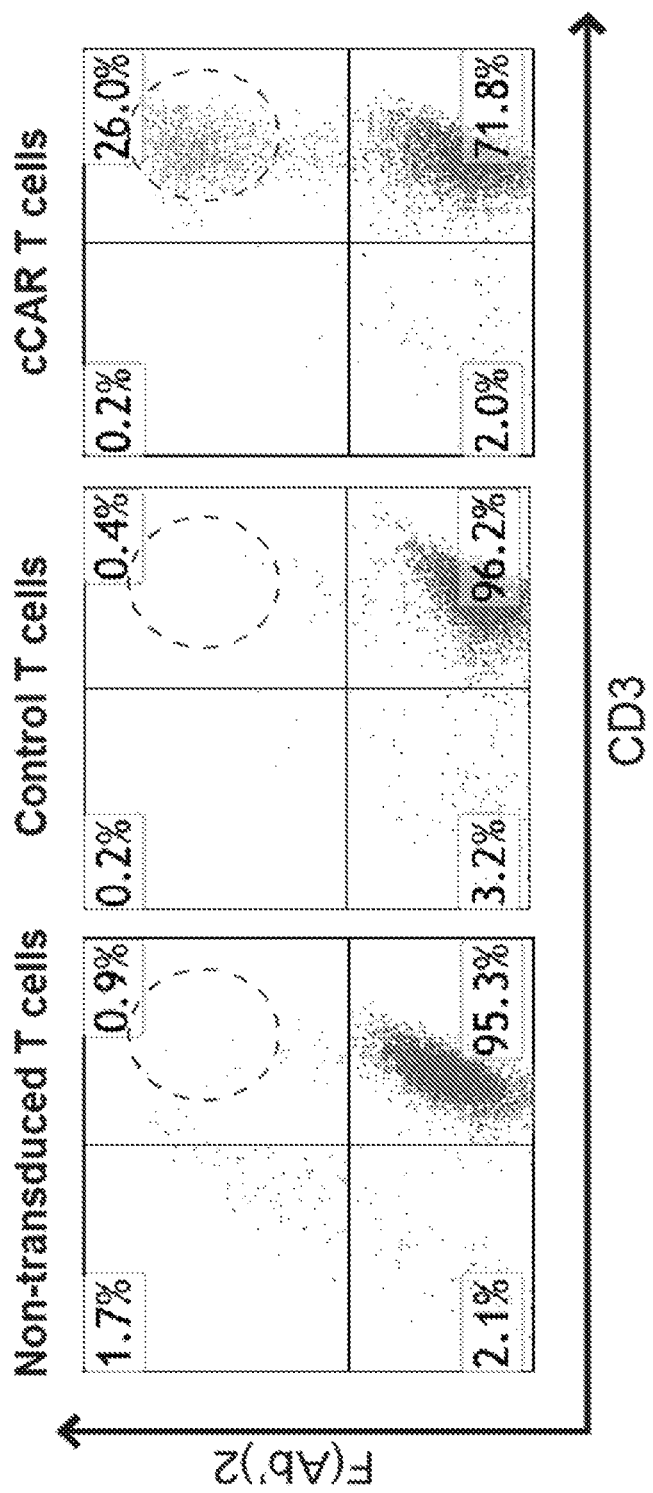

FIG. 20: Transduction efficiency of CD19b–CD123 cCAR
Activated T cells were transduced with thawed lentivirus expressing CD19b–CD123 cCAR on retronectin-coated plates. After transduction, cells are washed and expanded; flow analysis (F(Ab')2 labeling) is done to confirm CAR efficiency.

FIGS. 21A-21D: CD19b–CD123 cCAR T cells demonstrate specific and efficacious lysis of CD19+ and CD123+ leukemia/lymphoma cell lines.
(21A) Flow cytometry analysis of control T-cells and CD19b–CD123 cCAR T-cells against artificially-induced CD19+K562 cells and control K562 cells at 5:1 E:T ratios at 16 and 48 hours. The target cell population is contained within flattened ellipses. Non-transduced CD19-cells are contained within smaller round circles. (21B) Flow cytometry analysis of control T-cells and CD19b–CD123 cCAR T-cells against artificially-induced CD19+K562 cells and control K562 cells at 5:1 E:T ratios at 16 hours. The target cell population is depicted by scattered dots in the upper right lanes. Non-transduced CD123–Jurkat cells are depicted by scattered dots in the lower right lanes. (21C) Flow cytometry analysis of KG1a tumor cells (CD123+ CD19−) and SP53 cells (CD123-CD19+) at 5:1 E:T ratio, at 16 and 48 hours. (21D) Summary graph of tumor cell percent lysis.

FIGS. 22A-22D: CD19b–CD123 cCAR T cells demonstrate targeted lysis of primary patient cells.
(22A) Flow cytometry analysis of PT1 and PT2 tumor cell phenotypes. (22B) Flow cytometry analysis of control T-cells and CD19b–CD123 cCAR T-cells against PT1 tumor target cells a 5:1 E:T ratio, at 24 hours. The target cell population is depicted as scattered dots in the boxes on the right of the graphs red. (22C) Flow cytometry analysis of control T-cells and CD19b–CD123 cCAR T-cells against PT2 tumor target cells a 5:1 E:T ratio, at 24 and 48 hours. The target cell population is depicted as scattered dots in the right, upper boxes of the graphs. (22D) Percent lysis summary of CD19b–CD123 cCAR T-cells against patient samples at a 5:1 E:T ratio at 24 and 48 hours.

FIGS. 23A-23F: CD19b–CD123 cCAR T-cells demonstrate a profound anti-leukemic effect against MOLM13 and REH cell lines in two in vivo xenograft mouse models.
(23A) IVIS imaging of luciferase-expressing MOLM13 cells on days 3, 6, 8, and 11 allowing tumor burden visualization (represented mice for each group). (23B) Graphical representation of tumor burden comparison between CD19b–CD123 cCAR T-cell and control T-cell treated mice over time, tumor burden was measured both dorsally and ventrally. Tumor reduction is statistically significant from day 6 onward. (23C) Kaplan-Meier survival analysis curve represents survival outcomes (Mantel-Cox log-rank test p=0.0031). (23D) IVIS imaging of luciferase-expressing REH cells on day 16, allowing for tumor burden visualization (n=5 for each group). (23E) Graphical representation of tumor burden comparison between CD19b-CD123 cCAR T-cell and control T-cell treated mice over time. Tumor reduction is statistically significant. Tumor burden was measured dorsally and ventrally. (23F) Kaplan-Meier survival analysis curve represents survival outcomes (Mantel-Cox log-rank test p=0.0016).

Figure 24:
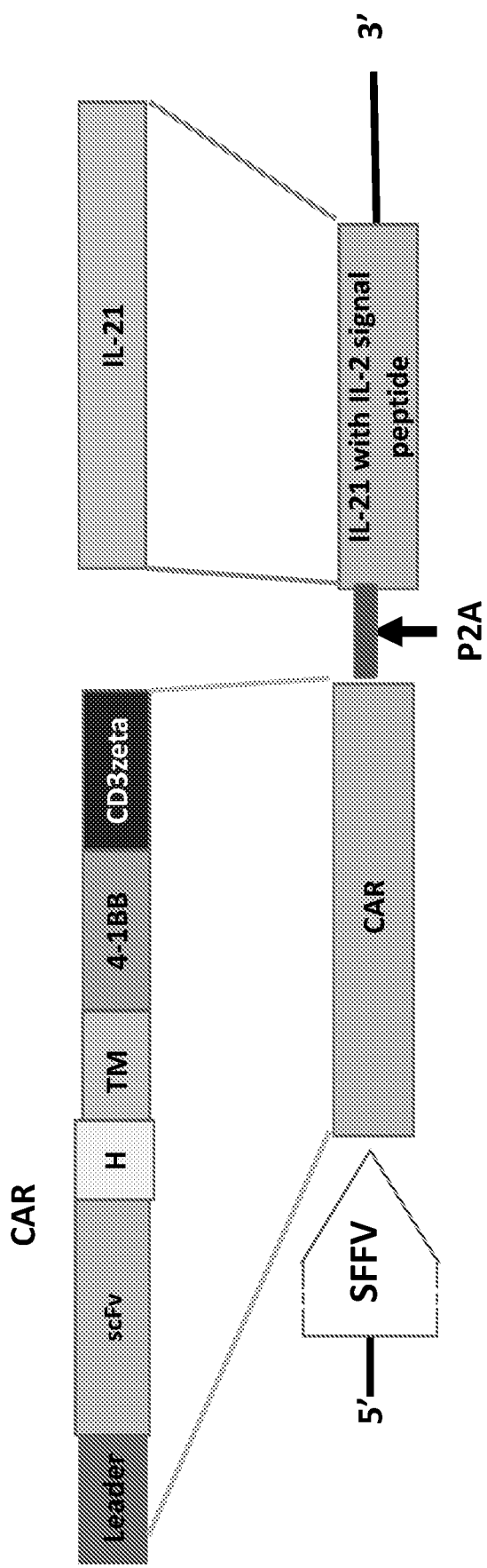

FIG. 24. A Link by P2A schematic showing CAR, 4-1BB and IL-21 in a single construct (CAR co-expressing IL-21) and its expression in T or NK cells.
The construct consists of a SFFV promoter driving the expression of CAR with costimulatory domain, 4-1BB). Upon cleavage of the linkers, a CAR and IL-21 split and engage upon targets expressing antigen. CAR T cells received not only costimulation through the 4-1BB or CD28 but also 4-1BB ligand (4-1BBL or CD137L) or IL-21. The CD3-zeta signaling domain complete the assembly of this CAR-T. The IL-21 signal peptide is replaced with IL-2 signal peptide for a better secretion of IL-21. H, CD8a hinge region, TM, CD8a transmembrane domain. Example of CAR with IL-21 can be CD19-IL-21 CAR, BCMA-IL-21 CAR, CD4-IL-21 CAR and CD45-IL-21 CAR.

Figure 25:
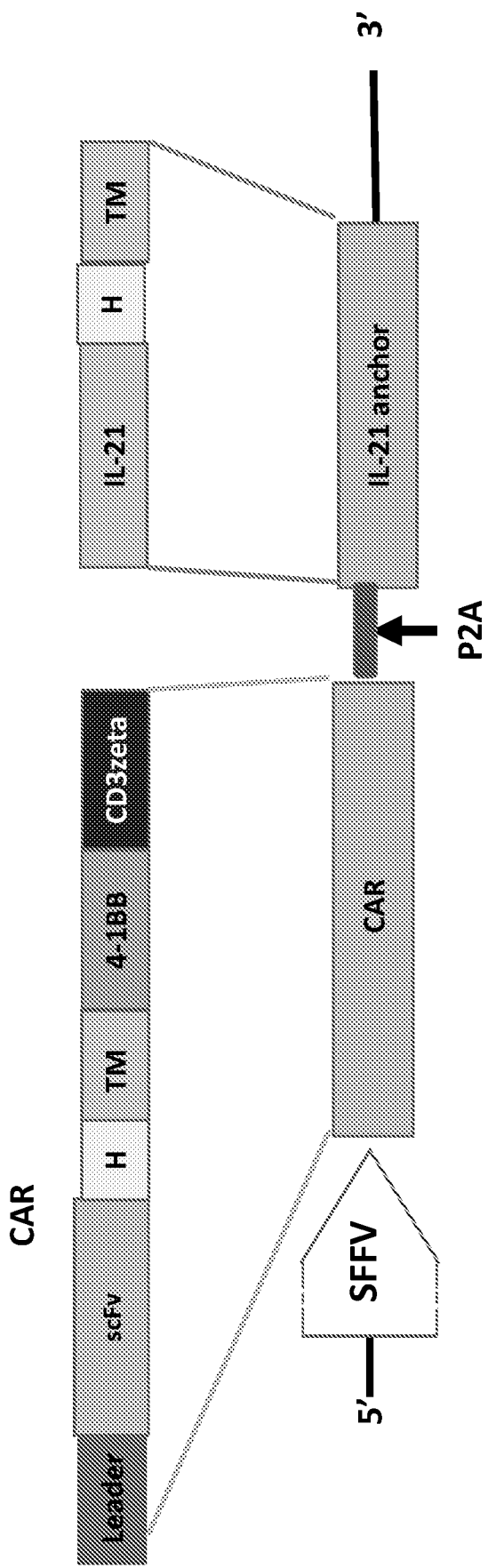

FIG. 25. Schematic diagram to elucidate the construct (CAR co-expressing IL-21 anchor) and its expression in T or NK cells.
A CAR with IL-21anchor is linked with the P2A self-cleaving sequence. The IL-21 anchor fusion is composed of IL-2 signal peptide fused to IL-21, and linked to CD8 hinge region and CD8 transmembrane domain. The combination of CAR and IL-21 fusion is assembled on an expression vector and their expression is driven by the SFFV promoter. The IL-21 signal peptide is replaced with IL-2 signal peptide for a better secretion of IL-21 and anchoring on the cell surface. Example of CAR with IL-21anchor can be CD19-IL-21 anchor CAR, BCMA-IL-21 anchor CAR, CD4-IL-21 anchor CAR and CD45-IL-21 anchor CAR.

Figure 26:
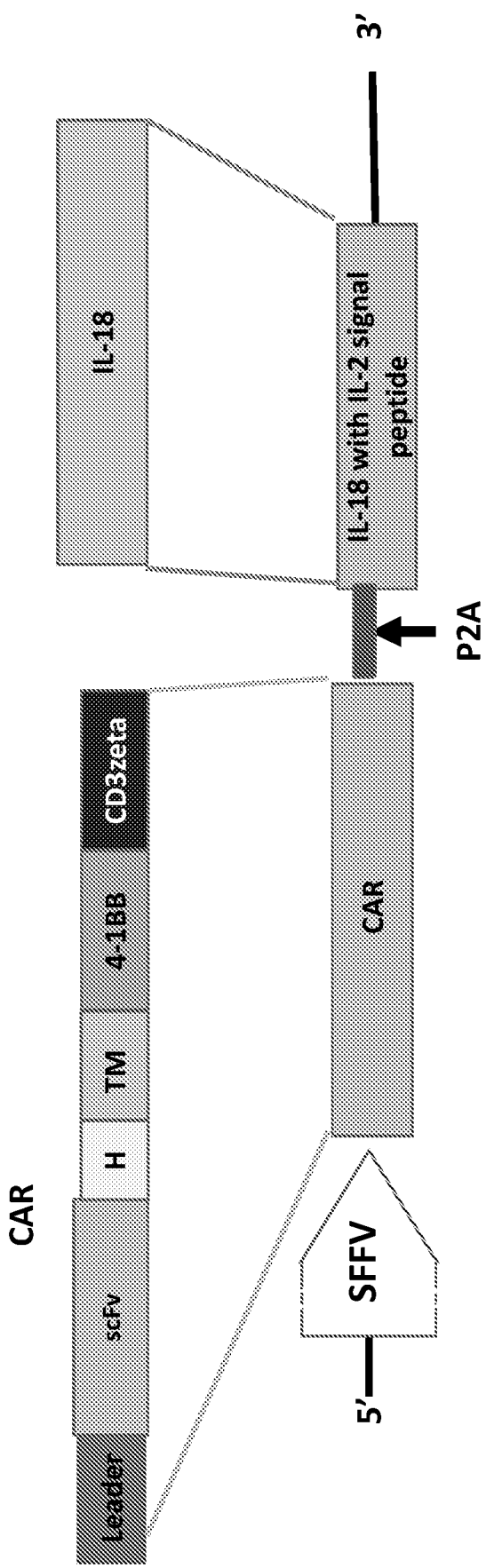

FIG. 26. A Link by P2A schematic showing CAR, 4-1BB and IL-18 in a single construct (CAR co-expressing IL-18) and its expression in T or NK cells.
The construct consists of a SFFV promoter driving the expression of CAR with costimulatory domain, 4-1BB). Upon cleavage of the linkers, a CAR and IL-18 split and engage upon targets expressing antigen. CAR T cells received not only costimulation through the 4-1BB or CD28 but also 4-1BB ligand (4-1BBL or CD137L) or IL-21. The CD3-zeta signaling domain complete the assembly of this CAR-T. The IL-21 signal peptide is replaced with IL-2 signal peptide for a better secretion of IL-18. H, CD8a hinge region, TM, CD8a transmembrane domain. The CD3-zeta signaling domain complete the assembly of this CAR-T. Example of CAR with IL-18 can be CD19-IL-18 CAR, BCMA-IL-18 CAR, CD4-IL-18 CAR and CD45-IL-18 CAR.

Figure 27:
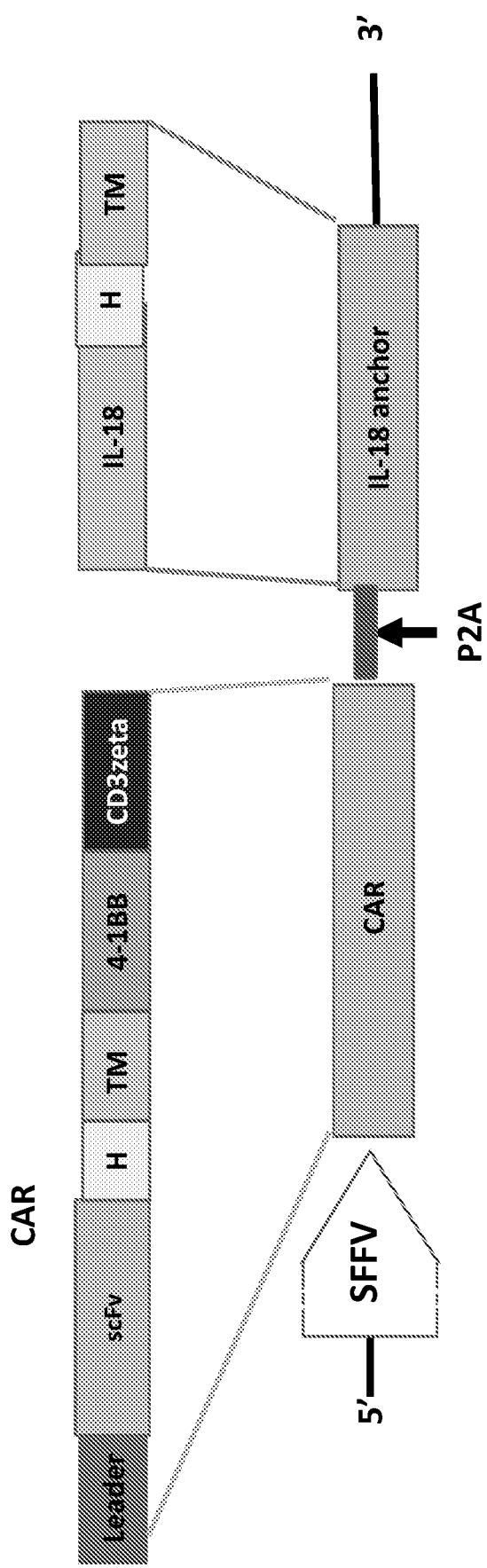

FIG. 27. Schematic diagram to elucidate the construct (CAR co-expressing IL-18 anchor) and its expression in T or NK cells.
A CAR with IL-18 anchor is linked with the P2A self-cleaving sequence. The IL-18 anchor fusion is composed of IL-2 signal peptide fused to IL-18 and linked to CD8 hinge region and CD8 transmembrane domain. The combination of CAR and IL-18 anchor fusion is assembled on an expression vector without CD3 zeta chain, and their expression is driven by the SFFV promoter. The IL-18 signal peptide is replaced with IL-2 signal peptide for a better secretion of IL-18 and then anchoring on the cell surface. Example of CAR with IL-18 anchor can be CD19-IL-18 anchor CAR, BCMA-IL-18 anchor CAR, CD4-IL-18 anchor CAR and CD45-IL-18 anchor CAR.

Figure 28A:
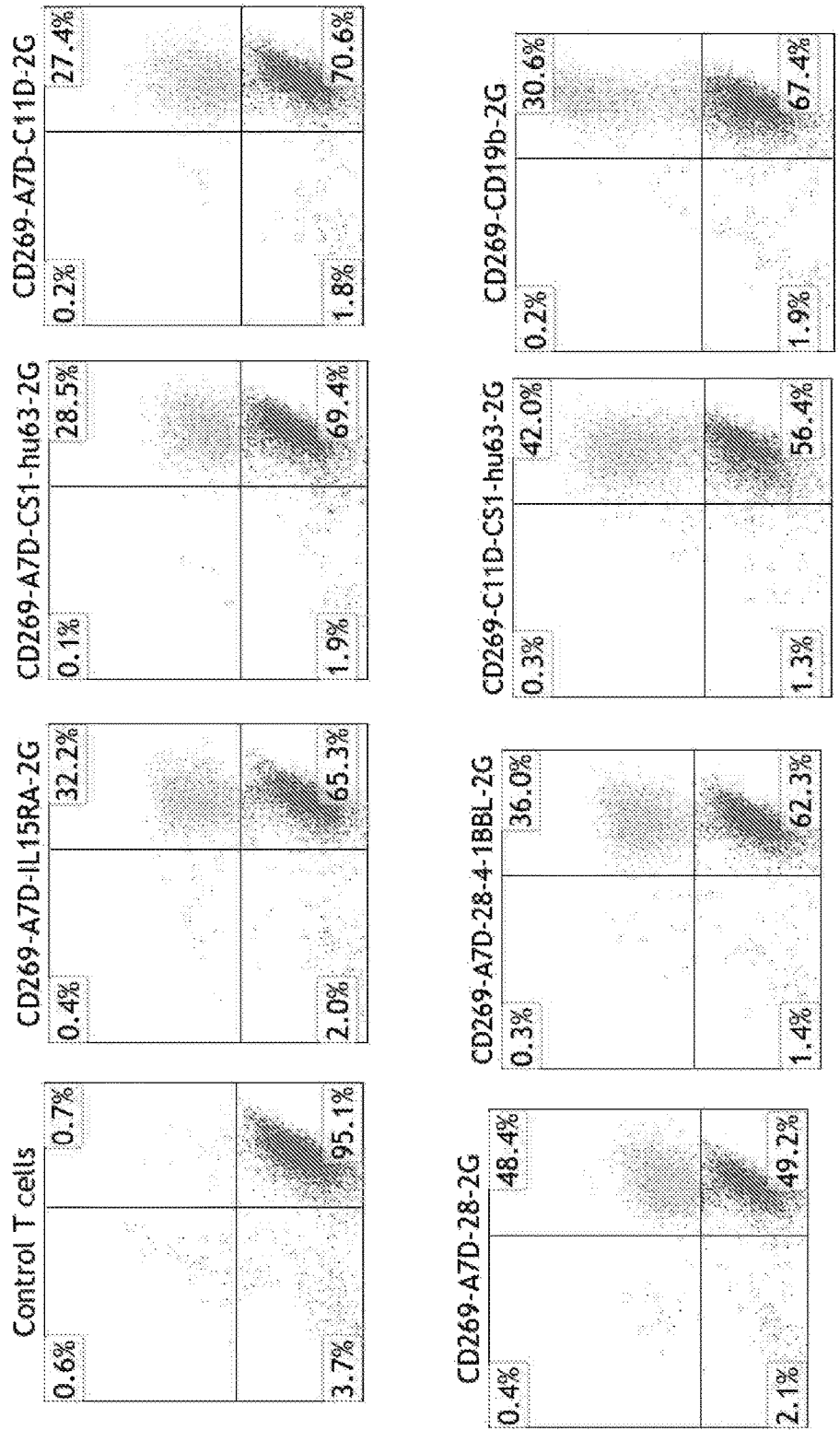

FIG. 28A. Expression of different versions of anti-BCMA CAR or cCAR T cells. Buffy coat cells were activated 3 days with anti-CD3 antibody.
Cells were transduced with either control vector (top left) or various CD269 CAR lentiviral supernatants. After 3 days of incubation, cells were harvested and labeled for flow cytometry.

Figure 28B:
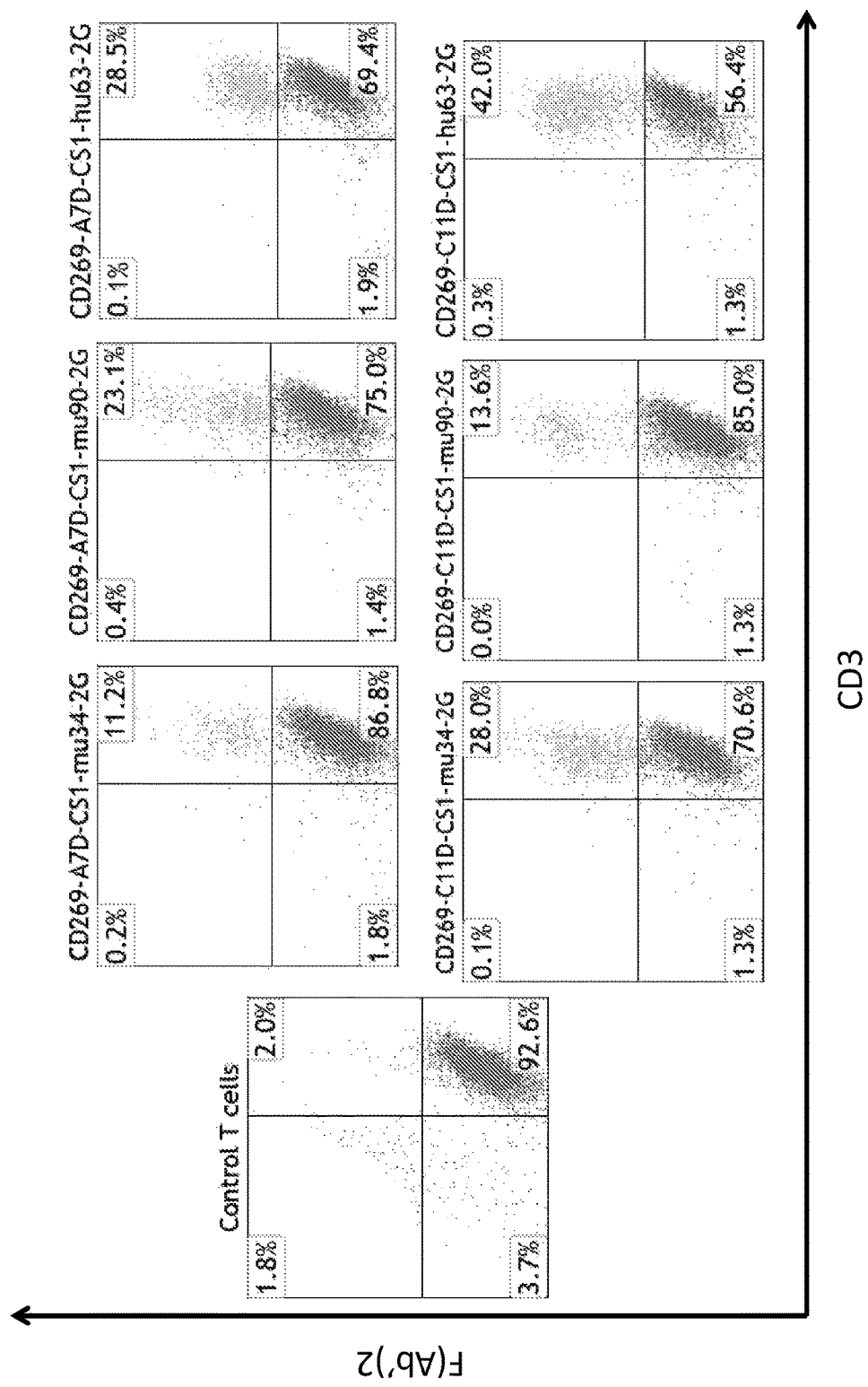

FIG. 28B. Expression of different versions of BCMA-CS1 cCAR T cells.
Buffy coat cells were activated 3 days with anti-CD3 antibody. Cells were transduced with either control vector (top left) or various CD269 cCAR lentiviral supernatants. After 3 days of incubation, cells were harvested and labeled for flow cytometry.

Figure 29A:
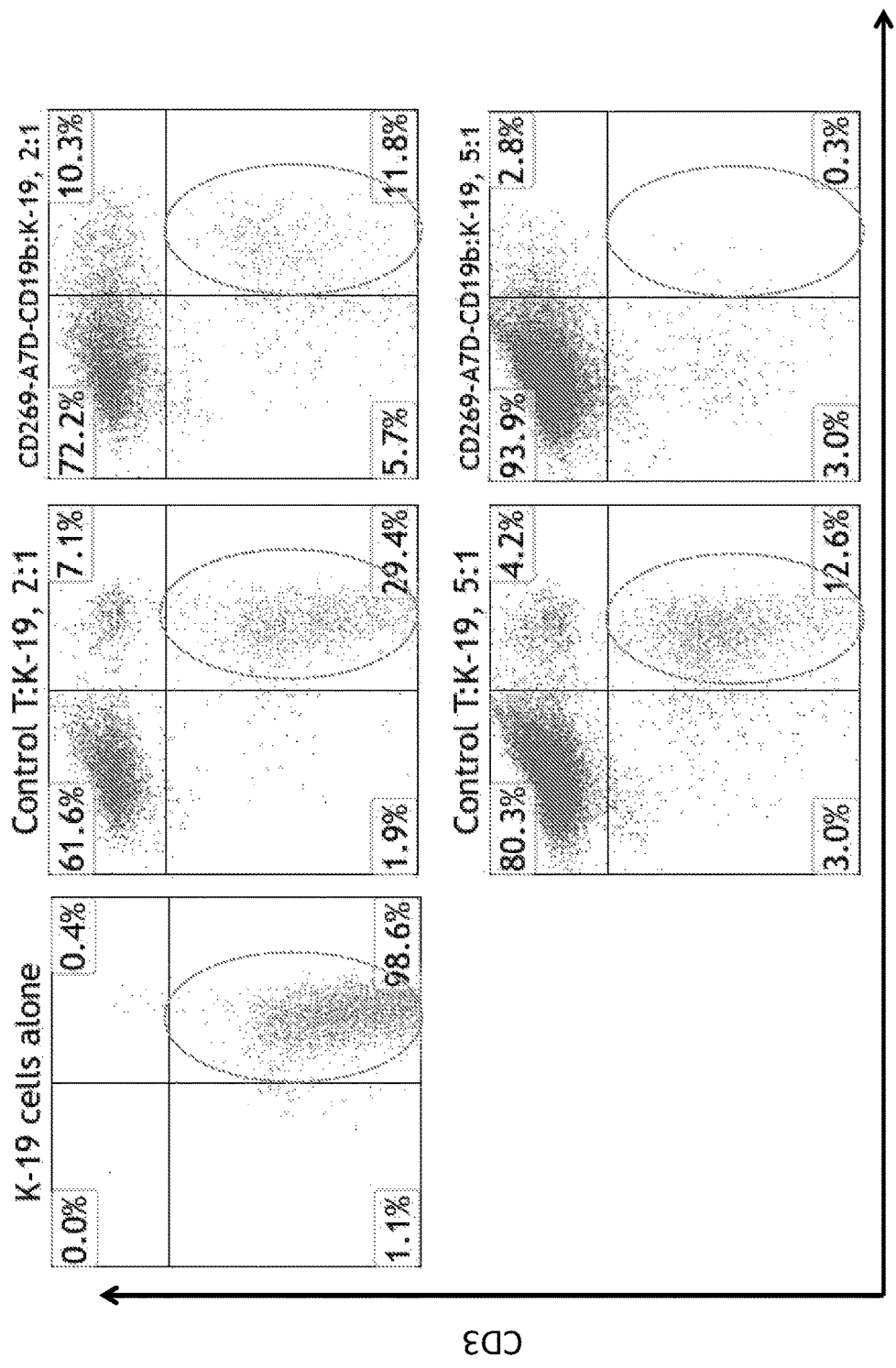

FIG. 29A. CD269-A7D-CD19b CAR T cells specifically lyse the K562 tumor cell line, which is synthetically expressing CD19 surface antigen (K-19), in co-culture assays. Co-culture experiments were performed at an effector to target ratio of 2:1 or 5:1 for 18 hours and were directly analyzed by flow cytometry for CD19 and CD3. Each assay consists of K-19 target cells alone (left), control T cells (center panels) and CD269-A7D-CD19b CAR T cells (right panels). K-19 cells are circled.

Figure 29B:
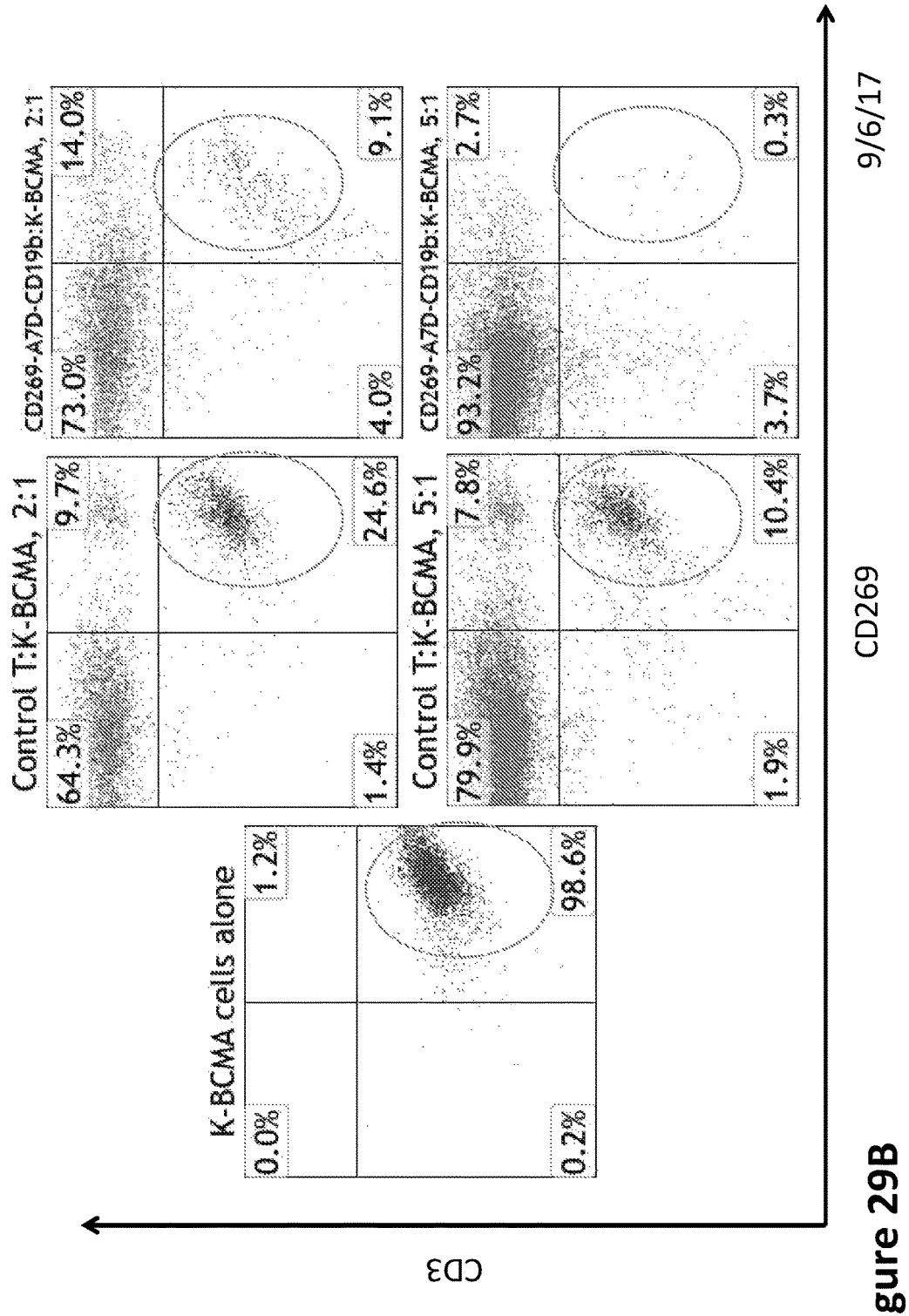

FIG. 29B. CD269-A7D-CD19b CAR T cells specifically lyse the K562 tumor cell line, which is synthetically expressing BCMA surface antigen (K-BCMA), in co-culture assays. Co-culture experiments were performed at an effector to target ratio of 2:1 or 5:1 for 18 hours and were directly analyzed by flow cytometry for CD269 and CD3. Each assay consists of K-BCMA target cells alone (left), control T cells (center panels) and CD269-A7D-CD19b CAR T cells (right panels). K-BCMA cells are circled.

Figure 30A:
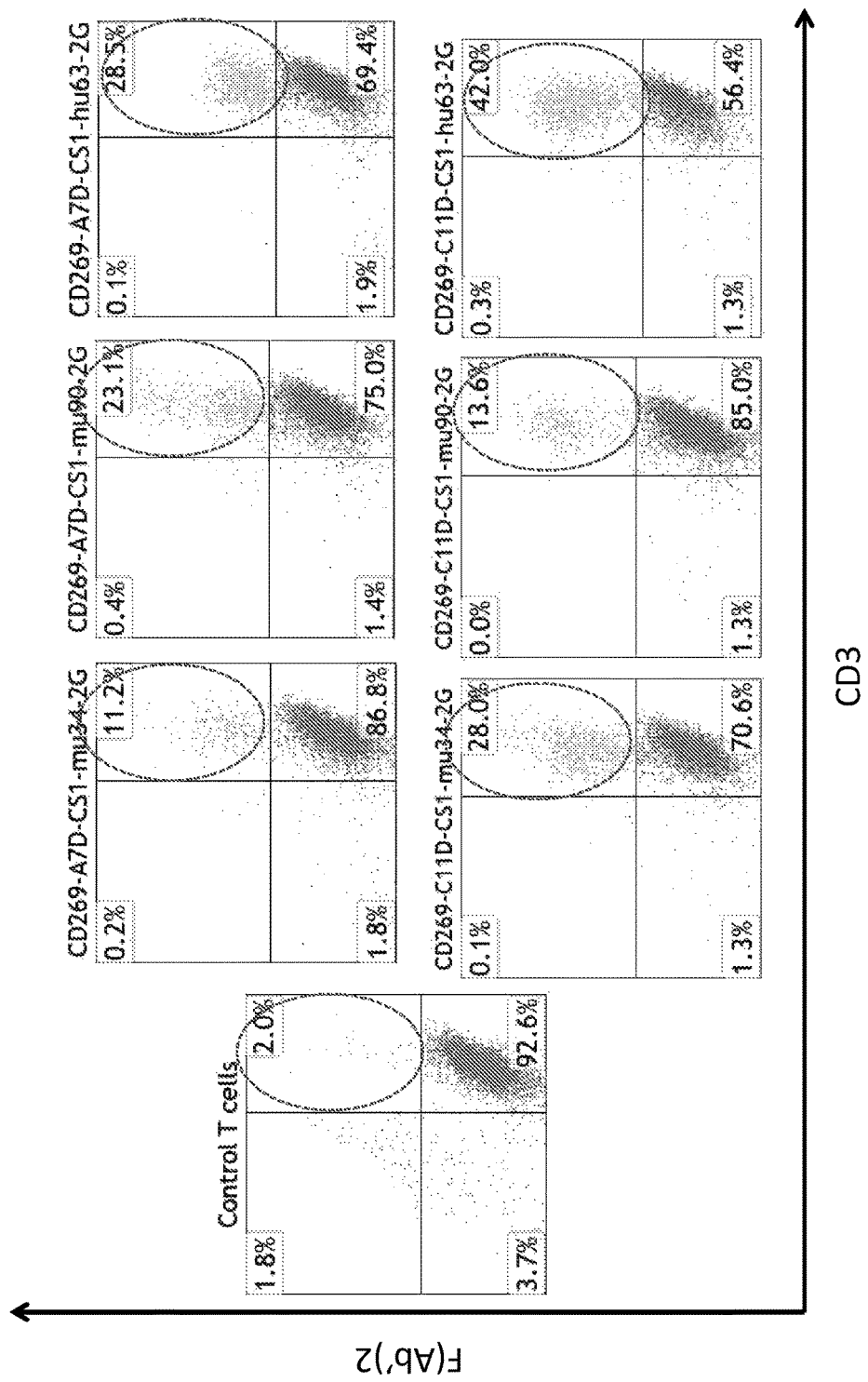

FIG. 30A. Expression of different versions of BCMA-CS1 cCAR T cells.
Buffy coat cells were activated 3 days with anti-CD3 antibody. Cells were transduced with either control vector (top left) or various CD269 (BCMA) cCAR lentiviral supernatants. After 3 days of incubation, cells were harvested and labeled for flow cytometry.

Figure 30B:
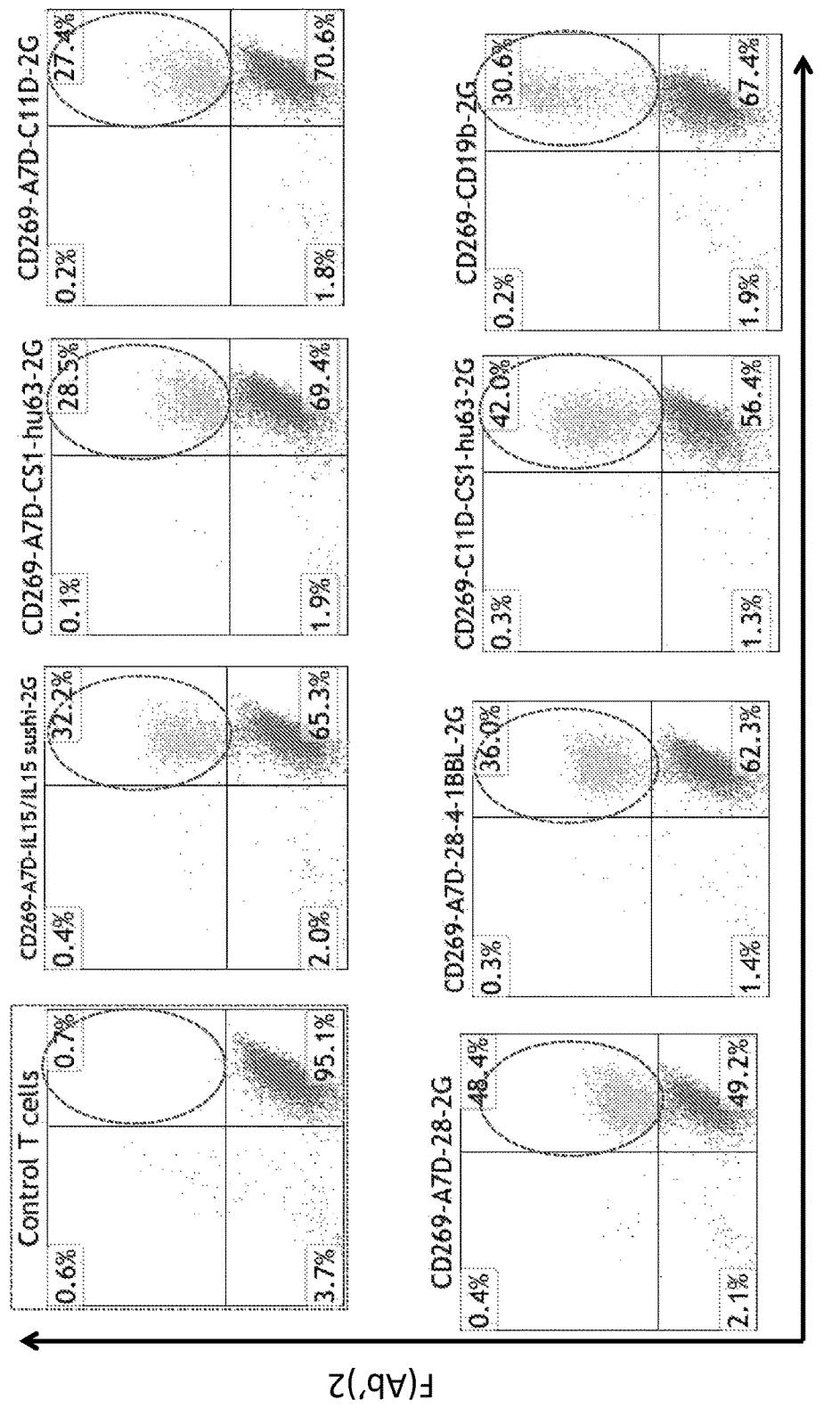

FIG. 30B. Expression of different versions of BCMA-CS1 cCAR T cells or enhanced BCMA CAR T cells.
Buffy coat cells were activated 3 days with anti-CD3 antibody. Cells were transduced with either control vector (top left) or various CD269 (BCMA) CAR lentiviral supernatants. After 3 days of incubation, cells were harvested and labeled for flow cytometry.

Figure 30C:
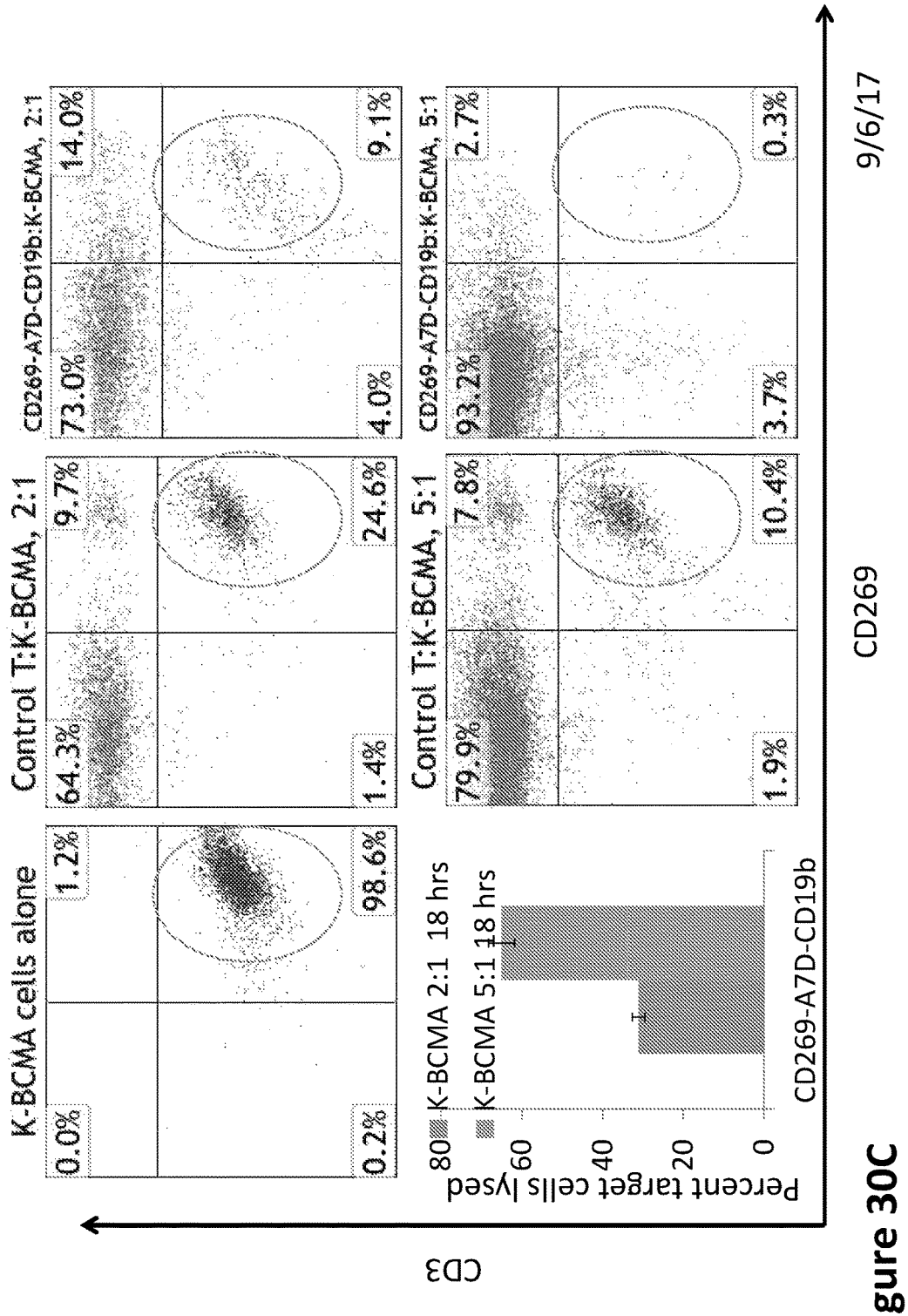

FIG. 30C. CD269-A7D-CD19b CAR T cells specifically lyse the K562 tumor cell line, which is synthetically expressing BCMA surface antigen (K-BCMA), in co-culture assays. Co-culture experiments were performed at an effector to target ratio of 2:1 or 5:1 for 18 hours and were directly analyzed by flow cytometry for CD269 and CD3. Each assay consists of K-BCMA target cells alone (left), control T cells (center panels) and CD269-A7D-CD19b CAR T cells (right panels). K-BCMA cells are circled.

Figure 30D:
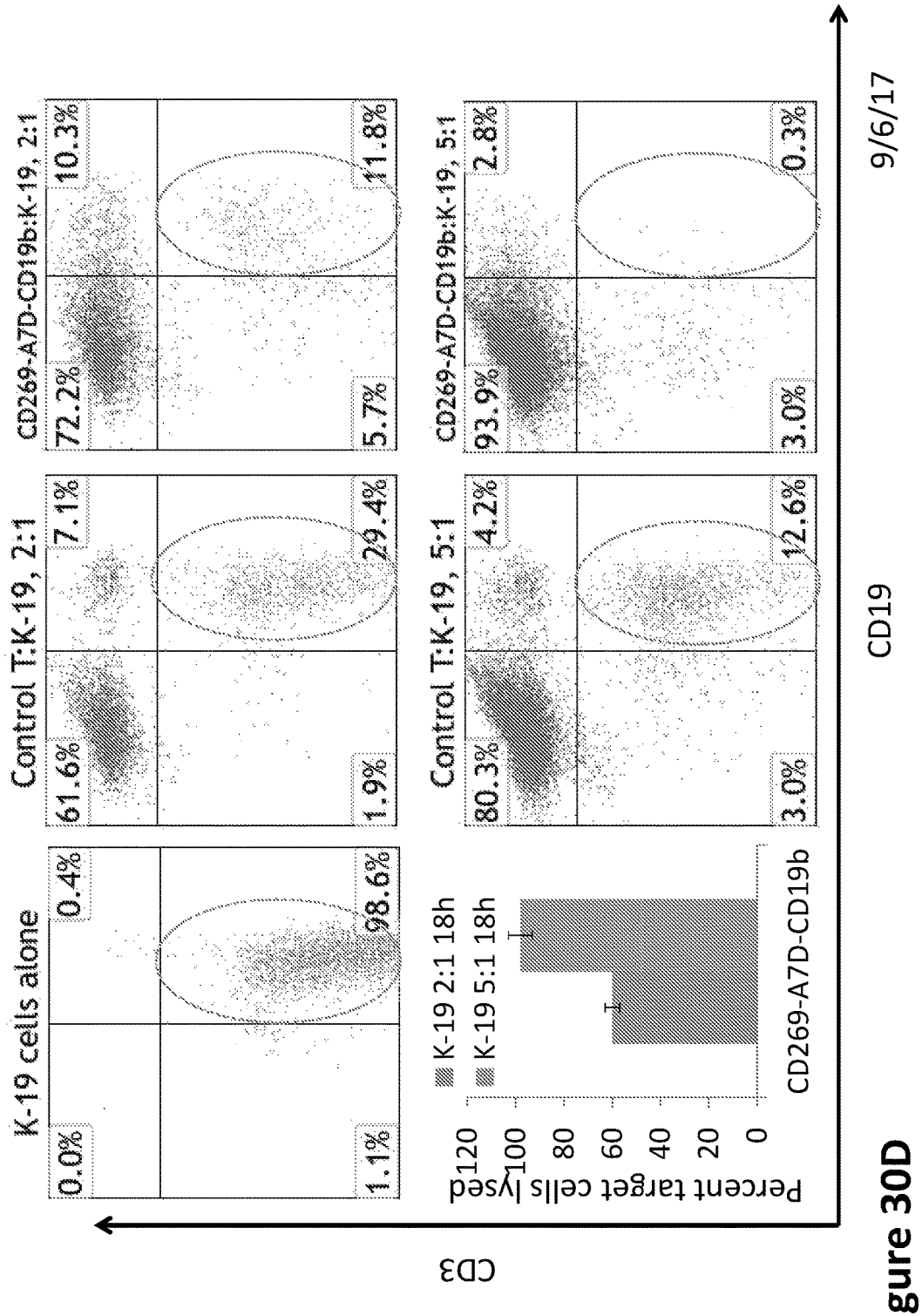

FIG. 30D. CD269-A7D-CD19b CAR T cells specifically lyse the K562 tumor cell line, which is synthetically expressing CD19 surface antigen (K-19), in co-culture assays. Co-culture experiments were performed at an effector to target ratio of 2:1 or 5:1 for 18 hours and were directly analyzed by flow cytometry for CD19 and CD3. Each assay consists of K-19 target cells alone (left), control T cells (center panels) and CD269-A7D-CD19b CAR T cells (right panels). K-19 cells are circled. Results are summarized in the graph in the lower left. (N=2).

Figure 30E:
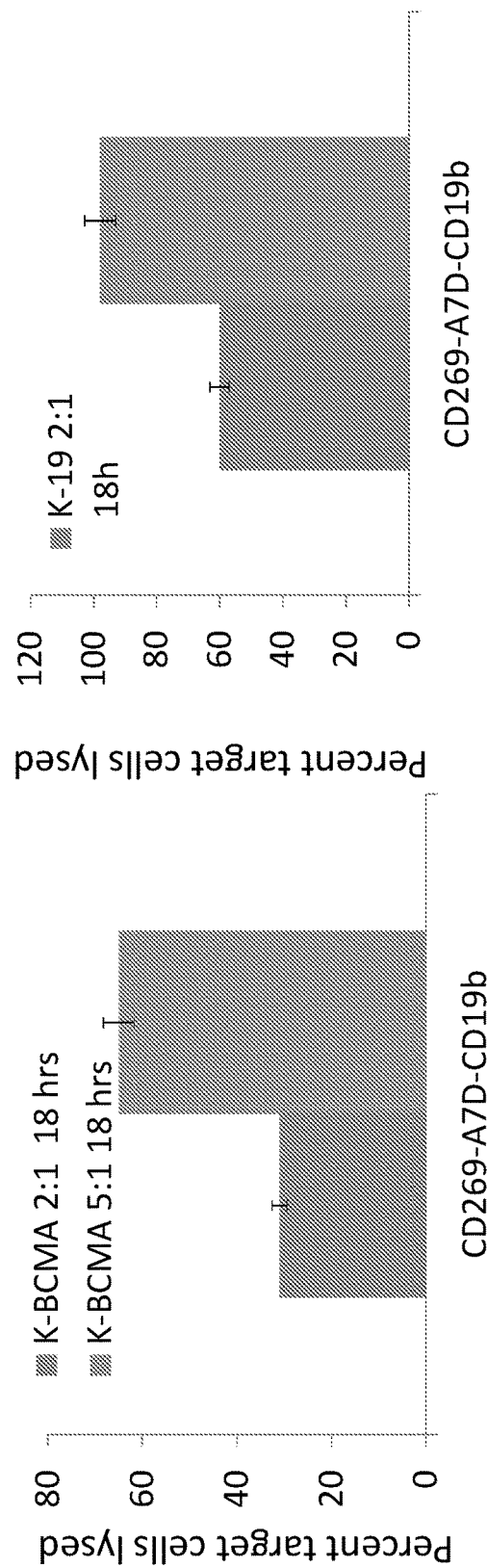

FIG. 30E. Summary lysis of K562-BCMA (K-BCMA) and K562-CD19 (K-19) cells by CD269-A-7D-CD19b cCAR T cells.

Figure 30F:
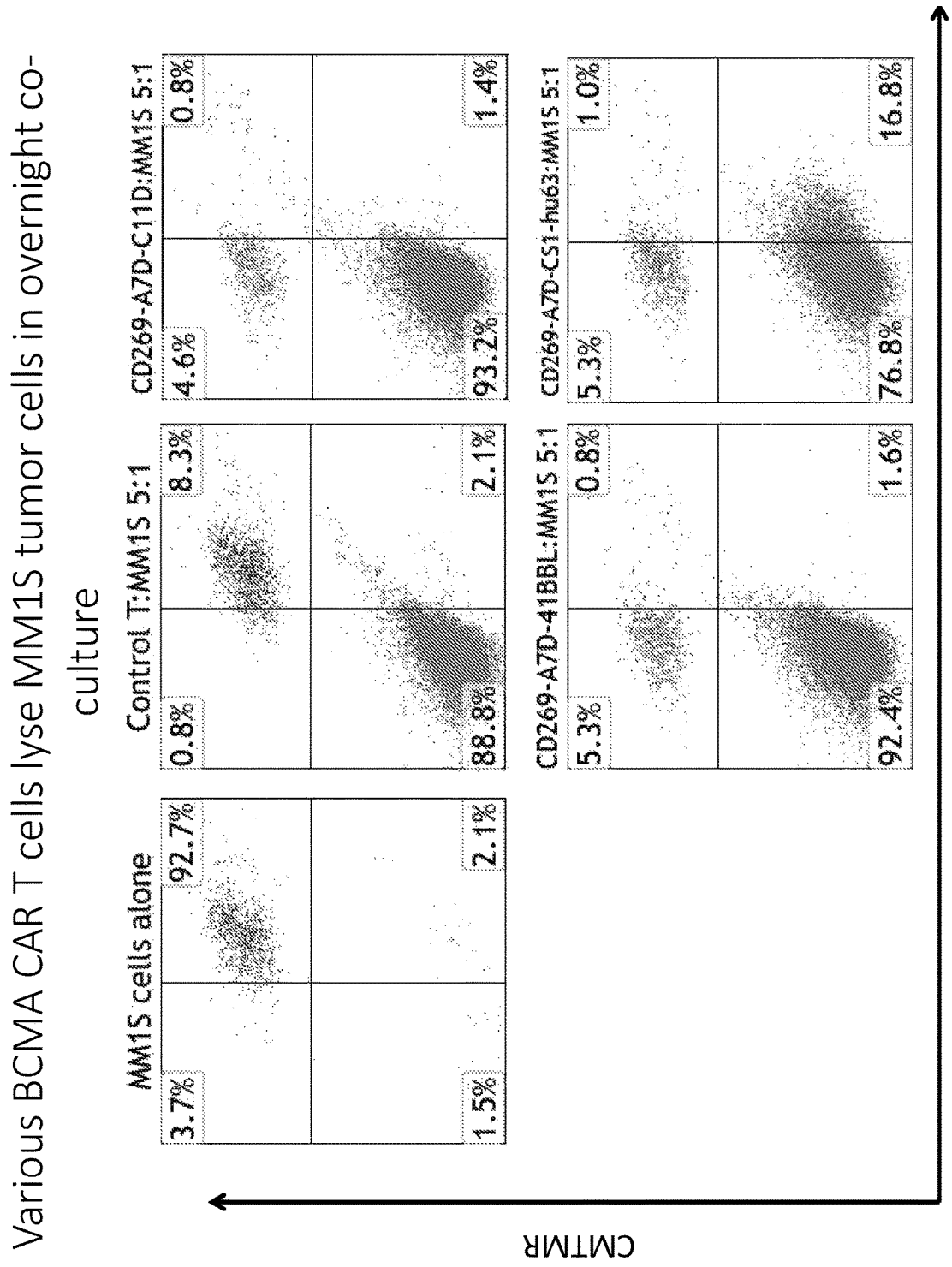

FIG. 30F. CD269-A7D cCAR T cells specifically lyse the MM1S tumor cell line in co-culture assays.
Co-culture experiments were performed at an effector to target ratio of 5:1 for 18 hours and were directly analyzed by flow cytometry for CD269 (BCMA) and CMTMR (Cell-Tracker). Each assay consists of MM1S target cells alone (left), control T cells (top center panel), CD269-A7D-41BBL (bottom center), CD269-A7D-C11D (top right) and CD269-A7D-CS1-hu63 cCAR T cells (bottom right). MM1S cells are represented by scattered dots in the upper, right boxes of the graphs. (N=2).

Figure 30G:
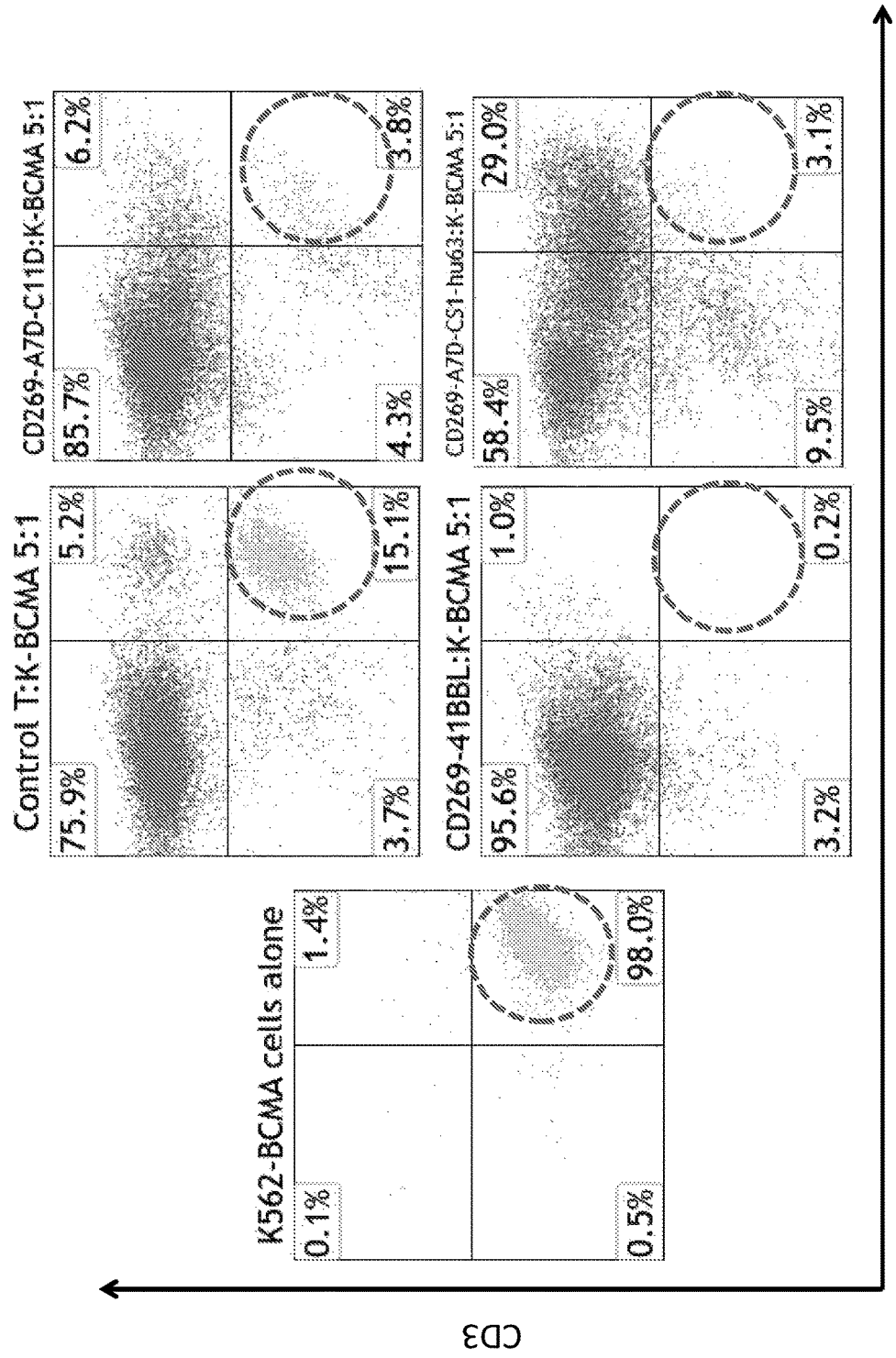

FIG. 30G. Different versions of CD269-CS1 cCAR or enhanced CD269 CAR T cells specifically lyse the K562-BCMA tumor cell line in co-culture assays.
Co-culture experiments were performed at an effector to target ratio of 5:1 for 18 hours and were directly analyzed by flow cytometry for CD269 and CD3. Each assay consists of MM1S target cells alone (left), control T cells (top center panel), CD269-A7D-41BBL (bottom center), CD269-A7D-C11D (a cCAR targeting two different epitopes of BCMA antigen) (top right) and CD269-A7D-CS1-hu63 CAR T cells (bottom right). K-BCMA cells are circled. (N=2).

Figure 30H:
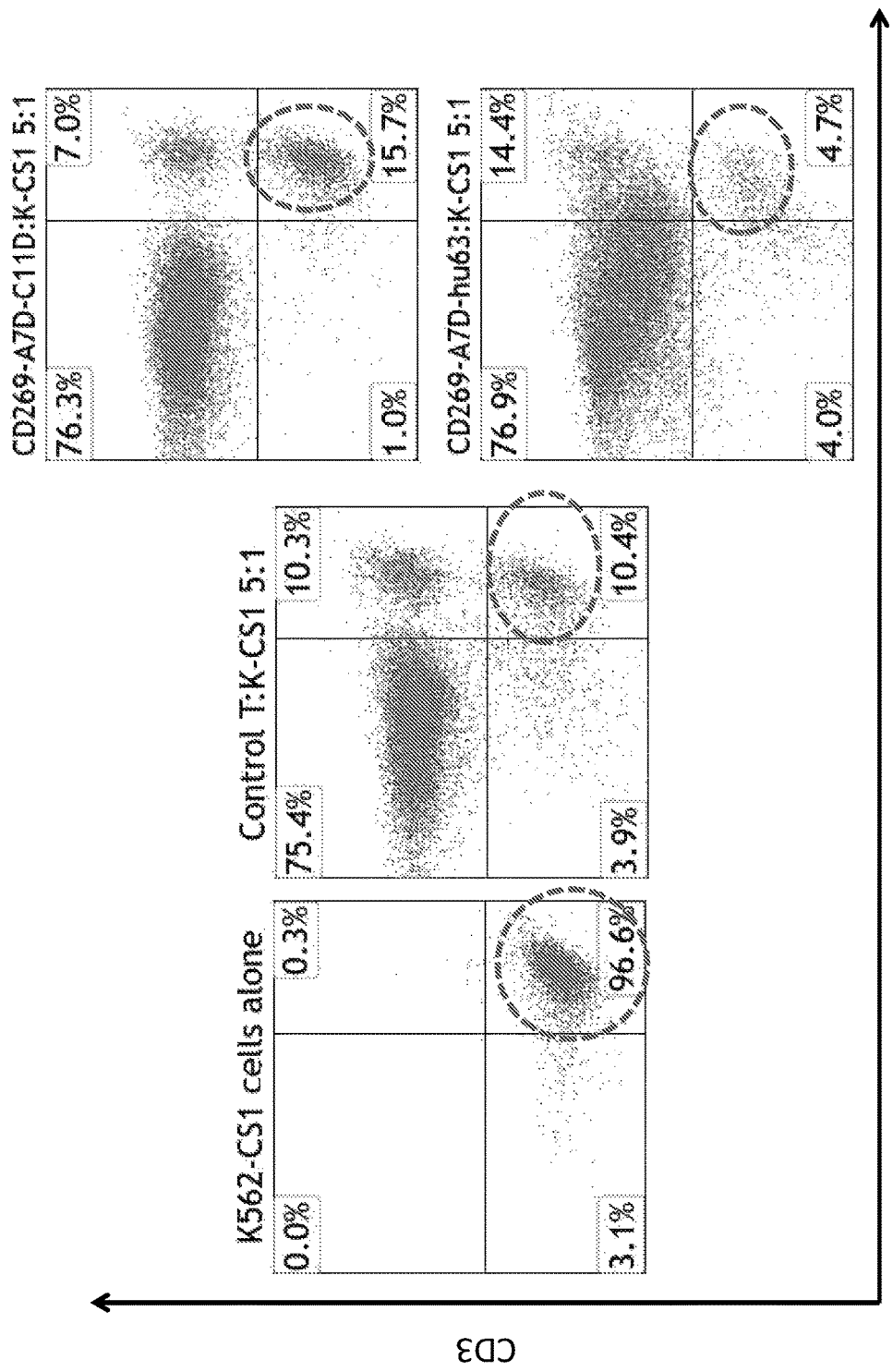

FIG. 30H. CD269-A7D-CS1-hu63 CAR T cells specifically lyse the K562-CS1 tumor cell line in co-culture assays, while CD269-A7D-C11D cCAR (a cCAR targeting different epitopes of BCMA antigen, without a CS1 CAR) do not. Co-culture experiments were performed at an effector to target ratio of 5:1 for 18 hours and were directly analyzed by flow cytometry for CD269 and CD3. Each assay consists of MM1S target cells alone (left), control T cells (center panel), CD269-A7D-C11D (top right) and CD269-A7D-CS1-hu63 CART cells (bottom right). K-CS1 cells are circled. (N=2).

Figure 30I:
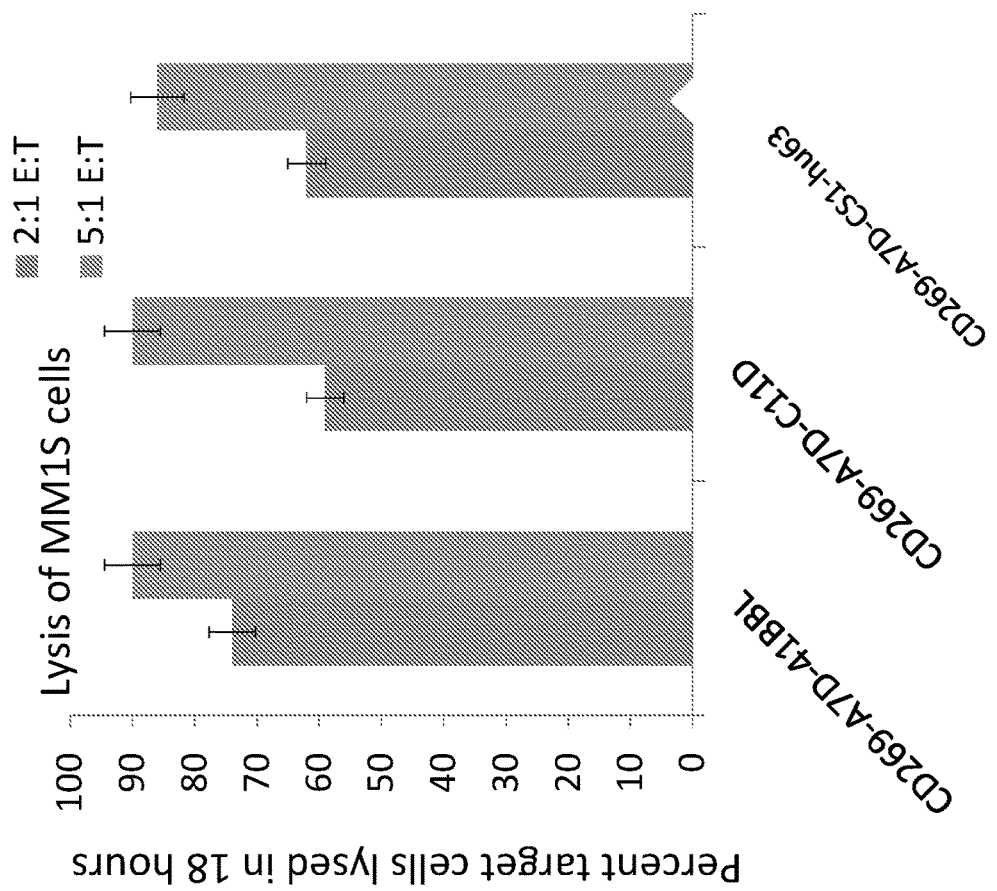

FIG. 30I. Summary lysis of MM1S myeloma cells by CD269-A7D-41BBL, CD269-A7D-C11D and CD269-CS1-hu63 CAR T cells.

Figure 30J:
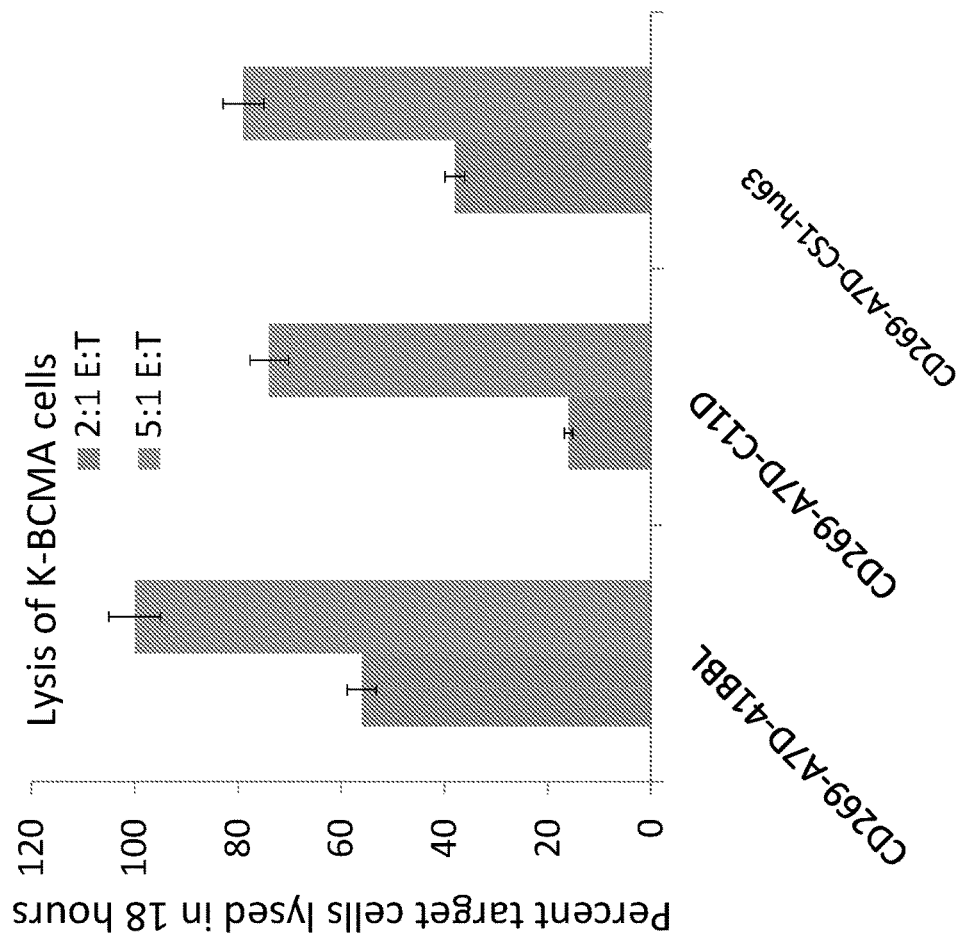

FIG. 30J. Summary lysis of K-BCMA (K562 expressing BCMA) cells by CD269-A7D-41BBL, CD269-A7D-C11D and CD269-CS1-hu63 CAR T cells.

Figure 30K:
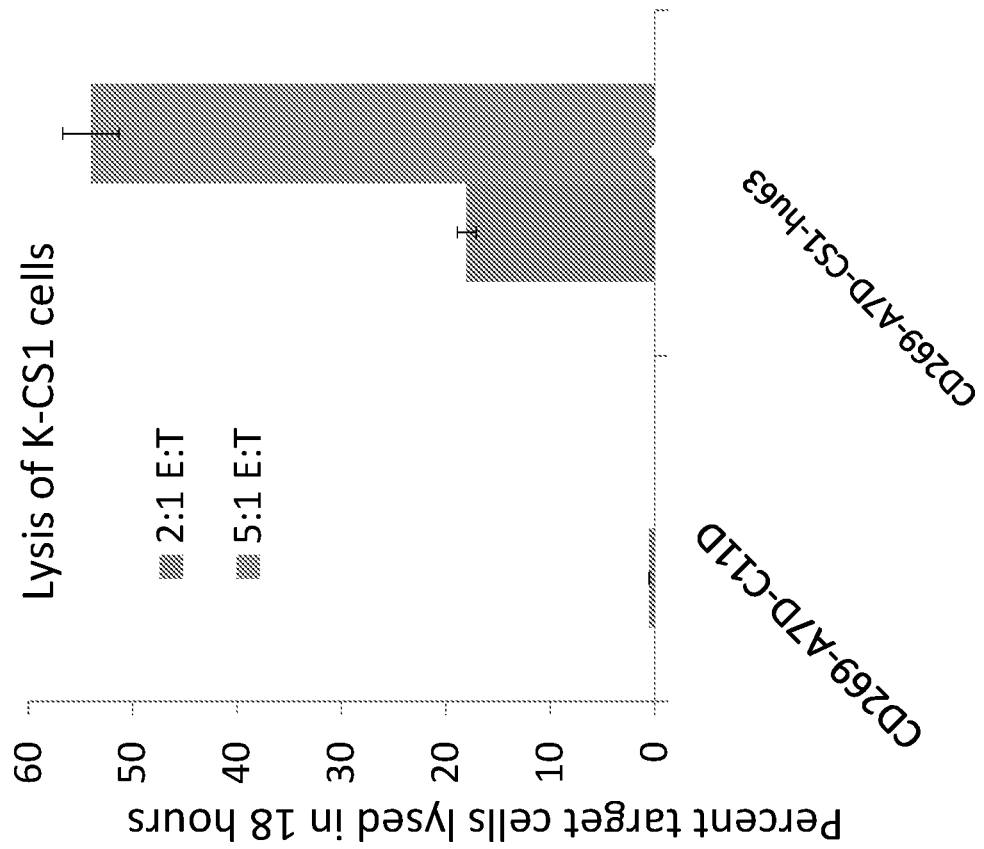

FIG. 30K. Summary lysis of K-CS1 (K562 expressing CS1) cells by CD269-A7D-C11D and CD269-CS1-hu63 cCAR T cells.

Figure 31:
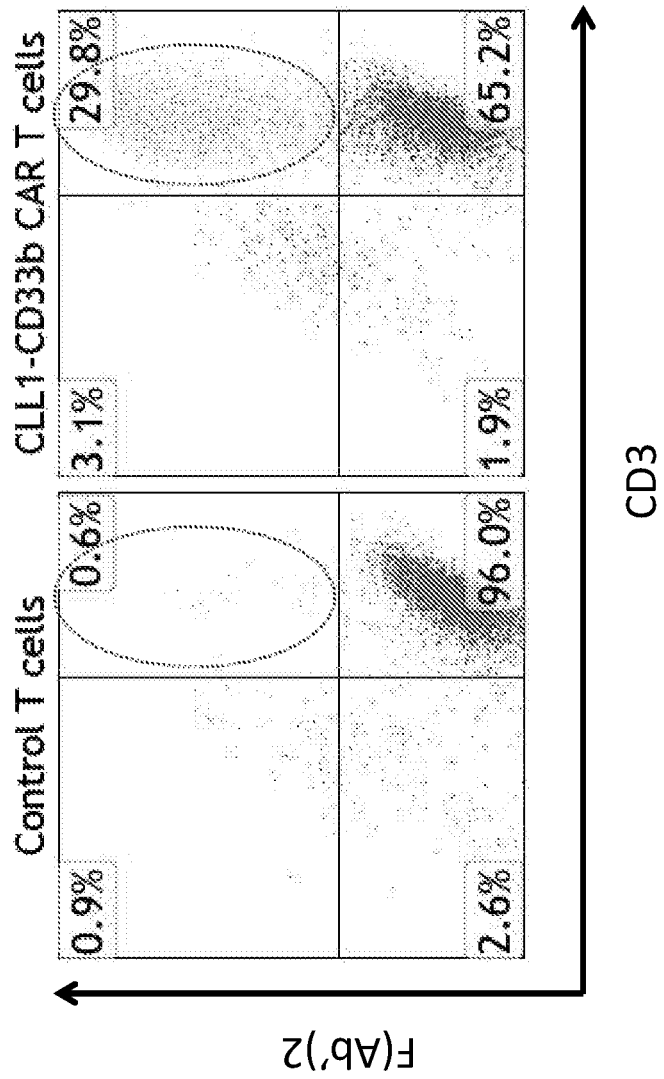

FIG. 31. Expression of CLL1-CD33b CAR T cells. Buffy coat cells were activated 3 days with anti-CD3 antibody. Cells were transduced with either control vector (left) or CLL1-CD33b CAR (right) lentiviral supernatant. After 3 days of incubation, cells were harvested and labeled for flow cytometry.

Figure 32A:
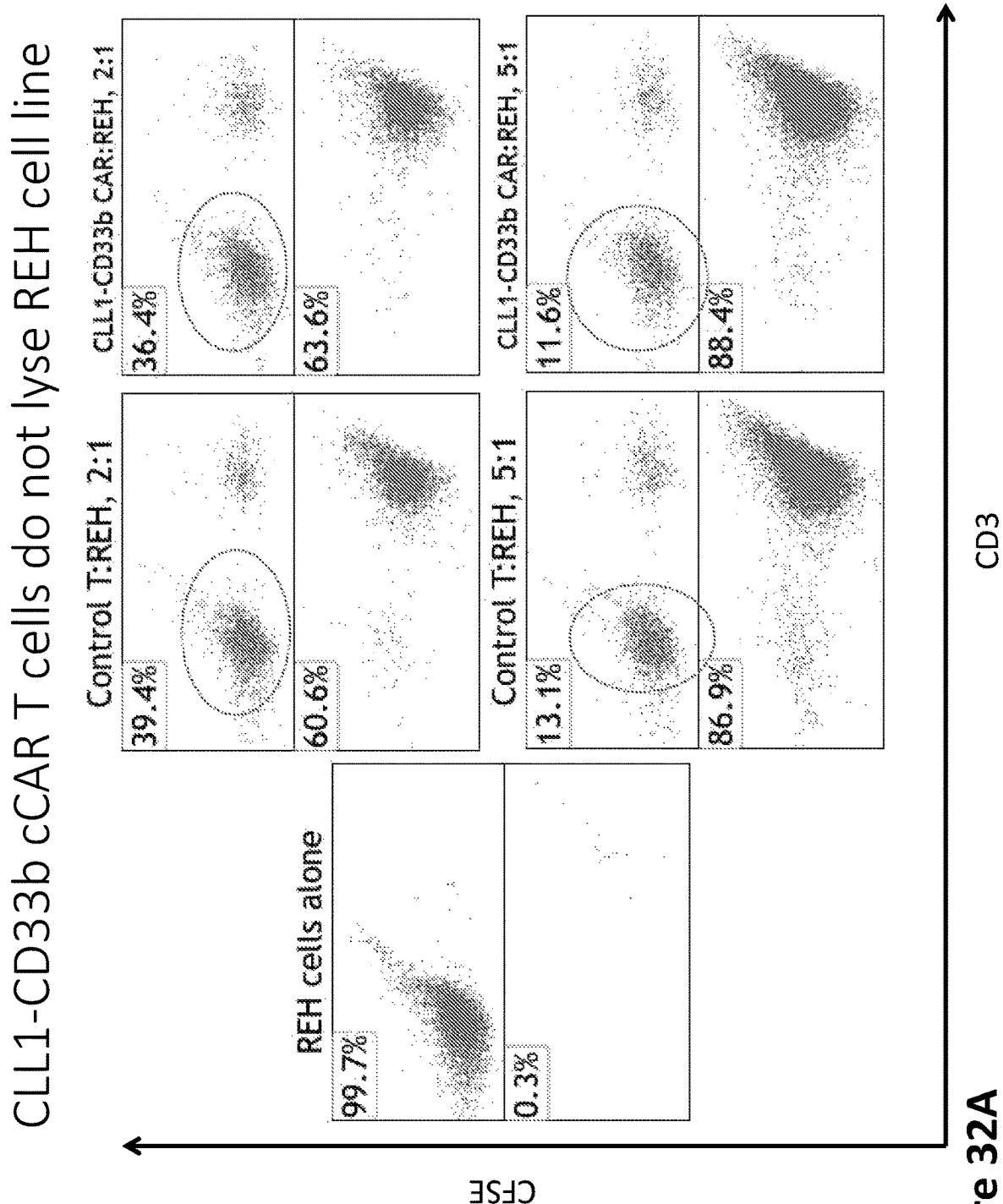

FIG. 32A. CLL1-CD33b CAR T cells do not lyse REH tumor cell line in co-culture assays.
Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of REH target cells alone (left), control T cells (center panels) and CLL1-CD33b CAR T cells (right panels). REH cells are circled. Note: REH cells do not express CLL1 (CLL-1) or CD33.

Figure 32B:
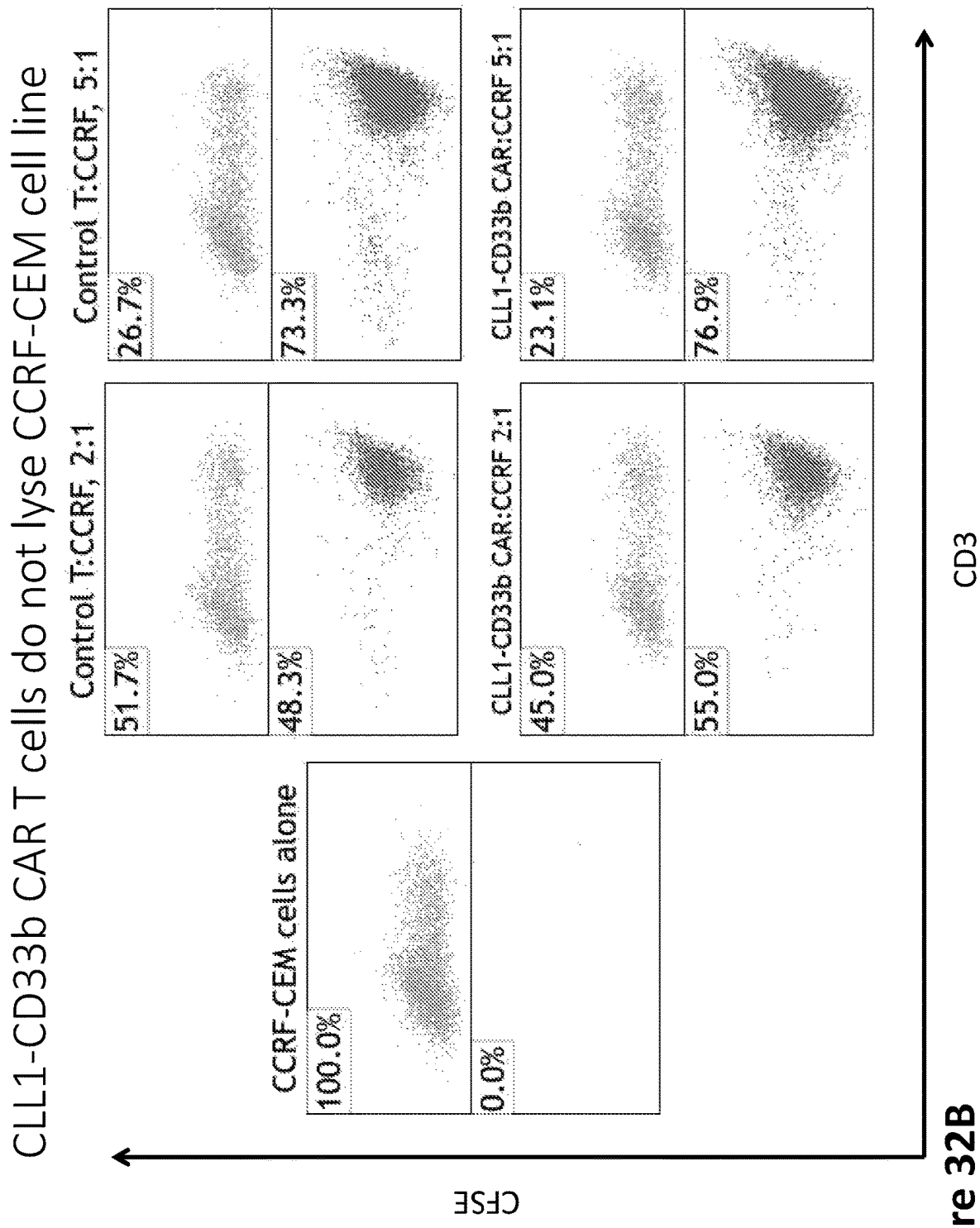

FIG. 32B. CLL1-CD33b CAR T cells do not lyse CCRF-CEM tumor cell line, in co-culture assays.
Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of CCRF-CEM target cells alone (left), control T cells (center panels) and CLL1-CD33b CAR T cells (right panels). CCRF-CEM cells are scattered dots in the upper boxes. Note: CCRF-CEM cells do not express CLL1 or CD33 antigen.

Figure 32C:
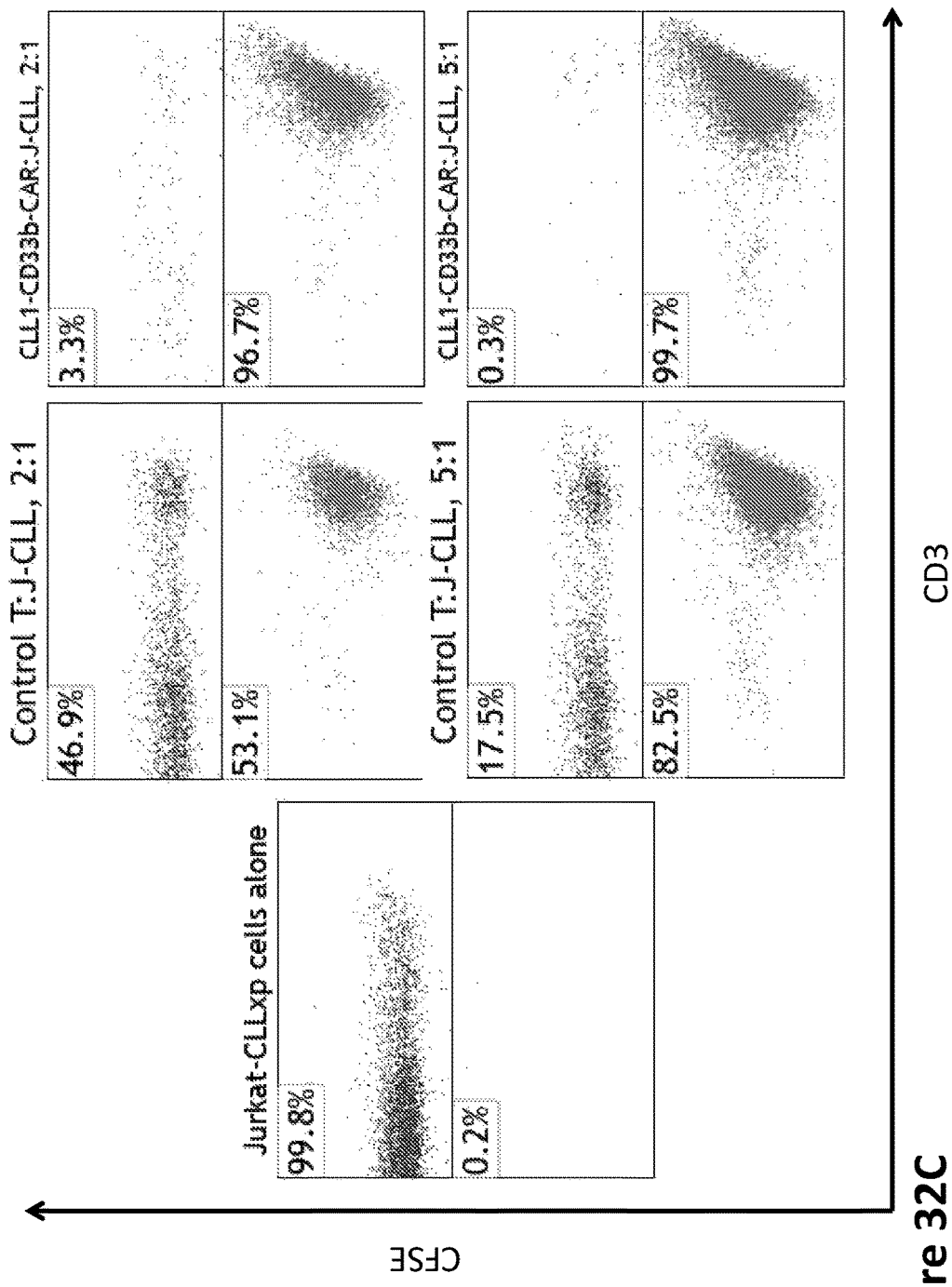

FIG. 32C. CLL1-CD33b CAR T cells specifically lyse the Jurkat tumor cell line, which is synthetically expressing CLL-1 surface antigen in co-culture assays.
Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of Jurkat-CLL1 (J-CLL) target cells alone (left), control T cells (center panels) and CLL1-CD33b CAR T cells (right panels). Jurkat-CLL cells are represented as scattered dots in the upper boxes.

Figure 32D:
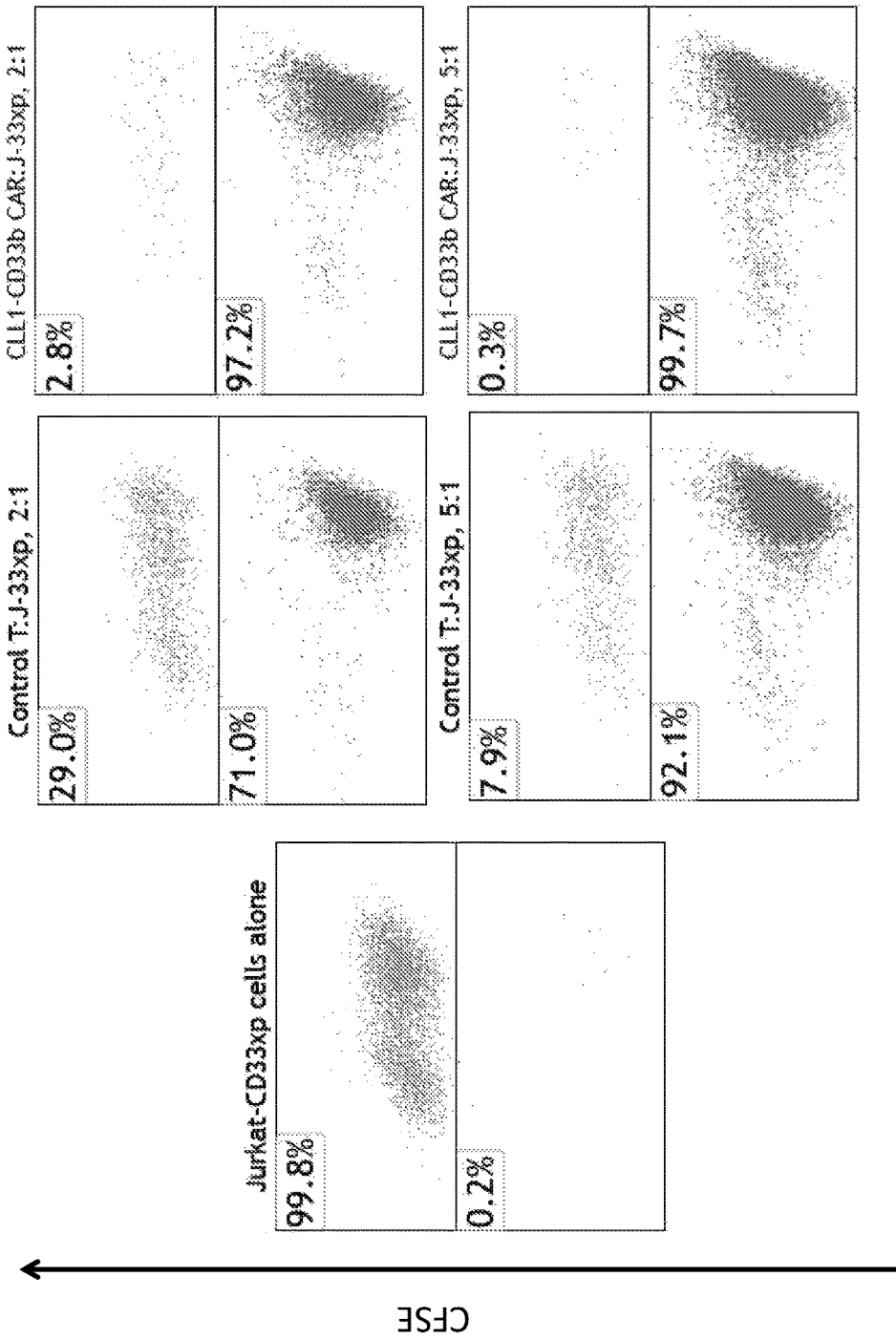

FIG. 32D. CLL1-CD33b CAR T cells specifically lyse the Jurkat tumor cell line, which is synthetically expressing CD33 surface antigen, in co-culture assays.
Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of Jurkat-CD33 (J-33xp) target cells alone (left), control T cells (center panels) and CLL1-CD33b CAR T cells (right panels). Jurkat-CD33 (J-33xp) cells are represented as scattered dots in the upper boxes.

Figure 32E:
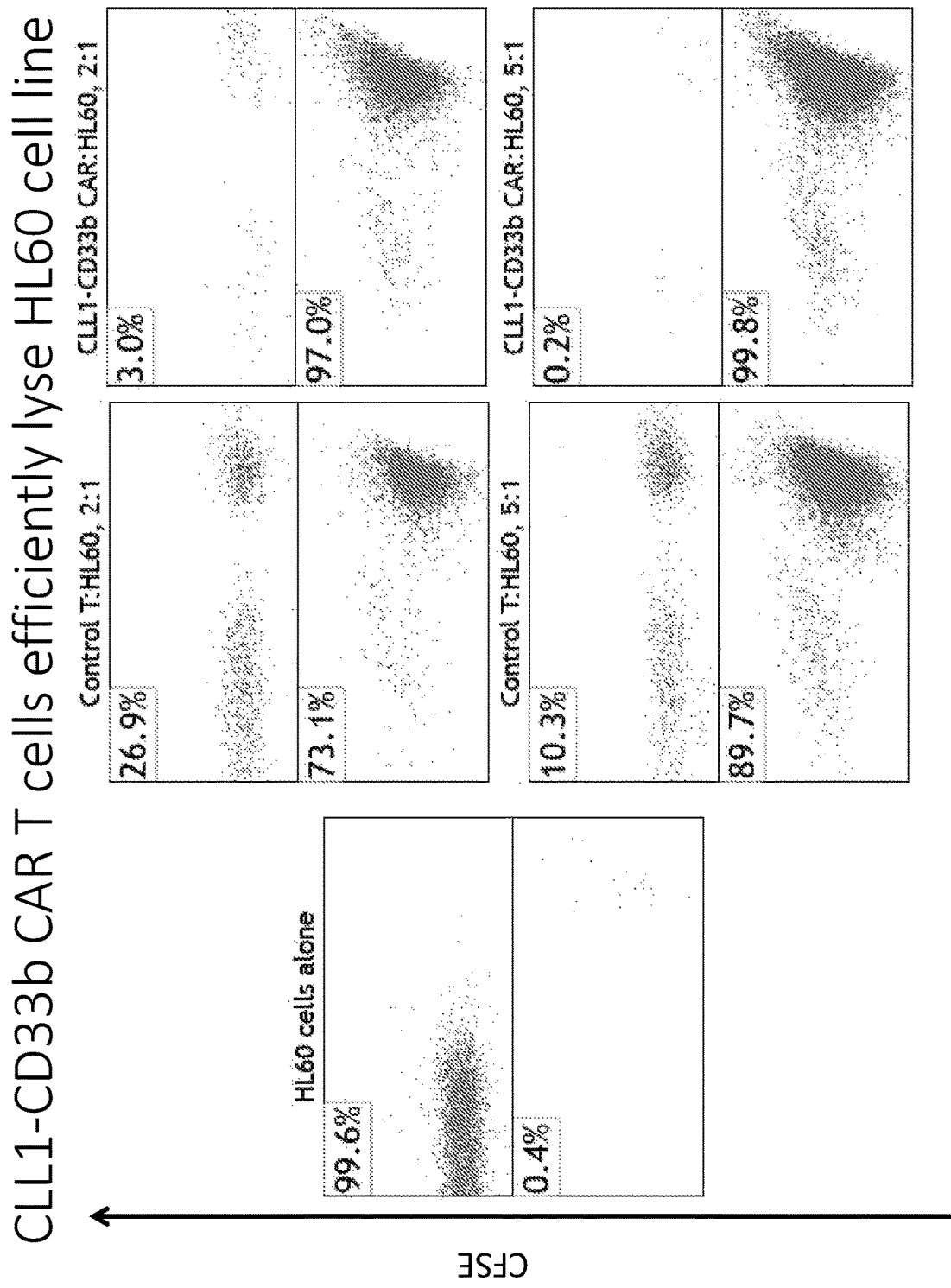

FIG. 32E. CLL1-CD33b cCAR T cells efficiently lyse HL60 tumor cell line in co-culture assays.
Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of HL60 target cells alone (left), control T cells (center panels) and CLL1-CD33b CAR T cells (right panels). HL60 cells are represented as scattered dots in the upper boxes.

Figure 32F:
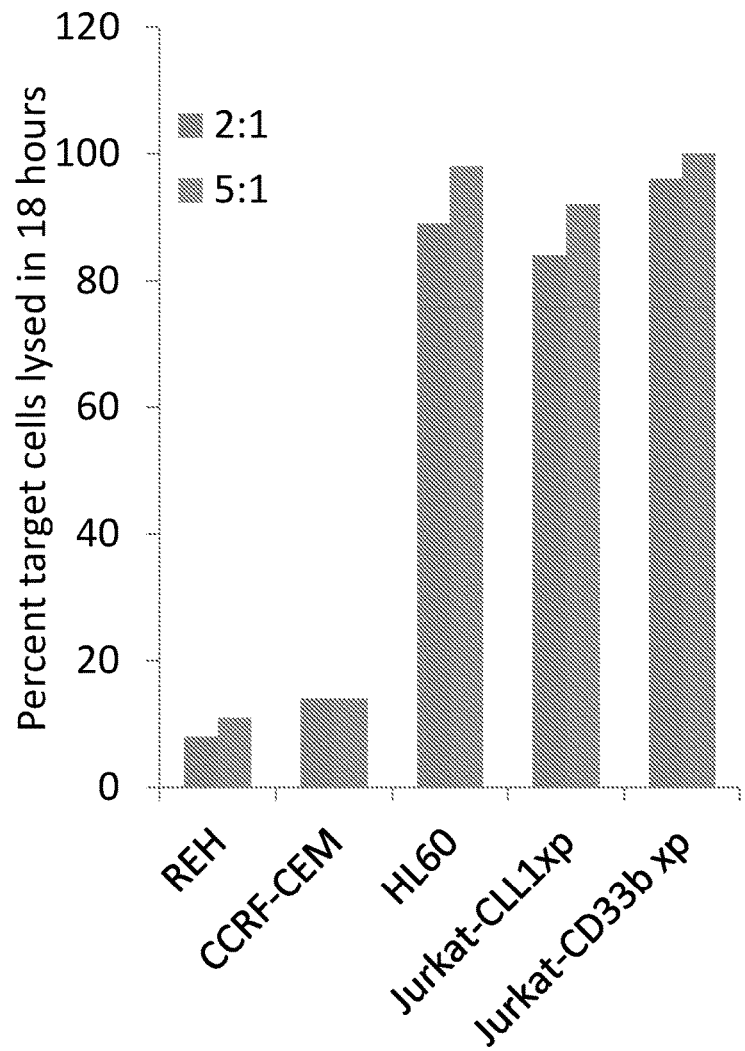

FIG. 32F. Summary of CLL1-CD33 cCAR (CLL-1-CD33 cCAR) lysis results in co-culture assays using different AML cell lines and Jurkat cells expressing either CLL-1 or CD33.

Figure 32G:
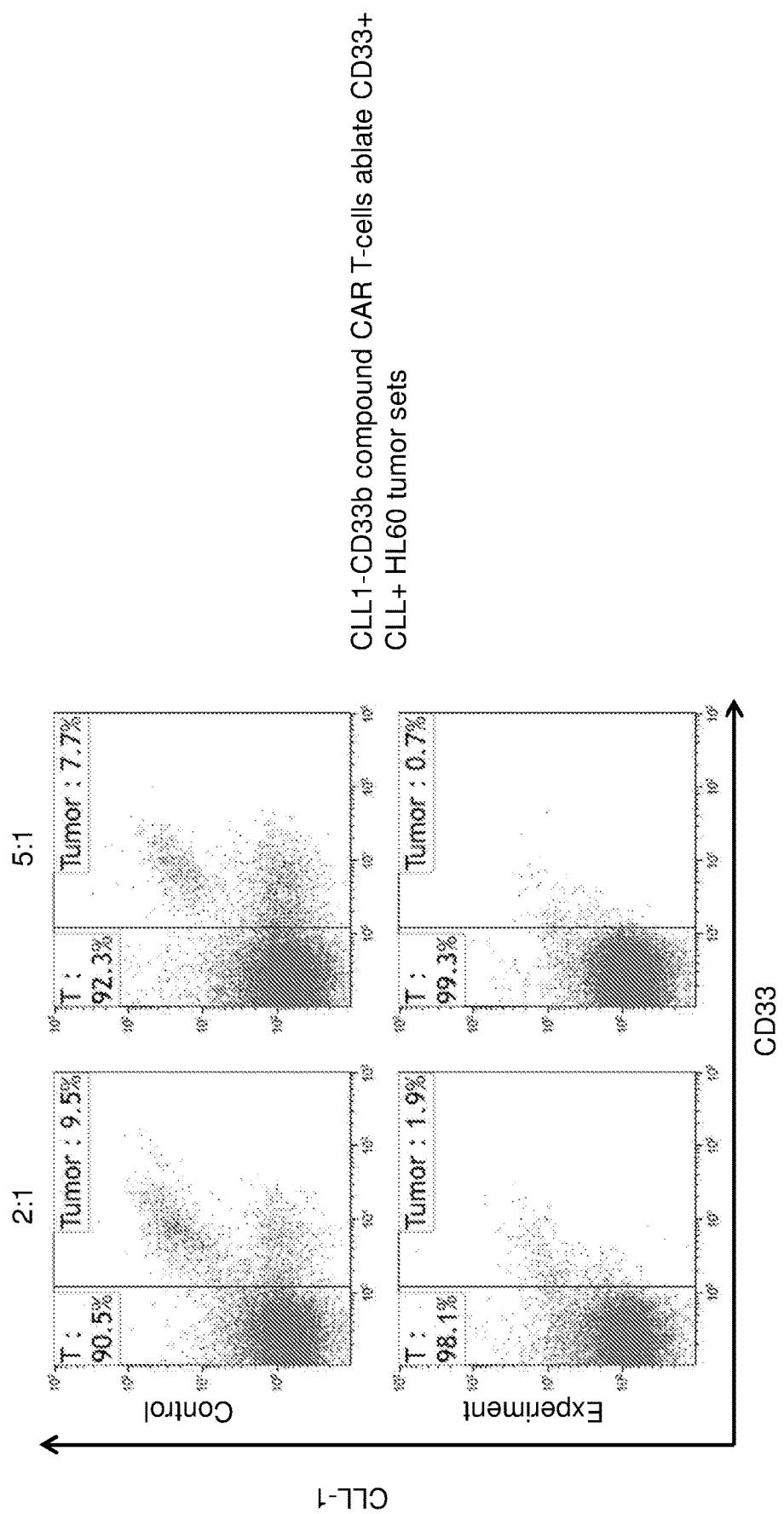

FIG. 32G—CLL1-CD33b compound CAR T cells ablate HL60 target tumor cells Cocultures were carried out overnight at E:T ratios of 2:1 and 5:1. Target HL60 cells mostly double positive for CLL-1 and CD33 were prelabeled with CFSE membrane dye. Flow cytometry acquisition (FACS) was conducted the next day using CD3, CLL-1, and CD33 antibodies.

Figure 32H:
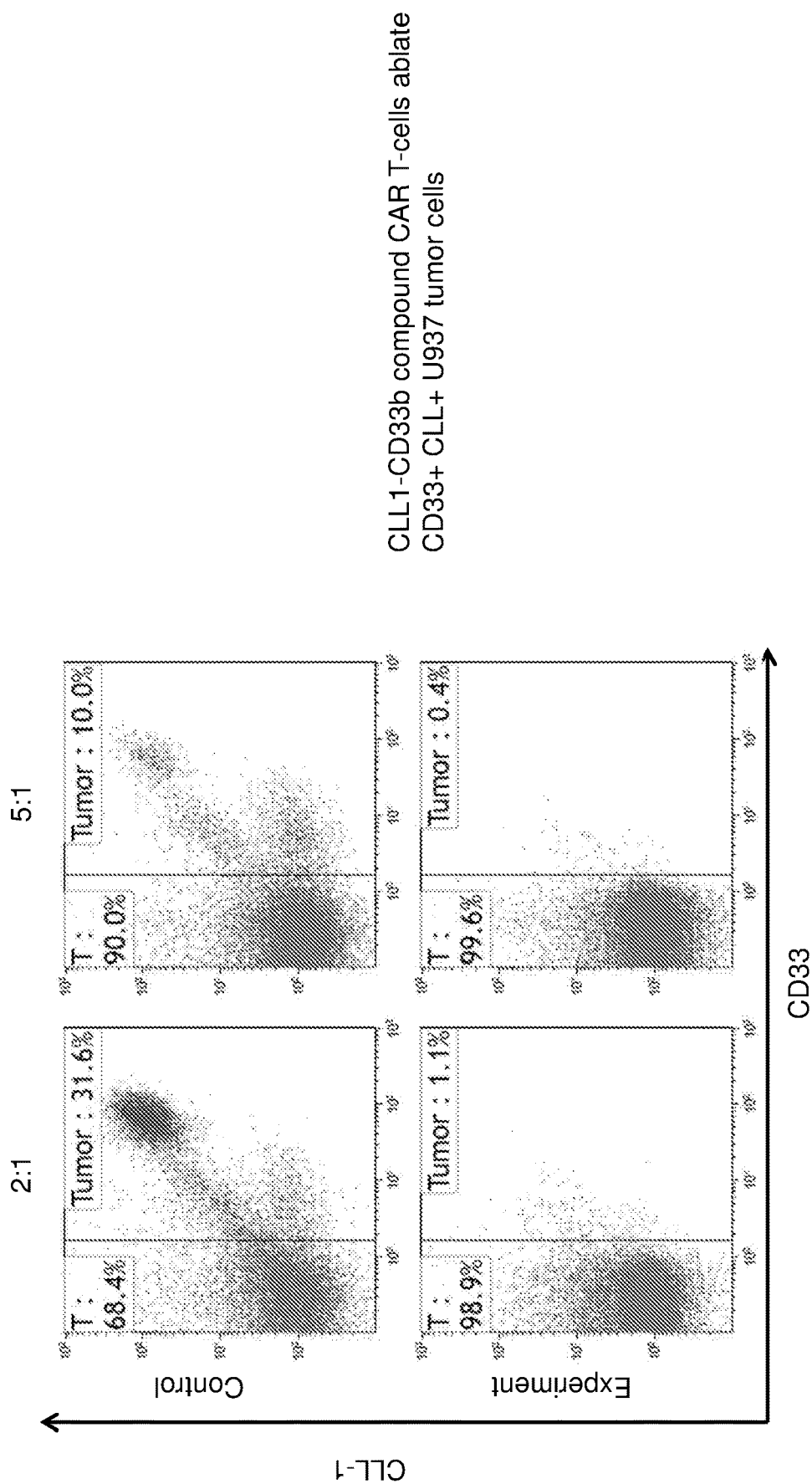

FIG. 32H—CLL1-CD33b compound CAR T cells ablate U937 target tumor cells Cocultures were carried out overnight at E:T ratios of 2:1 and 5:1. Target U937 cells are highly positive for both CLL-1 and CD33 and were prelabeled with CFSE membrane dye. Flow cytometry acquisition (FACS) was conducted the next day using CD3, CLL-1, and CD33 antibodies.

Figure 32I:
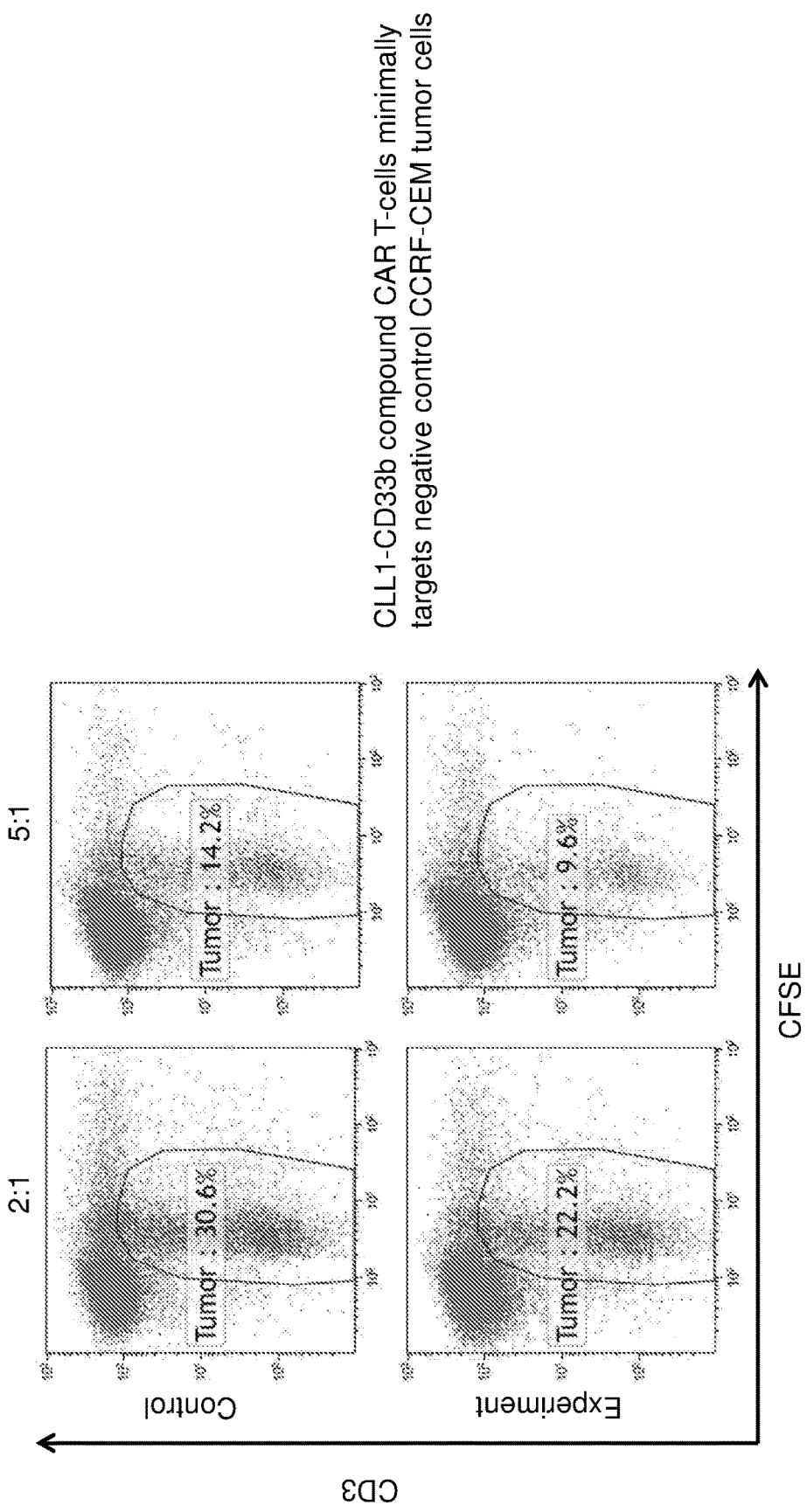

FIG. 32I—CLL1-CD33b compound CAR T cells minimally target negative control CCRF-CEM cells
Cocultures were carried out overnight at E:T ratios of 2:1 and 5:1. CCRF-CEM cells are predominantly negative for CLL-1 and CD33 and were prelabeled with CFSE membrane dye. Flow cytometry acquisition (FACS) was conducted the next day using CD3, CLL-1, and CD33 antibodies.

Figure 32J:
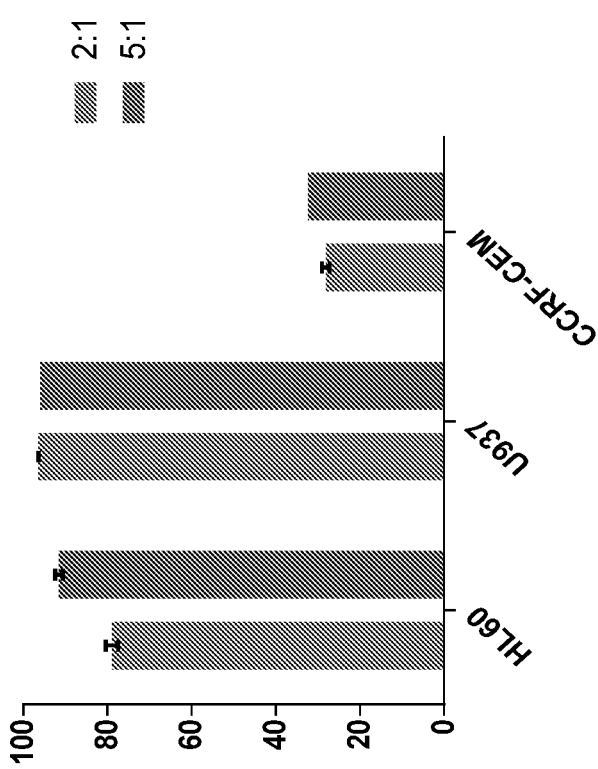
Figure 32J:
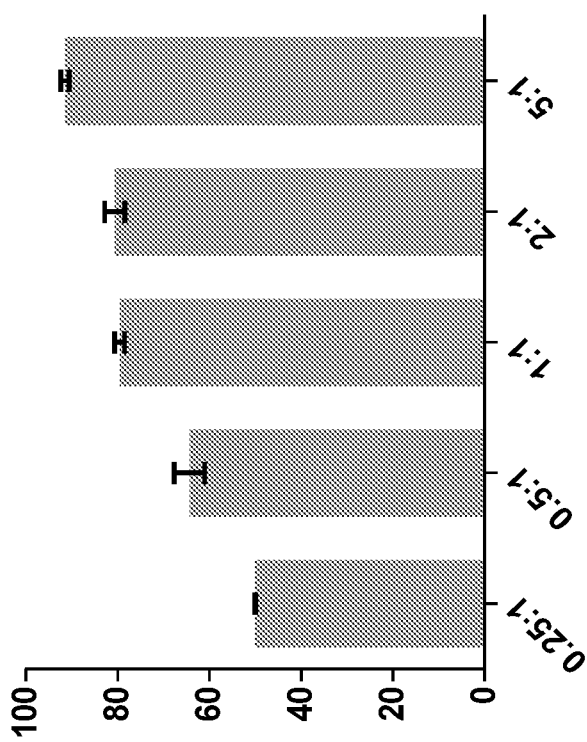

FIG. 32J—In vitro summary of CLL1-CD33b compound CAR T cells against target cell lines
All co-cultures were carried out overnight and target cells were prelabeled with CFSE membrane dye. Flow cytometry acquisition (FACS) was conducted the next day using CD3, CLL-1, and CD33 antibodies for all samples. Dose dependent co-cultures using HL60 target cells were conducted in an escalating E:T ratio scheme under identical co-culture conditions.

Figure 32K:
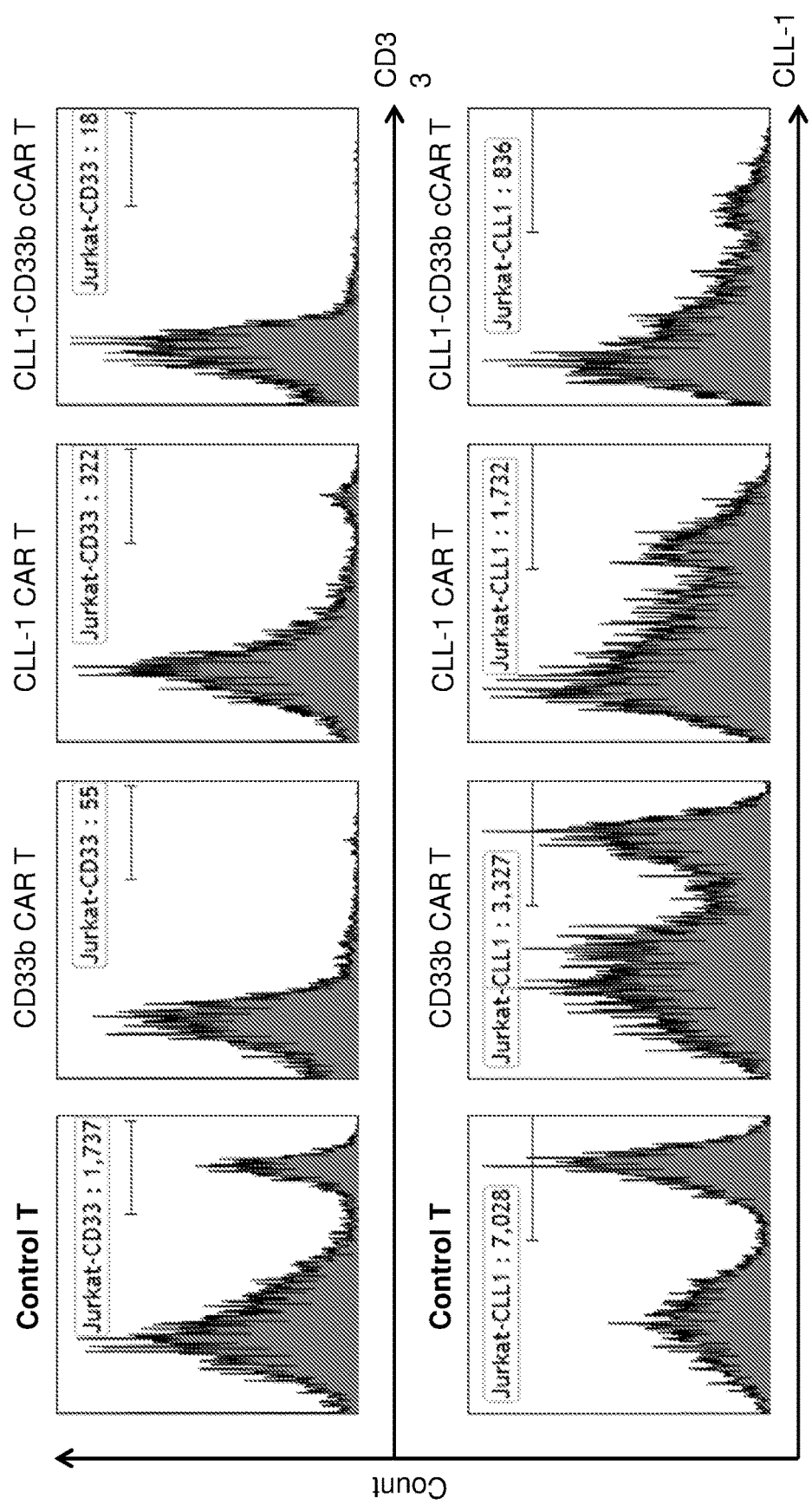

FIG. 32K—Antigen depletion by CLL1-CD33b compound CAR in relation to single CAR T cells in a mixed cell co-culture.
CD33 expressing and CLL-1 expressing Jurkat cells were produced by stable transfection of CD33 or CLL-1 expressing cDNA into wild type Jurkat cells. Jurkat cells were then sorted for expression to establish homogeneous stable cell lines expressing either CD33 or CLL-1. For mixed cell co-culture, Jurkat cells expressing CD33 (Jurkat-CD33) and Jurkat cells expressing CLL-1 (Jurkat-CLL1) were mixed together in an approximate 1:1 ratio totaling 200,000 cells. Effector cells were then added in a 1:2 ratio (effector:target), totaling 100,000 T-cells in an overnight culture. Flow cytometry acquisition (FACS) was conducted the next day using CD3, CLL-1, and CD33 antibodies for all samples. Histograms depicting antigen depletion under various CAR treatments are shown, with bars (left) depicting T-cell populations and antigen expressing Jurkat cells (right).

Figure 32L:
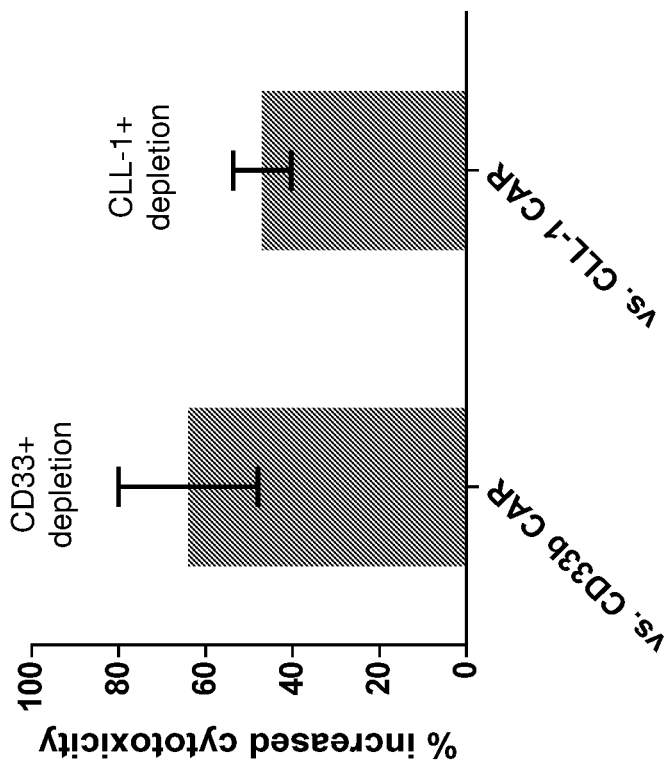
Figure 32L:
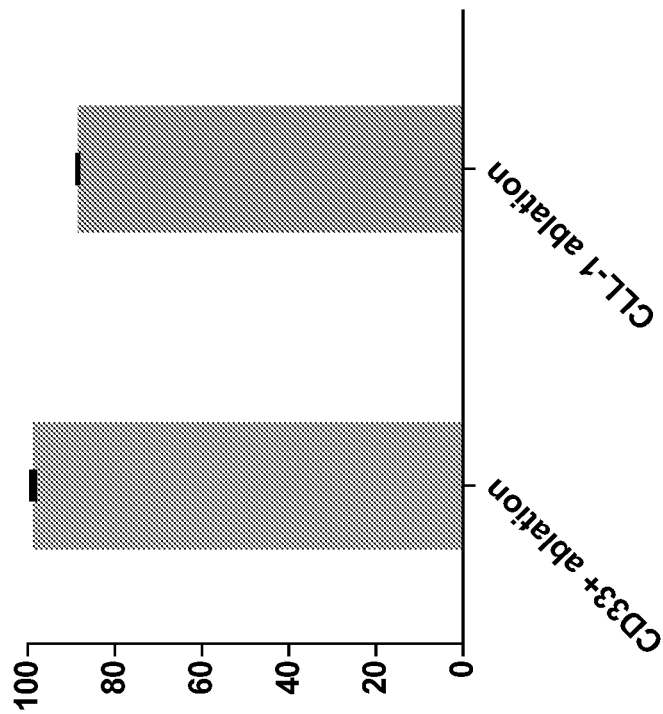

FIG. 32L—Summary of antigen depletion by CLL1-CD33b compound CAR in relation to single CAR T cells in a mixed cell co-culture.
Graphs summarizing histogram data of the previous figure. Overall, CLL1-CD33b compound CAR T cells exhibit potent and targeted cytotoxicity against both CD33 and CLL-1 expressing Jurkat cells with ablation rates of greater than 85% against both cell types. Furthermore, CLL1-CD33b compound CAR T cells were able to demonstrate superior cytotoxicity compared to a single anti-CD33b CAR T or a single anti-CLL-1 CAR T cell against their own respective antigen populations. The compound CAR was able to target CD33 60% better than a CD33 CAR T and CLL-1 40% better than a CLL-1 CAR T cell.

Figure 33A:
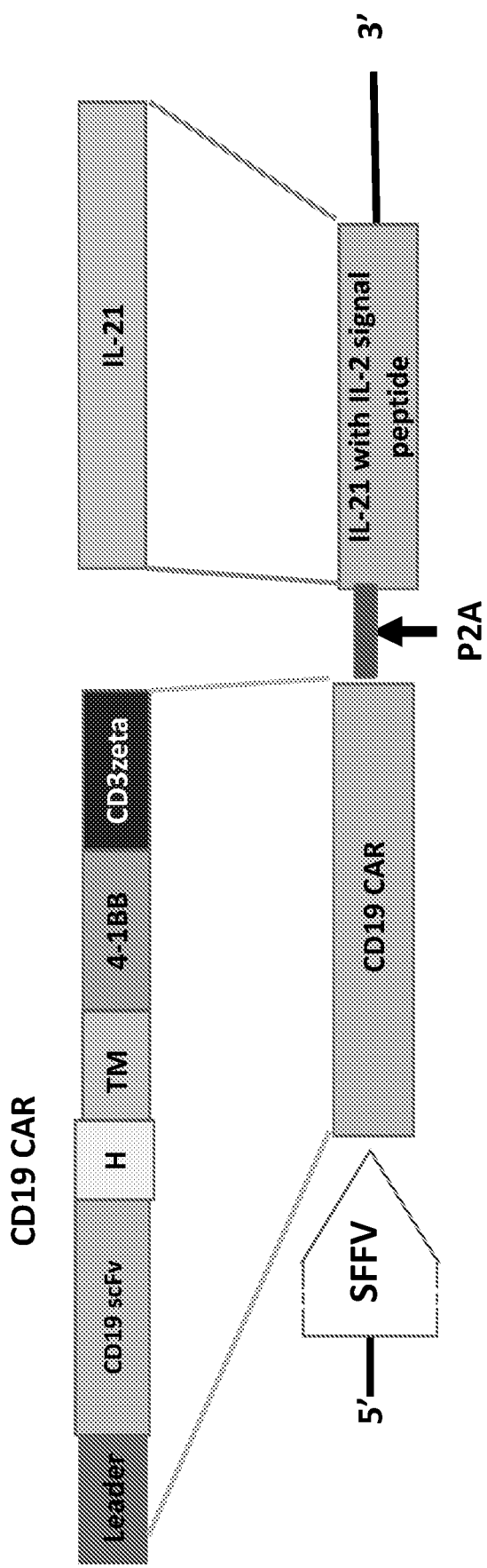

FIG. 33A. A Link by P2A schematic showing CD19 CAR and IL-21 in a single construct (Cd19 CAR co-expressing IL-21) and its expression in T or NK cells.

Figure 33B:
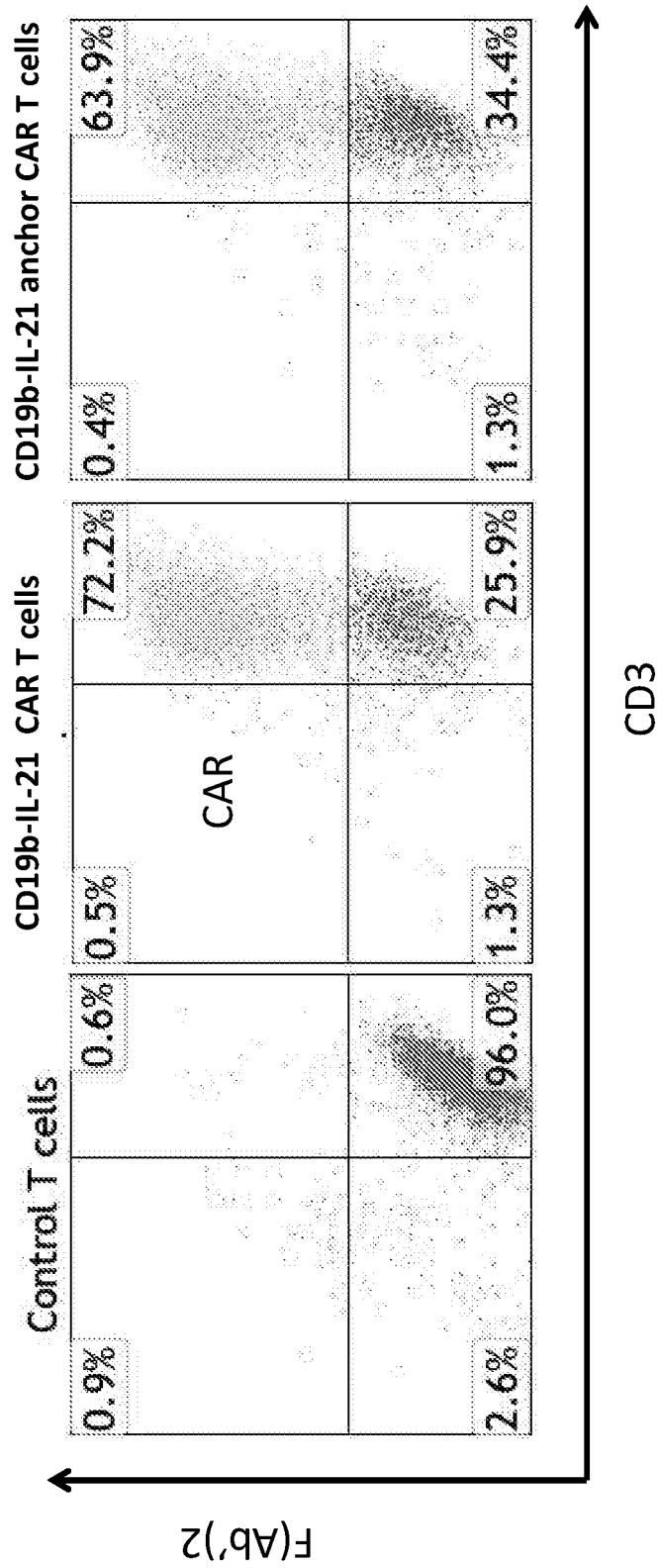

FIG. 33B. Expression of CD19b-IL-21 CAR T cells and CD19-IL-21 anchor. Buffy coat cells were activated 3 days with anti-CD3 antibody.
Cells were transduced with either control vector (left), CD19b-IL-21, or CD19b-IL21-anchor CAR (right) lentiviral supernatant. After 3 days of incubation, cells were harvested and labeled for flow cytometry.

Figure 34:
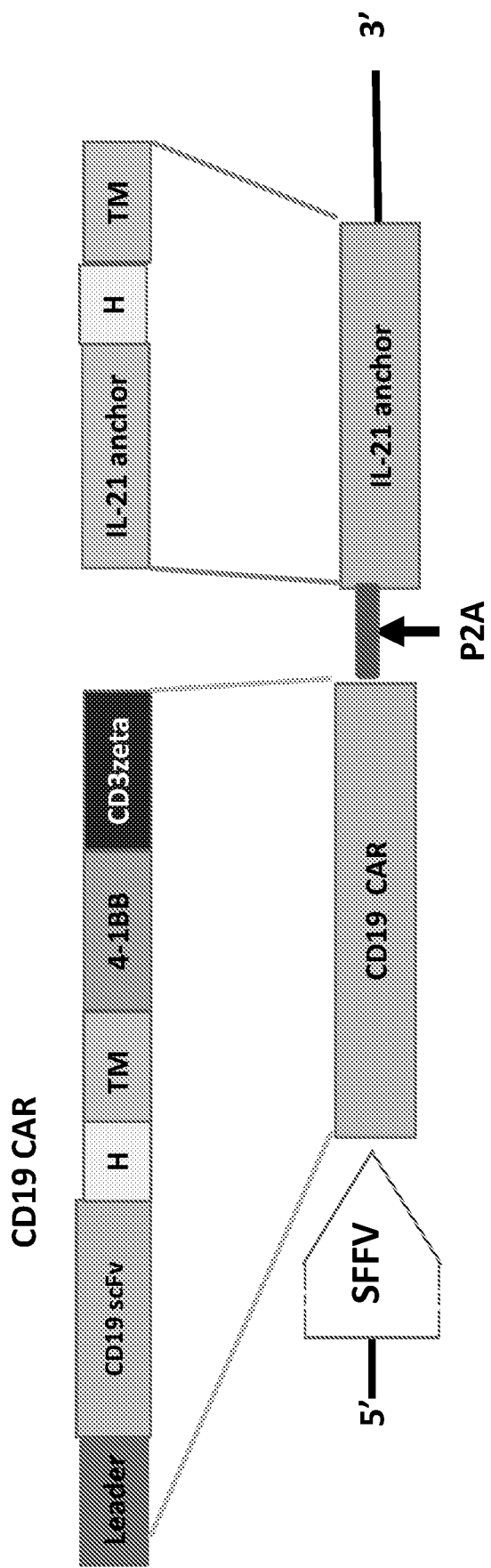

FIG. 34. Schematic diagram to elucidate the construct (CD19 CAR co-expressing IL-21 anchor) and its expression in T or NK cells.
CD19 CAR with IL-21anchor is linked with the P2A self-cleaving sequence. The IL-21 anchor fusion is composed of IL-2 signal peptide fused to IL-21, and linked to CD8 hinge region and CD8 transmembrane domain. The combination of CD19 CAR and IL-21 fusion is assembled on an expression vector and their expression is driven by the SFFV promoter. The IL-21 signal peptide is replaced with IL-2 signal peptide for a better secretion of IL-21 and anchoring on the cell surface.

Figure 35:
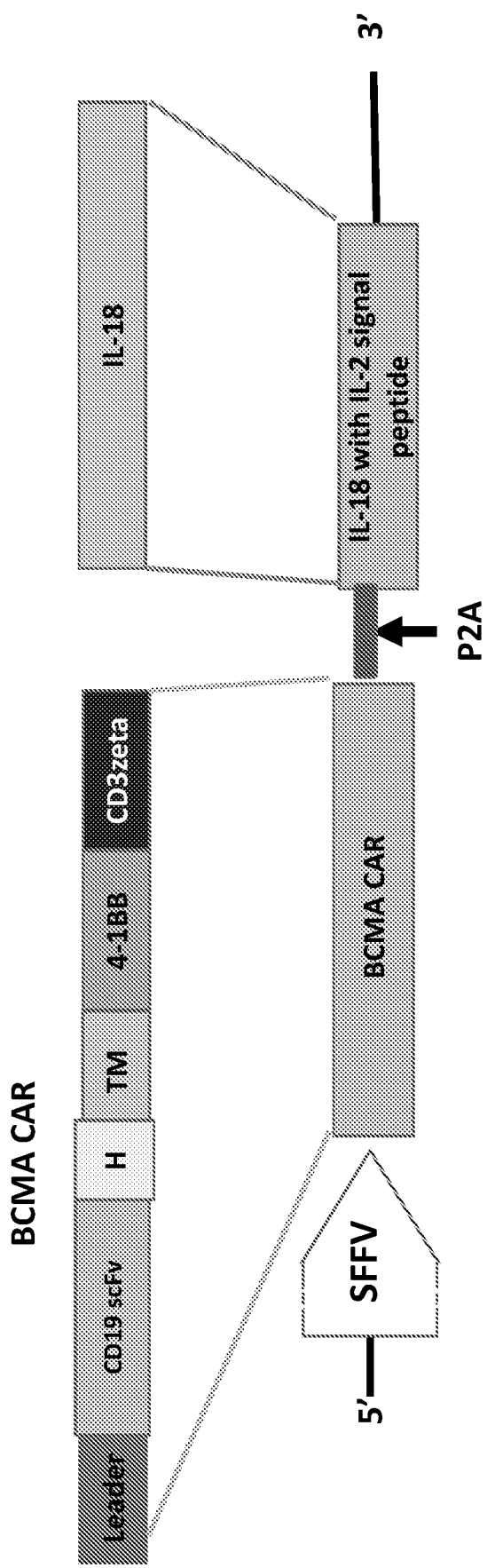

FIG. 35. A Link by P2A schematic showing BCMA CAR, and IL-18 in a single construct (BCMA CAR co-expressing IL-18) and its expression in T or NK cells.
The construct consists of a SFFV promoter driving the expression of CAR with costimulatory domain, 4-1BB). Upon cleavage of the linkers, BCMA CAR and IL-18 split and engage upon targets expressing antigen. CAR T cells received not only costimulation through the 4-1BB or CD28 but also 4-1BB ligand (4-1BBL or CD137L) or IL-18. The CD3-zeta signaling domain complete the assembly of this CAR-T. The IL-21 signal peptide is replaced with IL-2 signal peptide for a better secretion of IL-21. H, CD8a hinge region, TM, CD8a transmembrane domain.

Figure 36:
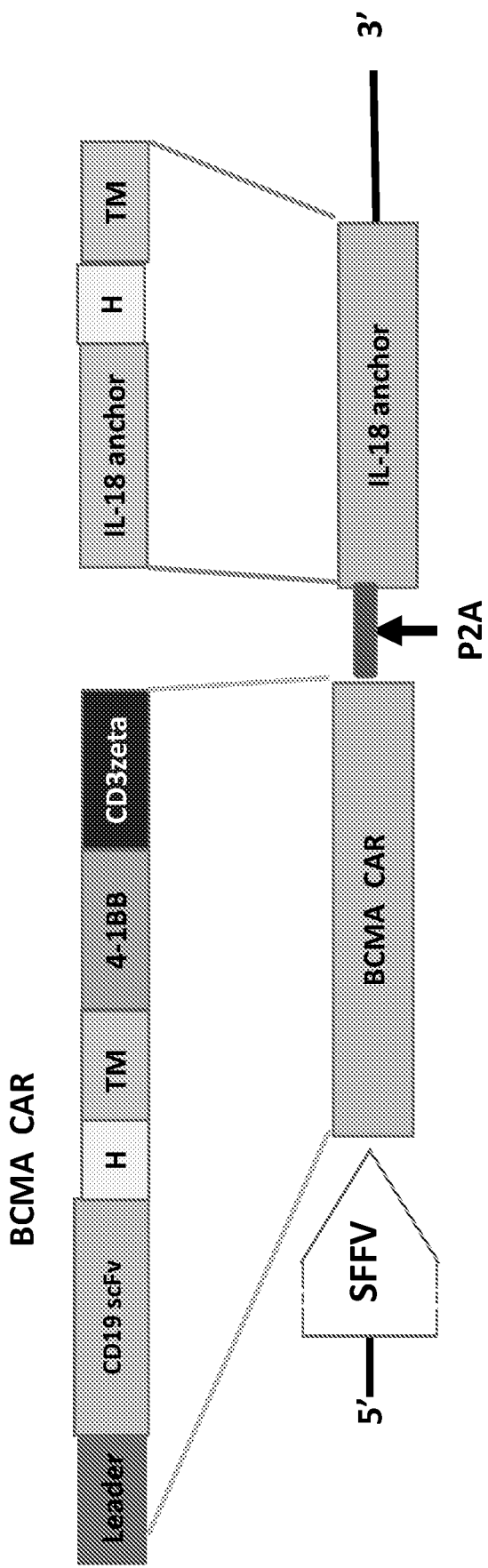

FIG. 36. Schematic diagram to elucidate the construct BCMA (CAR co-expressing IL-18 anchor) and its expression in T or NK cells.

A CAR with IL-18 anchor is linked with the P2A self-cleaving sequence. The IL-18 anchor fusion is composed of IL-2 signal peptide fused to IL-18, and linked to CD8 hinge region and CD8 transmembrane domain. The combination of BCMA CAR and IL-18 anchor fusion is assembled on an expression vector and their expression is driven by the SFFV promoter. The IL-18 signal peptide is replaced with IL-2 signal peptide for a better secretion of IL-18 and anchoring on the cell surface.

Figure 37:
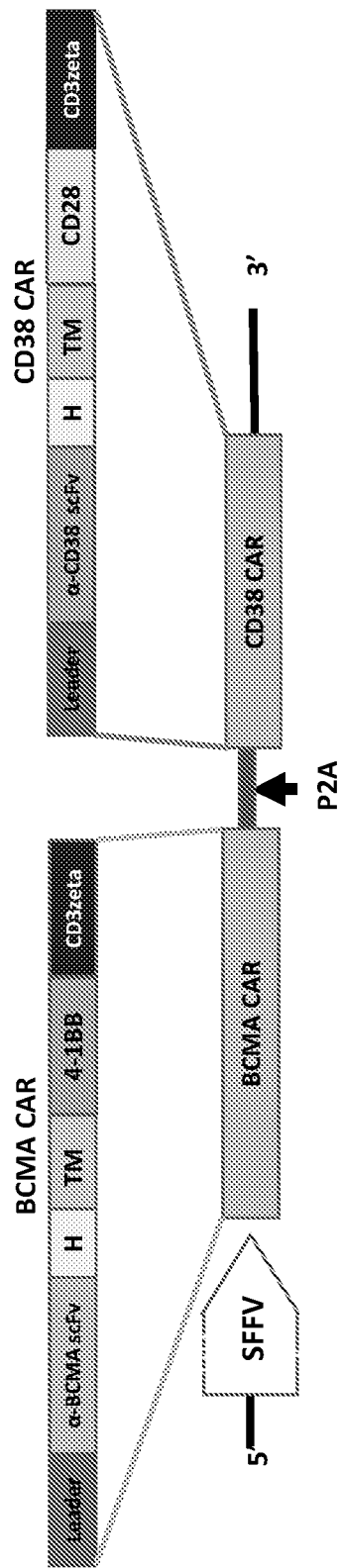

FIG. 37. A schematic representation of cCAR construct (BCMA–CD38 cCAR).

The construct comprises a SFFV promoter driving the expression of multiple modular units of CARs linked by a P2A cleavage peptide. Upon cleavage of the P2A linker, the cCARs split and engage upon targets expressing BCMA and/or CD38. Each unit of CAR bears a scFv against the antigen, a hinge domain (H), a transmembrane domain (TM), a co-stimulatory domain (including, but not limited to, CD28 or 4-1BB) and the intracellular signaling domain CD3 zeta chain. As a novel cCAR construct, the activation domains of the construct may include, but is not limited to, 4-1BB on the BCMA CAR segment and a CD28 region on the CD38 CAR.

Figure 38:
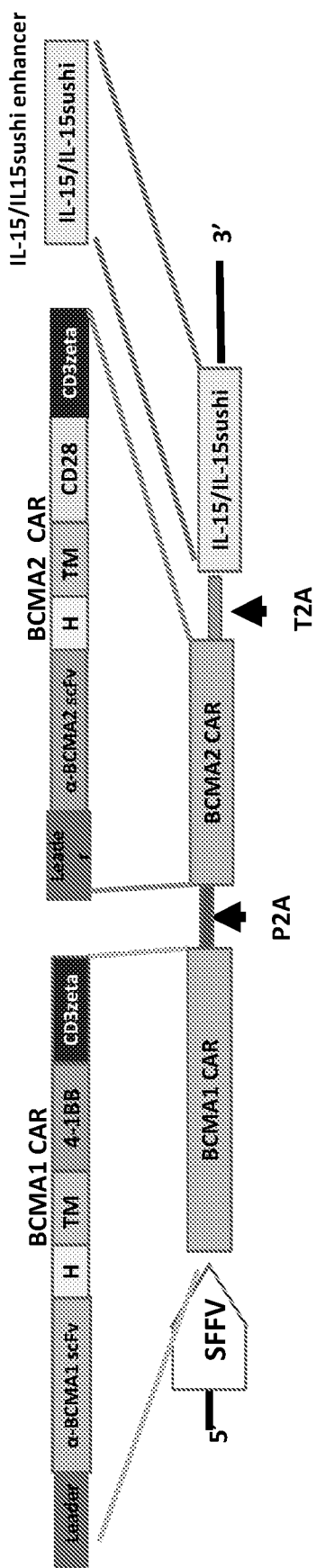

FIG. 38. A schematic representation of cCAR construct (BCMA1-BCMA2 cCAR).

The construct comprises a SFFV promoter driving the expression of multiple modular units of CARs linked by a P2A cleavage peptide. Upon cleavage of the P2A linker, the cCARs split and engage upon targets expressing BCMA1 (one of BCMA1 epitopes) and/or BMCA2 (another BCMA antigen epitope). Each unit of CAR bears a scFv against the antigen, a hinge domain (H), a transmembrane domain (TM), a co-stimulatory domain (including, but not limited to, CD28 or 4-1BB) and the intracellular signaling domain CD3 zeta chain. As a novel cCAR construct, the activation domains of the construct may include, but is not limited to, 4-1BB on the BCMA1 CAR segment and a CD28 region on the BCMA2 CAR. Each BCMA CAR targets its antigen epitope. The compound CAR, BCMA1-BCMA2 is able to recognize two distinct BCMA epitopes.

Figure 39A:
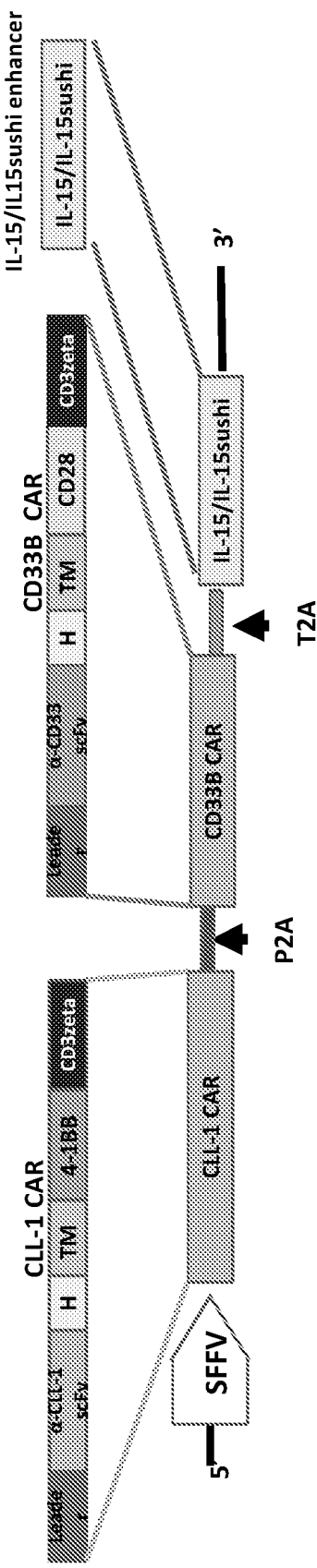

FIG. 39A. A schematic representation of cCAR-T with IL-15/IL15sushi enhancer construct. The construct comprises a SFFV promoter driving the expression of multiple modular units of CARs, and IL-15/IL-15sushi linked by P2A and T2A peptide respectively. Upon cleavage of the linker, the cCARs split and engage upon targets expressing CLL-1 and/or CD33 and a secreting enhancer fusion of IL-15/IL-15sushi. As a novel cCAR construct, the activation domains of the construct may include, but is not limited to, 4-1BB or CD28 on the CLL-1 CAR segment and a CD28 or 4-1BB region on the CD33B CAR segment. The peptide self cleavage peptides of the construct may include, but is not limited to, P2A, T2A, F2A and E2A. The secreting enhancer (s) of the construct may also include, but is not limited to, IL-15/IL-15sushi, IL-15, IL-21, IL-18, IL-7, and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Figure 39B:
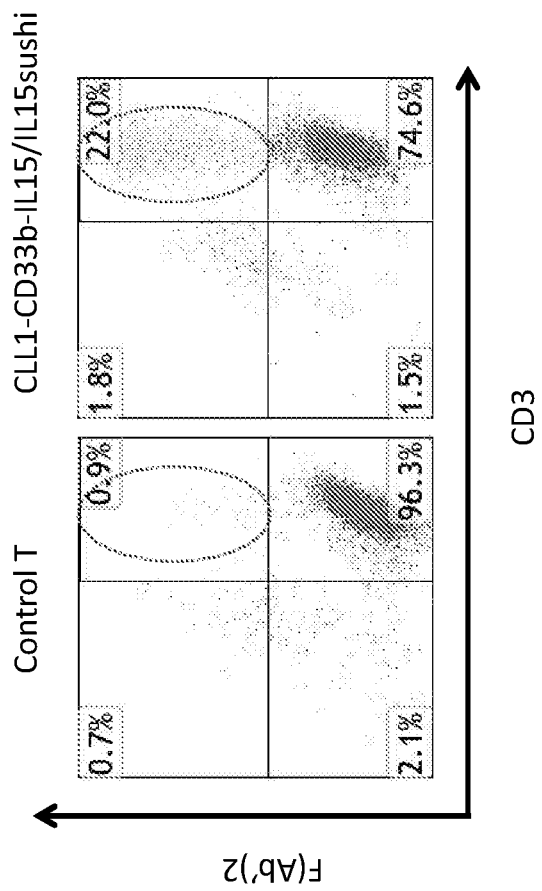

FIG. 39B. Expression of CLL1-CD33b-IL15/IL-15sushi CAR T cells. Human peripheral blood buffy coat cells were activated 3 days with anti-human CD3 antibody. Cells were transduced with either control vector (left), CLL1-CD33b-IL15/IL15sushi CAR (right) lentiviral supernatant. After 4 days of incubation, cells were harvested and labeled for flow cytometry with goat anti-human F(Ab')2 and mouse anti-human CD3 antibodies. CAR T cells are circled.

Figure 39C:
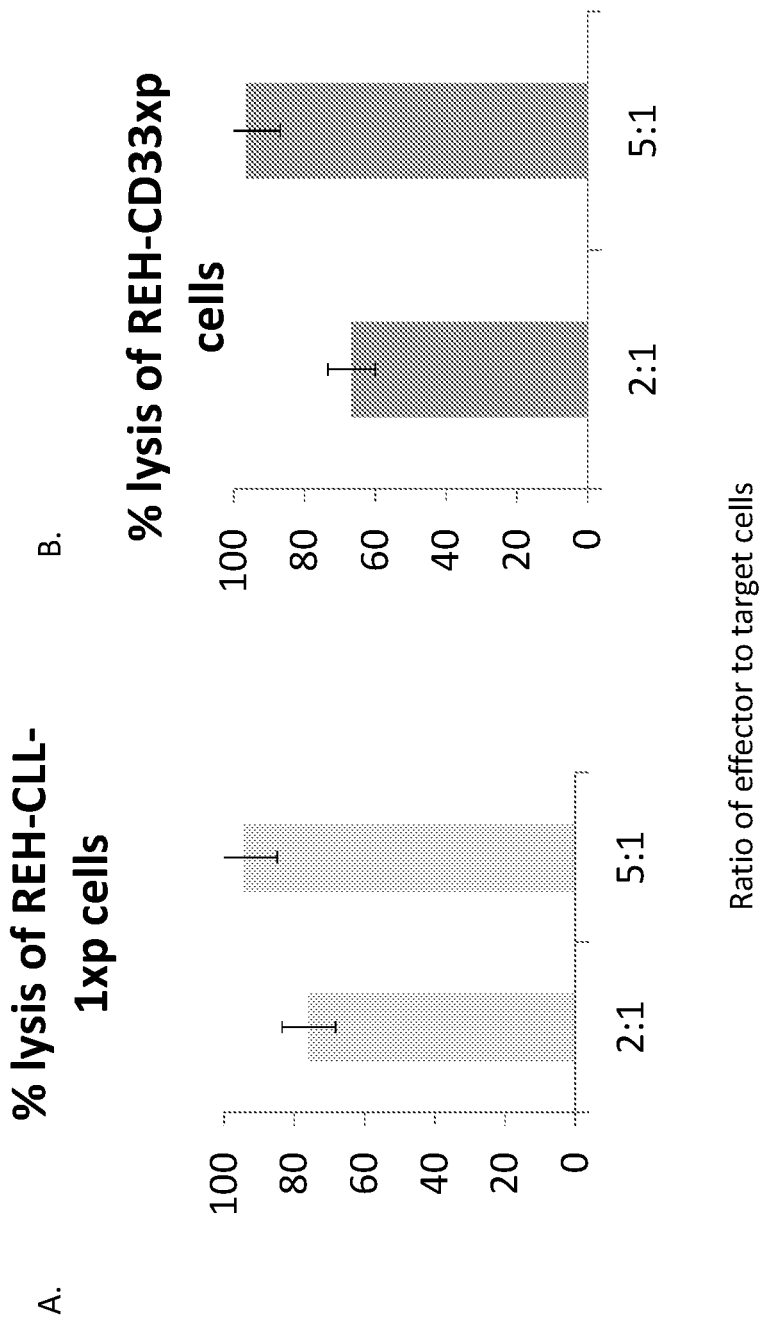

FIG. 39C CLL1-CD33b-IL15/IL15sushi CAR T cells specifically lyse the REH tumor cell line, which is synthetically expressing either CLL-1 or CD33 surface antigen, in co-culture assays. Each assay consisted of either REH-CLLxp (left graph) or REH-CD33xp target cells (right graph) co-cultured with control T cells or CLL1-CD33b-IL15/IL15sushi CAR T cells at 2:1 and 5:1 effector:target cell ratios. Co-culture experiments were performed for 24 hours and were directly analyzed by flow cytometry for anti-human CD3 and either CLL-1 or CD33.

Figure 40A:
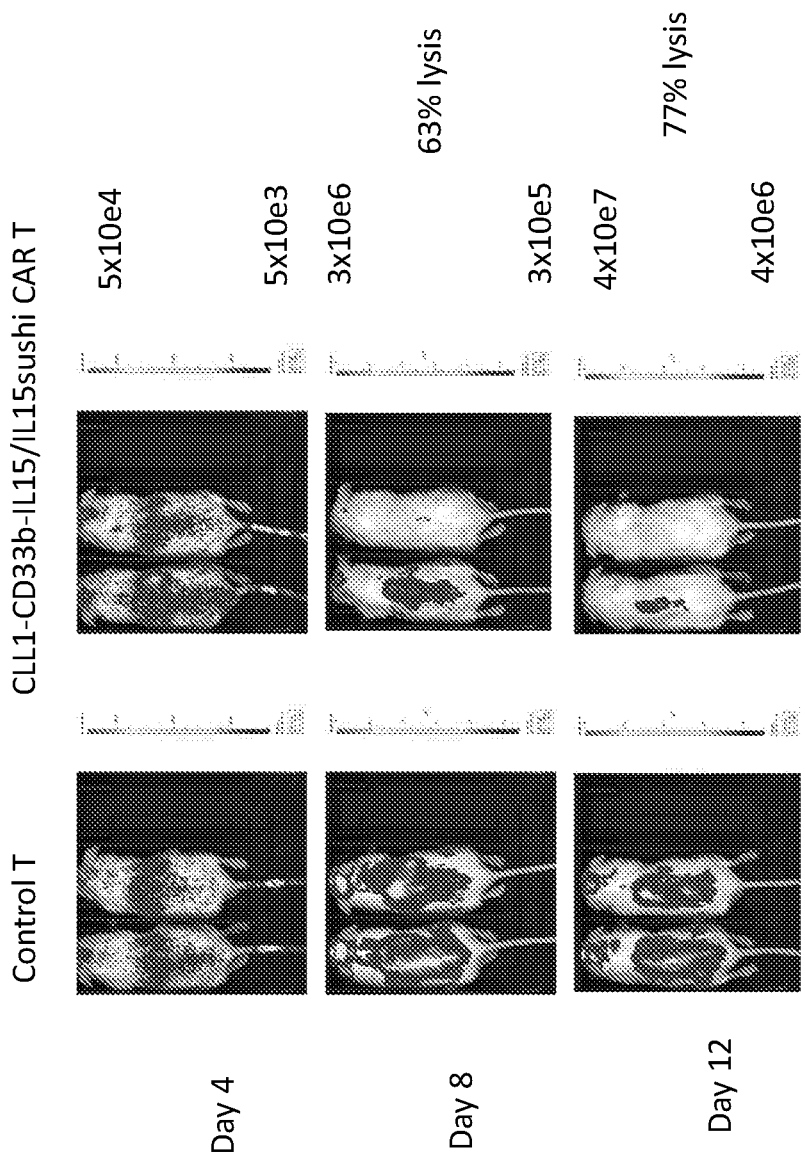

FIG. 40A. CLL1-CD33b-IL15/IL15sushi CAR T cells demonstrate strong anti-tumor effects in vivo against MOLM13 tumor cell line. NSG mice were sublethally irradiated and intravenously injected with $1.0 \times 10^6$ luciferase-expressing MOLM13 cells (Day 0) to induce measurable tumor formation. Starting 5 days after injection of tumor cells, mice were intravenously injected with a course of $15 \times 10^6$ either CLL1-CD33b-IL15/IL15sushi CAR T or vector control T cells. On days 4 (before T cell injection), 8 and 12, mice were injected subcutaneously with RediJect D-Luciferin and subjected to IVIS imaging. Dorsal view.

Figure 40B:
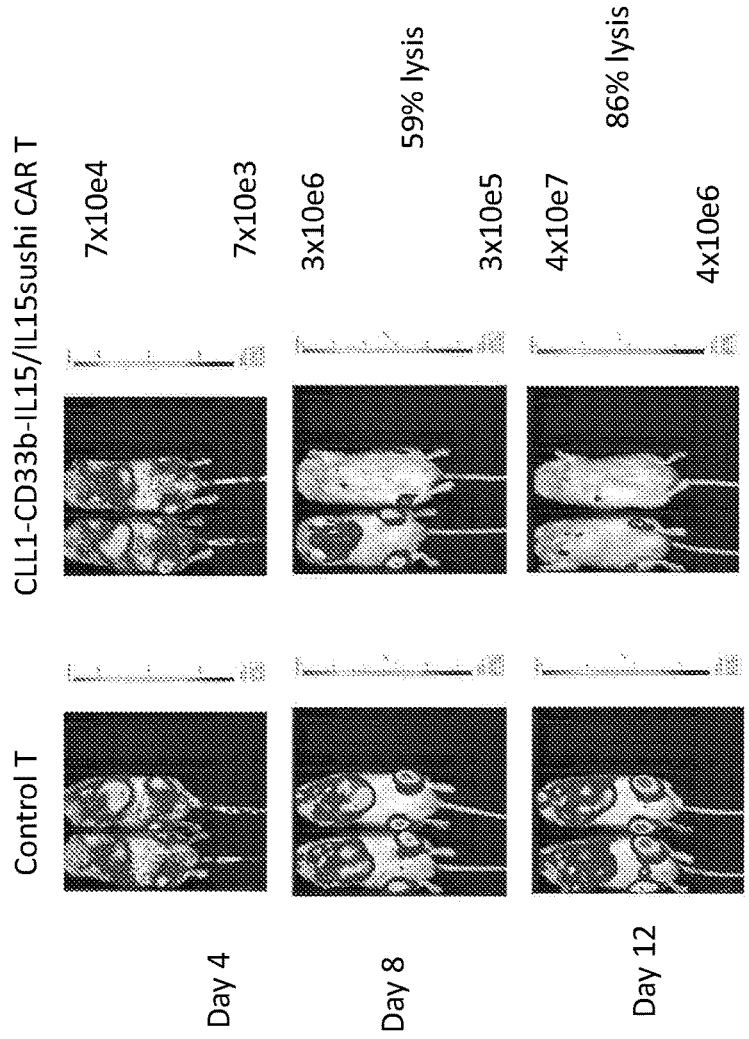

FIG. 40B. CLL1-CD33b-IL15/IL15sushi CAR T cells demonstrate strong anti-tumor effects in vivo against MOLM13 tumor cell line. NSG mice were sublethally irradiated and intravenously injected with $1.0 \times 10^6$ luciferase-expressing MOLM13 cells (Day 0) to induce measurable tumor formation. Starting 5 days after injection of tumor cells, mice were intravenously injected with a course of $15 \times 10^6$ either CLL1-CD33b-IL15/IL15sushi CAR T or vector control T cells. On days 4 (before T cell injection), 8 and 12, mice were injected subcutaneously with RediJect D-Luciferin and subjected to IVIS imaging. Ventral view.

Figure 40C:
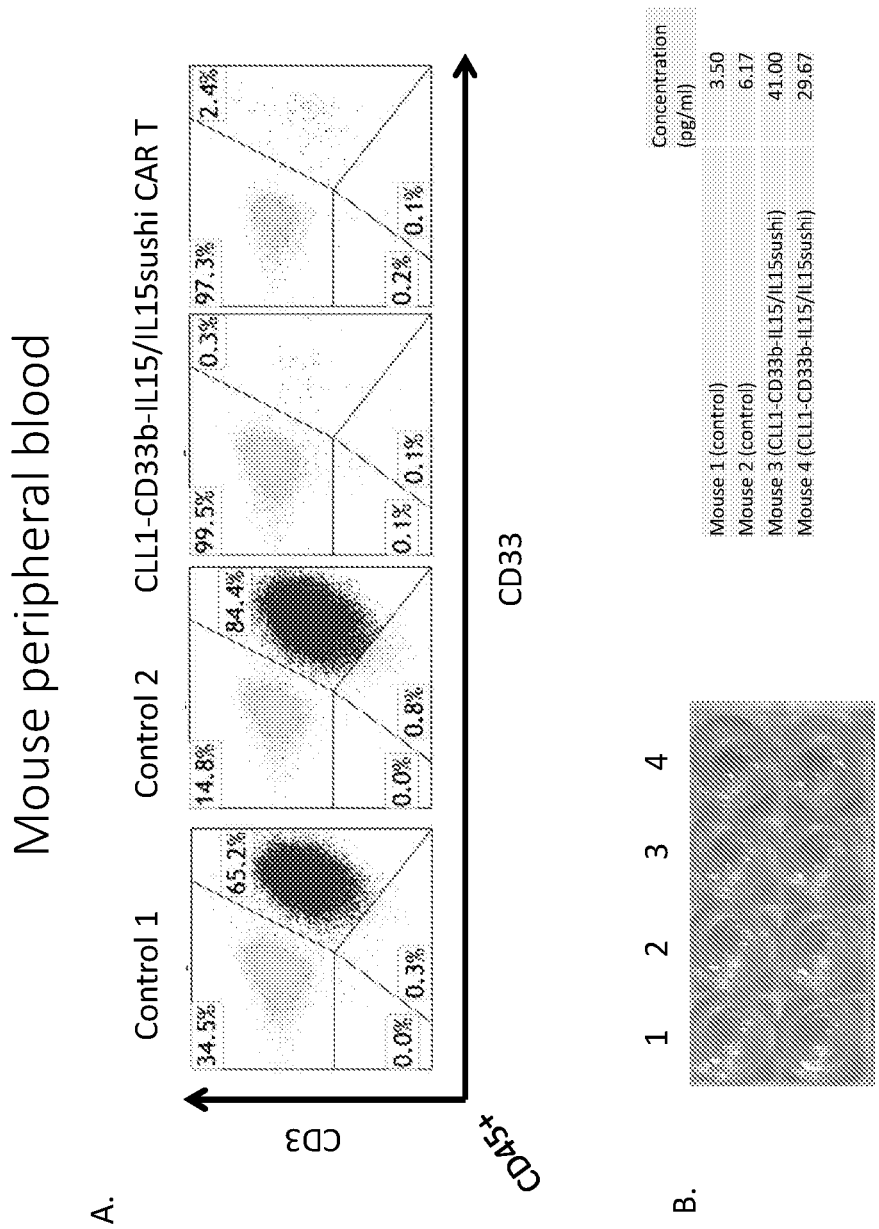

FIG. 40C. (A) Peripheral blood was removed from mice from FIG. 40A at time of sacrifice, labeled with mouse anti-human CD45, CD3 and CD33, and subjected to flow cytometry. Transplanted human cells were gated by CD45, and analyzed for T cell and MOLM13 cell populations. Results of two control mice are on the left, and the two mice treated with CLL1-CD33b-IL15/IL15sushi CAR T cells are on the right. (B) Plasma from the peripheral blood of each mouse was subjected to ELISA to quantify the amount of secreted human IL-15 fusion. Control mice, #1-2. Wells are in duplicate.

Figure 40D:
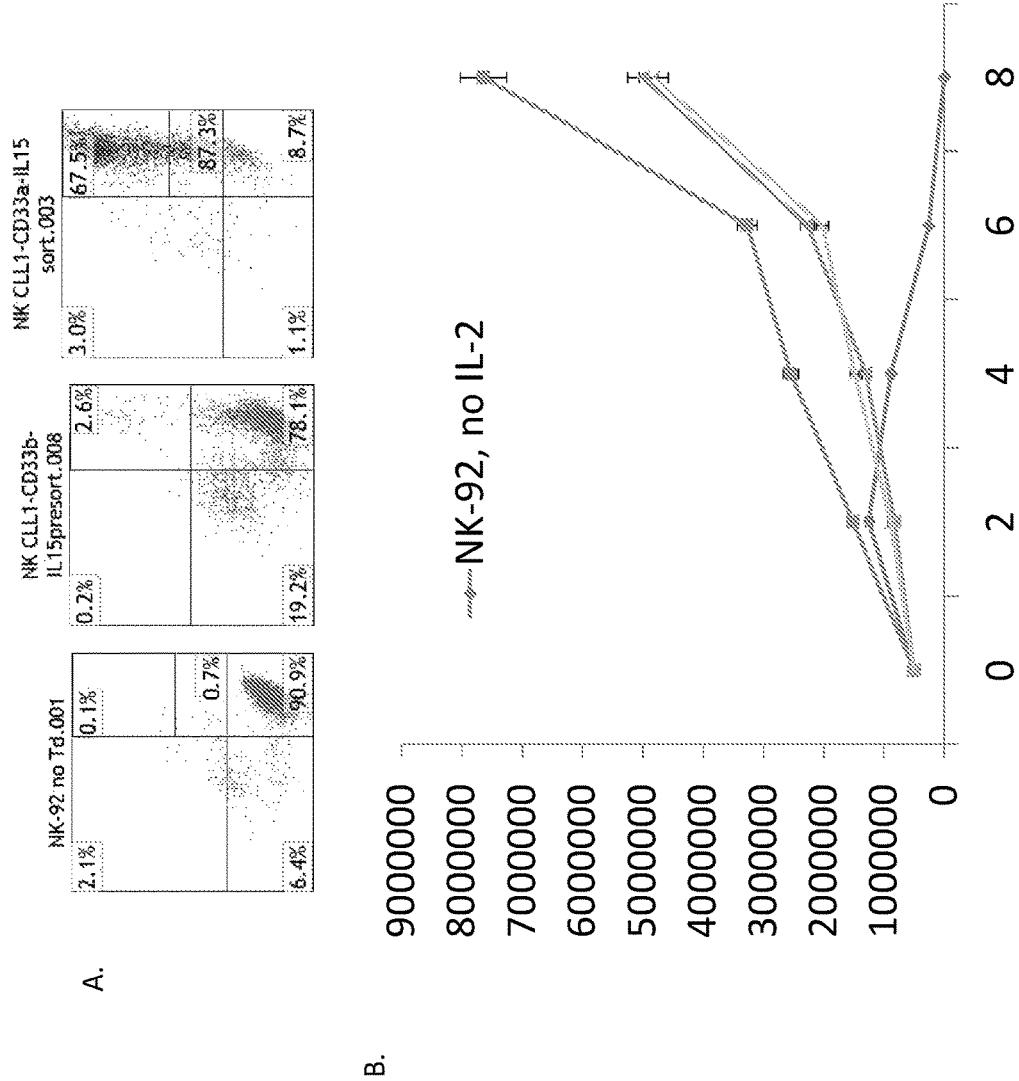

FIG. 40D. CLL1-CD33b-IL15/IL15sushi NK cells express functional IL-15/IL-15 fusion. NK-92 cell line was transduced with lentiviral vector containing CLL1-CD33b-IL15/IL15sushi CAR. (A) Cells were sorted on BD FACS Aria to select NK cells positive for the F(Ab')2 phenotype. (B) CLL1-CD33b-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted (B), and the volume increased to yield a concentration of approximately 0.5×10e6 cells/mL. This process was repeated on Days 4, 6 and 8.

Figure 40E:
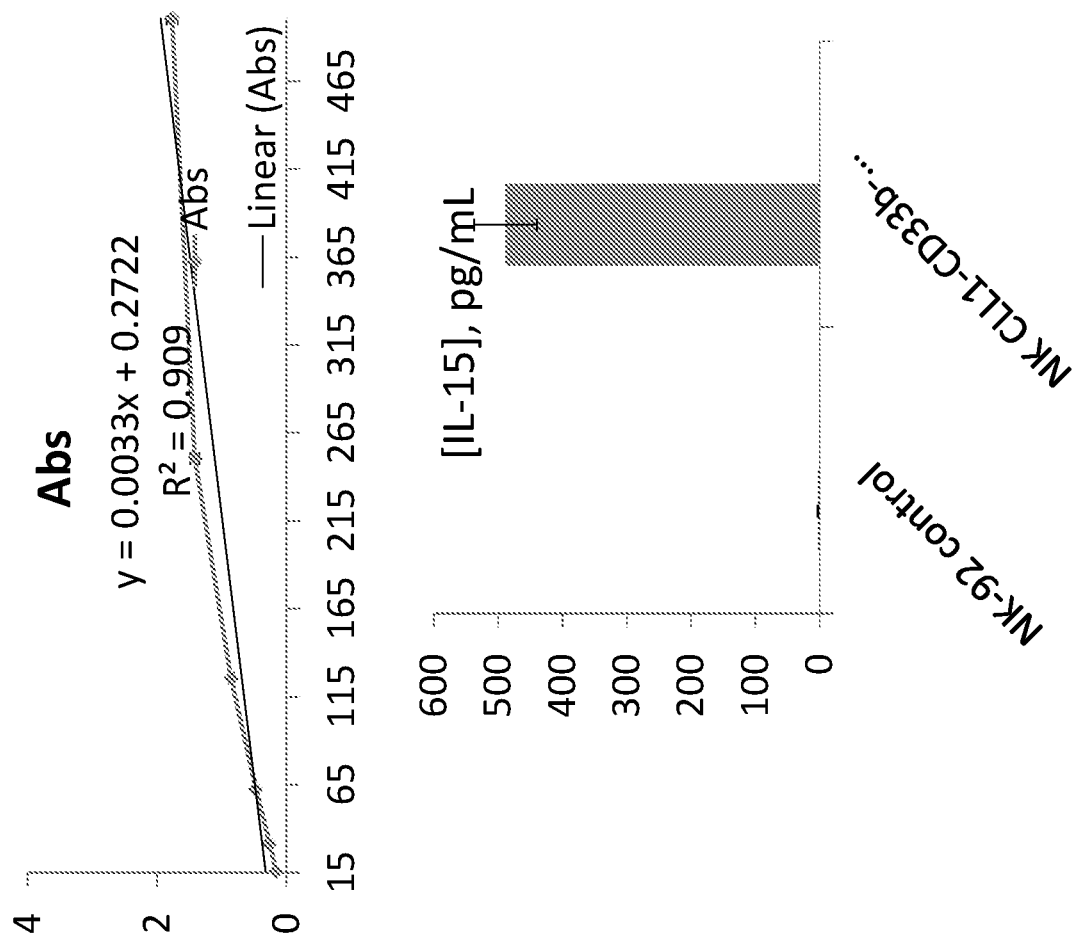

FIG. 40E. Sorted CLL1-CD33b-IL15/IL15sushi NK cells and wild-type control NK-92 cells were cultured in separate wells for 72 hours. Supernatant was collected and subjected to ELISA on 96-well plates precoated with IL-15 antibody. Following manufacturer's (Boster) directions, colorimetric results obtained on a plate reader were compared to a standard curve (A) generated with human IL-15 to determine concentration of IL-15 in the supernatants (B).

Figure 41A:
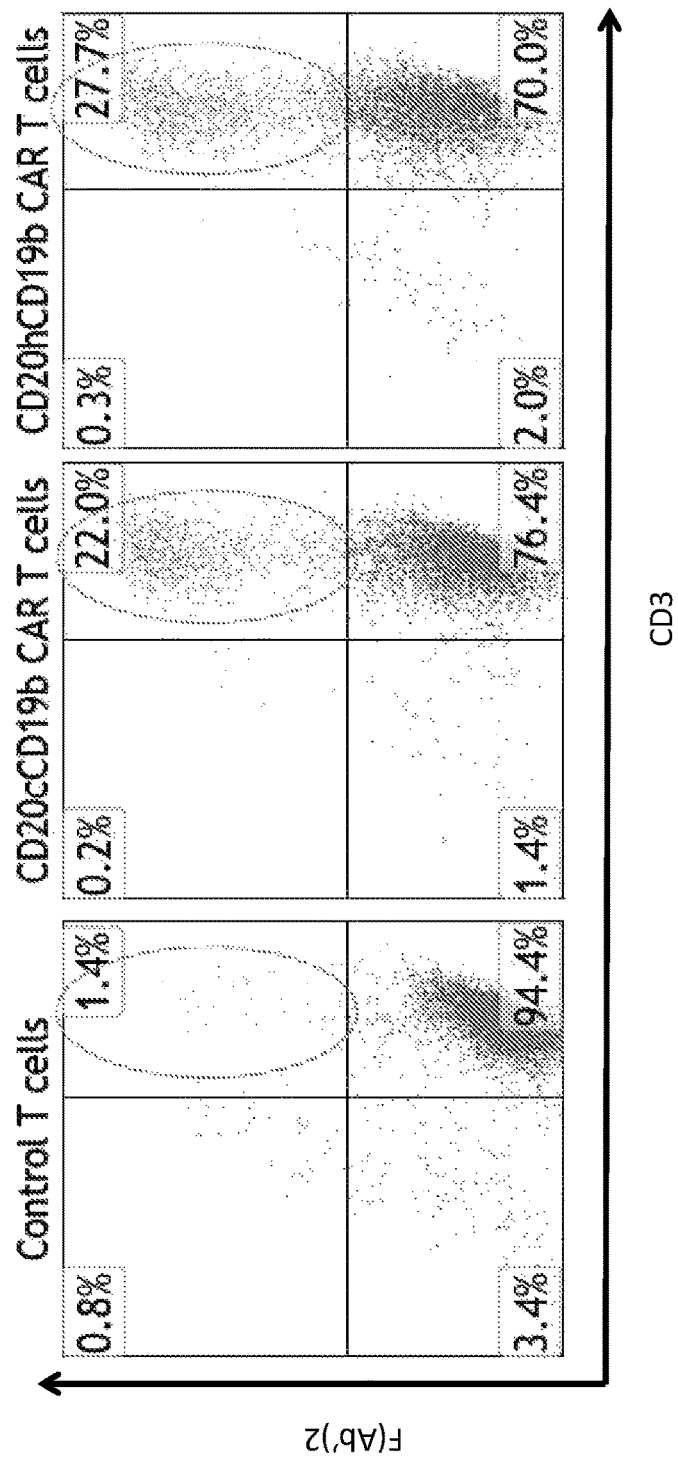

FIG. 41A. Expression of CD20cCD19b CAR T cells. Buffy coat cells were activated 3 days with anti-CD3 antibody. Cells were transduced with either control vector (left), CD20cCD19b or CD20hCD19b CAR (right) lentiviral supernatant. After 3 days of incubation, cells were harvested and labeled for flow cytometry.

Figure 41B:
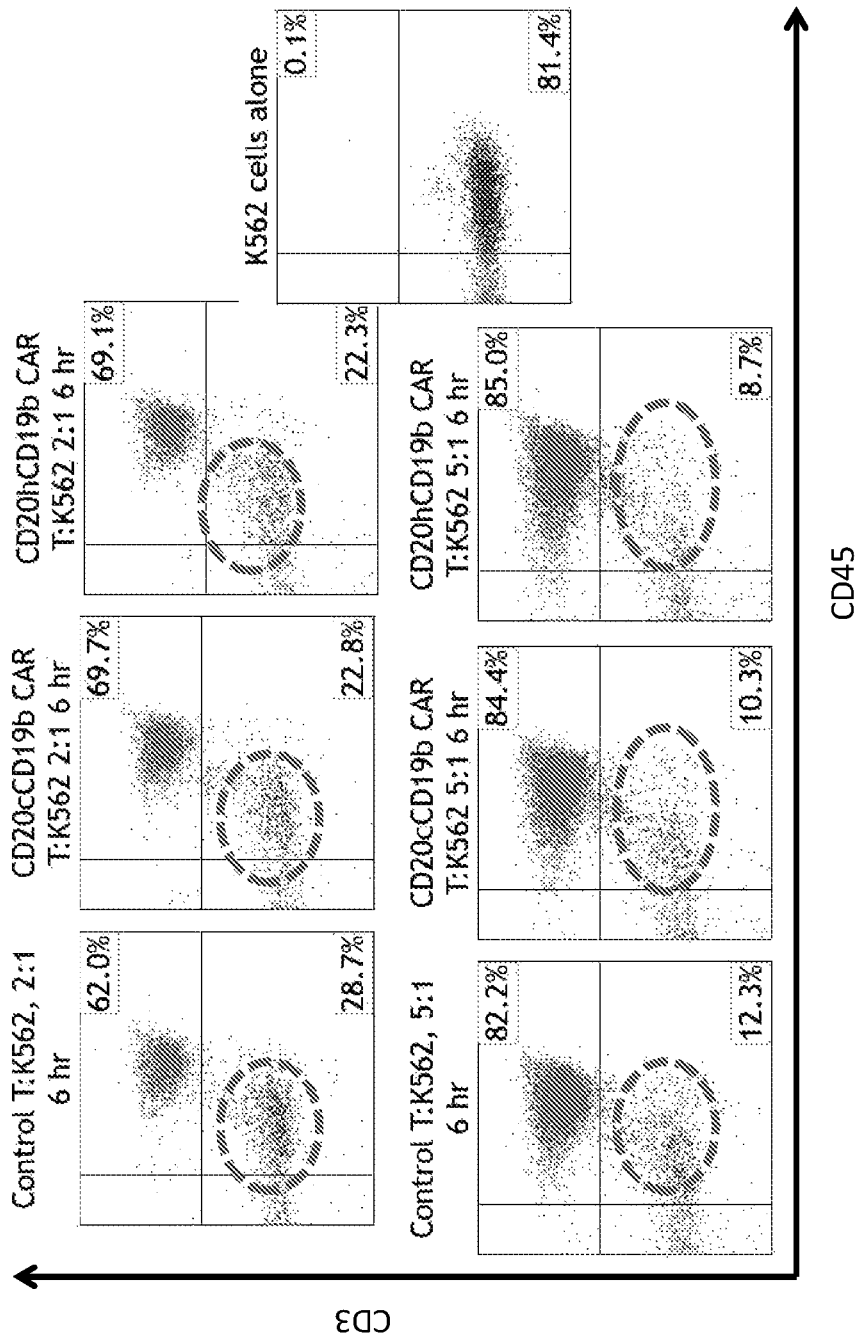

FIG. 41B. CD20cCD19b and CD20hCD19b CAR T cells do not lyse K562 tumor cell line in co-culture assays. Co-culture experiments were performed at an effector to target ratio of 2:1 or 5:1 for 6 hours and were directly analyzed by flow cytometry for CD3 and CD45. Each assay consists of K652 target cells alone (right), control T cells (left) and either CD20cCD19b or CD20hCD19b CAR T cells (center panels). (N=2)

Figure 41C:
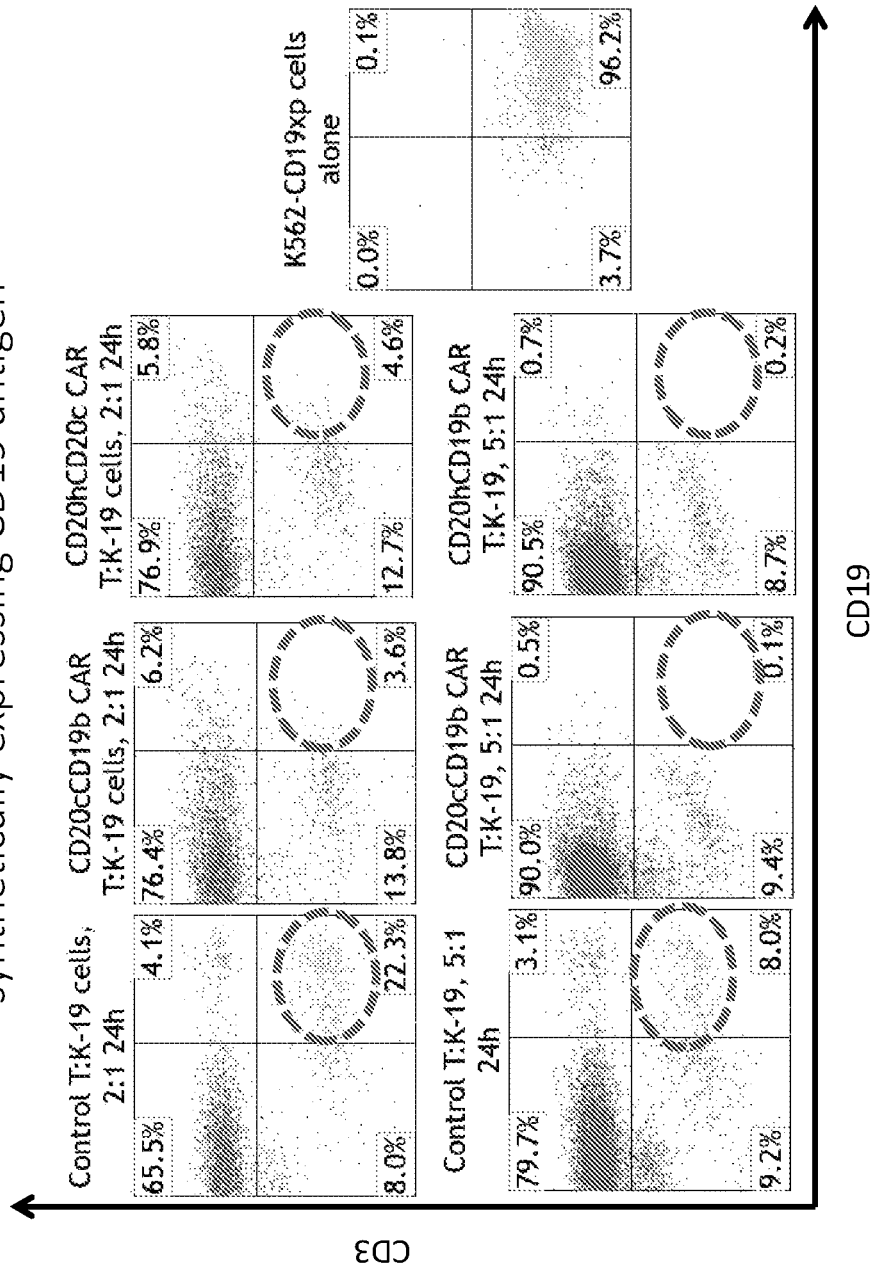

FIG. 41C. cCAR T cells lyse CD19 synthetically-expressing K562 tumor cell line in co-culture assays. Co-culture experiments were performed at an effector to target ratio of 2:1 or 5:1 for 24 hours and were directly analyzed by flow cytometry for CD19 and CD3. Each assay consists of K562-CD19xp target cells (K562 expressing CD19, K-19) alone (right side), control T cells (left panels) and either CD20cCD19b or CD20hCD19b CAR T cells (center panels).

Figure 41D:
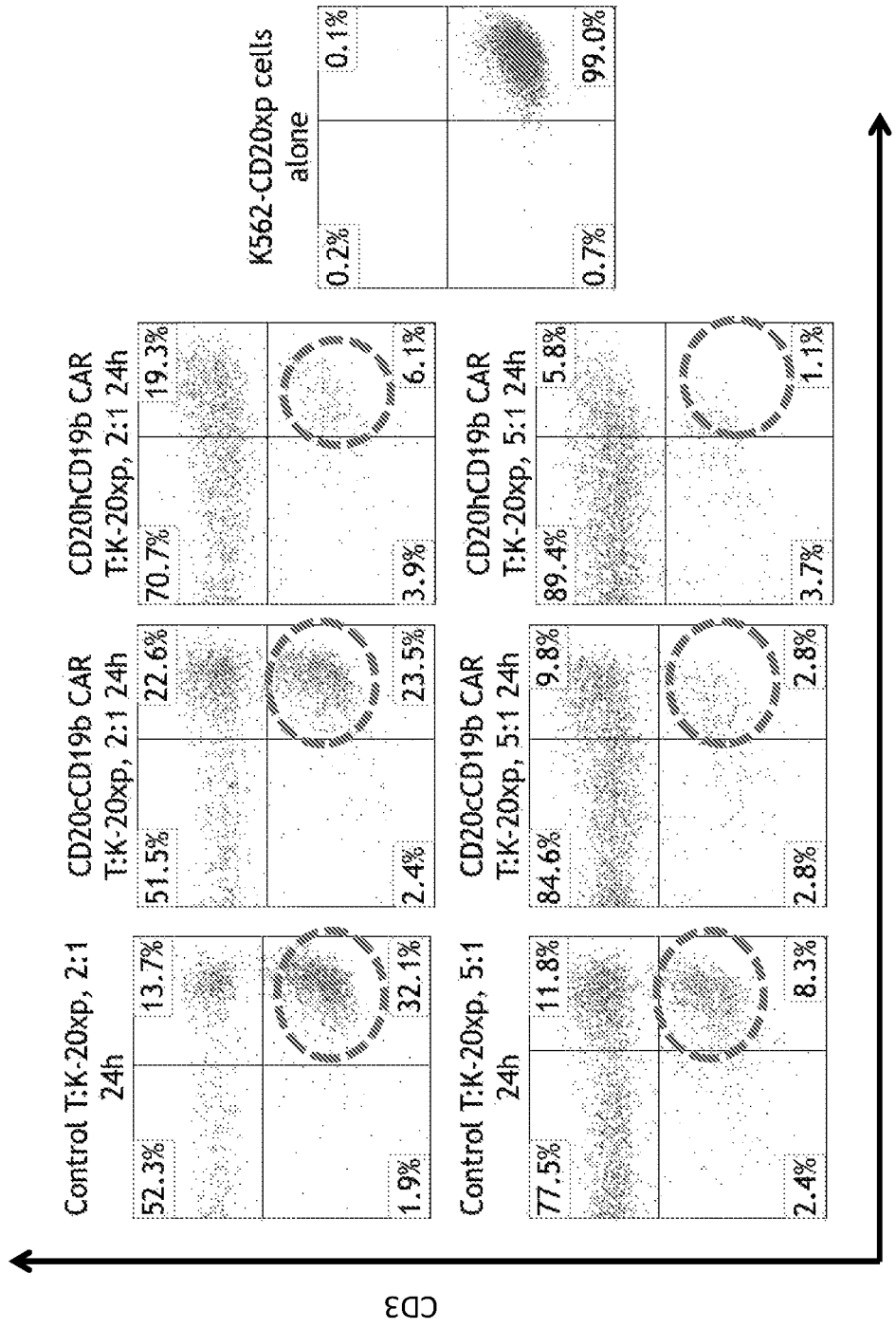

FIG. 41D. cCAR T cells lyse CD20 synthetically-expressing K562 tumor cell line, in co-culture assays. Co-culture experiments were performed at an effector to target ratio of 2:1 or 5:1 for 24 hours and were directly analyzed by flow cytometry for CD20 and CD3. Each assay consisted of K562-CD20xp target cells alone (right side), control T cells (left panels) and either CD20cCD19b or CD20hCD19b CAR T cells (center panels).

Figure 41E:
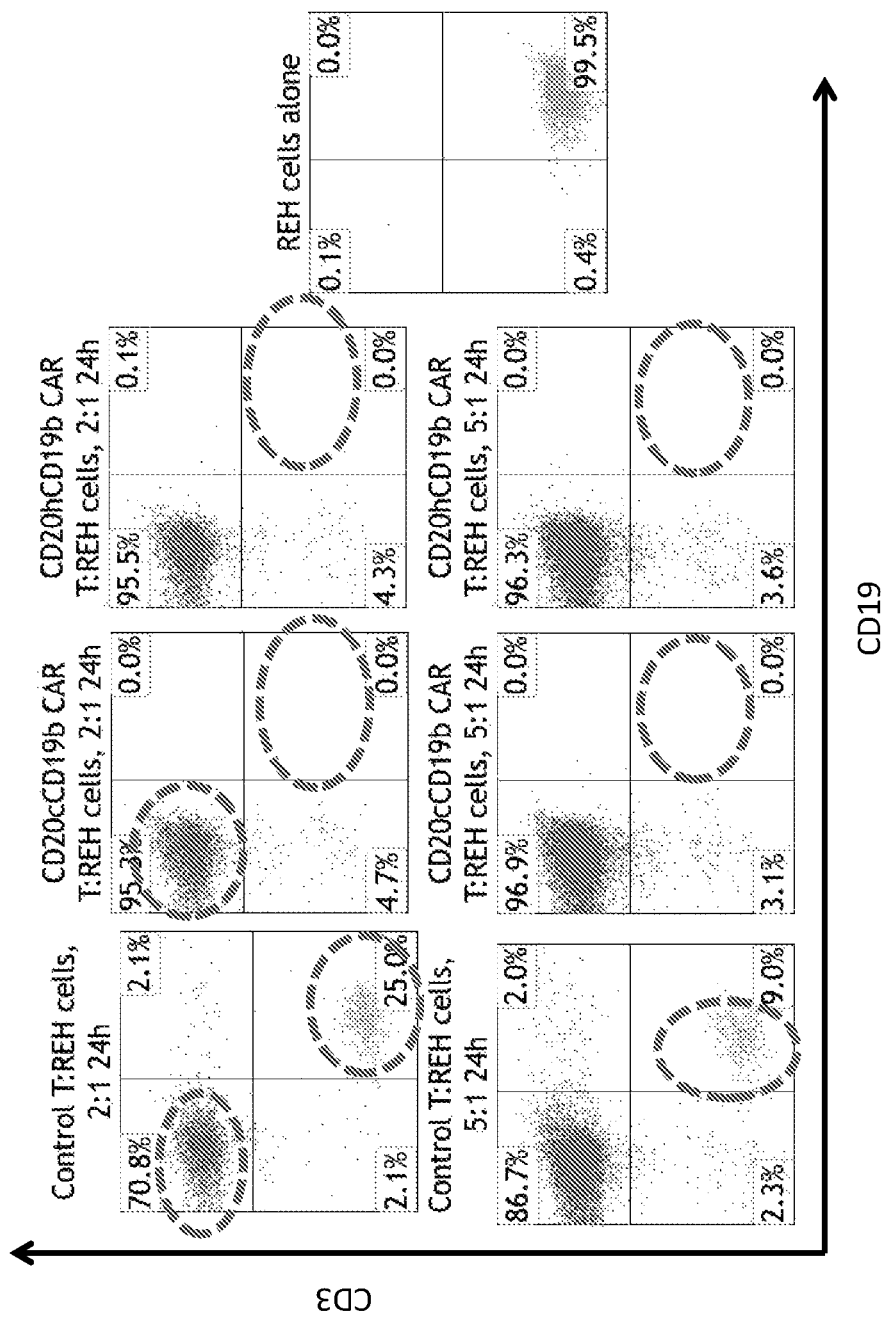

FIG. 41E. cCAR T cells completely lyse CD19-expressing REH tumor cell line in co-culture assays. Co-culture experiments were performed at an effector to target ratio of 2:1 or 5:1 for 24 hours and were directly analyzed by flow cytometry for CD19 and CD3. Each assay consisted of REH target cells alone (right side), control T cells (left panels) and either CD20cCD19b or CD20hCD19b CAR T cells (center panels).

Figure 41F:
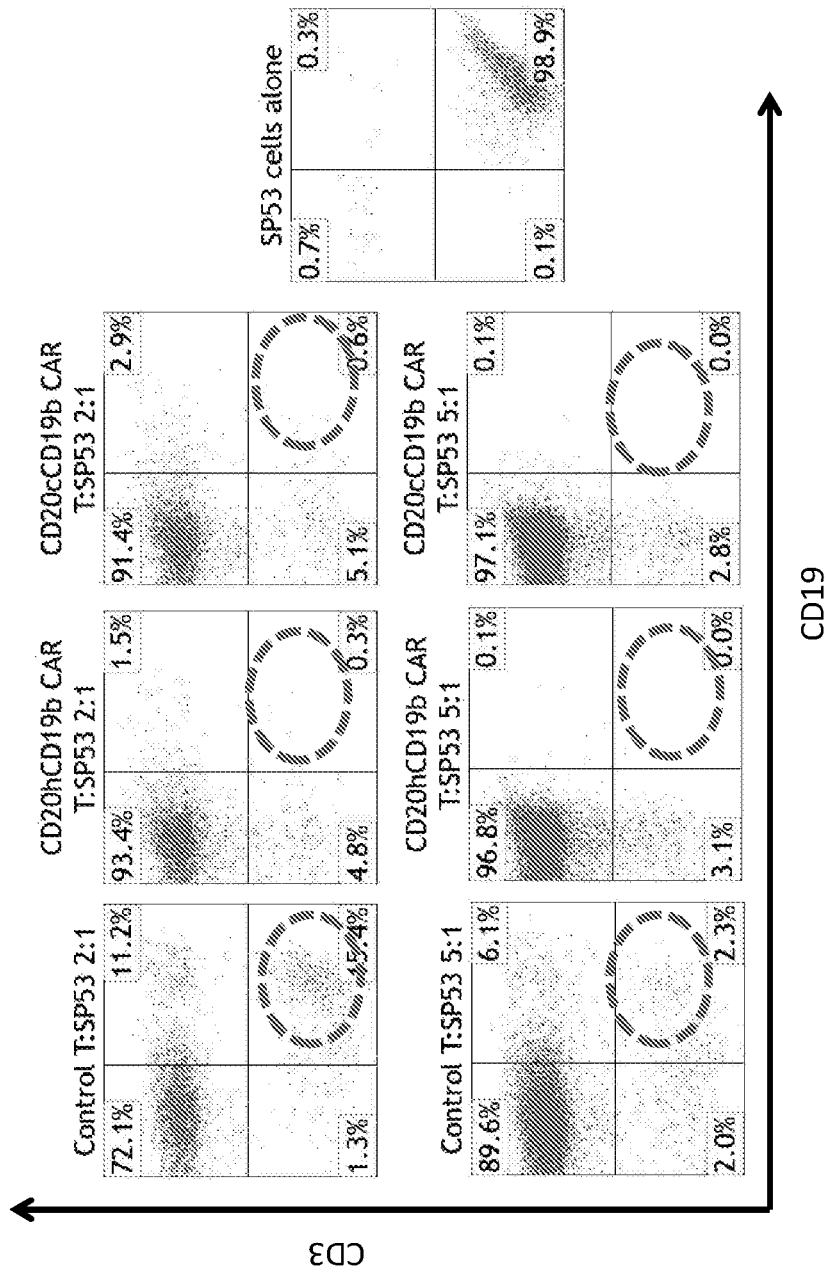

FIG. 41F. cCAR T cells completely lyse SP53 tumor cell line, which expresses both CD19 and CD20 antigens, in co-culture assay. Co-culture experiments were performed at an effector to target ratio of 2:1 or 5:1 for 24 hours and were directly analyzed by flow cytometry for CD19 and CD3. Each assay consisted of SP53 target cells alone (right side), control T cells (left panels) and either CD20cCD19b or CD20hCD19b CAR T cells (center panels). (N=2)

Figure 41G:
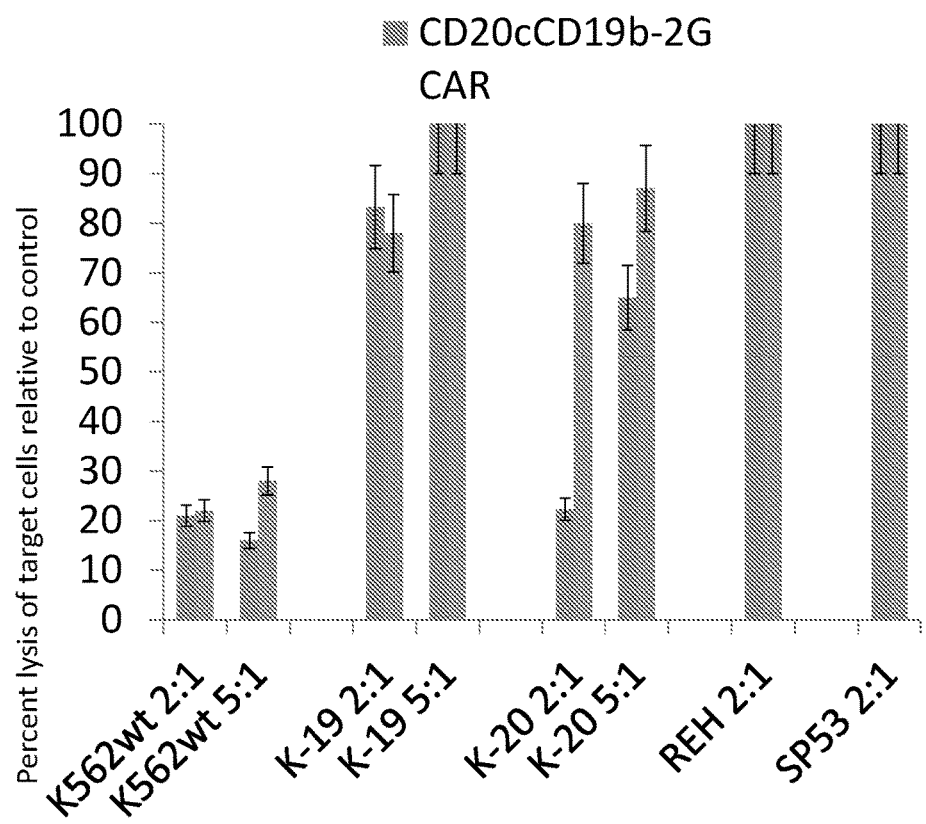

FIG. 41G. A summary of the co-culture results.

Figure 42A:
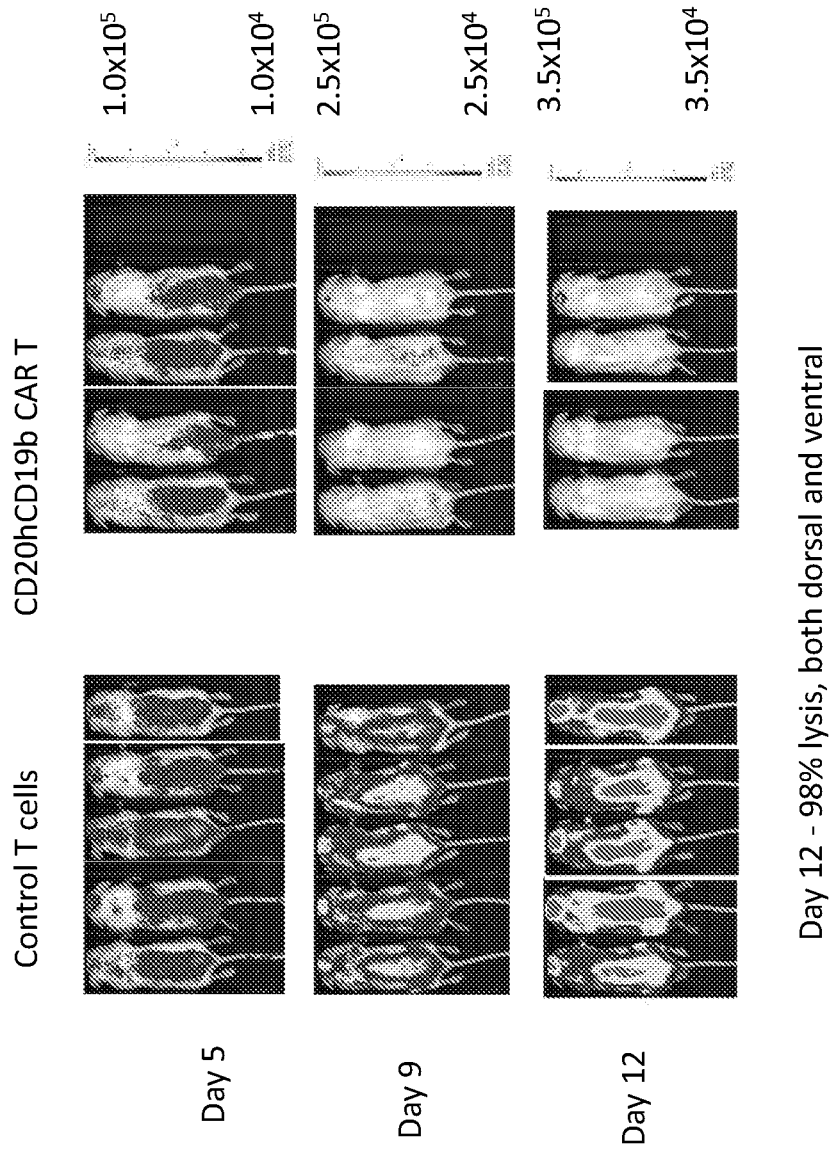

FIG. 42A. CD20hCD19b CAR T cells demonstrate anti-tumor effects in vivo against REH tumor cell line expressing CD19 antigen. NSG mice were sublethally irradiated and intravenously injected with $1.0 \times 10^6$ luciferase-expressing REH cells (Day 0) to induce measurable tumor formation. Starting 6 days after injection of tumor cells, mice were intravenously injected with a course of $10 \times 10^6$ CD20hCD19b CAR T cells or vector control T cells. On days 5, 9 and 12, mice were injected subcutaneously with RediJect D-Luciferin and subjected to IVIS imaging. Ventral view.

Figure 42B:
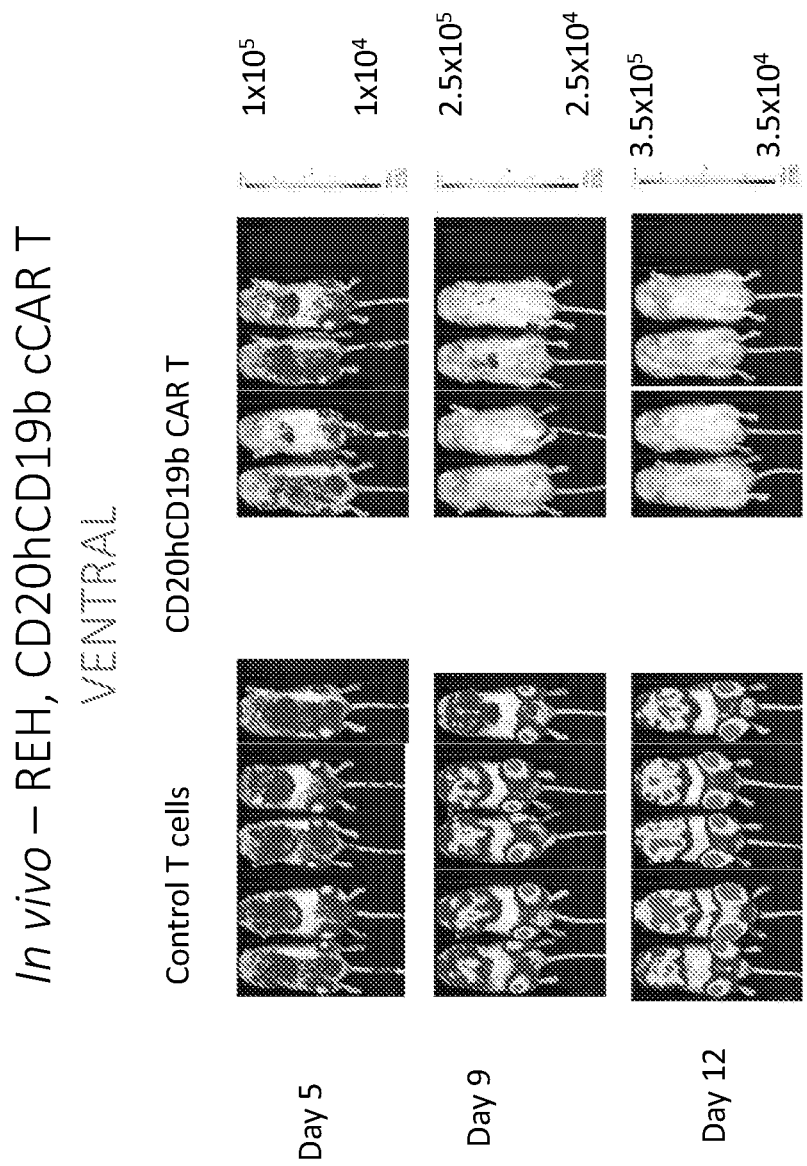

FIG. 42B. CD20hCD19b CAR T cells demonstrate anti-tumor effects in vivo against REH tumor cell line expressing CD19 antigen. NSG mice were sublethally irradiated and intravenously injected with $1.0 \times 10^6$ luciferase-expressing REH cells (Day 0) to induce measurable tumor formation. Starting 6 days after injection of tumor cells, mice were intravenously injected with a course of $10 \times 10^6$ CD20hCD19b CAR T cells or vector control T cells. On days 5, 9 and 12, mice were injected subcutaneously with RediJect D-Luciferin and subjected to IVIS imaging. Ventral view.

Figure 43A:
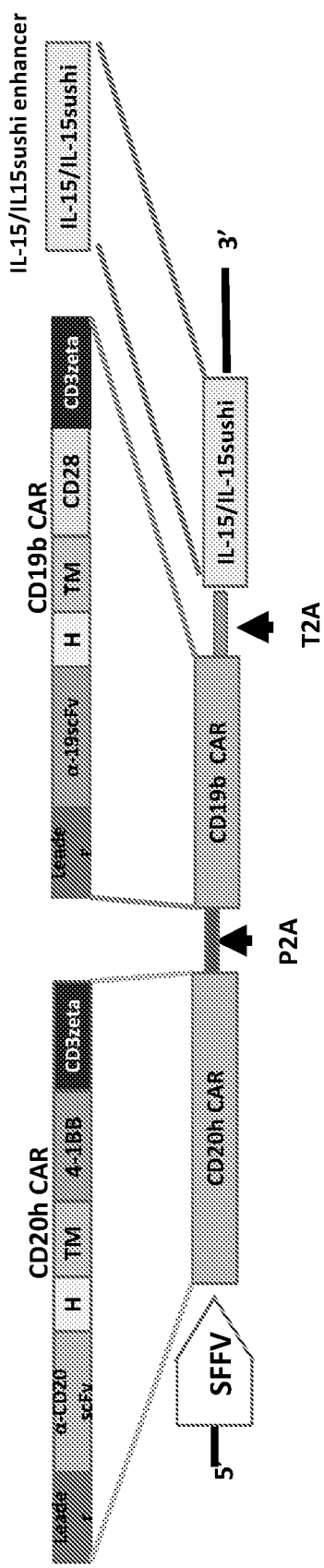

FIG. 43A. A schematic representation of cCAR-T with IL-15/IL15sushi enhancer construct. The construct comprises a SFFV promoter driving the expression of multiple modular units of CARs, and IL-15/IL-15sushi linked by P2A and T2A peptide respectively. Upon cleavage of the linker, the cCARs, CD20h–CD19b split and engage upon targets expressing CD20 and/or CD19 and a secreting enhancer fusion of IL-15/IL15sushi. As a novel cCAR construct, the activation domains of the construct may include, but is not limited to, 4-1BB or CD28 on the CD20h CAR segment and a CD28 or 4-1BB region on the CD19b CAR segment. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7, and IL-12. The secreting enhancer, such as IL-15/IL-15sushi enhances CAR T or NK T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects a by reprogramming body's immune system to fight cancers.

Figure 43B:
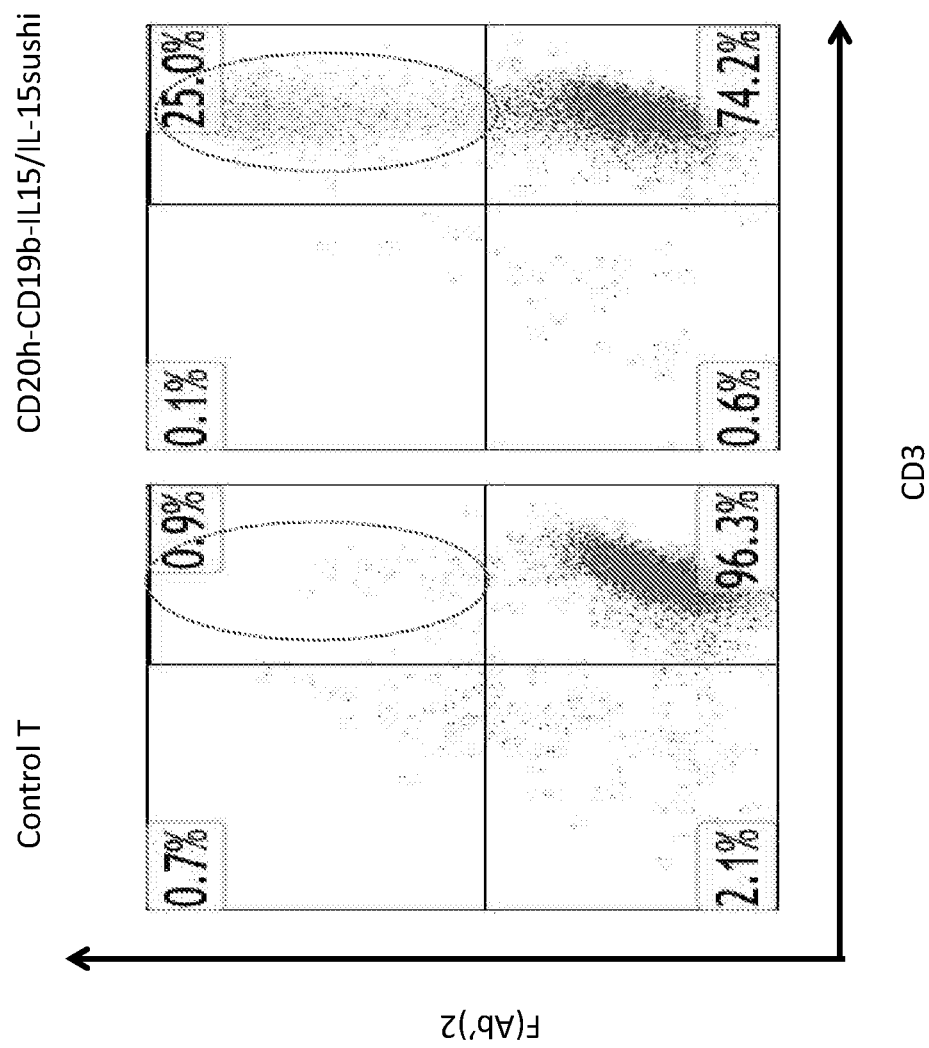

FIG. 43B. Expression of CD20h–CD19b-IL15/IL15sushi CAR T cells. Human peripheral blood buffy coat cells were activated 3 days with anti-human CD3 antibody. Cells were transduced with either control vector (left), or CD20h–CD19b-IL15/IL15sushi CAR (right) lentiviral supernatant. After 4 days of incubation, cells were harvested and labeled for flow cytometry with goat anti-human F(Ab')2 and mouse anti-human CD3 antibodies. CAR T cells circled.

Figure 43C:
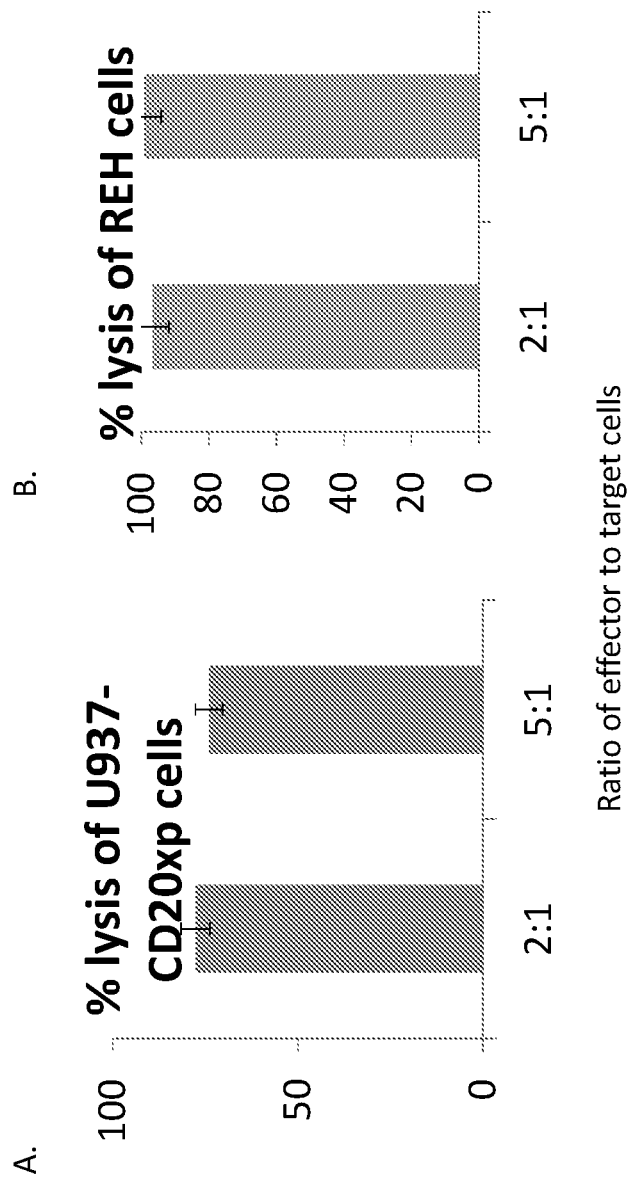

FIG. 43C. CD20h–CD19b-IL15/IL15sushi CAR T cells specifically lyse the U937 tumor cell line, which is synthetically expressing CD20 surface antigen (A), and REH tumor cells (B), which express the surface antigen CD19, in co-culture assays. Co-culture experiments were performed at an effector to target ratio of 2:1 or 5:1 for 48 hours and were directly analyzed by flow cytometry for anti-human CD20 and CD19, respectively.

Figure 44A:
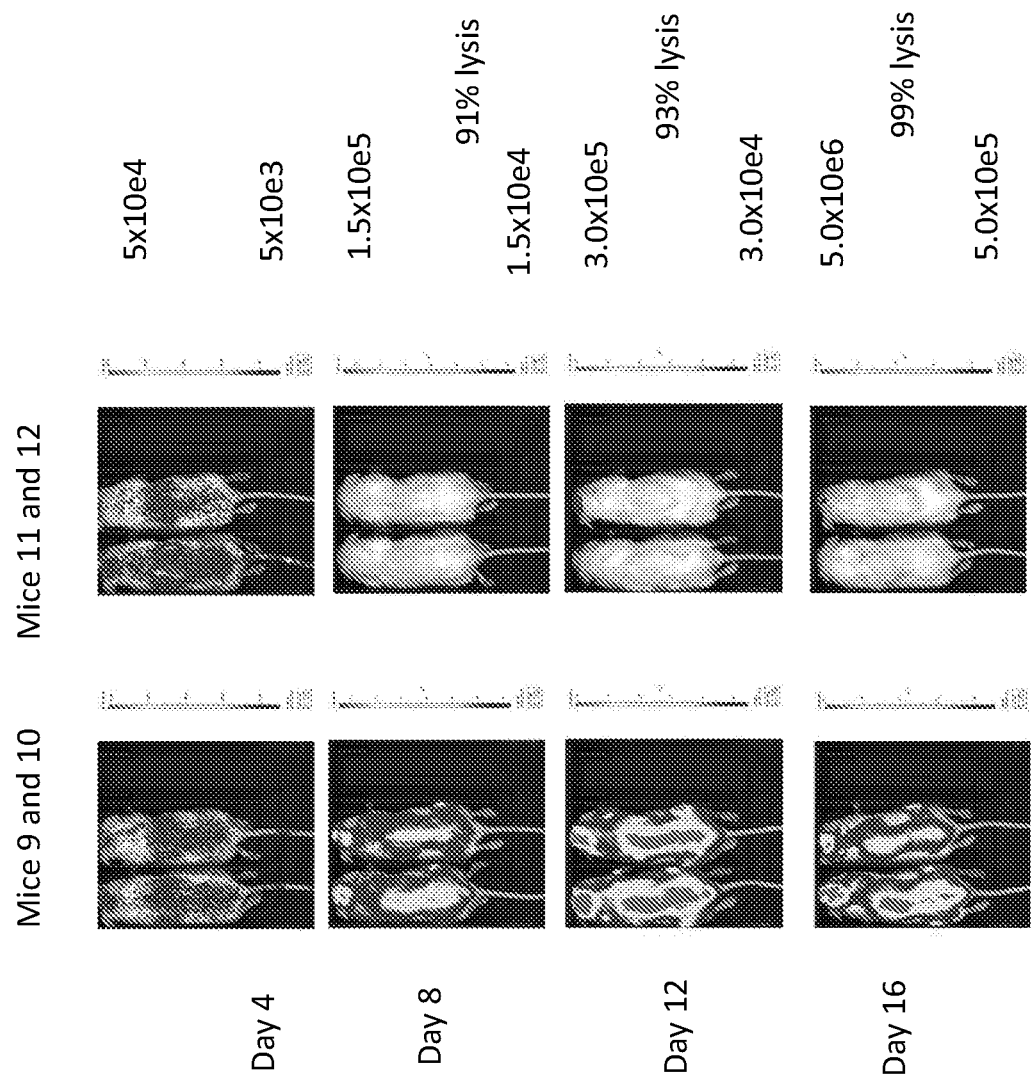

FIG. 44A. CD20h–CD19b-IL15/IL15sushi CAR T cells demonstrate strong anti-tumor effects in vivo against REH tumor cell line. NSG mice were sublethally irradiated and intravenously injected with $1.0 \times 10^6$ luciferase-expressing REH cells (Day 0) to induce measurable tumor formation. Starting 5 days after injection of tumor cells, mice were intravenously injected with a course of $15 \times 10^6$ either CD20h–CD19b-IL15/IL15sushi CAR T or vector control T cells. On days 4 (before T cell injection) 8 (72 hours after T cell injection), 12 and 16, mice were injected subcutaneously with RediJect D-Luciferin and subjected to IVIS imaging. Dorsal view.

Figure 44B:
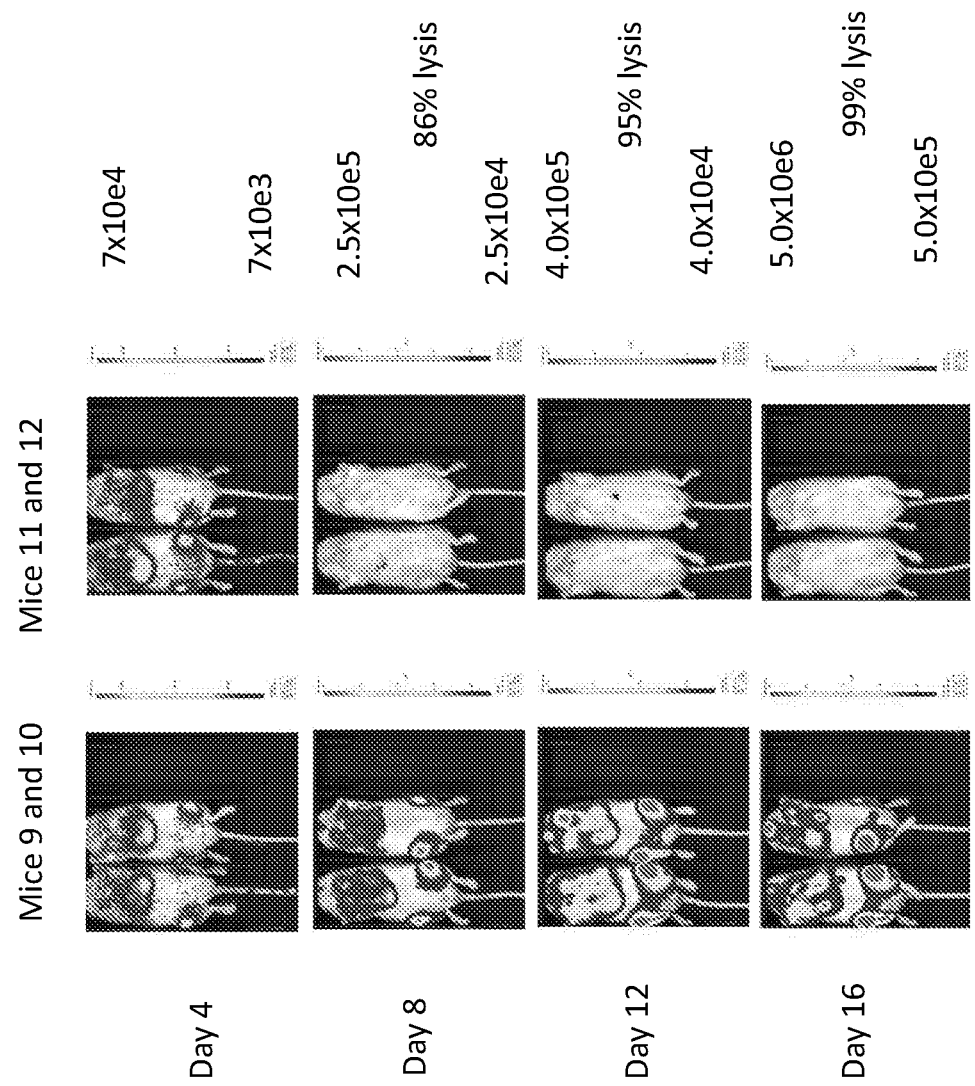

FIG. 44B. CD20h–CD19b-IL15/IL15sushi CAR T cells demonstrate strong anti-tumor effects in vivo against REH tumor cell line. NSG mice were sublethally irradiated and intravenously injected with $1.0 \times 10^6$ luciferase-expressing REH cells (Day 0) to induce measurable tumor formation. Starting 5 days after injection of tumor cells, mice were intravenously injected with a course of $15 \times 10^6$ either CD20h–CD19b-IL15/IL15sushi CAR T or vector control T cells. On days 4 (before T cell injection) 8 (72 hours after T cell injection), 12 and 16, mice were injected subcutaneously with RediJect D-Luciferin and subjected to IVIS imaging. Ventral view.

Figure 44C:
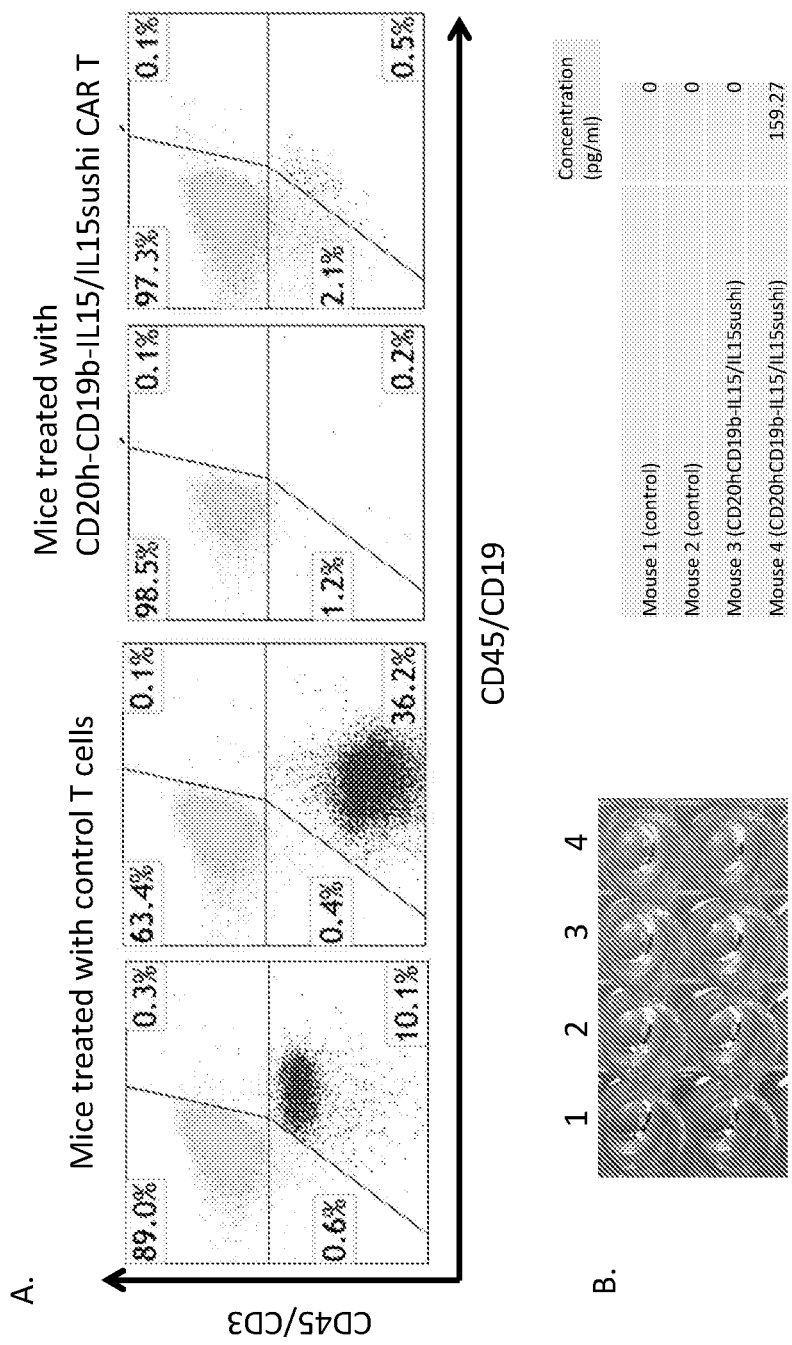

FIG. 44C. (A) Peripheral blood was removed from mice from FIG. 3 at time of sacrifice, labeled with mouse anti-human CD45, CD3 and CD19, and subjected to flow cytometry. Transplanted human cells were gated by CD45, and analyzed for T cell and REH cell populations. Results of two control mice are on the left, and the two mice treated with CD20h-CD19b-IL15/IL15sushi CAR T cells are on the right. (B) Plasma from the peripheral blood of each mouse was subjected to ELISA to quantify the amount of secreted IL-15. Control mice, #1-2.

Figure 44D:
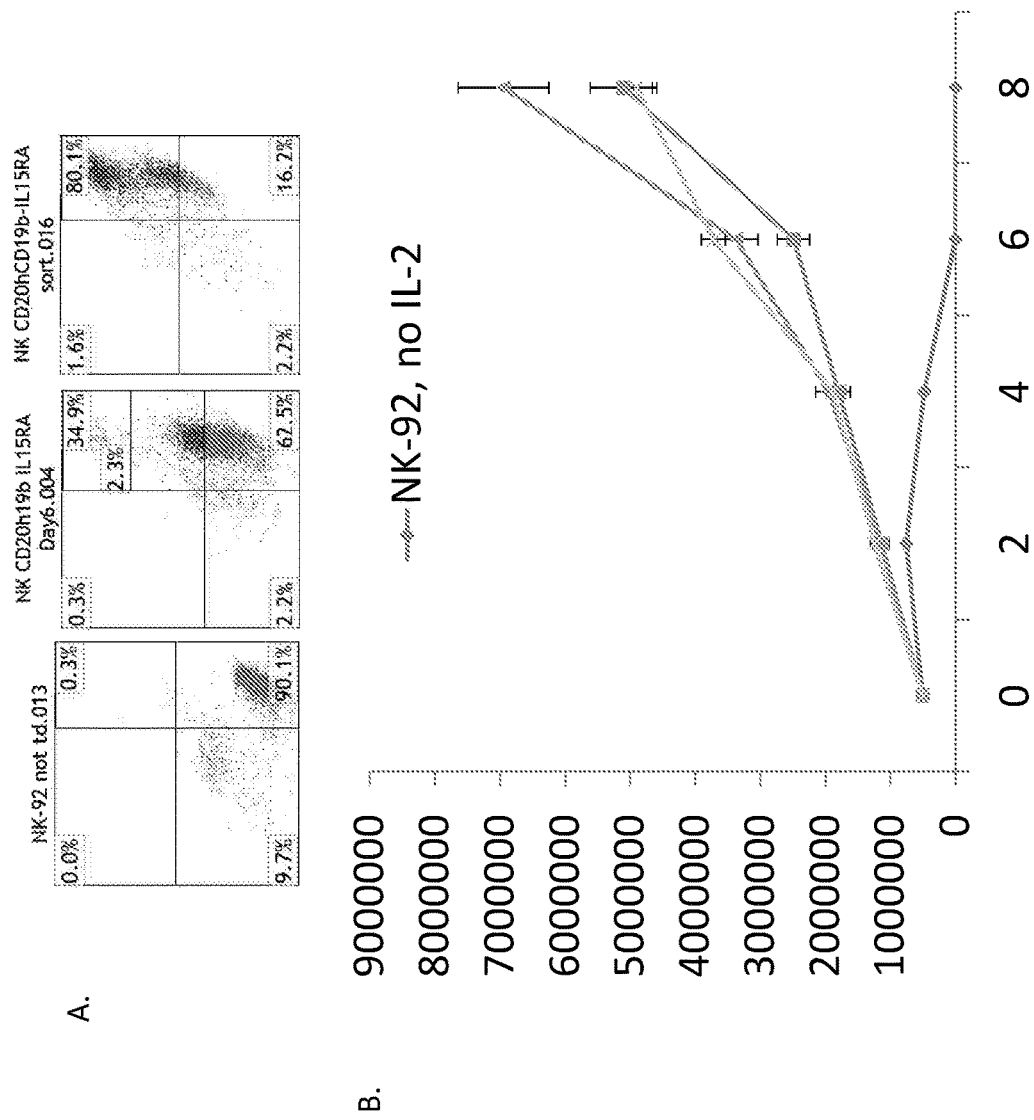

FIG. 44D. CD20h–CD19b-IL15/IL15sushi NK cells express functional IL15. NK-92 cell line was transduced with lentiviral vector containing CD20h–CD19b-IL15/IL15sushi-IL15/IL15sushi CAR. (A) Cells were sorted on BD FACS Aria to select NK cells positive for the F(Ab')2 phenotype. (B) CD20h–CD19b-IL15/IL15sushi-IL15/IL15sushi CAR NK cells, and wild-type NK-92 cells, were cultured in a 24-well plate at $0.5 \times 10e6$ cells per mL, in 1 mL total volume. Cells were added to duplicate wells; one well of each pair contained IL-2 at 300 IU/mL, the other well did not. After 48 hours (Day 2), cells were counted (B), and the volume increased to yield a concentration of approximately $0.5 \times 10e6$ cells/mL. This process was repeated on Days 4, 6 and 8.

Figure 44E:
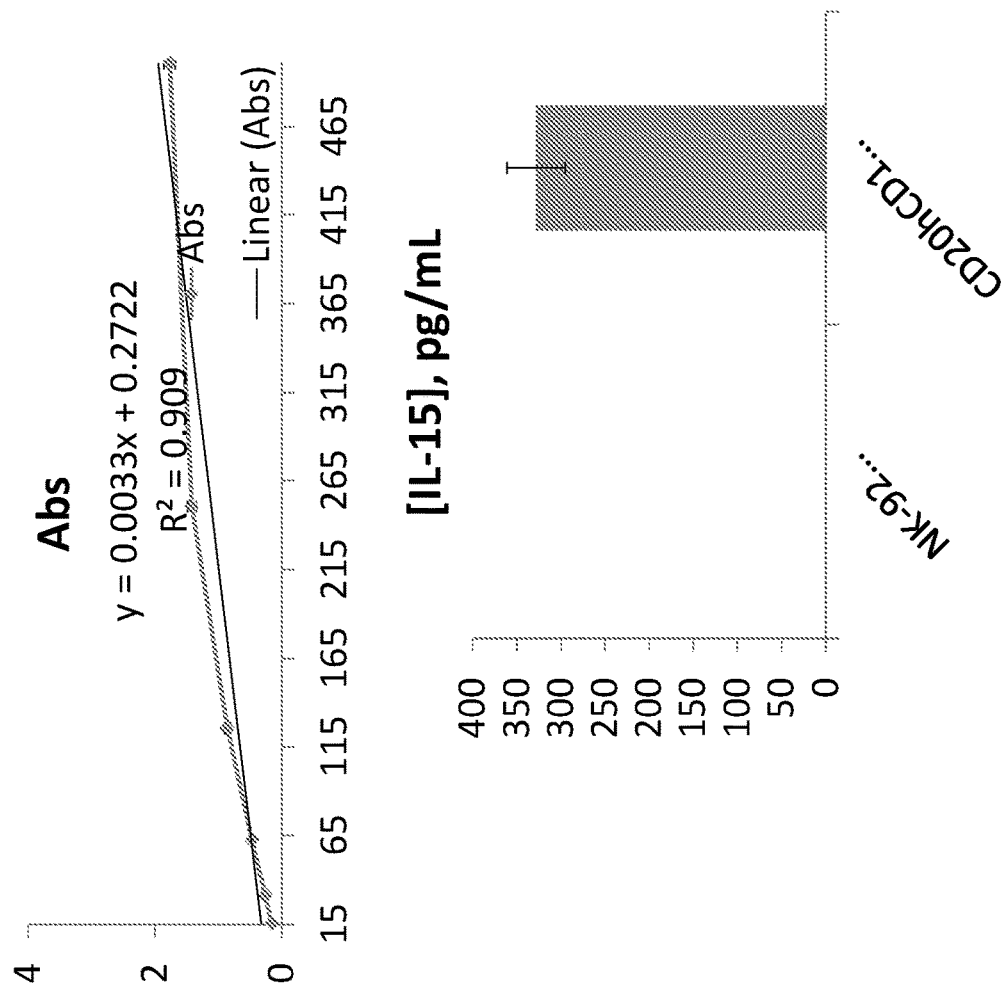

FIG. 44E. Sorted CD20h–CD19b-IL15/IL15sushi NK cells and wild-type control NK-92 cells were cultured in separate wells for 72 hours. Supernatant was collected and subjected to ELISA on 96-well plates precoated with IL-15 antibody. Following manufacturer's (Boster) directions, colorimetric results obtained on a plate reader were compared to a standard curve (A) generated with human IL-15 to determine concentration of IL-15 in the supernatants (B).

Figure 45A:
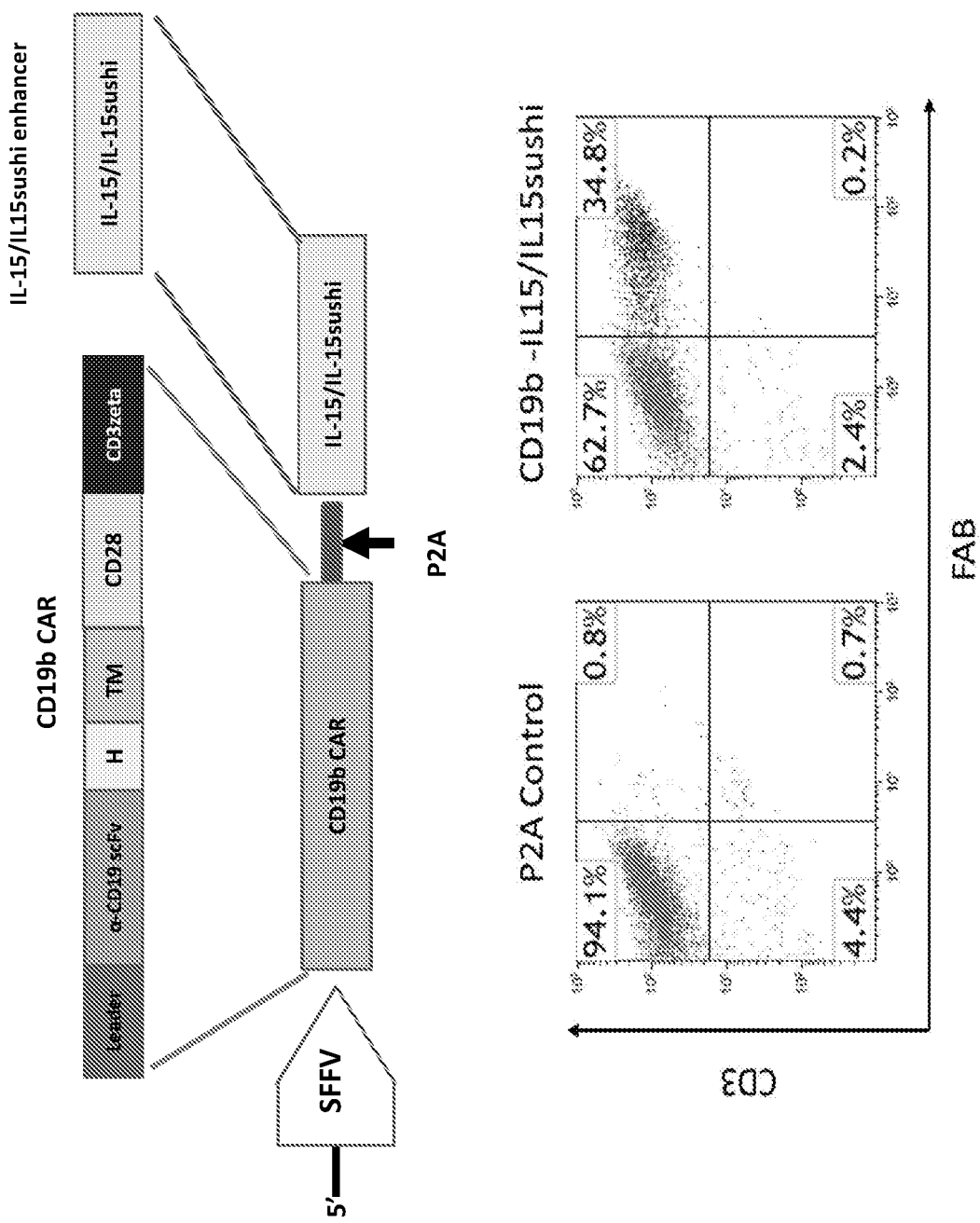

FIG. 45A. Expression was measured by FACS against control T-cells. Upper is the organization of CD19b-IL-15/IL-15sushi CAR. CD19b-IL15/IL-15sushi CAR T-cells are created by the viral transduction of patient or donor T-cells with lentiviruses expressing CD19b-IL-15/IL-15sushi CAR and the transduced T cells are able to secret IL-15/IL-15sushi fusion protein. FACS analysis shows that CD19b-IL-15/IL-15sushi CAR is able to be expressed on 35% of the T cells, (bottom) furthermore, the secreting IL-15/IL-15sushi fusion provides additional stimulation, proliferation, and potency enhancement to the CAR T cells or NK cells when compared to a standard CAR cell.

Figure 45B:
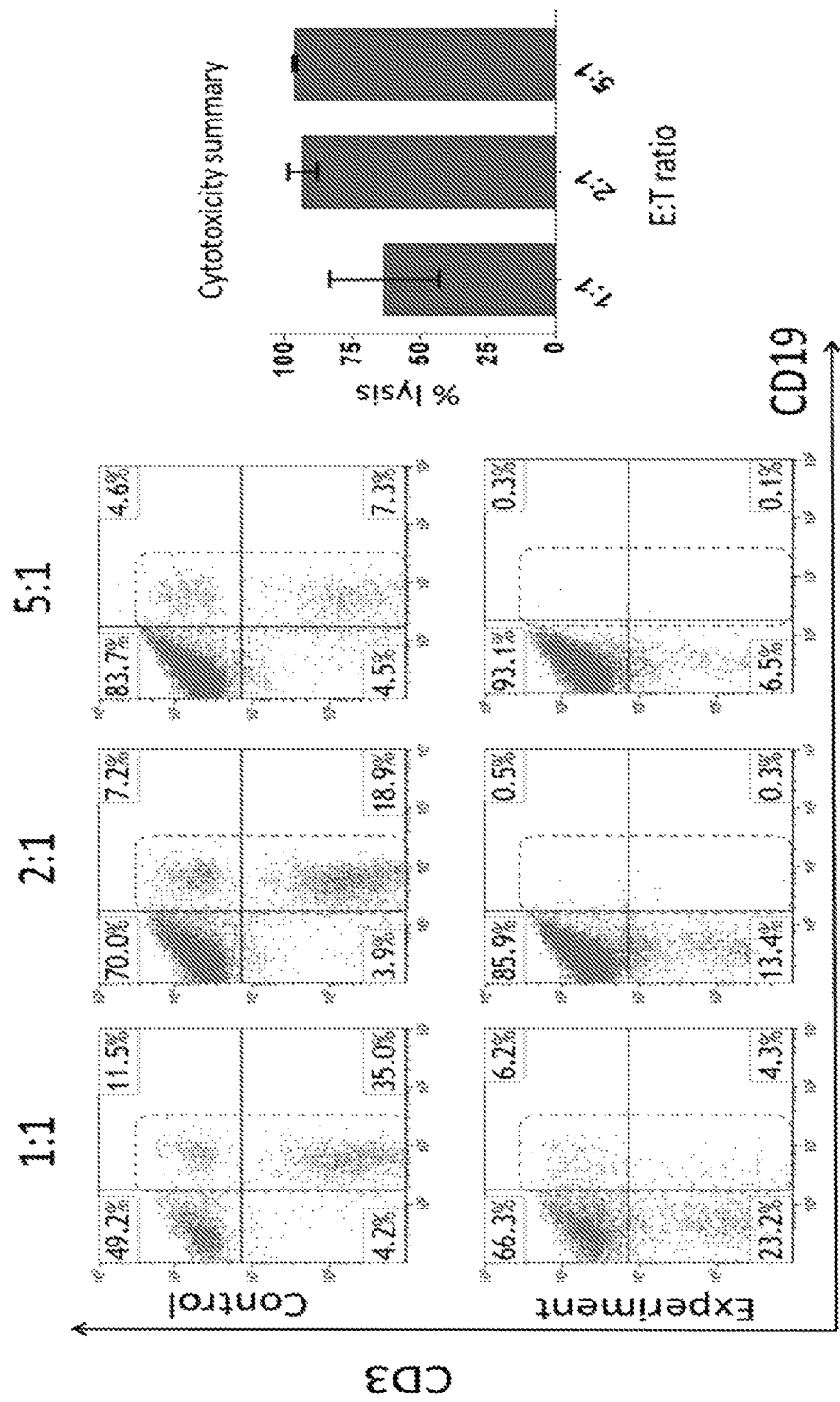

FIG. 45B: CD19b-IL15/IL15sushi CAR T-cells potently lyse CD19+Sp53 cells.

Figure 45C:
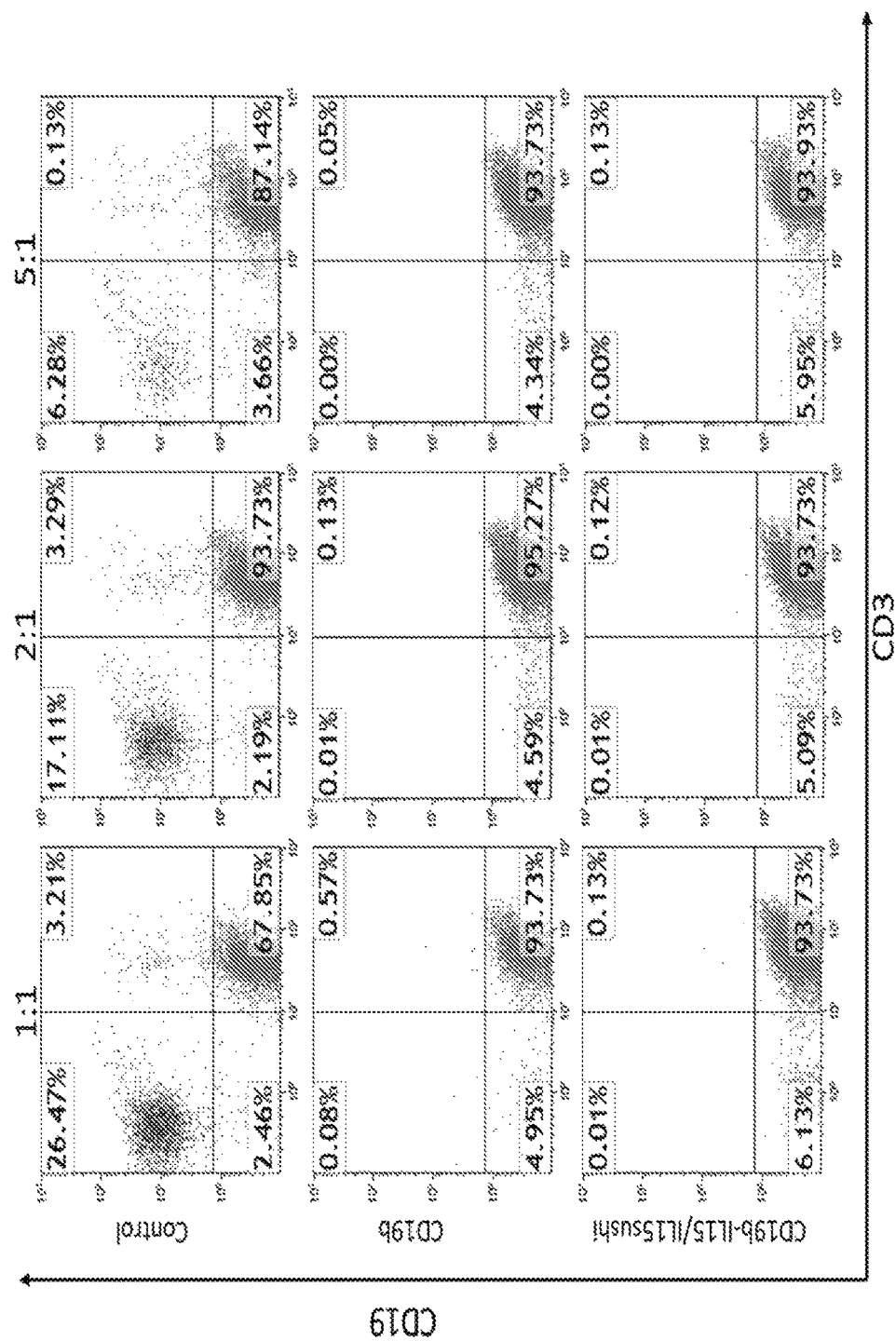

FIG. 45C: CD19b-IL-15/IL-15sushi CAR T-cells potently lyse CD19+Sp53 cells (with comparison to CD19b single CAR T).

Figure 46A:
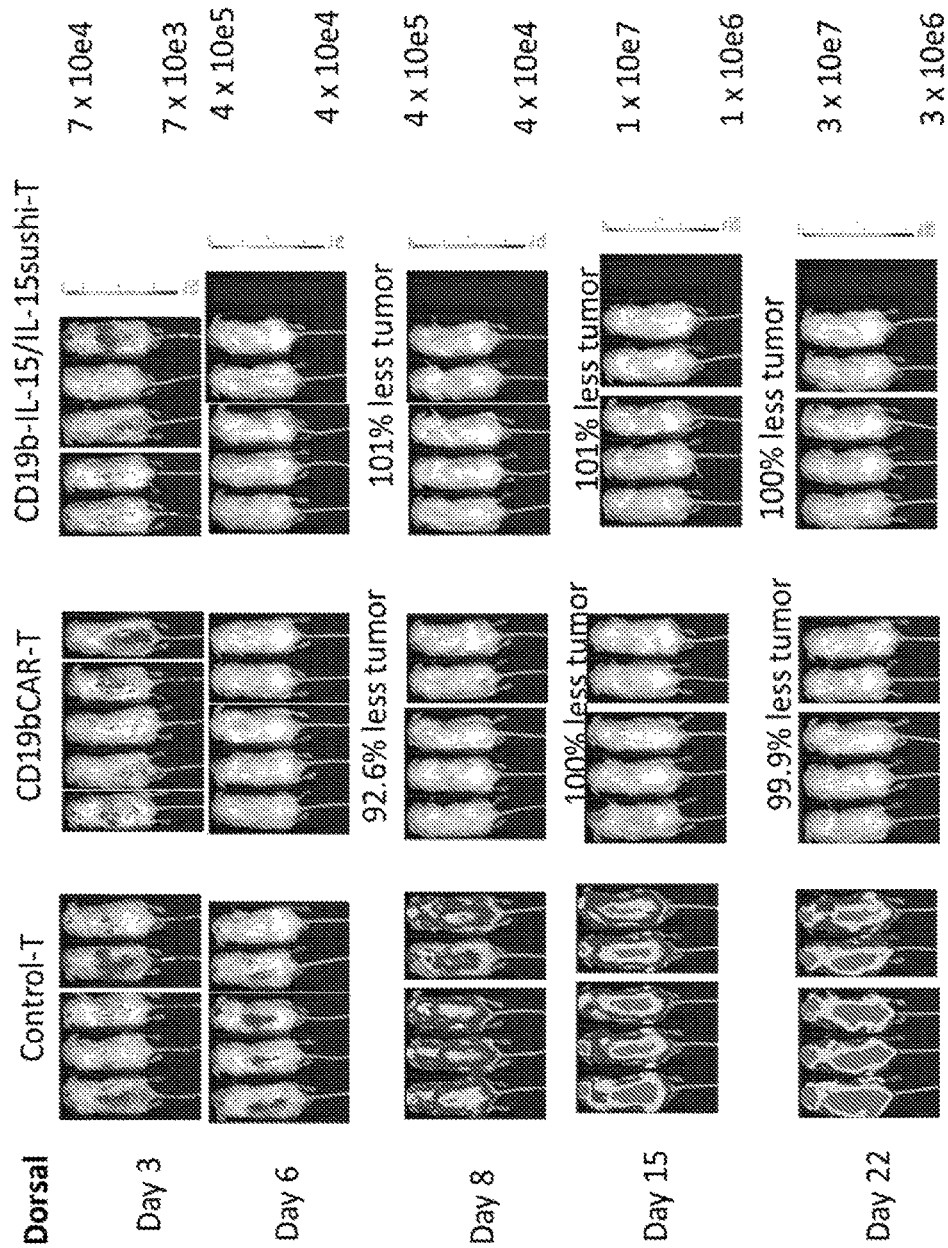

FIG. 46A—CD19 based CARs deplete Reh cells in vivo and IL-15/IL-15sushi conjugates augment anti-tumor response. Mice were injected with Reh tumor cells ($0.5 \times 10^6$ cells/mouse) expressing luciferase on Day 1. On Day 3 IVIS was conducted to assay the appearance of circulating Reh cells. On Day 4, control T-cells, CD19b CAR, and CD19b-IL15/IL-15sushi CAR T-cells were injected ($7.5 \times 10^6$ total cells/mouse) and on day 6 through 22, IVIS imaging was conducted to assay semi-quantitative assessment of tumor burden and subsequent tumor depletion and control of cell growth by T-cells. Here, both CAR T treatments demonstrated similar efficacy, with the IL-15 secreting CAR demonstrating comparable or better control of the Reh tumor growth when compared to standard CART19 cells.

Figure 46B:
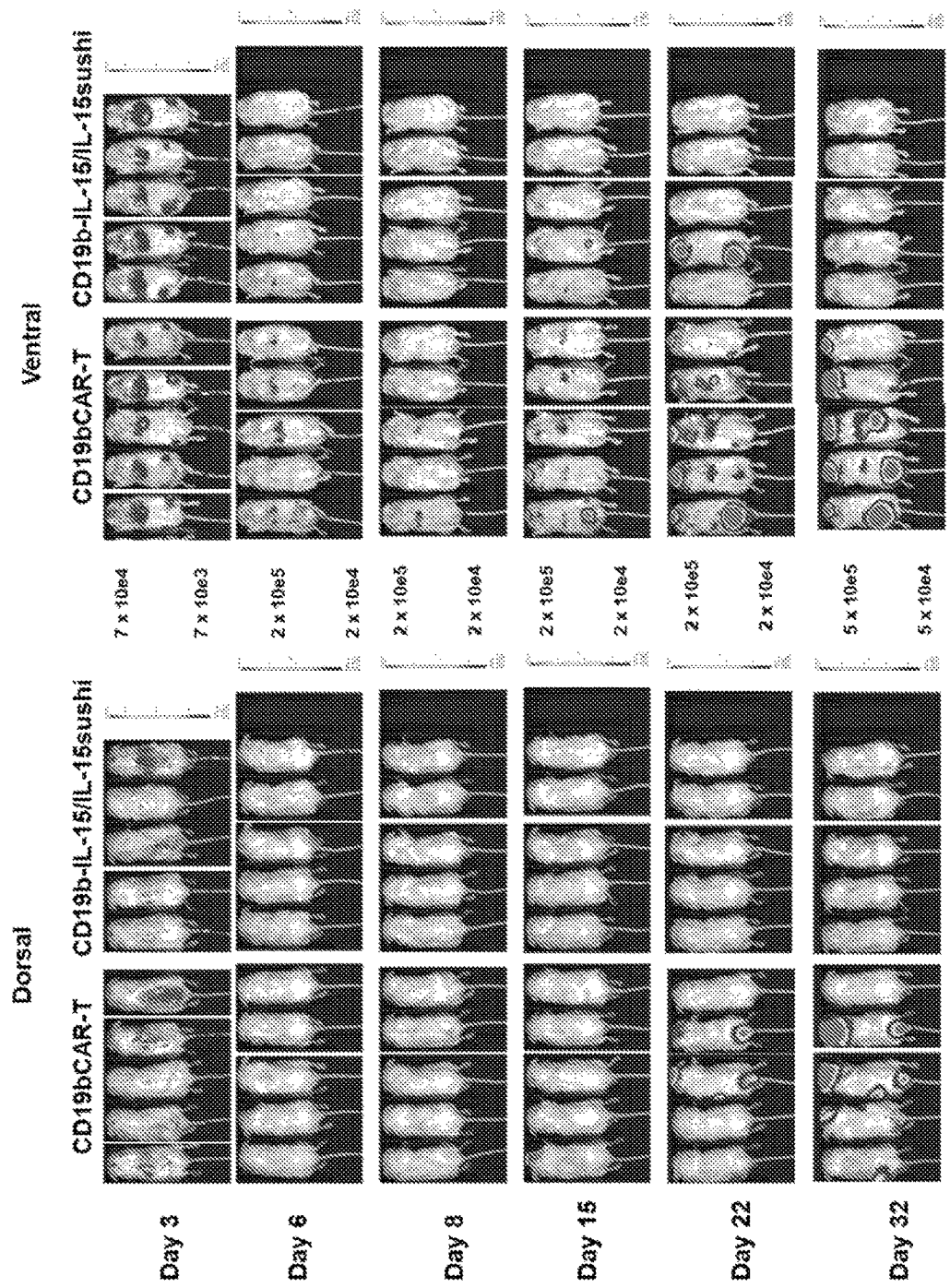

FIG. 46B—Comparison CD19b-CAR-T vs CD19b-IL-15/IL15sushi CAR-T against REH cells over long term. (TOP) Similar experimental scheme with identical IVIS methodology to above, however mice were followed until signs of tumor relapse were seen. Here, after day 30, we observed that aggressive Reh tumor relapse began to occur in standard CART19 treated mice. Clusters of tumor (indicated by red regions on the IVIS imaged mice) are seen in most CART19 mice, with a single CD19b-IL-15/IL-15sushi CART treated mice also showing tumor growth by day 22. However, after day 30, all CART19 mice show signs of severe tumor relapse, while CD19b-IL-15/IL-15sushi CART treated mice show no sign of tumor. Even the relapsed mouse on day 22 was absolved of its tumor by day 32, signifying that CD19b-IL-15/IL-15sushi CART cells were still in effective circulation.

Figure 46C:
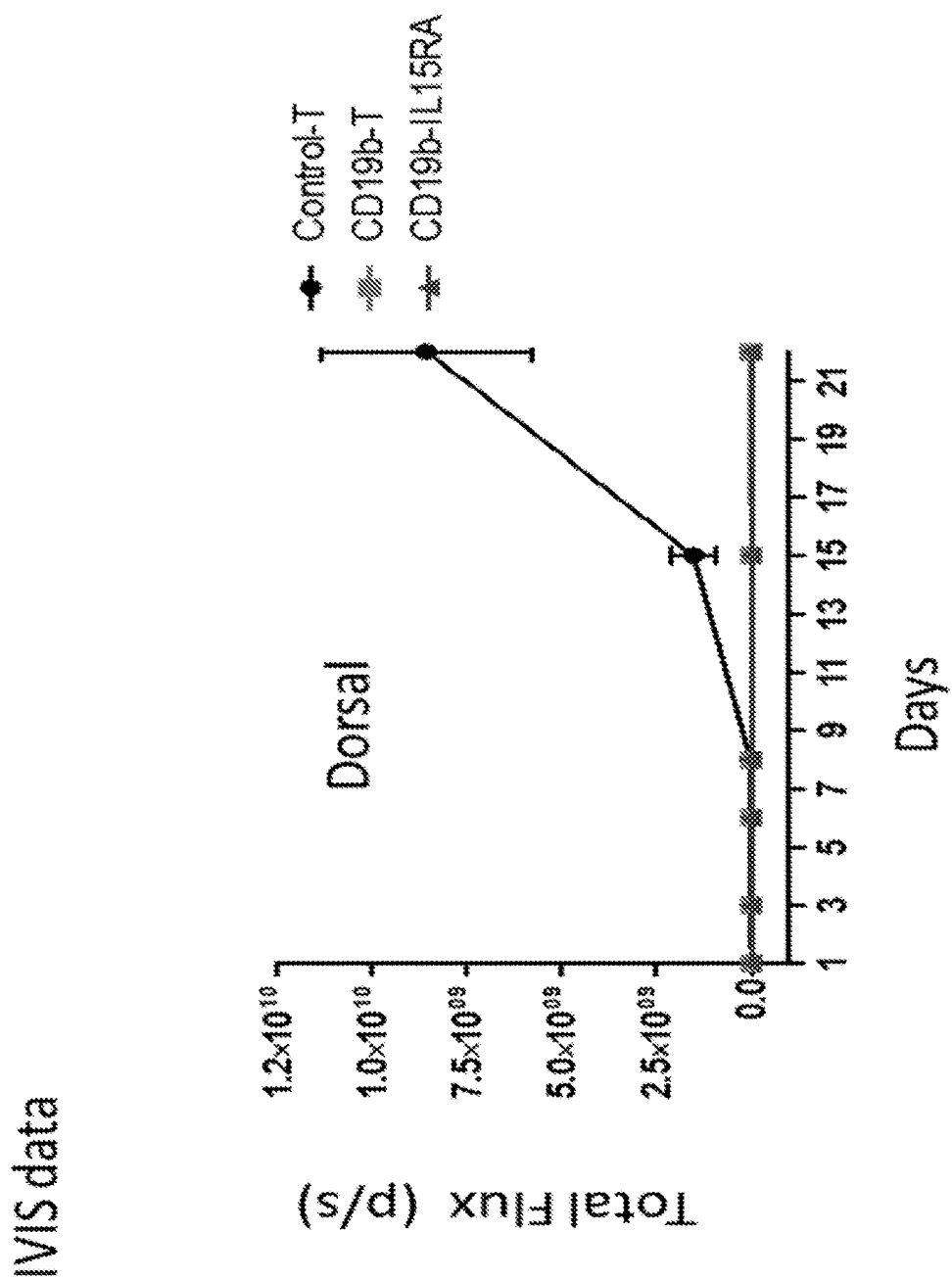

FIG. 46C. Line graph summarizing IVIS trend values estimating tumor growth over time for each treatment cohort. Past day 30, the tumor burden for the standard CD19b CAR (CART19) treated mice rises precipitously resulting in highly significant increases in tumor burden compared to the CD19b-IL-15/IL-15sushi CART treatment group which remained largely tumor free. Values are displayed for both views of the mice (dorsal image acquisition views).

Figure 46D:
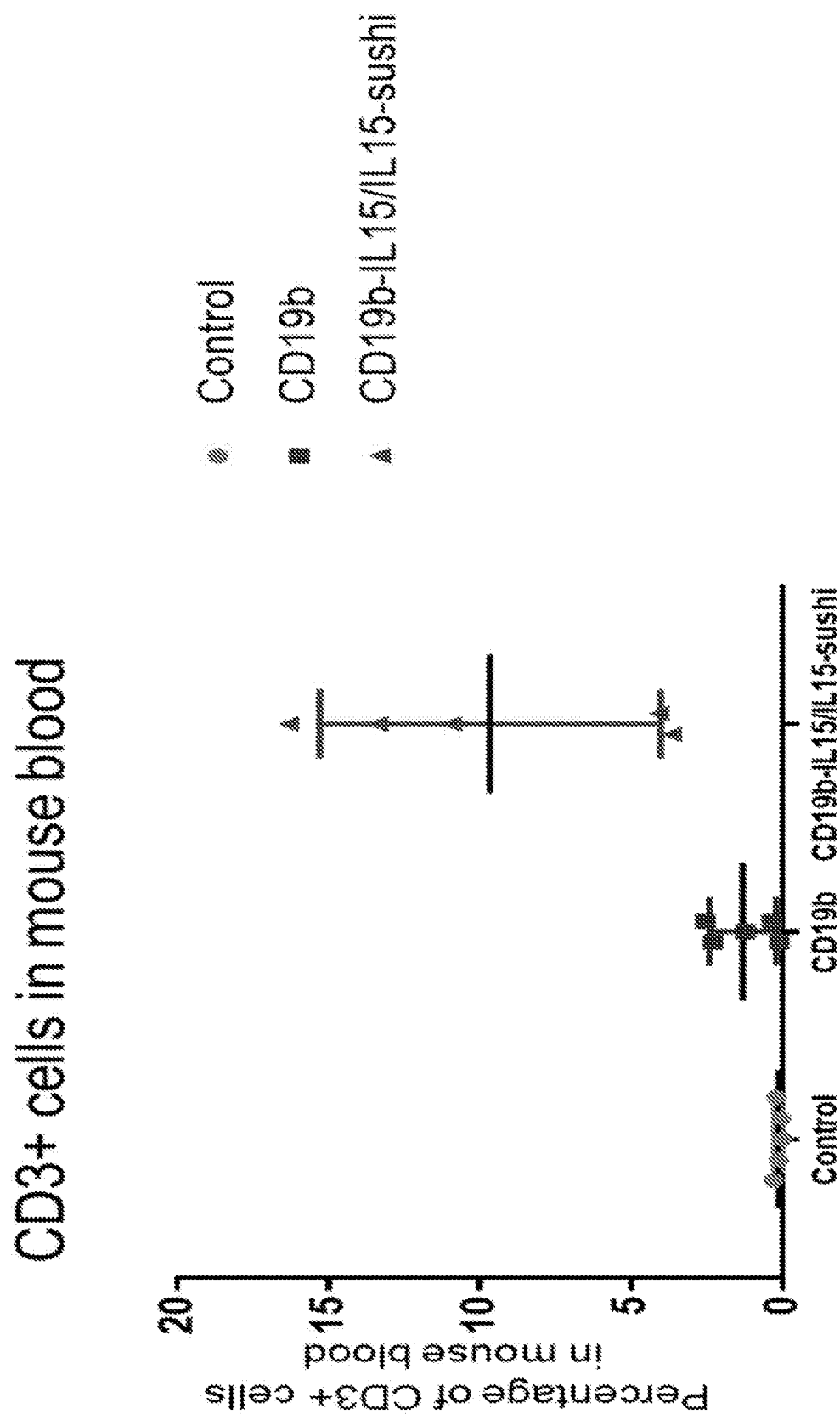

FIG. 46D—Overall summary of mice blood data-summarized persistence of T cells in mice. The overall persistence of T cells in mouse blood from the model in FIG. 3A-1 was assayed at survival endpoints and screened by flow cytometry using CD3 antibody for bulk T cell populations. To further dissect the persistency results of the CD19b-IL-15/IL-15sushi armored CAR, the collection of mouse blood is necessary to reveal the presence of durability of the engrafted human cells. Overall, we find by flow cytometry analysis that there is a higher average count of T cells in the IL-15/il-15sushi secreting CAR cohorts when compared to the standard CART19 groups. Control group T cells remain at baseline as expected due to minimal stimulation from circulating in vivo tumor.

Figure 46E:
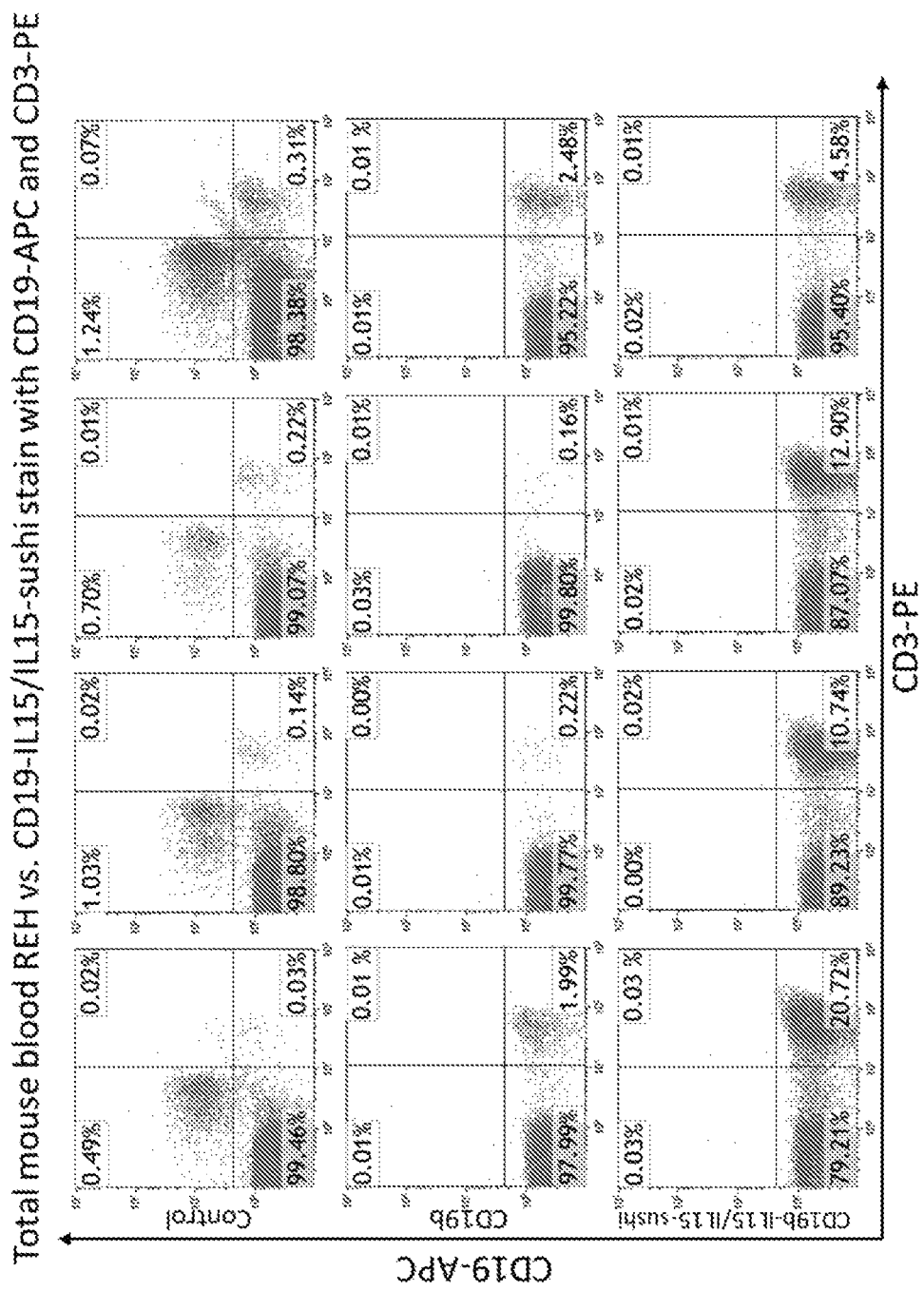

FIG. 46E—Mice blood data (individual). Representative mice from FIG. 3A-1 was assayed by flow cytometry at survival endpoints to screen for remaining tumor and T cell populations, revealed by CD19+ and CD3+ expressions respectively. These flow cytometry plots further analyze the conditions of each mouse at their survival endpoints revealing that significant tumor populations and diminished T cell counts are characteristic of control and most CART19 mice. Significant counts of T cells and few or absence tumor cells are characteristic of the CD19b-IL-15/IL-15sushi CAR cohort mice.

Figure 47A:
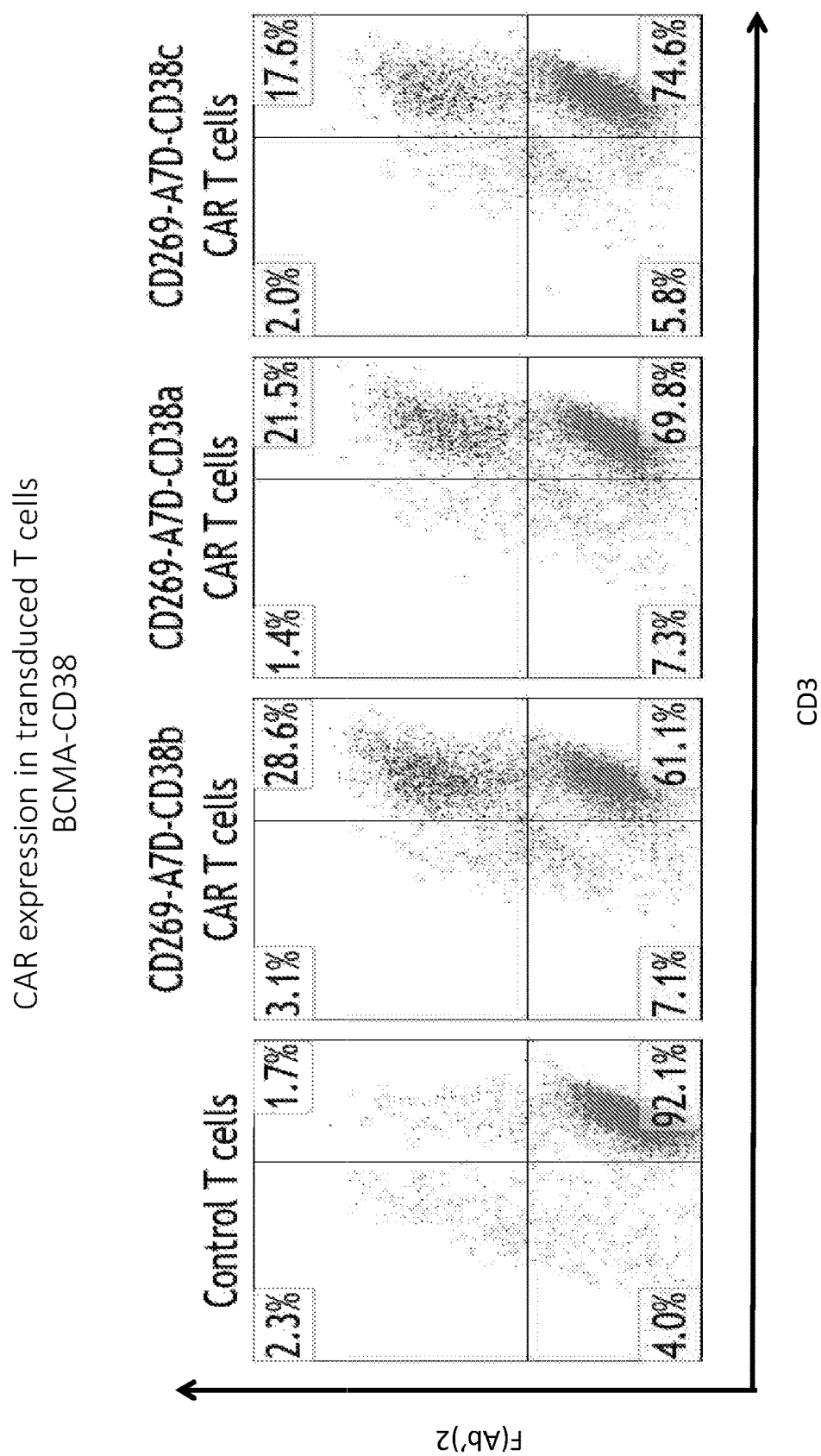

FIG. 47A. Expression of CD269-A7D-CD38 CAR T cells. Buffy coat cells were activated 3 days with anti-CD3 antibody. Cells were transduced with either control vector (left), CD269-A7D-CD38a, CD269-A7D-CD38b, or CD269-A7D-CD38c CAR (right) lentiviral supernatant. After 3 days of incubation, cells were harvested and labeled for flow cytometry.

Figure 47B:
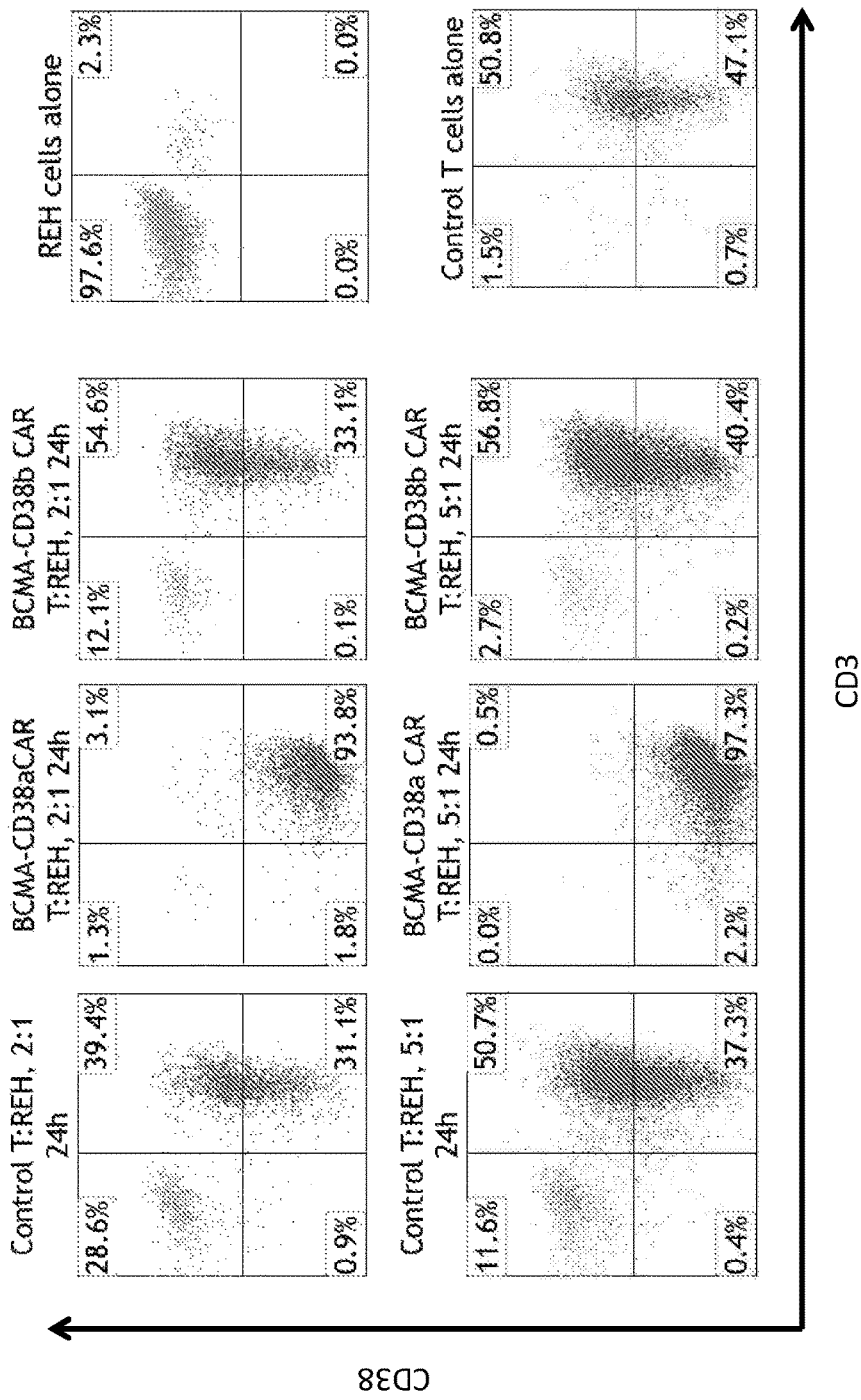

FIG. 47B. CD269-A7D-CD38 CAR T cells specifically lyse the REH tumor cell line, which expresses CD38 surface antigen, in co-culture assays. Co-culture experiments were performed at an effector to target ratio of 2:1 (top row) or 5:1 (bottom row) for 24 hours and were directly analyzed by flow cytometry for CD38 and CD3. Each assay consists of REH target cells incubated with control T cells (left panels), CD269-A7D-CD38a (center left panels) or CD269-A7D-CD38a CAR T cells (center-right panels), or cells alone (far right).

Figure 47C:
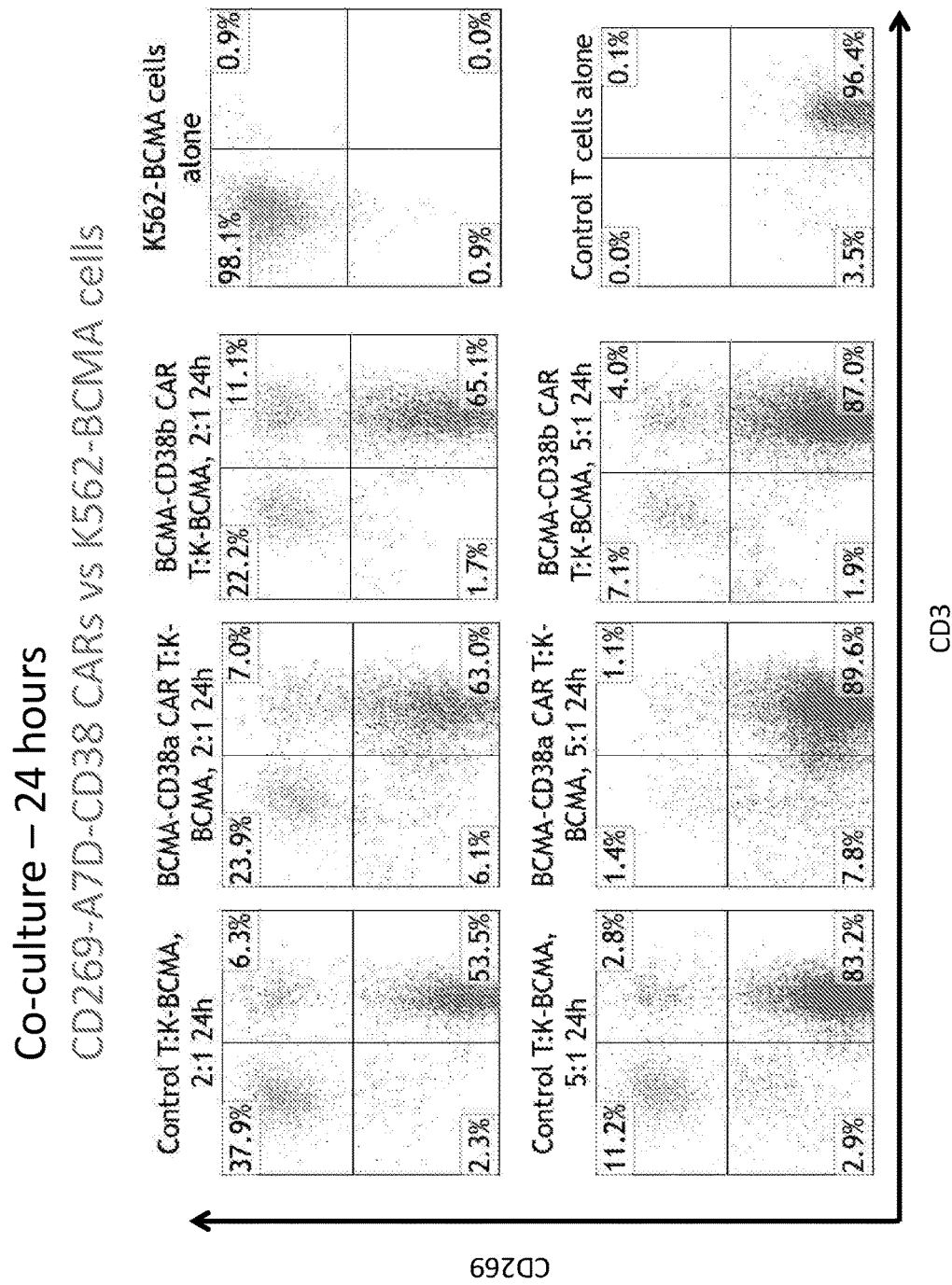

FIG. 47C. CD269-A7D-CD38 CAR T cells specifically lyse the K562 tumor cell line, which is synthetically expressing CD269 (BCMA) surface antigen, in co-culture assays. Co-culture experiments were performed at an effector to target ratio of 2:1 (top row) or 5:1 (bottom row) for 24 hours and were directly analyzed by flow cytometry for CD269 and CD3. Each assay consists of K562-BCMA target cells incubated with control T cells (left panels), CD269-A7D-CD38b (center left panels) or CD269-A7D-CD38a CAR T cells (center-right panels), or cells alone (far right).

Figure 48A:
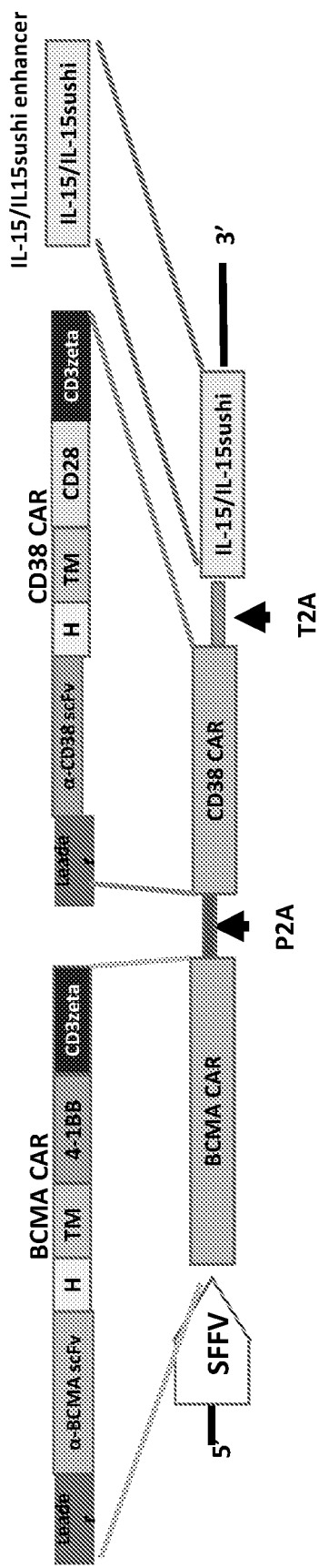

FIG. 48A. A schematic representation of cCAR-T with IL-15/IL15sushi enhancer construct. The construct comprises a SFFV promoter driving the expression of multiple modular units of CARs, and IL-15/IL-15sushi linked by P2A and T2A peptide respectively. Upon cleavage of the linker, the cCARs split and engage upon targets expressing BCMA and/or CD38 and a secreting enhancer fusion of IL-15/IL-15sushi. As a novel cCAR construct, the activation domains of the construct may include, but is not limited to, 4-1BB or CD28 on the BCMA CAR segment and a CD28 or 4-1BB region on the CD38 CAR segment. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7, and IL-12. The secreting enhancer, such as IL-15/IL15sushi enhances CAR T or NK T or NK cell expansion and persistency. The soluble IL-15/IL-15sushi fusion are stable and functions as an unexpected and powerful immunomodulatory for CAR T/NK cells or NK T cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects a by reprogramming body's immune system to fight cancers.

Figure 48B:
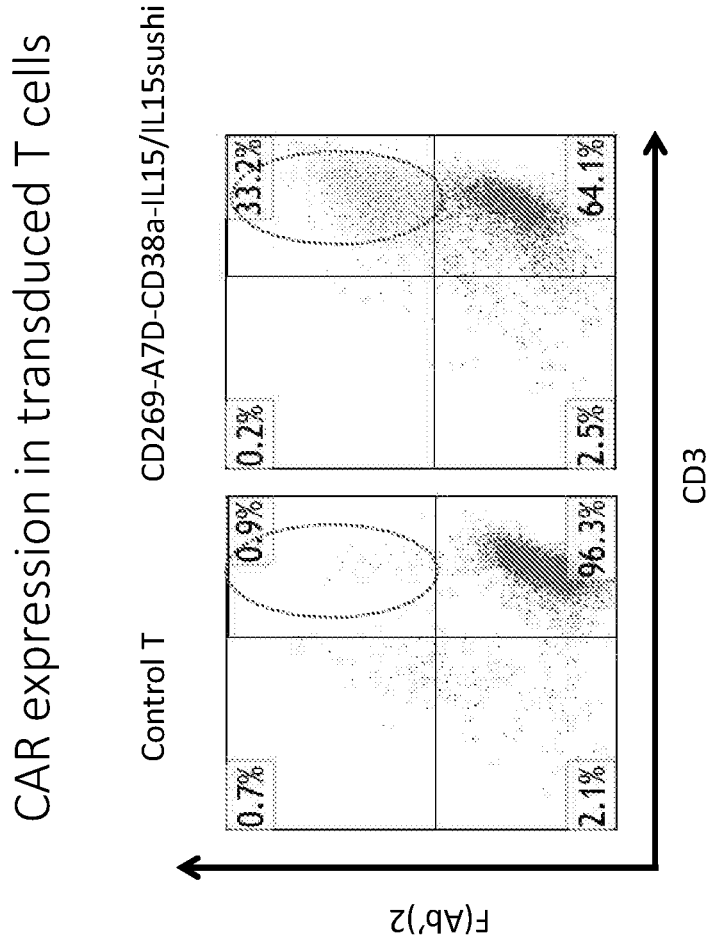

FIG. 48B. Expression of CD269-A7D-CD38a-IL15/IL15sushi CAR T cells. Human peripheral blood buffy coat cells were activated 3 days with anti-human CD3 antibody. Cells were transduced with either control vector (left), CD269-A7D-CD38a-IL15/IL15sushi CAR (right) lentiviral supernatant. After 4 days of incubation, cells were harvested and labeled for flow cytometry with goat anti-human F(Ab')2 and mouse anti-human CD3 antibodies. CAR T cells circled.

Figure 48C:
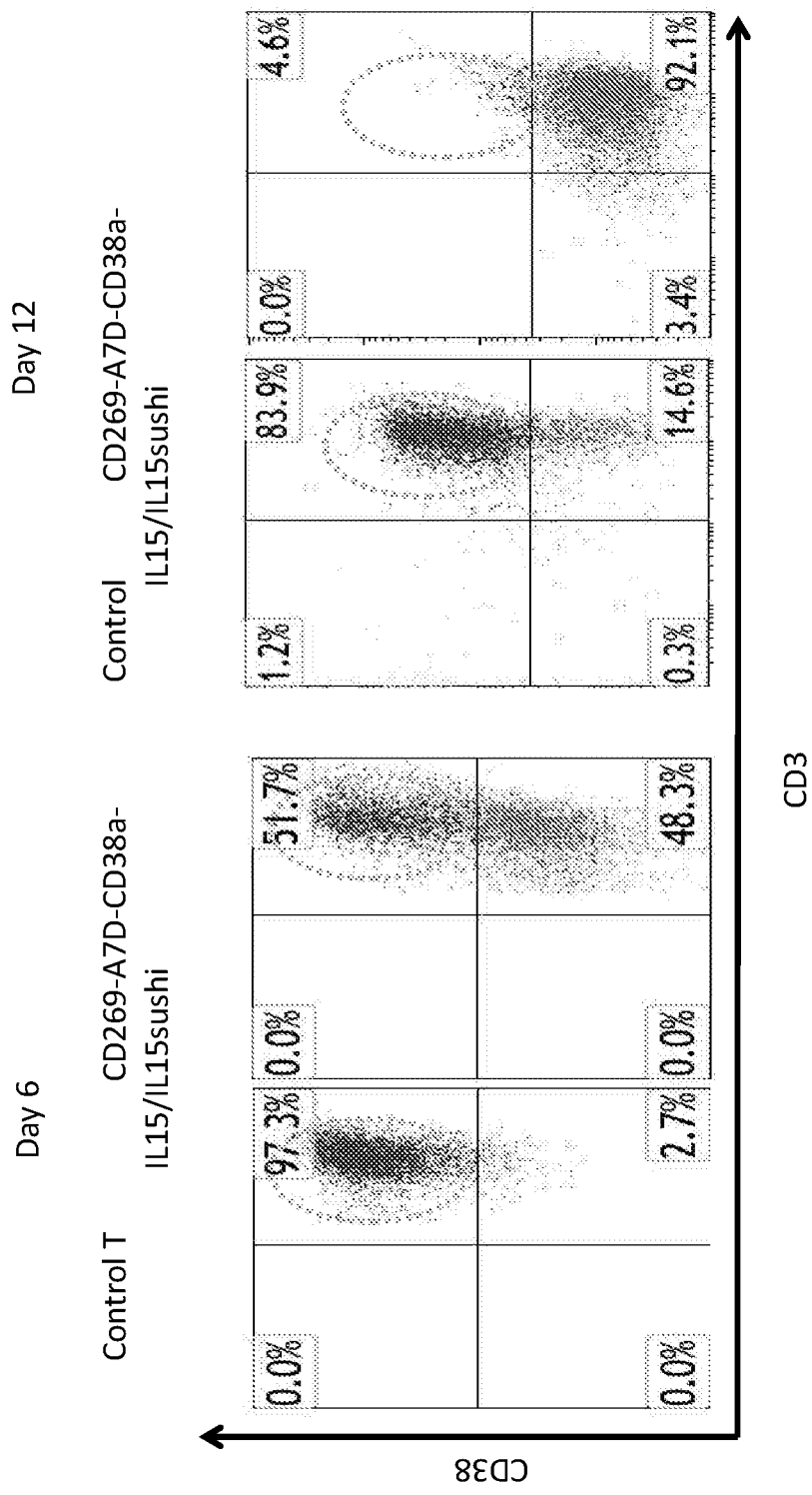

FIG. 48C. CD269-A7D-CD38a-IL15/IL15sushi CAR T cells lyse CD38+ T cells. Human peripheral blood buffy coat cells were activated 3 days with anti-human CD3 antibody. Cells were transduced with either control vector (left), CD269-A7D-CD38a-IL15/IL15sushi CAR (right) lentiviral supernatant. After 6 days (two left graphs) and 12 days (two right graphs) of incubation, cells were harvested and labeled for flow cytometry with mouse anti-human CD3 and CD38 antibodies. CD38+ T cells are circled.

Figure 48D:
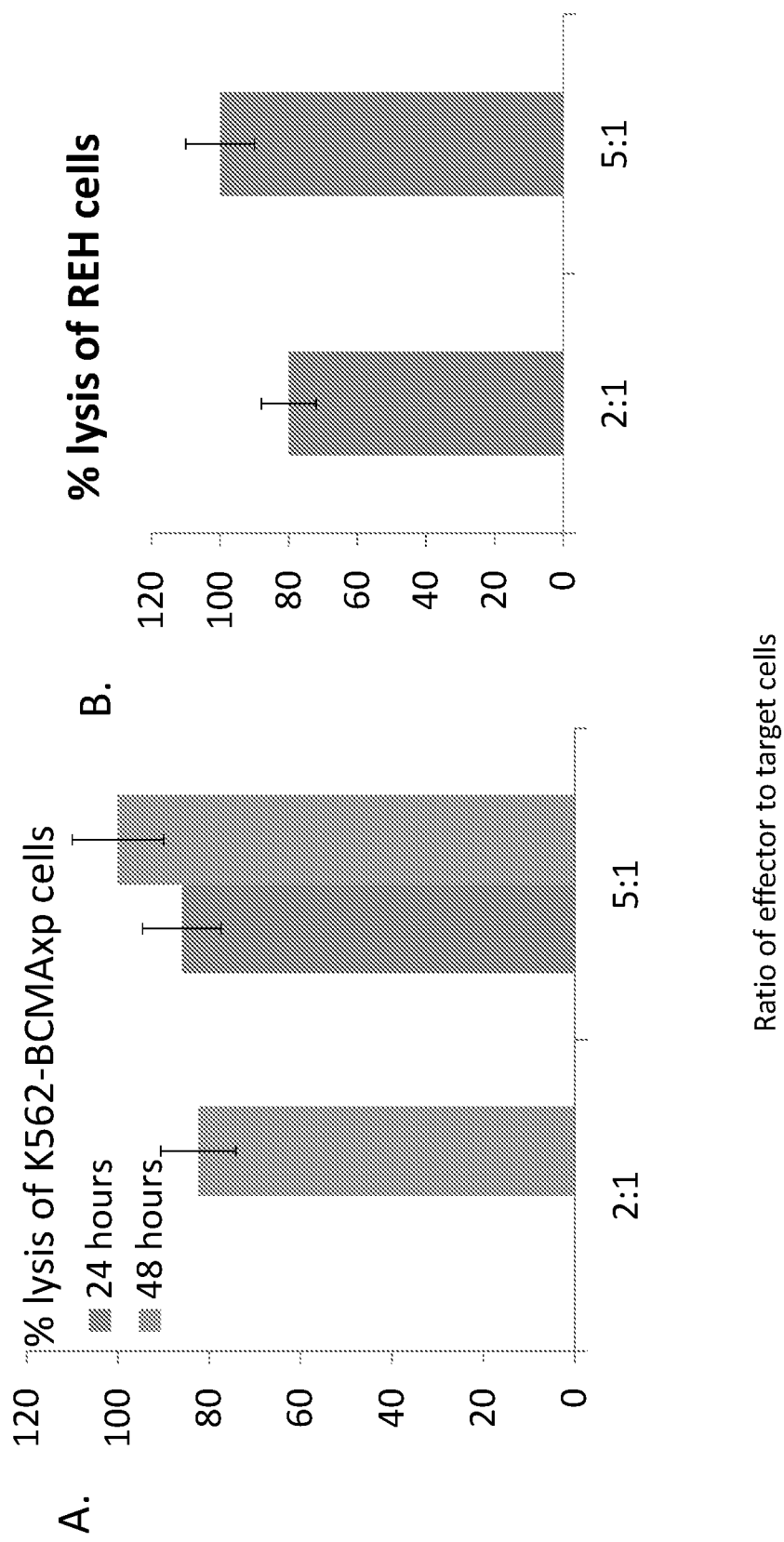

FIG. 48D. CD269-A7D-CD38a-IL15/IL15sushi CAR T cells specifically lyse the K562 tumor cell line, which is synthetically expressing BCMA (CD269) surface antigen, and wild-type REH cells, which naturally express CD38 antigen, in co-culture assays. Each assay consisted of either K562-BCMAxp (left graph) or REH target cells (right graph) co-cultured with control T cells or CD269-A7D-CD38a-IL15/IL15sushi CART cells at 2:1 and 5:1 effector:target cell ratios. Co-culture experiments were performed for 24 and 48 hours and were directly analyzed by flow cytometry for anti-human CD3 and either CD269 or CD38.

Figure 48E:
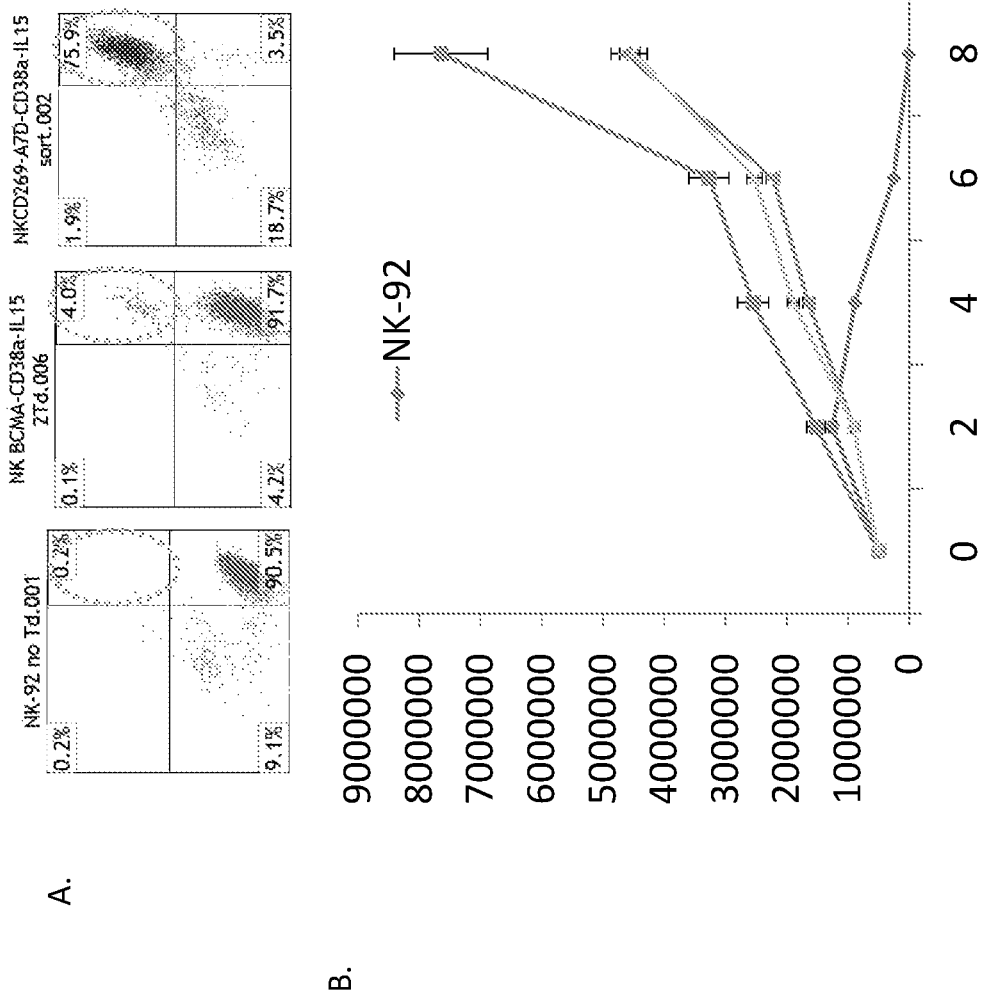

FIG. 48E. CD269-A7D-CD38a-IL15/IL15sushi NK cells express functional IL15. NK-92 cell line was transduced with lentiviral vector containing CD269-A7D-CD38a-IL15/IL15sushi CAR. (A) Cells were sorted on BD FACS Aria to select NK cells positive for the F(Ab')2 phenotype. NK CAR cells are circled. (B) CD269-A7D-CD38a-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted (B), and the volume increased to yield a concentration of approximately 0.5×10e6 cells/mL. This process was repeated on Days 4, 6, and 8.

Figure 48F:
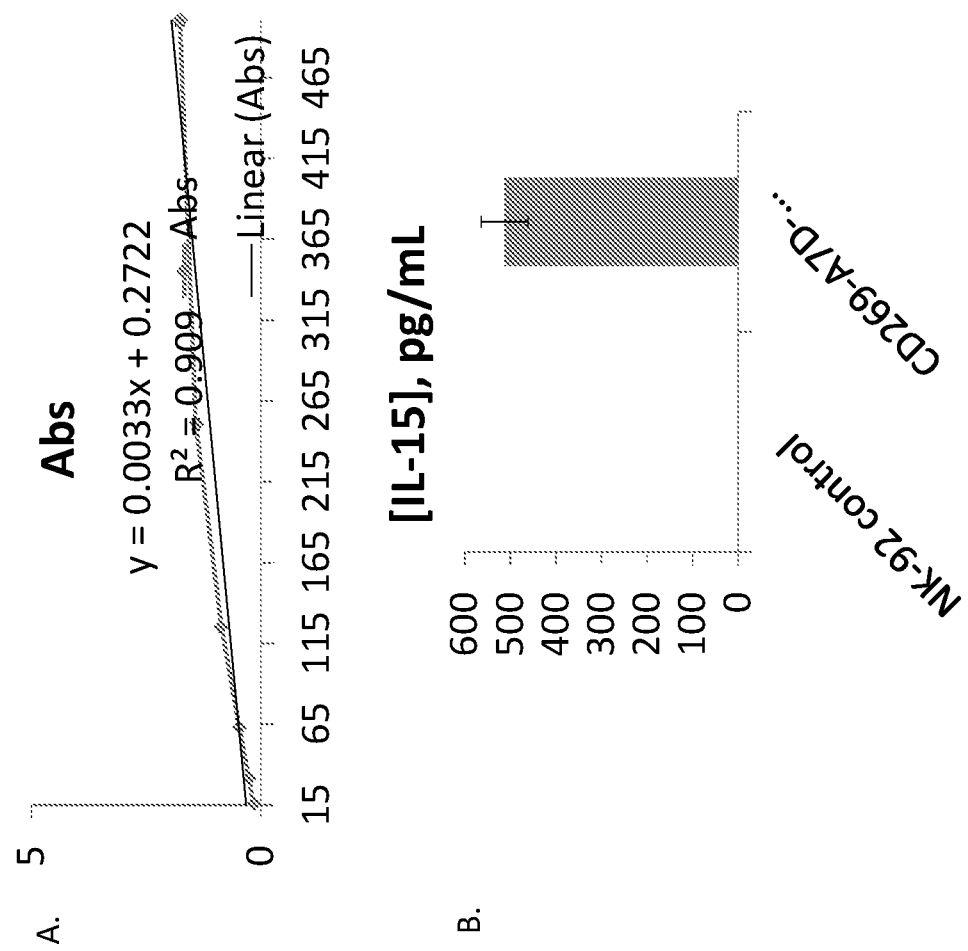

FIG. 48F. Sorted CD269-A7D-CD38a-IL15/IL15sushi NK cells and wild-type control NK-92 cells were cultured in separate wells for 72 hours. Supernatant was collected and subjected to ELISA on 96-well plates precoated with IL-15 antibody. Following manufacturer's (Boster) directions, colorimetric results obtained on a plate reader were compared to a standard curve (A) generated with human IL-15 to determine concentration of IL-15 in the supernatants (B).

Figure 49A:
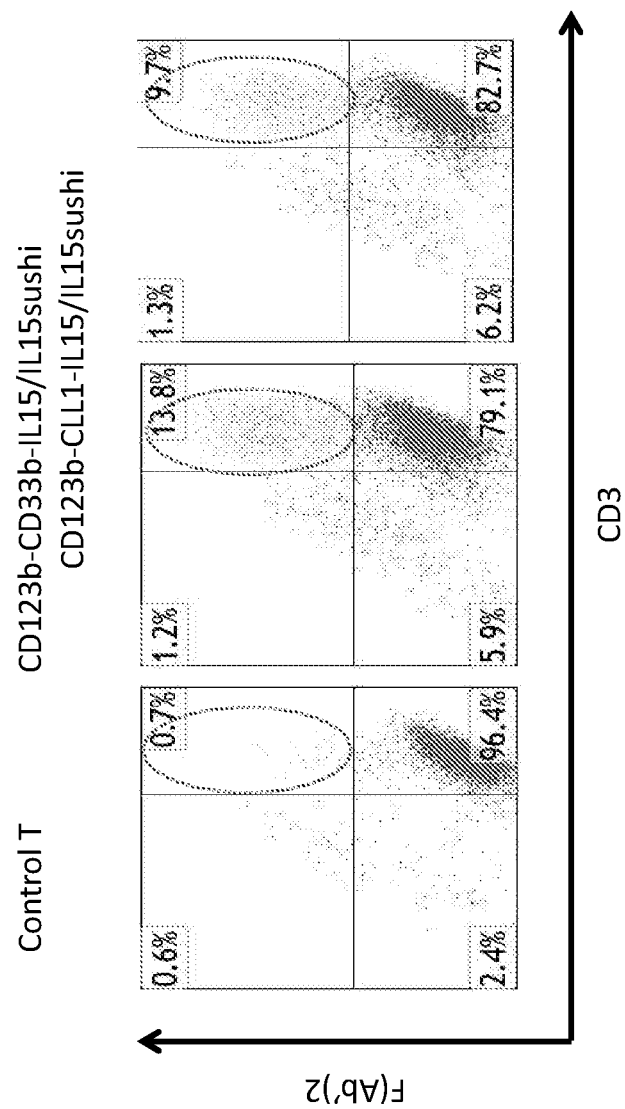

FIG. 49A. Expression of CD123b–CD33b-IL15/IL15sushi and CD123b-CLL1-IL15/IL15sushi CAR T cells. Human peripheral blood buffy coat cells were activated 3 days with anti-human CD3 antibody. Cells were transduced with either control vector (left), CD123b–CD33b-IL15/IL15sushi (center) or CD123b-CLL1-IL15/IL15sushi CAR (right) lentiviral supernatant. After 4 days of incubation, cells were harvested and labeled for flow cytometry with goat anti-human F(Ab')2 and mouse anti-human CD3 antibodies. CAR T cells are circled.

Figure 49B:
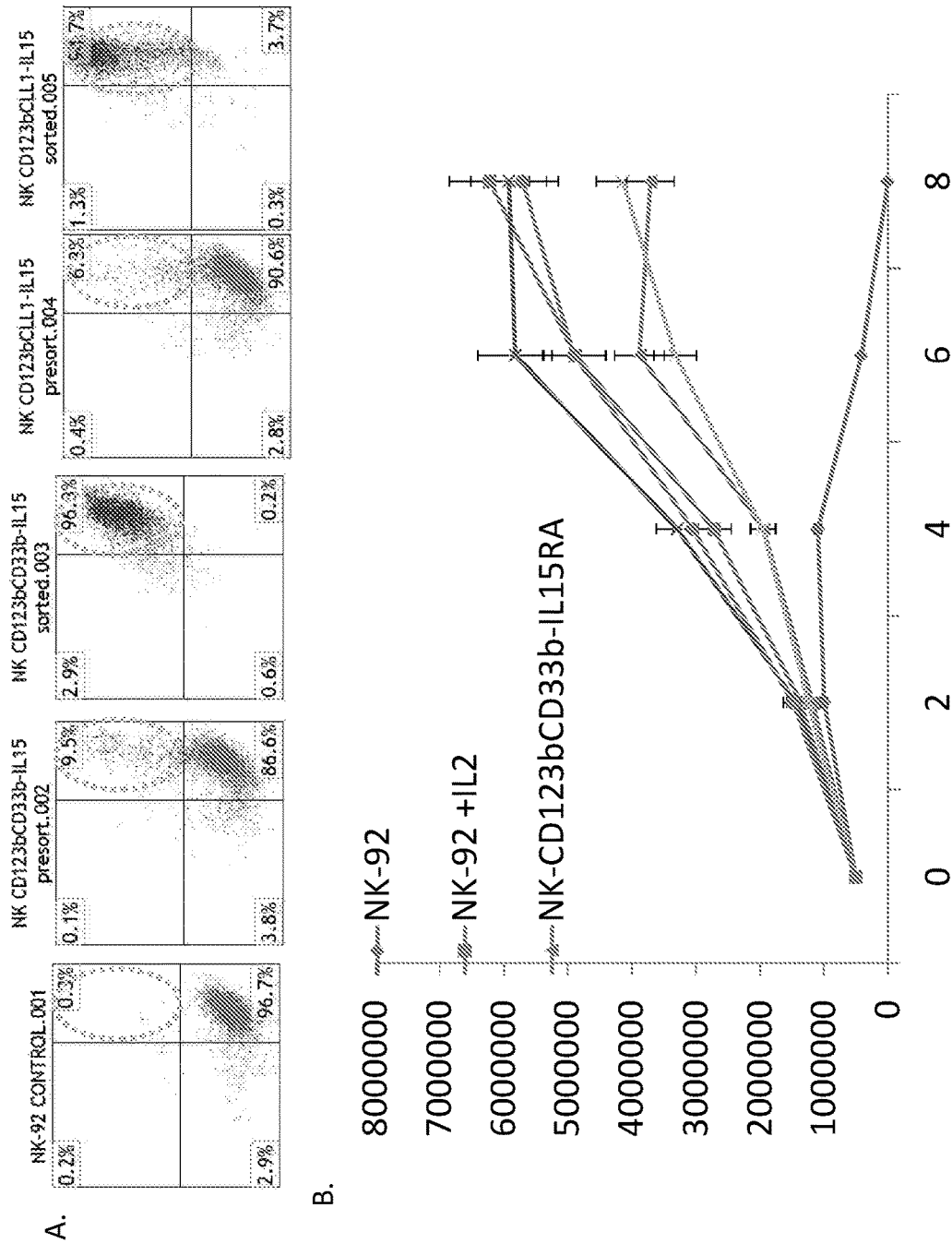

FIG. 49B. CD123b–CD33b-IL15/IL15sushi and CD123b-CLL1-IL15/IL15sushi NK cells express functional IL15. NK-92 cell line was transduced with lentiviral vector containing CD123b–CD33b-IL15/IL15sushi or CD123b-CLL1-IL15/IL15sushi CAR. (A) Cells were sorted on BD FACS Aria to select NK cells positive for the F(Ab')2 phenotype. NK CAR cells are circled. (B) CD123b–CD33b-IL15/IL15sushi and CD123b-CLL1-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted (B), and the volume increased to yield a concentration of approximately 0.5×10e6 cells/mL. This process was repeated on Days 4, 6, and 8.

Figure 49C:
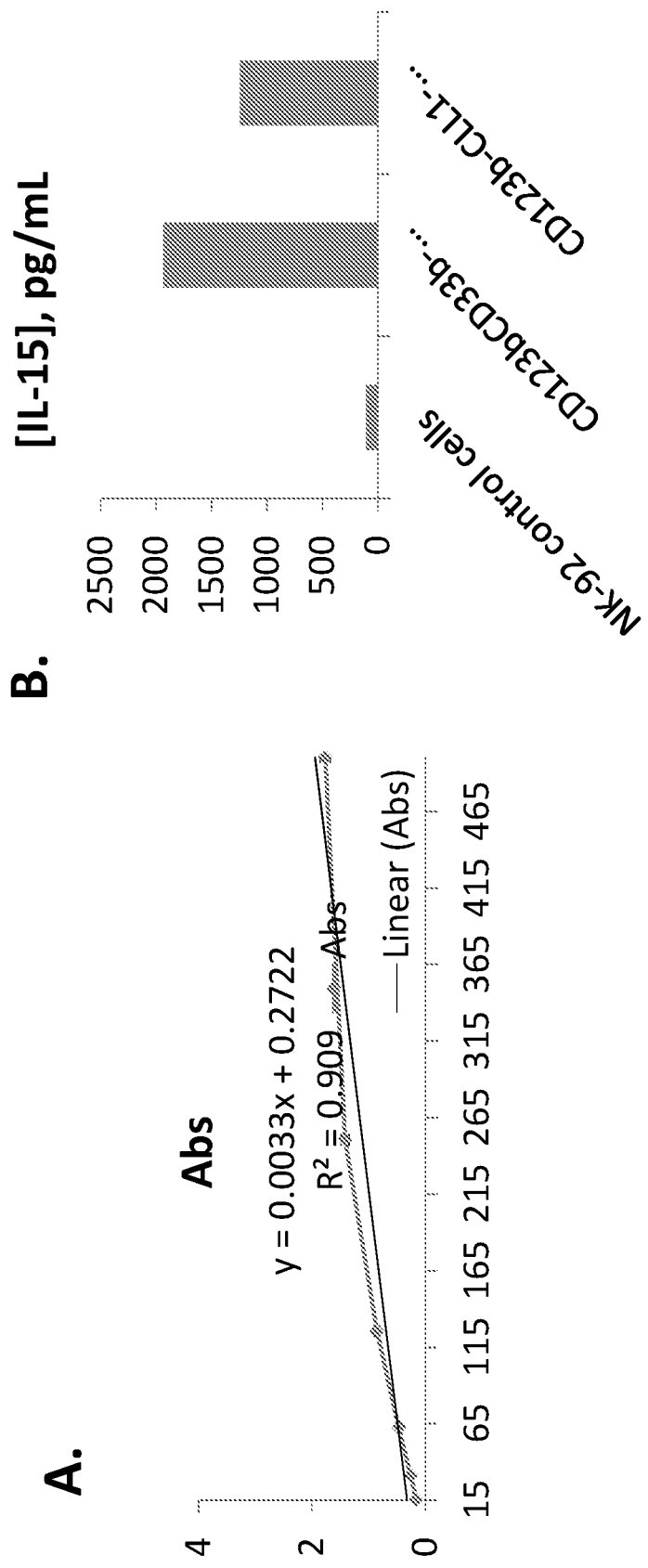

FIG. 49C. Sorted CD123b–CD33b-IL15/IL15sushi and CD123b-CLL1-IL15/IL15sushi NK cells and wild-type control NK-92 cells were cultured in separate wells for 72 hours. Supernatant was collected and subjected to ELISA on 96-well plates precoated with IL-15 antibody. Following manufacturer's (Boster) directions, colorimetric results obtained on a plate reader were compared to a standard curve (A) generated with human IL-15 to determine concentration of IL-15 in the supernatants (B).

Figure 50A:
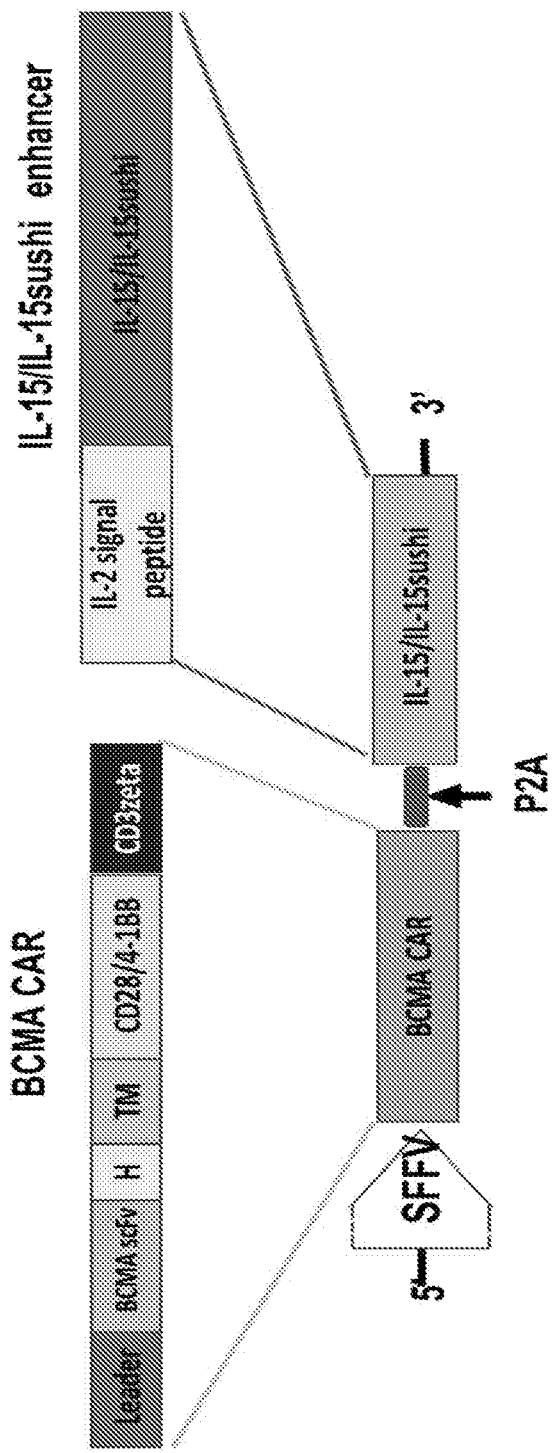

FIG. 50A. A schematic representation of anti-BCMA CAR with IL-15/IL15sushi enhancer construct (BCMA-IL-15/IL15sushi, also called CD269-A7D-IL-15/IL-15sushi). The construct comprises a SFFV promoter driving the expression of anti-BCMA CAR, and IL-15/IL-15sushi linked by P2A or T2A peptide respectively. Upon cleavage of the linker, the CAR split and engage upon targets expressing BCMA and a secreting enhancer fusion of IL-15/IL-15sushi. As a novel CAR construct, the activation domains of the construct may include, but is not limited to, CD28 or 4-1BB on the anti-BCMA CAR segment. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7 and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK or NK T cell persistency, stimulate tumor infiltrate lymphocyte proliferation, and anti-tumor activity. The soluble IL-15/IL-15sushi fusion provides anti-tumor vaccine-like effects a by reprogramming body's immune system particularly NK cells to fight cancers.

Figure 50B:
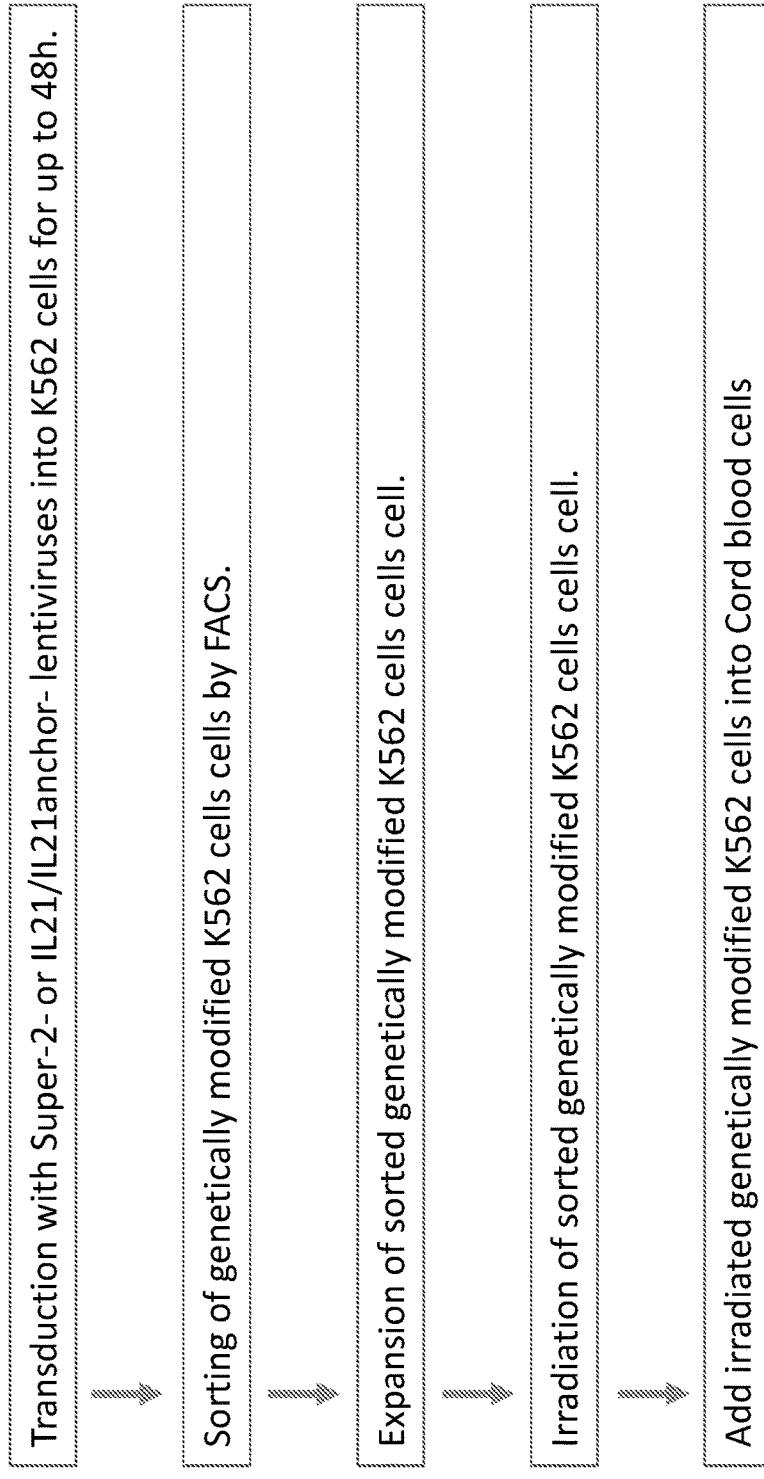

FIG. 50B. Steps for generation and preparation of irradiated genetically modified K562 cells as feeder cells for primary NK cell expansion.

Figure 50C:
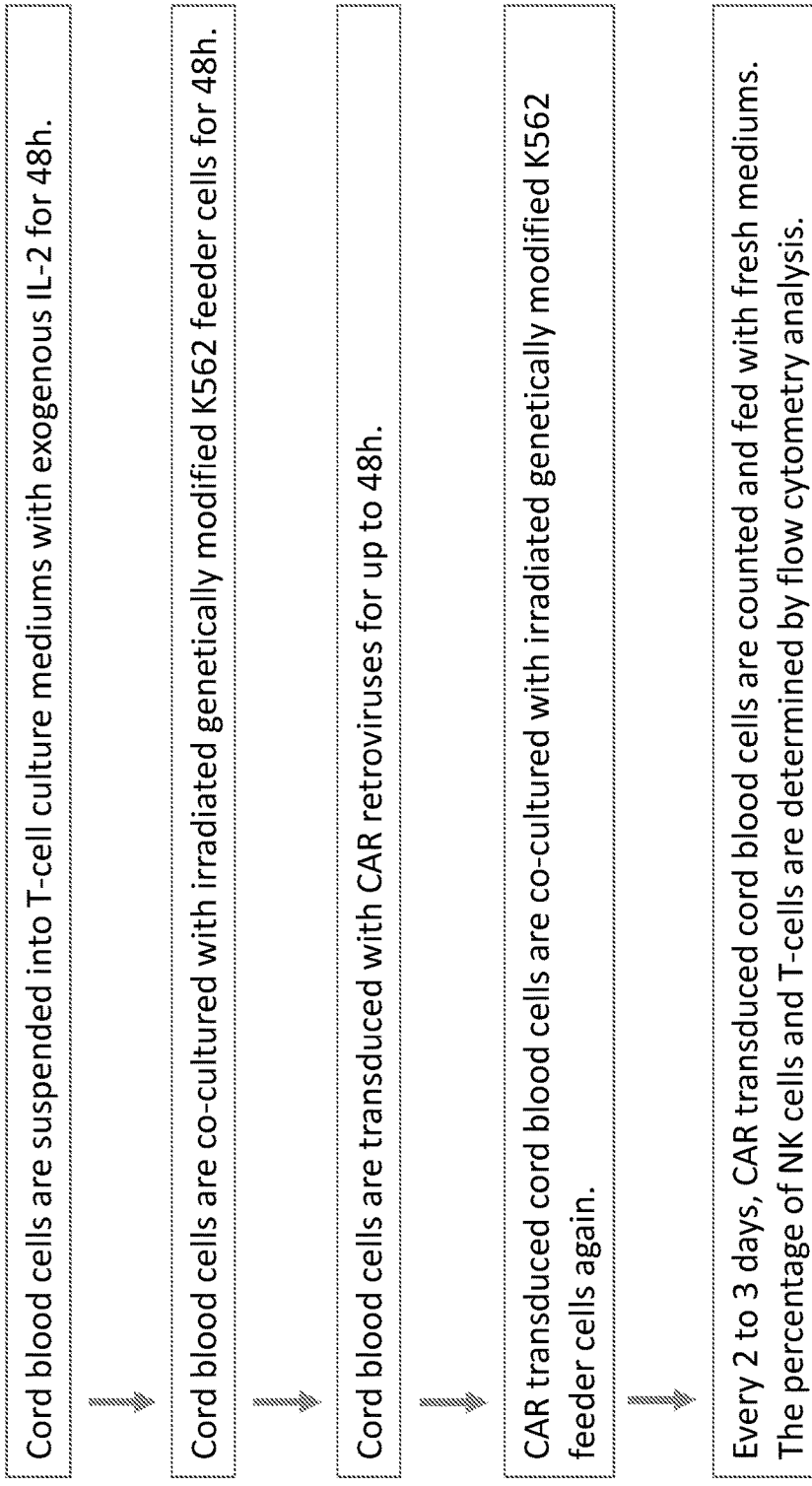

FIG. 50C. Steps for generation and expansion of CAR-transduced natural killer (NK) cells from umbilical cord blood by co-culture with irradiated genetically modified K562 cells (feeder cells)

Figure 51A:
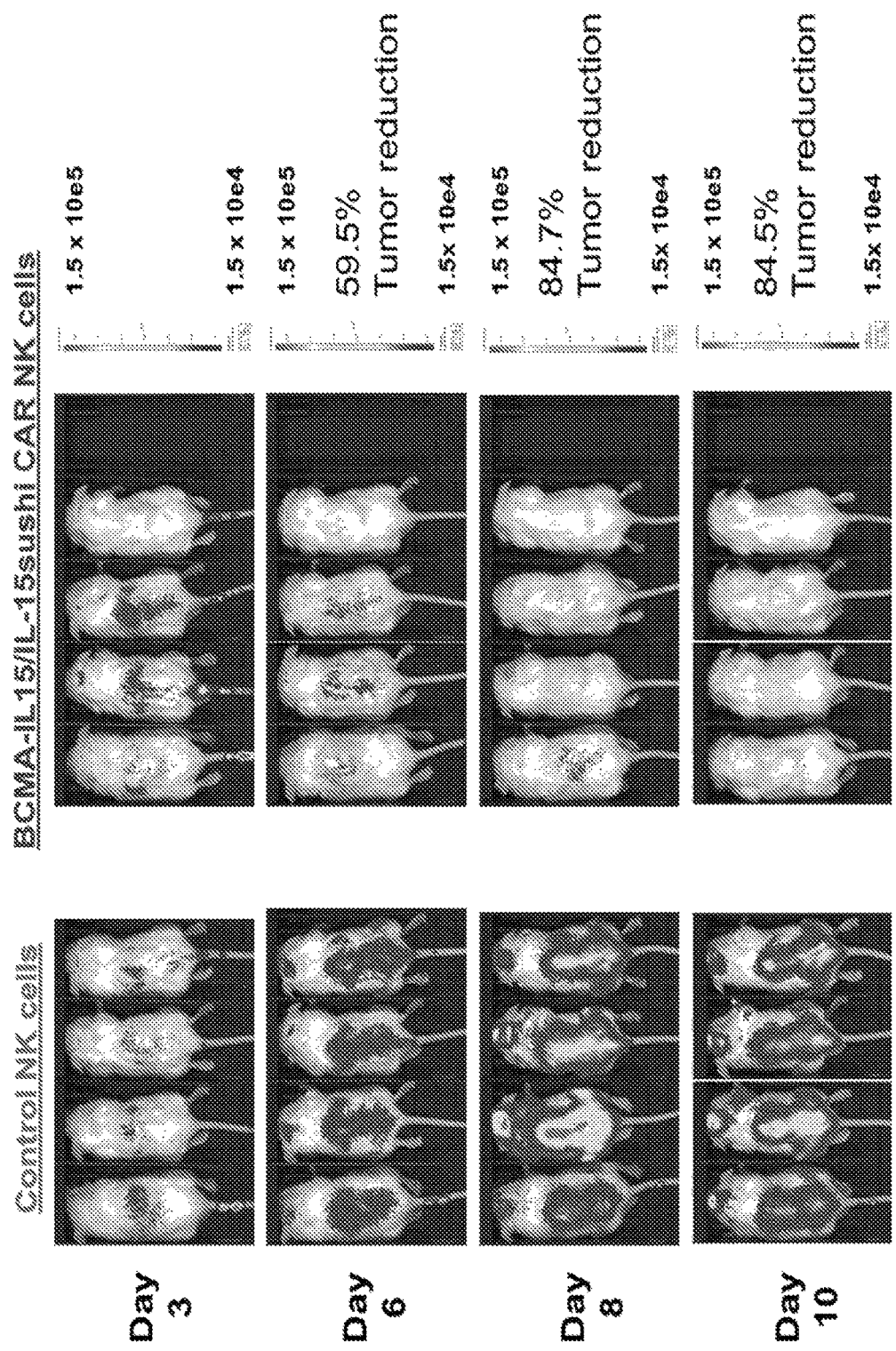

FIG. 51A. BCMA-IL15/IL15sushi-CAR NK cells demonstrate anti-leukemic effects in vivo mouse model. NSG mice were sublethally irradiated and intravenously injected the following day with luciferase-expressing MM1S multiple myeloma cells to induce measurable tumor formation. On Day 4, the mice were intravenously injected with $10 \times 10^6$ Control NK cells or BCMA-IL15/IL15sushi-CAR expressed NK cells. On Days 3, 6, 8 and 10, mice were injected subcutaneously with RediJect D-Luciferin and subjected to IVIS imaging.

Figure 51B:
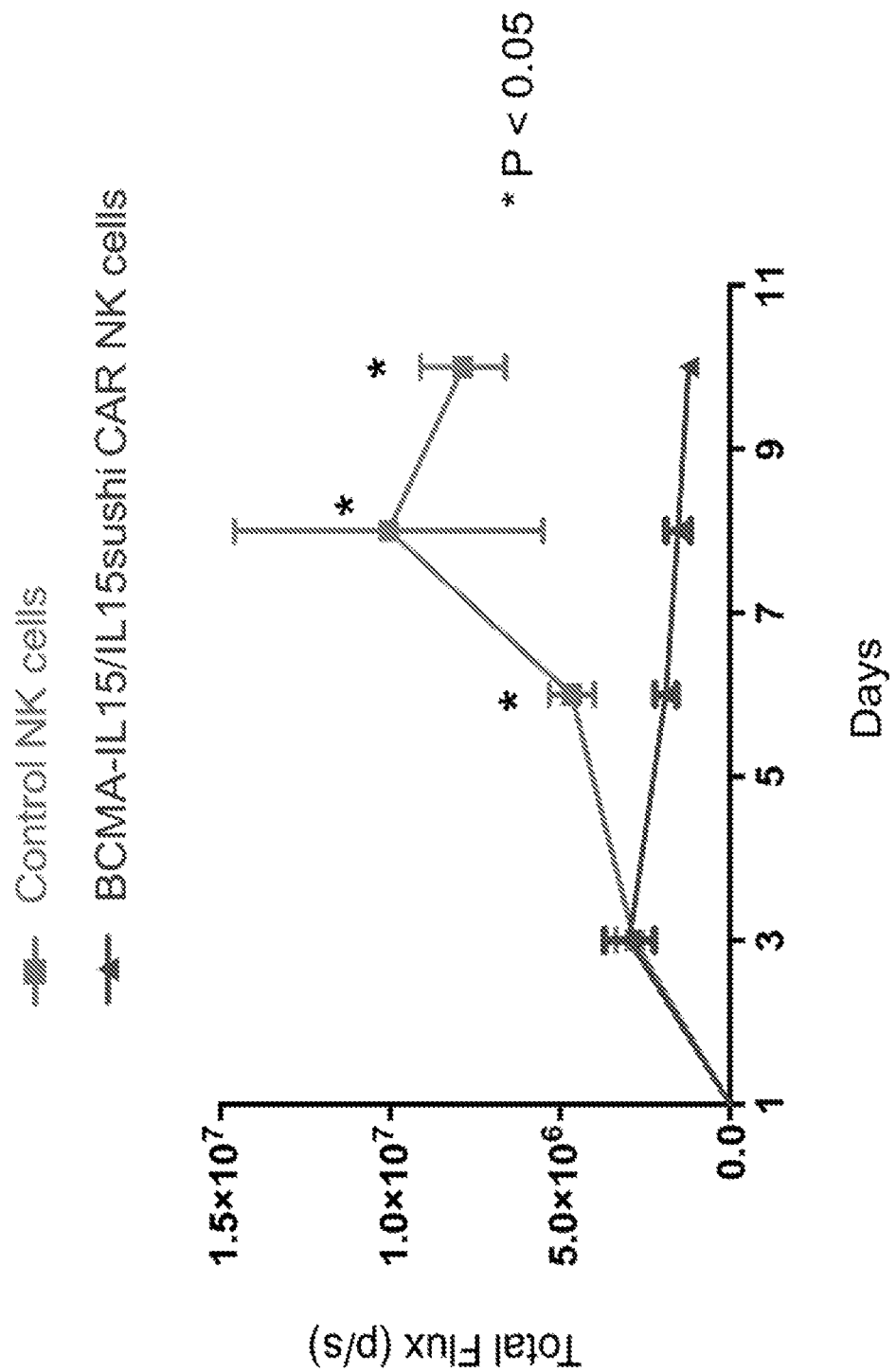

FIG. 51B. Comparison of total flux values (photons/sec) between control and BCMA-IL15/IL15sushi-CAR expressed NK cells treated mice over time. The data are presented as a mean+S.D. *, P<0.05 as compared to control NK-cells at indicated days.

Figure 51C:
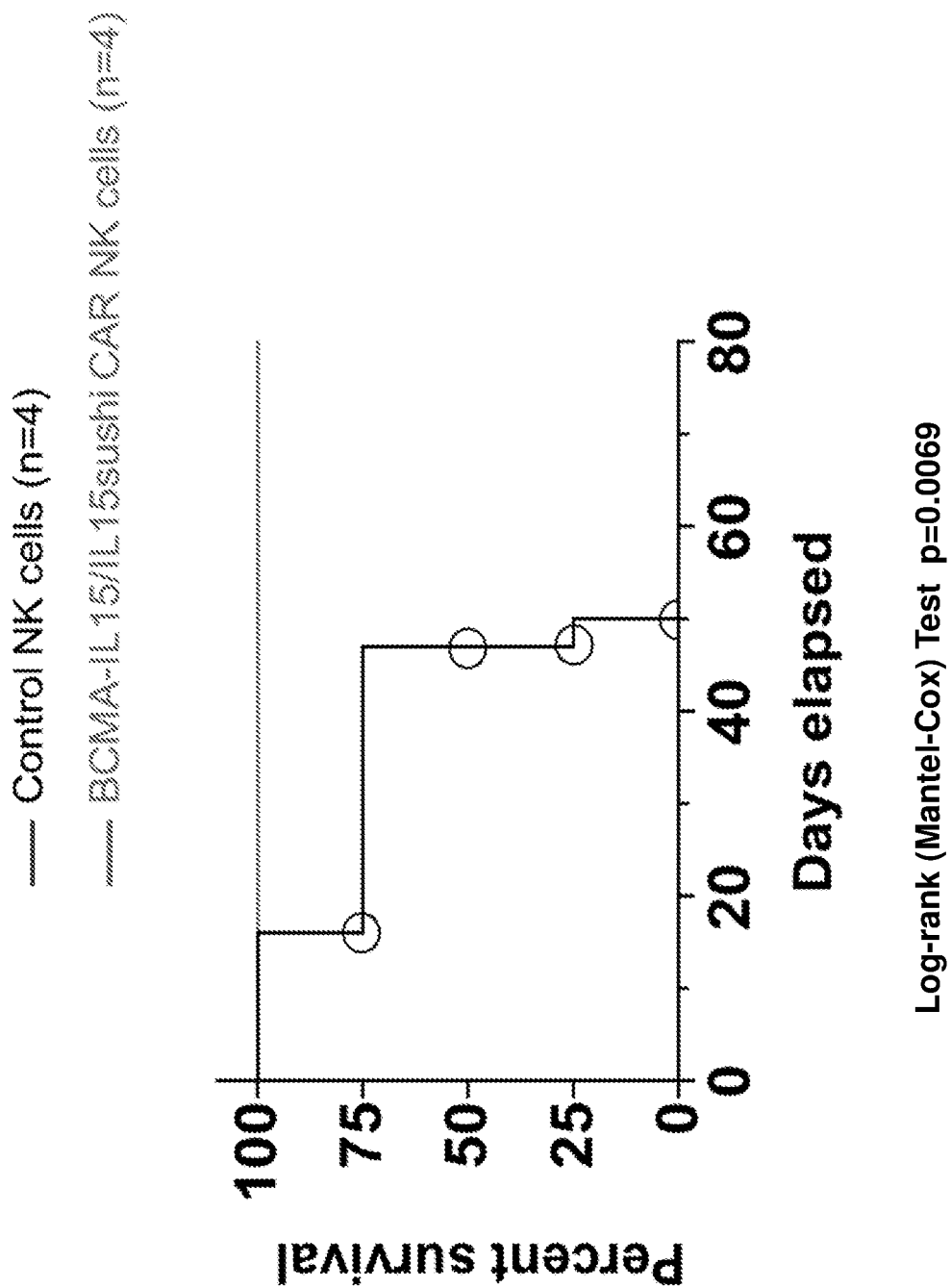

FIG. 51C. Survival comparison of mice injected with MM1S multiple myeloma cells between control mice and mice treated with BCMA-IL15/IL15sushi-CAR NK cells over time. A survival curve was generated to show the survival of mice over time, up to Day 80, with Log-rank (Mantel-Cox) Test p=0.0069.

Figure 52A:
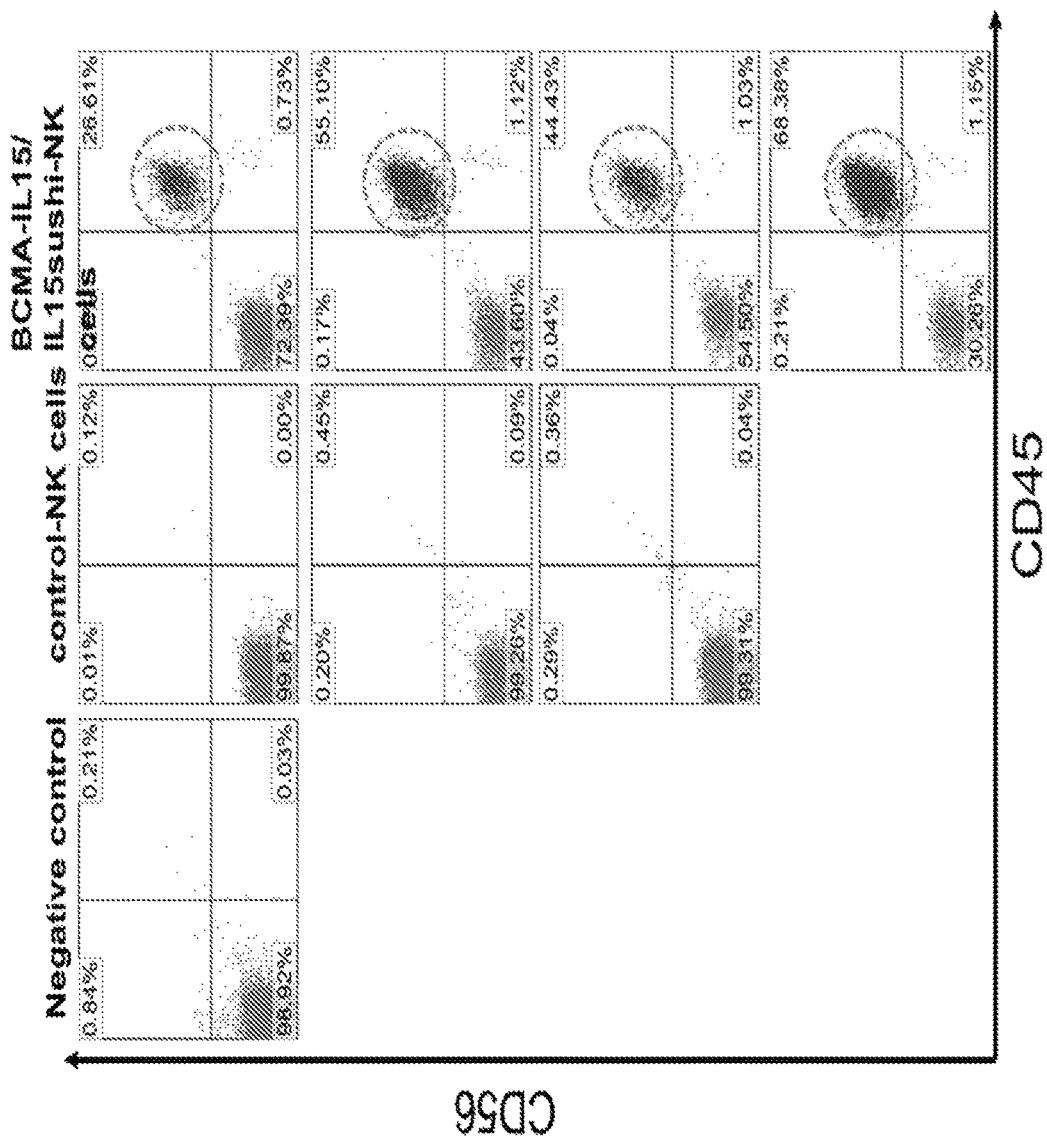

FIG. 52A. Evaluation of persistence of infused BCMA-A7D-IL15/IL15sushi CAR transduced NK cells in xenograft mouse model on Day 25 (D) and Day 60 (E). On Day 25 (21 days after control NK or CAR NK cells infused mice) and Day 60 (58 days after mice were infused with control NK or CAR NK cells), peripheral blood was collected from individual mice and cells were labeled using human CD56- and human CD45 antibodies to detect the presence of infused control- and/or CAR-NK cells. The persistence of control NK cells or BCMA-IL15/IL-15sushi CAR transduced NK cells in collected peripheral blood was determined by flow cytometry analysis. Left panels show the negative controls, in which an NK cells were uninfused. The middle panels show the group of mice infused with control NK cells. Right panels show the group of mice infused with BCMA-IL15/IL15sushi-CAR transduced NK cells.

Figure 52B:
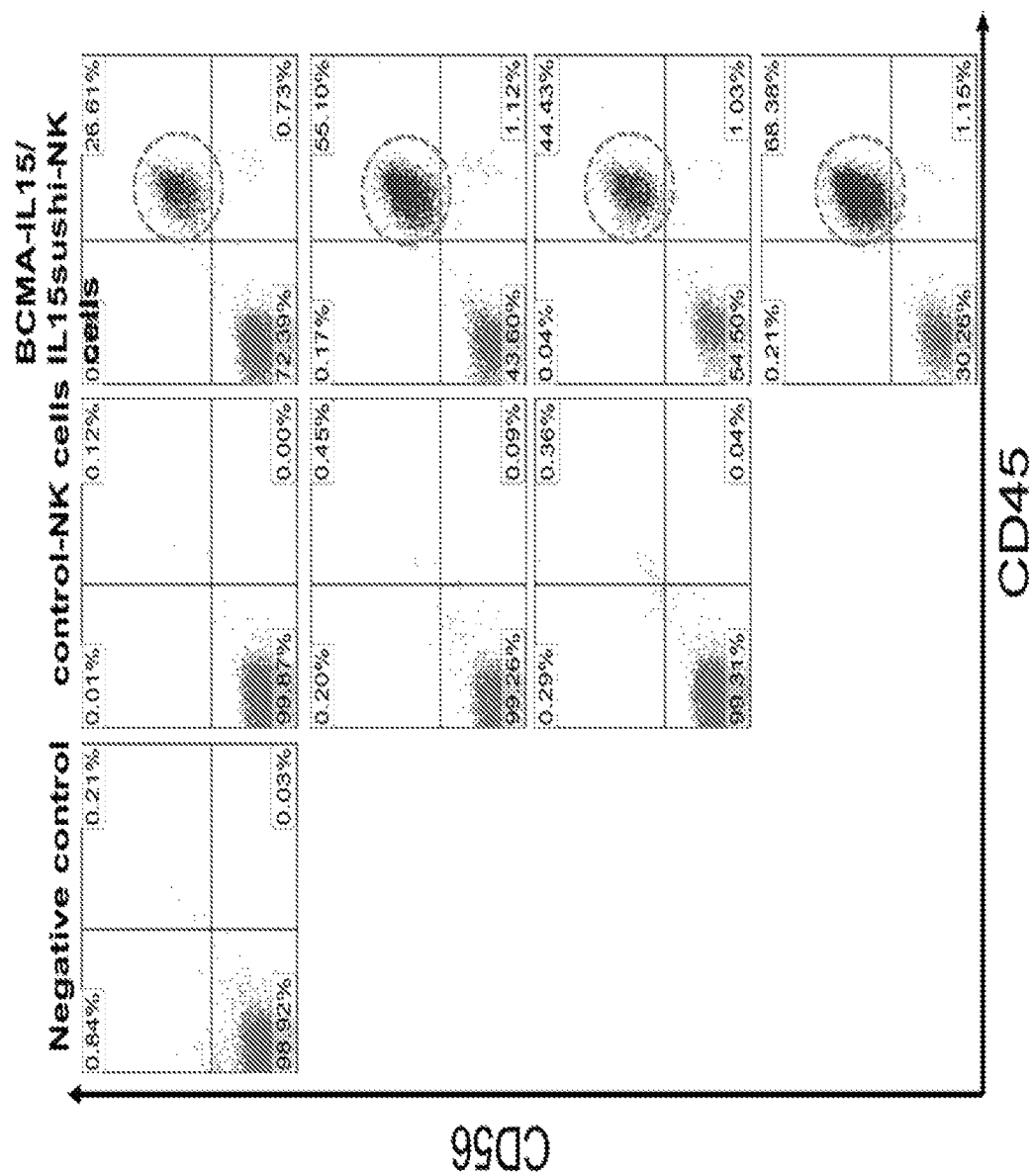

FIG. 52B. Evaluation of persistence of infused BCMA-A7D-IL15/IL15sushi CAR transduced NK cells in xenograft mouse model on Day 60.

FIG. 53. Schematic diagram to elucidate the construct of a CAR co-expressing a secreting IL-15/IL-15sushi fusion protein and its expression in T or NK cells. A) a combination of CAR (third or two generation) and IL15/sushi domain of the IL15 alpha receptor, is assembled on an expression vector, and their expression is driven by the SFFV promoter. CAR with IL-15/sushi is linked with the P2A self-cleaving sequence. The IL-15/sushi portion is composed of IL-2 signal peptide fused to IL-15 and linked to sushi domain via a 26-amino acid poly-proline linker. B) CAR and IL-15/sushi are present on the T or NK cells. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7 and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Figure 54A:
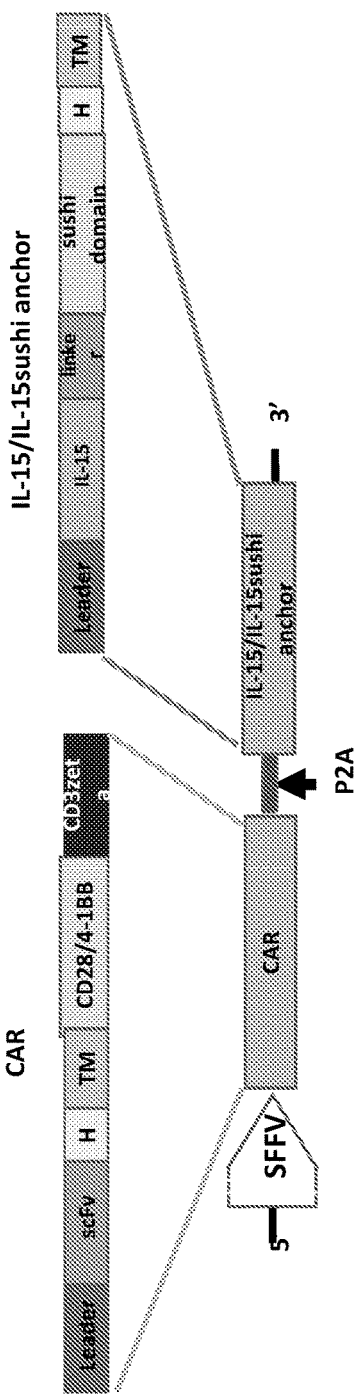
Figure 54B:
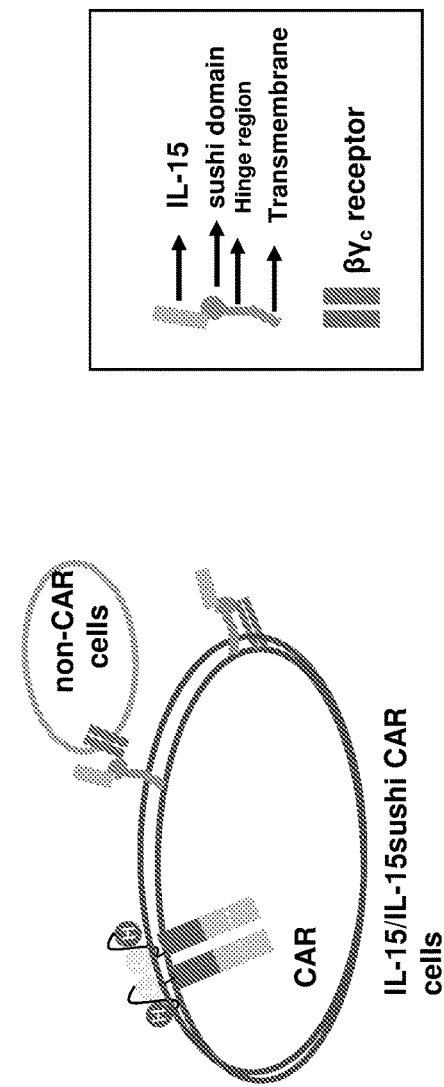

FIG. 54. A schematic showing a CAR equipped with IL-15/IL-15sushi anchor. A) the construct consists a SFFV promoter driving the expression of a CAR and an IL-15/IL-15sushi anchor (also called anchor) linked by a P2A peptide. Upon cleavage of this P2A peptide, IL-15/IL-15 anchor CAR splits to a CAR and an IL-15/IL-15suchi anchor. The IL-15/IL-15sushi portion of anchor is composed of IL-2 signal peptide fused to IL-15 and linked to sushi domain of IL-15 alpha receptor via a 26-amino acid poly-proline linker. Both CAR and anchor comprise a hinge (H) region, a transmembrane domain (TM). CAR also has scFv, costimulatory domain (including, but not limited to CD28 or 4-1BB) and intracellular signaling, CD3 zeta chain while anchor does not bear these components. B) IL-15/IL-15sushi is anchored on the surface of T or NK cells.

Figure 55:
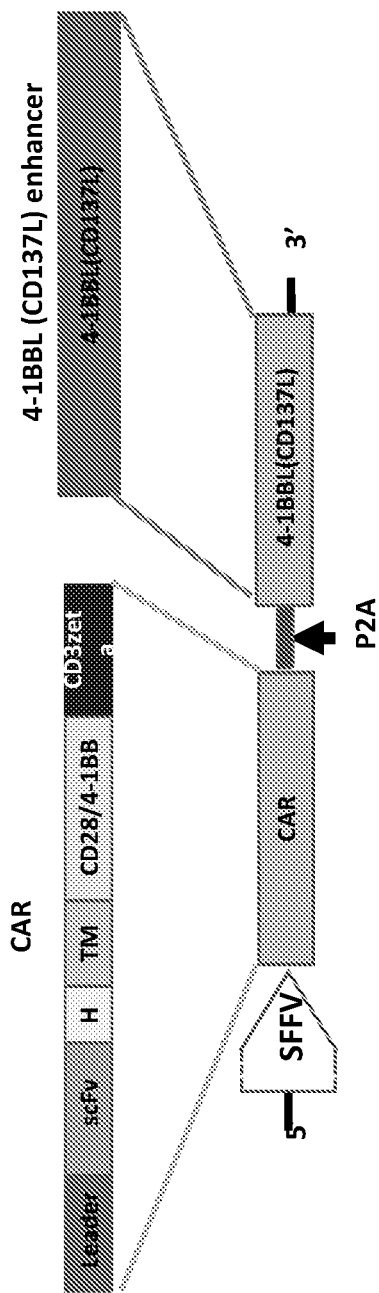

FIG. 55. A schematic showing a CAR enhancer construct. The construct consists a SFFV promoter driving the expression of a CAR and an enhancer, 4-1BBL (CD137L) linked by a P2A peptide. Upon cleavage of this P2A peptide, A CAR construct with 4-1BBL splits to a CAR and the full length of 4-1BBL protein. A CAR comprises a leader sequence and scFv, a hinge (H) region, a transmembrane domain (TM). CAR also has costimulatory domain (including, but not limited to, CD28 or 4-1BB) and intracellular signaling, CD3 zeta chain while 4-1BBL does not bear these components. 4-1BBL provides a synergistic effect of T cell activation or anti-tumor activity with CD28 or 4-1BB (but not limited to).

Figure 56:
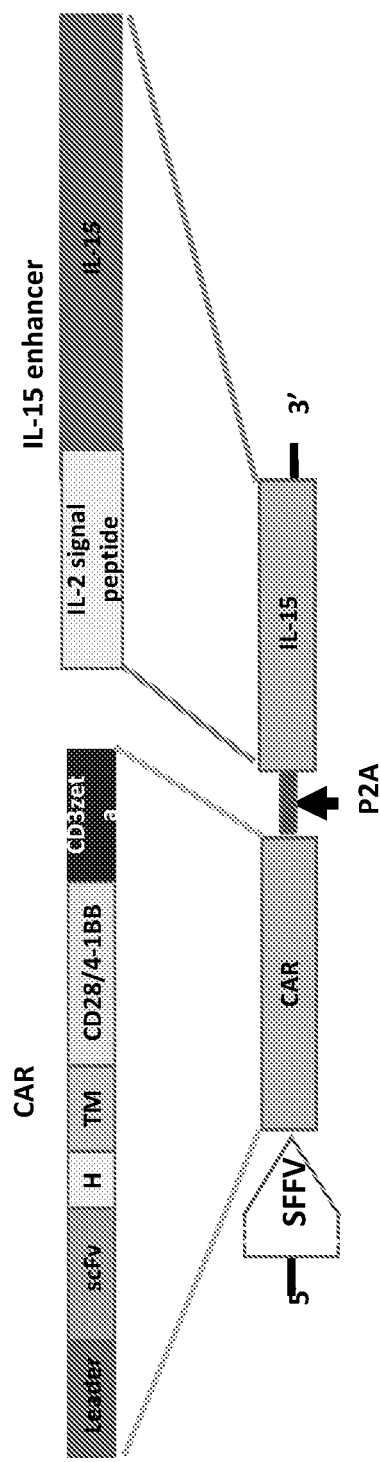

FIG. 56. A schematic showing a CAR enhancer construct. The construct consists a SFFV promoter driving the expression of a CAR and an enhancer, IL-15 linked by a P2A peptide. Upon cleavage of this P2A peptide, A CAR construct with IL-15 splits to a CAR and the full length of IL-15 protein. A CAR comprises a leader sequence and scFv, a hinge (H) region, a transmembrane domain (TM). CAR also has a costimulatory domain (including, but not limited to, CD28 or 4-1BB) and intracellular signaling, CD3 zeta chain while IL-15 does not bear these components. IL-15 provides a synergistic effect of T cell activation or expansion or anti-tumor activity with CD28 or 4-1BB. The IL-15 signal peptide in the IL-15 is replaced with IL-2 signal peptide (leader sequence), a strong signal peptide to provide a high efficiency of IL-15 secretion.

Figure 57:
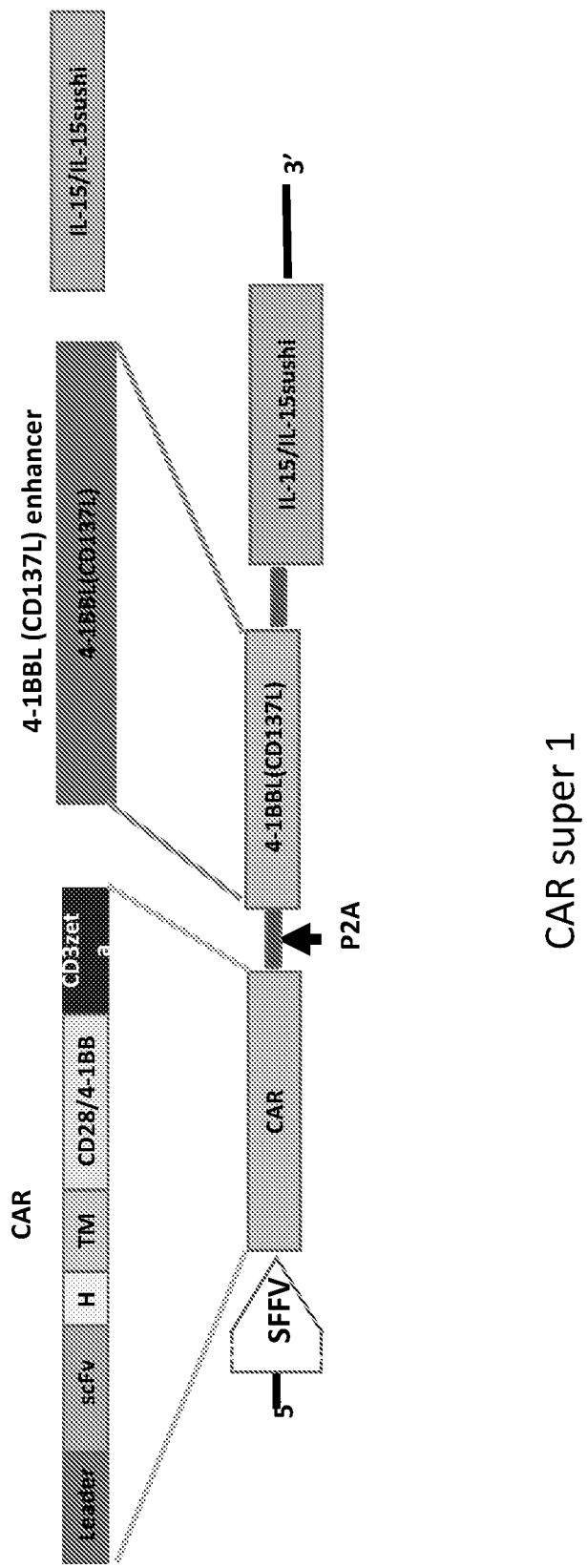

FIG. 57. A schematic showing a CAR construct with multiple enhancers (CAR super). The construct consists a SFFV promoter driving the expression of a CAR and enhancers, 4-1BBL (CD137L) and IL-15/IL-15sushi linked by a P2A and T2A peptide, respectively. Upon cleavage of this P2A and T2A peptides, A CAR construct with 4-1BBL and IL-15/IL-15sushi splits to a CAR and the full length of 4-1BBL protein, and secreting IL-15/IL-15sushi. A CAR comprises a leader sequence and scFv, a hinge (H) region, a transmembrane domain (TM). CAR also has costimulatory domain (including, but not limited to, CD28 or 4-1BB) and intracellular signaling, CD3 zeta chain. 4-1BBL ligand provides a synergistic effect of T or NK cell activation or anti-tumor activity with CD28 or 4-1BB (but not limited to). The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7, and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK or NK T cells and their neighbor tumor immune response cells. The soluble IL-15/IL-15sushi fusion are stable and enhances CAR T/NK or NK T cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Figure 58:
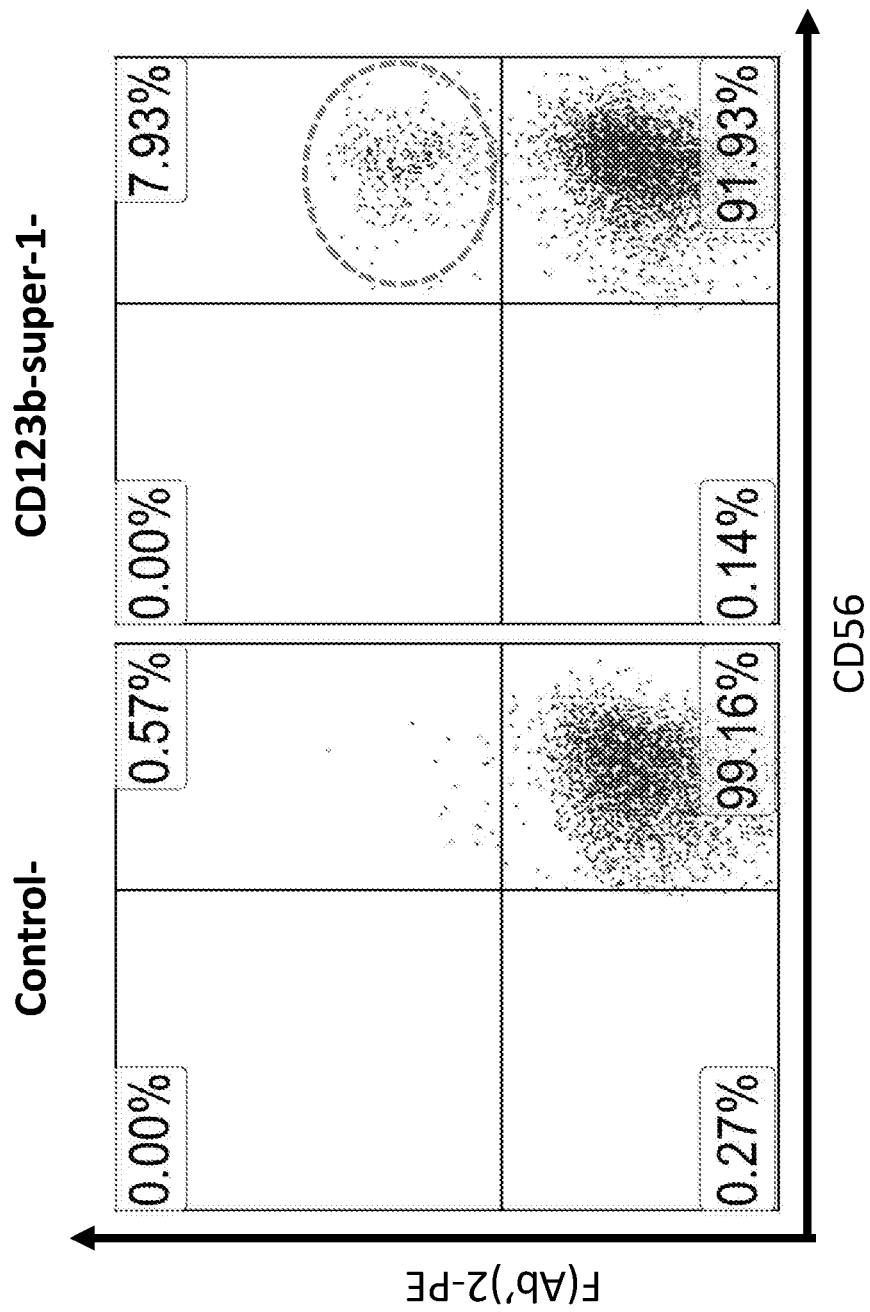

FIG. 58. Generation of CD123b-Super-1-CAR expressed human NK cells derived from human cord blood. Flow cytometry analysis showed the expression levels of CD123b-Super 1CAR on CD56 positive cells (circled in pink) in cord blood cells after transduction CD123b Super-1 CAR viruses in cord blood cells.

Figure 59:
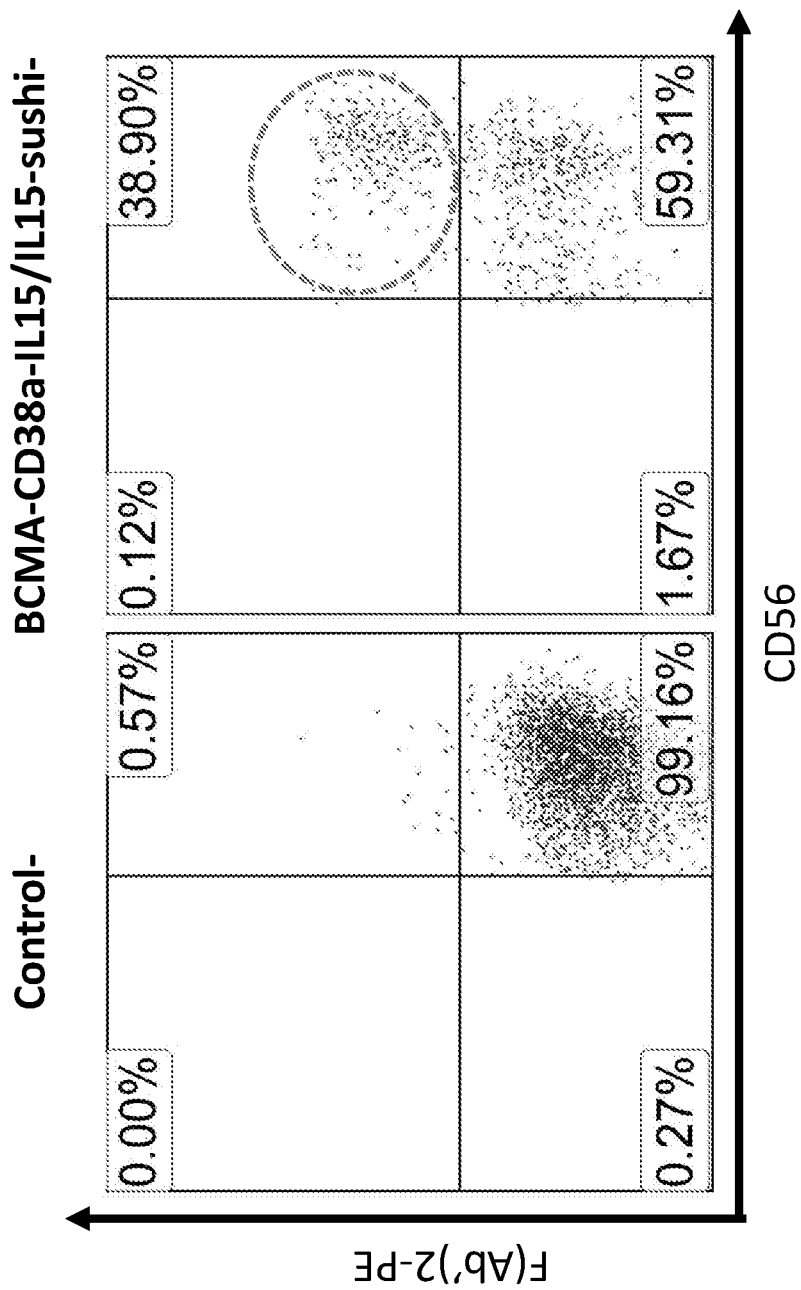

FIG. 59. Generation of BCMA–CD38a-IL15/IL15sushi cCAR (also called CD269-A7D-CD38a-IL15/IL15sushi) CAR. BCMA–CD38a-IL15/IL15sushi cCAR was expressed in human NK cells derived from human cord blood. Flow cytometry analysis showed the expression levels of BCMA–CD38a-IL15/IL-15sushi-cCAR on CD56 positive cells (circled) in cord blood cells after transduction BCMA–CD38a-IL15/IL-15sushi cCAR viruses in cord blood cells.

Figure 60A:
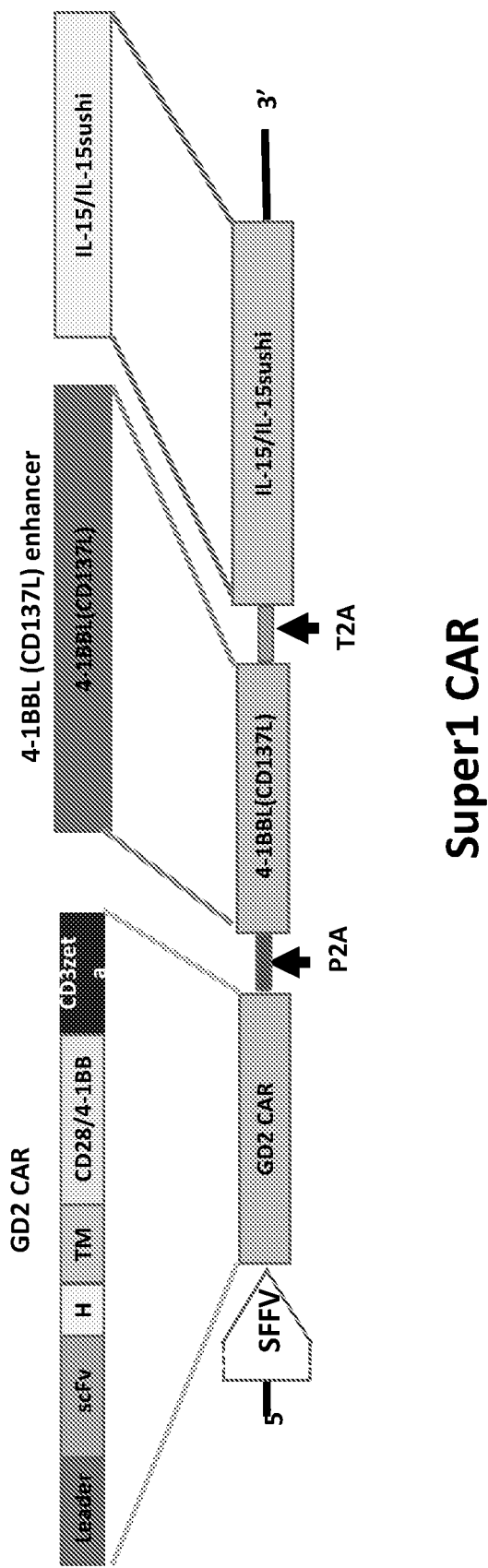

FIG. 60A. A schematic representation of a super1 CAR construct. Links by P2A and T2A schematic to generate a super1 CAR showing a CAR, GD2 CAR equipped with 4-1BBL and IL-15/IL-15sushi in a single construct. The construct consists of a SFFV promoter driving the expression of three segments, CAR, 4-1BBL and IL-15/IL-15sushi. Upon cleavage of the linkers (P2A and T2A), the CAR (GD2 CAR), 4-1BBL and IL-15/IL-15sushi split and engage upon a target (s). CAR has scFv, hinge region, transmembrane domain, costimulatory domain (including, but not limited to, CD28 or 4-1BB) and intracellular signaling, CD3 zeta chain. 4-1BBL or IL-15/IL-sushi or both provides a synergistic effect of T or NK cell activation and persistency or anti-tumor activity with CD28 or 4-1BB.

Figure 60B:
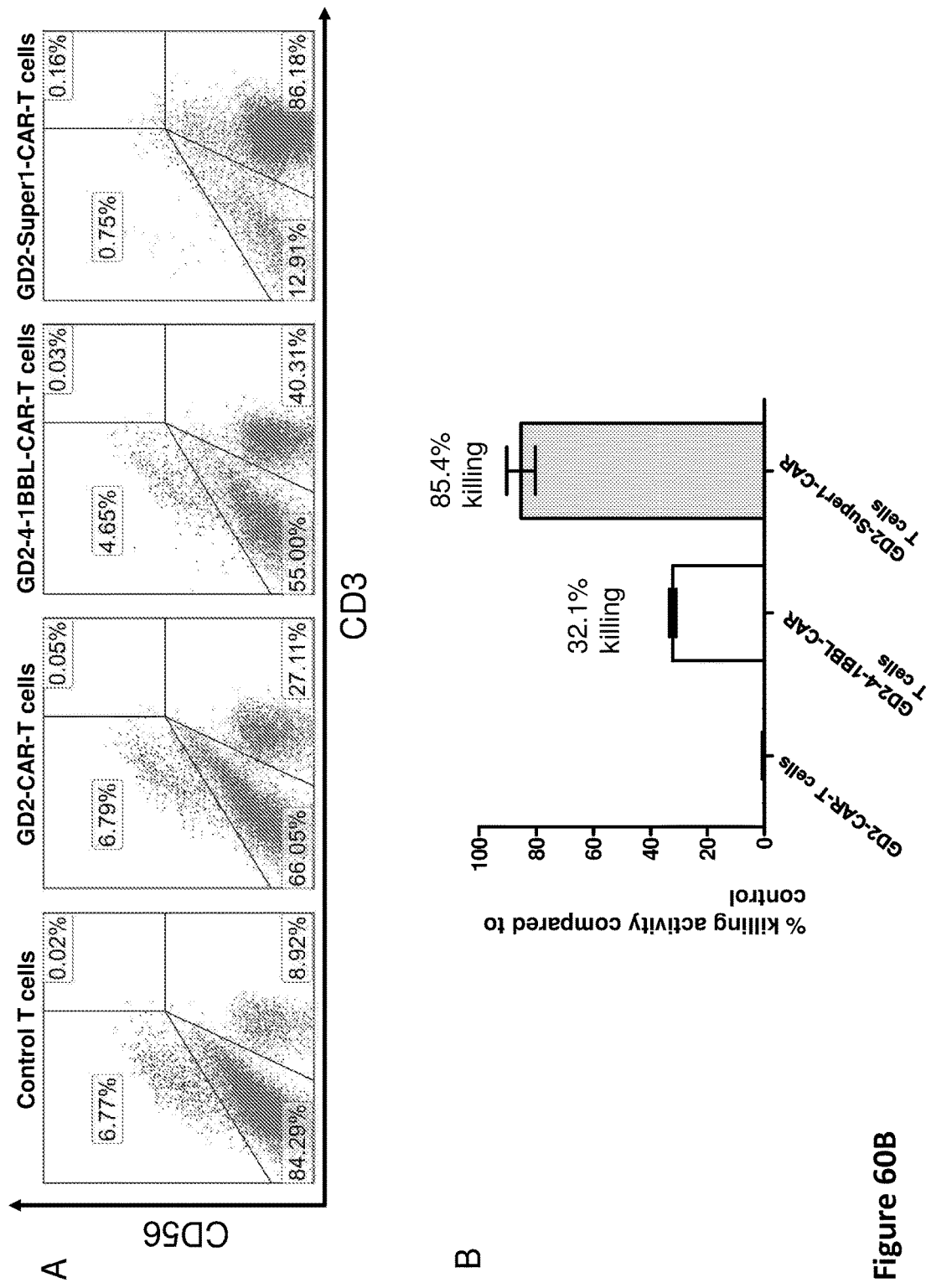

FIG. 60B. GD2-Super1-CAR-T cells virtually eliminate Y79 cells in mouse liver (A) Flow cytometry analysis shows persistence of Y79 tumor in the livers of mice treated with different forms of anti-GD2 CAR T cells. Three days after Y79 cells ($1 \times 10^6$ cells) were injected mice via tail vein, CAR T-cells ($10 \times 10^6$ cells) were infused into mice by I.V. injection. At day 30 after Y79 tumor injection, mice were euthanized and livers were homogenized to evaluate CAR T efficacy. Homogenized liver cells were labeled with mouse anti-human CD3 and CD56 antibodies to detect human T cells and Y79 tumor cells, respectively. A representation of a mouse given control T cells is shown on the left; mouse treated with GD2CAR (left center), GD2-4-1BBL CAR (right center), and GD2-Super1 CAR (right) T cells. Elimination of tumor cells was associated with high labels of T-cells. GD2-4-BBL CAR is a GD2 CAR co-expressing 4-1BBL ligand.

(B) Graph indicating percent killing activity against Y79 cells by each CAR treated mice compared to control mice (n=2). From these data, especially, only GD2 Super1 CAR T were able to virtually eliminate Y79 cells in liver.

Figure 60C:
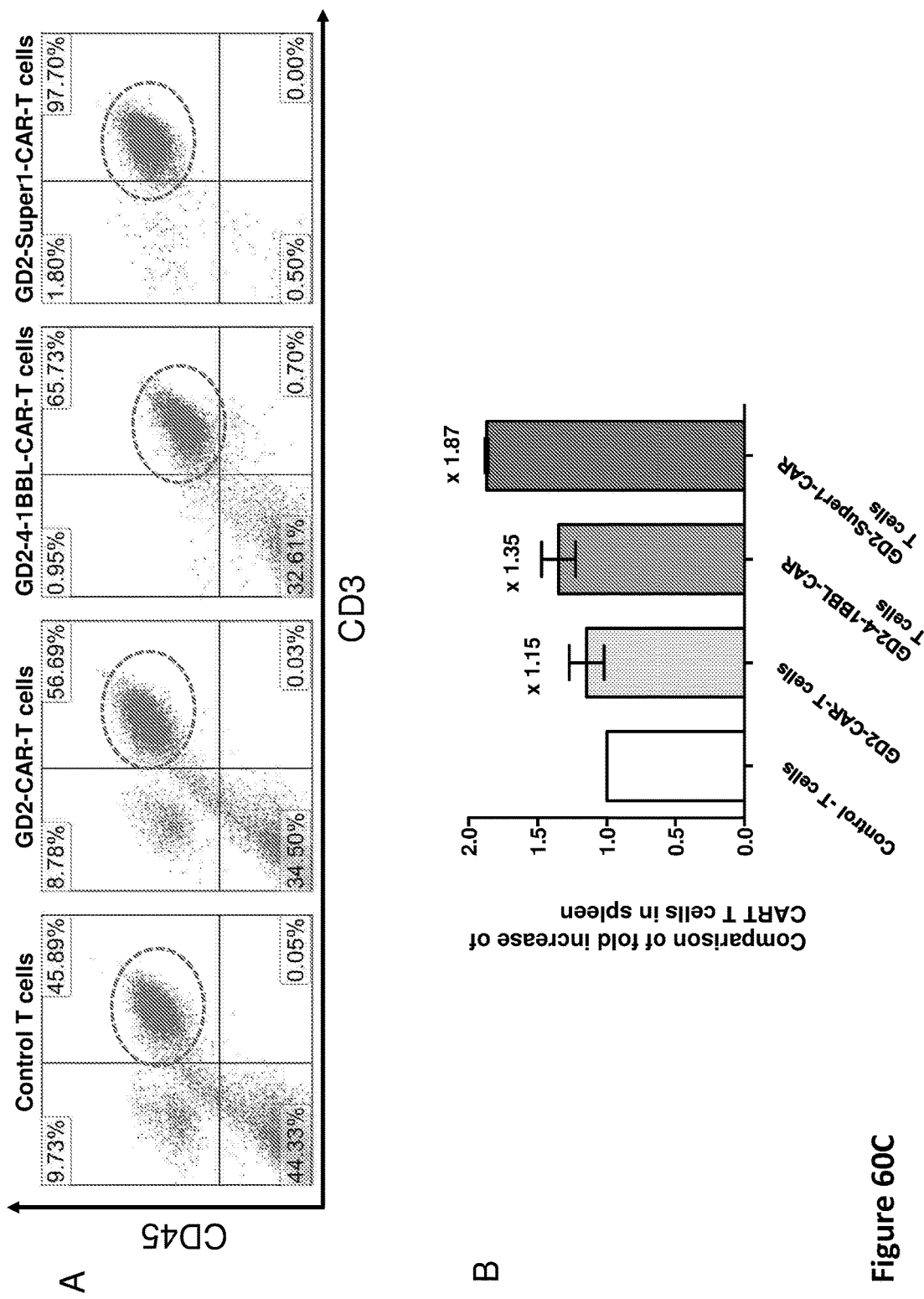

FIG. 60CA-60CB. GD2-Super1-CAR T cells exhibit greater persistence in mouse spleen (60CA) Flow cytometry analysis shows persistence of CAR T cells (circled) in the livers of mice treated with different forms of anti-GD2 CAR T cells. Three days after Y79 cells ($1 \times 10^6$ cells) were injected mice via tail vein, CAR T-cells ($10 \times 10^6$ cells) were infused into mice by I.V. injection. At day 30 after Y79 tumor injection, mice were euthanized and spleens were homogenized to evaluate CAR T efficacy. Homogenized spleen cells were labeled with mouse anti-human CD3 and CD45 antibodies to detect human T cells. A representation of a mouse given control T cells is shown on the left; mouse treated with GD2CAR (left center), GD2-4-1BBL CAR (right center), and GD2-super1 CAR (right) T cells.

(60CB) Graph indicating fold-increase of CAR T cells in treated mice compared to control T mice (n=2). From these data, especially, GD2-Super CAR T cells were well expanded compared to control T-cells in total mouse spleen cells.

Figure 60D:
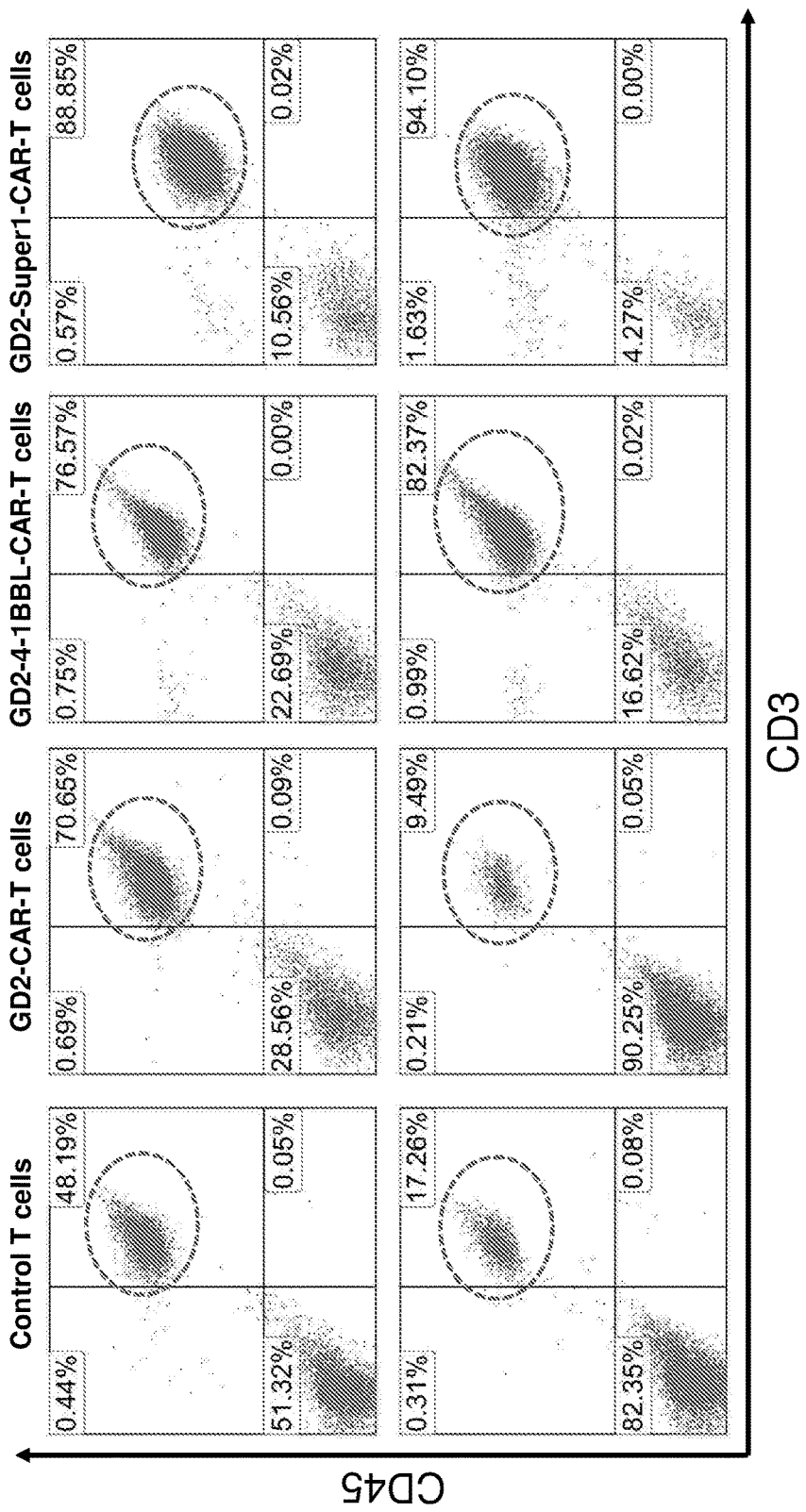

FIG. 60D. Persistence of CAR T cells in mouse blood (A) Flow cytometry analysis shows persistence of CAR T cells (circled) in the whole blood of mouse treated with different forms of anti-GD2 CAR T cells. Three days after Y79 cells ($1 \times 10^6$ cells) were injected mice via tail vein, CAR T-cells ($10 \times 10^6$ cells) were infused into mice by I.V. injection. At day 30 after Y79 tumor injection, mice were euthanized and whole blood was collected to evaluate CAR T persistence. Whole blood cells were labeled with mouse anti-human CD3 and CD45 antibodies, to detect human T cells. A representation of a mouse given control T cells is shown on the left; mice treated with GD2CAR (left center), GD2-4-1BBL CAR (right center), and GD2-Super1 CAR (right) T cells.

Figure 60E:
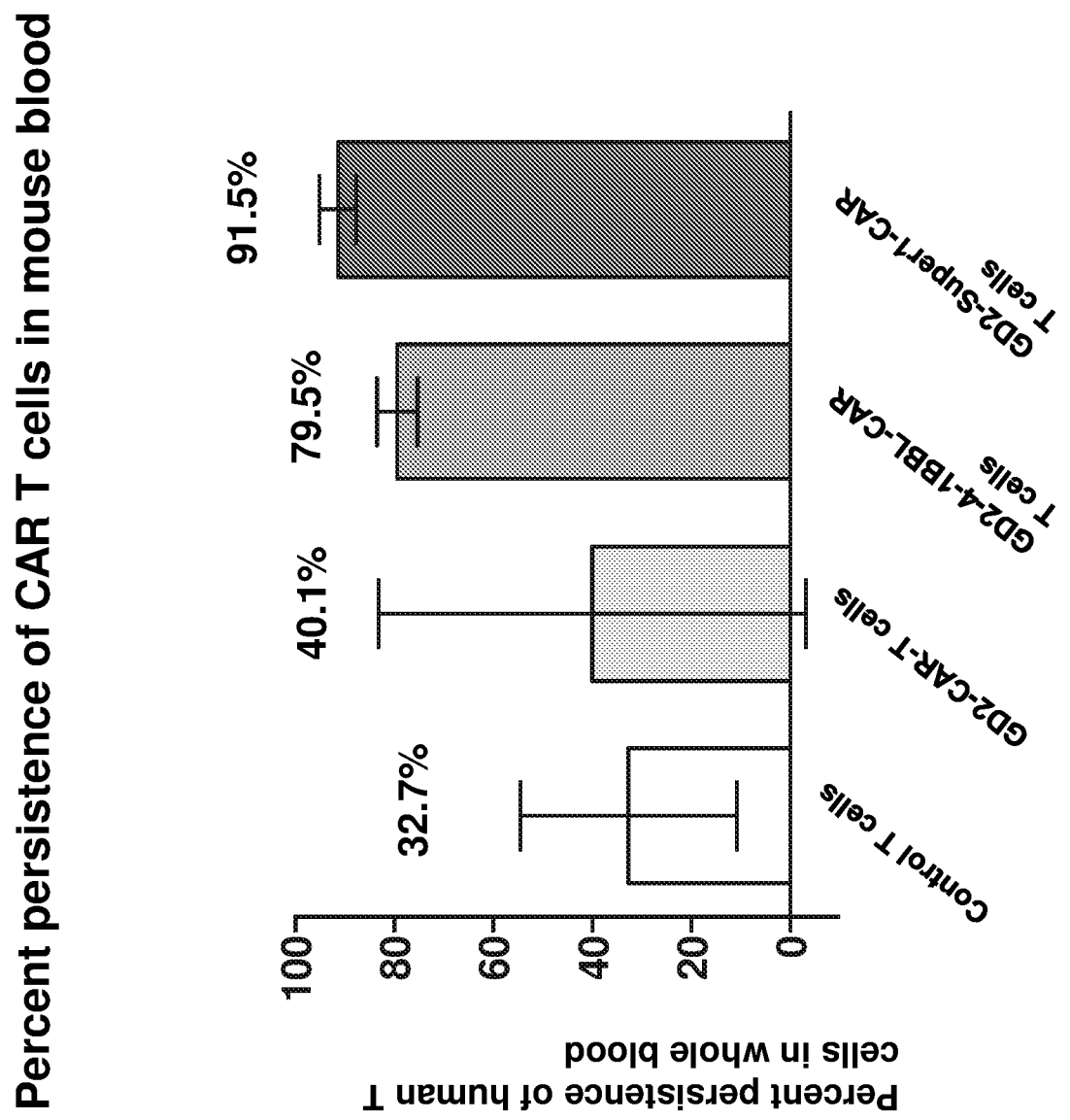

FIG. 60E. Bar graph representing the percent persistence of human T cells in whole blood samples, relative to the number of total cells analyzed by flow cytometry (n=2 each)

DETAILED DESCRIPTION

The disclosure provides chimeric antigen receptor (CAR) compositions, methods and making thereof, and methods of using the CAR compositions.

Compositions

Chimeric Antigen Receptor Polypeptides

In one embodiment, the disclosure provides a chimeric antigen receptor (CAR) polypeptide having a signal peptide, an antigen recognition domain, a hinge region, a transmembrane domain, at least one co-stimulatory domain, and a signaling domain.

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can include a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal peptide" includes a peptide sequence that directs the transport and localization of the peptide and any attached polypeptide within a cell, e.g. to a certain cell organelle (such as the endoplasmic reticulum) and/or the cell surface.

The signal peptide is a peptide of any secreted or transmembrane protein that directs the transport of the polypeptide of the disclosure to the cell membrane and cell surface, and provides correct localization of the polypeptide of the present disclosure. In particular, the signal peptide of the present disclosure directs the polypeptide of the present disclosure to the cellular membrane, wherein the extracellular portion of the polypeptide is displayed on the cell surface, the transmembrane portion spans the plasma membrane, and the active domain is in the cytoplasmic portion, or interior of the cell.

In one embodiment, the signal peptide is cleaved after passage through the endoplasmic reticulum (ER), i.e. is a cleavable signal peptide. In an embodiment, the signal peptide is human protein of type I, II, III, or IV. In an embodiment, the signal peptide includes an immunoglobulin heavy chain signal peptide.

The "antigen recognition domain" includes a polypeptide that is selective for an antigen, receptor, peptide ligand, or protein ligand of the target; or a polypeptide of the target.

The target specific antigen recognition domain preferably includes an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine, or a hormone) binding a receptor on the target, or a domain derived from a receptor (including but not limited to a growth factor receptor, a cytokine receptor or a hormone receptor) binding a peptide or protein ligand on the target. The target includes GD2 and GD3. In another embodiment, the target includes any portion of GD2 and GD3. In another embodiment, the target is gangliosides GD2 with its structure, GD2=bDGalpNAc(1-4)[aNeu5Ac(2-8)aNeu5Ac(2-3)]bDGalp(1-4)bDGlcp(1-1)Cer. In another embodiment, the target is the gangliosides GD3 with its structure, GD3=aNeu5Ac(2-8)aNeu5Ac(2-3)bDGalp(1-4)bDGlcp(1-1)Cer.

In one embodiment, the antigen recognition domain includes the binding portion or variable region of a monoclonal or polyclonal antibody directed against (selective for) the target.

In one embodiment, the antigen recognition domain includes antigen-binding fragment (Fab). In another embodiment, the antigen recognition domain includes a single-chain variable fragment (scFv). scFv is a fusion protein of the variable regions of the heavy (VH) and light chains (VL) of immunoglobulins, connected with a short linker peptide.

In another embodiment, the antigen recognition domain includes Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

In another embodiment, the antigen recognition domain includes ligands that engage their cognate receptor. In another embodiment, the antigen recognition domain is humanized.

It is understood that the antigen recognition domain may include some variability within its sequence and still be selective for the targets disclosed herein. Therefore, it is contemplated that the polypeptide of the antigen recognition domain may be at least 95%, at least 90%, at least 80%, or at least 70% identical to the antigen recognition domain polypeptide disclosed herein and still be selective for the targets described herein and be within the scope of the disclosure.

In another embodiment, the antigen recognition domain is selective for gangliosides GD2 and gangliosides GD3.

The hinge region is a sequence positioned between for example, including, but not limited to, the chimeric antigen receptor, and at least one co-stimulatory domain and a signaling domain. The hinge sequence may be obtained including, for example, from any suitable sequence from any genus, including human or a part thereof. Such hinge regions are known in the art. In one embodiment, the hinge region includes the hinge region of a human protein including CD-8 alpha, CD28, 4-1BB, OX40, CD3-zeta, T cell receptor α or β chain, a CD3 zeta chain, CD28, CD3, CD45, CD4, CD5, CD8, CD9, CD16, CD22, CD33, CD37, CD64, CD80, CD86, CD134, CD137, ICOS, CD154, functional derivatives thereof, and combinations thereof.

In one embodiment the hinge region includes the CD8a hinge region.

In some embodiments, the hinge region includes one selected from, but is not limited to, immunoglobulin (e.g. IgG1, IgG2, IgG3, IgG4, and IgD).

The transmembrane domain includes a hydrophobic polypeptide that spans the cellular membrane. In particular, the transmembrane domain spans from one side of a cell membrane (extracellular) through to the other side of the cell membrane (intracellular or cytoplasmic).

The transmembrane domain may be in the form of an alpha helix or a beta barrel, or combinations thereof. The transmembrane domain may include a polytopic protein, which has many transmembrane segments, each alpha-helical, beta sheets, or combinations thereof.

In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

For example, a transmembrane domain includes a transmembrane domain of a T-cell receptor α or β chain, a CD3 zeta chain, CD28, CD3, CD45, CD4, CD5, CD8, CD9, CD16, CD22, CD33, CD37, CD64, CD80, CD86, CD134, CD137, ICOS, CD154, functional derivatives thereof, and combinations thereof.

The artificially designed transmembrane domain is a polypeptide mainly comprising hydrophobic residues such as leucine and valine. In one embodiment, a triplet of phenylalanine, tryptophan and valine is found at each end of the synthetic transmembrane domain.

In one embodiment, the transmembrane domain is the CD8 transmembrane domain. In another embodiment, the transmembrane domain is the CD28 transmembrane domain. Such transmembrane domains are known in the art.

The signaling domain and co-stimulatory domain include polypeptides that provide activation of an immune cell to stimulate or activate at least some aspect of the immune cell signaling pathway.

In an embodiment, the signaling domain includes the polypeptide of a functional signaling domain of CD3 zeta, common FcR gamma (FCER1G), Fc gamma Rlla, FcR beta (Fc Epsilon Rib), CD3 gamma, CD3 delta, CD3 epsilon, CD79a, CD79b, DNAX-activating protein (DAP10), DNAX-activating protein 12 (DAP12), active fragments thereof, functional derivatives thereof, and combinations thereof. Such signaling domains are known in the art.

In an embodiment, the CAR polypeptide further includes one or more co-stimulatory domains. In an embodiment, the co-stimulatory domain is a functional signaling domain (s) selected from at least a protein including, but not limited to, IL-15 receptor alpha; IL-15 receptor alpha cytoplasmic domain; B7-1/CD80; CD28; 4-1BB, 4-1BBL, B7-2/CD86; CTLA-4; B7-H1/PD-L1; ICOS; B7-H2; PD-1; B7-H3; PD-L2; B7-H4; PDCD6; BTLA; 4-1BB/TNFRSF9/CD137; CD40 Ligand/TNFSF5; 4-1BB Ligand/TNFSF9; GITR/TNFRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNFSF7; OX40/TNFRSF4; CD30/TNFRSF8; OX40 Ligand/TNFSF4; CD30 Ligand/TNFSF8; TACI/TNFRSF13B; CD40/TNFRSF5; 2B4/CD244/SLAMF4; CD84/SLAMF5; BLAME/SLAMF8; CD229/SLAMF3; CD2, CD27, CRACC/SLAMF7; CD2F-10/SLAMF9; NTB-A/SLAMF6; CD48/SLAMF2; SLAM/CD150; CD58/LFA-3; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR.

The present disclosure further provides a polynucleotide encoding the chimeric antigen receptor polypeptide described above. The polynucleotide encoding the CAR is easily prepared from an amino acid sequence of the specified CAR by any conventional method. A base sequence encoding an amino acid sequence can be obtained from the aforementioned NCBI RefSeq IDs or accession numbers of GenBenk for an amino acid sequence of each domain, and the nucleic acid of the present disclosure can be prepared using a standard molecular biological and/or chemical procedure. For example, based on the base sequence, a polynucleotide can be synthesized, and the polynucleotide of the present disclosure can be prepared by combining DNA fragments which are obtained from a cDNA library using a polymerase chain reaction (PCR).

In one embodiment, the polynucleotide disclosed herein is part of a gene, or an expression or cloning cassette.

The term "polynucleotide" as used herein is defined as a chain of nucleotides. Polynucleotide includes DNA and RNA. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

Polynucleotide Vector

The polynucleotide described above can be cloned into a vector. A "vector" is a composition of matter which includes an isolated polynucleotide and which can be used to deliver the isolated polynucleotide to the interior of a cell. Numerous vectors are known in the art including, but not limited to, linear polynucleotides, polynucleotides associated with ionic or amphiphilic compounds, plasmids, phagemid, cosmid, and viruses. Viruses include phages, phage derivatives. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

In one embodiment, vectors include cloning vectors, expression vectors, replication vectors, probe generation vectors, integration vectors, and sequencing vectors.

In an embodiment, the vector is a viral vector. In an embodiment, the viral vector is a retroviral vector or a lentiviral vector. In an embodiment, the engineered cell is virally transduced to express the polynucleotide sequence.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Expression of chimeric antigen receptor polynucleotide may be achieved using, for example, expression vectors including, but not limited to, at least one of a SFFV (spleen focus-forming virus) or human elongation factor 11α (EF) promoter, CAG (chicken beta-actin promoter with CMV enhancer) promoter human elongation factor 1α (EF) promoter. Examples of less-strong/lower-expressing promoters utilized may include, but is not limited to, the simian virus 40 (SV40) early promoter, cytomegalovirus (CMV) immediate-early promoter, Ubiquitin C (UBC) promoter, and the phosphoglycerate kinase 1 (PGK) promoter, or a part thereof. Inducible expression of chimeric antigen receptor may be achieved using, for example, a tetracycline responsive promoter, including, but not limited to, TRE3GV (Tet-response element, including all generations and preferably, the 3rd generation), inducible promoter (Clontech Laboratories, Mountain View, CA) or a part or a combination thereof.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure should not be limited to the use of constitutive promoters, inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

"Expression vector" refers to a vector comprising a recombinant polynucleotide expression control sequence operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Additional promoter elements, e.g., enhancers, regulate the frequency of transcriptional initiation. Typically, these are located in the region 30-100 bp upstream of the start site, although a number of promoters have recently been shown to contain functional elements downstream of the start site as well. The spacing between promoter elements frequently is flexible, so that promoter function is preserved when elements are inverted or moved relative to one another, in the thymidine kinase (tk) promoter, the spacing between promoter elements can be increased to bp apart before activity begins to decline. Depending on the promoter, it appears that individual elements can function either cooperatively or independently to activate transcription.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors; in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyi phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyi phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 19 1 Glycobiology 5; 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous polynucleotides into a host cell or otherwise expose a cell to the polynucleotide of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Engineered Cell

In another embodiment, the disclosure provides an engineered cell expressing the chimeric antigen receptor polypeptide described above or polynucleotide encoding for the same, and described above.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a chimeric antigen receptor or chimeric antigen receptor complex and express the chimeric receptor on the cell surface. Isolated host cells and engineered cells may be used, for example, for enhancing an NK cell activity or a T lymphocyte activity, treatment of cancer, and treatment of infectious diseases.

Any cell capable of expressing and/or capable of integrating the chimeric antigen receptor polypeptide, as disclosed herein, into its membrane may be used.

In an embodiment, the engineered cell includes immunoregulatory cells. Immunoregulatory cells include T-cells, such as CD4 T-cells (Helper T-cells), CD8 T-cells (Cytotoxic T-cells, CTLs), and memory T cells or memory stem cell T cells. In another embodiment, T-cells include Natural Killer T-cells (NK T-cells).

T cells comprise of CD4 and CD8 cells. CD4 is a glycoprotein present on the surface of immune cells such as T helper cells, important in T cell activation and receptor for HIV. Some monocytes or macrophages also express CD4. CD4 is also called OKT4. Cytotoxic T cells are also known as CD8+ T cells or CD8 T cells expressing CD8 glycoprotein at their surfaces. These CD8+ T cells are activated once they are exposed to peptide antigens presented by MHC class I.

In an embodiment, the engineered cell includes NK T cells. NK T cells are well known in the art.

In an embodiment, the engineered cell includes Natural Killer cells. Natural killer cells are well known in the art. In one embodiment, natural killer cells include cell lines, such as NK-92 cells. Further examples of NK cell lines include NKG, YT, NK-YS, HANK-1, YTS cells, and NKL cells.

NK cells mediate anti-tumor effects without the risk of GvHD and are short-lived relative to T-cells. Accordingly, NK cells would be exhausted shortly after destroying cancer cells, decreasing the need for an inducible suicide gene on CAR constructs that would ablate the modified cells.

As used herein, CDXCAR refers to a chimeric antigen receptor having a CDX antigen recognition domain. As used herein CDX may be any one of GD2 and GD3.

TCR Deficient T Cells Used to Carry CAR

In one embodiment, engineered cells, in particular allogeneic T cells obtained from donors can be modified to inactivate components of TCR (T cell receptor) involved in MHC recognition. As a result, TCR deficient T cells would not cause graft versus host disease (GVHD).

Sources of Cells

The engineered cells may be obtained from peripheral blood, cord blood, bone marrow, tumor infiltrating lymphocytes, lymph node tissue, or thymus tissue. The host cells may include placental cells, embryonic stem cells, induced pluripotent stem cells, or hematopoietic stem cells. The cells may be obtained from humans, monkeys, chimpanzees, dogs, cats, mice, rats, and transgenic species thereof. The cells may be obtained from established cell lines.

The above cells may be obtained by any known means. The cells may be autologous, syngeneic, allogeneic, or xenogeneic to the recipient of the engineered cells.

The term "autologous" refer to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "syngeneic" refers to an extremely close genetic similarity or identity especially with respect to antigens or immunological reactions. Syngeneic systems include for example, models in which organs and cells (e.g. cancer cells and their non-cancerous counterparts) come from the same individual, and/or models in which the organs and cells come from different individual animals that are of the same inbred strain.

In certain embodiments, T and NK cells are derived from human peripheral blood mononuclear cells (PBMC), leukapheresis products (PBSC), human embryonic stem cells (hESCs), induced pluripotent stem cells (iPSCs), bone marrow, or umbilical cord blood.

The potential disadvantages of using NK cells in CAR therapy include a lack of persistency that may reduce long-term efficacy.

Finding matching donor T cells for generating CAR T cells could be a challenge as un-matched T cells could attach to the recipient's tissues, resulting in graft vs. host disease (GVHD).

Recent studies have shown that gene editing through CRISPR-Cas9 for generation of universal CAR T cells may increase cancer risk by creating unintentional mutations and disrupting the function of the p53 repair protein. Given this risk, it is important to seek methods that avoid genome editing when creating a CAR therapy for patients. The natural killer (NK) cell is an ideal platform for creating a universal CAR that avoids risks associated with genome editing. However, the life expectancy of NK CAR cells in vivo is very short, with a lifespan of approximately one week In one embodiment, the present disclosure comprises a method of generating chimeric antigen receptor (CAR)-modified NK cells with long-lived or long persistency in vivo potential for treating a disease. Surprisingly, it is found that CAR NK cells co-expressing IL-15/IL-15sushi or IL-15/IL-15 sushi anchor can extend survival for a long period of time.

In further embodiment, the extension of CAR NK cell survival can be achieved by co-expressing the IL-15/IL-15 anchor.

In some embodiments, CAR NK cells co-expressing IL-15/IL-15sushi or IL-15/IL-15sushi anchor can be scaled up and used as an off-the-shelf product.

In one embodiment, CAR NK cells co-expressing IL-15/IL-15 sushi or IL-15/IL-15sushi anchor are capable of continuing supportive cytokine signaling, which is critical to their survival post-infusion in a patient.

In some embodiments, CAR NK T cells co-expressing IL-15/IL-15sushi or IL-15/IL-15sushi anchor can be scaled up and used as an off-the-shelf product.

In one embodiment, CAR NK T cells co-expressing IL-15/IL-15 sushi or IL-15/IL-15sushi anchor are capable of continuing supportive cytokine signaling, which is critical to their survival post-infusion in a patient.

In further embodiment, the extension of CAR NK cell survival can be achieved by co-expressing a cytokine selected from a group of IL-7, IL-15, IL-15/IL-15 anchor, IL-15/IL-15RA, IL-12, IL-18 and IL-21.

In one embodiment, CAR NK T cells co-expressing IL-15/IL-15 sushi or IL-15/IL-15sushi anchor are capable of continuing supportive cytokine signaling, which is critical to their survival post-infusion in a patient.

In further embodiment, the extension of CAR NK T cell survival can be achieved by co-expressing a cytokine selected from a group of IL-7, IL-15, IL-15/IL-15 anchor, IL-15/IL-15RA, IL-12, IL-18 and IL-21.

Natural killer T (NK T) cells are a group of T cells that share properties of both T cells and natural killer cells.

In an embodiment, the IL-15 product is modified to create a disulfide bond linking the IL-15/sushi domain complex with an Fc region, such as from IgG1. In this embodiment, the IL-15/sushi complex can be linked to the Fc region, which will form a dimer with a disulfide bridge linking the two molecules. In an embodiment, the leucine at position 52 of the IL-15 is replaced with a cysteine and the serine at position 40 of the Sushi domain is replaced with a cysteine.

In an embodiment, the inducible promoter causes expression upon activation of cellular pathways, such as the T-cell receptor pathway. In this embodiment, expression of the gene of interest will be induced upon activation of the T cell receptor or similar pathways, including those activated by CARs. Those skilled in the art would understand this to include promoters such as those under the control of nuclear factor of activated T cells (NFAT) promoter including portions of the IL-2 promoter or synthetic promoters consisting of NFAT-binding motifs, the sequences of which are well-described. These are only examples of activation-induced promoters and are not limiting.

uCAR NK Cells

The majority of current clinical trials or therapies infuse autologous CAR T cells, as allogeneic CAR T cells are capable of inducing GVHD (graft-versus-host disease) in recipients. Although this autologous approach achieved remarkable clinical successes, the process of manufacturing a patient-specific T cell product is both time-consuming and expensive. Furthermore, it is not always possible to collect enough T cells from a heavily pretreated patient to successfully generate sufficient doses of CAR T cells. There is great demand for the development of an off-the-self allogeneic CAR product. NK cells are similar to T cells in that they are highly cytotoxic immune effectors. In contrast to T cells, NK cells bear the property of killing their targets through an on-specific manner. NK cells can be used as an off-the-self allogeneic product because they usually lack the potential to cause GVHD. The major disadvantage of using NK cells is their lack of persistence in vivo, with a half-life of only about a week.

In some embodiments, the present invention discloses a form of universal CAR-expressing NK cells or NK T cells from a healthy donor that can be stored and then infused into an individual on demand. In further embodiments, the invention comprises a method of generating of off-the-self universal CAR NKs from allogeneic healthy donors that can be infused to any patient without causing GVHD.

In some embodiments, NK cell or NK T is obtained from an umbilical cord blood bank and a peripheral blood bank. In a further embodiment, NK is an induced pluripotent stem cell or embryonic stem cell or NK-92 cell.

In some embodiments, the present disclosure comprises a method for having a CAR or compound CAR (cCAR) co-expressing IL-15/IL-15sushi in a NK cell. These engineered NK cells are called uCAR NK cells.

In some embodiments, uCAR NK cells have CAR or cCAR co-expressing IL-15/IL-15sushi. In further embodiments, uCAR NK cells is capable of persisting for more than one week in vivo.

In some embodiments, the present disclosure comprises a method for a uCAR NK cell with a vector expressing a CAR or cCAR with IL-15/IL-15sushi.

In some embodiments, co-expression of IL-15/IL-15sushi with a CAR or cCAR provides long-term persistence for a NK cell in a subject.

In some embodiments, co-expression of IL-15/IL-15sushi with a CAR or cCAR provides long-term durable remission in patients by increasing the sensitivity of CAR recognition of target cancer cells or by recruiting innate immune cells to cancer cells.

In some embodiments, the present disclosure comprises a method for generating a NK cell with one CAR or cCARs co-expressing IL-15/IL-15sushi. In further embodiments, a particular tumor antigen targeted by an antigen recognition domain in a CAR can be selected from the group of, but not limited to: GD2, GD3, interleukin 6 receptor, FSHR, ROR1, PSMA, PSCA (prostate stem cell antigen), MAGE A3, Glycolipid, glypican 3, F77, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, NKG2D, NKG2D receptors, immunoglobin kappa and lambda, CD38, CD52, CD47, CD200, CD70, CD56, CD19, CD20, CD22, CD38, BCMA, CS1, BAFF receptor, TACI, CD3, CD4, CD8, CD5, CD7, CD2, and CD138.

In some embodiments, the present disclosure comprises a method for the treatment of a disorder or disease by the infusion of a therapeutically effective amount of NK cells that are genetically engineered to express IL-15/IL-15sushi and/or a CAR with an antigen recognition domain for a particular tumor antigen. In further embodiments, a particular tumor antigen targeted by an antigen recognition domain can be selected from the group of, but not limited to: GD2, GD3, interleukin 6 receptor, FSHR, ROR1, PSMA, PSCA (prostate stem cell antigen), MAGE A3, Glycolipid, glypican 3, F77, WT1, CEA, HER-2/neu, MAGE-3, MAGE-4, MAGE-MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, NKG2D, NKG2D receptors, immunoglobin kappa and lambda, CD38, CD52, CD47, CD200, CD70, CD56, CD19, CD20, CD22, CD38, BCMA, CS1, BAFF receptor, TACI, CD3, CD4, CD8, CD5, CD7, CD2, and CD138.

In some embodiments, the administration of a high dose of uCAR NK cells can cause cytokine release syndrome (CRS). In present disclosure comprises a method of reduction or avoidance of CRS by providing a subject with a lower doses or split doses of uCAR NK cells.

Suicide and Safety Switch Systems

The engineered cells of the present disclosure may also include a suicide system. Suicide systems provide a mechanism whereby the engineered cell, as described above, may be deactivated or destroyed. Such a feature allows precise therapeutic control of any treatments wherein the engineered cells are used. As used herein, a suicide system provides a mechanism by which the cell having the suicide system can be deactivated or destroyed. Suicide systems are well known in the art.

In one embodiment, a suicide system includes a gene that can be pharmacologically activated to eliminate the containing cells as required. In specific aspects, the suicide gene is not immunogenic to the host harboring the polynucleotide or cell. In one example, the suicide system includes a gene that causes CD20 to be expressed on the cell surface of the engineered cell. Accordingly, administration of rituximab may be used to destroy the engineered cell containing the gene.

In some embodiments, the suicide system includes an epitope tag. Examples of epitope tags include a c-myc tag, CD52 streptavidin-binding peptide (SBP), and truncated EGFR gene (EGFRt). In this embodiment, the epitope tag is expressed in the engineered cell. Accordingly, administration of an antibody against the epitope tag may be used to destroy the engineered cell containing the gene.

In another embodiment, the suicide system includes a gene that causes truncated epidermal growth factor receptor to be expressed on the surface of the engineered cell. Accordingly, administration of cetuximab may be used to destroy the engineered cell containing the gene.

In another embodiment, the suicide system includes CD52 to be expressed on the surface of the engineered cell. Accordingly, administration of anti-52 monoclonal antibody (CAMPATH, alemtuzumab) may be used to destroy the engineered cell containing the gene.

In another embodiment, the suicide system includes CAMPATH (alemtuzumab). Accordingly, administration of anti-52 monoclonal antibody (CAMPATH) may be used to destroy the engineered cell without expressing a tag or a gene as CAR T cells or T cells highly express CD52.

In another embodiment, the suicide gene may include caspase 8 gene, caspase 9 gene, thymidine kinase, cytosine deaminase (CD), or cytochrome P450.

Examples of further suicide systems include those described by Jones et al. (Jones B S, Lamb L S, Goldman F and Di Stasi A (2014) Improving the safety of cell therapy products by suicide gene transfer. Front. Pharmacol. 5:254. doi: 10.3389/fphar.2014.00254), which is herein incorporated by reference in its entirety.

Compound CAR (cCAR)

As used herein, a compound CAR (cCAR) or multiple CAR refers to an engineered cell having at least two complete and distinct chimeric antigen receptor polypeptides. As used herein, a "distinct chimeric antigen receptor polypeptide" has a unique antigen recognition domain, a signal peptide, a hinge region, a transmembrane domain, at least one costimulatory domain, and a signaling domain. Therefore, two unique chimeric antigen receptor polypeptides will have different antigen recognition domains. The signal peptide, hinge region, transmembrane domain, at least one costimulatory domain, and signaling domain may be the same or different between the two distinct chimeric antigen receptor polypeptides. As used herein, a chimeric antigen receptor (CAR) unit refers to a distinct chimeric antigen receptor polypeptide, or a polynucleotide encoding for the same.

As used herein, a unique antigen recognition domain is one that is specific for or targets a single target, or a single epitope of a target.

As used herein, in the context of compound CAR. A single chimeric antigen receptor polypeptide has only one unique antigen recognition domain. By way of further explanation, this single antigen recognition domain recognizes and binds to a single antigen or a single antigen epitope only.

In some embodiments, the compound CAR targets the same antigen. For example, cCAR targets different epitopes or parts of a single antigen. In some embodiments, each of the CAR units present in the compound CAR targets different antigen specific to the same or different disease condition or side effects caused by a disease condition.

In some embodiments, the compound CAR targets two different antigens.

Creation of compound CARs bearing different CAR units can be quite challenging: (1) CAR-CAR interactions might have a deleterious effect and an appropriate CAR design is a key to offset this effect; (2) a compound CAR in a single construct could increase the length of the expression cassette, which may cause the reduction of the viral titer and level of protein expression; (3) an appropriate design to include various CAR body elements particularly to select a strategy to express multiple CARs in a single vector is required; (4) A strong promoter is particularly important for a compound CAR that bears additional units of CAR; (5) The hinge region in the CAR needs to be designed so that interaction of the hinge region between each CAR unit is avoided preferably; (6) two or more units of CARs expressing in a cell may cause toxic effects (CAR-CAR interaction). Applicants herein provide novel and surprising CAR compositions and methods to overcome these hurdles.

The transduction efficiency (percentage of CAR T cells) for cCARs is often lower than for a single-unit CAR. There are several ways to improve efficiency, at both the transfection and transduction steps. To improve viral titer for making cCARs, it is preferred to use LentiX™ 293 T (Clontech/Takara) packaging cell line, which is selected for high titer lentivirus production, instead of the commonly used HEK-293FT. It is also preferable to increase the amount of plasmid DNA (containing the cCAR construct) 1.5- to 2.0-fold when transfecting packaging cells, to increase transfection efficiency. The amount of viral packaging plasmids and transfection reagent remains the same during the forming of complexes. Transduction efficiency can be further enhanced by lowering the ratio of T cells to viral vector during the transduction step, to $0.3 \times 10^6$ cells per mL, and increasing the volume of lentiviral supernatant or lentiviruses.

In one embodiment, the present disclosure provides an engineered cell having multiple CAR units. This allows a single engineered cell to target multiple antigens. Targeting multiple surface markers or antigens simultaneously with a multiple CAR unit prevents selection of resistant clones and reduces tumor recurrence. Multiple CAR T cell immunotherapies, with each individual component CAR comprising various domains and activation sites has not yet been developed for any malignancies.

In one aspect of the present disclosure, cCAR includes multiple CAR units. In some embodiments, cCAR includes at least two CAR units. In another embodiment, the cCAR includes at least three CAR units. In another embodiment, the cCAR includes at least four units.

In one embodiment, the present disclosure provides an engineered cell having at least two distinct chimeric antigen receptor polypeptides, each having a different antigen recognition domain.

In one embodiment, the engineered cell having at least two distinct chimeric antigen receptor polypeptides is a T-cell or NK T-cell. The T-cell may be engineered so that it does not express a cell surface antigen. For example, a T-cell may be engineered so that it does not express a CD45 cell surface antigen.

In a preferred embodiment, the engineered cell having at least two distinct chimeric antigen receptor polypeptides is a primary NK cell or NK T cell isolated from the peripheral blood or cord blood and NK-92 cells, such that it is administered "off-the-shelf" to any mammal with a disease or cancer.

In one embodiment, the engineered cell includes (i.) a first chimeric antigen receptor polypeptide comprising a first antigen recognition domain, a first signal peptide, a first hinge region, a first transmembrane domain, a first co-stimulatory domain, and a first signaling domain; and (ii.) a second chimeric antigen receptor polypeptide comprising a second antigen recognition domain, a second signal peptide, a second hinge region, a second transmembrane domain, a second co-stimulatory domain, and a second signaling domain. The first antigen recognition domain is different from the second antigen recognition domain.

In a preferred embodiment, each engineered CAR unit polynucleotide has different nucleotide sequences in order to avoid homologous recombination.

In one embodiment, the target of the first antigen recognition domain is selected from the group of, but not limited to, GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, NKG2D, NKG2D receptors, immunoglobin kappa and lambda, CD38, CD52, CD19, CD20, CD22, CD38, BCMA, CS1, BAFF receptor, TACI, CD3, CD4, CD8, CD5, CD7, CD2, and CD138; and the target of the second recognition domain is selected from the group consisting of GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, NKG2D, NKG2D receptors, immunoglobin kappa and lambda, CD38, CD52, CD19, CD20, CD22, CD38, BCMA, CS1, BAFF, BAFF receptor, April receptor, TACI, CD3, CD4, CD8, CD5, CD7, CD2, and CD138.

In one embodiment, the target of the first antigen recognition domain is selected from the group of, but not limited to: GD2, GD3, CD19, CD20, CD22, CD38, CD138, BCMA, CS1, BAFF, BAFF receptor, TACI, April, April receptor, CD3, CD4, CD5, CD7, CD2, CLL-1, CD33, CD123, NKG2D receptors and CD30; the target of the second recognition domain is selected from a group consisting of GD2, GD3, CD19, CD20, CD22, CD38, CD138, BCMA, CS1, BAFF, April, April receptor, BAFF receptor, TACI, CD3, CD4, CD5, CD7, CD2, CLL-1, CD33, CD123, NKG2D receptors and CD30.

In one embodiment, each CAR unit includes the same or different hinge region. In another embodiment, each CAR unit includes the same or different transmembrane region. In another embodiment, each CAR unit includes the same or different intracellular domain.

In one embodiment, each CAR unit includes the CD3 zeta chain signaling domain.

In one embodiment, each distinct CAR unit includes different co-stimulatory domains. For example, the first chimeric antigen receptor polypeptide includes a 4-1BB co-stimulatory domain; and the second chimeric antigen receptor polypeptide includes a CD28 co-stimulatory domain.

In one embodiment, each distinct CAR unit includes the same co-stimulatory domains. For example, the first chimeric antigen receptor polypeptide includes a 4-1BB co-stimulatory domain; and the second chimeric antigen receptor polypeptide includes a 4-1BB co-stimulatory domain.

In another embodiment, the hinge region is designed to exclude amino acids that may cause undesired intra- or intermolecular interactions. For example, the hinge region may be designed to exclude or minimize cysteine residues to prevent formation of disulfide bonds. In another embodiment, the hinge region may be designed to exclude or minimize hydrophobic residues to prevent unwanted hydrophobic interactions.

Compound CAR can perform killing independently or in combination. Multiple or compound CAR comprises same or different hinge region, same or different transmembrane, same or different co-stimulatory and same or different intracellular domains. Preferably, the hinge region is selected to avoid the interaction site.

The compound CAR of the present disclosure may target same or different tumor populations in T or NK cells. The first CAR, for example, may target the bulky tumor population and the next or the second CAR, for example, may eradicate cancer or leukemic stem cells, to avoid cancer relapses.

In accordance with the present disclosure, it was surprisingly found that the compound CAR in a T or NK cells targeting different or same tumor populations combat tumor factors causing cancer cells resistant to the CAR killing activity, thereby producing down regulation of the target antigen from the cancer cell surface. It was also surprisingly found that this enables the cancer cell to "hide" from the CAR therapy referred to as "antigen escape" and tumor heterogeneity, by which different tumor cells can exhibit distinct surface antigen expression profiles. As present disclosure below, it is surprisingly found that the compound CAR has significant advantages over single-CAR therapies due to its multi-targeting ability. While loss of a single antigen under antigen-specific selection pressure is possible, loss of two major antigens simultaneously is much less likely.

In one embodiment, the antigen recognition domain includes the binding portion or variable region of a humanized monoclonal or humanized polyclonal antibody directed against (selective for) the target.

In one aspect to the invention, an antigen recognition domain can be a bispecific tandem chimeric antigen receptor that includes two targeting domains. In further embodiment, there is a multispecific tandem chimeric antigen receptor that includes three or more targeting domains.

In certain aspects to the invention, an antigen recognition domain can be a bispecific chimeric antigen receptor (derived from a bispecific antibody) that includes two targeting domains.

In one embodiment, a bispecific tandem chimeric antigen receptor or a bispecific chimeric antigen receptor effectively offsets tumor escape or antigen loss and increases the sensitivity of antigen recognition.

In another embodiment, the antigen recognition domain includes camelid single domain antibody, or portions thereof. In one embodiment, camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001) and also includes an isolated VHH antibody of camelid, a recombinant VHH antibody of camelid, or a synthetic VHH antibody of camelid.

Enhancers for CAR Functions and Promotion of T and Innate Cell Expansion or Proliferation IL-15/IL15sushi Enhancer In one embodiment, A CAR construct with IL-15/IL15sushi enhancer is shown in FIG. 53, A CAR is equipped with secreting IL-15/IL-15sushi complexes. A CAR with IL-15/IL-15 sushi is linked with the P2A self-cleaving sequence. The IL-15/IL-15sushi portion is composed of IL-2 signal peptide fused to IL-15 and linked to the sushi domain of IL-15 alpha receptor via a 26-amino acid poly-proline linker. CAR has scFv, costimulatory domain (including, but not limited to CD28 or 4-1BB) and intracellular signaling, CD3 zeta chain. The IL-15 signal peptide in the IL-15 is replaced with IL-2 signal peptide (leader sequence), a strong signal peptide to provide a high efficiency of IL-15/IL-15sushi secretion. The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7 and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

The IL-15 can be a variant, IL-15N72D described in elsewhere, U.S. Pat. No. 8,507,222 B2.

IL-15/IL15sushi Anchor Enhancers

In one embodiment, a CAR construct with IL-15/IL-15sushi anchor is shown in FIG. 54. A CAR IL-15/IL15sushi anchor construct consists a SFFV promoter driving the expression of a CAR and an IL-15/IL-15sushi anchor (also called anchor) linked by a P2A peptide. Upon cleavage of this P2A peptide, IL-15/IL-15 anchor CAR splits to a CAR and an IL-15/IL-15suchi anchor. The IL-15/IL-15sushi portion of anchor is composed of IL-2 signal peptide fused to IL-15 and linked to sushi domain of IL-15 alpha receptor via a 26-amino acid poly-proline linker. Both CAR and anchor comprise a hinge (H) region, a transmembrane domain (TM). CAR also has scFv, costimulatory domain (including, but not limited to CD28 or 4-1BB) and intracellular signaling, CD3 zeta chain while anchor does not bear these components. IL-15/IL-15sushi anchor provides a synergistic effect of T cell activation or anti-tumor activity with CD28 or 4-1BB. CAR is more powerful when equipped with IL-15/IL-15sushi anchor (FIG. 54)

The IL-15 can be a variant, IL-15N72D described in elsewhere, U.S. Pat. No. 8,507,222 B2

4-1BBL Enhancer

In another embodiment, a CAR construct with a 4-1BBL enhancer is shown in FIG. 55. A CAR 4-1BBL construct consists a SFFV promoter driving the expression of a CAR and an enhancer, 4-1BBL (CD137L) linked by a P2A peptide. Upon cleavage of this P2A peptide, A CAR construct with 4-1BBL splits to a CAR and the full length of 4-1BBL protein. A CAR comprises a leader sequence and scFv, a hinge (H) region, a transmembrane domain (TM). CAR also has costimulatory domain (including, but not limited to, CD28 or 4-1BB) and intracellular signaling, CD3 zeta chain while 4-1BBL does not bear these components. 4-1BBL provides a synergistic effect of T cell activation or anti-tumor activity with CD28 or 4-1BB. CAR is more powerful when equipped with 4-1BBL.

IL-15 Enhancer

A CAR function can be enhanced by incorporating a secreting enhancer, IL-15 shown in FIG. 56. A CAR 4-IL-15 construct consisted a SFFV promoter driving the expression of a CAR and an enhancer, IL-15 linked by a P2A peptide. Upon cleavage of this P2A peptide, A CAR construct with IL-15 splits to a CAR and the full length of IL-15 protein. A CAR comprises a leader sequence and scFv, a hinge (H) region, a transmembrane domain (TM). CAR also has costimulatory domain (including, but not limited to, CD28 or 4-1BB) and intracellular signaling, CD3 zeta chain while IL-15 does not bear these components. Secreting IL-15 provides a synergistic effect of T cell activation or anti-tumor activity with CD28 or 4-1BB. CAR is more powerful when secreting IL-15. The IL-15 signal peptide in the IL-15 was replaced with IL-2 signal peptide (leader sequence), a strong signal peptide to provide a high efficiency of IL-15 secretion.

A CAR with Multiple Enhancers

An example for generation of a CAR with multiple enhancers (CAR super). FIG. 57, a schematic showing a CAR enhancer construct. The construct consists a SFFV promoter driving the expression of a CAR and enhancers, 4-1BBL (CD137L) and IL-15/IL-15sushi linked by a P2A and T2A peptide, respectively. Upon cleavage of this P2A and T2A peptides, a CAR construct with 4-1BBL and IL-15/IL-15sushi splits to a CAR and the full length of 4-1BBL protein, and secreting IL-15/IL-15sushi. A CAR comprises a leader sequence and scFv, a hinge (H) region, a transmembrane domain (TM). CAR also has costimulatory domain (including, but not limited to, CD28 or 4-1BB) and intracellular signaling, CD3 zeta chain. 4-1BBL ligand provides a synergistic effect of T or NK cell activation or anti-tumor activity with CD28 or 4-1BB (but not limited to). The peptide self cleavage peptides of the construct may include, but is not limited to, P2A, T2A, F2A and E2A. The secreting enhancer (s) of the construct may also include, but is not limited to, IL-15/IL-15sush, IL-15, IL-21, IL-18, IL-7 and IL-12. The secreting enhancer, such as IL-15/IL-15sushi enhances CAR T or NK cell expansion and persistency. The soluble IL-15/IL-15sushi fusion are stable and functions as an unexpected and powerful immunomodulatory for CAR T/NK cells and their neighbor tumor immune response cells. The soluble IL-15/IL-15sushi fusion are stable and enhances CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

BCMA-CS1 Compound CAR (BCMA-CS1 cCAR)

Multiple myeloma (MM) is a blood cancer caused by the unusually rapid proliferation of plasma cells and accounts for 18% of all blood cancers in the United States. Treatment options for MM include chemotherapy, corticosteroid therapy, targeted therapy, high-dose chemotherapy with stem cell transplant, biological therapy, radiation therapy, monoclonal antibodies, proteasome inhibitors, and surgery. Even with these available treatments, the five-year survival rate for MM remains at 49.6%. However, there remains no cure for MM, and nearly all patients relapse after treatment.

Current CAR technology efforts in multiple myeloma involve the use of a BCMA (CD269) targeted CART-cell against bulk disease spearheaded by James Kochenderfer (NIH). Those patients in remission after BCMA CAR treatment eventually relapse and this may due to the fact that some myeloma cells are dim (weak) or negative expression for BCMA. Therefore, a single target for CAR based treatment may not be sufficient to prevent myeloma relapse. CS1 (SLAMF7) is another good target for myeloma as its expression is typically high and uniform in myeloma cells as well as being implicated in myeloma cell adhesion and tumorigenicity.

The present disclosure is composed of a single CAR T-cell expressing 2 discrete CAR units in a vector with independent signaling domains can be utilized as a novel approach for targeting multiple antigens and potentially avoiding tumor relapse. A compound CAR (cCAR) comprising of a BCMA CAR linked to a CS1 CAR via a self-cleaving P2A peptide and expressed both functional CAR molecules on the surface of a T cell.

In the present disclosure, it was surprisingly found that this BCMA-CS1 cCAR (BC1cCAR) T-cell exhibits potent and specific anti-tumor activity in vitro, as well as controlling significant tumor growth in vivo. We demonstrate, for the first time, a 2-unit discrete CAR is able to target effectively both antigens in vitro, with potential implications for more comprehensive clinical outcomes. It is unexpected that targeting multiple myeloma with a compound CAR targeting both BCMA and CS1 in combination is a very strong strategy. This novel approach circumvents the antigen escape (loss of a single antigen) from selection pressure of single CAR treatment due to combinatorial pressure from a compound design.

BCMA (B-cell maturation antigen) and CS1 (SLAMF7) were preferably chosen as targets for our compound CAR because the vast majority of myeloma cases express either or both surface antigens, and these antigens do not include hematopoietic stem cells. The use of two different targets widely expressed on plasma cells, BCMA and CS1, can increase coverage and efficaciously eradicate cancerous cells to prevent antigen escape In this disclosure, it is surprisingly found that the addition of CS1 as a target to the BCMA CAR enhanced the anti-tumor response by eliminating surviving BCMA⁻CS1+ myeloma cells to reduce the risk of relapse. BCMA and CS1 (CD319) are both widely expressed on MM cells, and this high expression allows the BCMA-CS1 cCAR to have a comprehensive coverage of all potentially cancerous cells. This allows for a more complete elimination of cancerous cells to reduce antigen escape by hitting hard with multiple targets simultaneously before resistance develops.

In one embodiment, BCMA-CS1 directed BCMA-CS1cCAR (BC1cCAR) therapy is as a "bridge" to bone marrow transplant (BMT) or combination with a heavy chemotherapy plus BMT. BCMA-CS1 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA-CS1 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, BCMA-CS1 cCAR therapy can have further applications for patients with BCMA+ and/or CS1+ multiple myelomas beyond a bridge to bone marrow transplantation. BCMA-CS1cCAR therapy as a standalone therapy, or as a part of a patient-individualized immunochemotherapy regimen. For elderly patients, or for those with comorbidities who cannot tolerate highly intensive chemotherapy or BMT, this might be a promising strategy to prolong patient's survival time and reserve better life quality.

In some embodiments, BCMA-CS1cCAR T-cell therapy can be developed as a "bridge to transplant," a supplement to chemotherapy, or as a standalone therapy for patients with multiple myeloma.

In some embodiments, the present disclosure provides a compound CAR polypeptide engineered cell that targets cells expressing BCMA or CS1 antigens or both. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

It was surprised to find that co-expression of IL-15/IL-15sushi with cCAR could provide long-term durable remission in patients by increasing the sensitivity of CAR recognition of target cancer cells or recruiting innate immune cells to cancer cells.

Without wishing to be bound by theory, it is believed that co-expression of IL-15/IL-15sushi anchor or 4-1BBL with BCMA-CS1 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with BCMA-CS1 cCAR provides long-term durable remission in patients by increasing the sensitivity of CAR recognition of target cancer cells or recruiting innate immune cells to cancer cells.

In one embodiment, the engineered cell includes a BCMA-CS1 cCAR polypeptide and IL-15/IL-15sushi (SEQ ID NO. 42), and corresponding nucleotides (SEQ ID NO. 43).

BCMA1-BCMA2 Compound CAR (BCMA1-BCMA2 cCAR) (FIG. 38)

Initial remission of most B-ALL can be seen in CD19 CAR T therapy but relapses with epitope loss occur in 10% to 20% of responders.

Current CAR technology efforts in multiple myeloma involve the use of a BCMA (CD269) targeted CAR T-cell against multiple myeloma spearheaded by James Kochenderfer (NIH). Those patients in initial remission after BCMA CAR treatment eventually relapse and this may due to the fact that some myeloma cells are dim (weak) or negative expression for BCMA. In addition, potency of a single CAR is also an issue for eliminating multiple myeloma cells in the patients. Therefore, a single target for CAR based treatment may not be sufficient to prevent myeloma relapse.

In one embodiment, the antibody recognition domain includes the binding variable region of a monoclonal antibody, single chain fragment variable (scFv). The scFv includes one light and heavy of antibody. In a particular embodiment, antigen recognition domain is composed of two different heavy chain domains (VHH). Each heavy chain domain binds to a different epitope of the same antigen or different antigen. A VHH antibody is more stable and robust than a whole antibody.

In some embodiments, the compound CAR targets the same antigen. For example, cCAR targets different epitopes or parts of a single antigen. In some embodiments, each of the CAR units present in the compound CAR targets different epitopes specific to the same antigen but different locations.

In some embodiments, a compound CAR targets different epitopes on one antigen.

The present disclosure is composed of a single CAR T-cell expressing two discrete CAR units in a vector with independent signaling domains can be utilized as a novel approach for targeting different epitopes on one antigen, and potentially avoiding tumor epitope skipping or epitope loss or epitope escape. A compound cCAR (BCMA1-BCMA2 cCAR) is comprising of one BCMA CAR (BCMA1 CAR) linked to another BCMA CAR (BCMA2 CAR) via a self-cleaving P2A peptide and expressed both functional CAR molecules on the surface of a T cell. Both units of CARs in cCAR target the same antigen, BCMA.

In one embodiment, the engineered cell includes a first chimeric antigen receptor polypeptide having a BCMA antigen recognition epitope and second chimeric antigen receptor polypeptide having a different BCMA recognition epitope. In one embodiment, this engineered cell includes a polypeptide of SEQ ID NO. 3 and corresponding polynucleotide of SEQ ID NO. 4.

In the present disclosure, it was surprisingly found that this BCMA1-BCMA2 cCAR T-cell exhibits potent and specific anti-tumor activity in vitro, as well as controlling significant tumor growth in vivo. We demonstrate, for the first time, a 2-unit discrete CAR is able to target effectively both different epitopes on one antigen, BCMA in vitro, with potential implications for more comprehensive clinical outcomes. It is unexpected that targeting multiple myeloma with a compound CAR targeting different epitopes in combination is a very strong strategy. This novel approach circumvents the epitope escape (loss of a single epitope or epitope skipping) from selection pressure of single CAR treatment due to combinatorial pressure from a compound design.

In this disclosure, it is surprisingly found that the addition of epitope as a target to the BCMA CAR enhances the anti-tumor response and reduces the risk of multiple myeloma relapse due to the loss of BCMA epitope.

In one embodiment, BCMA1-BCMA2 directed therapy is as a "bridge" to bone marrow transplant (BMT) or combination with a heavy chemotherapy plus BMT. BCMA1-BCMA2 cCAR can increase the sensitivity of recognition of BCMA antigen, and offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA1-BCMA2 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In some embodiments, the present disclosure provides a compound CAR polypeptide engineered cell that targets two different epitopes on the BCMA antigen. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

Without wishing to be bound by theory, it is believed that co-expression of IL-15/IL-15sushi or IL-15/IL-15sushi anchor or 4-1BBL with BCMA1-BCMA2 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with BCMA1-BCMA2 cCAR provides long-term durable remission in patients by increasing the sensitivity of CAR recognition of target cancer cells or recruiting innate immune cells to cancer cells.

CD123-CD33 Compound CAR (CD123-CD33 cCAR)

Translating CAR success to AML requires a careful understanding of characteristics unique to the disease. AML is characterized by the presence of blast cells, which are highly aggressive and rapidly dividing cells that form the bulk of disease. Unlike B-cell malignancies, AML is uniquely challenging to treat due to the role of leukemic stem cells (LSCs). LSCs are a population of cells expressing markers of hematopoietic stem cells (CD34+CD38−) that are capable of initiating and maintaining hematopoietic malignancy, producing clonal cell populations that overtake healthy bone marrow. Since LSCs remain mostly in the quiescent phase of the cell cycle, chemotherapy directed against rapidly dividing tumor populations leaves LSCs untouched. Most often it is this elusive population that comprises minimal residual disease (MRD) and is responsible for inevitable relapse after AML treatment. Successful translation of CAR therapy to AML to completely eliminate disease and ensure no relapse requires careful antigen selection that will enable eradication of not just bulk leukemic disease, but also leukemic stem cells.

It is expected that a CD123-CD33 cCAR that will ablate both CD33+ and CD123+ cells without causing a CAR and CAR interaction. A useful analogy in this case would be to consider AML as a cancer tree with leaves and roots. While the leaves make up the majority/bulk of the disease (these are the CD33+ AML blast cells), trimming these leaves does not prevent the tree from growing further unless you also pull the tree from its root (these are the CD123+CD34+CD38−LSCs). A study of 319 AML patients and found that 87.8% of cases expressed CD33, so it follows that targeting CD33 might most leukemic cells. However, patients treated with gentuzumab ozogamicin, an anti-CD33 antibody therapy linked to calicheamicin, relapsed with CD33+ AML likely due to acquired chemoresistance to calicheamicin. Therefore, while targeting CD33 eliminates the majority of disease, the chemoresistant LSCs must also be targeted or relapse will occur. This can be achieved by targeting CD123, which is overexpressed on CD34+CD38−LSCs as compared to healthy hematopoietic stem cells. Considering that 97.2% of AML cases express at least one of the two targets, targeting both CD123 and CD33 would therefore eliminate all cancer cells in the majority of patients, increasing treatment efficacy and uprooting the cancer tree.

AML is a rapidly progressing blood cancer that accounts for about 15-20% of acute childhood leukemias and 80% of acute adult leukemia cases. Patients are nowadays still treated by high-dose multi-agent chemotherapy potentially followed by hematopoietic stem cell transplantation. Despite such intensive therapies, which are often associated with considerable toxicities and even death, about 60-70% of AML patients still relapse due to acquired therapy resistance or LSC re-emergence. Moreover, the five-year survival rate from AML remains at a dismal 27%. However, there are a limited number of clinical trials attempting the use of CARs to treat AM.

The present disclosure is composed of a single CAR T-cell expressing two discrete CAR units in a vector with independent signaling domains can be utilized as a novel approach for targeting multiple antigens and potentially avoiding tumor relapse. A compound CAR (cCAR) comprising of a CD123 CAR linked to a CD33 CAR via a self-cleaving P2A peptide and expressed both functional CAR molecules on the surface of a T cell.

In the present disclosure, it was surprisingly found that this CD123-CD33 cCAR T-cell exhibits potent and specific anti-tumor activity in vitro, as well as controlling significant tumor growth in vivo. We demonstrate, for the first time, a 2-unit discrete CAR is able to target effectively both antigens in vitro, with potential implications for more comprehensive clinical outcomes. It is unexpected that targeting AML with a compound CAR targeting both CD123 and Cd33 in combination is a very strong strategy. This novel approach circumvents disease relapses associated with LSCs, and antigen escape (loss of a single antigen) from selection pressure of single CAR treatment due to combinatorial pressure from a compound design.

In this disclosure, it is surprisingly found that the addition of CD123 as a target to the CD33 CAR enhanced the anti-tumor response by eliminating both leukemic blasts and its root, LSCs to reduce the risk of relapse. This allows for a more complete elimination of cancerous cells to reduce disease relapse by deleting both slowly growing LSCs and proliferative leukemic cells.

In this disclosure, it is surprisingly found that CD123-CD33 cCAR T-cells are able to eliminate regular leukemic cells and leukemic precursor cells to reduce the risk of relapse, and enhance anti-tumor activities.

In this disclosure, it is also surprisingly found that CD123-CD33 cCAR T-cells exhibit a more complete elimination of cancerous cells to reduce antigen escape by hitting hard with multiple targets simultaneously before resistance develops.

In one embodiment, CD123-CD33cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to, acute myeloid leukemia, myelodysplastic syndromes, chronic myeloid leukemia and chronic myeloproliferative disorders.

In another embodiment, CD123-CD33cCAR T-cell therapy can use to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, CD123-CD33cCAR T-cell therapy can have further applications for patients with Cd123+ and/or CD33+ leukemic patients beyond a bridge to bone marrow transplantation. CD123-CD33cCAR T-cell therapy as a standalone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

Without wishing to be bound by theory, it is believed that co-expression of IL-15/IL-15sushi or IL-15/IL-15sushi anchor or 4-1BBL with CD123-CD33 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD123-CD33 cCAR provides long-term durable remission in patients by increasing the sensitivity of CAR recognition of target cancer cells or recruiting innate immune cells to cancer cells.

In one embodiment, the engineered cell includes a CD123-CD33 cCAR polypeptide and IL-15/IL-15sushi (SEQ ID NO. 34), and corresponding nucleotides (SEQ ID NO. 35).

CLL-1-CD33 Compound CAR (CLL-1-CD33 cCAR)

A cCAR contains two units of CARs, CLL-1CAR and CD33 CAR targeting tumor cells expressing CLL-1 and CD33, respectively. CD33b CAR and CLL-1 CAR were used to construct a version of cCAR shown in FIG. 92. The construct comprises a SFFV promoter driving the expression of multiple modular units of CARs linked by a P2A peptide. Upon cleavage of the linker, the cCARs split and engage upon targets expressing CD33 and CLL-1. The activation domains of the construct included 4-1BB on the CD33b (CD33) CAR unit and a CD28 on the CLL-1 CAR unit. This CD33b-CLL-1 cCAR was designed to delete myeloid leukemic cells including leukemic stem cells.

At the present, therapies for MDS, MPN (chronic myeloproliferative neoplasms) and AML have focused on the leukemic blast cells because they are very abundant and clearly represent the most immediate problem for patients. Importantly, leukemic stem cells (LSCs) are quite different from most of the other leukemia cells ("blast" cells), and they constitute a rare subpopulation. While killing blast cells can provide short-term relief, LSCs, if not destroyed, will always re-grow, causing the patient to relapse. It is imperative that LSCs be destroyed in order to achieve durable cures for MDS disease. Unfortunately, standard drug regimens are not effective against MDS or MPN or AML LSCs. Therefore, it is critical to develop new therapies that can specifically target both the leukemic stem cell population and the bulky leukemic population. The compound CAR disclosed in the present disclosure target both populations and is embodied herein.

In one aspect of the present disclosure, CLL-1 antigen is one of the targets for cCAR therapy. C-type lectin-like-1 (CLL-1) is also known as MICL, CLEC12A, CLEC-1 and DCAL2. CLL-1 is a glycoprotein receptor and is expressed in hematopoietic cells. CLL-1 is absent on uncommitted CD34+/CD38− or CD34+/CD33−stem cells but present on subsets of CD34+/CD38+ or CD34+/CD33+ progenitor cells (Bakker et al, 2004). In addition, CLL-1 is not expressed in any other tissue.

CLL-1 expression is seen in acute myeloid leukemia (AML) blasts and leukemic stem cells. CLL-1 is expressed in a variety of leukemias including myelomonocytic leukemia (M4), acute monocytic leukemia (M5), acute promyelocytic leukemia (M3), chronic myeloid leukemia (CML), chronic myeloproliferative neoplasms and myelodysplastic syndromes (MDS).

CLL-1 is expressed on a subset of leukemic cells related to leukemic stem cells (LSCs), the ablation of which is essential in preventing disease refractoriness and relapse.

CD33 (Siglec-3) is a myeloid lineage-specific antigen expressed on early myeloid progenitors, most monocytic cells and approximately 90% of AML blasts, but absent on normal HSCs.

In one aspect of the present disclosure, CD33 antigen is one of the targets for cCAR therapy. CD33 is a transmembrane receptor expressed on 90% of malignant cells in acute myeloid leukemia. Thus, according to the present disclosure, CLL-1 and CD33 target antigens are particularly attractive from a safety standpoint.

In accordance with the present disclosure, the compound CLL-1-CD33 cCARs may be highly effective for therapeutic treatment of chronic myeloid leukemia (CML) population. In chronic myeloid leukemia (CML), there is a rare subset of cells that are CD34+CD38−. This population is considered as comprised of LSCs. Increased number of LSCs is associated with the progression of the disease. A small-molecule Bcr-Abl tyrosine kinase inhibitor (TKI) is shown to significantly improve the overall survival in CP-CML patients. However, LSCs are thought to be resistant to TKI therapy. A novel therapy targeting CML resistant LSCs is urgently needed for treatment of CML and the novel therapy is embodied in the compound CD33CLL-1 CAR disclosed in the present disclosure. CLL-1 expression is high in the CD34+CD38-population. In accordance with the present disclosure, the compound CD33CLL-1 CARs is highly effective for therapeutic treatment of this population.

In one embodiment of the present disclosure, leukemic cells expressing both CD33 and CLL-1 in the cCAR are used as a therapeutic treatment. CD33 is expressed on cells of myeloid lineage, myeloid leukemic blasts, and mature monocytes but not normal pluripotent hematopoietic stem cells. CD33 is widely expressed in leukemic cells in CML, myeloproliferative neoplasms, and MDS.

Since a significant number of patients with acute myeloid leukemia (AML) are refractory to standard chemotherapy regimens or experience disease relapse following treatment (Burnett 2012), the development of CAR T cell immunotherapy for AML has the potential to address a great clinical need. In the majority of these patients, leukemic cells express both CLL-1 and CD33, giving broad clinical applicability to the compound CLL-1-CD33 cCAR disclosed herein. Thus, the present disclosure discloses a novel multiple cCAR T/NK cell construct comprising multiple CARs targeting multiple leukemia-associated antigens, thereby offsetting antigen escape mechanism, targeting leukemia cells, including leukemic stem cells, by synergistic effects of co-stimulatory domain activation, thereby providing a more potent, safe and effective therapy.

In further embodiments, the present disclosure provides a method of eradicating or killing leukemic stem cells (LSCs) or bulk leukemic cells expressing CLL-1 or CD33, or both.

In this embodiment, a T or NK engineered cell having a CD33 unit and a CLL-1 unit is administered to a patient in need thereof.

In further embodiments, a compound CAR in a T or NK cell may be used to eradicate or kill CD34+CD38–leukemic stem cells or bulk leukemic cells expressing CLL-1 or CD33 or both.

The present disclosure further discloses a compound CAR construct with enhanced potency of anti-tumor activity against cells co-expressing target antigens, and yet retains sensitivity to tumor cells only expressing one antigen. In addition, each CAR of the compound CAR includes one or two co-stimulatory domains and exhibits potent killing capability in the presence of the specific target.

In this disclosure, it is surprisingly found that CLL-1-CD33 cCAR T-cells are able to eliminate regular leukemic cells and leukemic precursor cells to reduce the risk of relapse, and enhance anti-tumor activities.

In this disclosure, it is also surprisingly found that CLL-1-CD33 cCAR T-cells exhibit a more complete elimination of cancerous cells to reduce antigen escape by hitting hard with multiple targets simultaneously before resistance develops.

In one embodiment, CLL-1-CD33 cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to, acute myeloid leukemia, myelodysplastic syndromes, chronic myeloid leukemia and chronic myeloproliferative disorders.

In another embodiment, CLL-1-CD33cCAR T-cell therapy can use to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, CLL-1-CD33 cCAR T-cell therapy can have further applications for patients with CLL-1+ and/or CD33+ leukemic patients beyond a bridge to bone marrow transplantation. CLL-1-CD33cCAR T-cell therapy as a standalone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

Without wishing to be bound by theory, it is believed that co-expression of IL-15/IL-15sushi or IL-15/IL-15sushi anchor or 4-1BBL with CLL-1-CD33 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CLL-1-CD33 cCAR provides long-term durable remission in patients by increasing the sensitivity of CAR recognition of target cancer cells or recruiting innate immune cells to cancer cells.

In one embodiment, the engineered cell includes a CLL1-CD33 cCAR polypeptide and IL-15/IL-15sushi (SEQ ID NO.60), and corresponding nucleotides (SEQ ID NO. 61).

In one embodiment, the engineered cell includes a CLL-1 CAR polypeptide, 4-1BBL and IL-15/IL-15sushi (SEQ ID NO. 44), and corresponding nucleotides (SEQ ID NO. 45).

In one embodiment, the engineered cell includes a CD33 CAR polypeptide, 4-1BBL and IL-15/IL-15sushi (SEQ ID NO.20), and corresponding nucleotides (SEQ ID NO. 21).

CD123-NKG2D cCAR or CLL-1-NKG2D cCAR or CD33-NKG2D cCAR or BCMA-NKG2D cCAR

NKG2D (NKG2D receptor) is considered a transmembrane protein belonging to the CD94/NKG2 family of C-type lectin-like receptors. NKG2D can bind to at least 8 different ligands that are naturally expressed in AML, multiple myeloma or other leukemias. NKG2D ligands are induced-self proteins which are virtually absent or present only at very low levels on surface of normal cells but are overexpressed in cancer cells, including AML, and multiple myeloma. Therefore, they are good candidates for CAR targeting.

A cCAR contains two units of CARs, a CD123 CAR and NKG2D CAR that target tumor cells expressing CD123 and NKG2D ligands, respectively.

A cCAR contains two units of CARs, a CLL-1 CAR and NKG2D CAR that target tumor cells expressing CLL-1 and NKG2D ligands, respectively.

CD123-NKG2D cCAR or CLL-1-NKG2D cCAR or CD33-NKG2D cCAR are able to eliminate leukemias including AML, MDS, CML, and MPN.

In the present disclosure, BCMA-NKG2D cCAR is able to eliminate multiple myeloma.

In this disclosure, the addition of NKG2D as a target to the CD123 CAR or CLL-1 CAR or CD33 CAR enhances the anti-tumor response and reduces the risk of antigen escape associated with disease relapse because NKG2D is widely expressed on AML, MDS, CML and MPN.

BCMA and NKG2D ligands are both widely expressed on multiple myeloma cells, and this high expression allows the BCMA-NKG2D cCAR to have a comprehensive coverage of all potentially cancerous cells. This allows for a more complete elimination of cancerous cells to reduce antigen escape by hitting hard with multiple targets simultaneously before resistance develops.

BCMA–CD38 Compound CAR (BCMA–CD38 cCAR)

Current CAR technology efforts in multiple myeloma involve the use of a BCMA (CD269) targeted CART-cell against bulk disease spearheaded by James Kochenderfer (NIH). Those patients in remission after BCMA CAR treatment eventually relapse and this may due to the fact that some myeloma cells are dim (weak) or negative expression for BCMA. Therefore, a single target for CAR based treatment may not be sufficient to prevent myeloma relapse.

CD38 also known as cyclic ADP ribose hydrolase is a glycoprotein is found on the surface of many immune cells including CD4+, CD8+, B lymphocytes, plasma cells, and natural killer cells.

CD38 is another good target for myeloma as its expression is typically high and uniform in myeloma cells and lymphoma cells.

The present disclosure is composed of a single CAR T-cell expressing 2 discrete CAR units in a vector with independent signaling domains can be utilized as a novel approach for targeting multiple antigens and potentially avoiding tumor relapse. A compound CAR (cCAR) comprising of a BCMA CAR linked to a CD38 CAR via a self-cleaving P2A peptide and expressed both functional CAR molecules on the surface of a T cell. This compound cCAR expression is controlled by a strong promoter, SFFV to ensure adequate CAR expression.

In the present disclosure, BCMA–CD38 cCAR T-cell can provide potent and specific anti-tumor activity in controlling myeloma (FIG. 37). Targeting multiple myeloma with a compound CAR targeting both BCMA and CD38 in combination is a very strong strategy. This novel approach circumvents the antigen escape (loss of a single antigen)

from selection pressure of single CAR treatment due to combinatorial pressure from a compound design.

In this disclosure, the addition of CD38 as a target to the BCMA CAR enhanced the anti-tumor response by eliminating surviving BCMA⁻CD38+ myeloma cells to reduce the risk of relapse.

BCMA and CD38 are both widely expressed on multiple myeloma cells, and this high expression allows the BCMA-CD38 cCAR to have a comprehensive coverage of all potentially cancerous cells. This allows for a more complete elimination of cancerous cells to reduce antigen escape by hitting hard with multiple targets simultaneously before resistance develops.

In one embodiment, BCMA-CD38 directed BCMA-CD38 cCAR therapy is as a "bridge" to bone marrow transplant (BMT) or combination with a heavy chemotherapy plus BMT. BCMA-CD38 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA-CD38 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, BCMA-CD38 cCAR therapy can have further applications for patients with BCMA+ and/or CD38+ multiple myelomas beyond a bridge to bone marrow transplantation. BCMA-CD38 cCAR therapy as a stand-alone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

In some embodiments, the present disclosure provides a compound CAR polypeptide engineered cell that targets cells expressing BCMA or CD38 antigens or both. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

It was surprised to find that co-expression of IL-15/IL-15sushi or IL-15/IL-15sushi anchor or 4-1BBL with BCMA-CD38 cCAR provides long-term durable disease remission by increasing the sensitivity of CAR recognition of target cancer cells or recruiting innate immune cells to cancer cells.

Without wishing to be bound by theory, it is believed that co-expression of IL-21 or IL-21 anchor with BCMA-CD38 cCAR provides long-term durable remission in patients by increasing the sensitivity of CAR recognition of target cancer cells or recruiting innate immune cells to cancer cells.

In one embodiment, the engineered cell includes a BCMA-CD38 cCAR polypeptide, 4-1BBL and IL-15/IL-15sushi (SEQ ID NO.40), and corresponding nucleotides (SEQ ID NO. 41).

Without wishing to be bound by theory, it is believed that BCMA-CD38 compound CAR engineered cells provide a better therapeutic outcome in patients suffering from an autoimmune disorder or organ rejection by depletion of B-cells and plasma cells associated with autoimmune disorders.

In some embodiments, a compound CAR (BCMA-CD38 cCAR) targets cells expressing BCMA or CD38 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

BCMA-CD38 cCAR targeted cells are 13 cells, immature B cells, memory B cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis. Addison's disease, antigen-antibody complex mediated diseases, and anti-glomerular basement membrane disease.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjögren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, pemphigus vulgaris (PV) and pemphigus foliaceus (PF). Pemphigus vulgaris (PV) and pemphigus foliaceus (PF) are chronic and life-threatening blistering diseases caused by autoantibodies.

Compound CD123-CLL-1

Unlike B-cell and plasma cell malignancies, AML is uniquely challenging to treat due to the role of leukemic stem cells (LSCs). LSCs are a population of cells expressing markers of hematopoietic stem cells (CD34+CD38−) that are capable of initiating and maintaining hematopoietic malignancy, producing clonal cell populations that overtake healthy bone marrow. Since LSCs remain mostly in the quiescent phase of the cell cycle, chemotherapy directed against rapidly dividing tumor populations leaves LSCs untouched. Most often it is this elusive population that comprises minimal residual disease (MRD) and is responsible for inevitable relapse after AML treatment. The successful translation of CAR therapy to AML to completely eliminate disease and ensure no relapse occurs will require careful antigen selection to enable the eradication of not just bulk leukemic disease, but also leukemic stem cells.

Single-CAR therapy has recently made breakthroughs in achieving high remission rates in the treatment of previously refractory and relapsed B cell malignancies. Conversely, new treatment approaches for AML are lacking, and CAR therapy offers a beacon of hope. In particular, the application of a compound CAR therapy to AML has the potential to transform its treatment entirely.

CD123 and C-type lectin-like molecule-1 (CLL-1) are present on AML CD34+CD38-cells in the majority of AML patients. Without wishing to be bound by theory, it is believed that a compound CAR presents the idea in which a single T-cell encoding two discrete CAR units can simultaneously and more broadly target and eradicate LSCs, preventing disease relapse.

The present disclosure is composed of a single CAR T-cell expressing two discrete CAR units in a vector with independent signaling domains that can be utilized as a novel approach for targeting multiple antigens and potentially avoiding tumor relapse. A compound CAR (cCAR) is comprised of a CD123 CAR linked to a CLL-1 CAR via a self-cleaving P2A peptide and expressed both functional CAR molecules on the surface of a T cell.

In one embodiment, CD123-CLL-1 cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to: acute myeloid leukemia, myelodysplastic syndromes, chronic myeloid leukemia and chronic myeloproliferative disorders.

In another embodiment, CD123-CLL-1 cCAR T-cell therapy can be used to thoroughly eliminate MRD. It can be expected that the relapse rate will decrease and long-term disease-free survival rate will increase, and patient outcomes will be dramatically improved.

In one embodiment, CD123-CLL1 cCAR T-cell therapy can have further applications for patients with CD123+ and/or CLL-1+ leukemic patients beyond a bridge to bone marrow transplantation. CD123-CLL-1 cCAR T-cell therapy can be used as a standalone therapy or as a part of a patient-individualized immuno-chemotherapy regimen. For elderly patients or for those with comorbidities who cannot tolerate highly intensive chemotherapy or BMT, this might be a promising strategy to prolong patients' survival time and reserve a better quality of life.

Without wishing to be bound by theory, it is believed that co-expression of IL-15/IL-15sushi or IL-15/IL-15sushi anchor or 4-1BBL with CD123-CDLL-1 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD123-CLL-1 cCAR provides long-term durable remission in patients by increasing the sensitivity of CAR recognition of target cancer cells or by recruiting innate immune cells to cancer cells.

Compound CD38 CARs for T Cell Malignancies

The present disclosure is composed of a single T-cell expressing two discrete CAR units in a vector with independent signaling domains that can be utilized as a novel approach for targeting multiple antigens and potentially avoiding tumor relapse. A CD38-based compound CAR (cCAR) is comprised of a CD4 CAR or CD5 CAR or CD3 CAR or CD7 CAR linked to a CD38 CAR via a self-cleaving P2A peptide and expresses both functional CAR molecules on the surface of a T cell.

The present disclosure is composed of a single NK-cell expressing two discrete CAR units in a vector with independent signaling domains that can be utilized as a novel approach for targeting multiple antigens and potentially avoiding tumor relapse. A CD38-based compound CAR (cCAR) is comprised of a CD4 CAR or CD5 CAR or CD3 CAR or CD7 CAR linked to a CD38 CAR via a self-cleaving P2A peptide and expresses both functional CAR molecules on the surface of a T cell.

Without wishing to be bound by theory, it is believed that the CD38-based compound cCAR T or NK-cells are able to eliminate T cell lymphoma/leukemic cells to reduce the risk of relapse due to the antigen escape and enhance anti-tumor activities.

A CD4-CD38 compound CAR (cCAR) comprising of a CD4 CAR is linked to a CD38 CAR via a self-cleaving P2A peptide and expresses both functional CAR molecules on the surface of a T cell.

A CD5-CD38 compound CAR (cCAR) comprising of a CD5 CAR is linked to a CD38 CAR via a self-cleaving P2A peptide and expresses both functional CAR molecules on the surface of a T cell.

In one embodiment, the engineered cell includes a CD5-CD38 chimeric antigen receptor polypeptide (SEQ ID NO. 18), and corresponding nucleotides (SEQ ID NO. 19).

A CD7-CD38 compound CAR (cCAR) comprising of a CD4 CAR is linked to a CD38 CAR via a self-cleaving P2A peptide and expresses both functional CAR molecules on the surface of a T cell.

CD56-CD38 CARs for Lymphoma/Leukemia

CD56 is a glycoprotein and functions as the neural cell adhesion molecule. The antigen is expressed on NK cells. CD56 or CD38 is usually present in most cases of 1) aggressive NK cells leukemia/lymphoma, 2) extranodal NK/T lymphoma (nasal type), hepatopleenic T cell lymphoma, and 4) chronic NK cell lymphocytosis.

Like CD38, CD56 is also expressed in non-hematologic cells, such as brain cells. The off-target effects would be severe for a patient administered CD56 or CD38 CAR T cells alone.

Without wishing to be bound by theory, it is believed that compound cCAR T cells bearing two CARs and targeting different antigens have a higher affinity of binding to a cell bearing two antigens targeted by cCAR than that of a cell carrying a single cCAR targeted antigen. As a result, it is believed that the compound CAR T cells have a higher capability of trafficking to the tumor than a single CAR T cells. Thus, applicants surprisingly discovered that there was significantly reduced concern of off-target effects when a compound CAR cell based therapy was used.

CD56 is a glycoprotein and functions as the neural cell adhesion molecule. The antigen is expressed on NK cells. Like CD38, CD56 is also expressed in non-hematologic cells, such as brain cells. The off-target effects would be severe for a patient administered CD56 CAR or CD38 CAR T cells. Thus, the invention disclosure provides a method of generating CD56-CD38 cCAR to reduce concerns of off-target effects associated with using CD56 CAR or CD38 CAR alone.

The present invention is composed of a single T-cell expressing two discrete CAR units in a vector with independent signaling domains that can be utilized as a novel approach for targeting CD56 and CD38 simultaneously and potentially avoiding tumor relapse. A CD56-CD38 compound CAR (cCAR) bears CD56 CAR linked to a CD38 CAR via a self-cleaving P2A peptide and expresses both functional CAR molecules on the surface of a T cell.

The present invention is composed of a single T-cell expressing two discrete CAR units in a vector with independent signaling domains that can be utilized as a novel approach for targeting CD56 and CD38 simultaneously and potentially avoiding tumor relapse. A CD56-CD38 compound CAR (cCAR) bears CD56 CAR linked to a CD38 CAR via a self-cleaving P2A peptide and expresses both functional CAR molecules on the surface of a NK cell.
CD19-CD38 Compound CAR (CD19-CD38 cCAR)

While initial remission rates of approximately 90% are commonly seen in patients with B-ALL using CD19CAR, most patients relapse within a year. The relapse is at least in part due to antigen escape. Thus, more effective CAR T cell treatments to prevent relapse are urgently needed.

CD38 is another good target for lymphomas as its expression is typically high and uniform in lymphoma cells. CD38 is expressed in a variety of lymphomas including chronic lymphocytic lymphoma/small lymphocytic lymphoma, follicular lymphoma, primary effusion lymphoma, diffuse large cell lymphoma, lymphoplasmacytic lymphoma.

The present disclosure is composed of a single CAR T-cell expressing two discrete CAR units in a vector with independent signaling domains can be utilized as a novel approach for targeting multiple antigens and potentially avoiding tumor relapse. A compound CAR (cCAR) comprising of a CD19 CAR linked to a CD38 CAR via a self-cleaving P2A peptide and expressed both functional CAR molecules on the surface of a T cell. This compound cCAR expression is controlled by a strong promoter, SFFV to ensure adequate CAR expression.

In the present disclosure, CD19-CD38 cCAR T-cell can provide potent and specific anti-tumor activity in controlling lymphoma. Targeting multiple myeloma with a compound CAR targeting both BCMA and CD19 in combination is a very strong strategy. This novel approach circumvents the antigen escape (loss of a single antigen) from selection pressure of single CAR treatment due to combinatorial pressure from a compound design.

In this disclosure, the addition of CD38 as a target to the BCMA CAR enhanced the anti-tumor response by eliminating surviving BCMA⁻CD38+ lymphomas to reduce the risk of relapse. CD19 and CD38 are both widely expressed on multiple myeloma cells, and this high expression allows the CD19-CD38 cCAR to have a comprehensive coverage of all potentially lymphoma cells. This allows for a more complete elimination of cancerous cells to reduce antigen escape by hitting hard with multiple targets simultaneously before resistance develops.

In one embodiment, CD19-CD38 directed BCMA–CD38 cCAR therapy is as a "bridge" to bone marrow transplant (BMT) or combination with a heavy chemotherapy plus BMT. CD19-CD38 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, CD19-CD38 cCAR therapy is able to bring down disease burden to the lowest possible level prior to transplant or thoroughly eliminate MRD, it can be expected that the relapse rate will decrease and long-term disease-free survival rate for lymphoma will increase, and patient outcomes will be dramatically improved.

In one embodiment, CD19-CD38 cCAR therapy can have further applications for patients with CD19+ and/or CD38+ multiple myelomas beyond a bridge to bone marrow transplantation. CD19-CD38 cCAR therapy as a standalone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

In some embodiments, the present disclosure provides a compound CAR polypeptide engineered cell that targets cells expressing CD19 or CD38 antigens or both. The targeted cells may be cancer cells, such as, but not limited to, lymphomas. In further embodiments, lymphomas are selected from without limiting, B-ALL, high grade B cell lymphoma, low grade B-cell lymphoma, diffuse large B cell lymphoma, Burkett lymphoma, mantle cell lymphoma, CLL, marginal zone B cell lymphoma and follicular lymphoma.

Without wishing to be bound by theory, it is believed that co-expression of IL-15/IL-15sushi or IL-15/IL-15sushi anchor or 4-1BBL with CD19-CD38 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD19-CD38 cCAR provides long-term durable remission in patients by increasing the sensitivity of CAR recognition of target cancer cells or recruiting innate immune cells to cancer cells.

Without wishing to be bound by theory, it is believed that CD19-CD38 compound CAR engineered cells provide a better therapeutic outcome in patients suffering from an autoimmune disorder or organ rejection by depletion of B-cells and plasma cells associated with autoimmune disorders.

In some embodiments, a compound CAR (BCMA–CD38 cCAR) targets cells expressing BCMA or CD38 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

BCMA–CD38 cCAR targeted cells are B cells, immature B cells, memory 13 cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis, Addison's disease, antigen-antibody complex mediated diseases, and anti-glomerular basement membrane disease.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjögren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, pemphigus vulgaris (PV) and pemphigus foliaceus (PF). Pemphigus vulgaris (PV) and pemphigus foliaceus (PF) are chronic and life-threatening blistering diseases caused by autoantibodies.

BCMA-CD19 Compound CAR (BCMA-CD19 cCAR)

While killing multiple myeloma cells can provide short-term relief, LSCs (myeloma leukemic stem cells), if not destroyed, will always re-grow, causing the patient to relapse. It is imperative that LSCs be destroyed to achieve durable cures for multiple myeloma disease. Without wishing to be bound by theory, it is believed that a small subset of multiple myeloma cells is stem cells that are CD19 positive and associated with disease progression and relapses, and a bulky myeloma cell population is BCMA positive. Therefore, it is critical to develop new therapies that can specifically target both the myeloma stem cell population and the bulky myeloma population. A compound CAR in the present disclosure targets BCMA+ and/or CD19+ positive populations of multiple myeloma cells and is embodied herein.

In some embodiments, the present disclosure provides a method of eradicating or killing myeloma stem cells (LSCs) or bulk myeloma cells expressing CD19 and/or BCMA. In this embodiment, a T or NK engineered cell having a BCMA unit and a CD19 unit is administered to a patient in need thereof.

In some embodiments, the disclosed disclosure comprises methods and compositions of deleting both BCMA and CD19 populations in multiple myeloma to prevent relapses using a BCMA-CD19 cCAR. CAR is more powerful in eliminating myeloma cells when combination of two units of BCMA and CD19 (BCMA-CD19) together in a vector or a cell.

In further embodiments, a compound CAR, BCMA-CD19 cCAR in a T or NK cell may be used to eradicate or kill BCMA+CD19+ or BCMA+CD19− or BCMA-CD19+ populations.

In some embodiments, the disclosed disclosure comprises methods and compositions of deleting both BCMA and CD19 populations in multiple myeloma to prevent relapses using a BCMA-CD19 cCAR. CAR is more powerful in eliminating myeloma cells when combination of two units of BCMA and CD19 (BCMA-CD19) together in a vector or a cell.

In some embodiments, CD19+ populations can be early precursors for multiple myeloma cells, and CD19-BCMA+ cells can be more differentiated malignant multiple myeloma cells. In some embodiments, the disclosed invention comprises methods and compositions of deleting both early precursor of multiple myeloma cells and more differential malignant multiple myeloma cells using a BCMA-CD19b cCAR (a version of BCMA-CD19 cCAR) T or NK cell. In a further embodiment, the disclosed disclosure comprises methods and compositions of targeting both early precursor and more differential malignant cells to completely eliminate malignant clones for multiple myeloma using a BCMA-CD19b cCAR T or NK cell.

The present disclosure further discloses a compound CAR construct with enhanced potency of anti-myeloma cell activity against cells co-expressing target antigens, and yet retains sensitivity to tumor cells only expressing one antigen. In addition, each CAR of the compound CAR includes one or two co-stimulatory domains and exhibits potent killing capability in the presence of the specific target.

Without wishing to be bound by theory, it is believed that co-expression of IL-15/IL-15sushi or IL-15/IL-15sushi anchor or 4-1BBL with BCMA-CD19 cCAR provides long-term durable remission in patients by increasing the sensitivity of CAR recognition of target myeloma cells or recruiting innate immune cells to myeloma cells.

In some embodiments, a compound CAR (BCMA-CD19 cCAR) targets cells expressing BCMA or CD19 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

Without wishing to be bound by theory, it is believed that co-expression of IL-21 or IL-IL-21 anchor with BCMA-CD19 cCAR provides long-term durable remission in patients by increasing the sensitivity of CAR recognition of target myeloma cells or recruiting innate immune cells to myeloma cells.

Without wishing to be bound by theory, it is believed that co-expression of IL-18 or IL-IL-18 anchor with BCMA-CD19 cCAR provides long-term durable remission in patients by increasing the sensitivity of CAR recognition of target myeloma cells or recruiting innate immune cells to myeloma cells.

In some embodiments, the disclosure provides a method of depleting B cells, immature B cells, memory B cells, plasmablasts, long lived plasma cells, or plasma cells in patients with an autoimmune disease by administering to patients CAR or compound CAR (BCMA-CD19 cCAR) T cells or NK cells.

BCMA-CD19 cCAR targeted cells are B cells, immature B cells, memory B cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis, Addison's disease, antigen-antibody complex mediated diseases, and antiglomerular basement membrane disease.

In some embodiments, immune cells including B cells, immature B cells, memory B cells, plasmablasts, long lived plasma cells, or plasma cells in patients with autoimmune diseases can be eliminated by a BCMA and CD19 bispecific CAR T cell or bispecific antibody.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjögren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, Pemphigus vulgaris (PV) and pemphigus foliaceus (PF).

An organ transplant represents a new life for a person and organs that can be transplanted could include the kidneys, heart, lungs, pancreas and intestine. However, many patients are unable to receive a potentially life-saving organ because of pre-existing or developing donor-specific antibody against the donor's antigens such human leukocyte antigens (HLA). Thus, patients may lose the donated organ. Currently there are few treatment options available for antibody mediated rejection, and an enormous unmet need in the field for efficacious treatment of antibody mediated rejection. Deletion of B cells or plasma cells or both using CAR T/NK cell provide a therapy for antibody-mediated rejection.

BCMA-CD19 cCAR or CD19-CD3S cCAR or BCMA-CD38 cCAR targeted cells are B cells, immature B cells, memory B cells, plasmablasts, long lived plasma cells or plasma cells in patients with the antibody-mediated rejection associated with organ rejections.

Engineered Cell Having CAR Polypeptide and Enhancer

In another embodiment, the present disclosure provides an engineered cell having at least one chimeric antigen receptor polypeptide and an enhancer.

In another embodiment, the present disclosure provides an engineered cell having at least one chimeric antigen receptor polypeptide and at least one enhancer.

In one embodiment, the present disclosure provides an engineered cell having at least two distinct chimeric antigen receptor polypeptides and an enhancer.

In one embodiment, the present disclosure provides an engineered cell having at least two distinct chimeric antigen receptor polypeptides and at least one enhancer.

As used herein, an enhancer includes a biological molecule that promotes or enhances the activity of the engineered cell having the chimeric antigen receptor polypeptide. Enhancers include cytokines. In another embodiment, enhancers include IL-2, IL-7, IL-12, IL-15, IL-18, IL-21, IL-21 anchor, PD-1, PD-L1, CSF1R, CTAL-4, TIM-3, and TGFR beta, receptors for the same, and functional fragments thereof.

Enhancers may be expressed by the engineered cell described herein and displayed on the surface of the engineered cell or the enhancer may be secreted into the surrounding extracellular space by the engineered cell. Methods of surface display and secretion are well known in the art. For example, the enhancer may be a fusion protein with a peptide that provides surface display or secretion into the extracellular space.

The effect of the enhancer may be complemented by additional factors such as enhancer receptors and functional fragments thereof. The additional factors may be co-expressed with the enhancer as a fusion protein, or expressed as a separate polypeptide and secreted into the extracellular space.

Enhancers can be cytokines secreted from engineered CAR cells and are designed to co-express with the CAR polypeptide. A massive release occurs upon CAR engagement of cognate antigen Inflammatory cells surrounding tumor cells have a significant correlation with cancer cell progression and metastasis. Inflammatory cells could include T cells and innate immune response cells, such as NK cells, macrophages, and dendritic cells and their proliferation and anti-tumor activity are regulated by cytokines. CAR cells such as CAR T or NK cells bind to targeted cancer cells and trigger massive secretion of enhancers from the expansion of CAR T/NK cells. The secreted enhancers efficiently promote survival, differentiation and activation of immune response cells against cancer cells. The co-expression of an enhancer(s) with CAR can supplement the defect that CAR T or NK cells are unable to eliminate non-targeting cancer cells CAR cells can be a carrier of cytokines, and cytokines can be delivered to targeted cancer sites by CAR cells to reduce systemic toxicity with high-dose exogenous cytokines.

To improve sustained survival or long-lived persistence of CAR cells, a membrane bound enhancer (s) can be co-expressed with CAR to improve CAR persistency In one embodiment, the enhancer is IL-15. In this instance, the additional factor described above is the IL-15 receptor, and functional fragments thereof. Functional fragments include the IL-15 receptor, IL-15RA, and the sushi domain of IL-15RA (IL-15sushi). Soluble IL-15RA or IL15sushi profoundly potentiates IL-15 functional activity by prevention of IL-15 degradation. Soluble IL-15/IL-15RA or IL-15/IL-15sushi complexes are stable and much more stimulatory than IL-15 alone in vivo.

In one embodiment, IL-15 is co-expressed as a fusion protein with at least one of IL-15 receptor, IL-15RA, and the sushi domain of IL-15RA (IL-15sushi). In one embodiment, the IL-15 receptor, IL-15RA, or the sushi domain of IL-15RA (IL-15sushi) is at the N-terminus of IL-15. In another embodiment, the IL-15 receptor, IL-15RA, or the sushi domain of IL-15RA (IL-15sushi) is at the C-terminus of IL-15. As used herein, IL-15/IL-15 sushi denotes that IL-15 sushi is at the C-terminus of IL-15 in a fusion protein; and IL-15sushi/il-15 denotes that IL-15 sushi is at the N-terminus of IL-15 in a fusion protein.

In some embodiments, IL-15 and the IL-15 receptor or functional fragments thereof polypeptide is on a single polypeptide molecule and is separated by a peptide linker, the peptide linker may be 1-25 amino acid residues in length, 25-100 amino acid residues in length, or 50-200 amino acid residues in length. This linker may include a high efficiency cleavage site described herein.

Interleukin (IL)-15 and its specific receptor chain, IL-15Rα (IL-15-RA) play a key functional role in various effector cells, including NK and CD8 T cells. CD8+ T cells can be modified to express autocrine growth factors including, but not limited to, IL-2, 11-7, IL-21 or IL-15, to sustain survival following transfer in vivo. Without wishing to be bound by theory, it is believed that IL-15 overcomes the CD4 deficiency to induce primary and recall memory CD8T cells. Overexpression of IL-15-RA or an IL-15 IL-RA fusion on CD8 T cells significantly enhances its survival and proliferation in-vitro and in-vivo. In some embodiments, CD4 CAR or CD3 CAR or CD5 CAR or CD20 CAR, CD33 CAR, CLL-1 or CD123 CAR, CD19 CAR or CD45 CAR or GD2 CAR, BCMA CAR or any CAR is co-expressed with at least one of IL-15, IL15RA and IL-15/IL-15RA or IL15-RA/IL-15 or IL-15/IL-15sush, or a part or a combination thereof, to enhance survival or proliferation of CAR T or NK, and to improve expansion of memory CAR CD8+ T cells or NK cells.

CD4 CAR or CD7 CAR, CD3 CAR or CD5 CAR or CD20 CAR, CD33 CAR, CLL-1 or CD123 CAR, CD19 CAR or GD2 CAR or CD45 CAR or BCMA CAR or any CARs co-expressed with at least one of IL-15/IL-15sushi or a part or a combination thereof, to enhance survival or proliferation of CAR NK, and to improve expansion of memory CAR CD8+ T cells.

It is surprisingly found that CAR co-expression of IL-15/IL-15sushi is important for the longer persistence and enhanced activity of the T cells and NK cells targeting tumor cells.

It is surprisingly found that CAR co-expression of IL-15/IL-15sushi is important for the T cells or NK T cells, and NK cells targeting tumor cells and preventing cancer relapses.

It is surprisingly found that CAR NK cells or NK cells can extend survival when co-expressing with IL-15/IL-15sushi.

The present disclosure provides an engineered cell having a CAR polypeptide as described herein and at least one of IL-15, IL-15RA, IL-15sushi, IL-15/IL-15RA, IL-15-RA/IL-15, IL-15/IL-15sushi, IL15sushi/IL-15, fragment thereof, a combination thereof, to enhance survival or persistence or proliferation of CAR T or NK T or NK cells for treating cancer in a patient.

In one embodiment, the engineered cell includes a CD5 chimeric antigen receptor polypeptide and IL-15/IL-15sushi (SEQ ID NO. 48), and corresponding nucleotides (SEQ ID NO. 49).

In one embodiment, the engineered cell includes a CD4 chimeric antigen receptor polypeptide and IL-15/IL-15sushi (SEQ ID NO. 22), and corresponding nucleotides (SEQ ID NO. 23).

In one embodiment, the engineered cell includes a CD4 chimeric antigen receptor polypeptide, 4-1BBL and IL-15/IL-15sushi (SEQ ID NO. 20), and corresponding nucleotides (SEQ ID NO. 21).

In one embodiment, the engineered cell includes a CD3 chimeric antigen receptor polypeptide, 4-1BBL and IL-15/IL-15sushi (SEQ ID NO. 18), and corresponding nucleotides (SEQ ID NO. 19).

In one embodiment, the engineered cell includes a CD19 chimeric antigen receptor polypeptide and IL-15/IL-15sushi (SEQ ID NO. 24), and corresponding nucleotides (SEQ ID NO. 25).

In one embodiment, the engineered cell includes a CD19 chimeric antigen receptor polypeptide, 4-1BBL and IL-15/IL-15sushi (SEQ ID NO. 26), and corresponding nucleotides (SEQ ID NO. 27).

In one embodiment, the engineered cell includes a CD33 chimeric antigen receptor polypeptide, 4-1BBL and IL-15/IL-15sushi (SEQ ID NO. 30), and corresponding nucleotides (SEQ ID NO. 31).

In one embodiment, the engineered cell includes a CD123 chimeric antigen receptor polypeptide, 4-1BBL and IL-15/IL-15sushi (SEQ ID NO. 32), and corresponding nucleotides (SEQ ID NO. 33).

In one embodiment, the engineered cell includes a BCMA chimeric antigen receptor polypeptide, 4-1BBL and IL-15/IL-15sushi (SEQ ID NO. 38), and corresponding nucleotides (SEQ ID NO. 39).

In one embodiment, the engineered cell includes a GD2 chimeric antigen receptor polypeptide, 4-1BBL and IL-15/IL-15sushi (SEQ ID NO. 46), and corresponding nucleotides (SEQ ID NO. 47).

In one embodiment, the engineered cell includes a GD2 chimeric antigen receptor polypeptide (SEQ ID NO. 56), and corresponding nucleotides (SEQ ID NO. 57).

In one embodiment, the engineered cell includes a GD2 chimeric antigen receptor polypeptide and 4-1BBL (SEQ ID NO. 56), and corresponding nucleotides (SEQ ID NO. 57).

In one embodiment, the engineered cell includes a CD45 chimeric antigen receptor polypeptide and IL-15/IL-15sushi (SEQ ID NO. 54), and corresponding nucleotides (SEQ ID NO. 55).

In another embodiment, the present disclosure provides an engineered cell having at least one of recombinant IL-15, IL-15RA, IL-15sushi, IL-15/IL-15RA, IL15-RA/IL-15, IL-15/IL-15sushi, IL15sushi/IL-15, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD19, CD20, CD22, CD38, BCMA, CS1, BAFF receptor, TACI, CD3, CD4, CD8, CD5, CD7, CD2, and CD138.

Without wishing to be bound by theory, it is believed that IL-15/IL-15sushi and other types of IL-15 or IL-15RA proteins or protein fragments thereof provide synergistic efficacy of a CAR polypeptide when combined with checkpoint inhibitors or modulators (e.g. anti-PD-1).

In one embodiment, the present disclosure provides a method of providing long-term durable remission in patients suffering from cancer by administering a CAR engineered cell that co-expresses IL-21 or IL-12 anchor to a patient in need thereof (FIGS. 24 and 25). Without wishing to be bound by theory, it is believed that co-expression of IL-21 or IL-21 anchor with a CAR provides long-term durable remission in patients by increasing the persistence of CAR engineered cells.

Without wishing to be bound by theory, it is also believed that co-expression of secreting IL-21 with a CAR polypeptide provides long-term durable remission in patients by affecting tumor micro-environment resulting in reduction of immunosuppression and promotion of innate cell proliferation or functions.

Without wishing to be bound by theory, it is believed that CAR co-expression of secreting IL-21 or IL-21 anchor is important for the longer persistence and enhanced activity of the T cells, NK T cells and NK cells targeting tumor cells. CAR NK cells or NK cells or NK T cells can extend survival when co-expressing with IL-21 or IL-21 anchor.

In one embodiment, the present disclosure provides a method related to that CAR T or NK cells targeting tumor cells can be a carrier to delivery an enhancer, IL-21 to the tumor micro-environment. CAR T or NK cells are engineered to co-express a secretory IL-21. Engineered CAR T or NK T cells or NK cells in tumor microenvironment, target tumor cells, binding to the CAR targeting antigen, and triggering lysis of tumor cells and massive secretion of soluble IL-21 from the expansion of CAR T or NK T cells or NK cells.

In particular embodiments, elimination of tumor can be achieved by combination of at least one or more of the following steps:
(1) binding of an CAR engineered T cell or NK cell or NK T cell disclosed herein to a portion of tumor cells by targeting CAR antigen(s);
(2) Triggering of a massive secretion of IL-21 from expansion of CAR T/NK cells, which co-express this molecule;
(3) Recruiting and stimulating a variety of innate and adaptive immune cells against tumor;
(4) Reducing tumor suppression that is present in tumor by administration of a checkpoint blockage such as PD-L1 and CTLA-4 inhibitor.

Without wishing to be bound by theory, it is believed that the combination of steps described above provide potent anti-tumor effects via a concerted innate and adaptive immune response.

In another embodiment, the present disclosure provides an engineered cell having IL-21 or IL-21 anchor, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD19, CD20, CD22, CD38, BCMA, CS1, BAFF receptor, TACI, CD3, CD4, CD8, CD5, CD7, CD2, and CD138.

In one embodiment, the present disclosure provides a method of providing long-term durable remission in patients suffering from cancer by administering a CAR engineered cell that co-expresses IL-18 or IL-18 anchor to a patient in need thereof (FIGS. 26 and 27). Without wishing to be bound by theory, it is believed that co-expression of IL-18 or IL-18 anchor with a CAR provides long-term durable remission in patients by increasing the persistence of CAR engineered cells.

Without wishing to be bound by theory, it is also believed that co-expression of secreting IL-18 with a CAR polypeptide provides long-term durable remission in patients by affecting tumor micro-environment resulting in reduction of immunosuppression and promotion of innate cell proliferation or functions.

Without wishing to be bound by theory, it is believed that CAR co-expression of secreting IL-18 or IL-18 anchor is important for the longer persistence and enhanced activity of the T cells and NK cells targeting tumor cells. CAR NK cells or NK cells can extend survival when co-expressing with IL-18 or IL-18 anchor.

In one embodiment, the present disclosure provides a method related to that CAR T or NK cells targeting tumor cells can be a carrier to delivery an enhancer, IL-18 to the tumor micro-environment. CAR T or NK cells are engineered to co-express a secretory IL-18. Engineered CAR T or NK cells in tumor microenvironment, target tumor cells, binding to the CAR targeting antigen, and triggering lysis of tumor cells and massive secretion of soluble IL-18 from the expansion of CAR T or NK cells.

In particular embodiments, elimination of tumor can be achieved by combination of at least one or more of the following steps:
(1) binding of an CAR engineered T cell or NK cell disclosed herein to a portion of tumor cells by targeting CAR antigen(s);
(2) Triggering of a massive secretion of IL-18 from expansion of CAR T/NK cells, which co-express this molecule;
(3) Recruiting and stimulating a variety of innate and adaptive immune cells against tumor;
(4) Reducing tumor suppression that is present in tumor by administration of a checkpoint blockage such as PD-L1 and CTLA-4 inhibitor.

Without wishing to be bound by theory, it is believed that the combination of steps described above provide potent anti-tumor effects via a concerted innate and adaptive immune response.

In another embodiment, the present disclosure provides an engineered cell having IL-18 or IL-18 anchor, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD19, CD20, CD22, CD38, BCMA, CS1, BAFF receptor, TACI, CD3, CD4, CD8, CD5, CD7, CD2, and CD138.

In some embodiments, targeting more than one different antigen can be achieved by pooled CAR engineered cells, which are generated by at least two separate CAR T or NK cells. As used herein, pooled CAR engineered cells include a population of engineered cells having more than one distinct CAR polypeptide unit. By way of example, pooled engineered cells include a population of engineered cells with a distinct CAR polypeptide and a population of engineered cells with a different and distinct CAR polypeptide. Furthermore, the pooled CAR engineered cells include engineered cells having cCAR polypeptides.

Methods of Generating Engineered Cells

Any of the polynucleotides disclosed herein may be introduced into an engineered cell by any method known in the art.

In one embodiment, CAR polynucleotides are delivered to the engineered cell by any viral vector as disclosed herein.

In one embodiment, to achieve enhanced safety profile or therapeutic index, the any of the engineered cells disclosed herein be constructed as a transient RNA-modified "biodegradable" version or derivatives, or a combination thereof. The RNA-modified CARs of the present disclosure may be electroporated into T cells or NK cells. The expression of the compound CAR may be gradually diminished over few days.

In some embodiments of the present disclosure, any of the engineered cells disclosed herein may be constructed in a transponson system (also called a "Sleeping Beauty"), which integrates the CAR DNA into the host genome without a viral vector.

In some embodiments of the present disclosure, any of the engineered cells disclosed herein may be introduced by two vectors, and each vector bears a unit of CAR or an enhancer.

Methods of Generating an Engineered Cell Having Multiple CAR Units

In another embodiment, the present disclosure provides a method making an engineered cell having at least two CAR units.

In some embodiments, multiple units of CAR are expressed in a T or NK cell using bicistronic or multicistronic expression vectors. There are several strategies which can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (4) insertion of internal ribosomal entry sites (IRESs); (5) separate two vectors to express different units of CAR.

In a preferred embodiment, multiple CAR units are expressed in a single open reading frame (ORF), thereby creating a single polypeptide having multiple CAR units. In this embodiment, an amino acid sequence or linker containing a high efficiency cleavage site is disposed between each CAR unit.

As used herein, high cleavage efficiency is defined as more than 50%, more than 70%, more than 80%, or more than 90% of the translated protein is cleaved. Cleavage efficiency may be measured by Western Blot analysis, as described by Kim 2011.

Furthermore, in a preferred embodiment, there are equal amounts of cleavage product, as shown on a Western Blot analysis.

Examples of high efficiency cleavage sites include porcine teschovirus-1 2A (P2A), FMDV 2A (abbreviated herein as F2A); equine rhinitis A virus (ERAV) 2A (E2A); and Thoseaasigna virus 2A (T2A), cytoplasmic polyhedrosis virus 2A (BmCPV2A) and flacherie Virus 2A (BmIFV2A), or a combination thereof. In a preferred embodiment, the high efficiency cleavage site is P2A. High efficiency cleavage sites are described in Kim J H, Lee S-R, Li L-H, Park H-J, Park J-H, Lee K Y, et al. (2011) High Cleavage Efficiency of a 2A Peptide Derived from Porcine Teschovirus-1 in Human Cell Lines, Zebrafish and Mice. PLoS ONE 6(4): e18556, the contents of which are incorporated herein by reference.

In embodiments, wherein multiple CAR units are expressed in a single open reading frame (ORF), expression is under the control of a strong promoter. Examples of strong promoters include the SFFV promoter, and derivatives thereof.

When designing longer gene constructs, the level of protein expression drops significantly with each 1 kb of additional length. Therefore, an initial screen of several antigen recognition sequences is preferred to find the combination that yields both the highest transduction efficiency along with highest target cell lysis. Additionally, it is preferred to avoid very high CAR expression which leads to tonic effects and poor lysis caused by single chain aggregation on the cell surface.

In embodiments, wherein multiple CAR units are expressed in a cell, CAR-CAR interaction between the hinge region of each individual CAR is preferred to be avoided. The interaction site of the hinge is preferred to be excluded or each unit of CARs uses different hinge regions to avoid their interaction.

In some embodiments, wherein multiple CAR units are expressed in a cell, different nucleotide sequences for each domain in common, such as leader sequence, hinge and transmembrane regions, and CD3zeta region, are preferred to avoid homologous recombination, while maintaining the same amino acid sequence.

In some embodiments, wherein multiple CAR units are created, the choice of target antigen is preferred based on which will give the best therapeutic effect, based on medical knowledge and background.

In some embodiments, targeting more than one different antigen can be achieved by pooled CAR engineered cells, which are generated by at least two separate CAR T or NK cells.

It is preferred that co-culture lysis experiments be performed on both on-target cell lines, and off-target cell lines using CAR T or NK cells, to test specificity. Additionally, it is preferred that cell lines expressing only one targeted antigen each be used to demonstrate the ability of each component CAR to lyse. To do this, it is preferred that an off-target cell line be made to synthetically express the desired antigen(s).

In some embodiments, targeting more than one different antigen can be achieved by pooled CAR engineered cells, which are generated by at least two separate CAR T or NK cells.

As used herein, pooled CAR engineered cells include a population of engineered cells having more than one distinct CAR polypeptide unit. By way of example, pooled engineered cells include a population of engineered cells with a distinct CAR polypeptide and a population of engineered cells with a different and distinct CAR polypeptide. Furthermore, the pooled CAR engineered cells include engineered cells having cCAR polypeptides.

Engineered Cell Having CAR Polypeptide and Enhancer

In another embodiment, the present disclosure provides a method making an engineered cell that expresses at least one CAR unit and an enhancer.

In some embodiments, at least one CAR unit and enhancer is expressed in a T or NK cell using bicistronic or multicistronic expression vectors. There are several strategies which can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (4) insertion of internal ribosomal entry sites (IRESs).

In some embodiments, at least one CAR and an enhancer (s) expressing in a T cell or NK cell can be achieved by two separate vectors or viruses.

In a preferred embodiment, at least one CAR unit and an enhancer are expressed in a single open reading frame (ORF), thereby creating a single polypeptide having at least one CAR unit and an enhancer. In this embodiment, an amino acid sequence or linker containing a high efficiency cleavage site is disposed between each CAR unit and between a CAR unit and enhancer. In this embodiment, the ORF is under the control of a strong promoter. Examples of strong promoters include the SFFV promoter, and derivatives thereof.

Furthermore, in a preferred embodiment, there are equal amounts of cleavage product, as shown on a Western Blot analysis.

Combination Therapy

The compositions and methods of this disclosure can be used to generate a population of CAR T lymphocyte or NK cells that deliver both primary and co-stimulatory signals for use in immunotherapy in the treatment of cancer. In further embodiments, the present invention for clinical aspects are combined with other agents effective in the treatment of hyperproliferative diseases, such as anti-cancer agents. Anti-cancer agents are capable of reduction of tumor burdens in a subject. Anti-cancer agents include chemotherapy, radiotherapy and immunotherapy.

More than 50% of persons with cancer will undergo surgery of some type. Curative surgery includes resection in which all or part of cancerous tissue is physically removed, excised, and/or destroyed.

The compositions and methods described in the present disclosure may be utilized in conjunction with other types of therapy for cancer, such as chemotherapy, surgery, radiation, gene therapy, and so forth.

In accordance with the present disclosure, natural killer (NK) cells represent alternative cytotoxic effectors for CAR driven killing. Unlike T-cells, NK cells do not need pre-activation and constitutively exhibit cytolytic functions. Further expression of cCARs in NK cells allow NK cells to effectively kill cancers, particularly cancer cells that are resistant to NK cell treatment.

Further, NK cells are known to mediate anti-cancer effects without the risk of inducing graft-versus-host disease (GvHD).

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure Administration of any of the engineered cells described herein may be supplemented with the co-administration of a CAR enhancing agent. Examples of CAR enhancing agents include immunomodulatory drugs that enhance CAR activities, such as, but not limited to agents that target immune-checkpoint pathways, inhibitors of colony stimulating factor-1 receptor (CSF1R) for better therapeutic outcomes. Agents that target immune-checkpoint pathways include small molecules, proteins, or antibodies that bind inhibitory immune receptors CTLA-4, PD-1, and PD-L1, and result in CTLA-4 and PD-1/PD-L1 blockades. As used herein, enhancing agent includes enhancer as described above.

As used herein, "patient" includes mammals. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human. A patient includes subject.

In certain embodiments, the patient is a human 0 to 6 months old, 6 to 12 months old, 1 to years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

The terms "effective amount" and "therapeutically effective amount" of an engineered cell as used herein mean a sufficient amount of the engineered cell to provide the desired therapeutic or physiological or effect or outcome. Such, an effect or outcome includes reduction or amelioration of the symptoms of cellular disease. Undesirable effects, e.g. side effects, are sometimes manifested along with the desired therapeutic effect; hence, a practitioner balances the potential benefits against the potential risks in determining what an appropriate "effective amount" is. The exact amount required will vary from patient to patient, depending on the species, age and general condition of the patient, mode of administration and the like. Thus, it may not be possible to specify an exact "effective amount". However, an appropriate "effective amount" in any individual case may be determined by one of ordinary skill in the art using only routine experimentation. Generally, the engineered cell or engineered cells is/are given in an amount and under conditions sufficient to reduce proliferation of target cells.

Following administration of the delivery system for treating, inhibiting, or preventing a cancer, the efficacy of the therapeutic engineered cell can be assessed in various ways well known to the skilled practitioner. For instance, one of ordinary skill in the art will understand that a therapeutic engineered cell delivered in conjunction with the chemoadjuvant is efficacious in treating or inhibiting a cancer in a patient by observing that the therapeutic engineered cell reduces the cancer cell load or prevents a further increase in cancer cell load. Cancer cell loads can be measured by methods that are known in the art, for example, using polymerase chain reaction assays to detect the presence of certain cancer cell nucleic acids or identification of certain cancer cell markers in the blood using, for example, an antibody assay to detect the presence of the markers in a sample (e.g., but not limited to, blood) from a subject or patient, or by measuring the level of circulating cancer cell antibody levels in the patient.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

As used herein, a XXXX antigen recognition domain is a polypeptide that is selective for XXXX. "XXXX" denotes the target as discussed herein and above. For example, a CD38 antigen recognition domain is a polypeptide that is specific for CD38.

As used herein, CDXCAR refers to a chimeric antigen receptor having a CDX antigen recognition domain.

EXAMPLES

Figure 1A:
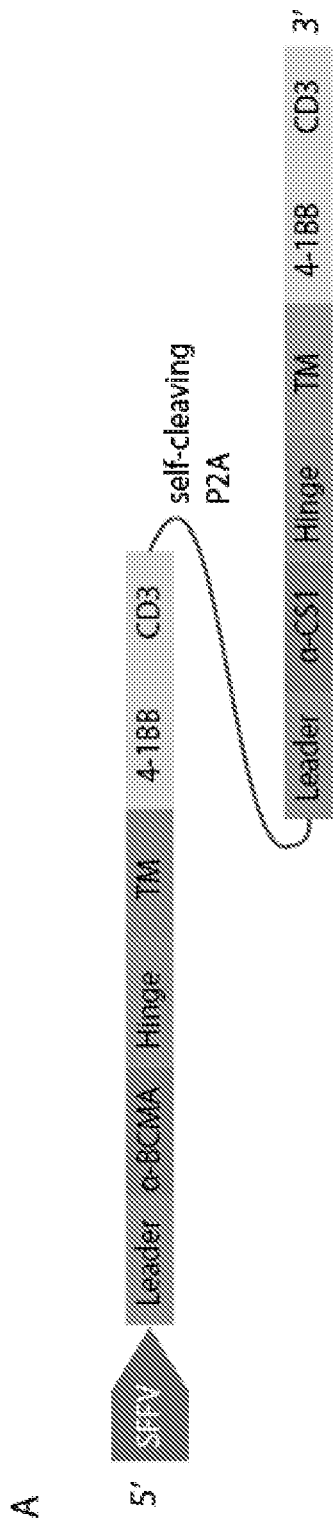
FIGS. 1A-1B: CAR construction and expression
(1A) Two discrete CAR units: an anti-BCMA CAR comprised of: a CD8-derived hinge (H) and transmembrane (TM) regions, and 4-1BB co-activation domains linked to the CD3ζ signaling domain is fused to a complete anti-CS1 CAR by a self-cleaving P2A peptide. A strong spleen focus forming virus promoter (SFFV) and a CD8 leader sequence were used for efficient expression of the BC1cCAR (BCMA-CS1 cCAR) molecule on the T-cell surface. (2B) Expression of BC1cCAR was measured by FACS against control T-cells. BCMA also called CD269.
Figure 1B:
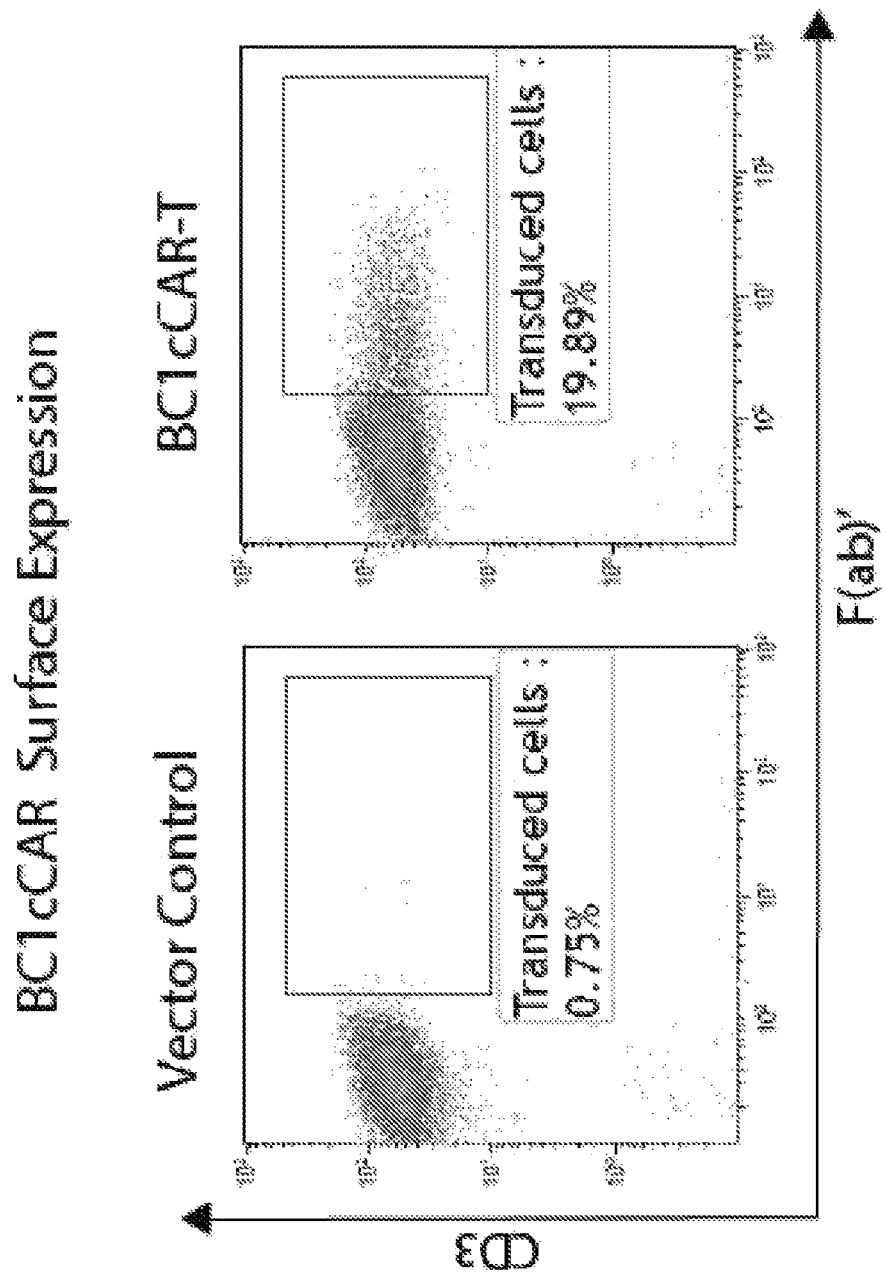

BCMA-CS1 cCAR Targeting Plasma Cell Diseases Such as Multiple Myeloma Generation of BCMA-CS1 cCAR (BC1cCAR) T-Cells The BC1cCAR construct is a 2-unit CAR composed of a complete BCMA-CAR fused to a complete CS1-CAR by a self-cleaving P2A peptide, enabling independent expression of both CAR receptors separately on the T-cell surface (FIG. 1A). Expression assayed by FACS revealed distinct transduced cells (FIG. 1B). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the BCMA-CS1 cCAR molecule on the T-cell surface.

BC1cCAR T-Cells Specifically Lyse BCMA$^+$ and CS1$^+$ Myeloma Cell Lines

Figure 2A:
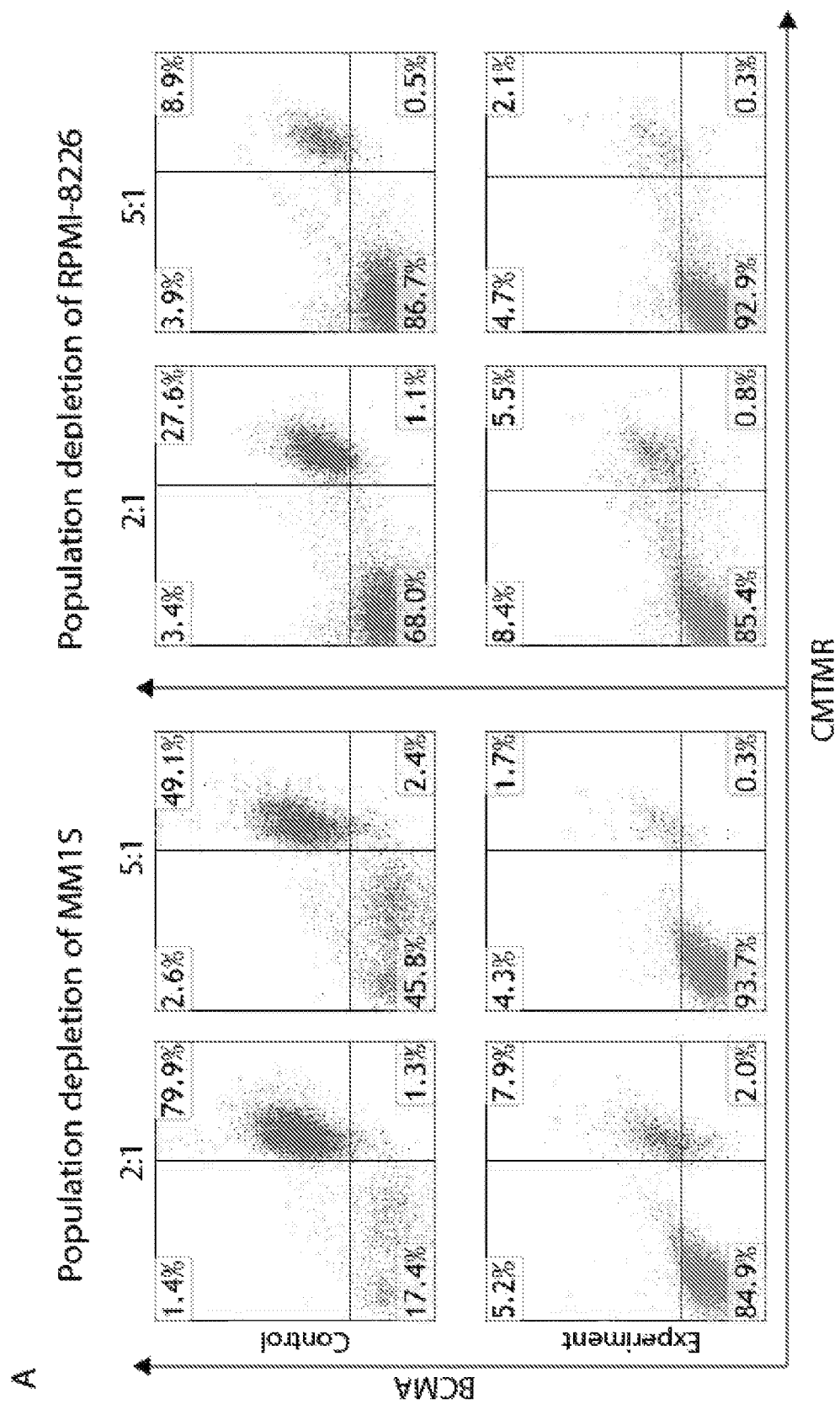
FIGS. 2A-2C: In vitro evaluation of BC1cCAR T-cells against myeloma cell lines
(2A) BC1cCAR and control T-cells cultured with MM1S and RPMI-8226 cells for 24 hours at E:T ratios of 2:1 and 5:1. Target cells were stained by Cytotracker dye (CMTMR) to distinguish them from effector T-cells, and are indicated in red. Populations were gated by BCMA, CS1, and CMTMR. (2B) BC1cCAR and control T-cells were incubated with U266 (BCMA$^+$CS1$^{dim}$) cells under similar conditions. (2C) Graphical summary of BC1cCAR T-cell in vitro cytotoxicity against various myeloma cell lines.
Figure 2B:
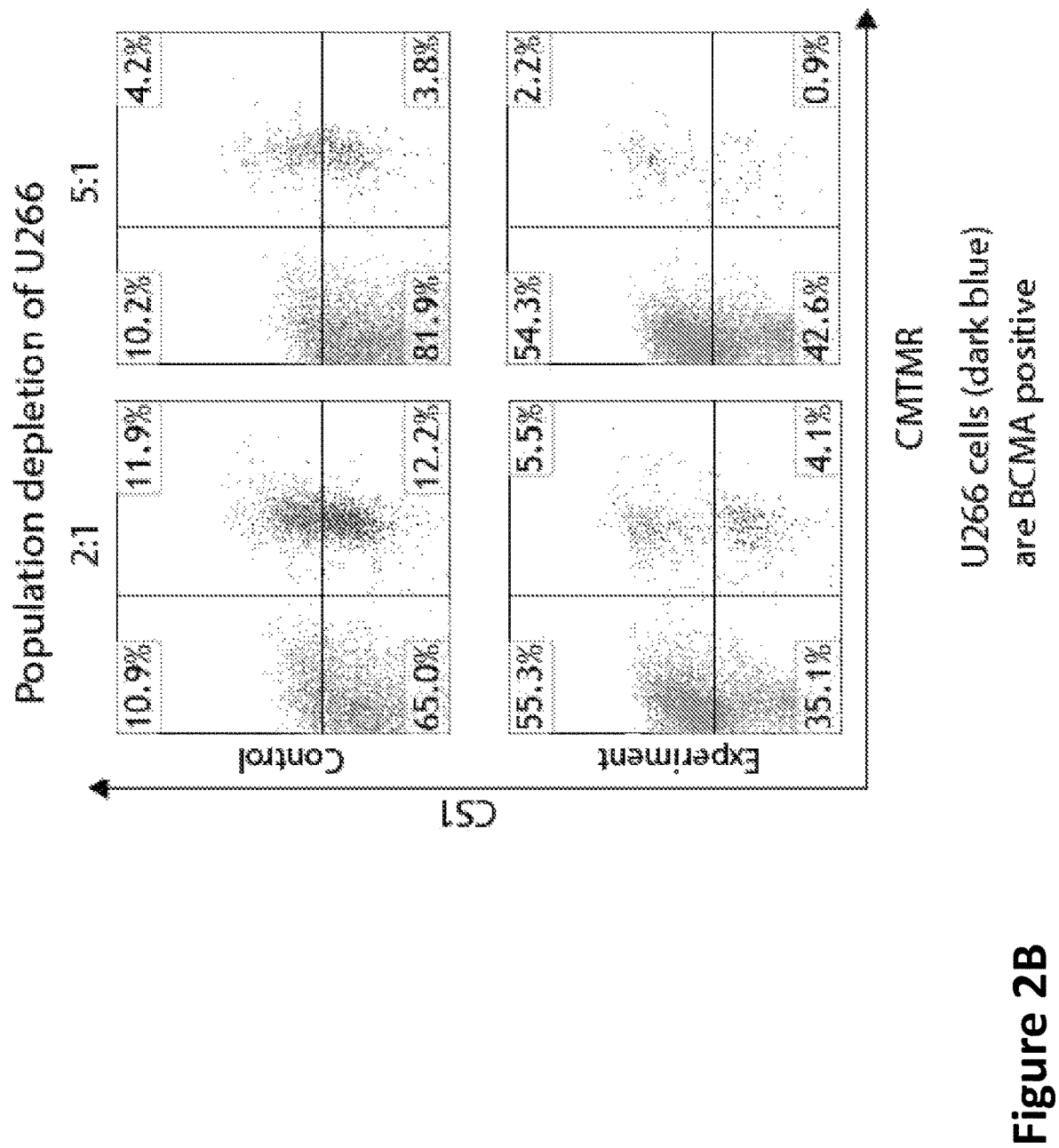
Figure 2C:
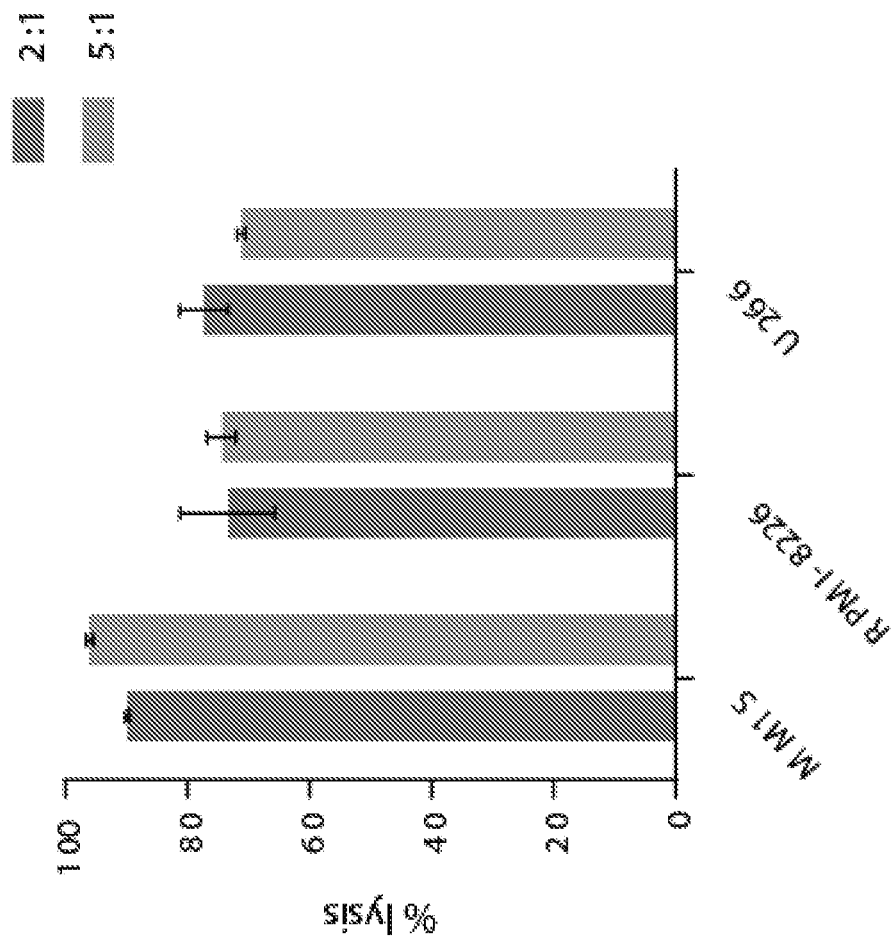

To assess the cytotoxicity of BC1cCAR T-cells, we conducted co-culture assays against myeloma cell lines: MM1S (BMCA$^+$CS1$^+$), RPMI-8226 (BCMA$^+$CS1$^{dim}$), and U266 (BCMA$^+$CS1$^{dim}$). FACS analysis of BC1cCAR cytotoxicity in 24 hour co-cultures show virtually complete lysis of MM1S cells (>90%) at all E:T ratios (FIG. 2A). Similar trends were observed against RPMI-8226 and U266 cells in culture (FIG. 2A, 2B), demonstrating effective bulk cytotoxicity against target populations with varying levels of antigen expression (FIG. 2C).

Figure 3:
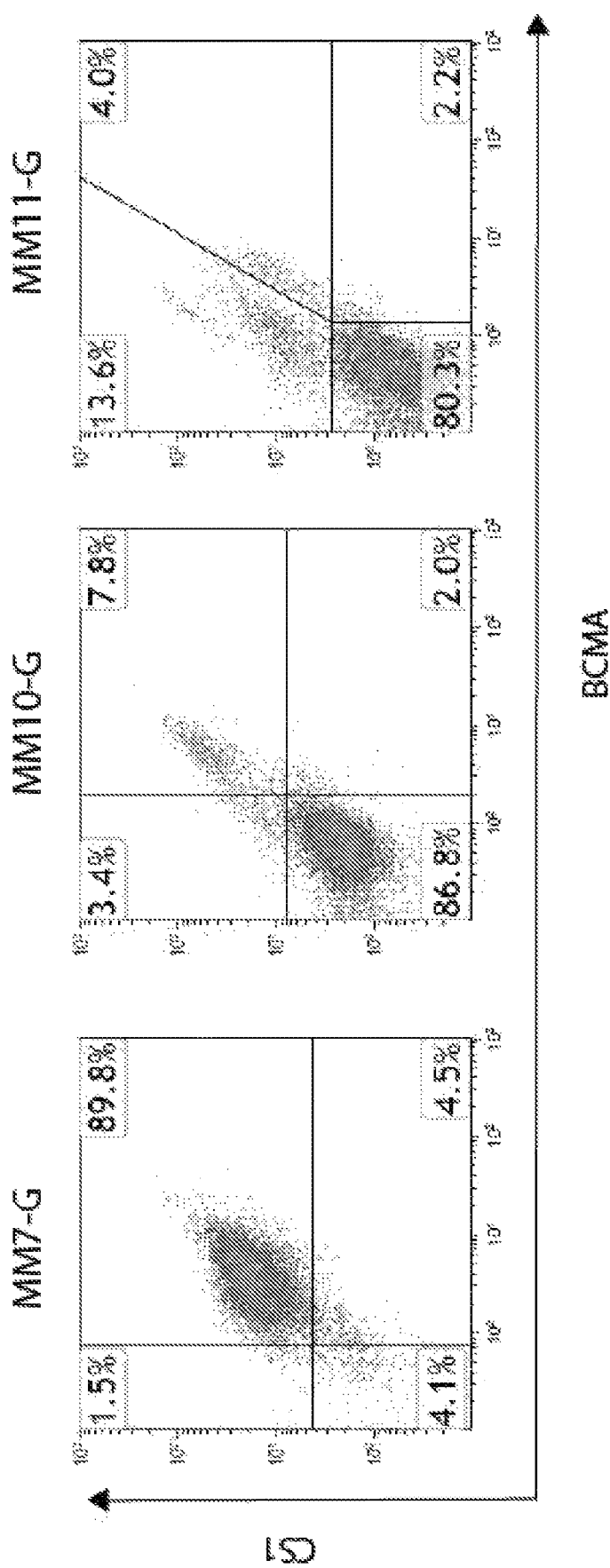
FIG. 3: Primary patient cell phenotypes
Primary cells were assayed by FACS for BCMA and CS1 expression. Density plots represent major antigen populations.
Figure 4A:
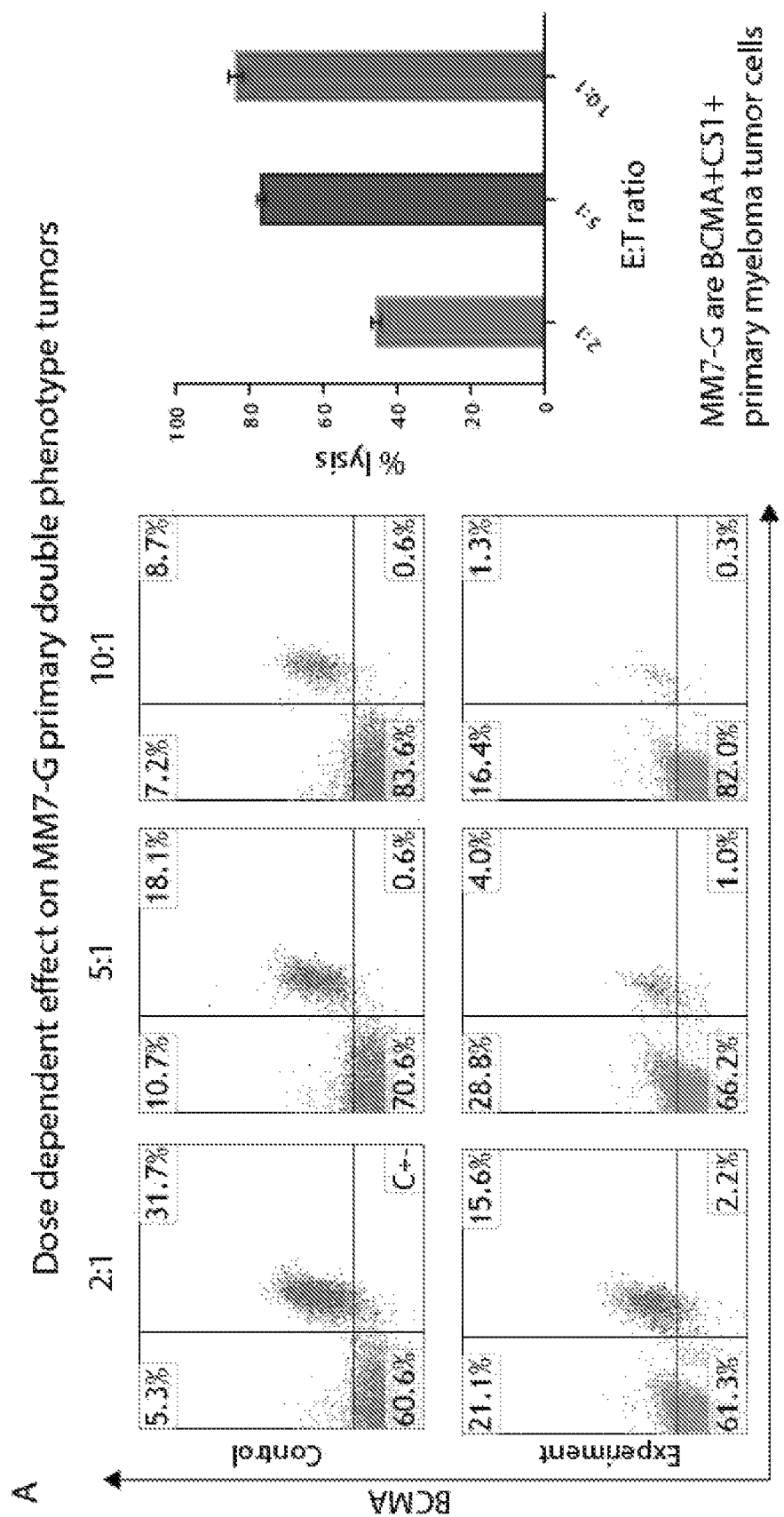
FIGS. 4A-4D: Characterization of BC1cCAR T-cell antitumor activity against primary myeloma tumor cells
(4A) Co-cultures against BCMA+CS1+ primary myeloma cells (MM7-G) were carried out over 24 hours and target cells pre-stained with CMTMR. Populations were gated by BCMA and CS1, along with CMTMR, and flow cytometry plots show target tumor populations (left). Bar graph summarizing in vitro cytotoxicity (right). (4B) Co-cultures with MM10-G primary cells were conducted under similar conditions. BCMA⁺CS1⁺ double positive populations and CS1⁺ only populations by FACS. Specific cytotoxicity summarized (below). (4C) BCMA$^{dim}$CS1$^{dim}$ primary cells (MM11-G) show BC1cCAR anti-tumor activity over a range of E:T dosages. (4D) Summary panel graph showing results of BC1cCAR in vitro screening.

BC1cCAR T-Cells Specifically Target BCMA$^+$ and CS1$^+$ Populations in Primary Myeloma Samples To further evaluate the BC1cCAR's ability to kill diverse primary myeloma cell types, primary samples were chosen to exhibit a spectrum of target antigen expression (FIG. 3). Flow cytometry analysis of the MM10-G sample revealed a mixed tumor with double positive BCMA CS1$^+$ as well as CS1$^+$ only population subsets. MM7-G sample showed a complete BCMA CS1+ phenotype while bone marrow aspirate MM11-G exhibited a noisy BCMA$^{dim}$ CS1$^{dim}$ phenotype. BC1cCAR T-cells showed robust (>80%) dose-dependent ablation of the MM7-G primary patient sample (FIG. 4A).

Figure 4B:
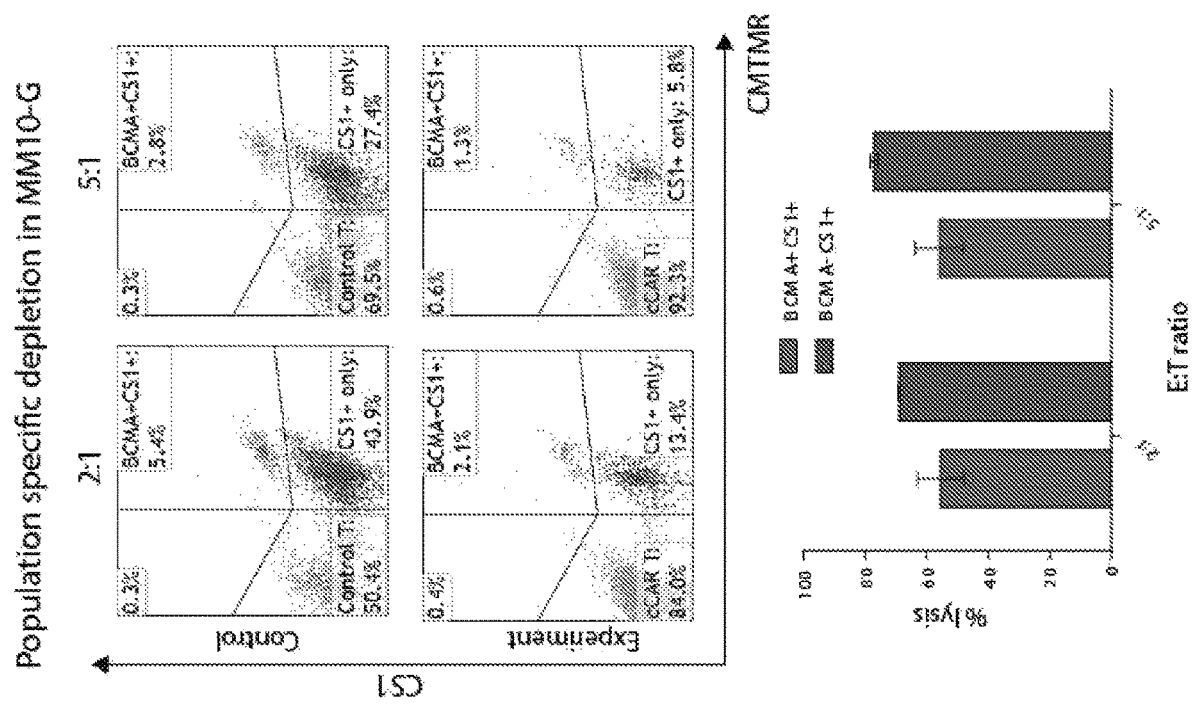
Figure 4C:
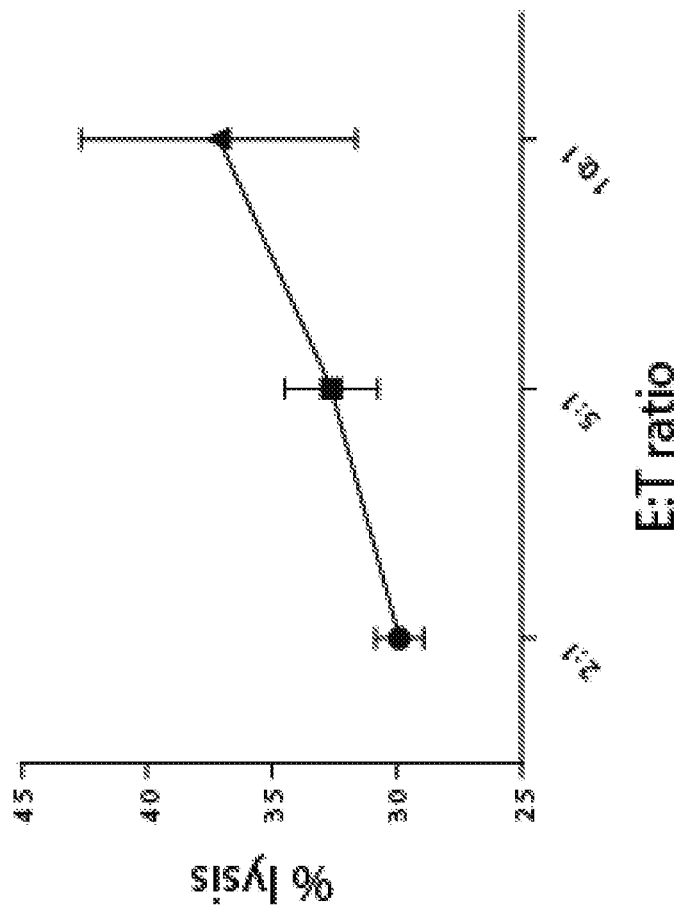
Figure 4D:
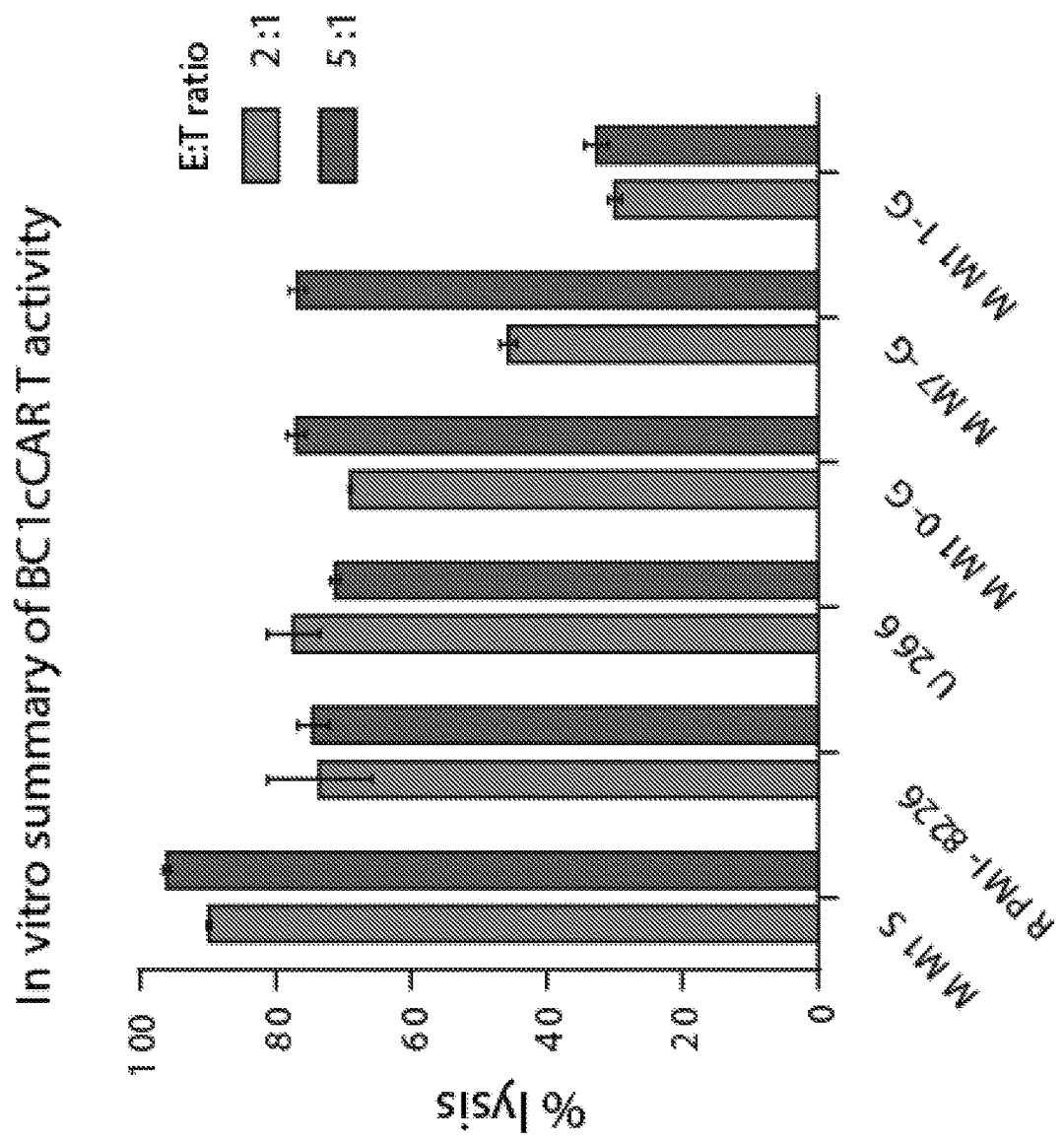

BC1cCAR also showed targeted and specific lysis ability, by significantly ablating both BCMA$^+$CS1$^+$ and BCMA$^-$CS1$^+$ population subsets in MM10-G co-cultures. At an E:T ratio of 2:1, BC1cCAR T-cells ablated over 60% of the BCMA$^+$CS1$^+$ population, and 70% of the CS1$^+$ only population with slight dose dependent increases (FIG. 4B). BC1cCAR T-cells were also able to demonstrate dose-dependent cytotoxic activity against the MM11-G cells (FIG. 4C). Across the cytotoxicity screening, BC1cCAR T cells exhibited robust anti-tumor activity against both myeloma cell lines and primary tumor cells expressing different combinations of BCMA and CS1 (FIG. 4D)

Functional Evaluation of BC1cCAR Antigen Specific Activity

Figure 5A:
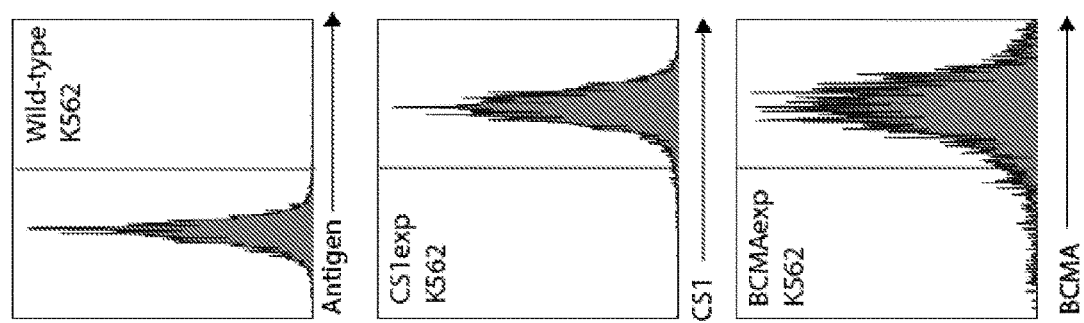
FIGS. 5A-5C: Functional validation of BC1cCAR antigen specificity (5A) A CML cell line (K562) was transduced to stably express either BCMA or CS1. Histogram population shifts in their respective antigen expression ranges show expression. (5B) Short term (4 hour-8 hour) cultures of BC1cCAR T-cells against either BCMA-K562 or CS1-K562 show antigen specific cytotoxicity correlating with E:T dosage increase. Wild-type K562 cells were used as a negative control. A CS1 single CAR (red bar) was generated to compare efficacy with BC1cCAR against CS1-K562 cells. (5C) Long-term cultures (48 hours) conducted with a 1:1 mixture of BCMA-K562 cells and CS1-K562 cells. BC1cCAR, CS1-CAR, BCMA-CAR, and control T-cells were added at a 5:1 E:T ratio to each treatment well. Histogram plots showing residual populations (% gated) of BCMA or CS1 cells are shown per treatment condition, with red lines demarcating T-cell or target tumor populations.

We established a model that allowed us to test the BC1cCAR scFv functionality independently. A CML cell line, K562, negative for myeloma markers was overexpressed with either CS1 (CS1-K562) or BCMA (BCMA-K562). After confirming independent antigen expression in each cell line (FIG. 5A), we determined BC1cCAR T-cell targeting functionality through co-culture experiments.

Figure 5B:
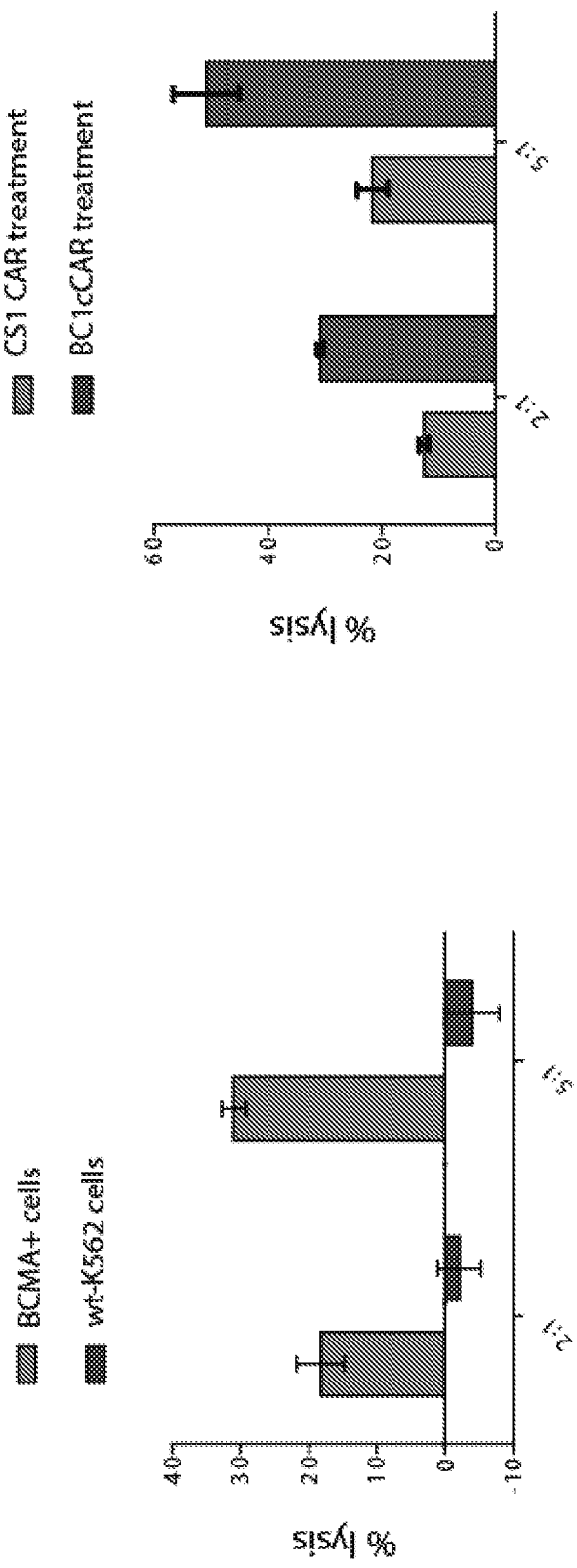

In short-term cultures (overnight), BC1cCAR T-cells exhibited cytotoxic activity against BCMA-K562 cells. There were no off-target effects against wild-type K562 cells negative for either antigen (FIG. 5B). Short-term cultures against CS1-K562 cells also showed similar responses against CS1-expressing target cells. In addition, BC1cCAR T-cells appeared to have a stronger cytotoxic effect than a CS1-specific CAR against CS1-K562 cells (FIG. 5B).

Figure 5C:
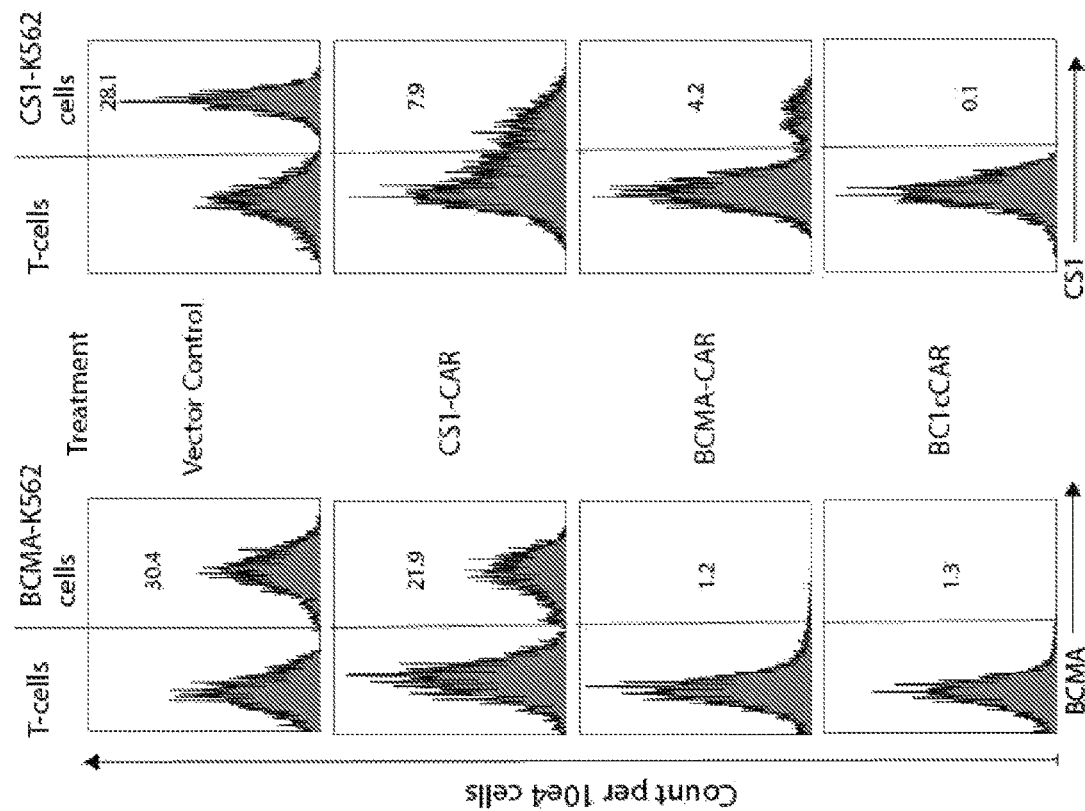

Residual tumor populations possessing a non-target antigen may lead to relapse in patients who have undergone treatment using a single-antigen CAR. Thus, to model more clinically relevant mixed antigen-expressing cell populations, we conducted combined co-culture experiments. BCMA-K562 and CS1-K562 cells were mixed in 1:1 ratios in a sustained (48 h) culture to assay for residual antigen positive populations. Next, histograms were constructed that represented populations of T-cells and target tumor cells with residual gated target tumor populations marked (FIG. 5C). We found that compared to control T-cells, BCMA-specific CAR and CS1-specific CAR had profound cytotoxic effects against their respective target populations. However, CS1-CAR left a significant residual BCMA$^+$ population, whereas BCMA-CAR achieved a high degree of cytotoxicity but left a small CS1$^+$ population. In contrast, the BC1cCAR T-cells effectively depleted both target populations (FIG. 5C).

Tumor Re-Challenge Demonstrates Sequential Killing Ability of BC1cCAR T-Cells

Figure 6A:
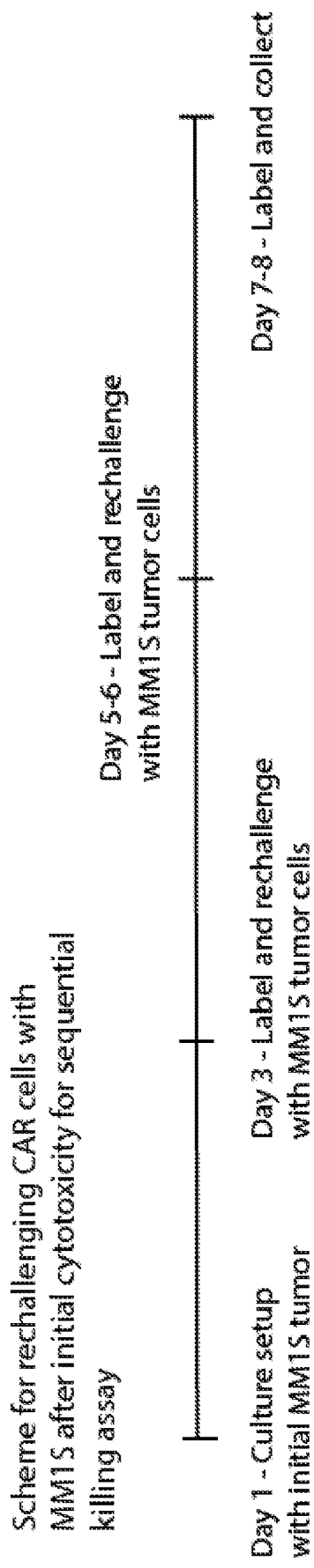
FIGS. 6A-6C: Long-term sequential killing assay and tumor re-challenge (6A) Assay was conducted over a period of 168 hours without exogenous cytokines and initial culture was performed using a 1:1 E:T ratio of CAR cells or control cells mixed with BCMA⁺CS1⁺ MM1S cells. After 48 hours, flow cytometry analysis was acquired for a small sample collection and MM1S cells were re-introduced into each treatment well. Repeated through the 168 hour time-point. (6B) T-cell proliferation and response after 48 hours. Images were taken on the day of flow cytometry acquisition and cells were stained with anti-BCMA, anti-CS1, and anti-CD3 antibodies, MM1S cells (circled). (6C) Similar image acquisition and FACS analysis was performed at the 108 hour time mark.
Figure 6B:
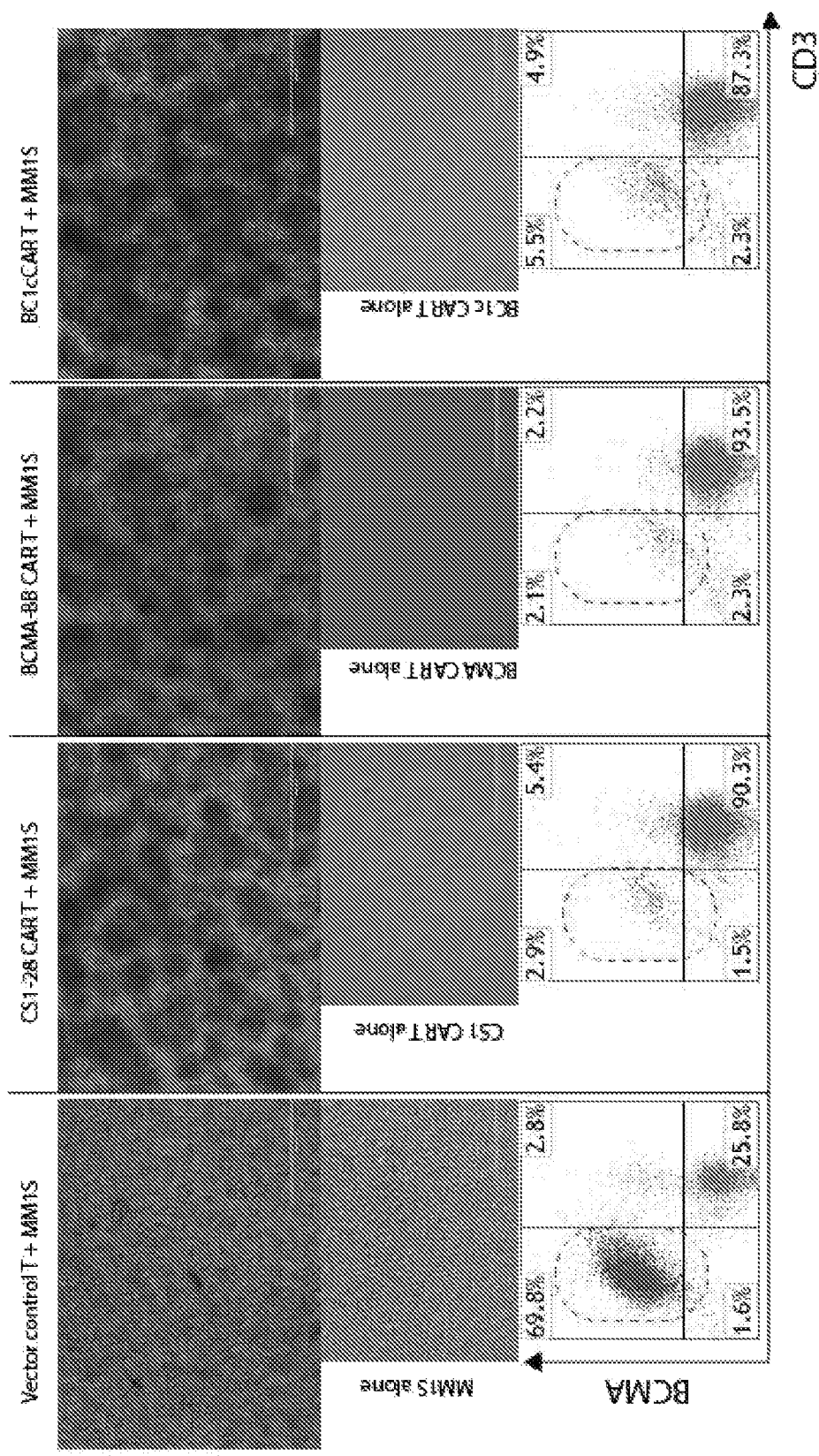
Figure 6C:
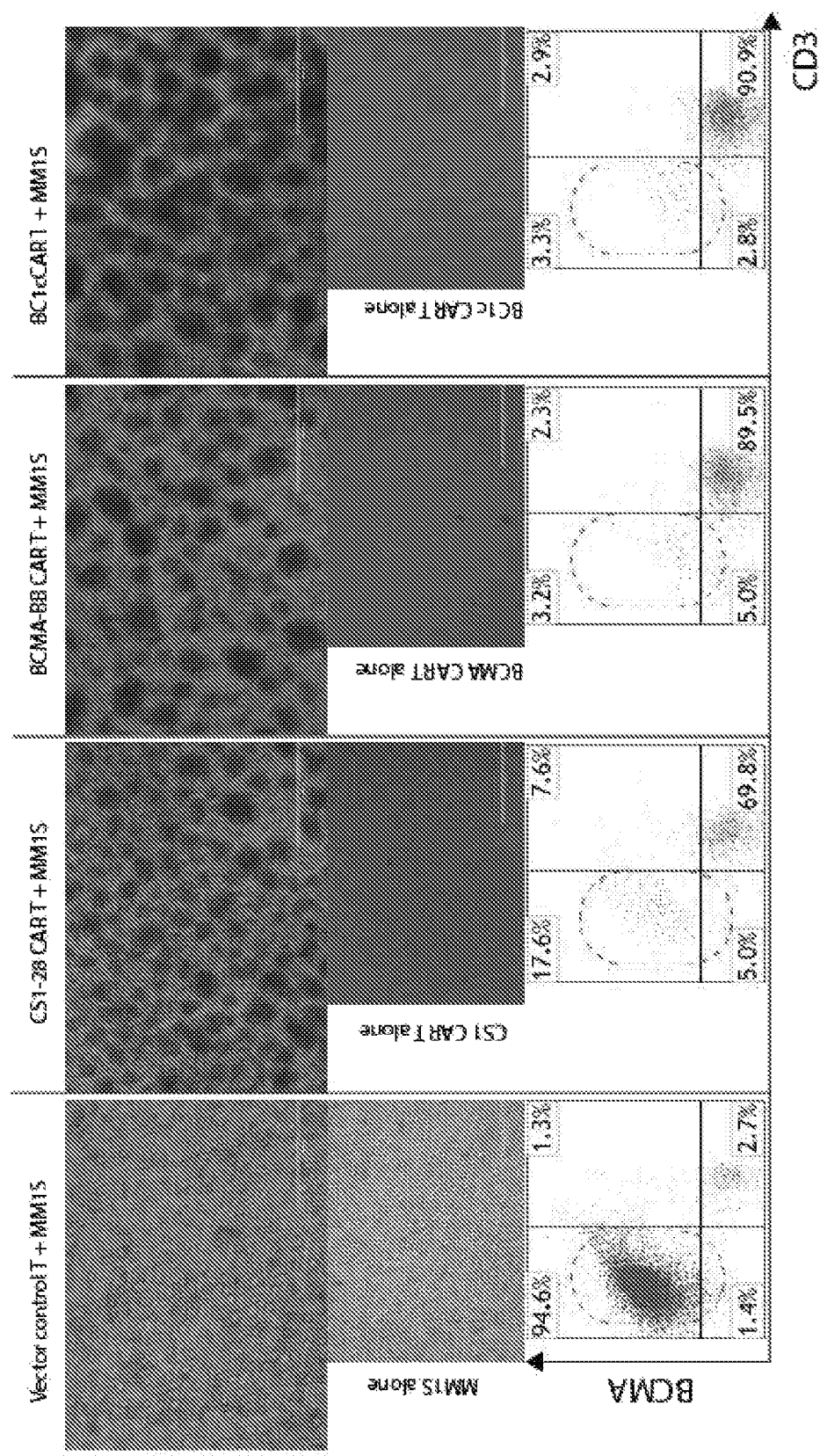

We next investigated the ability of BC1cCAR T-cells to kill tumor cells in a sequential manner under unfavorable microenvironments caused by cell lysis, debris, and tumor re-challenge. Using the scheme in FIG. 6A, we conducted long-term co-cultures using MM1S cells as a model myeloma tumor and periodically re-challenged BC1cCAR T-cells and single BCMA-CAR and CS1-CAR T-cells with fresh MM1S cells to simulate tumor expansion or relapse. Even without exogenous cytokines, we found that all CAR treatments depleted target antigens after 48 hours, with significant clustering and T-cell proliferation (FIG. 6B). In contrast, control T-cells showed no response or proliferation, and yielded a tumor cell population twice its initial size. After re-challenging all treatment wells with fresh MM1S cells we found that all CARs still retained a high degree of cytotoxicity. By 108 hours, new MM1S cells were virtually depleted by both BCMA-CAR and the BC1cCAR, while the CS1-CAR displayed incomplete killing of the new MM1S cells (FIG. 6C). All CAR-mediated tumor lysis and cytotoxicity stopped after 168 hours, however, BCMA-CAR and BC1cCAR still showed detectable minority T-cell populations while control T-cells and CS1-CAR T-cells were virtually undetectable (data not shown).

BC1cCAR T-Cells Exhibit Significant Control and Reduction of Tumor In Vivo

Figure 7A:
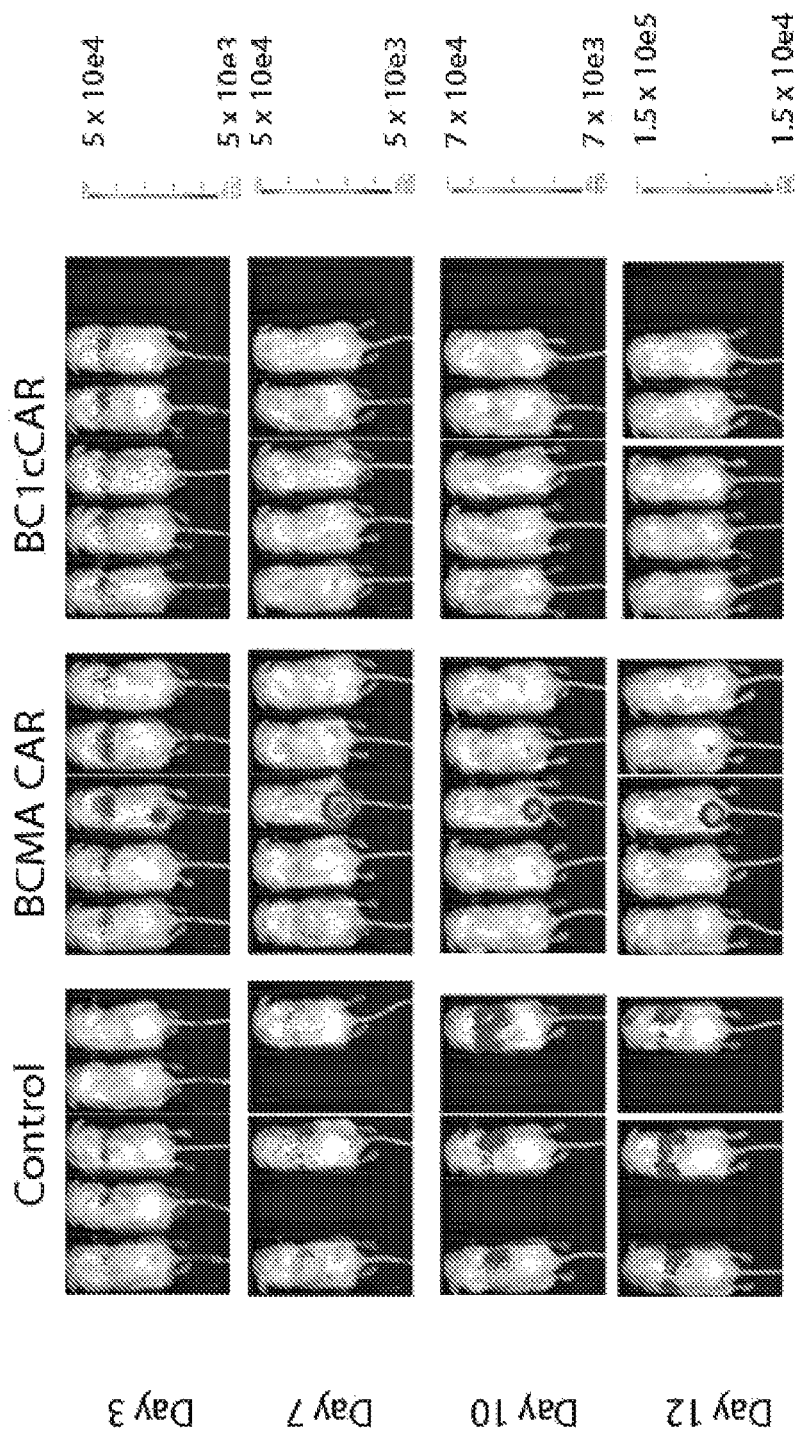
FIGS. 7A-7C: BC1cCAR T-cells demonstrate anti-leukemic effects in vivo.
Figure 7B:
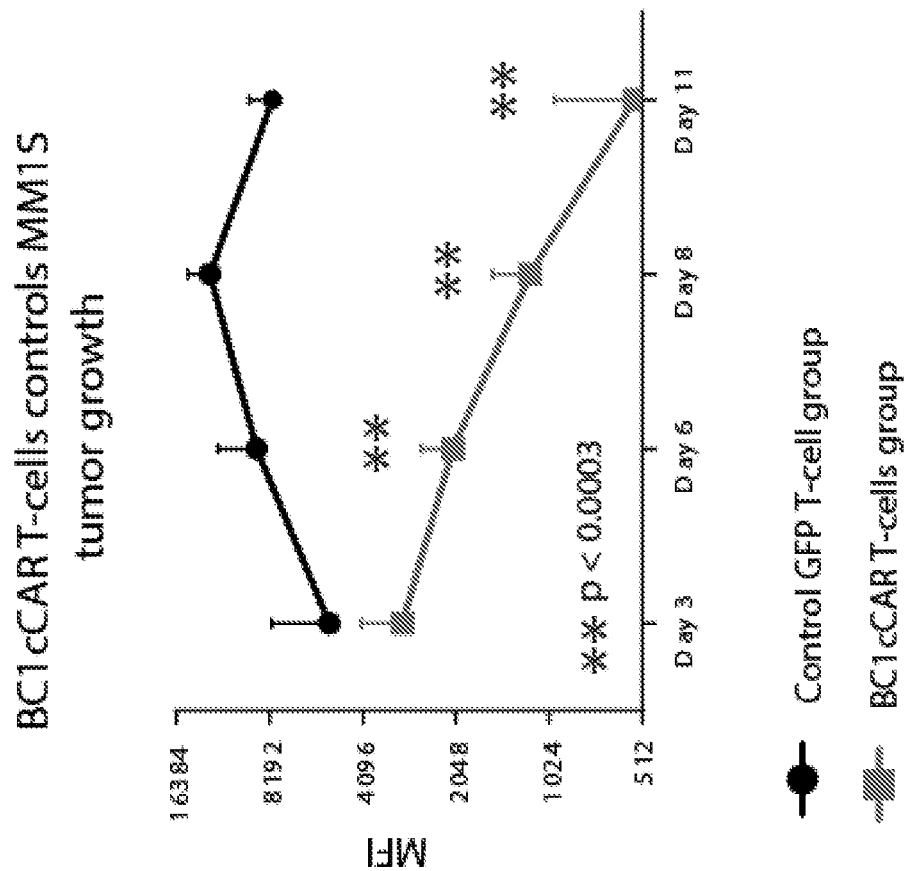
Figure 7C:
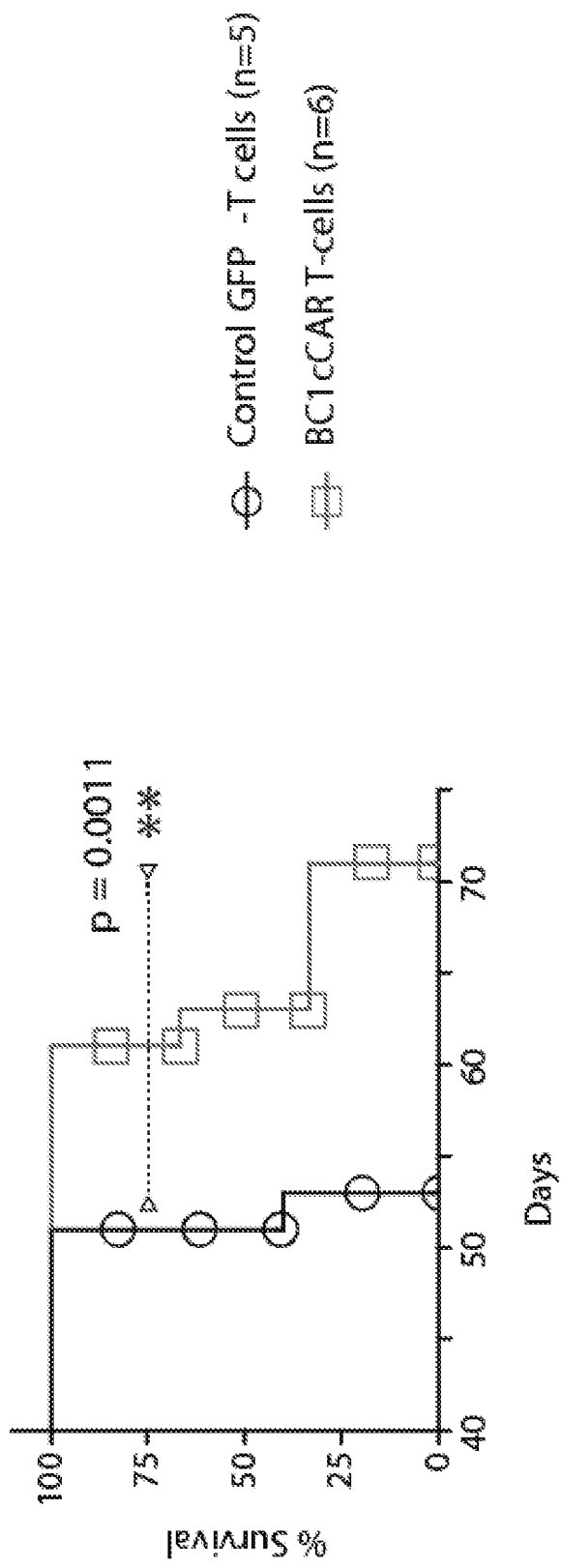

In order to evaluate the in vivo activity of BC1cCAR T-cells, we developed a myeloma mouse model with luciferase-expressing MM1S cells to induce fluorescence visible tumor formation. The BC1cCAR T-cells significantly reduced tumor burden and prolonged survival in MM1S-injected mice when compared to control T-cells. Mice were given a single dose of BC1cCAR or control T-cells and tumor burden assayed by IVIS imaging (FIG. 7A). There was a highly significant difference (P<0.0003) in IVIS measurement of tumor burdens between the control group and the BC1cCAR treatment group from Day 6 onwards (FIG. 7B). CAR injected mice also had significantly more favorable survival outcomes (FIG. 7C).

Mixed Antigen Population Mouse Models Demonstrate Superior Tumor Burden Control by cCAR Expressing Cells Vs Single CAR Expressing Cells To model heterogeneous cell populations and potential antigen escape, we injected mice with a 4:1 mix of BCMA: CS1-expressing K562 cells and treated on day 3 with $7.5 \times 10^6$ of either control, BCMA-CAR, or BC1cCAR T-cells. CS1-CAR T-cells were excluded on the basis of inferior in vitro efficacy. On day 3, two control mice died as a result of the injection procedure and were excluded from analysis. Tumor burden was visualized by fluorescence (FIG. 8A). At day 10, both CARs exhibited over 50% tumor reduction compared to GFP control, increasing to over 60% by day 12 (FIG. 8A—right). By day 10, BC1cCAR outpaced BCMA-CAR in tumor suppression by 6% and this spread increased to 17% by day 12, potentially modeling the inability of BCMA-CAR to lyse residual CS1-K562 cells (20% of tumor injected). Survival outcomes for all CAR T-cell treated mice were significantly improved over the control group. There was also a significant improvement ($p<0.05$) in survival for the BC1cCAR group versus the BCMA-CAR group (FIG. 8B). While both CARs were efficacious in controlling tumor growth, the BC1cCAR demonstrates more robust control compared to a single target option.

Enhanced T-Cell Persistency and Maintenance of Tumor Depletion by Compound CAR T-Cells in Independent Antigen Mouse Models To assay specific BCMA and CS1 antigen-expressing cell depletion and verify compound scFv efficacy, a third mouse model was constructed in which 4 groups consisting of 5 mice each were injected with either BCMA-K562 or CS1-K562 cells, with control and BC1cCAR T-cells administered to each tumor group (n=19 as a result of an early spontaneous mouse death). At times of sacrifice (various: day 30-80+), mice whole blood and liver tissues were screened for T-cell and tumor populations. Both hematological tissue types show consistent tumor presence in control groups when compared to cCAR groups (FIG. 9A, 9B, 10A, 10B). Aggregate tissue analysis of averaged tumor cell populations in both tissues show consistent trends of depleted tumor burden in cCAR treated mice groups (FIG. 9B). In both the blood and liver, control T-cells were unable to persist beyond the 30 day mark and exhibited significant tumor burden in both tissue types (FIG. 9B, 9C). In contrast, cCAR treated mice showed significant T-cell expansion and persistency compared to control T-cells across all mice even at day $30^+$ (FIG. 9C), correlating with observed increased anti-tumor activity and supporting overall improved survival.

Structural Organization of BCMA-CS1-IL-15/IL-15Sushi (CD269-A7D-CS1-Hu63-IL15/IL15Sushi)

BCMA-CS1-IL-15/IL-15sushi (FIG. 11A) contains two independent units of CARs, CD269-A7D (also called BCMA CAR or anti-CD269 CAR), and CS1 CAR (also called CS1-hu63 CAR or anti-CS1 CAR). BCMA-CS1-IL-15/IL-15sushi CAR is able to secret IL-15/IL-15sushi. The soluble IL-15/IL-15sushi fusion are stable and functions as an unexpected and powerful immunomodulatory for CAR T/NK cells and their neighbor tumor immune response cells. The soluble IL-15/IL-15sushi fusion can enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers CAR Expression Activated human peripheral blood T cells were transduced with the lentiviral vector from CD269-A7D-CS1-hu63-IL15/IL15sushi. CAR. FIG. 11B shows the transduction efficiency between activated T cells transduced with either control vector, or CD269-A7D-hu63-IL15/IL15sushi CAR vector, as determined by labeling with goat anti-mouse F(Ab')2 antibody. Activated T cells transduced with the CAR vectors resulted in 23.7% F(Ab')2 positive cells for CD269-A7D-hu63-IL15/IL15sushi (FIG. 11B). These CAR T cells were used in the following in vitro killing assays.

CD269-A7D-CS1-Hu63-IL15/IL15sushi CAR T Cells are Able to Lyse Tumor Cell Lines Expressing Either CD269 or CS1 Antigens in In Vitro Assays CD269-A7D-CS1-hu63-IL15/IL15sushi CART cells from FIG. 11B were assayed for their ability to specifically lyse both K562 cells synthetically expressing either CD269 (BCMA) or CS1 (CD319) antigen. Wild-type K562 cells were transduced with lentiviral vector for CD269 antigen or CS1 antigen expression, and positively selected by FACS (FACS-Aria, BD). Co-cultures with either K562-BCMAxp or K562-CS1xp synthetic expression cells were set up at 2:1 and 5:1 effector cell:target cell ratios, for 48 hours. Following this incubation, cells were stained using mouse anti-human CD3 antibody (in all cases), and either mouse anti-human CD269 or CS1, and analyzed by flow cytometry. At the 2:1 E:T ratio, 58% of the K562-BCMAxp tumor cells were lysed, while at the 5:1 ratio, 91% tumor cells were lysed (FIG. 11C). For co-cultures with K562-CS1-xp tumor cells, the percent lysis was 33 and 72%, respectively (FIG. 11C). These results demonstrate that each CAR component of the CD269-A7D-CS1-hu63-IL15/IL15sushi CAR T cell is able to lyse its intended target cells.

CD269-A7D-CS1-Hu63-IL15/IL15sushi CAR T Cells Exhibit Significant Anti-Tumor Activity in Xenogeneic Mouse Model In order to evaluate the specific in vivo anti-tumor activity of CD269-A7D-CS1-hu63-IL15/IL15sushi CAR T cells against human tumor cell lines, we developed a xenogeneic mouse model using NSG mice sublethally irradiated and intravenously injected with $4 \times 10^6$ of luciferase-expressing MM.1S wild type multiple myeloma cells, to induce measurable tumor formation. Eight days following tumor cell injection, all mice were intravenously injected with a course of $15 \times 10^6$ of either control T cells or CD269-A7D-CS1-hu63-IL15/IL15sushi CAR T cells. On Day 8 (the day before T cell treatment), and Day 12 (72 hours after treatment), mice were subjected to IVIS imaging to measure tumor burden. Average light intensity measured for the MM.1S mice injected with CD269-A7D-CS1-hu63-IL15/IL15sushi CART cells was compared to that of mice injected with the control T cells to determine percent lysis of targeted cells. Results showed that only 3 days following treatment with T cells (Day 12), mice treated with CD269-A7D-CS1-hu63-IL15/IL15sushi CAR T cells had 90% lower tumor burden than mice given control T cells (FIG. 11D). These results show the efficacy of CD269-A7D-CS1-IL15/IL15sushi CAR T cells against multiple myeloma cell line in vivo. In addition, blood drawn at sacrifice showed that MM.1S mice injected with CD269-A7D-CS1-IL15/IL15sushi CART cells had a significant higher level of human IL-15/IL-15sushi than the control mice which were undetectable.

Function of IL15 in CD269-A7D-CS1-Hu63-IL15/IL15sushi CAR NK Cells.

To further determine if IL-15/IL15sushi is being secreted, NK-92 cell line was transduced with lentiviral vector containing CD269-A7D-CS1-hu63-IL15/IL15sushi CAR. Cells were sorted on BD FACS Aria to select NK cells positive for the F(Ab')2 phenotype (FIG. 11E). Sorted cells were expanded, and after 72 hours supernatant was collected and subjected to ELISA on 96-well plates precoated with IL-15 antibody. Following manufacturer's (Boster) directions, colorimetric results obtained on a plate reader were compared to a standard curve generated with human IL-15 to determine concentration of IL-15 in the supernatant. It was determined that IL-15 was detected in the supernatant at 285.9 pg/mL (FIG. 11F). By comparison, supernatant containing the same number of wild-type control NK-92 cells had a concentration of only 0.33 pg/mL.

IL15/IL15sushi Secreted from CD269-A7D-CS1-Hu63-IL15/IL15sushi CAR NK Cells can Substitute for the Function of IL-2 In Vitro for T Cell Expansion NK-92 cell culture requires the presence of IL-2. IL-15 can replace the absence of IL-2 for NK-92 cell growth or expansion in vitro. This system was used to test the function of IL-15/IL-15sushi fusion secreting from CD269-A7D-CS1-hu63-IL15/IL15sushi CAR transduced NK cells. Sorted CD269-A7D-CS1-hu63-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted, and the volume increased to yield a concentration of approximately 0.5×10e6 cells/mL. This process was repeated on Days 4, 6, and 8. As shown in the graph in FIG. 11E, CD269-A7D-CS1-hu63-IL15/IL15sushi NK CAR cells cultured for 8 days without IL-2 in the culture expanded at the same rate as wild-type NK-92 cells cultured with IL-2 added, whereas wild-type NK-92 cultured without IL-2 had all died by Day 6. This indicates that IL-15 secreted by the NK CAR cells can substitute for the expansion activity of IL-2.

In one embodiment, the engineered cell includes a BCMA-CS1 cCAR polypeptide and IL-15/IL-15sushi (SEQ ID NO. 42), and corresponding nucleotides (SEQ ID NO. 43).

Examples for Targeting CD123+ and/or CD33+ Leukemia/Lymphomas by CD123b-CD33b cCAR (a Version of CD123-CD33 cCAR) T Cells Generation of CD123b-CD33b cCAR T-Cells Lentivirus transfected cytotoxic effector T-cells were engineered to express two complete units of CAR linked by a self-cleaving P2A peptide (FIG. 12A). The resulting compound CAR (CD123b-CD33b cCAR) is capable of targeting CD123+ and/or CD33+ leukemic cells (FIG. 12B). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the CD123b-CD33b cCAR molecule on the T-cell surface.

CD123b-CD33b cCAR T-Cell Transduction Efficiency

To evaluate CD123b-CD33b cCAR expression levels on the T-cell surface after transduction, flow cytometry analysis was used (FIG. 13). The transduction efficiency was determined to be 25%.

CD123b-CD33b cCAR T-Cells Effectively Lyse Acute Myeloid Leukemia Cell Lines

Figure 14A:
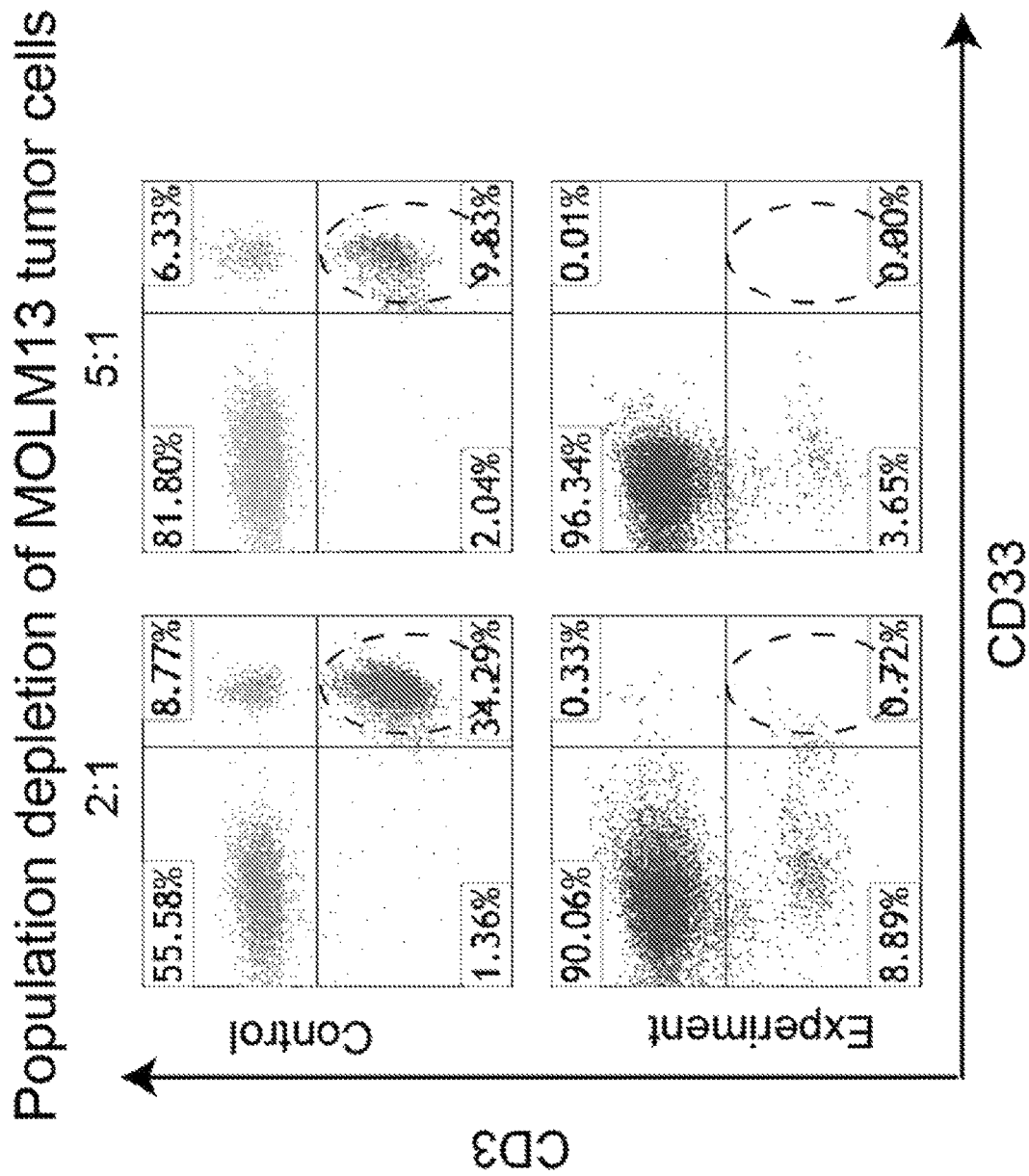
Figure 14B:
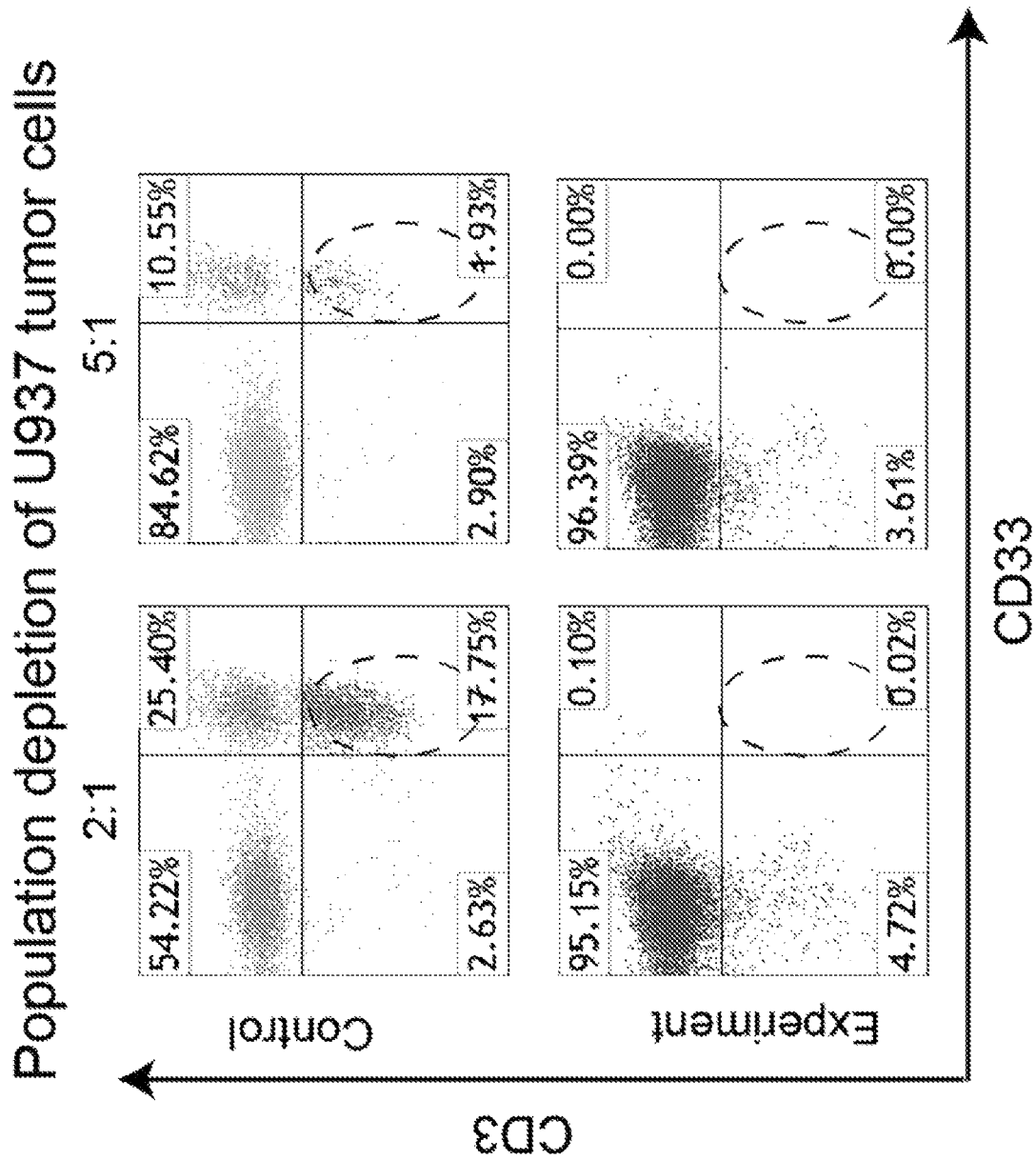
Figure 14C:
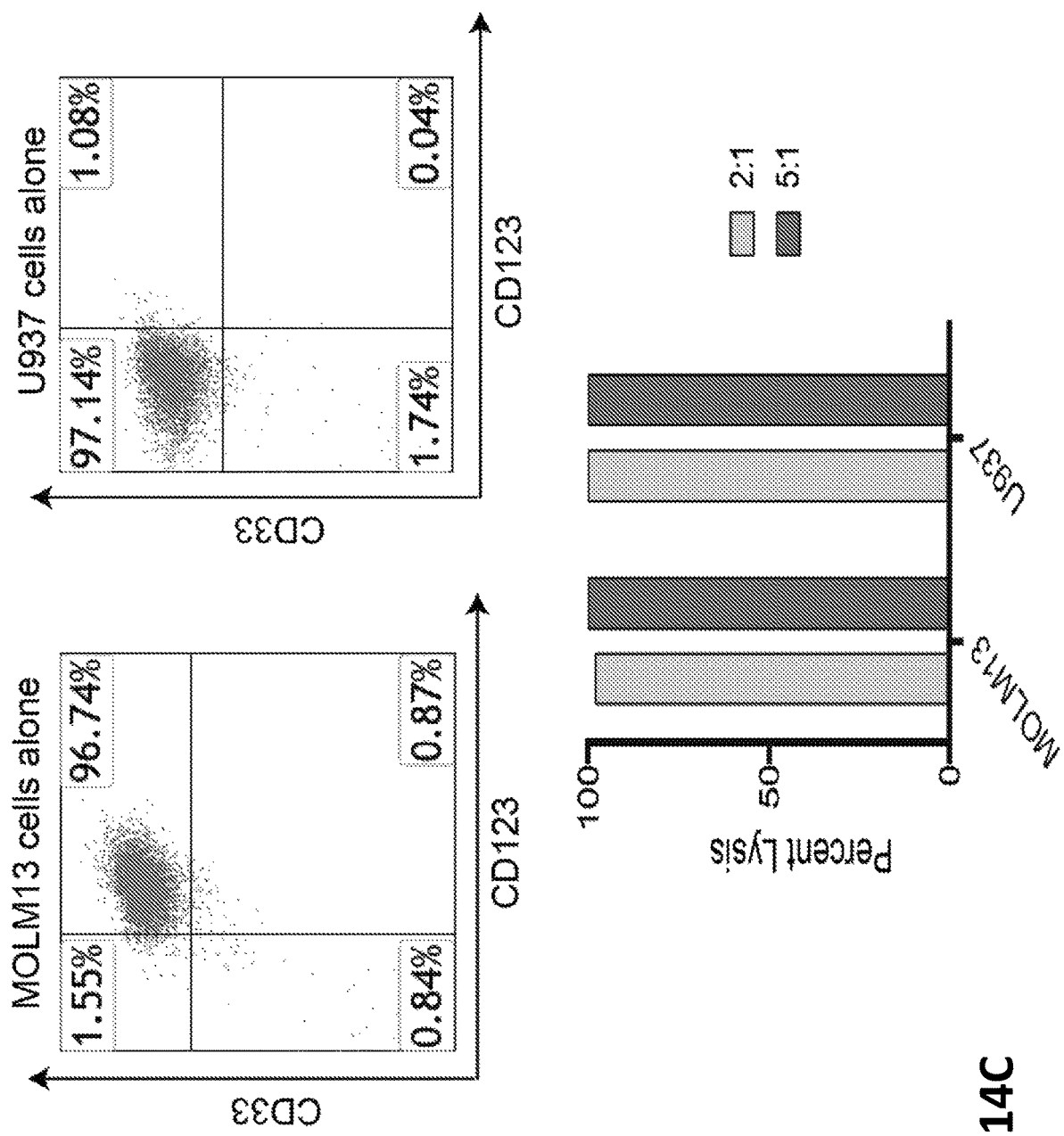

To evaluate the anti-tumor activity of the CD123b-CD33b cCAR (CD123b-CD33b cCAR) T-cells, we performed co-cultures using the AML cell line MOLM13 (CD33+CD123+) and the promonocytic U937 cell line (CD33$^+$CD123-). To distinguish between the target leukemia calls (MOLM13 and U927; both are CD3-) and effector T-cells (CD3$^+$) during flow cytometry, cells were stained with CD3. Co-culture assays were performed at effector to target (E:T) ratios of 2:1 and 5:1 for 24 hours, and flow cytometry analysis was used to determine cell lysis rates by CD123b-CD33b cCAR T-cells or control T-cells (FIG. 14A, 14B). At the 2:1 E:T ratio, CD123b-CD33b cCAR T-cells were able to lyse around 98% of CD123+CD33+ MOLM13 cells and 99.9% of CD33+U937 cells when compared to control T-cells. Furthermore, at the 5:1 ratio, 100% lysis of both cell lines was observed (FIG. 14C). We also validated the surface markers expressed on both the MOLM13 and U937 cell lines (FIG. 14C). Overall, these results suggest that CD123b-CD33b cCAR T-cells specifically and robustly eliminate tumor cells expressing either or both antigens. Moreover, the finding that the CD123b-CD33b cCAR T-cells effectively ablated U937 cells expressing only CD33 and not CD123 supports the fact that each discrete unit of the compound CAR can independently target its antigen and eliminate a target expressing only one antigen or both antigens.

Figure 14D:
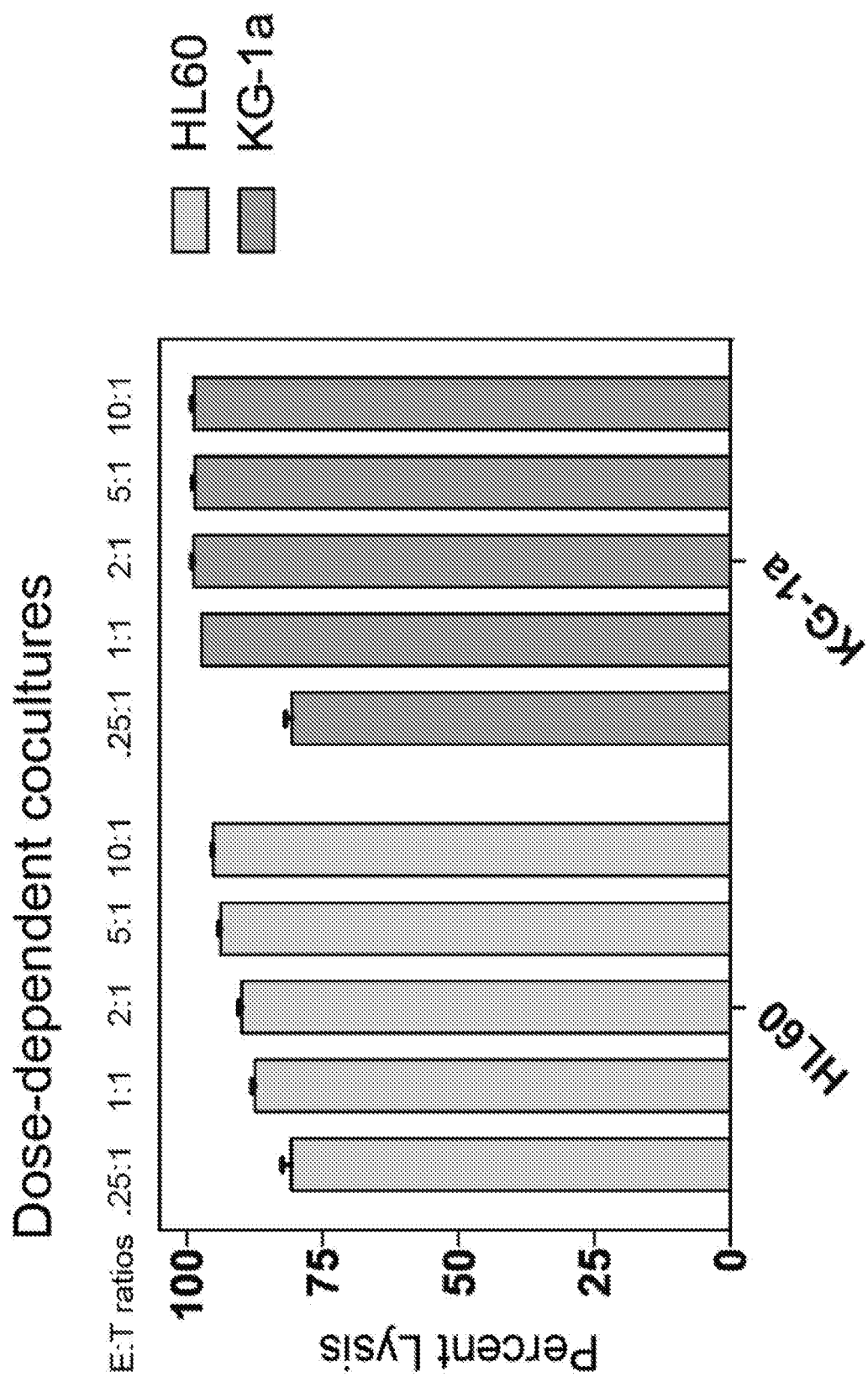

We further evaluated the dose-dependent tumor lysis ability of the CD123b-CD33b cCAR T-cells by varying and decreasing the E:T ratio against two other cell lines: KG1a (CD123dimCD33+) and HL60 (CD123dimCD33+). CD123b-CD33b cCAR T-cells were cultured against KG1a and HL60 cell lines in 0.25:1, 0.5:1, 1:1, 2:1, 5:1, and 10:1 E:T ratios, showing over 75% tumor lysis ability at even a 0.25:1 ratio. Overall, there was a strong correlation between dose and tumor-lysis until saturation at the 5:1 ratio (FIG. 14D).

CD123b-CD33b cCAR T-Cells Effectively Lyse Primary Myeloid Leukemia Tumor Cells

We next established the anti-tumor properties of the CD123b-CD33b cCAR T-cells against primary tumor cells. Cells were stained with CD3 to distinguish the CAR T-cells from the CD3-leukemia samples. Different primary patient leukemia samples including two CD123+CD33+ AML and two CD123+B-ALL samples (PT1:AML, PT2:B-ALL, PT3: AML, and PT4:B-ALL) were assayed in this panel and flow cytometry analysis was performed to verify tumor lysis with depleted target populations encircled (FIG. 15). Compared to the previous anti-tumor cytotoxicity results for AML cell lines (FIG. 14), CD123b-CD33b cCAR T-cells showed similarly positive results against all patient samples, with over 80% tumor lysis at the 2:1 ratio and more than 98% tumor lysis at the 5:1 E:T ratio (FIG. 15). Moreover, similarly to our cell lines, the finding that the CD123b-CD33b cCAR T-cells effectively ablated PT2 cells expressing only CD123 and not CD33 supports the fact that each discrete unit of the compound CAR can independently target its antigen and eliminate a cell expressing only one of its target antigens (as seen against CD33+U937 and CD123+ PT2 cells) or both target antigens (as seen against CD123+CD33+ MOLM13 and PT1 cells). Overall, these results suggest that CD123b-CD33b cCAR T-cells display high killing efficacy against patient tumor cells expressing either or both antigens.

Figure 15A:
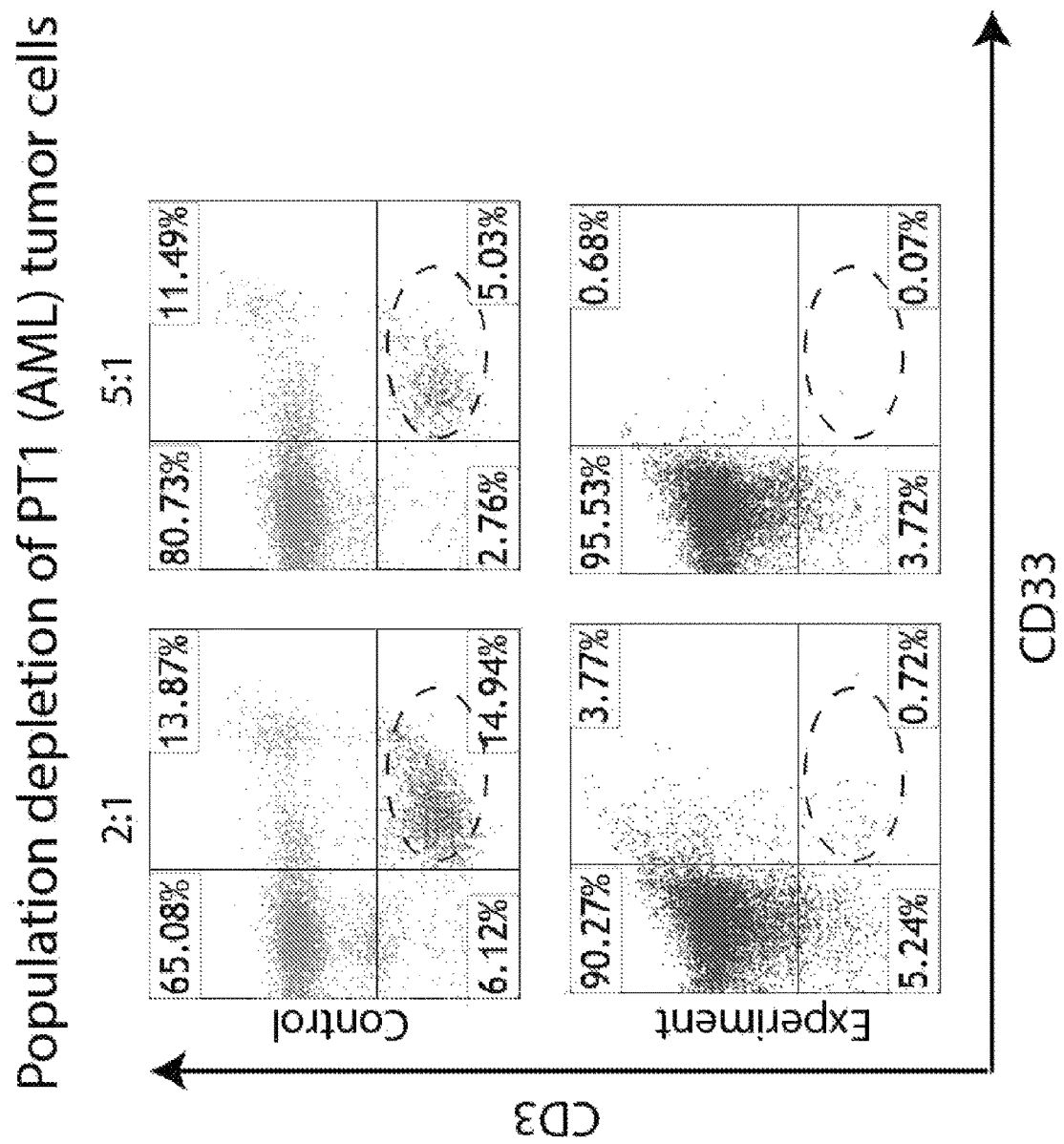
Figure 15B:
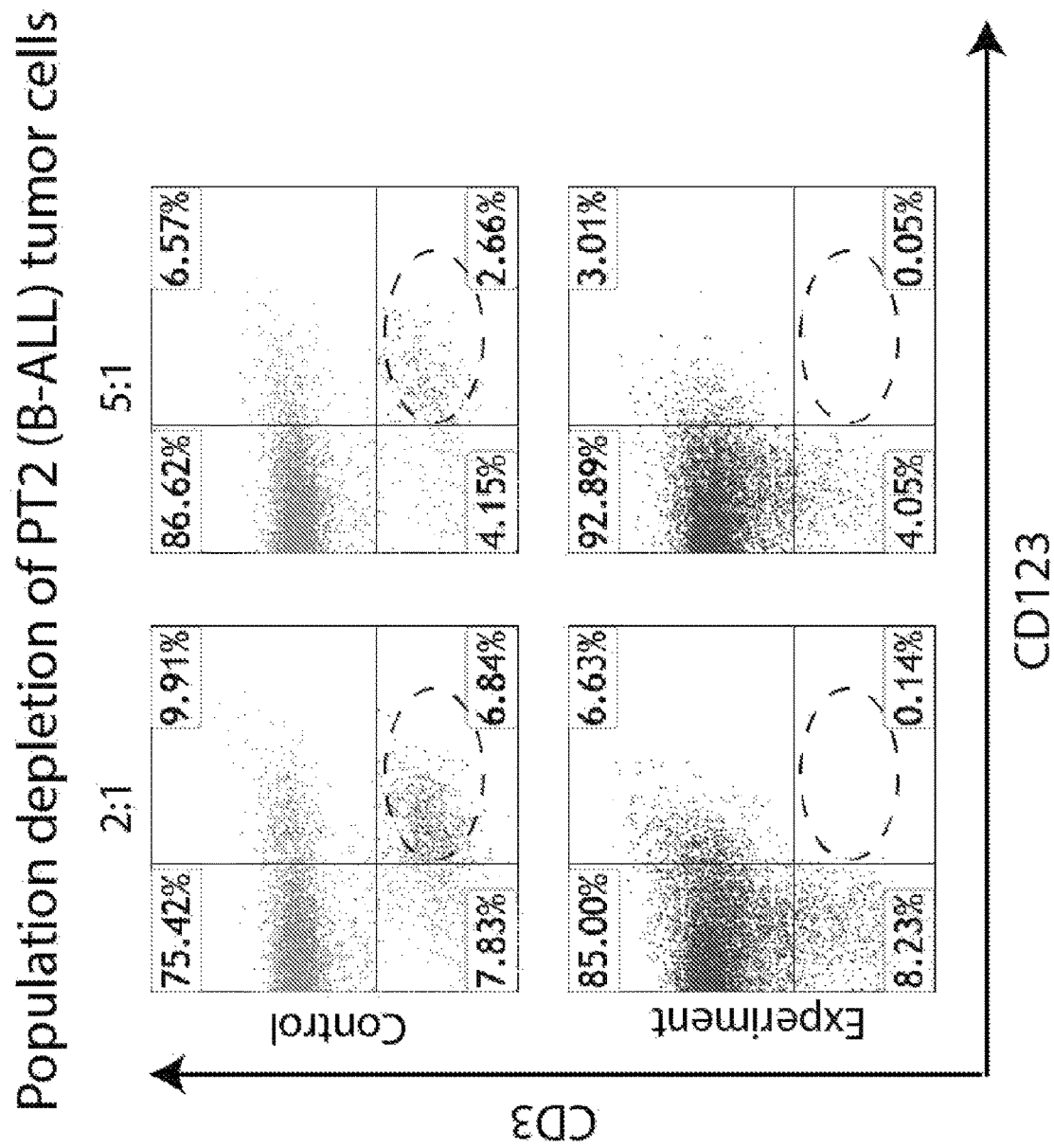
Figure 15C:
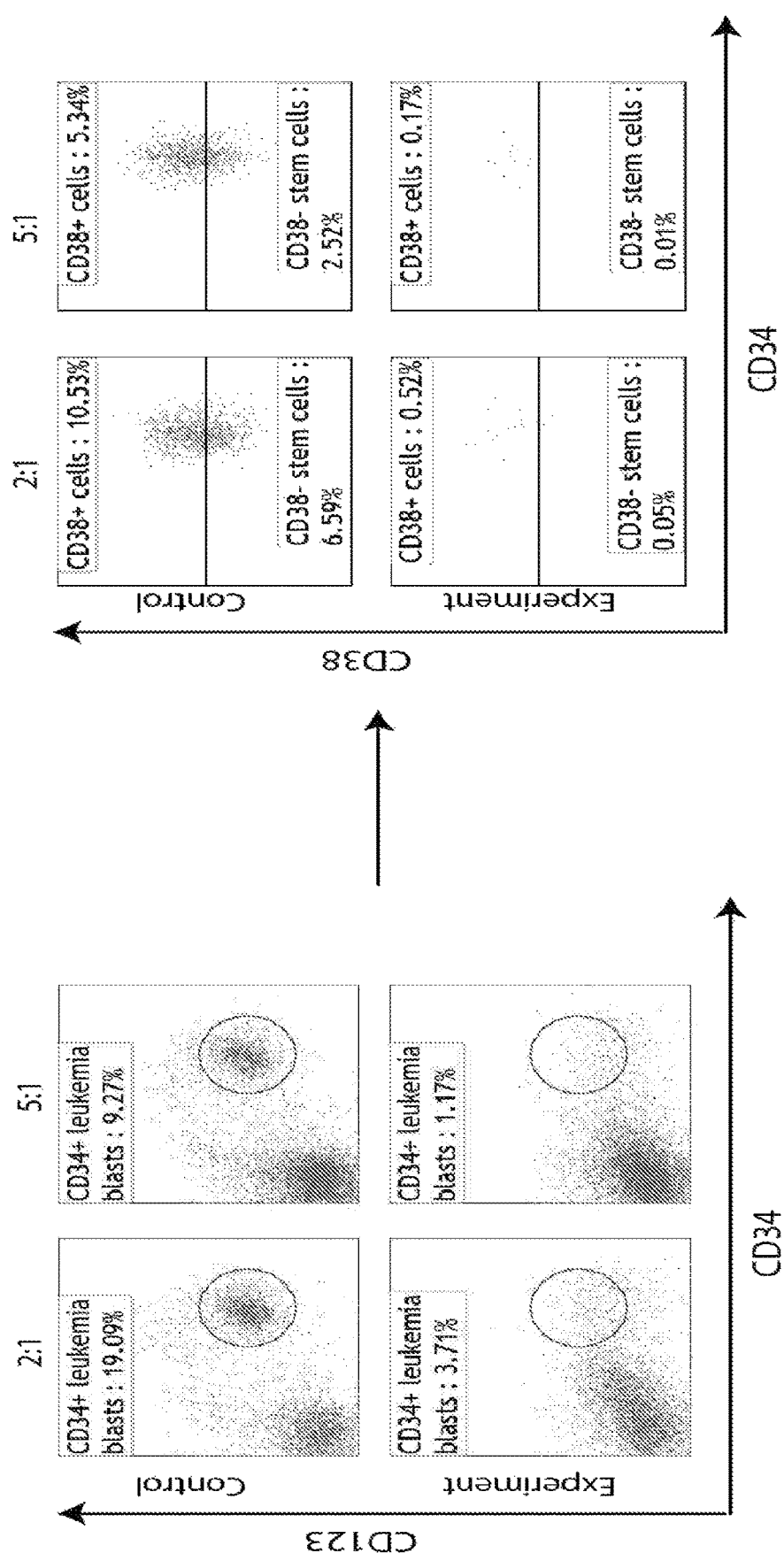
Figure 15D:
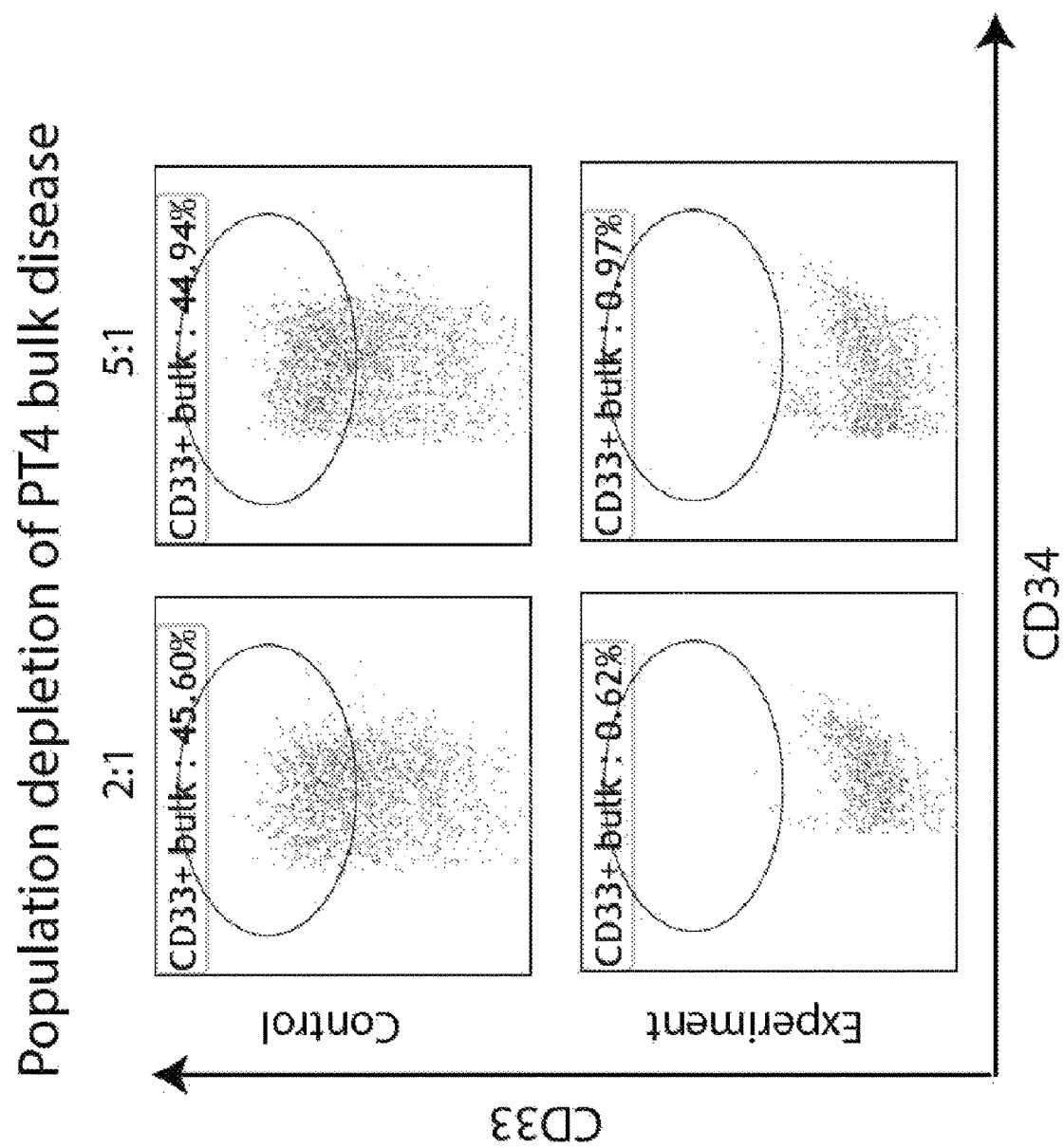
Figure 15E:
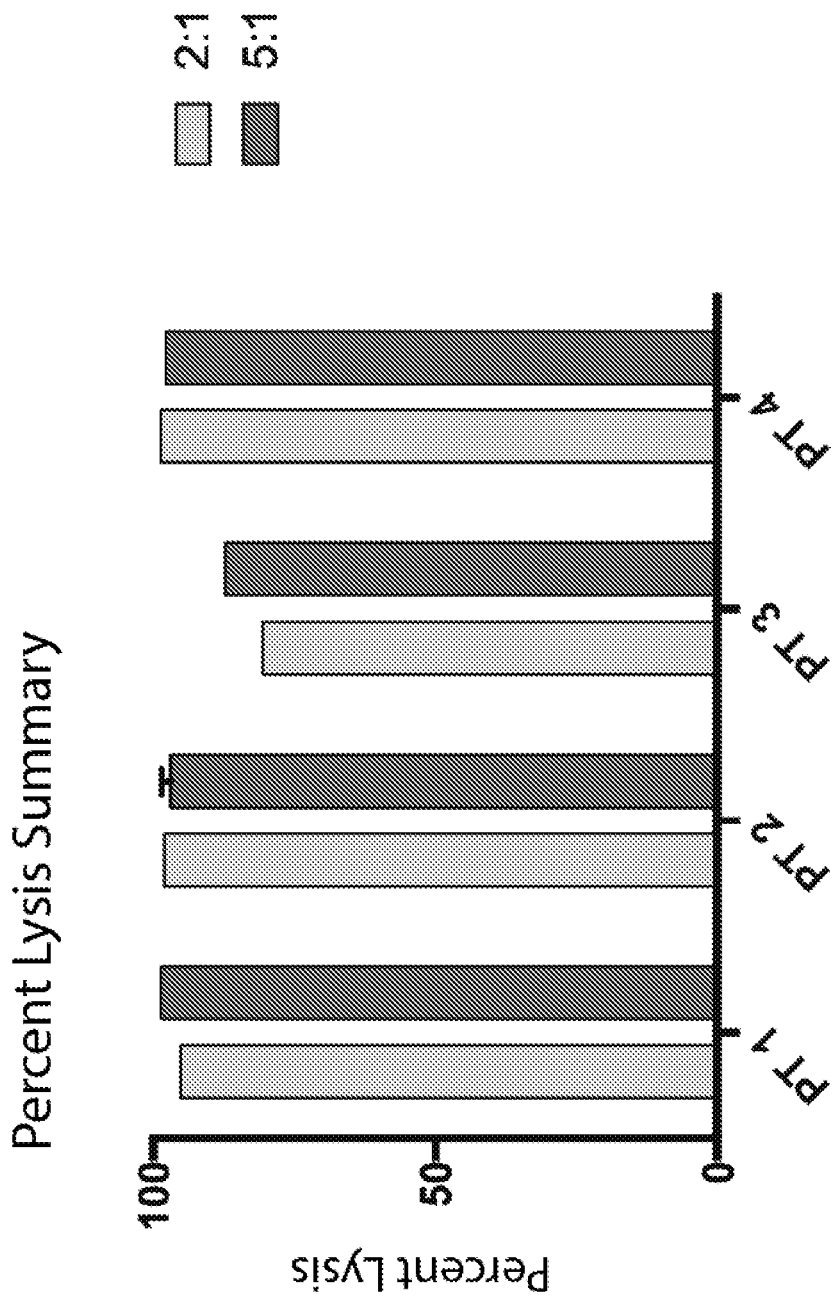

We also specifically examined the ability of our CD123b-CD33b cCAR to eliminate specific cell populations including leukemic stem cells (CD123+CD34+CD38-) in the PT3 sample and myeloid leukemia bulk disease (CD34variableCD33+) in the PT4 sample (FIG. 15D). We found that CD123b-CD33b cCAR T-cells successfully ablated both LSCs and bulk disease cells.

CD123b–CD33b cCAR T-Cells' Discrete Receptor Units Independently Lyse Target Cells in an Antigen-Specific Manner To further confirm our cCAR's independent antigen targeting ability, we generated Jurkat artificial cell lines expressing either CD123 or CD33 and tested CD123b–CD33b cCAR T-cells against these cells in addition to wild-type Jurkat cells expressing neither antigen (FIG. 16). We found that the CD123b–CD33b cCAR T-cells specifically and potently ablated cells expressing either the CD123 or CD33 antigen when compared to wild-type Jurkat cells expressing neither antigen (FIGS. 16A, 16B and 16C). Overall, we conclude that the our CD123b–CD33b cCAR T-cells can act via stimulation of either CAR receptor, and are able to target cells expressing only one target antigen or both equally well, and eliminate targets with high efficacy.

CD123b–CD33b cCAR T-Cells Exhibit Profound Anti-Tumor Activity in Two Xenograft Mouse Models of AML Using MOLM13 and U937 Cells In order to evaluate the in vivo anti-tumor activity of CD123b–CD33b cCAR T-cells as a predictor of their therapeutic efficacy in patients, we developed two xenograft mouse models (FIG. 17). NSG mice were sublethally (2.0 Gy) irradiated and intravenously injected with either $1.0 \times 10^6$ firefly luciferase-expressing MOLM13 cells or $1.0 \times 10^6$ firefly luciferase-expressing U937 cells. On day 4 following MOLM13 or U937 engraftment, mice were intravenously injected with a $10 \times 10^6$ cells of either CD123b–CD33b cCAR or control T-cells. To evaluate tumor burden in mice, RediJect D-Luciferin (Perkin-Elmer) was injected intraperitoneally on days 6, 9, and 13, and mice were subjected to IVIS imaging to quantify the luciferase activity (Caliper LifeSciences) (FIG. 17A, 17B). As observed by IVIS imaging, total flux levels continually increased in control mice with drastic tumor burden growth. In contrast, CD123b–CD33b cCAR treated mice significantly suppressed tumor burden as early as day 3. By day 6, mice treated with the cCAR had over 80% reduction in tumor burden in both models (FIG. 17A, 17B). This tumor suppression was maintained and increased in potency through day 13, as total flux in CD123b–CD33b cCAR treated mice remained near background null values with statistically significant differences from control T-cell treated mice.

We also evaluated tumor cell and CAR T-cell persistency at the time of sacrifice. Peripheral blood was collected from each experimental mouse at the time of sacrifice along with control mice, and analyzed via flow cytometry for the presence of transplanted tumor (MOLM13 or U937 cells) and T-cells (cCAR or control). MOLM13 and U937 cells are CD3– cells, allowing them to be distinguished from CD3+ CAR or control T-cells. Murine peripheral blood cells were gated by side scatter and human CD45 antibody, and then broken down into CD3 vs. CD33. While control treated mice showed significant residual tumor populations (~75-87%) in the peripheral blood, CD123b–CD33b cCAR treated mice showed virtual depletion of all tumor comparable to control mice (FIG. 17C). In addition, CD123b–CD33b cCAR treated mice showed significant T cell expansion with virtually all human cells in the peripheral blood that were CAR T cells. This confirms the potency and persistency of our cCAR T-cells in maintaining long-term responses. Furthermore, CD123b–CD33b cCAR treated mice showed significantly increased survival outcomes as compared to control treated mice (FIG. 17A, 17B).

In Vivo Depletion of Infused cCAR T-Cells Following Treatment with CAMPATH

For clinical treatment using CAR T-cells against acute myeloid leukemias, establishment of safety methods to eliminate CAR T-cells from patients may be necessary after tumor depletion or in emergency cases due to unexpected side effects caused by CAR therapy. T-cells and B-cells express CD52 on the cell surface and a CD52 specific antibody, CAMPATH (alemtuzumab), can eliminate CD52+ cells from circulation. To assess the effect of CAR elimination by CAMPATH treatment, we conducted in vivo procedures as described (FIG. 18A). We intravenously injected $10 \times 10^6$ cCAR T-cells into irradiated mice. On the next day, we administered 0.1 mg/kg of either CAMPATH or PBS via IP injection to 3 mice of each group. At 6 and 24 hours following CAMPATH treatment, we collected peripheral blood and determined the presence of cCAR T-cells by FACS analysis. cCAR T-cells were gated by side scatter (SSC) and CD3 expression and CD3 and CD45 expression to distinguish them from mouse cells. CAMPATH injection depleted cCAR T-cells in blood at both 6 h and 24 h (FIG. 18B, 18C). These findings support the use of CAMPATH as a safety switch to rapidly deplete CAR-T cells from the circulation.

In one embodiment, the engineered cell includes a CD123-CD33 cCAR polypeptide, and IL-15/IL-15sushi (SEQ ID NO. 34), and corresponding nucleotides (SEQ ID NO. 35).

In one embodiment, the engineered cell includes a CD123-CLL1 cCAR polypeptide, and IL-15/IL-15sushi (SEQ ID NO. 36), and corresponding nucleotides (SEQ ID NO. 37).

Examples for Targeting B-ALL and Other Leukemias by CD19b–CD123 cCAR (a Version of CD19-CD123 cCAR)

Generation of CD19b–CD123 cCAR T Cells

Lentivirus transfected cytotoxic effector cells, namely T cells, are engineered to express an anti-CD19 single-chain variable fragment (scFv1, CD19b) region fused to an anti-CD123 fragment (scFv2, CD123) by a self-cleaving P2A peptide. These antibody domains are linked by CD8-derived hinge (H) and transmembrane (TM) regions to 4-1BB and CD28 co-activation domains and a CD3ζ signaling domain (FIG. 19). A strong spleen focus forming virus promoter (SFFV) and a CD8 leader sequence were used for efficient expression of the CD19b-CD123 cCAR molecule on the T-cell surface.

CD19b–CD123 cCAR T-Cell Transduction Efficiency

T-cells isolated from umbilical cord blood (UCB) buffy coats were transduced with CD19b-CD123 cCAR lentivirus after 2 days of activation. The CD19b–CD123 cCAR transduction efficiency was determined to be 26% by flow cytometry (FIG. 20).

Figure 21A:
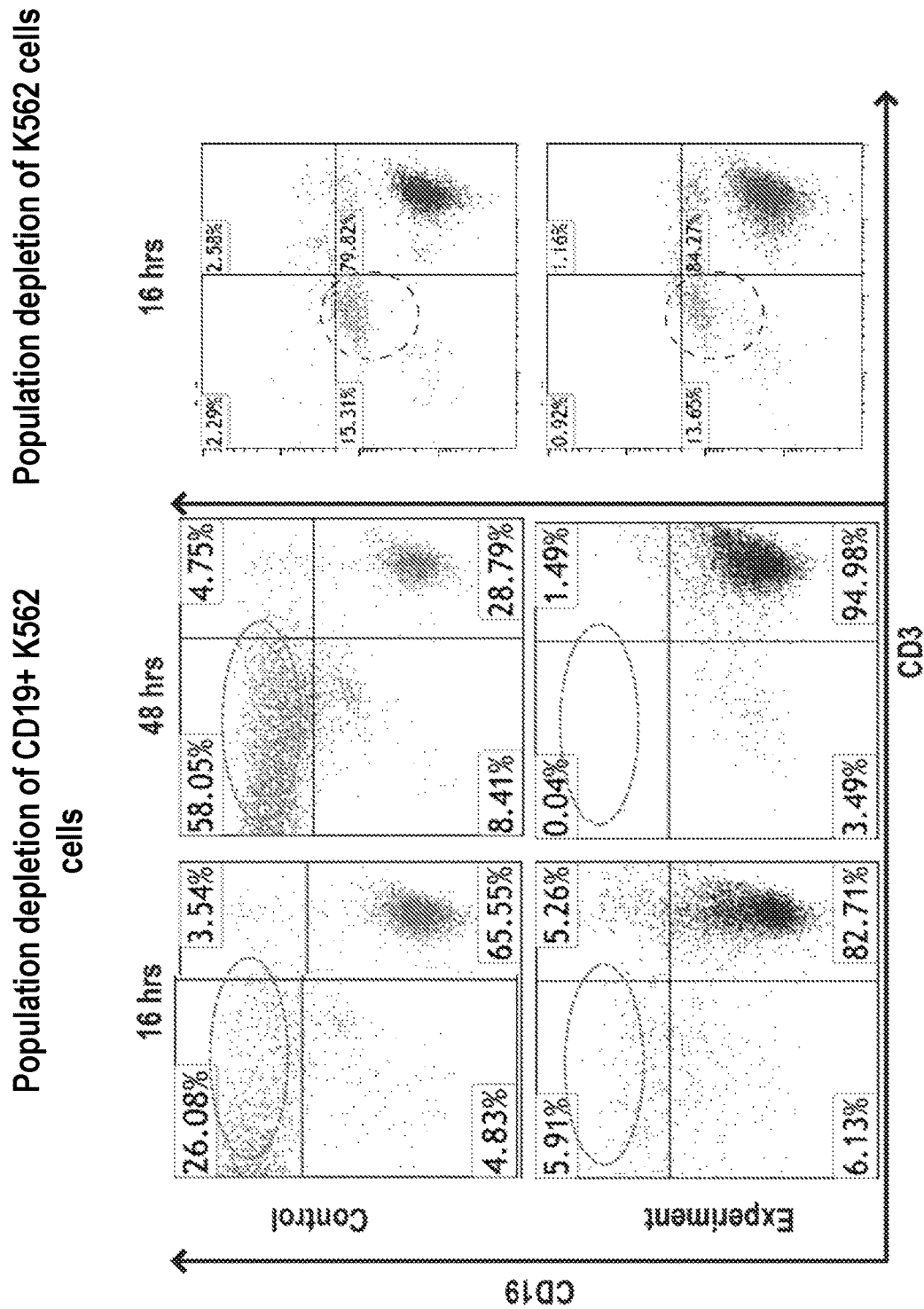
Figure 21B:
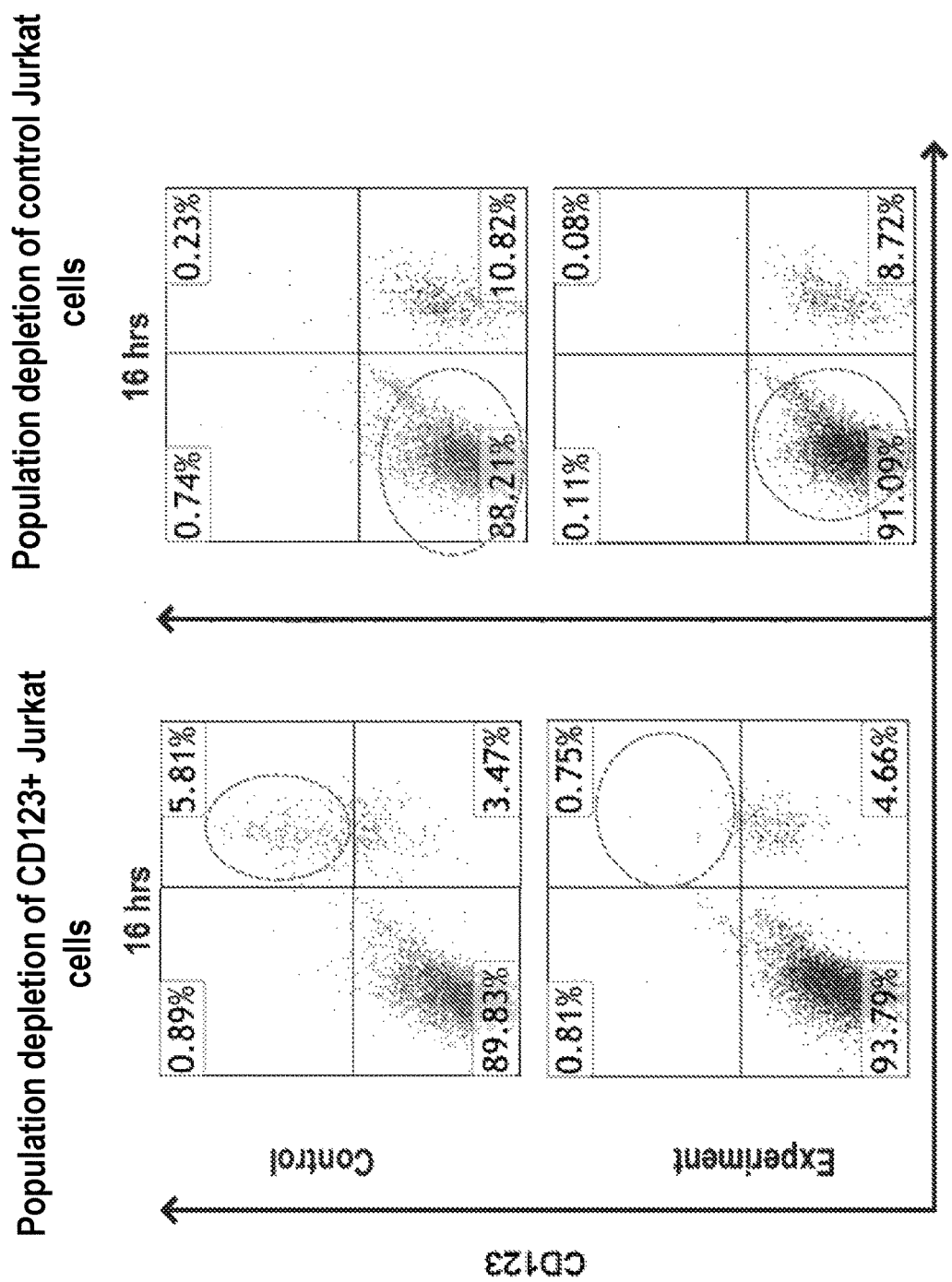

CD19b–CD123 cCAR-2G T-Cells Effectively Lyse CD19-Positive and CD123-Positive Leukemic Cell Lines To assess the cytotoxicity of CD19b–CD123 cCAR T-cells, we conducted co-culture assays at a 5:1 effector:target (E:T) ratio against leukemia/lymphoma cell lines with artificially expressing CD19 and CD123. K562 cells (a myeloid leukemia cell line) were used to express CD19 antigen by lentiviral infection (named K19), and wild type K562 cell line was used as a control. Jurkat cells were similarly used to express CD123 antigen (named J123), and wild-type Jurkat cells were used as a control. CD19b–CD123 cCAR T-cells lysis of target cells was quantified by flow cytometry. In 16 hour co-cultures, CD19b–CD123 cCAR T-cells lysed over 66% of K19 cells at 16 hours, and over 99% at 48 hours (FIG. 21A). Over 88% of J123 cells were lysed at 16 hours, reaching saturation (FIGS. 21B and 21D). Control K562 and control Jurkat cells were not significantly lysed, with less than 20% lysis. The finding that the CD19b-CD123 cCAR T-cells effectively ablate both artificially-induced singly-positive CD19 and CD123 cells supports the idea that each discrete unit of the compound CAR can independently target its antigen and eliminate a target expressing only one antigen or both antigens. Furthermore, the lack of cell lysis of control K562 and Jurkat cells demonstrates that CD19b-CD123 cCAR T-cells exhibit antigen-specific cytotoxicity.

We next assessed the ability of CD19b–CD123 cCAR T-cells to target leukemia/lymphoma cell lines with naturally occurring CD19/CD123 antigen expression: human mantle cell lymphoma SP53 (CD19+CD123−) and human acute myeloid leukemia KG1a (CD19−CD123+). In 16 hour co-cultures, the CD19b–CD123 cCAR exhibited virtually complete lysis of SP53 cells, with 86% depletion of target cells, reaching saturation (FIG. 21C).

Figure 21C:
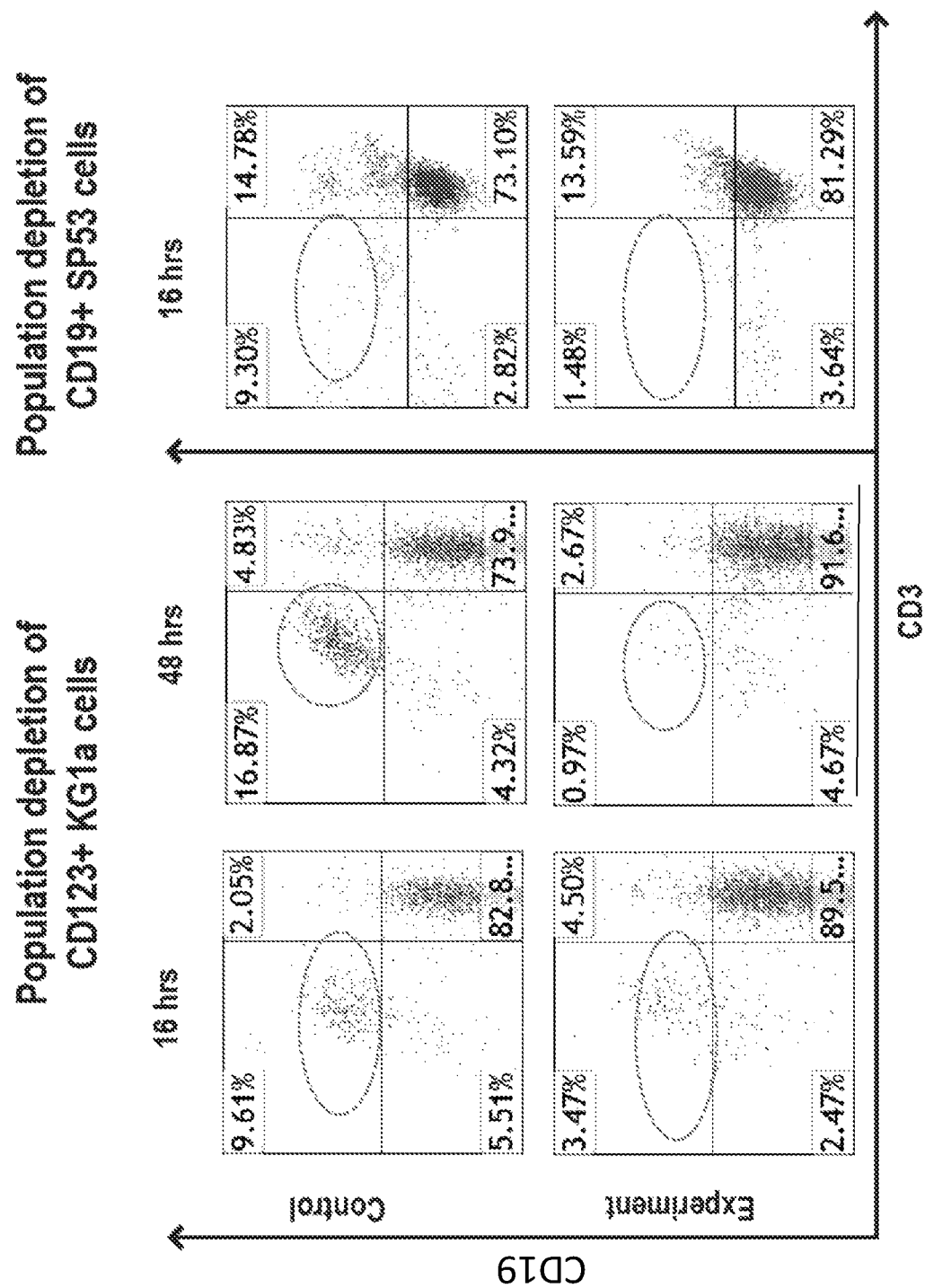
Figure 21D:
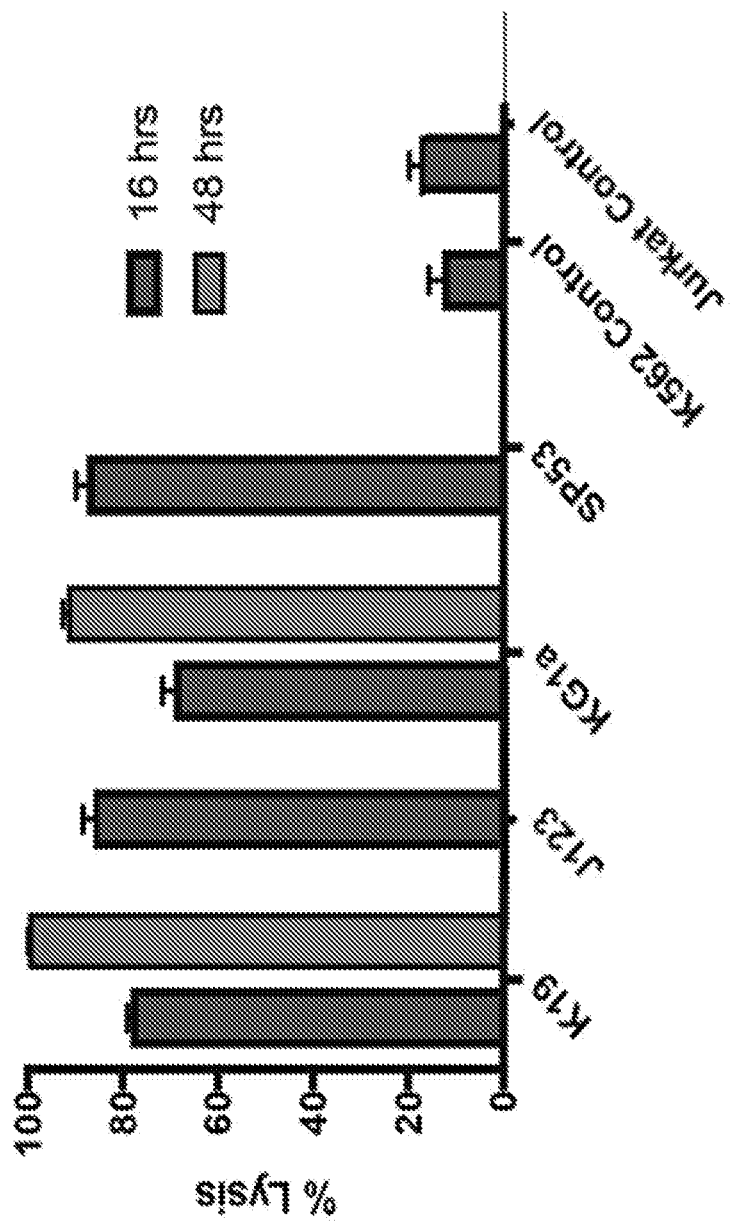

In KG1a, CD19b–CD123 cCAR lysed over 69% of CD123+ target cells at 16 hours, and over 94% at 48 hours (FIGS. 21C and 21D). Overall, CD19b–CD123 cCAR T-cells specifically and effectively lysed target populations expressing either antigen target, displaying effective bulk cytotoxicity.

Figure 22A:
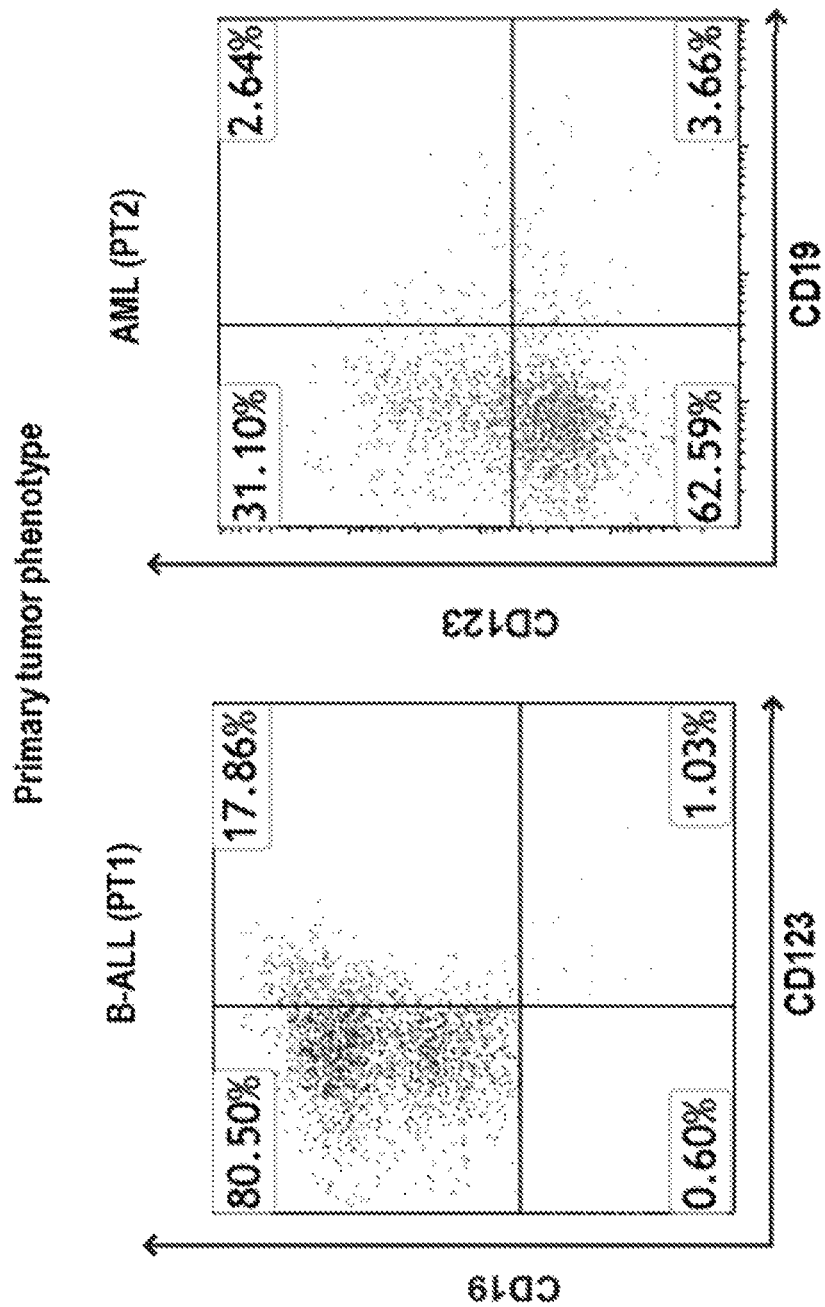
Figure 22B:
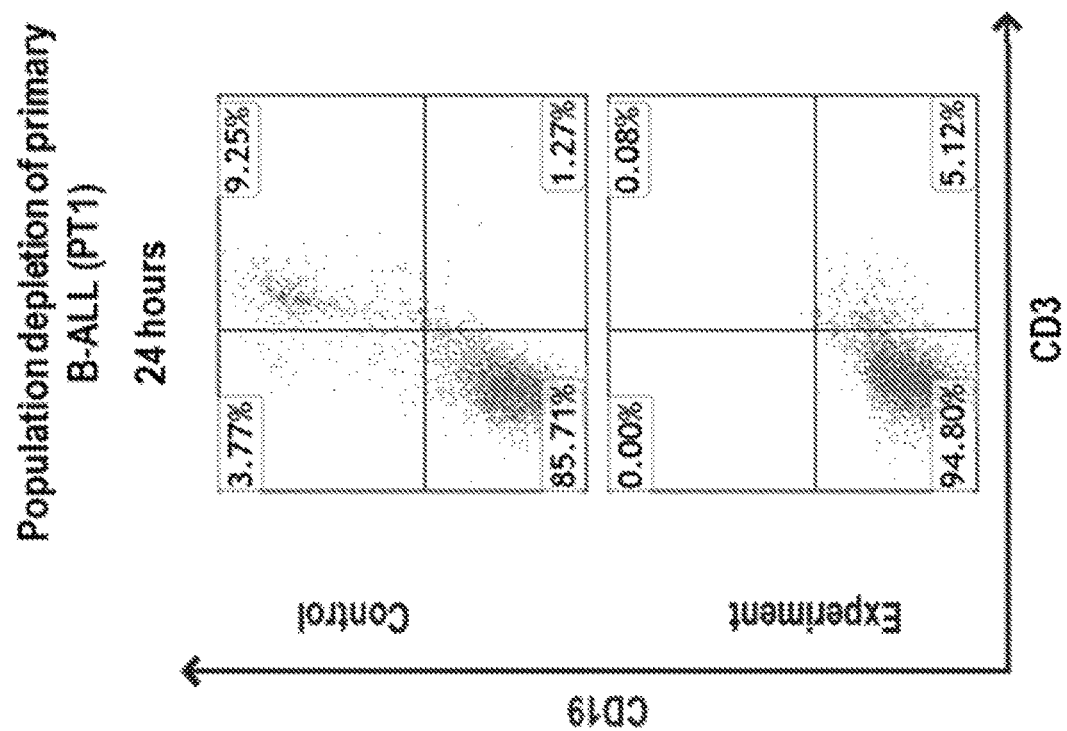
Figure 22C:
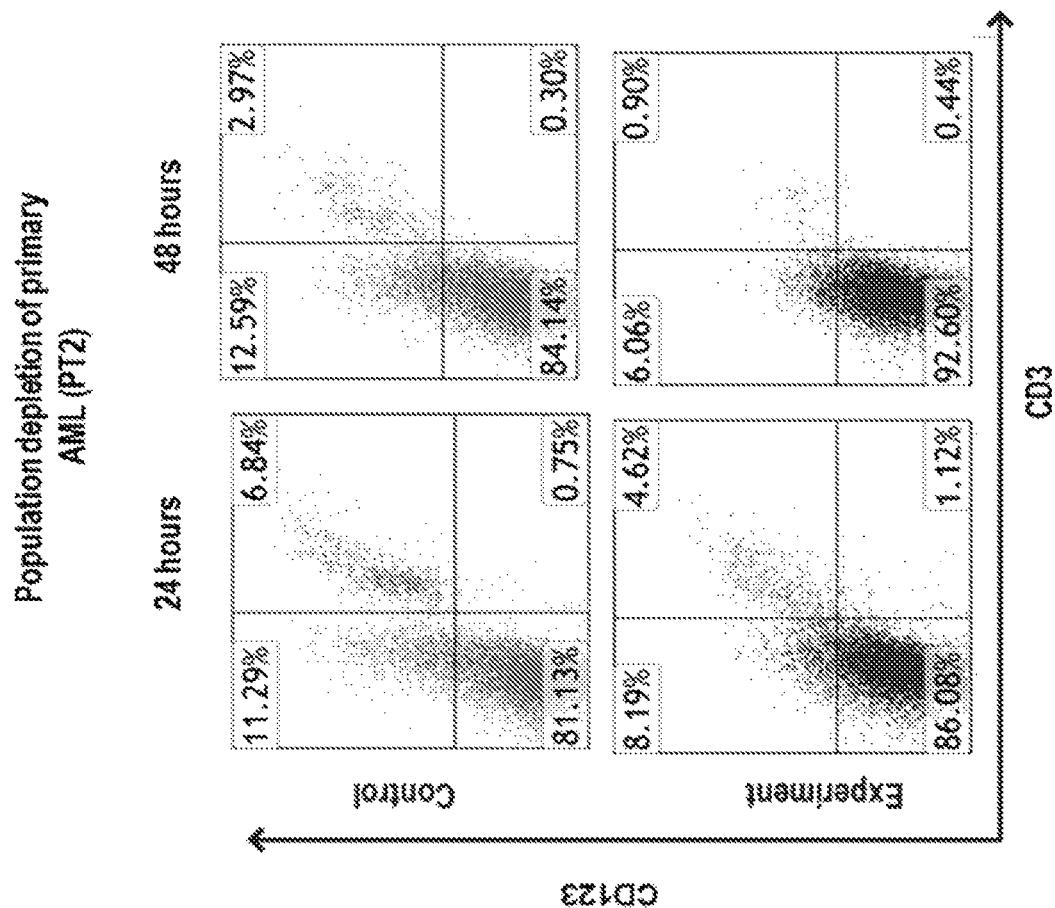
Figure 22D:
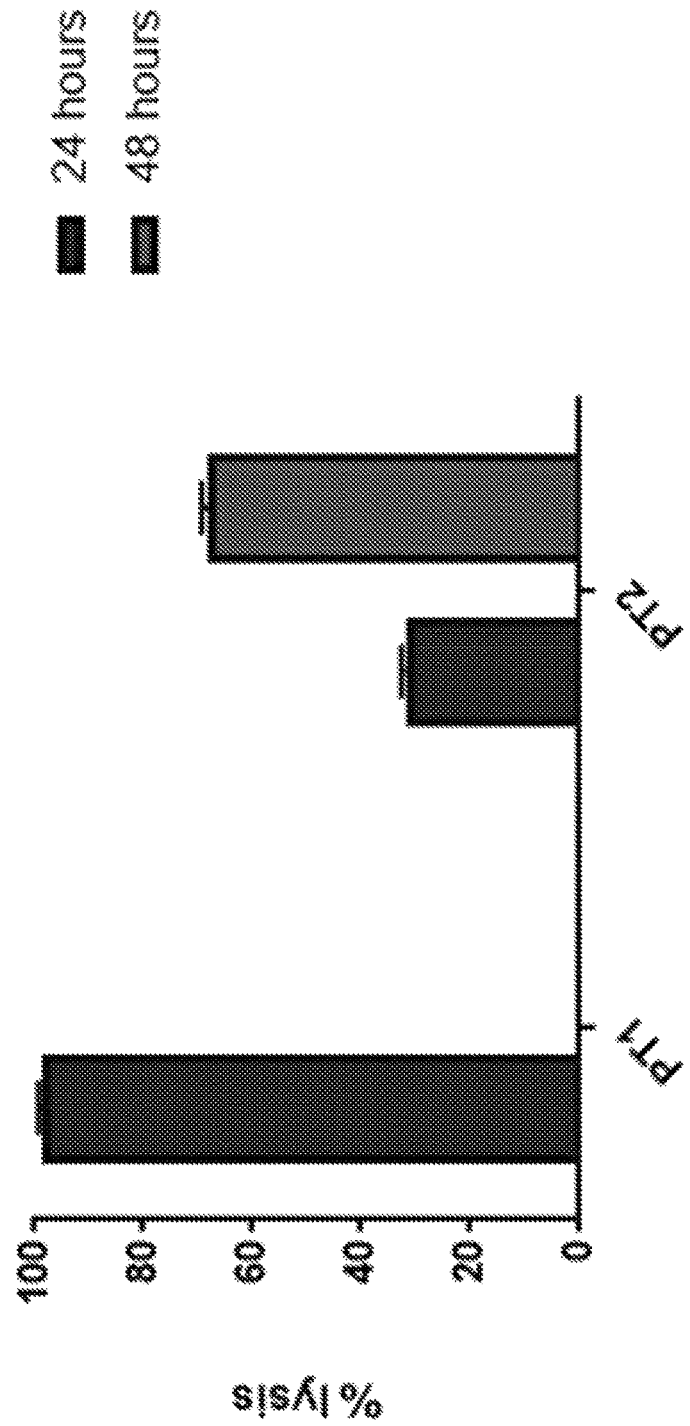

CD19b–CD123 cCAR-2G T-Cells Effectively Lyse Primary B-Cell Acute Lymphoblastic Leukemia (B-ALL) and Acute Myeloid Leukemia (AML) Tumor Cells We conducted co-cultures using CD19b–CD123 cCAR T-cells against primary tumor cells to evaluate their ability to kill diverse primary leukemia cell types. Patient samples were stained with CMTMR Cytotracker Dye to distinguish primary tumor cells from CAR T-cells. Co-cultures were performed with two samples, PT1:B-ALL and PT2:AML, and flow cytometry was performed to verify tumor-lysis. Flow cytometry analysis of the PT1 sample showed a near complete CD19+ phenotype, with a distinct CD19+CD123+ population. The PT2 sample showed a mixed tumor phenotype with a partial CD123+CD19− phenotype (FIG. 22A). CD19b–CD123 cCAR T-cells showed robust ablation of the PT1 primary B-ALL sample, with near complete lysis at an E:T ratio of 5:1 at 24 hours (FIGS. 22B and 22D). CD19b–CD123 cCAR T-cells also ablated the PT2 primary AML sample, with 31% lysis at 24 hours and 67% lysis at 48 hours (FIGS. 22C and 22D). In summary, CD19b–CD123 cCAR T cells exhibited robust anti-tumor activity against both leukemia cell lines and primary tumor cells expressing different combinations of CD19 and CD123 (FIG. 22D).

CD19b–CD123 cCAR-3G T-Cells Exhibit Profound Anti-Tumor Activity in Two Xenograft Mouse Models of AML and B-ALL Using MOLM-13 and REH Cells.

Figure 23A:
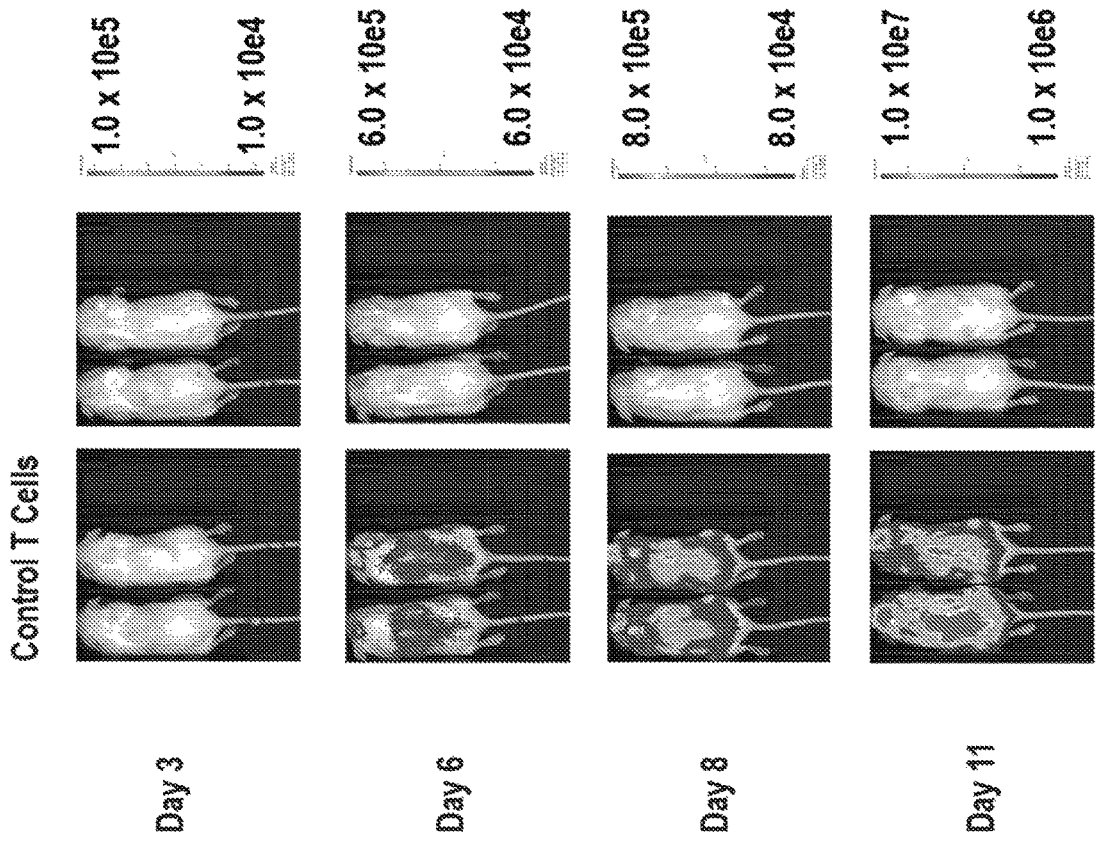
Figure 23B:
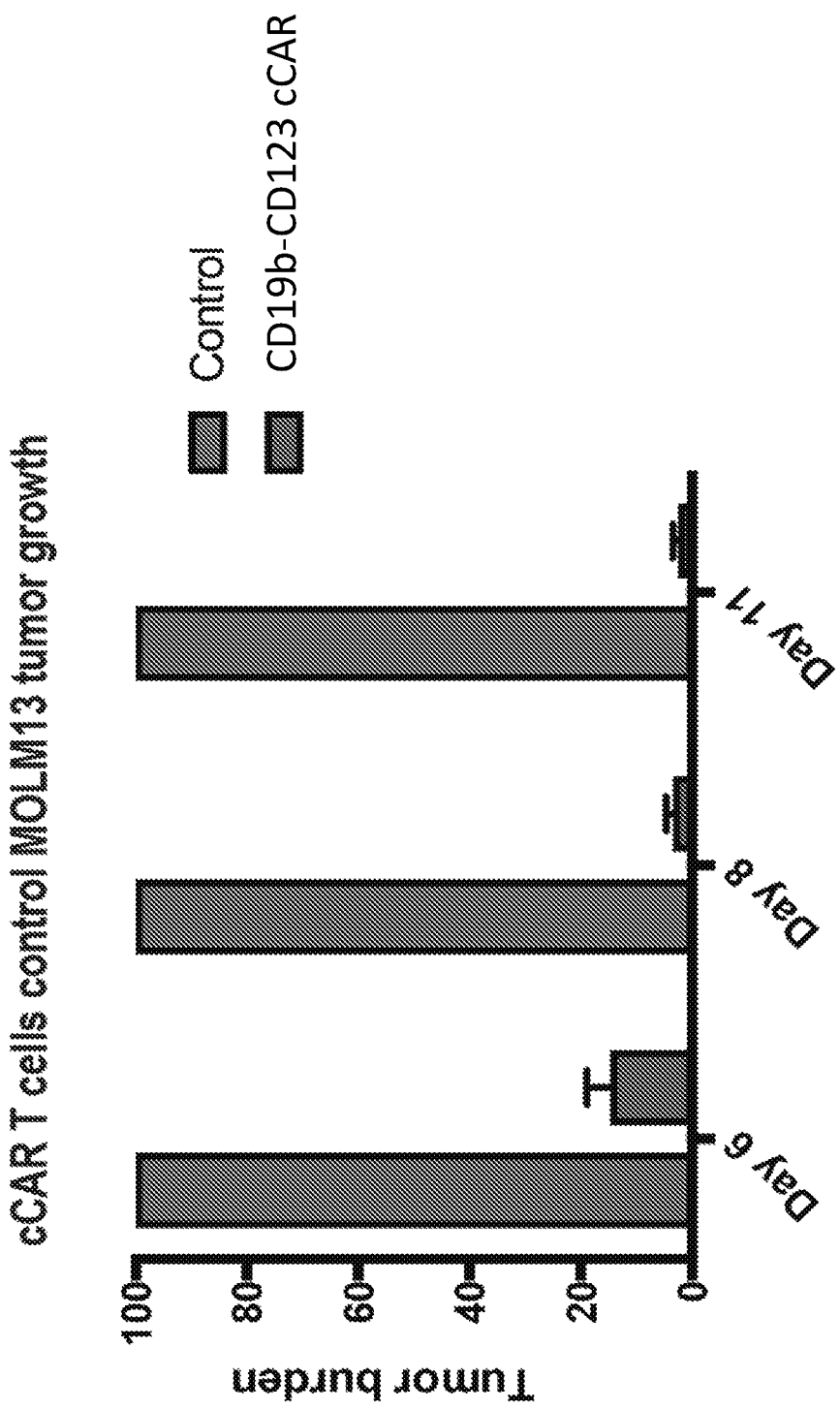
Figure 23C:
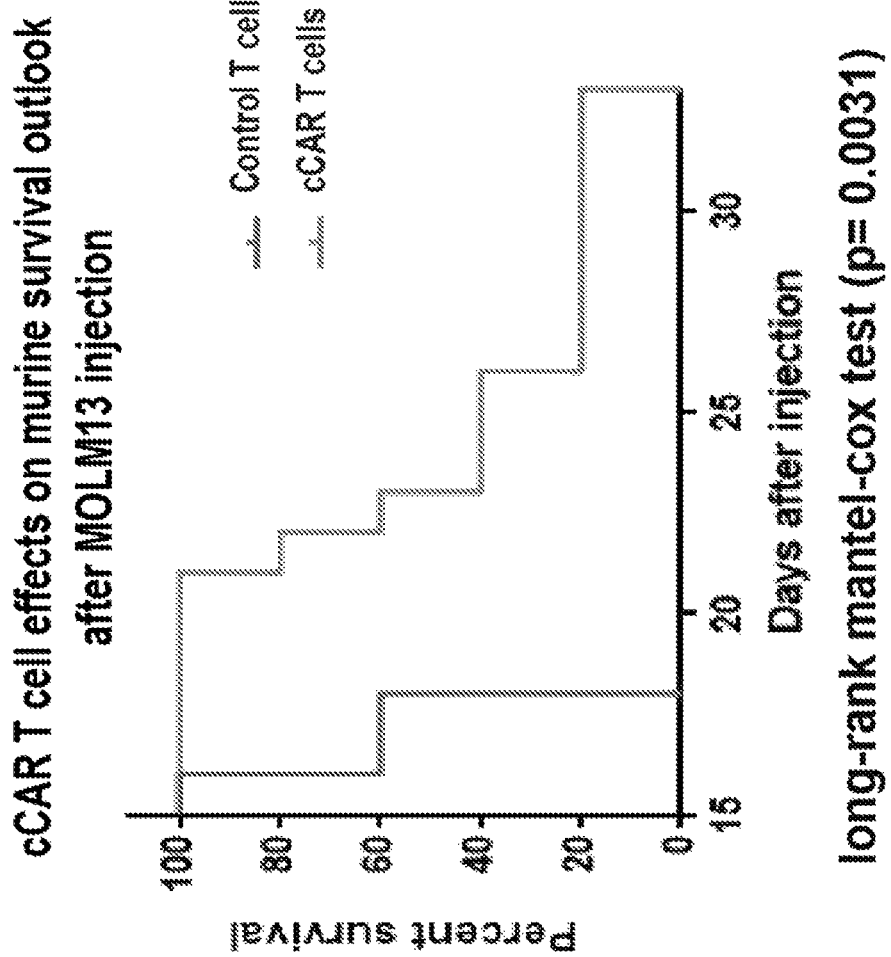

In order to evaluate the in vivo anti-tumor activity of CD19b–CD123 cCAR T-cells, we developed two models, one with luciferase-expressing MOLM13 cells (CD123+ CD19−), and one with luciferase-expressing REH cells (CD19+CD123−) to induce measurable tumor formation. Mice were given a single dose of CD19b–CD123 cCAR T-cells or control GFP cells, and tumor burden was measured on days 3, 6, 8 and 11 (FIG. 23A). In the MOLM13 model, there was a significant difference (P<0.01) between the cCAR treated and control groups by day 6, with less light intensity and thus less tumor burden in the CD19b–CD123 cCAR T-cell injected group compared to control (FIG. 23B). Mice injected with CD19b–CD123 CAR T-cells had 99% less tumor burden than control mice by day 11. Next, we compared mouse survival across the two groups. Following the IVIS imaging experiments previously described, mice were observed every day for symptoms of severe illness and were sacrificed once movement was greatly impaired. All control mice died by day 18, while the CD19b–CD123 CAR T treated mice survived longer than control mice by up to 15 days (p=0.0031) (FIG. 23C).

Figure 23D:
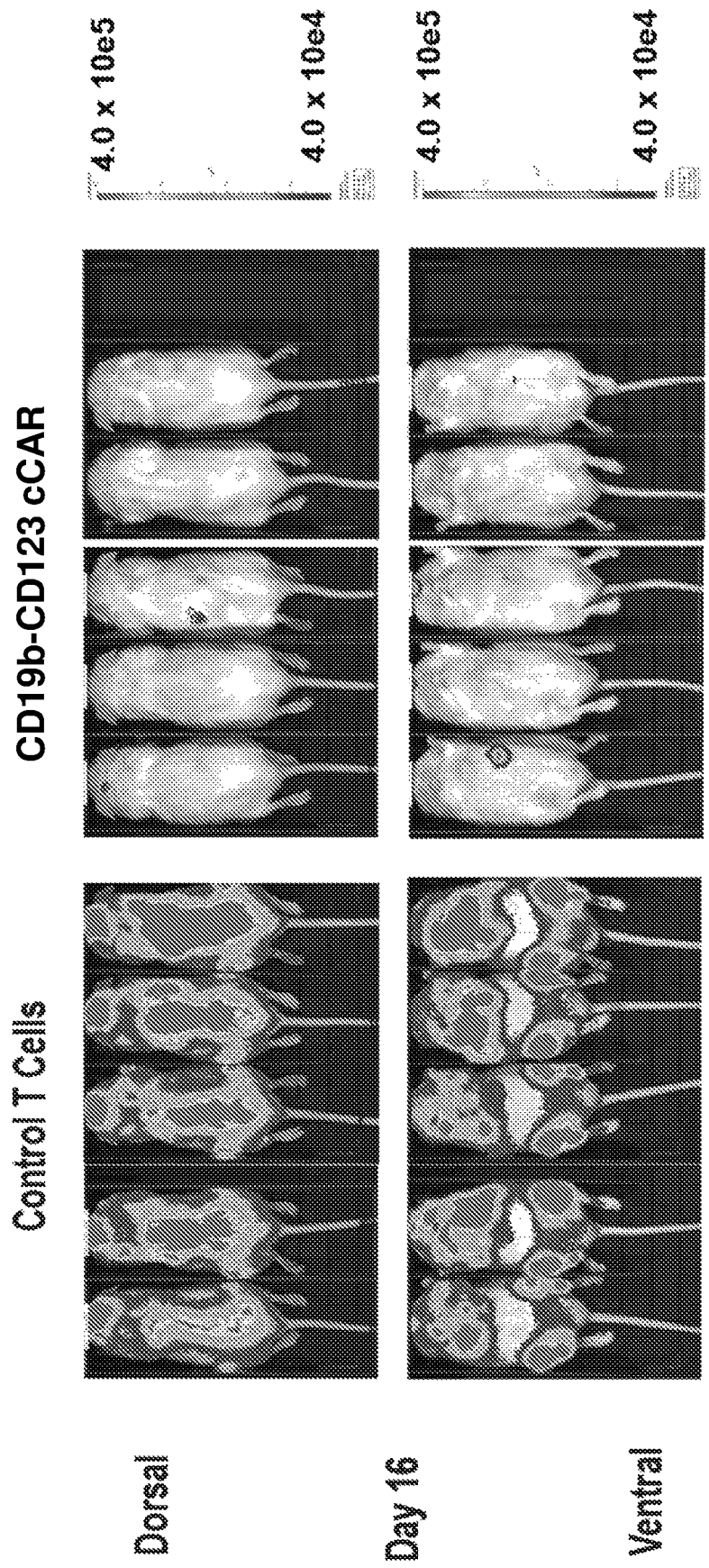
Figure 23E:
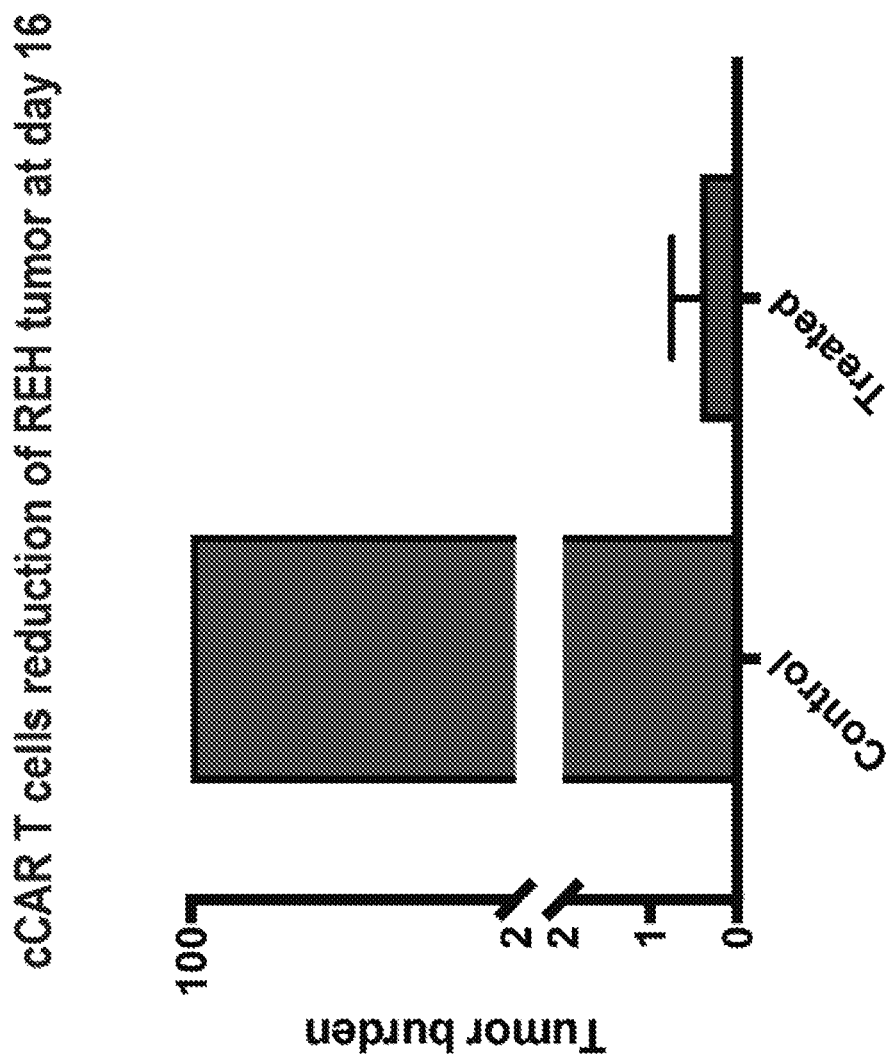
Figure 23F:
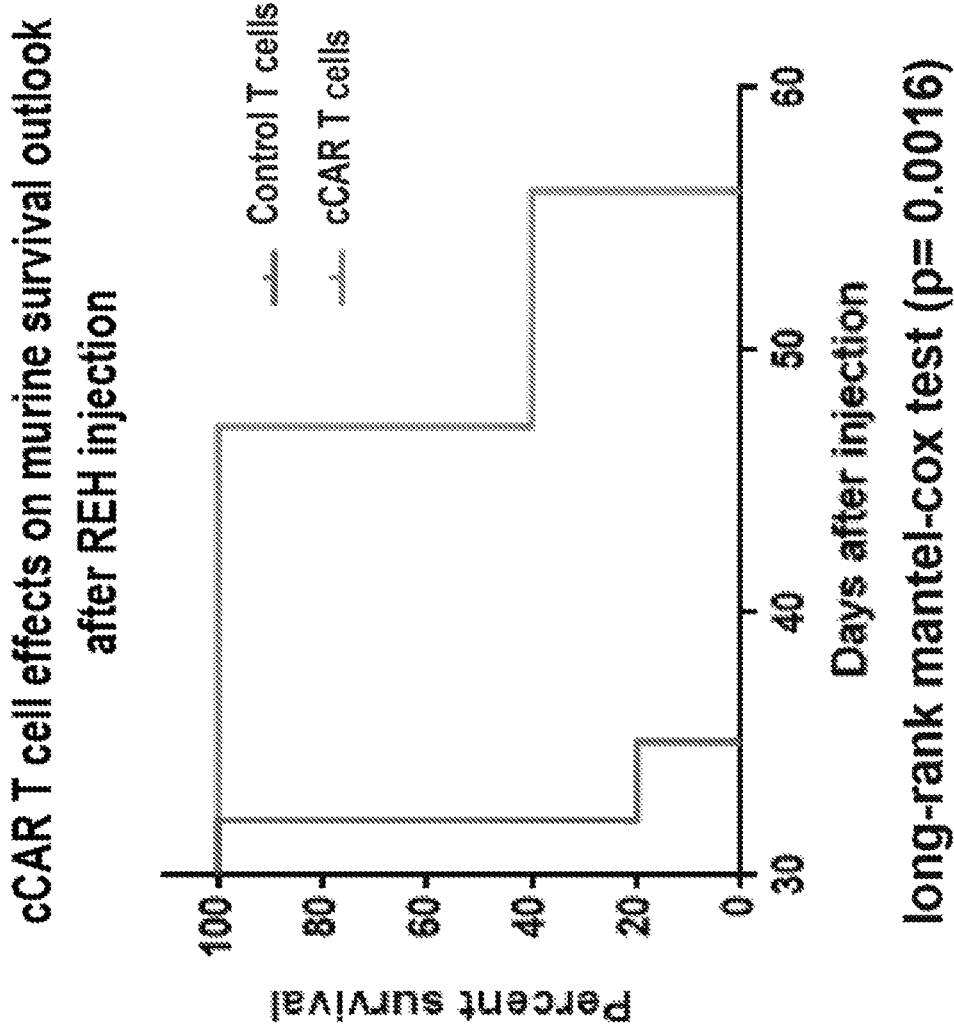

0A1 similar result was seen in the REH mouse model (FIG. 23D). REH leukemic mice injected with CD19b–CD123 cCAR T cells had 99% less tumor burden than control mice on day 16 (FIG. 23E). When comparing mouse survival across cCAR and control treated groups, CD19b–CD123 cCAR T injected mice survived much longer than control mice (FIG. 23F)(p=0.0031). In summary, these in vivo data indicate that CD19b–CD123 cCAR T-cells significantly reduce tumor burden and prolong survival in MOLM13-injected and REH-injected NSG mice when compared to control T-cells.

Screening and Evaluation of Several Versions of cCARs Targeting BCMA+ and/or CS1+ Leukemic Cells, Particularly Multiple Myeloma Cells Using Co-Culture Killing Assays.

1. Generations of Different Versions of BCMA (CD269)-CS1 cCARs.

As described above, creation of compound CARs bearing different CAR units can be quite challenging. We selected various CAR body elements to express multiple units of CARs in a single vector using a strong promoter and P2A self-cleaving site. The hinge region in the CAR was chosen so that interaction of the hinge region between each CAR unit could be avoided. Lentivirus transfected cytotoxic effector cells, namely T cells, were engineered to express an anti-BCMA (CD269) single-chain variable fragment (scFv1) region fused to an anti-CS1 fragment (scFv2) by a self-cleaving P2A peptide. These scFv domains are linked by CD8-derived hinge (H) and transmembrane (TM) regions to 4-1BB and CD28 co-activation domains and a CD3 (CD3) signaling domain (FIG. 30). A strong spleen focus forming virus promoter (SFFV) and a CD8 leader sequence were used for efficient expression of the compound CAR molecule on the T-cell surface. Finally, the generated constructs were screened and evaluated for their expression and functions. scFv1 represents different scFv versions (A7D or C11D) against BCMA antigen. scFv 2 represents different scFv versions (hu63 or mu34 or mu90) against CS1 antigen.

2. Varied Level of CAR Expression in T Cells Transduced with Various Versions of BCMA-CS1 cCAR Lentiviruses.

Peripheral blood mononuclear buffy coat cells were activated for three days and transduced with the lentiviral vector for 6 different sequence variations cCARs comprised of CD269 (A7D or C11D) combined with CS1 (hu63, mu34 or mu90) CAR, or control vector. Expression of CAR on the T-cell surface was demonstrated three days after transduction by staining transduced T cells with goat anti-mouse Fab antibody and mouse anti-human CD3. FIG. 30A shows surface expression for each of the CD269-CS1 CARs: for A7D-mu34, 11.2%; A7D-mu90, 23.1%; A7D-hu63, 28.5%; C11D-mu34, 28.0%; C11Dmu90 13.6%; and C11Dhu63, 42%. This demonstrates the need to find a pairing of CAR units that result in the highest level of CAR expression. A high efficiency lentiviral packaging cell line is critical for generation of a high titer for these constructs (FIG. 30B). We used lenti-X 293 T cell line as a packaging system to generate high viral titers for compound CAR constructs. Lenti-X 293T packaging cell line clearly outperformed the other cell lines and produced over 2 to 6-times as many viruses as 293 FT cells.

The transduction efficiency (percentage of CAR T cells) for cCARs is often lower than for a single-unit CAR. There are several ways to improve efficiency, at both the transfection and transduction steps. To improve viral titer for making cCARs, it is preferred to use LentiX™ 293 T (Clontech/ Takara) packaging cell line, which is selected for high titer lentivirus production, instead of the commonly used HEK-293FT. It is also preferable to increase the amount of plasmid DNA (containing the cCAR construct) 1.5- to 2.0-fold when transfecting packaging cells, to increase transfection efficiency. The amount of viral packaging plasmids and transfection reagent remains the same during the forming of complexes. Transduction efficiency can be further enhanced by lowering the ratio of T cells to viral vector during the transduction step, to $0.3 \times 10^6$ cells per mL, and increasing the volume of lentiviral supernatant or lentiviruses.

3. Testing CAR Expression in T Cells Transduced with Various Anti-BCMA Lentiviral Vectors.

Based on the above studies, CD269-A7D (also called A7D) and CS1-hu63 (also called hu63) were chose as good candidates for generation of enhanced CARs or compound CAR (cCAR). We also generated a cCAR (CD269-A7D-C11D-2G) targeting two epitopes on the same antigen, BCMA. In this cCAR, each unit of CARs bears different scFv targeting different epitopes of BCMA. Enhanced CARs are CD269-A7D-IL15/IL15sushi and CD269-A7D-41BBL-2G targeting BCMA antigen. Compound CARs are CD269-A7D-CD19b-2G targeting BCMA and CD19 antigens, and CD269-A7D-CS1-hu63 or CD269-C11D-CS1-hu63-BB targeting BCMA and CS1 antigens.

Peripheral blood mononuclear buffy coat cells were activated for three days and transduced with the anti-BCMA lentiviral vectors for single CARs (CD269-A7D-2G, CD269-A7D-IL15/IL15sushi, CD269-A7D-41BBL-2G) and cCARs (CD269-A7D-C11D-2G, CD269-A7D-CD19b-2G, CD269-A7D-CS1-hu63, CD269-C11D-CS1-hu63-BB) or control vector (FIG. 30B). Expression of CAR on the T-cell surface was demonstrated three days after transduction by staining transduced T cells with goat anti-mouse Fab antibody and mouse anti-human CD3. FIG. 30B shows surface expression for each of the lentiviral CARs: for CD269-A7D-2G, 48.4%; CD269-A7D-IL15/IL15sushi, 32.2%; CD269-A7D-41BBL-2G, 36%; CD269-A7D-C11D-2G, 27.4%; CD269-A7D-CD19b-2G, 30.6%; CD269-A7D-CS1-hu63, 28.5%; and CD269-C11D-CS1-hu63-BB, 42.0%.

4. CD269-A7D-CD19b cCAR T Cells Efficiently Lyse Both BCMA and/or CD19-Expressing Tumor Cell Lines The CD269-A7D-CD19b cCAR T cells were tested for their ability to lyse individual target cell lines in in vitro co-culture assays (FIGS. 30C and 30D). K562 cells were modified to synthetically express either BCMA (CD269) (called K-BCMA) or CD19 (called K-19) on the cell surface. After 18-hour co-incubation, cells were labeled with anti-human CD3 and either anti-human CD269 or CD19, and analyzed by flow cytometry (FIG. 30C and CD30E). CD269-A7D-CD19b cCAR T cells were able to lyse 31% of the target K-BCMA cells at the 2:1 E:T ratio, and 65% at 5:1 ratio. CD269-A7D-CD19b cCAR T cells were also able to lyse 60% of the target K-CD19 cells at the 2:1 E:T ratio, and nearly all at 5:1 ratio (FIG. 30D and CD30E). These results confirm that each CAR unit—CD269 and CD19b CAR—effectively lyses its specific target cells.

CD269-A7D-41BBL, CD269-A7D-CS1-Hu63, and CD269-A7D-C11D cCAR T Cells Efficiently Lyse MM1S Tumor Cell Line Various versions of BCMA-CS1 cCAR T cells generated above were tested for their ability to lyse specific target cell lines in in vitro co-culture assays. The human multiple myeloma cell line, MM1S, was co-cultured with CD269-A7D-41BBL CAR, CD269-A7D-CS1-hu63 cCAR, CD269-A7D-C11D cCAR T cells, or control T cells, at 2:1 and 5:1 E:T ratios (FIG. 30F). After 18-hour co-incubation, cells were labeled with CMTMR (Cell Tracker) and anti-human CD269 and analyzed by flow cytometry. CD269-A7D-41BBL CAR T cells were able to lyse 74% of the target MM1S cells at the 2:1 E:T ratio, and 90% at 5:1 ratio, while CD269-A7D-CS1-hu63 cCAR T cells lysed 59% and 90%, and CD269-A7D-C11D CART cells lysed 62% and 86% of the MM1S cells at 2:1 and 5:1 ratios, respectively (FIG. 30F). These compound CARs did not appeared to show any evidence of the CAR to CAR interaction. In vivo anti-tumor activities, cell killing is performed in a xenogeneic mouse model and targeted cells expressing BCMA or CS1 or both are eliminated or suppressed by cCAR T or NK cells using methods described in PCT/US2016/019953 and PCT/US2016/039306

6. CD269-A7D-41BBL, CD269-A7D-CS1-Hu63, and CD269-A7D-C11D CART Cells Efficiently Lyse the Cell Line K562 Synthetically Expressing BCMA or CS1

Various versions of BCMA-CS1 cCAR T cells generated above were tested for their ability to lyse specific target cell lines in in vitro co-culture assays. K562 cells were modified to synthetically express either BCMA (CD269) or CS1 on the cell surface, and were subsequently co-cultured with CD269-A7D-41BBL, CD269-A7D-CS1-hu63, CD269-A7D-C11D cCAR T cells, or control T cells, at 2:1 and 5:1 E:T ratios. After 18 hour co-incubation, cells were labeled with anti-human CD3 and anti-human CD269 (or CS1) and analyzed by flow cytometry. CD269-A7D-41BBL CART cells were able to lyse 56% of the target K-BCMA cells at the 2:1 E:T ratio, and completely eliminated all target cells at 5:1 ratio, while CD269-A7D-CS1-hu63 cCAR T cells lysed 38% and 79%, and CD269-A7D-C11D CART cells lysed 16% and 74% of the K-BCMA cells at 2:1 and 5:1 ratios, respectively (FIG. 30G). Only CD269-A7D-CS1-hu63, CD269-A7D-C11D cCAR T cells were tested in co-culture against the K-CS1 cells (FIG. 30H. CD269-A7D-CS1-hu63 cCAR T cells lysed 18% and 54%, of the K-562 cells at 2:1 and 5:1 ratios, respectively, while the CD269-A7D-C11D cCAR T cells, a compound CARs targeting two different epitopes on the BCMA antigen, showed no ability to lyse the K-CS1 cells at either ratio, which was expected, due to the absence of a CS1 CAR unit. (FIG. 30H). These results demonstrate the ability of each CAR unit to specifically lyse its target population.

Examples for Targeting CLL1+ and/or CD33+ Leukemic Cells by CLL1-CD33b cCAR (a Version of CLL1-CD33)

Transduced T Cells Efficiently Express the CLL1-CD33b cCAR (CLL1-CD33b CAR)

Peripheral blood mononuclear buffy coat cells were activated for two or three days and transduced with either CLL1-CD33b cCAR or control vector. Expression of CLL1-CD33b cCAR on the T-cell surface was demonstrated three days after transduction by staining transduced T cells with goat anti-mouse Fab antibody and mouse anti-human CD3. FIG. 31 shows that 29.7% of cells transduced with the CLL1-CD33b cCAR viruses were positive for both F(ab')2 and CD3 as determined by flow cytometry.

CLL1-CD33b cCAR T Cells Specifically Target Both CLL1 (CLL-1) and CD33-Expressing Tumor Cell Lines T cell coculture killing assays were performed to determine the ability of CLL1-CD33b cCAR T cells to effectively and specifically lyse CLL1 (CLL-1) and CD33-expressing cell lines: the acute myeloid leukemia cell line HL60, which expresses both antigens on the cell surface naturally; and Jurkat cells which were modified to synthetically express either CLL1 (called Jurkat-CLL-1xp) or CD33 (called Jurkate-CD33xp). In addition, CLL1-CD33b cCAR T cells were co-cultured against the REH and CCRF-CEM cell lines, which are negative for CLL1 and CD33 (FIGS. 32A and 32B). All target cells were pre-labeled with CFSE membrane dye to distinguish them from T cells. After 18 hour co-incubation, cells were labeled with anti-human CD3 and analyzed by flow cytometry. At the low 2:1 effector: target ratio, CLL1-CD33b cCAR T cells were able to effectively lyse HL60 cells (89%), Jurkat-CLL-1xp cells (84%) and Jurkat—CD33xp cells (96%) (FIGS. 32C, 32D and 32E); at the 5:1 E:T ratio, nearly all target cells were depleted (FIG. 2a-d). However, the REH (8%) and CCRF-CEM cells (14%), both off-target, showed very little cell lysis (FIGS. 32A and 32B). This demonstrates remarkable potency and specificity of the CLL1-CD33b cCAR T lysis. The results are summarized in the bar graph (FIG. 32F).

CLL1-CD33b Compound CAR T Cells are Able to Demonstrate Potent and Directed Cytotoxicity In Vitro.

We conducted co-culture assays using target AML cell lines HL60 and U937 expressing high amounts of both CLL-1 and CD33. We found that the CLL-1 CART cell was able to potently ablate both of these cell types at high efficiency >90% (FIGS. 32G and 32H). Furthermore, the compound CAR exhibited minimal targeting of negative control cell line CCRF-CEM with basal levels of activity (FIG. 32I).

In addition, the CLL1-CD33b cCAR demonstrated potent dose dependent cytotoxicity in an escalating dosage scheme, with ~50% activity even at the lowest dose threshold of 0.25:1 (effector:target) cell ratio (FIG. 32J).

Compared to Single CAR T Options, the CLL1-CD33b cCAR T Cells Demonstrate Superior Anti-Tumor Activity Jurkat cells expressing either CLL-1 or CD33 were combined in a 1:1 ratio and incubated with 100,000 effector cells for a final effective E:T ratio of 1:2. The results show that the compound CAR exhibited highly specific and potent cytotoxicity against either CLL-1 or CD33 expressing sets of Jurkat cells (>85%) while demonstrating increased cytotoxicity over single CAR options for their respective antigens (FIGS. 32K and 32L).

CD19b-IL-21 CAR (a Version of CD19-IL-21 CAR)

Example

An engineered CD19b-IL-21 (CD19b-IL21) CAR cell was prepared in accordance with the present disclosure (FIG. 33A). CD19b CAR is equipped with secreting IL-2 to lyse leukemia/lymphoma expressing CD19 antigen.

Peripheral blood mononuclear buffy coat cells were activated for two or three days and transduced with either CD19b-IL-21 or control vector. Expression of CD19b-IL-21 on the T-cell surface was demonstrated three days after transduction by staining transduced T cells with goat anti-mouse Fab antibody and mouse anti-human CD3. FIG. 33B shows that 63.9% of cells transduced with the CD19b-IL-21 CAR viruses were positive for both F(ab')2 and CD3 as determined by flow cytometry.

Cell killing assay is performed and targeted cells expressing CD19 are lysed by IL-19-IL-21 CAR.

In vivo anti-tumor activities, cell killing is performed in a xenogeneic mouse model and targeted cells expressing CD19 are eliminated or suppressed by CD19b-IL-21 CAR T or NK cells using methods described in PCT/US2016/019953 and PCT/US2016/039306

Similar assays can be used for BCMA-IL-18 CAR (FIG. 35)

In one embodiment, the engineered cell includes a CD19 chimeric antigen receptor polypeptide and IL-21 (SEQ ID NO. 16), and corresponding nucleotides (SEQ ID NO. 17).

In one embodiment, the engineered cell includes a CD19 chimeric antigen receptor polypeptide and IL-21 anchor (SEQ ID NO. 1), and corresponding nucleotides (SEQ ID NO. 2).

In one embodiment, the engineered cell includes a BCMA chimeric antigen receptor polypeptide and IL-18 (SEQ ID NO. 11), and corresponding nucleotides (SEQ ID NO. 12).

In one embodiment, the engineered cell includes a BCMA chimeric antigen receptor polypeptide and IL-18 anchor (SEQ ID NO. 13), and corresponding nucleotides (SEQ ID NO. 14).

CD19b-IL-21 Anchor CAR (a Version of CD19-IL-21 Anchor)

Example

An engineered CD19b-IL-21 anchor (CD19b-IL21) CAR cell was prepared in accordance with the present disclosure (FIG. 34). CD19b-IL-21 anchor CAR is to lyse leukemia/lymphoma expressing CD19 antigen.

Cell killing assay is performed and targeted cells expressing CD19 are lysed by IL-19-IL-21 anchor CAR.

In vivo anti-tumor activities, cell killing is performed in a xenogeneic mouse model and targeted cells expressing CD19 are eliminated or suppressed by CD19b-IL-21 anchor CAR T or NK cells using methods described in PCT/US2016/019953 and PCT/US2016/039306

Similar assays can be used for BCMA-IL-18 anchor CAR (FIG. 36)

Examples for Targeting Multiple Myeloma by BCMA–CD38 cCAR

Example

An engineered BCMA–CD38 cCAR cell was prepared in accordance with the present disclosure (FIG. 37). Lentivirus transfected cytotoxic effector T or NK-cells were engineered to express two complete units of CAR linked by a self-cleaving P2A peptide. The resulting compound CAR) is capable of targeting BCMA+ and/or CD38+ multiple myeloma cells or abnormal plasma cells (FIG. 37). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the BCMA–CD38 cCAR molecule on the T or NK-cell surface.

BCMA–CD38 cCAR is to lyse multiple myeloma cells or abnormal plasma cells expressing BCMA and/or CD38 antigen.

Cell killing assay is performed and targeted cells expressing BCMA and/or CD38 antigen are lysed by BCMA–CD38 cCAR.

In vivo anti-tumor activities, cell killing is performed in a xenogeneic mouse model and targeted cells expressing BCMA and/or CD38 antigen are eliminated or suppressed by BCMA-CD38 cCAR T or NK cells using methods described in PCT/US2016/019953 and PCT/US2016/039306.

In one embodiment, the CD38 antigen recognition domain includes SEQ ID NO. 15.

In one embodiment, the engineered cell includes a first chimeric antigen receptor polypeptide having a BCMA antigen recognition domain and second chimeric antigen receptor polypeptide having a CD38 recognition domain. In one embodiment, this engineered cell includes a polypeptide of SEQ ID NO. 5, 7, 9 and corresponding polynucleotide of SEQ ID NO. 6, 8, 10.

Structural organization of CLL1-CD33b-IL-15/IL-15sushi (CLL1-CD33-IL-15/IL-15sushi)

CLL1-CD33b-IL-15/IL-15sushi (FIG. 39A) contains two independent units of CARs, CLL-1 CAR (also called anti-CD371 CAR or anti-CLL1 CAR), and CD33b CAR (also called anti-CD33 CAR). CLL1-CD33b-IL-15/IL-15sushi is able to secret IL-15/IL-15sushi. The soluble IL-15/IL-15sushi fusion are stable and functions as an unexpected and powerful immunomodulatory for CAR T/NK or NK T cells and their neighbor tumor immune response cells. The soluble IL-15/IL-15sushi fusion can enhance CAR T/NK or NK T cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

CAR Expression

Activated human peripheral blood T cells were transduced with the lentiviral vector from CLL1-CD33b-IL15/IL15sushi. CAR. FIG. 39B shows the transduction efficiency between activated T cells transduced with either control vector, or CLL1-CD33b-IL15/IL-15sushi CAR vector, as determined by labeling with goat anti-mouse F(Ab')2 antibody. Activated T cells transduced with the CAR vectors resulted in 22% F(Ab')2 positive cells for CLL1-CD33b-IL15/IL15sushi (FIG. 39B). These CAR T cells were used in the following in vitro killing assays.

CLL1-CD33b-IL15/IL15sushi CAR T Cells are Able to Lyse Tumor Cell Lines Expressing Either CLL-1 or CD33 Antigens in In Vitro Assays CLL1-CD33b-IL15/IL15sushi CAR T cells from FIG. 39B were assayed for their ability to specifically lyse REH cells synthetically expressing either CLL-1 antigen or CD33 antigen. Wild-type REH cells were transduced with a lentiviral vector for CLL-1 or CD33 antigen expression and positively selected by FACS (FACS-Aria, BD) to create REH-CLL1xp and REH-CD33xp cell lines. Co-cultures with control T cells or CLL1-CD33b-IL15/IL-15sushi CAR T cells, and either REH-CLL1xp (REH cells expressing CLL-1 antigen) or REH-CD33xp (REH cells expressing CD33 antigen) cells were set up at 2:1 and 5:1 effector cell:target cell ratios, for 24 hours. Following this incubation, cells were stained using mouse anti-human CD3 antibody (in all cases), and either mouse anti-human CLL1 or CD33, and analyzed by flow cytometry. At the 2:1 E:T ratio, 76% of the REH-CLL1xp tumor cells were lysed, while at the 5:1 ratio, 94% tumor cells were lysed (FIG. 39C). For co-cultures with REH-CD33xp cells, the lysis was also robust, 66.7% for 2:1 and 96% for 5:1 (FIG. 39C). These results demonstrate that each CAR component of the CLL1-CD33b-IL15/IL15sushi CAR T cell is able to lyse its intended target cells.

CLL1-CD33b-IL15/IL15sushi CAR T Cells Exhibit Significant Anti-Tumor Activity in Xenogeneic Mouse Model In order to evaluate the specific in vivo anti-tumor activity of CLL1-CD33b-IL15/IL-15sushi CAR T cells against human tumor cell lines, we developed a xenogeneic mouse model using NSG mice sublethally irradiated and intravenously injected with $1 \times 10^6$ of luciferase-expressing MOLM13 wild type acute myeloid leukemia tumor cells, which express CD33 on the cell surface, to induce measurable tumor formation. Four days following tumor cell injection, all mice were intravenously injected with a course of $15 \times 10^6$ of either control T cells or CLL1-CD33b-IL15/IL-15sushi CAR T cells. On Day 4 (the day before T cell treatment), and days 8 (72 hours after treatment), and 12, mice were subjected to IVIS imaging to measure tumor burden. Average light intensity measured for the MOLM13 mice injected with CLL1-CD33b-IL15/IL15sushi CAR T cells was compared to that of mice injected with the control T cells to determine percent lysis of targeted cells. Results showed that only 3 days following treatment with T cells (Day 8), mice treated with CLL1-CD33b-IL15/IL15sushi CAR T cells had 63% less (dorsal view) and 59% (ventral view) lower tumor burden than mice given control T cells (FIG. 40A, 40B). By Day 12, percent lysis had increased to 77% and 86%, respectively. These results show the efficacy of CLL1-CD33b-IL15/IL15sushi CAR T cells against an AML cell line in vivo.

IL-15/IL15sushi Secretion Results in Persistence of CLL1-CD33b-IL15/IL15sushi CAR T Cells in Peripheral Blood of Mice Blood was drawn from each of the 4 mice at sacrifice; each of the control mice was euthanized on Day 18, once the animals had exhibited signs of paralysis due to spreading of the MOLM13 tumor cells to various organs. The two CAR T cell treated mice were euthanized on Days 21 and 23. Peripheral blood was collected and labeled with mouse anti-human CD45, CD3 and CD33, and subjected to flow cytometry. Transplanted human cells were gated by CD45, and analyzed for T cell and MOLM13 cell populations. As shown in FIG. 40C, control mice had a large population of tumor cells (blue dots), while the blood of CAR T-treated mice appeared to be nearly tumor-free. Despite the lack of tumor cells in the blood, these mice still maintained large populations of CAR T cells (green dots), an indication of CAR T cell persistence, and protection of the mouse from engraftment of MOLM13 tumor cells sequestered in other organs. To determine if this persistence could be due to secretion of IL15/IL-15sushi, the plasma from each mouse was subjected to ELISA to quantify the amount of secreted human IL-15 fusion. As shown in FIG. 40C, IL-15 was not detected in the two control mice, but low level concentrations of 30 and 40 pg/mL was detected in CAR T cell treated mice.

Function of IL15 in CLL1-CD33b-IL15/IL15sushi CAR NK Cells.

To determine if IL-15 is being secreted, NK-92 cell line was transduced with lentiviral vector containing CLL1-CD33b-IL15/IL-15sushi CAR. Cells were sorted on BD FACS Aria to select NK cells positive for the F(Ab')2 phenotype (FIG. 40D). Sorted cells were expanded, and after 72 hours supernatant was collected and subjected to ELISA on 96-well plates precoated with IL-15 antibody. Following manufacturer's (Boster) directions, colorimetric results obtained on a plate reader were compared to a standard curve generated with human IL-15 to determine concentration of IL-15 in the supernatant (FIG. 40E). It was determined that IL-15 was detected in the supernatant at 488 pg/mL. By comparison, supernatant containing approximately the same number of wild-type control NK-92 cells had a background concentration of only 0.33 pg/mL.

IL15/IL-15Sushi Secreted from CLL1-CD33b-IL15/IL15sushi CAR NK Cells can Substitute for the Function of IL-2 In Vitro Sorted CLL1-CD33b-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted, and the volume increased to yield a concentration of approximately 0.5×10e6 cells/mL. This process was repeated on Days 4, 6 and 8. As shown in the graph in FIG. 40D, CLL1-CD33b-IL15/IL15sushi NK CAR cells cultured for 8 days without IL-2 in the culture expanded at close to the same rate as wild-type NK-92 cells cultured with IL-2 added, whereas wild-type NK-92 cultured without IL-2 had all died by Day 6. This indicates that IL-15 secreted by the NK CAR cells can substitute for the expansion activity of IL-2.

Generation and Characterization of CD20cCD19b and CD20hCD19b CARs

The construct comprises a SFFV promoter driving the expression of multiple modular units of CARs linked by a P2A peptide. Upon cleavage of the linker, the cCARs, CD20h–CD19b or CD20h–CD19b cCAR split and engage upon targets expressing CD20 and/or CD19. As a novel cCAR construct, the activation domains of the construct may include, but is not limited to, 4-1BB on the CD20h CAR or CD20c CAR segment, and a CD28 region on the CD19b CAR segment. The CD20h CAR section in the cCAR contains a humanized anti-CD20 scFv targeting CD20 expressing cells.

Two versions of compound CARs of CD20-CD19 targeting CD20 and/or CD19 expressing cells are CD20c-CD19b (CD20cCD19b) and CD20h–CD19b CAR (CD20hCD19b) used a similar method described above. The percent expression of two compound CARs, CD20cCD19b and CD20hCD19b CAR on transduced T cells was found to be 22% and 28%, respectively (FIG. 41A). Buffy coat cells were activated after 3 days with anti-CD3 antibody. Cells were transduced with either control vector (left), CD20cCD19b or CD20hCD19b CAR (right) lentiviral supernatant. After 3 days of incubation, cells were harvested and labeled for flow cytometry.

To assess the specificity of CD20cCD19b and CD20hCD19b CAR T cells on non-target wild-type K562 cells, co-culture experiments were performed at an effector to target ratio of 2:1 or 5:1 for 6 hours and were directly analyzed by flow cytometry for CD3 and CD45 (FIG. 41B). Each assay consisted of K652 target cells alone (right), control T cells (left) and either CD20cCD19b or CD20hCD19b CAR T cells (center panels). Target cells are represented as blue dots (N=2). CD20cCD19b and CD20hCD19b CAR T cells did not lyse K562 tumor cell line that did not expressing either CD20 or CD19 in co-culture assays.

To assess the ability of CD20cCD19b and CD20hCD19b CART cells to lyse target cells expressing CD19, co-culture experiments were then performed with target K562 cell line synthetically expressing the CD19 antigen (K-19) at an effector to target ratio of 2:1 or 5:1 for 24 hours and were directly analyzed by flow cytometry for CD19 and CD3 (FIG. 41C). Each assay consisted of K562-CD19xp target cells alone (right side), control T cells (left panels) and either CD20cCD19b or CD20hCD19b CAR T cells (center panels). Target cells are represented as green dots. Both types of compound CAR T cells lysed CD19 synthetically-expressing K562 tumor cell line in co-culture assays.

To assess CD20cCD19b and CD20hCD19b CAR T cells' ability to lyse on-target cells expressing CD20, co-culture experiments were performed with target K562 cell line synthetically expressing the CD20 antigen (K-20xp) at an effector to target ratio of 2:1 or 5:1 for 24 hours and were directly analyzed by flow cytometry for CD20 and CD3 (FIG. 41D). Each assay consisted of K562-CD20xp target cells (K-20xP) alone (right side), control T cells (left panels) and either CD20cCD19b or CD20hCD19b CAR T cells (center panels). Target cells are represented as purple dots. Both types of compound CAR T cells lysed CD19 or CD20 synthetically-expressing K562 tumor cell line in co-culture assays (FIGS. 41C and 41D)

To assess the specificity of CD20cCD19b and CD20hCD19b CAR T cells on-target REH cells expressing CD19, co-culture experiments were performed with CD19-expressing REH cell lines at an effector to target ratio of 2:1 or 5:1 for 24 hours and were directly analyzed by flow cytometry for CD19 and CD3 (FIG. 41E). Each assay consisted of REH target cells alone (right side), control T cells (left panels) and either CD20cCD19b or CD20hCD19b CAR T cells (center panels). Target cells are represented as orange dots. Both types of compound CAR T cells were found to completely lyse CD19-expressing REH tumor cell line in co-culture assays (FIG. 41E).

To assess the ability of CD20cCD19b and CD20hCD19b CART cells to lyse on-target cells expressing both CD19 and CD20 antigens, co-culture experiments were also performed with the CD19– and CD20-expressing SP53 B-cell lymphoma cell line at an effector to target ratio of 2:1 or 5:1 for 24 hours and were directly analyzed by flow cytometry for CD19 and CD3 (FIG. 41F). Each assay consisted of SP53 target cells alone (right side), control T cells (left panels) and either CD20cCD19b or CD20hCD19b CAR T cells (center panels). Target cells are represented as turquoise dots (N=2). Both types of compound CAR T cells completely lysed SP53 tumor cell line, which expresses both CD19 and CD20 antigens, in co-culture assays.

A summary of the co-culture results is shown in FIG. 41G, with K562 wt (Wild type) performed at a 6 hour co-culture and the others at 24 hours (N=2). Both compound CAR types exhibited superior on-target lysis relative to the control T cells, with CD20hCD19b-2G CAR T cells demonstrating more robust killing of target K562 cells synthetically expressing the CD20 antigen when compared to CD20cCD19b-2G CAR T cells.

To characterize anti-tumor activity of CD20h–CD19 CAR T cells in vivo, NSG mice were sublethally irradiated and intravenously injected with $1.0 \times 10^6$ luciferase-expressing REH cells (Day 0) to induce measurable tumor formation (FIG. 42A, B). Starting 6 days after injection of tumor cells, mice were intravenously injected with a course of $10 \times 10^6$ CD20hCD19b CAR T cells or vector control T cells. On days 5, 9 and 12, mice were injected subcutaneously with RediJect D-Luciferin and subjected to IVIS imaging. By day 12, CD20h–CD19 CAR T cells achieved 98% lysis of tumor cells for both dorsal and ventral sides. These results demonstrate that CD20h–CD19 CAR T cells exhibit robust lysis of REH cells expressing the CD19 antigen.

Structural Organization of CD20h–CD19b-IL-15/IL-15Sushi (CD20hCD19b-IL-15/IL-15sushi)

Compound CAR (cCAR), CD20h–CD19b-IL-15/IL-15sushi (FIG. 43A) contains two independent units of CARs, CD20h CAR (also called anti-CD20 CAR), and CD19b CAR (also called anti-CD19 CAR). CD20h–CD19b-IL-15/IL-15sushi is able to secret IL-15/IL-15sushi. The soluble IL-15/IL-15sushi fusion are stable and functions as an unexpected and powerful immunomodulatory for CAR T/NK cells and their neighbor tumor immune response cells. The soluble IL-15/IL-15sushi fusion can enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

CAR Expression

Activated human peripheral blood T cells were transduced with the lentiviral vector from CD20h–CD19b-IL15/IL15sushi. FIG. 43B shows the transduction efficiency between activated T cells transduced with either control vector, or CD20h–CD19b-IL15/IL15sushi CAR vector, as determined by labeling with goat anti-mouse F(Ab')2 antibody. Activated T cells transduced with the CAR vectors resulted in 25% F(Ab')2 positive cells for CD20h–CD19b-IL15/IL15sushi (FIG. 43B). These CAR T cells were used in the following in vitro killing assays.

CD20h–CD19b-IL15/IL15sushi CAR T Cells are Able to Lyse Tumor Cell Lines Expressing Either CD20 or CD19 Antigens or Both in In Vitro Assays CD20h–CD19b-IL15/IL15sushi CAR T cells from FIG. 43B were assayed for their ability to specifically lyse both U937 cells synthetically expressing CD20 (also called U937-CD20xp or U-CD20xp) and REH cells naturally expressing CD19 antigen. Wild-type U937 cells were transduced with lentiviral vector for CD20 antigen expression and positively selected by FACS (U-CD20xp; FACS-Aria, BD). Co-cultures with control T cells or CD20h–CD19b-IL15/IL15sushi CAR T cells, and either U-CD20xp cells, or with REH wild-type cells were set up at 2:1 and 5:1 effector cell:target cell ratios, for 24 hours. Following this incubation, cells were stained using mouse anti-human CD3 antibody (in all cases), and either mouse anti-human CD20 or CD19, and analyzed by flow cytometry. At the 2:1 E:T ratio, 77% of the U-CD20xp tumor cells were lysed, while at the 5:1 ratio, 74% tumor cells were lysed (FIG. 43C). For co-cultures with REH tumor cells, the lysis was near complete, 96% for 2:1 and 99% for 5:1 (FIG. 43C). These results demonstrate that each CAR component of the CD20h–CD19b-IL15/IL15sushi CAR T cell is able to lyse its intended target cells.

CD20h–CD19b-IL15/IL-15Sushi CAR T Cells Exhibit Significant Anti-Tumor Activity in Xenogeneic Mouse Model In order to evaluate the specific in vivo anti-tumor activity of CD20h–CD19b-IL15/IL15sushi CAR T cells against human tumor cell lines, we developed a xenogeneic mouse model using NSG mice sublethally irradiated and intravenously injected with 1×10$^6$ of luciferase-expressing REH wild type B-ALL tumor cells, to induce measurable tumor formation. Four days following tumor cell injection, all mice were intravenously injected with a course of 15×10$^6$ of either control T cells or CD20h–CD19b-IL15/IL-15sushi CART cells. On Day 4 (the day before T cell treatment), and days 8 (72 hours after treatment), 12 and 16, mice were subjected to IVIS imaging to measure tumor burden. Average light intensity measured for the REH mice injected with CD20h–CD19b-IL15/IL-15sushi CAR T cells was compared to that of mice injected with the control T cells to determine percent lysis of targeted cells. Results showed that only 3 days following treatment with T cells (Day 8), mice treated with CD20h–CD19b-IL15/IL15sushi CAR T cells had >90% less (dorsal view) and >86% (ventral view) lower tumor burden than mice given control T cells (FIG. 44A, B). By Day 16, no tumor could be detected. These results show the efficacy of CD20h–CD19b-IL15/IL15sushi CAR T cells against acute lymphoblastic lymphoma cell line in vivo.

IL15/IL-15Sushi Secretion Results in Persistence of CD20h–CD19b-IL15/IL-15Sushi CAR T Cells in Peripheral Blood of Mice Blood was drawn from each of the 4 mice at sacrifice; each of the control mice was euthanized on Days 28 and 30, once the animals had exhibited signs of paralysis due to spreading of the REH tumor cells to various organs. The two CAR T cell treated mice were euthanized on Days 33 and 36; however, the mouse euthanized on Day 36 was still relatively mobile. Peripheral blood was collected and labeled with mouse anti-human CD45, CD3 and CD19, and subjected to flow cytometry. Transplanted human cells were gated by CD45, and analyzed for T cell and REH cell populations. As shown in FIG. 44C, control mice had a large population of tumor cells (blue dots), while the blood of CAR T treated mice appeared to be tumor-free. Despite the lack of tumor cells in the blood, these mice still maintained large populations of CAR T cells (green dots), an indication of CAR T cell persistence, and protection of the mouse from engraftment of REH tumor cells sequestered in other organs. To determine if this persistence could be due to secretion of IL15/IL-15sushi, the plasma from each mouse was subjected to ELISA to quantify the amount of secreted IL15. As shown in FIG. 44C, human IL-15 was not detected in the two control mice, but a concentration of 159 pg/mL was detected in the CAR T cell treated mouse that still appeared to be relatively healthy on Day 36, when it was euthanized.

Function of IL15 in CD20h–CD19b-IL15/IL-15Sushi CAR NK Cells.

To further determine if IL-15 is being secreted, NK-92 cell line was transduced with lentiviral vector containing CD20h–CD19b-IL15/IL-15sushi CAR. Cells were sorted on BD FACS Aria to select NK cells positive for the F(Ab')2 phenotype (FIG. 44D). Sorted cells were expanded, and after 72 hours supernatant was collected and subjected to ELISA on 96-well plates precoated with IL-15 antibody. Following manufacturer's (Boster) directions, colorimetric results obtained on a plate reader were compared to a standard curve generated with human IL-15 to determine concentration of IL-15 in the supernatant (FIG. 44E). It was determined that IL-15 was detected in the supernatant at 328 pg/mL. By comparison, supernatant containing approximately the same number of wild-type control NK-92 cells had a background concentration of only 0.33 pg/mL.

IL15/IL15sushi Secreted from CD20h–CD19b-IL15/IL15sushi CAR NK Cells can Substitute for the Function of IL-2 In Vitro Related to Expansion and Growth.

Sorted CD20h–CD19b-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted, and the volume increased to yield a concentration of approximately 0.5×10e6 cells/mL. This process was repeated on Days 4, 6 and 8. As shown in the graph in FIG. 44D, CD20h–CD19b-IL15/IL-15sushi NK CAR cells cultured for 8 days without IL-2 in the culture expanded at the same rate as wild-type NK-92 cells cultured with IL-2 added, whereas wild-type NK-92 cultured without IL-2 had all died by Day 6. This indicates that IL-15 secreted by the NK CAR cells can substitute for the expansion activity of IL-2.

In one embodiment, the engineered cell includes a CD20-CD19 cCAR polypeptide, and IL-15/IL-15sushi (SEQ ID NO. 28), and corresponding nucleotides (SEQ ID NO. 29).

In one embodiment, the engineered cell includes a CD20-CD19 cCAR polypeptide (SEQ ID NO. 52), and corresponding nucleotides (SEQ ID NO. 53).

Generation of CD19b-IL-15/IL-15Sushi CAR

CD19b-IL-15/IL-15sushi CAR T-cells were generated by transduction of primary peripheral blood T-cells with the lentiviral construct as previously described (Pinz, 2015). CD19b-IL-15/IL-15sushi CAR construct contains one unit of CAR, anti-CD19 CAR (also called CD19b CAR). CD19b-IL-15/IL-15sushi CAR is able to secret IL-15/IL-15sushi (FIG. 45A). The soluble IL-15/IL-15sushi fusion are stable and functions as an unexpected and powerful immunomodulatory for CAR T/NK cells and their neighbor tumor immune response cells. The soluble IL-15/IL-15sushi fusion can enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Flow cytometry analysis showed that ~35% of T cells expressed the CD19b-IL-15/IL-15sushi CAR F(Ab')2 fragment after transduction (FIG. 45A). This CD19b-IL-15/IL15suhsi CAR was designed to: 1) delete targeted tumor cells, 2) enhance anti-tumor cytotoxicity, 3) robustly increase CAR potency and persistency by secreting theIL-15/IL15-sushi fusion.

Co-culture experiments were performed at an effector to target (E:T) ratio of spanning from 1:1 to 5:1 for 24 hours and were directly analyzed by flow cytometry with mouse anti-human CD3pPerCp and mouse anti-human CD19-PE. Each assay consists of target cells (Sp53 all CD19+) incubated with either P2A control or CAR T-cells. This experiment revealed the dose-dependent nature of the CD19b-IL-15/IL-15sushi CAR T cells, where even at low E:T ratios such as 1:1, there was potent lysis of tumor cells of greater than 60%. At 2:1, saturation of killing ability was observed with all tumor cells lysed (FIG. 45B).

CD19b-IL-15/IL-15Sushi CAR T-Cells Potently Lyse CD19+Sp53 Cells (with Comparison to CD19b Single CART Cells)

Similar cocultures conditions were used as above (FIG. 45B), in this experimental scheme, anti-CD19 CAR co-expressing IL-15/IL-15sushi (CD19b-IL-15/IL-15sushi) CAR T cells were cultured against CD19 positive Reh cells in comparison to both control P2A and single anti-CD19b CAR T cells. Anti-CD19b CART cells were generated with the same methodology and expression on T cell surfaces was verified to be ~50% (of all T cells, data not shown). The results here demonstrate that even at low E:T ratios such as 1:1, both CART treatments are equally effective, with potent and virtual deletion of all antigen-positive Reh cells. The "secreting IL-15/IL-15sushi fusion" does not have a deleterious effect on the cytotoxicity of the CAR T cells.

CD19b-IL-15/IL-15Sushi CART Constructs Provide Enhanced Persistency and Biologic Activity Compared to Standard CD19 CAR To characterize the CAR secreting IL-15/IL-15sushi as a viable option to current CAR T/NK cell paradigms we analyzed for 3 broad factors: 1) ability to kill target cells (efficacy), 2) enhanced persistence for increased bioavailability and surveillance, and 3) proliferation of more potent CAR T phenotypes. We found that the CD19b-IL-15/IL-15sushi CAR construct was able to control Reh model tumor growth in vivo with comparable and slightly better efficacy than standard CART-19 (CD19b CAR) (FIG. 46A). In a second Reh model, we showed that as time goes on, Reh tumor relapsed in standard CAR T(CD19b CAR) treatment, however, the IL-15/IL-15sushi secreting CAR persists and deletes relapsed tumor and keeps mice disease free (FIGS. 46B and 46C). Furthermore, by survival endpoints, CD19b-IL-15/IL-15sushi CAR T cells administered mice revealed distinct populations of cytotoxic T cells remaining in circulation with a higher level, compared to CD19b CAR without secreting IL-15/IL-15sushi (FIG. 46D). In addition, the population of remaining T cells in both treatment groups showed that the CAR T cells (CD19b-IL-15/IL-15sushi) secreting IL-15/IL-15sushi resulted in a more cytotoxic T cell population, comprised of a higher population of CD8+ cells (FIGS. 46D and E).

Generation of BCMA-CD38 Compound CARs

Three versions of compound CARs, CD269-A7D-CD38b, CD269-A7D-CD38a, and CD269-A7D-CD38c were created and their CAR T cells were generated by transduction of primary peripheral blood T-cells with the lentiviral construct as previously described (Pinz, 2015). Flow cytometry analysis showed various levels of CAR T cell expression with F(Ab')2 fragment after transduction (FIG. 45A).

CD269-A7D-CD38a or CD269-A7D-CD38b CAR T cells from FIG. 45A were assayed for their ability to specifically lyse REH naturally expressing CD38. Co-cultures with control T cells or CD269-A7D-CD38a or CD269-A7D-CD38b CAR T cells with REH wild-type cells were set up at 2:1 and 5:1 effector cell:target cell ratios, for 24 hours. Both CAR T cells demonstrated robustly lysed targeted cells (FIG. 47B).

CD269-A7D-CD38a or CD269-A7D-CD38b CAR T cells were also tested for their ability of targeting K562 cells synthetically expressing BCMA. Co-cultures with control T cells or CD269-A7D-CD38a or CD269-A7D-CD38b with either wild type or K562 expressing BCMA (k-BCMA) cells were set up at 2:1 and 5:1 effector cell:target cell ratios, for 24 hours. Following this incubation, cells were stained using mouse anti-human CD3 antibody (in all cases), and either mouse anti-human BCMA (CD269), and analyzed by flow cytomety. Both CAR T cells showed remarkably lysed targeted cells (FIG. 47C).

Structural Organization of CD269-A7D-CD38a-IL15/IL15sushi CAR (Also Called BCMA-CD38-IL-15/IL-15Sushi CAR)

CD269-A7D-CD38a-IL15/IL15sushi (FIG. 48A) contains two independent units of two CARs, CD269-A7D (also called anti-BCMA CAR or anti-CD269 CAR), and CD38a CAR (also called anti-CD38). CD269-A7D-CD38a-IL15/IL15sushi is able to secret IL-15/IL-15sushi. The soluble IL-15/IL-15sushi fusion are stable and functions as an unexpected and powerful immunomodulatory for CAR T/NK cells and their neighbor tumor immune response cells. The soluble IL-15/IL-15sushi fusion can enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers CAR Expression Activated human peripheral blood T cells were transduced with the lentiviral vector from CD269-A7D-CD38a-IL15/IL15sushi. CAR. FIG. 1 shows the transduction efficiency between activated T cells transduced with either control vector, or CD269-A7D-CD38a-IL15/IL15sushi CAR vector, as determined by labeling with goat anti-mouse F(Ab')2 antibody. Activated T cells transduced with the CAR vectors resulted in 33% F(Ab')2 positive cells for CD269-A7D-CD38a-IL15/IL15sushi (FIG. 48B). These CAR T cells were used in the following in vitro killing assays.

T Cells Transduced with CD269-A7D-CD38a-IL15/IL15sushi CAR Exhibit Self-Killing of CD38+ T Cells To determine if T cells transduced with CD269-A7D-CD38a-IL15/IL15sushi CAR would be lysed by the CD38a CAR domain, cells were harvested on Day 6 (the same day as anti-F(Ab')2 labeling, above) and Day 12. Cells were labeled with mouse anti-human CD3 and CD38, and analyzed by flow cytometry. As shown in FIG. 2, the number of CAR T cells on Day 6 expressing CD38 was cut nearly in half (97% to 51%) in comparison to the control T cells, while nearly all CAR cells by Day 12 were CD38−. This confirms the fratricide, or self-killing, of CD38+ T cells, by CD38a CAR.

CD269-A7D-CD38a-IL15/IL15sushi CAR T Cells are Able to Lyse Tumor Cell Lines Expressing Either BCMA (CD269) or CD38 Antigens In Vitro Assays CD269-A7D-CD38a-IL15/IL15sushi CAR T cells from FIG. 48B were assayed for their ability to specifically lyse K562 cells synthetically expressing BCMA (CD269) antigen or wild-type REH cells, which naturally express CD38 antigen. Wild-type K562 cells were transduced with lentiviral vector for BCMA antigen expression and positively selected by FACS (FACS-Aria, BD) to create K-BCMAxp cell line. Co-cultures with control T cells or CD269-A7D-CD38a-IL15/IL15sushi CAR T cells, and either K-BCMAxp or REH cells were set up at 2:1 and 5:1 effector cell:target cell ratios, for 24 or 48 hours. Following this incubation, cells were stained using mouse anti-human CD3 antibody (in all cases), and either mouse anti-human CD269 or CD38, and analyzed by flow cytometry. The results demonstrated that each CAR component of the CD269-A7D-CD38a-IL15/IL15sushi CAR T cell was able to lyse its intended target cells (FIG. 48D).

Function of IL-15 in CD269-A7D-CD38a-IL15/IL15sushi CAR NK Cells.

To determine if IL-15 is being secreted, NK-92 cell line was transduced with lentiviral vector containing CD269-A7D-CD38a-IL15/IL15sushi CAR. Cells were sorted on BD FACS Aria to select NK cells positive for the F(Ab')2 phenotype (FIG. 48E). Sorted cells were expanded, and after 72 hours supernatant was collected and subjected to ELISA on 96-well plates precoated with IL-15 antibody. Following manufacturer's (Boster) directions, colorimetric results obtained on a plate reader were compared to a standard curve generated with human IL-15 to determine concentration of IL-15 in the supernatant (FIG. 48F). It was determined that IL-15 was detected in the supernatant at 512 pg/mL. By comparison, supernatant containing approximately the same number of wild-type control NK-92 cells had a background concentration of only 0.

IL15/IL15sushi Secreted from CD269-A7D-CD38a-IL15/IL15sushi CAR NK Cells can Substitute for the Function of IL-2 In Vitro Related to the Expansion and Growth Sorted CD269-A7D-CD38a-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted, and the volume increased to yield a concentration of approximately 0.5×10e6 cells/mL. This process was repeated on Days 4, 6 and 8. As shown in the graph in FIG. 48E, CD269-A7D-CD38a-IL15/IL15sushi NK CAR cells cultured for 8 days without IL-2 in the culture expanded at the same rate as wild-type NK-92 cells cultured with IL-2 added, whereas wild-type NK-92 cultured without IL-2 had all died by Day 6. This indicates that IL-15 secreted by the NK CAR cells can substitute for the expansion activity of IL-2.

CD123b–CD33b-IL15/IL15sushi cCAR

Structural Organization of CD123b–CD33b-IL15/IL15sushi (Also Called CD123-CD33-IL-15/IL-15Sushi) and CD123b-CLL1-IL15/IL15sushi (Also Called CD123-CLL1-IL15/IL-15Sushi) cCARs CD123b–CD33b-IL15/IL15sushi contains two independent units of two CARs, CD123b CAR (also called anti-CD123 CAR), and CD33b CAR (also called anti-CD33 CAR).

CD123b-CLL1-IL15/IL15sushi also contains two independent units of two CARs, CD123b CAR (also called anti-CD123 CAR), and CLL-1 CAR (also called anti-CLL1 CAR). Both CAR constructs were generated using a similar method described.

Both CARs were able to secret IL-15/IL-15sushi. The soluble IL-15/IL-15sushi fusion are stable and functions as an unexpected and powerful immunomodulatory for CAR T/NK cells or NK T cells, and their neighbor tumor immune response cells. The soluble IL-15/IL-15sushi fusion can enhance CAR T/NK or NK T cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Function of IL-15 in CD123b–CD33b-IL15/IL15sushi and CD123b-CLL1-IL15/IL15sushi CARs To determine if IL-15 is being secreted, NK-92 cell line was transduced with lentiviral vector containing CD123b–CD33b-IL15/IL15sushi or CD123b-CLL1-IL15/IL15sush. Cells were sorted on BD FACS Aria to select NK cells positive for the F(Ab')2 phenotype (FIG. 49B). Sorted cells were expanded, and after 72 hours supernatant was collected and subjected to ELISA on 96-well plates precoated with IL-15 antibody. Following manufacturer's (Boster) directions, colorimetric results obtained on a plate reader were compared to a standard curve generated with human IL-15/IL-15sushi to determine concentration of IL-15sushi in the supernatant (FIG. 49C). It was determined that IL-15sushi was detected in the supernatant at >1500 pg/mL and >1000 pg/mL from CD123b–CD33b-IL-15/IL-15sushi and CD123b-CLL1-IL-15/IL-15sushi NK cells, respectively. By comparison, supernatant containing approximately the same number of wild-type control NK-92 cells had a background concentration close to 0.

IL15/IL15sushi Secreted from CD123b–CD33b-IL15/IL15sushi and CD123b-CLL1-IL15/IL15sushi CAR NK Cells can Substitute for the Function of IL-2 In Vitro Related to the Expansion and Growth CD123b–CD33b-IL15/IL15sushi and CD123b-CLL1-IL15/IL15sush Sorted CD123b–CD33b-IL15/IL15sushi or CD123b-CLL1-IL15/IL15sushi CAR NK cells, and wild-type NK-92 cells, were cultured in a 24-well plate at 0.5×10e6 cells per mL, in 1 mL total volume. Cells were added to duplicate wells; one well of each pair contained IL-2 at 300 IU/mL, the other well did not. After 48 hours (Day 2), cells were counted, and the volume increased to yield a concentration of approximately 0.5×10e6 cells/mL. This process was repeated on Days 4, 6 and 8. As shown in the graph in FIG. 49B, CD123b–CD33b-IL15/IL15sushi or CD123b-CLL1-IL15/IL15sushi NK CAR cells cultured for 8 days without IL-2 in the culture expanded at the same rate as wild-type NK-92 cells cultured with IL-2 added, whereas wild-type NK-92 cultured without IL-2 had all died by Day 8. This indicates that IL-15 secreted by the NK CAR cells can substitute for the expansion activity of IL-2.

Examples for Generation of UCAR (Universal CAR)

Generation of BCMA15/IL-15Sushi-CAR Expressed Human NK Cells Prepared from Human Cord Blood BCMA15/IL-15sushi-CAR construct (also called CD269-A7D-IL-15/IL-15sushi or BCMA CARVac) contains one unit of CAR, CD269-A7D (also called anti-BCMA CAR or anti-CD269 CAR) (FIG. 50A). BCMA15/IL-15sushi-CAR is able to secret IL-15/IL-15sushi. The soluble IL-15/IL-15sushi fusion are stable and functions as an unexpected and powerful immunomodulatory for CAR T/NK cells and their neighbor tumor immune response cells. The soluble IL-15/IL-15sushi fusion can enhance CAR T/NK cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

Generation of Feeder Cells for Expansion of Cord Blood NK Cells:

The steps for generation of feeder cells are shown in FIG. 50B with a flowchart. K562 cells are transduced with lentiviruses expressing a surface anchor protein or scFv tagged IL-21 (IL-21 anchor) (see FIG. 55) or scFv tagged 4-1BBL and IL-15/IL-15sushi anchor (also called super 2)(FIG. 54 and FIG. 55).

In one embodiment, the engineered K562 cell includes IL-21 anchor polypeptide (SEQ ID NO. 1), and corresponding nucleotides (SEQ ID NO. 2).

In one embodiment, the engineered K562 cell includes super2 polypeptide (SEQ ID NO. 50), and corresponding nucleotides (SEQ ID NO. 51).

K562 were transduced with IL-21 anchor or super 2 lentiviruses for 48 hours. After transduction, cells are expanded and labeled by antibodies for sorting of genetically modified K562 cells by FACS. Sorted genetically modified K562 cells are expanded, irradiated (10-100Gy) and frozen down until use. Irradiated genetically modified K562 cells are added into cord blood cell to stimulus and expand NK cells as feeder cells.

Expansion of Human NK Cells from Human Cord Blood (FIG. 50C).

Flowchart (FIG. 50C) shows the steps for generation and expansion of CAR-transduced natural killer (NK) cells from umbilical cord blood by co-culture with irradiated genetically modified K562 cells. Cord blood cells are suspended into T-cell culture mediums with 300 U/ml IL-2 for 48 h. Irradiated genetically modified K562 cells are added into cord blood cell to stimulus and expand NK cells for 48 h. Stimulated cord blood cells are transduced with CAR lentiviruses and incubated for up to 48 h. CAR transduced cord blood cells are co-cultured with irradiated genetically modified K562 feeder cells again.

Every 2 to 3 days, CAR transduced cord blood cells are counted and fed with fresh mediums to maintain cell condition. Exogenous IL-2 is added in all of cell culture medium.

After 2 weeks, fold expansion of NK cells become 220-680 times compared to first day. After 3 weeks, fold expansion of NK cells become 450-1500 times compared to first day.

The percentage of NK cells and T-cells, and expression of CAR on NK cells are determined by flow cytometry analysis using antibodies again murine Fab fragment.

Flow cytometry analysis showed the expression levels of BCMA-IL15/IL15sushi-CAR on CD56 positive cells (blue dots circled in pink) in cord blood cells after transduction BCMA-IL15/IL15sushi-CAR-viruses in cord blood cells.

These data indicate that transduction of BCMA-IL15/IL15sushi-CAR-viruses into cord blood NK cells successfully generate BCMA-IL15/IL15sushi-CAR-expressed NK cells.

BCMA-IL-15/IL15sushi-CAR NK Cells Demonstrate Remarkably and Unexpected Anti-Leukemic Effects In Vivo Mouse Model.

In order to evaluate the specific in vivo anti-tumor activity of BCMA-IL-15/IL-15sushi-CAR expressed NK cells derived human cord blood, we developed a xenogeneic mouse model using NSG mice sublethally irradiated and intravenously injected with luciferase-expressing MM1S multiple myeloma cells to induce measurable tumor formation. At day 4, the mice were intravenously injected with $10 \times 10^6$ control NK cells or BCMA-IL15/IL15sushi-CAR expressed NK cells. On days 3, 6, 8 and 10, mice were injected subcutaneously with RediJect D-Luciferin and subjected to IVIS imaging. As observed by IVIS imaging, total flux levels continually increased in control mice with tumor burden growth. In contrast, BCMA-IL15/IL15sushi-CAR-NK cells injected mice significantly suppressed tumor burden as early as day 6 with a 59.5% reduction in tumor burden. Results showed that only 10 days following treatment with CAR NK cells (Day 6), mice treated with BCMA-IL-15/IL-15sushi CAR NK cells had >84% lower tumor burden than mice given control NK cells (FIGS. 51A and 51B). In addition, CAR NK cell-treated mice also had very significantly more favorable survival outcomes. A survival curve was generated to show the survival of CAR NK cell-treated mice over time, more than 80 days, with Log-rank (Mantel-Cox) Test p=0.0069 as compared to controls, which only survived up to 45 days (FIG. 51C).

Evaluation of Persistence of Infused BCMA-A7D-IL15/IL15sushi CAR Transduced NK Cells In Vivo.

In order to evaluate the persistence of BCMA-A-7D-IL-15/IL-15sushi (also called CD269-IL-15/IL-15sushi) NK cells, we developed a xenogeneic mouse model using NSG mice sub-lethally irradiated and intravenously injected with $1 \times 10^6$ of luciferase-expressing MM1S multiple myeloma cells to induce measurable tumor formation. On Day 4, leukemic mice were intravenously injected with $10 \times 10^6$ BCMA-A-7D-IL-15/IL-15sushi NK cells derived human cord blood. Evaluation of persistence of infused BCMA-A7D-IL15/IL15sushi CAR transduced NK cells in xenograft mouse model were done on Day 25 (FIG. 52A) and Day 60 (FIG. 52B). On Day 25 (21 days after control NK or CAR NK cells infused mice) and Day 60 (58 days after mice were infused with control NK or CAR NK cells), peripheral blood was collected from individual mice and cells were labeled using human CD56– and human CD45 antibodies to detect the presence of infused control- and/or CAR-NK cells. MM1S myeloma cell line is negative for CD56 and CD45 (FIG. 52A left panel), which can be used to monitor human NK cells in mice. The persistence of control NK cells or BCMA-IL15/IL15sushi CAR transduced NK cells in collected peripheral blood was determined by flow cytometry analysis. Left panels show that MM1S was negative for CD56 and CD45. BCMA-IL15/IL15sushi-CAR transduced NK cells persisted more than 25 days (FIG. 52A) and 60 days (FIG. 52B) after infusion, while non-transduced NK cells (control) were un-detectable in mice. In addition, further evaluation showed that BCMA-IL15/IL15sushi-CAR transduced NK cells could persist more than three months. In general, human non-transduced NK cells usually persist less than one or two weeks in mice.

The natural killer cell is an ideal platform for creating a universal CAR that avoids risks associated with genome editing. However, the life expectancy of NK CAR cells in vivo is very short, with a lifespan of one or two weeks. Ideally, the NK cell persistency should be one or two months to be considered adequate for therapy. We have developed a NK cell platform for a universal CAR therapy with improved persistency and killing using IL-15/IL-15sushi fusion. The invented studies demonstrate CAR NK cells co-expressing secretory IL-15/IL-15sushi can be used as non-gene-editing universal CAR platform for treatment of a variety of diseases.

CD123 CAR Super1

Structural Organization of CD123 CAR Super 1

CD123 CAR super 1 (FIG. 57) contains a CAR, CD123 CAR (also called anti-CD123 CAR or CD123b CAR). CD123b CAR super 1 also co-expresses 4-1BBL ligand to enhance CAR function, and a secreting IL-15/IL-15sushi fusion. The soluble IL-15/IL-15sushi fusion is stable and functions as an unexpected and powerful immunomodulatory for CAR T/NK or NK T cells and their neighbor tumor immune response cells. The soluble IL-15/IL-15sushi fusion can enhance CAR T/NK or NK T cell persistency, stimulate tumor infiltrate lymphocyte proliferation, and anti-tumor activity. The soluble IL-15/IL-15sushi fusion provides anti-tumor vaccine-like effects by reprogramming body's immune system to fight cancers.

CAR Expression

NK cells from cord blood were transduced with the lentiviral vector expressing CD123b CAR super 1. FIG. 58 shows the transduction efficiency between NK cells transduced with either control vector, or CD123b super 1, as determined by labeling with goat anti-mouse F(Ab')2 antibody. Activated T cells transduced with the CAR vectors resulted in 8% F(Ab')2 positive cells for CD123b super 1(FIG. 58). These CAR T cells were used in the following in vitro killing assays. The functional testing will be performed as described above in vitro and in vivo.

In one embodiment, the engineered cell includes a CD123b chimeric antigen receptor polypeptide and 4-1BBL ligand, and IL-15/IL-15sushi (SEQ ID NO. 32), and corresponding nucleotides (SEQ ID NO. 33).

BCMA–CD38a-IL15/IL15sushi cCAR in NK Cells Derived from Human Cord Blood

NK cells from cord blood were transduced with the lentiviral vector expressing BCMA-CD38a-IL15/IL15sushi cCAR. FIG. 59 shows the transduction efficiency between NK cells transduced with either control vector, or BCMA–CD38a-IL15/IL15sushi cCAR, as determined by labeling with goat anti-mouse F(Ab')2 antibody. Activated T cells transduced with the CAR vectors resulted in 40% F(Ab')2 positive cells for BCMA–CD38a-IL15/IL15sushi cCAR (FIG. 59). These CAR T cells were used in the following in vitro killing assays. The functional testing will be performed as described above in vitro and in vivo.

In one embodiment, the engineered cell includes BCMA–CD38a chimeric antigen receptor polypeptides and 4-1BBL ligand, and IL-15/IL-15sushi (SEQ ID NO. 40), and corresponding nucleotides (SEQ ID NO. 41).

GD2-Super1-CAR

Example

The structural organization of GD2 super1 CAR shown in FIG. 60A. Links by P2A and T2A schematic to generate a super1 CAR showing a CAR, GD2 CAR equipped with 4-1BBL and IL-15/IL-15sushi in a single construct. The construct consists of a SFFV promoter driving the expression of three segments, CAR, 4-1BBL and IL-15/IL-15sushi. Upon cleavage of the linkers (P2A and T2A), the CAR, 4-1BBL and IL-15/IL-15sushi split and engage upon a target (s). CAR has scFV, hinge region, transmembrane domain, costimulatory domain (including, but not limited to, CD28 or 4-1BB) and intracellular signaling, CD3 zeta chain. 4-1BBL or IL-15/IL-sushi or both provides a synergistic effect of T or NK cell activation and persistency or anti-tumor activity with CD28 or 4-1BB.

In order to evaluate the in vivo anti-tumor activity of various GD2-targeting CAR constructs, we developed a xenogeneic mouse model using NSG mice sublethally irradiated and intravenously injected with luciferase-expressing Y79 retinoblastoma cells to induce measurable tumor formation. Three days following tumor cell injection, mice were intravenously injected with a course of 10×10e6 of either GD2-CAR, GD2-4-1BBL CAR, or GD2-super1 CAR, or vector control T cells. To determine the persistence of CAR T cells, mice were euthanized on Day 30. Liver, spleen and whole blood was collected from each mouse.

Flow cytometry analysis shows persistence of Y79 tumor (blue dots) in the livers of mice treated with different forms of anti-GD2 CAR T cells (FIG. 60B). Homogenized liver cells were labeled with mouse anti-human CD3 and CD56 antibodies, to detect human T cells and Y79 tumor cells, respectively. A representation of a mouse given control T cells is shown on the left; mouse treated with GD2CAR (left center), GD2-4-1BBL CAR (right center), and GD2-super1 CAR (right) T cells. FIG. 60B shows that GD2CAR T cells were unable to eliminate Y79 cells from the liver, relative to the mouse given control T cells, while mice treated with GD2-4-1-BBL CAR T cells had 32% fewer tumor cells. By contrast, the GD2-super1 CAR treated mice had 85% less tumor cells in the liver. A graph was then constructed to indicate percent killing activity against Y79 cells by each CAR treated mice compared to control mice (n=2) (FIG. 60B). From these data, especially, GD2-Super CAR eliminates Y79 cells in liver. Analysis of mice spleen showed a 1.87-fold increase in human T cells in GD2-super1 treated mice compared to control mice (FIG. 60C), and higher than GD2CAR (1.15×) and GD2-4-1BBL (1.35). This increase in GD2-super1 T cells is even more pronounced in the analysis of mouse whole blood, where there is a nearly 3-fold increase over control mice, and more than double the percentage of GD2CAR (FIG. 60D). A graph was then created to indicate the persistence of human T cells in whole blood samples, relative to the number of total cells analyzed by flow cytometry (n=2 each) (FIG. 60E). These data strongly suggest that GD2-super1 CAR, with both secreted IL-15/IL-15sushi and 4-1BBL domains, lyses GD2-expressing tumor cells and exhibits greater persistence than GD2CAR or GD2-41BBL CAR T cells.

In one embodiment, the engineered cell includes GD2 chimeric antigen receptor polypeptides and 4-1BBL ligand (SEQ ID NO. 58), and corresponding nucleotides (SEQ ID NO. 59).

In one embodiment, the engineered cell includes GD2 chimeric antigen receptor polypeptides SEQ ID NO. 56), and corresponding nucleotides (SEQ ID NO. 57).

In one embodiment, the engineered cell includes GD2 chimeric antigen receptor polypeptides, 4-1BBL ligand and IL-15/IL-15sushi (SEQ ID NO. 58), and corresponding nucleotides (SEQ ID NO. 59).

DESCRIPTION OF THE SEQUENCE LISTING

| SEQ ID NO. | DESCRIPTION |
| --- | --- |
| SEQ ID NO: 1 | CD19b-IL-21 anchor CAR amino acid sequence |
| SEQ ID NO: 2 | CD19b-IL-21 anchor CAR nucleotide sequence |
| SEQ ID NO: 3 | CD269-A7D-C11D cCAR, also called Ab269-7-11 CAR amino acid sequences |
| SEQ ID NO: 4 | CD269-A7D-C11D cCAR, also called Ab269-7-11 CAR nucleotide sequence |
| SEQ ID NO: 5 | CD269-7D-CD38-3077-2G amino acid |
| SEQ ID NO: 6 | CD269-7D-CD38-3077-2G CAR nucleotide sequence |
| SEQ ID NO: 7 | CD269-A7D-CD38-3079 CAR amino acid sequence |
| SEQ ID NO: 8 | CD269-A7D-CD38-3079 CAR nucleotide sequence |
| SEQ ID NO: 9 | CD269-A7D-CD38 CAR amino acid sequence |
| SEQ ID NO: 10 | CD269-A7D-CD38 CAR nucleotide sequence |
| SEQ ID NO: 11 | BCMA-A7D-IL-18 CAR amino acid sequence |
| SEQ ID NO: 12 | BCMA-A7D-IL-18 CAR nucleotide sequence |
| SEQ ID NO: 13 | BCMA-A7D-IL-18 anchor CAR amino acid sequence |
| SEQ ID NO: 14 | BCMA-A7D-IL-18 anchor CAR nucleotide sequence |
| SEQ ID NO: 15 | CD38 extracellular domain, CD38 XP |
| SEQ ID NO: 16 | CD19b-IL-21 CAR amino acid sequence |
| SEQ ID NO: 17 | CD19b-IL-21 CAR nucleotide sequence |
| SEQ ID NO: 18 | CD3 -28-super1CAR amino acid sequence |
| SEQ ID NO: 19 | CD3 -28-super1CAR nucleotide sequence |
| SEQ ID NO: 20 | CD4 -28-super1-2G CAR amino acid sequence |
| SEQ ID NO: 21 | CD4 -28-super1-2G CAR nucleotide sequence |
| SEQ ID NO: 22 | CD4-IL15/IL15sushi-3G CAR amino acid sequence |
| SEQ ID NO: 23 | CD4-IL15/IL15sushi-3G CAR nucleotide sequence |
| SEQ ID NO: 24 | CD19b-28-IL-15/IL15sushi-2G CAR amino acid sequence |
| SEQ ID NO: 25 | CD19b-28-IL-15/IL15sushi-2G CAR nucleotide sequence |
| SEQ ID NO: 26 | CD19b-28-super1-2G CAR amino acid sequence |
| SEQ ID NO: 27 | CD19b-28-super1-2G CAR nucleotide sequence |
| SEQ ID NO: 28 | CD20hCD19b-IL15/IL15sushi-2G CAR amino acid sequence |
| SEQ ID NO: 29 | CD20hCD19b-IL15/IL15sushi-2G CAR nucleotide sequence |
| SEQ ID NO: 30 | CD33b-28-super1-2G CAR amino acid sequence |
| SEQ ID NO: 31 | CD33b-28-super1-2G CAR nucleotide sequence |

DESCRIPTION OF THE SEQUENCE LISTING

| SEQ ID NO. | DESCRIPTION |
| --- | --- |
| SEQ ID NO: 32 | CD123b-28-super1-2G CAR amino acid sequence |
| SEQ ID NO: 33 | CD123b-28-super1 CAR nucleotide sequence |
| SEQ ID NO: 34 | CD123b-CD33b-IL15/IL15sushi-2G CAR amino acid sequence |
| SEQ ID NO: 35 | CD123b-CD33b-IL15/IL15sushi-2G CAR nucleotide sequence |
| SEQ ID NO: 36 | CD123b-CLL1-28-IL/IL15sushi-2G CAR amino acid sequence |
| SEQ ID NO: 37 | CD123b-CLL1-28-IL/IL15sushi-2G CAR nucleotide sequence |
| SEQ ID NO: 38 | CD269-A7D-28-super1-2G CAR amino acid sequence |
| SEQ ID NO: 39 | CD269-A7D-28-super1-2G CAR nucleotide sequence |
| SEQ ID NO: 40 | CD269-A7D-CD38a -IL15/IL15sushi-2G CAR amino acid sequence |
| SEQ ID NO: 41 | CD269-A7D-CD38a -IL15/IL15sushi-2G CAR nucleotide sequence |
| SEQ ID NO: 42 | CD269-A7D-CS1-hu63-28-IL15/IL15sushi-2G CAR amino acid sequence |
| SEQ ID NO: 43 | CD269-A7D-CS1-hu63-28-IL15/IL15sushi-2G CAR nucleotide sequence |
| SEQ ID NO: 44 | CLL1-28-super1-2G CAR amino acid sequence |
| SEQ ID NO: 45 | CLL1-28-super1-2G nucleotide sequence CAR nucleotide sequence |
| SEQ ID NO: 46 | GD2-28-super1-2G CAR amino acid sequence |
| SEQ ID NO: 47 | GD2-28-super1-2G CAR nucleotide sequence |
| SEQ ID NO: 48 | L45-CD5-28-52-IL-15/IL-15sushi-2G CAR amino acid sequence |
| SEQ ID NO: 49 | L45-CD5-28-52-IL15/IL-15sushi-2G CAR nucleotide sequence |
| SEQ ID NO: 50 | CD269-A7D-super2-2G CAR amino acid sequence |
| SEQ ID NO: 51 | CD269-A7D-super2-2G CAR nucleotide sequence |
| SEQ ID NO: 52 | D20h-CD19b-28-2G CAR amino acid sequence |
| SEQ ID NO: 53 | CD20hCD19b-28-2G CAR nucleotide sequence |
| SEQ ID NO: 54 | CD45b-28-2G-IL-15/IL-15sushi amino acid sequence |
| SEQ ID NO: 55 | CD45b-28-2G-IL-15/IL-15sushi nucleotide sequence |
| SEQ ID NO: 56 | GD2-28-2G CAR amino acid sequence |
| SEQ ID NO: 57 | GD2-28-2G CAR nucleotide sequence |
| SEQ ID NO: 58 | GD2-28-4-1BBL-2G CAR amino acid sequence |
| SEQ ID NO: 59 | GD2-28-41BBL-2G CAR nucleotide sequence |
| SEQ ID NO: 60 | CLL1-CD33b-IL15/IL15sushi-2G CAR amino acid sequence |
| SEQ ID NO: 61 | CLL1-CD33b-IL15/IL15sushi-2G CAR nucleotide sequence |

The invention claimed is:

1. An ex vivo engineered T cell or NK cell co-expressing two distinct chimeric antigen receptor (CAR) units at the cell surface, wherein the engineered T cell or NK cell comprises a nucleotide sequence comprising from 5' to 3' a first polynucleotide encoding a first chimeric antigen receptor polypeptide (first CAR), a second polynucleotide encoding a second chimeric antigen receptor polypeptide (second CAR), a nucleotide encoding porcine teschovirus-1 2A (P2A), thoseaasigna virus 2A (T2A), FMDV 2A (F2A) or equine rhinitis A virus (ERAV) 2A (E2A1 disposed between the first CAR and second CAR, under the transcriptional control of a single promoter, wherein:
   (i.) the first CAR polypeptide comprises a first antigen recognition domain; a first signal peptide; a first hinge region; a first transmembrane domain; a first co-stimulatory domain; and a first signaling domain; and
   (ii.) the second CAR comprises a second antigen recognition domain; a second signal peptide; a second hinge region; a second transmembrane domain; a second co-stimulatory domain; and a second signaling domain; wherein the first antigen recognition domain and the second antigen recognition domain are different;
   wherein the engineered T cell or NK cell comprises an enhancer selected from the group consisting of IL-15/IL-15sushi, IL-15/IL-15 sushi anchor, 4-1BBL, and IL-15: and
   wherein the engineered T cell or NK cell comprises SEQ ID NO: 1, SEQ ID NO: 28, SEQ ID NO: 34, SEQ ID NO: 36, SEQ ID NO: 40, SEQ ID NO: 42, SEQ ID NO: 50, SEQ ID NO: 52, or SEQ ID NO: 60.

2. The engineered cell according to claim 1, wherein the engineered T cell or NK cell comprises SEQ ID NO: 60.

3. The engineered cell according to claim 1, wherein the enhancer is secreted by the engineered cell.

4. The engineered cell according to claim 1, wherein the engineered T cell is an NK T cell.

5. A method of treating a cell proliferative disease comprising administering an engineered T cell or NK cell according to claim 1 to a patient in need thereof.

6. The method according to claim 5, wherein the cell proliferative disease comprises a t-cell malignancy, leukemia, or a lymphoma.

7. The method according to claim 5, wherein the engineered T cell is an NK T cell.

* * * * *

UNITED STATES PATENT AND TRADEMARK OFFICE
CERTIFICATE OF CORRECTION

PATENT NO. : 11,905,528 B2
APPLICATION NO. : 16/753951
DATED : February 20, 2024
INVENTOR(S) : Yupo Ma et al.

It is certified that error appears in the above-identified patent and that said Letters Patent is hereby corrected as shown below:

In the Specification

Column 4, Line 61:
Now reads: "(4A) Co-cultures against BCMA+CS1+ primary myeloma"
Should read: --(4A) Co-cultures against $BCMA^+CS1^+$ primary myeloma--

Column 8, Line 28:
Now reads: "Jurkat xp123 cells ata 2:1 E:T ratio."
Should read: --Jurkat xp123 cells at a 2:1 E:T ratio.--

Column 8, Line 58:
Now reads: "–24 hours later, CAMPATH (0.1mg/kg)"
Should read: --~24 hours later, CAMPATH (0.1mg/kg)--

Column 9, Line 29:
Now reads: "CD19+K562 cells and control K562 cells at 5:1 E:T ratios"
Should read: --$CD19^+$K562 cells and control K562 cells at 5:1 E:T ratios--

Column 9, Lines 33-34:
Now reads: "analysis of control T-cells and CD19b–CD123 cCAR T-cells against artificially-induced CD19+K562 cells and"
Should read: --analysis of control T-cells and $CD19b^-$CD123 cCAR T-cells against artificially-induced $CD19^+$K562 cells and--

Column 9, Lines 39-40:
Now reads: "Flow cytometry analysis of KG1a tumor cells (CD123+CD19–) and SP53 cells (CD123-CD19+) at 5:1 E:T ratio, at"
Should read: --Flow cytometry analysis of KG1a tumor cells ($CD123^+CD19^-$) and SP53 cells ($CD123^-CD19^+$) at 5:1 E:T ratio, at--

Signed and Sealed this
Twenty-eighth Day of October, 2025

John A. Squires
*Director of the United States Patent and Trademark Office*

CERTIFICATE OF CORRECTION (continued)
U.S. Pat. No. 11,905,528 B2

Column 20, Lines 4-5:
Now reads: "IL-15/IL-15sushi CAR T-cells were injected (7.5×10$^6$ total cells/mouse) and on day 6 through 22, IVIS imaging was"
Should read: --IL15/IL-15sushi CAR T-cells were injected (~7.5×10$^6$ total cells/mouse) and on day 6 through 22, IVIS imaging was--

Column 28, Line 54:
Now reads: "β chain, a CD3 zeta chain, CD28, CD3, CD45, CD4, CD5,"
Should read: --β chain, a CD3 zeta chain, CD28, CD3$_e$, CD45, CD4, CD5,--

Column 29, Line 16:
Now reads: "zeta chain, CD28, CD3, CD45, CD4, CD5, CD8, CD9,"
Should read: --zeta chain, CD28, CD3$_e$, CD45, CD4, CD5, CD8, CD9,--

Column 29, Line 37:
Now reads: "CD79a, CD79b, DNAX-activating protein (DAP10),"
Should read: --CD79a, CD79b, DNAX-activating protein 10 (DAP10),--

Column 42, Line 21:
Now reads: "IL-15/IL-15 sushi is linked with the P2A self-cleaving"
Should read: --IL-15/IL-15sushi is linked with the P2A self-cleaving--

Column 44, Line 54:
Now reads: "anti-tumor response by eliminating surviving BCMA$^-$CS1+"
Should read: --anti-tumor response by eliminating surviving BCMA$^-$CS1$^+$--

Column 53, Line 5:
Now reads: "surviving BCMA$^-$CD38+ myeloma cells to reduce the"
Should read: --surviving BCMA$^-$CD38$^+$ myeloma cells to reduce the--

Column 54, Line 18:
Now reads: "BCMA–CD38 cCAR targeted cells are 13 cells, immature"
Should read: --BCMA–CD38 cCAR targeted cells are 1B cells, immature--

Column 54, Line 25:
Now reads: "Sjorgen's syndrome, polymyositis, pulmonary alveolar"
Should read: --Sjorgen syndrome, polymyositis, pulmonary alveolar--

Column 57, Line 36:
Now reads: "surviving BCMA$^-$CD38+ lymphomas to reduce the risk"
Should read: --surviving BCMA$^-$CD38$^+$ lymphomas to reduce the risk--

Column 58, Line 44:
Now reads: "B cells, memory 13 cells, plasma blasts, long lived plasma"
Should read: --B cells, memory B cells, plasma blasts, long lived plasma--

Column 58, Line 50:
Now reads: "Sjorgen's syndrome, polymyositis, pulmonary alveolar"
Should read: --Sjorgen syndrome, polymyositis, pulmonary alveolar--

Column 60, Line 39:
Now reads: "Sjorgen's syndrome, polymyositis, pulmonary alveolar"
Should read: --Sjorgen syndrome, polymyositis, pulmonary alveolar--

Column 69, Line 27:
Now reads: "months old, 6 to 12 months old, 1 to years old, 5 to 10 years"
Should read: --months old, 6 to 12 months old, 1 to 5 years old, 5 to 10 years--

Column 71, Line 40:
Now reads: "mixed tumor with double positive BCMA $CS1^+$ as well as"
Should read: --mixed tumor with double positive $BCMA^+$ $CS1^+$ as well as--

Column 71, Line 42:
Now reads: "complete BCMA $CS1^+$ phenotype while bone marrow"
Should read: --complete $BCMA^+$ $CS1^+$ phenotype while bone marrow--

Column 73, Line 47:
Now reads: "compared to control T-cells across all mice even at day $30^+$"
Should read: --compared to control T-cells across all mice even at day 30+--

Column 73, Line 50:
Now reads: "Structural Organization of BCMA-CS1-IL-15/IL-15Sushi"
Should read: --Structural Organization of BCMA-CS1-IL-15/IL-15sushi--

Column 80, Lines 33-34:
Now reads: "to 4-1BB and CD28 co-activation domains and a CD3 (CD3) signaling domain (FIG. 30). A strong spleen focus"
Should read: --to 4-1BB and CD28 co-activation domains and a CD3$\zeta$ (CD3) signaling domain (FIG. 30). A strong spleen focus--

Column 87, Line 57:
Now reads: "CART cells to lyse target cells expressing CD19, co-culture"
Should read: --CAR T-cells to lyse target cells expressing CD19, co-culture--

Column 88, Line 27:
Now reads: "CART cells to lyse on-target cells expressing both CD19 and"
Should read: --CAR T-cells to lyse on-target cells expressing both CD19 and--

Column 88, Lines 60-61:
Now reads: "Structural Organization of CD20h-CD19b-IL-15/IL-15Sushi (CD20hCD19b-IL-15/IL-15sushi)"

CERTIFICATE OF CORRECTION (continued)
U.S. Pat. No. 11,905,528 B2

Should read: --Structural Organization of CD20h-CD19b-IL-15/IL-15sushi (CD20hCD19b-IL-15/IL-15sushi)--

Column 89, Line 44:
Now reads: "CD20h-CD19b-IL15/IL-15Sushi CAR T Cells Exhibit"
Should read: --CD20h-CD19b-IL15/IL-15sushi CAR T Cells Exhibit--

Column 89, Line 56:
Now reads: "CART cells. On Day 4 (the day before T cell treatment), and"
Should read: --CAR T-cells. On Day 4 (the day before T cell treatment), and--

Column 91, Line 20:
Now reads: "Flow cytometry analysis showed that -35% of T cells"
Should read: --Flow cytometry analysis showed that ~35% of T cells--

Column 91, Line 25-26:
Now reads: "increase CAR potency and persistency by secreting theIL-15/IL15-sushi fusion."
Should read: --increase CAR potency and persistency by secreting the IL-15/IL15-sushi fusion.--

Column 95, Line 10:
Now reads: "Generation of BCMA15/IL-15Sushi-CAR Expressed"
Should read: --Generation of BCMA15/IL-15sushi-CAR Expressed--

SEQUENCE LISTING

```
<160> NUMBER OF SEQ ID NOS: 61

<210> SEQ ID NO 1
<211> LENGTH: 734
<212> TYPE: PRT
<213> ORGANISM: Artificial Sequence
<220> FEATURE:
<223> OTHER INFORMATION: Synthetic Sequence
```

<400> SEQUENCE: 1

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
130                 135                 140

Gly Gly Ser Gly Gly Gly Ser Gly Gly Gly Ser Asp Ile Val
145                 150                 155                 160

Met Thr Gln Ala Ala Pro Ser Ile Pro Val Thr Pro Gly Glu Ser Val
            165                 170                 175

Ser Ile Ser Cys Arg Ser Ser Lys Ser Leu Leu Asn Ser Asn Gly Asn
        180                 185                 190

Thr Tyr Leu Tyr Trp Phe Leu Gln Arg Pro Gly Gln Ser Pro Gln Leu
    195                 200                 205

Leu Ile Tyr Arg Met Ser Asn Leu Ala Ser Gly Val Pro Asp Arg Phe
210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
            245                 250                 255

Pro Phe Thr Phe Gly Ala Gly Thr Lys Leu Glu Leu Lys Arg Thr Thr
        260                 265                 270

Thr Pro Ala Pro Arg Pro Pro Thr Pro Ala Pro Thr Ile Ala Ser Gln
    275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Arg Ser Lys Arg Ser Arg Leu Leu His Ser Asp Tyr Met
        340                 345                 350

Asn Met Thr Pro Arg Arg Pro Gly Pro Thr Arg Lys His Tyr Gln Pro
    355                 360                 365

Tyr Ala Pro Pro Arg Asp Phe Ala Ala Tyr Arg Ser Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
```

```
              405                 410                 415
Lys Arg Arg Gly Arg Asp Pro Glu Met Gly Gly Lys Pro Gln Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Ser Gly
                485                 490                 495

Glu Gly Arg Gly Ser Leu Leu Thr Cys Gly Asp Val Glu Glu Asn Pro
            500                 505                 510

Gly Pro Met Tyr Arg Met Gln Leu Leu Ser Cys Ile Ala Leu Ser Leu
        515                 520                 525

Ala Leu Val Thr Asn Ser Gln Gly Gln Asp Arg His Met Ile Arg Met
    530                 535                 540

Arg Gln Leu Ile Asp Ile Val Asp Gln Leu Lys Asn Tyr Val Asn Asp
545                 550                 555                 560

Leu Val Pro Glu Phe Leu Pro Ala Pro Glu Asp Val Glu Thr Asn Cys
                565                 570                 575

Glu Trp Ser Ala Phe Ser Cys Phe Gln Lys Ala Gln Leu Lys Ser Ala
            580                 585                 590

Asn Thr Gly Asn Asn Glu Arg Ile Ile Asn Val Ser Ile Lys Lys Leu
        595                 600                 605

Lys Arg Lys Pro Pro Ser Thr Asn Ala Gly Arg Arg Gln Lys His Arg
    610                 615                 620

Leu Thr Cys Pro Ser Cys Asp Ser Tyr Glu Lys Lys Pro Pro Lys Glu
625                 630                 635                 640

Phe Leu Glu Arg Phe Lys Ser Leu Leu Gln Lys Met Ile His Gln His
                645                 650                 655

Leu Ser Ser Arg Thr His Gly Ser Glu Asp Ser Thr Thr Thr Pro Ala
            660                 665                 670

Pro Arg Pro Pro Thr Pro Ala Pro Thr Ile Ala Ser Gln Pro Leu Ser
        675                 680                 685

Leu Arg Pro Glu Ala Cys Arg Pro Ala Ala Gly Gly Ala Val His Thr
    690                 695                 700

Arg Gly Leu Asp Phe Ala Cys Asp Val Ala Ile Ser Thr Ser Thr Val
705                 710                 715                 720

Leu Leu Cys Gly Leu Ser Ala Val Ser Leu Leu Ala Cys Tyr
                725                 730
```

<210> SEQ ID NO 2
<211> LENGTH: 2221
<212> TYPE: DNA
<213> ORGANISM: Artificial Sequence
<220> FEATURE:
<223> OTHER INFORMATION: Synthetic Sequence

<400> SEQUENCE: 2

```
gcgatcgcat ggccttacca gtgaccgcct tgctcctgcc gctggccttg ctgctccacg      60
ccgccaggcc ggaggtccag ctgcagcagt ctggacctga gctgataaag cctggggctt     120
cagtgaagat gtcctgcaag gcttctggat acacattcac tagctatgtt atgcactggg     180
tgaagcagaa gcctgggcag ggccttgagt ggattggata tattaatcct tacaatgatg     240
```

```
gtactaagta caatgagaag ttcaaaggca aggccacact gacttcagac aaatcctcca    300
gcacagccta catggagctc agcagcctga cctctgagga ctctgcggtc tattactgtg    360
caagagggac ttattactac ggtagtaggg tatttgacta ctggggccaa ggcaccactc    420
tcacagtctc ctcaggtgga gggggctcag gcggaggtgg ctctggggt ggaggctcgg    480 acattgtgat gactcaggct gcaccctcta tacctgtcac tcctggagag tcagtatcca    540
tctcctgcag gtctagtaag agtctcctga atagtaatgg caacacttac ttgtattggt    600
tcctgcagag gccaggccag tctcctcagc tcctgatata tcggatgtcc aaccttgcct    660
caggagtccc agacaggttc agtggcagtg ggtcaggaac tgctttcaca ctgagaatca    720
gtagagtgga ggctgaggat gtgggtgttt attactgtat gcaacatcta gaatatccgt    780
tcacgttcgg tgctgggacc aagctggagc tgaaacggac cacgacgcca gcgccgcgac    840
caccaacacc ggcgcccacc atcgcgtcgc agcccctgtc cctgcgccca gaggcgtgcc    900
ggccagcggc gggggggcgca gtgcacacga gggggctgga cttcgcctgt gatatctaca    960
tctgggcgcc cttggccggg acttgtgggg tccttctcct gtcactggtt atcaccctt    1020 actgcaggag taagaggagc aggctcctgc acagtgacta catgaacatg actccccgcc    1080
gccccgggcc cacccgcaag cattaccagc cctatgcccc accacgcgac ttcgcagcct    1140
atcgctccag agtgaagttc agcaggagcc agacgccccc gcgtaccag cagggccaga    1200 accagctcta taacgagctc aatctaggac gaagagagga gtacgatgtt ttggacaaga    1260
gacgtggccg ggaccctgag atgggggaa agccgcagag aaggaagaac cctcaggaag    1320
gcctgtacaa tgaactgcag aaagataaga tggcggaggc ctacagtgag attgggatga    1380
aaggcgagcg ccggagggc aaggggcacg atggccttta ccagggtctc agtacagcca    1440
ccaaggacac ctacgacgcc cttcacatgc aggccctgcc ccctcgcggc agcggcgaag    1500
gccgcggcag cctgctgacc tgcggcgatg tggaagaaaa cccgggcccc atgtacagaa    1560
tgcagctgct gagctgcatc gccctgagcc tggcctggt gaccaacagc cagggccagg    1620
acaggcacat gatcaggatg aggcagctga tcgacatcgt ggaccagctg aagaactacg    1680
tgaacgacct ggtgcccgag ttcctgcccg ccccgagga cgtggagacc aactgcgagt    1740
ggagcgcctt cagctgcttc cagaaggccc agctgaagag cgccaacacc ggcaacaacg    1800
agaggatcat caacgtgagc atcaagaagc tgaagaggaa gccccccagc accaacgccg    1860
gcaggaggca gaagcacagg ctgacctgcc ccagctgcga cagctacgag aagaagcccc    1920
ccaaggagtt cctggagagg ttcaagagcc tgctgcagaa gatgatccac cagcacctga    1980
gcagcaggac ccacggcagc gaggacagca ccaccacccc cgcccccagg cccccaccc    2040 ccgcccccac catcgccagc cagccctga gcctgaggcc cgaggcctgc aggccgccg    2100 ccggcggcgc cgtgcacacc aggggcctgg acttcgcctg cgacgtggct atctccacgt    2160
ccactgtcct gctgtgtggg ctgagcgctg tgtctctcct ggcatgctac taagtttaaa    2220
c                                                                   2221
```

<210> SEQ ID NO 3
<211> LENGTH: 997
<212> TYPE: PRT
<213> ORGANISM: Artificial Sequence
<220> FEATURE:
<223> OTHER INFORMATION: Synthetic Sequence

<400> SEQUENCE: 3

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
            195                 200                 205

Gly Arg Phe Ala Phe Ser Val Glu Thr Ser Ala Thr Thr Ala Tyr Leu
210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270

Pro Pro Thr Pro Ala Pro Thr Ile Ala Ser Gln Pro Leu Ser Leu Arg
    275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
```

```
                420             425             430
Gly Leu Tyr Asn Glu Leu Gln Lys Asp Lys Met Ala Glu Ala Tyr Ser
            435             440             445

Glu Ile Gly Met Lys Gly Arg Arg Gly Lys Gly His Asp Gly
            450             455             460

Leu Tyr Gln Gly Leu Ser Thr Ala Thr Lys Asp Thr Tyr Asp Ala Leu
465             470             475             480

His Met Gln Ala Leu Pro Pro Arg Gly Ser Gly Ala Thr Asn Phe Ser
            485             490             495

Leu Leu Lys Gln Ala Gly Asp Val Glu Glu Asn Pro Gly Pro Met Ala
            500             505             510

Leu Pro Val Thr Ala Leu Leu Leu Pro Leu Ala Leu Leu Leu His Ala
            515             520             525

Ala Arg Pro Asp Ile Val Leu Thr Gln Ser Pro Pro Ser Leu Ala Met
            530             535             540

Ser Leu Gly Lys Arg Ala Thr Ile Ser Cys Arg Ala Ser Glu Ser Val
545             550             555             560

Thr Ile Leu Gly Ser His Leu Ile His Trp Tyr Gln Gln Lys Pro Gly
            565             570             575

Gln Pro Pro Thr Leu Leu Ile Gln Leu Ala Ser Asn Val Gln Thr Gly
            580             585             590

Val Pro Ala Arg Phe Ser Gly Ser Gly Ser Arg Thr Asp Phe Thr Leu
            595             600             605

Thr Ile Asp Pro Val Glu Glu Asp Asp Val Ala Val Tyr Tyr Cys Leu
            610             615             620

Gln Ser Arg Thr Ile Pro Arg Thr Phe Gly Gly Gly Thr Lys Leu Glu
625             630             635             640

Ile Lys Gly Gly Gly Gly Ser Gly Gly Gly Gly Ser Gly Gly Gly Gly
            645             650             655

Ser Gln Ile Gln Leu Val Gln Ser Gly Pro Glu Leu Lys Lys Pro Gly
            660             665             670

Glu Thr Val Lys Ile Ser Cys Lys Ala Ser Gly Tyr Thr Phe Thr Asp
            675             680             685

Tyr Ser Ile Asn Trp Val Lys Arg Ala Pro Gly Lys Gly Leu Lys Trp
            690             695             700

Met Gly Trp Ile Asn Thr Glu Thr Arg Glu Pro Ala Tyr Ala Tyr Asp
705             710             715             720

Phe Arg Gly Arg Phe Ala Phe Ser Leu Glu Thr Ser Ala Ser Thr Ala
            725             730             735

Tyr Leu Gln Ile Asn Asn Leu Lys Tyr Glu Asp Thr Ala Thr Tyr Phe
            740             745             750

Cys Ala Leu Asp Tyr Ser Tyr Ala Met Asp Tyr Trp Gly Gln Gly Thr
            755             760             765

Ser Val Thr Val Ser Ser Thr Thr Thr Pro Ala Pro Arg Pro Pro Thr
770             775             780

Pro Ala Pro Thr Ile Ala Ser Gln Pro Leu Ser Leu Arg Pro Glu Ala
785             790             795             800

Cys Arg Pro Ala Ala Gly Gly Ala Val His Thr Arg Gly Leu Asp Phe
            805             810             815

Ala Cys Asp Ile Tyr Ile Trp Ala Pro Leu Ala Gly Thr Cys Gly Val
            820             825             830

Leu Leu Leu Ser Leu Val Ile Thr Leu Tyr Cys Arg Ser Lys Arg Ser
            835             840             845
```

Arg Leu Leu His Ser Asp Tyr Met Asn Met Thr Pro Arg Arg Pro Gly
            850                 855                 860

Pro Thr Arg Lys His Tyr Gln Pro Tyr Ala Pro Pro Arg Asp Phe Ala
865                 870                 875                 880

Ala Tyr Arg Ser Arg Val Lys Phe Ser Arg Ser Ala Asp Ala Pro Ala
                885                 890                 895

Tyr Gln Gln Gly Gln Asn Gln Leu Tyr Asn Glu Leu Asn Leu Gly Arg
            900                 905                 910

Arg Glu Glu Tyr Asp Val Leu Asp Lys Arg Arg Gly Arg Asp Pro Glu
            915                 920                 925

Met Gly Gly Lys Pro Gln Arg Arg Lys Asn Pro Gln Glu Gly Leu Tyr
            930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
                965                 970                 975

Gly Leu Ser Thr Ala Thr Lys Asp Thr Tyr Asp Ala Leu His Met Gln
            980                 985                 990

Ala Leu Pro Pro Arg
            995

<210> SEQ ID NO 4
<211> LENGTH: 3013
<212> TYPE: DNA
<213> ORGANISM: Artificial Sequence
<220> FEATURE:
<223> OTHER INFORMATION: Synthetic Sequence

<400> SEQUENCE: 4

| ggcgatcgca | ccatggcctt | accagtgacc | gccttgctcc | tgccgctggc | cttgctgctc | 60 |
| cacgccgcca | ggccggacgt | ggtgatgacc | cagaccacag | gttcatgagc | accagcgtgg | 120 |
| gcgacagggt | gagcatcacc | tgcagggcca | gccaggacgt | gaacaccgcc | gtgagctggt | 180 |
| accagcagaa | gcccggccag | agccccaagc | tgctgatctt | cagcgccagc | tacaggtaca | 240 |
| ccggcgtgcc | cgacaggttc | accggcagcg | gcagcggcgc | cgacttcacc | ctgaccatca | 300 |
| gcagcgtgca | ggccgaggac | ctggccgtgt | actactgcca | gcagcactac | agcaccccct | 360 |
| ggaccttcgg | cggcggcacc | aagctggaca | tcaaggaggg | ggggggatcc | ggggaggag | 420 |
| gctccggcgg | aggcggaagc | cagatccagc | tggtgcagag | cggccccgac | ctgaagaagc | 480 |
| ccggcgagac | cgtgaagctg | agctgcaagg | ccagcggcta | caccttcacc | aacttcggca | 540 |
| tgaactgggt | gaagcaggcc | cccggcaagg | gcttcaagtg | gatggcctgg | atcaacacct | 600 |
| acaccggcga | gagctacttc | gccgacgact | tcaagggcag | gttcgccttc | agcgtggaga | 660 |
| ccagcgccac | caccgcctac | ctgcagatca | caaacctgaa | gaccgaggac | accgccacct | 720 |
| acttctgcgc | caggggcgag | atctactacg | gctacgacgg | cggcttcgcc | tactggggcc | 780 |
| agggcaccct | ggtgaccgtg | agcgccacca | cgacgccagc | gccgcgacca | ccaacaccgg | 840 |
| cgcccaccat | cgcgtcgcag | cccctgtccc | tgcgcccaga | ggcgtgccgg | ccagcggcgg | 900 |
| ggggcgcagt | gcacacgagg | gggctggact | tcgcctgtga | tatctacatc | tgggcgccct | 960 |
| tggccgggac | ttgtgggtc | cttctcctgt | cactggttat | cacccttac | tgcaggagta | 1020 |
| agaggagcag | gctcctgcac | agtgactaca | tgaacatgac | tccccgccgc | cccgggccca | 1080 |
| cccgcaagca | ttaccagccc | tatgccccac | cacgcgactt | cgcagcctat | cgctccagag | 1140 |

```
tgaagttcag caggagcgca gacgcccccg cgtaccagca gggccagaac cagctctata    1200
acgagctcaa tctaggacga agagaggagt acgatgtttt ggacaagaga cgtggccggg    1260
accctgagat gggggggaaag ccgcagagaa ggaagaaccc tcaggaaggc ctgtacaatg    1320
aactgcagaa agataagatg gcggaggcct acagtgagat tgggatgaaa ggcgagcgcc    1380 ggagggggcaa ggggcacgat ggcctttacc agggtctcag tacagccacc aaggacacct    1440
acgacgccct tcacatgcag gccctgcccc ctcgcggaag cggagccacc aacttcagcc    1500
tgctgaagca ggccggcgac gtggaggaga accccggccc catggcctta ccagtgaccg    1560
ccttgctcct gccgctggcc ttgctgctcc acgccgccag gccggacatc gtgctgaccc    1620
agagcccccc cagcctggcc atgagcctgg gcaagagggc caccatcagc tgcagggcca    1680
gcgagagcgt gaccatcctg gcagccaccc tgatccactg gtaccagcag aagcccggcc    1740
agccccccac cctgctgatc cagctggcca gcaacgtgca gaccggcgtg cccgccaggt    1800
tcagcggcag cggcagcagg accgacttca ccctgaccat cgaccccgtg gaggaggacg    1860
acgtggccgt gtactactgc ctgcagagca ggaccatccc caggaccttc ggcggcggca    1920
ccaagctgga gatcaaggga gggggggggat ccggggggagg aggctccggc ggaggcggaa    1980
gccagatcca gctggtgcag agcggccccg agctgaagaa gcccggcgag accgtgaaga    2040
tcagctgcaa ggccagcggc tacaccttca ccgactacag catcaactgg gtgaagaggg    2100
cccccggcaa gggcctgaag tggatgggct ggatcaacac cgagaccagg gagcccgcct    2160
acgcctacga cttcagggcc aggttcgcct tcagcctgga gaccagcgcc agcaccgcct    2220
acctgcagat caacaacctg aagtacgagg acaccgccac ctacttctgc gccctggact    2280
acagctacgc catggactac tggggccagg gcaccagcgt gaccgtgagc agcaccacga    2340
cgccagcgcc gcgaccacca caccggcgcc caccatcgc gtcgcagccc ctgtccctgc    2400
gcccagaggc gtgccggcca cggcggggg gcgcagtgca cacgagggg ctggacttcg    2460 cctgtgatat ctacatctgg gcgccccttgg ccgggacttg tggggtcctt ctcctgtcac    2520
tggttatcac cctttactgc aggagtaaga ggagcaggct cctgcacagt gactacatga    2580
acatgactcc ccgccgcccc gggcccaccc gcaagcatta ccagccctat gccccaccac    2640
gcgacttcgc agcctatcgc tccagagtga agttcagcag gagcgcagac gcccccgcgt    2700
accagcaggg ccagaaccag ctctataacg agctcaatct aggacgaaga gaggagtacg    2760 atgtttttgga caagagacgt ggccgggacc ctgagatggg gggaaagccg cagagaagga    2820
agaaccctca ggaaggcctg tacaatgaac tgcagaaaga taagatggcg gaggcctaca    2880
gtgagattgg gatgaaaggc gagcgccgga ggggcaaggg gcacgatggc ctttaccagg    2940
gtctcagtac agccaccaag gacacctacg acgccttca catgcaggcc ctgccccctc    3000
gctaagttta aac                                                      3013
```

<210> SEQ ID NO 5
<211> LENGTH: 1005
<212> TYPE: PRT
<213> ORGANISM: Artificial Sequence
<220> FEATURE:
<223> OTHER INFORMATION: Synthetic Sequence

<400> SEQUENCE: 5

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30
```

```
Ser Thr Ser Val Gly Asp Arg Val Ser Ile Thr Cys Arg Ala Ser Gln
         35                  40                  45

Asp Val Asn Thr Ala Val Ser Trp Tyr Gln Gln Lys Pro Gly Gln Ser
 50                  55                  60

Pro Lys Leu Leu Ile Phe Ser Ala Ser Tyr Arg Tyr Thr Gly Val Pro
 65                  70                  75                  80

Asp Arg Phe Thr Gly Ser Gly Ser Gly Ala Asp Phe Thr Leu Thr Ile
                 85                  90                  95

Ser Ser Val Gln Ala Glu Asp Leu Ala Val Tyr Tyr Cys Gln Gln His
                100                 105                 110

Tyr Ser Thr Pro Trp Thr Phe Gly Gly Gly Thr Lys Leu Asp Ile Lys
                115                 120                 125

Gly Gly Gly Gly Ser Gly Gly Gly Ser Gly Gly Gly Gly Ser Gln
                130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
                180                 185                 190

Trp Ile Asn Thr Tyr Thr Gly Glu Ser Tyr Phe Ala Asp Asp Phe Lys
                195                 200                 205

Gly Arg Phe Ala Phe Ser Val Glu Thr Ser Ala Thr Thr Ala Tyr Leu
                210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
                290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
                355                 360                 365

Asp Phe Ala Ala Tyr Arg Ser Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
                420                 425                 430

Gly Leu Tyr Asn Glu Leu Gln Lys Asp Lys Met Ala Glu Ala Tyr Ser
                435                 440                 445
```

```
Glu Ile Gly Met Lys Gly Glu Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Leu Pro Val Thr Ala Leu Leu Leu Pro Leu Ala Leu Leu Leu His Ala
        515                 520                 525

Ala Arg Pro Asp Ile Val Met Thr Gln Ser Pro Leu Ser Leu Pro Val
530                 535                 540

Thr Pro Gly Glu Pro Ala Ser Ile Ser Cys Arg Ser Ser Gln Ser Leu
545                 550                 555                 560

Leu Phe Ile Asp Gly Asn Asn Tyr Leu Asn Trp Tyr Leu Gln Lys Pro
                565                 570                 575

Gly Gln Ser Pro Gln Leu Leu Ile Tyr Leu Gly Ser Asn Arg Ala Ser
            580                 585                 590

Gly Val Pro Asp Arg Phe Ser Gly Ser Gly Ser Gly Thr Asp Phe Thr
            595                 600                 605

Leu Lys Ile Ser Arg Val Glu Ala Glu Asp Val Gly Val Tyr Tyr Cys
    610                 615                 620

Gln Gln Tyr Ser Ser Lys Ser Ala Thr Phe Gly Gln Gly Thr Lys Val
625                 630                 635                 640

Glu Ile Lys Arg Thr Gly Gly Gly Gly Ser Gly Gly Gly Gly Ser Gly
                645                 650                 655

Gly Gly Gly Ser Gln Val Gln Leu Val Gln Ser Gly Ala Glu Val Lys
            660                 665                 670

Lys Pro Gly Ala Ser Val Lys Val Ser Cys Lys Ala Ser Gly Tyr Thr
        675                 680                 685

Phe Thr Ser Tyr Ser Ile Asn Trp Val Arg Gln Ala Pro Gly Gln Gly
        690                 695                 700

Leu Glu Trp Met Gly Tyr Ile Asp Pro Asn Arg Gly Asn Thr Asn Tyr
705                 710                 715                 720

Ala Gln Lys Phe Gln Gly Arg Val Thr Met Thr Arg Asp Thr Ser Ile
                725                 730                 735

Ser Thr Ala Tyr Met Glu Leu Ser Ser Leu Arg Ser Glu Asp Thr Ala
            740                 745                 750

Val Tyr Tyr Cys Ala Arg Glu Tyr Ile Tyr Phe Ile His Gly Met Leu
        755                 760                 765

Asp Phe Trp Gly Gln Gly Thr Leu Val Thr Val Ser Ser Thr Thr Thr
770                 775                 780

Pro Ala Pro Arg Pro Pro Thr Pro Ala Pro Thr Ile Ala Ser Gln Pro
785                 790                 795                 800

Leu Ser Leu Arg Pro Glu Ala Cys Arg Pro Ala Ala Gly Gly Ala Val
                805                 810                 815

His Thr Arg Gly Leu Asp Phe Ala Cys Asp Ile Tyr Ile Trp Ala Pro
            820                 825                 830

Leu Ala Gly Thr Cys Gly Val Leu Leu Leu Ser Leu Val Ile Thr Leu
        835                 840                 845

Tyr Cys Lys Arg Gly Arg Lys Lys Leu Leu Tyr Ile Phe Lys Gln Pro
850                 855                 860

Phe Met Arg Pro Val Gln Thr Thr Gln Glu Glu Asp Gly Cys Ser Cys
```

```
              865               870               875               880
Arg Phe Pro Glu Glu Glu Gly Gly Cys Glu Leu Arg Val Lys Phe
                885               890               895
Ser Arg Ser Ala Asp Ala Pro Ala Tyr Gln Gln Gly Gln Asn Gln Leu
                900               905               910
Tyr Asn Glu Leu Asn Leu Gly Arg Arg Glu Glu Tyr Asp Val Leu Asp
                915               920               925
Lys Arg Arg Gly Arg Asp Pro Glu Met Gly Gly Lys Pro Gln Arg Arg
            930               935               940
Lys Asn Pro Gln Glu Gly Leu Tyr Asn Glu Leu Gln Lys Asp Lys Met
945               950               955               960
Ala Glu Ala Tyr Ser Glu Ile Gly Met Lys Gly Glu Arg Arg Arg Gly
                965               970               975
Lys Gly His Asp Gly Leu Tyr Gln Gly Leu Ser Thr Ala Thr Lys Asp
                980               985               990
Thr Tyr Asp Ala Leu His Met Gln  Ala Leu Pro Pro Arg
            995               1000              1005

<210> SEQ ID NO 6
<211> LENGTH: 2966
<212> TYPE: DNA
<213> ORGANISM: Artificial Sequence
<220> FEATURE:
<223> OTHER INFORMATION: Synthetic Sequence

<400> SEQUENCE: 6
```

| | | | | | |
|---|---|---|---|---|---|
| atggccttac | cagtgaccgc | cttgctcctg | ccgctggcct | tgctgctcca | cgccgccagg | 60 |
| ccggacgtgg | tgatgaccca | gagccacagg | ttcatgagca | ccagcgtggg | cgacagggtg | 120 |
| agcatcacct | gcagggccag | ccaggacgtg | aacaccgccg | tgagctggta | ccagcagaag | 180 |
| cccggccaga | gccccaagct | gctgatcttc | agcgccagct | acaggtacac | cggcgtgccc | 240 |
| gacaggttca | ccggcagcgg | cagcggcgcc | gacttcaccc | tgaccatcag | cagcgtgcag | 300 |
| gccgaggacc | tggccgtgta | ctactgccag | cagcactaca | cgccccctg | accttcggc | 360 |
| ggcggcacca | agctggacat | caaggggaggg | ggggatccg | ggggaggagg | ctccggcgga | 420 |
| ggcggaagcc | agatccagct | ggtgcagagc | ggccccgacc | tgaagaagcc | cggcgagacc | 480 |
| gtgaagctga | gctgcaaggc | cagcggctac | accttcacca | acttcggcat | gaactgggtg | 540 |
| aagcaggccc | ccggcaaggg | cttcaagtgg | atggcctgga | tcaacaccta | caccggcgag | 600 |
| agctacttcg | ccgacgactt | caagggcagg | ttcgccttca | gcgtggagac | cagcgccacc | 660 |
| accgcctacc | tgcagatcaa | caacctgaag | accgaggaca | ccgccaccta | cttctgcgcc | 720 |
| aggggcgaga | tctactacgg | ctacgacggc | ggcttcgcct | actggggcca | gggcaccctg | 780 |
| gtgaccgtga | gcgccaccac | gacgccagcg | ccgcgaccac | caacaccggc | gcccaccatc | 840 |
| gcgtcgcagc | ccctgtccct | gcgcccagag | gcgtgccggc | cagcggcggg | gggcgcagtg | 900 |
| cacacgaggg | ggctggactt | cgcctgtgat | atctacatct | gggcgccctt | ggccgggact | 960 |
| tgtgggtcc | ttctcctgtc | actggttatc | acccttact | gcaggagtaa | gaggagcagg | 1020 |
| ctcctgcaca | gtgactacat | gaacatgact | ccccgccgcc | ccgggcccac | ccgcaagcat | 1080 |
| taccagccct | atgccccacc | acgcgacttc | gcagcctatc | gctccagagt | gaagttcagc | 1140 |
| aggagcgcag | acgcccccgc | gtaccagcag | ggccagaacc | agctctataa | cgagctcaat | 1200 |
| ctaggacgaa | gagaggagta | cgatgttttg | gacaagagac | gtggccggga | ccctgagatg | 1260 |
| gggggaaagc | cgcagagaag | gaagaaccct | caggaaggcc | tgtacaatga | actgcagaaa | 1320 |

-continued

```
gataagatgg cggaggccta cagtgagatt gggatgaaag gcgagcgccg gaggggcaag    1380
gggcacgatg gcctttacca gggtctcagt acagccacca aggacaccta cgacgccctt    1440
cacatgcagg ccctgccccc tcgcggaagc ggagccacca acttcagcct gctgaagcag    1500
gccggcgacg tggaggagaa ccccggcccc atggccctgc ccgtgaccgc cctgctgctg    1560
cccctggccc tgctgctgca cgccgccagg cccgacatcg tgatgaccca gagccccctg    1620
agcctgcccg tgaccccggc cgagcccgcc agctacctgc agaagcccgg ccagagcccc    1680
cagctgctga tctacctggg cagcaacagg gccagcggcg tgcccgacag gttcagcggc    1740
agcggcagcg gcaccgactt caccctgaag atcagcaggg tggaggccga ggacgtgggc    1800
gtgtactact gccagcagta cagcagcaag agcgccacct tcggccaggg caccaaggtg    1860
gagatcaaga ggaccggcgg cggcggcagc ggcggcggcg gcagcggcgg cggcggcagc    1920
caggtgcagc tggtgcagag cggcgccgag gtgaagaagc ccggcgccag cgtgaaggtg    1980
agctgcaagg ccagcggcta caccttcacc agctacagca tcaactgggt gaggcaggcc    2040
cccggccagg gcctggagtg gatgggctac atcgacccca cagggggcaa caccaactac    2100
gcccagaagt tccagggcag ggtgaccatg accaggdaca ccagcatcag caccgcctac    2160
atggagctga gcagcctgag gagcgaggac accgccgtgt actactgcgc cagggagtac    2220
atctacttca tccacggcat gctggacttc tggggccagg gcaccctggt gaccgtgagc    2280
agcaccacca ccccgcccc caggccccc acccccgccc ccaccatcgc cagccagccc    2340
ctgagcctga ggcccgaggc ctgcaggccc gccgccggcg gcgccgtgca caccaggggc    2400
ctggacttcg cctgcgacat ctacatctgg gcccccctgg ccggcacctg cggcgtgctg    2460
ctgctgagcc tggtgatcac cctgtactgc aaacggggca gaaagaaact cctgtatata    2520
ttcaaacaac catttatgag accagtacaa actactcaag aggaagatgg ctgtagctgc    2580
cgatttccag aagaagaaga aggaggatgt gaactgaggg tgaagttcag caggagcgcc    2640
gacgcccccg cctaccagca gggccagaac cagctgtaca cgagctgaa cctgggcagg    2700 agggaggagt acgacgtgct ggacaagagg gggcaggg accccgagat gggcggcaag    2760
ccccagagga ggaagaaccc ccaggagggc ctgtacaacg agctgcagaa ggacaagatg    2820
gccgaggcct acagcgagat cggcatgaag ggcgagagga gaggggcaa gggccacgac    2880 ggcctgtacc agggcctgag caccgccacc aaggacacct acgacgccct gcacatgcag    2940
gccctgcccc ccaggtaagt ttaaac                                        2966
```

<210> SEQ ID NO 7
<211> LENGTH: 1001
<212> TYPE: PRT
<213> ORGANISM: Artificial Sequence
<220> FEATURE:
<223> OTHER INFORMATION: Synthetic Sequence

<400> SEQUENCE: 7

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln
            35                  40                  45

Asp Val Asn Thr Ala Val Ser Trp Tyr Gln Gln Lys Pro Gly Gln Ser
        50                  55                  60
```

```
Pro Lys Leu Leu Ile Phe Ser Ala Ser Tyr Arg Tyr Thr Gly Val Pro
 65                  70                  75                  80

Asp Arg Phe Thr Gly Ser Gly Ser Gly Ala Asp Phe Thr Leu Thr Ile
                 85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
```

```
                    485                 490                 495
Leu Leu Lys Gln Ala Gly Asp Val Glu Glu Asn Pro Gly Pro Met Ala
            500                 505                 510
Leu Pro Val Thr Ala Leu Leu Pro Leu Ala Leu Leu Leu His Ala
        515                 520                 525
Ala Arg Pro Asp Ile Gln Met Thr Gln Ser Pro Ser Ser Leu Ser Ala
        530                 535                 540
Ser Val Gly Asp Arg Val Thr Ile Thr Cys Arg Ala Ser Gln Asp Ile
545                 550                 555                 560
Ser Ala Phe Leu Asn Trp Tyr Gln Gln Lys Pro Gly Lys Ala Pro Lys
                565                 570                 575
Leu Leu Ile Thr Lys Val Ser Asn Leu Gln Ser Gly Val Pro Ser Arg
            580                 585                 590
Phe Ser Gly Ser Gly Ser Gly Thr Asp Phe Thr Leu Thr Ile Ser Ser
        595                 600                 605
Leu Gln Pro Glu Asp Phe Ala Thr Tyr Tyr Cys Gln Gln Ala Tyr Ser
        610                 615                 620
Gly Ser Ile Thr Phe Gly Gln Gly Thr Lys Val Glu Ile Lys Arg Thr
625                 630                 635                 640
Gly Gly Gly Gly Ser Gly Gly Gly Gly Ser Gly Gly Gly Gly Ser Gln
                645                 650                 655
Val Gln Leu Val Glu Ser Gly Gly Leu Val Gln Pro Gly Gly Ser
            660                 665                 670
Leu Arg Leu Ser Cys Ala Ala Ser Gly Phe Thr Phe Ser Asn Tyr Gly
        675                 680                 685
Met His Trp Val Arg Gln Ala Pro Gly Lys Gly Leu Glu Trp Val Ser
        690                 695                 700
Asn Ile Arg Ser Asp Gly Ser Trp Thr Tyr Tyr Ala Asp Ser Val Lys
705                 710                 715                 720
Gly Arg Phe Thr Ile Ser Arg Asp Asn Ser Lys Asn Thr Leu Tyr Leu
                725                 730                 735
Gln Met Asn Ser Leu Arg Ala Glu Asp Thr Ala Val Tyr Tyr Cys Ala
            740                 745                 750
Arg Arg Tyr Trp Ser Lys Ser His Ala Ser Val Thr Asp Tyr Trp Gly
        755                 760                 765
Gln Gly Thr Leu Val Thr Val Ser Ser Thr Thr Thr Pro Ala Pro Arg
        770                 775                 780
Pro Pro Thr Pro Ala Pro Thr Ile Ala Ser Gln Pro Leu Ser Leu Arg
785                 790                 795                 800
Pro Glu Ala Cys Arg Pro Ala Ala Gly Gly Ala Val His Thr Arg Gly
                805                 810                 815
Leu Asp Phe Ala Cys Asp Ile Tyr Ile Trp Ala Pro Leu Ala Gly Thr
            820                 825                 830
Cys Gly Val Leu Leu Leu Ser Leu Val Ile Thr Leu Tyr Cys Lys Arg
        835                 840                 845
Gly Arg Lys Lys Leu Leu Tyr Ile Phe Lys Gln Pro Phe Met Arg Pro
        850                 855                 860
Val Gln Thr Thr Gln Glu Glu Asp Gly Cys Ser Cys Arg Phe Pro Glu
865                 870                 875                 880
Glu Glu Glu Gly Gly Cys Glu Leu Arg Val Lys Phe Ser Arg Ser Ala
                885                 890                 895
Asp Ala Pro Ala Tyr Gln Gln Gly Gln Asn Gln Leu Tyr Asn Glu Leu
            900                 905                 910
```

```
Asn Leu Gly Arg Arg Glu Glu Tyr Asp Val Leu Asp Lys Arg Arg Gly
            915                 920                 925

Arg Asp Pro Glu Met Gly Gly Lys Pro Gln Arg Arg Lys Asn Pro Gln
        930                 935                 940

Glu Gly Leu Tyr Asn Glu Leu Gln Lys Asp Lys Met Ala Glu Ala Tyr
945                 950                 955                 960

Ser Glu Ile Gly Met Lys Gly Glu Arg Arg Gly Lys Gly His Asp
                965                 970                 975

Gly Leu Tyr Gln Gly Leu Ser Thr Ala Thr Lys Asp Thr Tyr Asp Ala
            980                 985                 990

Leu His Met Gln Ala Leu Pro Pro  Arg
            995                 1000

<210> SEQ ID NO 8
<211> LENGTH: 3014
<212> TYPE: DNA
<213> ORGANISM: Artificial Sequence
<220> FEATURE:
<223> OTHER INFORMATION: Synthetic Sequences

<400> SEQUENCE: 8
atggccttac cagtgaccgc cttgctcctg ccgctggcct tgctgctcca cgccgccagg     60
ccggacgtgg tgatgaccca gagccacagg ttcatgagca ccagcgtggg cgacagggtg    120
agcatcacct gcagggccag ccaggacgtg aacaccgccg tgagctggta ccagcagaag    180
cccggccaga gccccaagct gctgatcttc agcgccagct acaggtacac cggcgtgccc    240
gacaggttca ccggcagcgg cagcggcgcc gacttcaccc tgaccatcag cagcgtgcag    300
gccgaggacc tggccgtgta ctactgccag cagcactaca gcaccccctg gaccttcggc    360
ggcggcacca agctggacat caaggagggg ggggatccg gggaggagg ctccggcgga    420 ggcggaagcc agatccagct ggtgcagagc ggccccgacc tgaagaagcc cggcgagacc    480
gtgaagctga gctgcaaggc cagcggctac accttcacca acttcggcat gaactgggtg    540
aagcaggccc ccggcaaggg cttcaagtgg atggcctgga tcaacaccta caccggcgag    600
agctacttcg ccgacgactt caagggcagg ttcgccttca gcgtggagac cagcgccacc    660
accgcctacc tgcagatcaa caacctgaag accgaggaca ccgccaccta cttctgcgcc    720
aggggcgaga tctactacgg ctacgacggc ggcttcgcct actggggcca gggcaccctg    780
gtgaccgtga gcgccaccac gacgccagcg ccgcgaccac caacaccggc gcccaccatc    840
gcgtcgcagc ccctgtccct gcgcccagag gcgtgccggc cagcggcggg gggcgcagtg    900
cacacgaggg ggctggactt cgcctgtgat atctacatct gggcgccctt ggccgggact    960 tgtgggggtcc ttctcctgtc actggttatc accctttact gcaggagtaa gaggagcagg   1020
ctcctgcaca gtgactacat gaacatgact ccccgccgcc ccgggcccac cgcaagcat    1080 taccagccct atgccccacc acgcgacttc gcagcctatc gctccagagt gaagttcagc    1140
aggagcgcag acgcccccgc gtaccagcag gccagaaacc agctctataa cgagctcaat    1200
ctaggacgaa gagaggagta cgatgttttg gacaagagac gtggccggga ccctgagatg    1260 ggggggaaagc cgcagagaag gaagaaccct caggaaggcc tgtacaatga actgcagaaa    1320
gataagatgg cggaggccta cagtgagatt gggatgaaag gcgagcgccg gaggggcaag    1380
gggcacgatg gcctttacca gggtctcagt acagccacca aggacaccta cgacgccctt    1440
cacatgcagg ccctgccccc tcgcggaagc ggagccacca acttcagcct gctgaagcag    1500
```

| | |
|---|---|
| gccggcgacg tggaggagaa ccccggcccc atggccctgc ccgtgaccgc cctgctgctg | 1560 |
| cccctggccc tgctgctgca cgccgccagg cccgacatcc agatgaccca gagccccagc | 1620 |
| agcctgagcg ccagcgtggg cgacagggtg accatcacct gcagggccag ccaggacatc | 1680 |
| agcgccttcc tgaactggta ccagcagaag cccggcaagg cccccaagct gctgatcacc | 1740 |
| aaggtgagca acctgcagag cggcgtgccc agcaggttca gcggcagcgg cagcggcacc | 1800 |
| gacttcaccc tgaccatcag cagcctgcag cccgaggact cgccaccta ctactgccag | 1860 |
| caggcctaca gcggcagcat caccttcggc cagggcacca aggtggagat caagaggacc | 1920 |
| ggcggcggcg gcagcggcgg cggcggcagc ggcggcggcg gcagccaggt gcagctggtg | 1980 |
| gagagcggcg gcggcctggt gcagcccggc ggcagcctga gctgagctg cgccgccagc | 2040 |
| ggcttcacct tcagcaacta cggcatgcac tgggtgaggc aggccccggg caagggcctg | 2100 |
| gagtgggtga gcaacatcag gagcgacggc agctggacct actacgccga cagcgtgaag | 2160 |
| ggcaggttca ccatcagcag ggacaacagc aagaacaccc tgtacctgca gatgaacagc | 2220 |
| ctgagggccg aggacaccgc cgtgtactac tgcgccagga ggtactggag caagagccac | 2280 |
| gccagcgtga ccgactactg gggccagggc accctggtga ccgtgagcag caccaccacc | 2340 |
| cccgccccca ggcccccac cccgccccc accatcgcca gcagcccct gagcctgagg | 2400 |
| cccgaggcct gcaggcccgc cgccggcggc gccgtgcaca ccaggggcct ggacttcgcc | 2460 |
| tgcgacatct acatctgggc cccctggccc ggcacctgcg cgtgctgct gctgagcctg | 2520 |
| gtgatcaccc tgtactgcaa cgggcaga aagaaactcc tgtatatat caaacaacca | 2580 |
| tttatgagac cagtacaaac tactcaagag gaagatggct gtagctgccg atttccagaa | 2640 |
| gaagaagaag gaggatgtga actgagggtg aagttcagca ggagcgccga cgccccgcc | 2700 |
| taccagcagg gccagaacca gctgtacaac gagctgaacc tgggcaggag ggaggagtac | 2760 |
| gacgtgctgg acaagaggag gggcagggac cccgagatgg gcggcaagcc cagaggagg | 2820 |
| aagaaccccc aggagggcct gtacaacgag ctgcagaagg acaagatggc cgaggcctac | 2880 |
| agcgagatcg gcatgaaggg cgagaggagg aggggcaagg ccacgacgg cctgtaccag | 2940 |
| ggcctgagca ccgccaccaa ggacacctac gacgccctgc acatgcaggc cctgccccc | 3000 |
| aggtaagttt aaac | 3014 |

<210> SEQ ID NO 9
<211> LENGTH: 1004
<212> TYPE: PRT
<213> ORGANISM: Artificial Sequence
<220> FEATURE:
<223> OTHER INFORMATION: Synthetic Sequence

<400> SEQUENCE: 9

Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

```
Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Gly Ser Gln
130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
            500                 505                 510
```

-continued

Leu Pro Val Thr Ala Leu Leu Leu Pro Leu Ala Leu Leu His Ala
    515                 520                 525

Ala Arg Pro Ala Gln Pro Ala Met Ala Lys Val Gln Leu Gln Glu Ser
530                 535                 540

Gly Pro Ser Leu Val Gln Pro Ser Gln Arg Leu Ser Ile Thr Cys Thr
545                 550                 555                 560

Val Ser Gly Phe Ser Leu Ile Ser Tyr Gly Val His Trp Val Arg Gln
                565                 570                 575

Ser Pro Gly Lys Gly Leu Glu Trp Leu Gly Val Ile Trp Arg Gly Gly
            580                 585                 590

Ser Thr Asp Tyr Asn Ala Ala Phe Met Ser Arg Leu Ser Ile Thr Lys
        595                 600                 605

Asp Asn Ser Lys Ser Gln Val Phe Phe Lys Met Asn Ser Leu Gln Ala
    610                 615                 620

Asp Asp Thr Ala Ile Tyr Phe Cys Ala Lys Thr Leu Ile Thr Thr Gly
625                 630                 635                 640

Tyr Ala Met Asp Tyr Trp Gly Gln Gly Thr Thr Val Thr Val Ser Ser
                645                 650                 655

Gly Gly Gly Gly Ser Gly Gly Gly Ser Gly Gly Gly Gly Ser Asp
            660                 665                 670

Ile Glu Leu Thr Gln Ser Pro Ser Ser Phe Ser Val Ser Leu Gly Asp
        675                 680                 685

Arg Val Thr Ile Thr Cys Lys Ala Ser Glu Asp Ile Tyr Asn Arg Leu
    690                 695                 700

Ala Trp Tyr Gln Gln Lys Pro Gly Asn Ala Pro Arg Leu Leu Ile Ser
705                 710                 715                 720

Gly Ala Thr Ser Leu Glu Thr Gly Val Pro Ser Arg Phe Ser Gly Ser
                725                 730                 735

Gly Ser Gly Lys Asp Tyr Thr Leu Ser Ile Thr Ser Leu Gln Thr Glu
            740                 745                 750

Asp Val Ala Thr Tyr Tyr Cys Gln Gln Tyr Trp Ser Thr Pro Thr Phe
        755                 760                 765

Gly Gly Gly Thr Lys Leu Glu Ile Lys Arg Ala Ala Thr Thr Thr Pro
    770                 775                 780

Ala Pro Arg Pro Pro Thr Pro Ala Pro Thr Ile Ala Ser Gln Pro Leu
785                 790                 795                 800

Ser Leu Arg Pro Glu Ala Cys Arg Pro Ala Ala Gly Gly Ala Val His
                805                 810                 815

Thr Arg Gly Leu Asp Phe Ala Cys Asp Ile Tyr Ile Trp Ala Pro Leu
            820                 825                 830

Ala Gly Thr Cys Gly Val Leu Leu Leu Ser Leu Val Ile Thr Leu Tyr
        835                 840                 845

Cys Lys Arg Gly Arg Lys Lys Leu Leu Tyr Ile Phe Lys Gln Pro Phe
    850                 855                 860

Met Arg Pro Val Gln Thr Thr Gln Glu Glu Asp Gly Cys Ser Cys Arg
865                 870                 875                 880

Phe Pro Glu Glu Glu Glu Gly Gly Cys Glu Leu Arg Val Lys Phe Ser
                885                 890                 895

Arg Ser Ala Asp Ala Pro Ala Tyr Gln Gln Gly Gln Asn Gln Leu Tyr
            900                 905                 910

Asn Glu Leu Asn Leu Gly Arg Arg Glu Glu Tyr Asp Val Leu Asp Lys
        915                 920                 925

Arg Arg Gly Arg Asp Pro Glu Met Gly Gly Lys Pro Gln Arg Arg Lys

```
                    930               935               940
Asn Pro Gln Glu Gly Leu Tyr Asn Glu Leu Gln Lys Asp Lys Met Ala
945                 950               955               960

Glu Ala Tyr Ser Glu Ile Gly Met Lys Gly Glu Arg Arg Arg Gly Lys
                965               970               975

Gly His Asp Gly Leu Tyr Gln Gly Leu Ser Thr Ala Thr Lys Asp Thr
                980               985               990

Tyr Asp Ala Leu His Met Gln Ala  Leu Pro Pro Arg
            995               1000

<210> SEQ ID NO 10
<211> LENGTH: 3023
<212> TYPE: DNA
<213> ORGANISM: Artificial Sequence
<220> FEATURE:
<223> OTHER INFORMATION: Synthetic Sequence

<400> SEQUENCE: 10
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcacccctg gaccttcggc     360 ggcggcacca gctggacat caagggaggg ggggatccg ggggaggagg ctccggcgga      420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
accgcctacc tgcagatcaa caacctgaag accgaggaca ccgccaccta cttctgcgcc     720
aggggcgaga tctactacgg ctacgacggc ggcttcgcct actggggcca gggcacccctg    780 gtgaccgtga gcgccaccac gacgccagcg ccgcgaccac caacaccggc gcccaccatc     840
gcgtcgcagc cctgtccct gcgcccagag gcgtgccggc cagcggcggg gggcgcagtg     900
cacacgaggg ggctggactt cgcctgtgat atctacatct gggcgccctt ggccgggact     960 tgtgggtcc ttctcctgtc actggttatc acccttact gcaggagtaa gaggagcagg      1020
ctcctgcaca gtgactacat gaacatgact ccccgccgcc ccgggcccac ccgcaagcat     1080
taccagccct atgccccacc acgcgacttc gcagcctatc gctccagagt gaagttcagc     1140
aggagcgcag acgcccccgc gtaccagcag gccagaacc agctctataa cgagctcaat     1200
ctaggacgaa gagaggagta cgatgttttg gacaagagac gtggccggga ccctgagatg     1260
gggggaaagc cgcagagaag gaagaaccct caggaaggcc tgtacaatga actgcagaaa     1320
gataagatgg cggaggccta cagtgagatt gggatgaaag gcgagcgccg gaggggcaag     1380
gggcacgatg gcctttacca gggtctcagt acagccacca aggacaccta cgacgccctt     1440
cacatgcagg ccctgccccc tcgcggaagc ggagccacca acttcagcct gctgaagcag     1500
gccggcgacg tggaggagaa ccccggcccc atggccctgc cgtgaccgc cctgctgctg     1560 cccctggccc tgctgctgca cgccgccagg cccgcccagc ccgccatggc caaggtgcag     1620
ctgcaggaga gcggccccag cctggtgcag cccagccaga ggctgagcat cacctgcacc     1680
```

```
gtgagcggct tcagcctgat cagctacggc gtgcactggg tgaggcagag ccccggcaag    1740
ggcctggagt ggctgggcgt gatctggagg ggcggcagca ccgactacaa cgccgccttc    1800
atgagcaggc tgagcatcac caaggacaac agcaagagcc aggtgttctt caagatgaac    1860
agcctgcagc ccgacgacac cgccatctac ttctgcgcca agaccctgat caccaccggc    1920
tacgccatgg actactgggg ccagggcacc accgtgaccg tgagcagcgg cggcggcggc    1980
agcggcggcg gcggcagcgg cggcggcggc agcgacatcg agctgaccca gagccccagc    2040
agcttcagcg tgagcctggg cgacagggtg accatcacct gcaaggccag cgaggacatc    2100
tacaacaggc tggcctggta ccagcagaag cccggcaacg cccccaggct gctgatcagc    2160
ggcgccacca gcctggagac cggcgtgccc agcaggttca gcggcagcgg cagcggcaag    2220
gactacaccc tgagcatcac cagcctgcag accgaggacg tggccaccta ctactgccag    2280
cagtactgga gcaccccca cttcggcggc ggcaccaagc tggagatcaa gagggccgcc    2340
accaccaccc ccgcccccag gcccccaccc ccgcccccca ccatcgccag ccagcccctg    2400
agcctgaggc ccgaggcctg caggcccgcc gccggcggcg ccgtgcacac caggggcctg    2460
gacttcgcct gcgacatcta catctgggcc cccctggccg gcacctgcgg cgtgctgctg    2520
ctgagcctgg tgatcaccct gtactgcaaa cggggcagaa agaaactcct gtatatattc    2580
aaacaaccat ttatgagacc agtacaaact actcaagagg aagatggctg tagctgccga    2640
tttccagaag aagaagaagg aggatgtgaa ctgagggtga agttcagcag gagcgccgac    2700
gcccccgcct accagcaggg ccagaaccag ctgtacaacg agctgaacct gggcaggagg    2760
gaggagtacg acgtgctgga caagaggagg ggcagggacc ccgagatggg cggcaagccc    2820
cagaggagga gaacccccca ggagggcctg tacaacgagc tgcagaagga caagatggcc    2880
gaggcctaca gcgagatcgg catgaagggc gagaggagga ggggcaaggg ccacgacggc    2940
ctgtaccagg gcctgagcac cgccaccaag gacacctacg acgccctgca catgcaggcc    3000 ctgccccca ggtaagttta aac                                              3023
```

<210> SEQ ID NO 11
<211> LENGTH: 687
<212> TYPE: PRT
<213> ORGANISM: Artificial Sequence
<220> FEATURE:
<223> OTHER INFORMATION: Synthetic Sequence

<400> SEQUENCE: 11

```
Met Ala Leu Pro Val Thr Ala Leu Leu Leu Pro Leu Ala Leu Leu Leu
1               5                  10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
```

```
            115                 120                 125
Gly Gly Gly Gly Ser Gly Gly Gly Ser Gly Gly Gly Ser Gln
            130                 135                 140
Ile Gln Leu Val Gln Ser Gly Pro Asp Leu Lys Lys Pro Gly Glu Thr
145                 150                 155                 160
Val Lys Leu Ser Cys Lys Ala Ser Gly Tyr Thr Phe Thr Asn Phe Gly
                165                 170                 175
Met Asn Trp Val Lys Gln Ala Pro Gly Lys Gly Phe Lys Trp Met Ala
            180                 185                 190
Trp Ile Asn Thr Tyr Thr Gly Glu Ser Tyr Phe Ala Asp Asp Phe Lys
            195                 200                 205
Gly Arg Phe Ala Phe Ser Val Glu Thr Ser Ala Thr Thr Ala Tyr Leu
            210                 215                 220
Gln Ile Asn Asn Leu Lys Thr Glu Asp Thr Ala Thr Tyr Phe Cys Ala
225                 230                 235                 240
Arg Gly Glu Ile Tyr Tyr Gly Tyr Asp Gly Gly Phe Ala Tyr Trp Gly
                245                 250                 255
Gln Gly Thr Leu Val Thr Val Ser Ala Thr Thr Thr Pro Ala Pro Arg
            260                 265                 270
Pro Pro Thr Pro Ala Pro Thr Ile Ala Ser Gln Pro Leu Ser Leu Arg
            275                 280                 285
Pro Glu Ala Cys Arg Pro Ala Ala Gly Gly Ala Val His Thr Arg Gly
            290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Arg Ser
                325                 330                 335
Lys Arg Ser Arg Leu Leu His Ser Asp Tyr Met Asn Met Thr Pro Arg
            340                 345                 350
Arg Pro Gly Pro Thr Arg Lys His Tyr Gln Pro Tyr Ala Pro Pro Arg
            355                 360                 365
Asp Phe Ala Ala Tyr Arg Ser Arg Val Lys Phe Ser Arg Ser Ala Asp
            370                 375                 380
Ala Pro Ala Tyr Gln Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Gln Arg Arg Lys Asn Pro Gln Glu
            420                 425                 430
Gly Leu Tyr Asn Glu Leu Gln Lys Asp Lys Met Ala Glu Ala Tyr Ser
            435                 440                 445
Glu Ile Gly Met Lys Gly Glu Arg Arg Arg Gly Lys Gly His Asp Gly
            450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg Gly Ser Gly Ala Thr Asn Phe Ser
                485                 490                 495
Leu Leu Lys Gln Ala Gly Asp Val Glu Glu Asn Pro Gly Pro Met Tyr
            500                 505                 510
Arg Met Gln Leu Leu Ser Cys Ile Ala Leu Ser Leu Ala Leu Val Thr
            515                 520                 525
Asn Ser Tyr Phe Gly Lys Leu Glu Ser Lys Leu Ser Val Ile Arg Asn
            530                 535                 540
```

Leu Asn Asp Gln Val Leu Phe Ile Asp Gln Gly Asn Arg Pro Leu Phe
545                 550                 555                 560

Glu Asp Met Thr Asp Ser Asp Cys Arg Asp Asn Ala Pro Arg Thr Ile
                565                 570                 575

Phe Ile Ile Ser Met Tyr Lys Asp Ser Gln Pro Arg Gly Met Ala Val
            580                 585                 590

Thr Ile Ser Val Lys Cys Glu Lys Ile Ser Thr Leu Ser Cys Glu Asn
        595                 600                 605

Lys Ile Ile Ser Phe Lys Glu Met Asn Pro Pro Asp Asn Ile Lys Asp
    610                 615                 620

Thr Lys Ser Asp Ile Ile Phe Phe Gln Arg Ser Val Pro Gly His Asp
625                 630                 635                 640

Asn Lys Met Gln Phe Glu Ser Ser Ser Tyr Glu Gly Tyr Phe Leu Ala
                645                 650                 655

Cys Glu Lys Glu Arg Asp Leu Phe Lys Leu Ile Leu Lys Lys Glu Asp
                660                 665                 670

Glu Leu Gly Asp Arg Ser Ile Met Phe Thr Val Gln Asn Glu Asp
            675                 680                 685

<210> SEQ ID NO 12
<211> LENGTH: 2061
<212> TYPE: DNA
<213> ORGANISM: Artificial Sequence
<220> FEATURE:
<223> OTHER INFORMATION: Synthetic Sequence

<400> SEQUENCE: 12
atggccttac cagtgaccgc cttgctcctg ccgctggcct tgctgctcca cgccgccagg     60
ccggacgtgg tgatgaccca gagccacagg ttcatgagca ccagcgtggg cgacagggtg    120
agcatcacct gcagggccag ccaggacgtg aacaccgccg tgagctggta ccagcagaag    180
cccggccaga gccccaagct gctgatcttc agcgccagct acaggtacac cggcgtgccc    240
gacaggttca ccggcagcgg cagcggcgcc gacttcaccc tgaccatcag cagcgtgcag    300
gccgaggacc tggccgtgta ctactgccag cagcactaca gcaccccctg gaccttcggc    360
ggcggcacca agctggacat caagggaggg gggggatccg gggaggagg ctccggcgga    420 ggcggaagcc agatccagct ggtgcagagc ggccccgacc tgaagaagcc cggcgagacc    480
gtgaagctga gctgcaaggc cagcggctac accttcacca acttcggcat gaactgggtg    540
aagcaggccc ccggcaaggg cttcaagtgg atggcctgga tcaacaccta caccggcgag    600
agctacttcg ccgacgactt caagggcagg ttcgccttca gcgtggagac cagcgccacc    660
accgcctacc tgcagatcaa caacctgaag accgaggaca ccgccaccta cttctgcgcc    720
aggggcgaga tctactacgg ctacgacggc ggcttcgcct actggggcca gggcaccctg    780
gtgaccgtga gcgccaccac gacgccagcg ccgcgaccac caacaccggc gcccaccatc    840
gcgtcgcagc ccctgtccct gcgcccagag gcgtgccggc cagcggcggg gggcgcagtg    900
cacacgaggg ggctggactt cgcctgtgat atctacatct gggcgccctt ggccgggact    960 tgtgggggtcc ttctcctgtc actggttatc acccttact gcaggagtaa gaggagcagg   1020
ctcctgcaca gtgactacat gaacatgact ccccgccgcc ccgggccac ccgcaagcat   1080 taccagccct atgccccacc acgcgacttc gcagcctatc gctccagagt gaagttcagc   1140
aggagcgcag acgccccgc gtaccagcag ggccagaacc agctctataa cgagctcaat   1200
ctaggacgaa gagaggagta cgatgttttg gacaagagac gtggccggga ccctgagatg   1260

```
ggggggaaagc cgcagagaag gaagaaccct caggaaggcc tgtacaatga actgcagaaa  1320
gataagatgg cggaggccta cagtgagatt gggatgaaag gcgagcgccg gaggggcaag  1380
gggcacgatg gcctttacca gggtctcagt acagccacca aggacaccta cgacgccctt  1440
cacatgcagg ccctgccccc tcgcggaagc ggagccacca acttcagcct gctgaagcag  1500
gccggcgacg tggaggagaa ccccggcccc atgtacagaa tgcagctgct gagctgcatc  1560
gccctgagcc tggccctggt gaccaacagc tacttcggca agctggagag caagctgagc  1620
gtgatcagga acctgaacga ccaggtgctg ttcatcgacc agggcaacag gcccctgttc  1680
gaggacatga ccgacagcga ctgcagggac aaccccccca ggaccatctt catcatcagc  1740
atgtacaagg acagccagcc caggggcatg gccgtgacca tcagcgtgaa gtgcgagaag  1800
atcagcaccc tgagctgcga gaacaagatc atcagcttca aggagatgaa ccccccccgac  1860 aacatcaagg acaccaagag cgacatcatc ttcttccaga ggagcgtgcc cggccacgac  1920
aacaagatgc agttcgagag cagcagctac gagggctact ccctggcctg cgagaaggag  1980
agggacctgt tcaagctgat cctgaagaag gaggacgagc tgggcgacag gagcatcatg  2040
ttcaccgtgc agaacgagga c  2061
```

<210> SEQ ID NO 13
<211> LENGTH: 754
<212> TYPE: PRT
<213> ORGANISM: Artificial Sequence
<220> FEATURE:
<223> OTHER INFORMATION: Synthetic Sequence

<400> SEQUENCE: 13

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln
            35                  40                  45

Asp Val Asn Thr Ala Val Ser Trp Tyr Gln Gln Lys Pro Gly Gln Ser
        50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
                100                 105                 110

Tyr Ser Thr Pro Trp Thr Phe Gly Gly Gly Thr Lys Leu Asp Ile Lys
            115                 120                 125

Gly Gly Gly Gly Ser Gly Gly Gly Ser Gly Gly Gly Ser Gln
        130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
                180                 185                 190

Trp Ile Asn Thr Tyr Thr Gly Glu Ser Tyr Phe Ala Asp Asp Phe Lys
            195                 200                 205

Gly Arg Phe Ala Phe Ser Val Glu Thr Ser Ala Thr Thr Ala Tyr Leu
```

```
              210                 215                 220
Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                    245                 250                 255

Gln Gly Thr Leu Val Thr Val Ser Ala Thr Thr Thr Pro Ala Pro Arg
                260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                    325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
            355                 360                 365

Asp Phe Ala Ala Tyr Arg Ser Arg Val Lys Phe Ser Arg Ser Ala Asp
        370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                    405                 410                 415

Asp Pro Glu Met Gly Gly Lys Pro Gln Arg Arg Lys Asn Pro Gln Glu
                420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                    485                 490                 495

Leu Leu Lys Gln Ala Gly Asp Val Glu Glu Asn Pro Gly Pro Met Tyr
                500                 505                 510

Arg Met Gln Leu Leu Ser Cys Ile Ala Leu Ser Leu Ala Leu Val Thr
            515                 520                 525

Asn Ser Tyr Phe Gly Lys Leu Glu Ser Lys Leu Ser Val Ile Arg Asn
        530                 535                 540

Leu Asn Asp Gln Val Leu Phe Ile Asp Gln Gly Asn Arg Pro Leu Phe
545                 550                 555                 560

Glu Asp Met Thr Asp Ser Asp Cys Arg Asp Asn Ala Pro Arg Thr Ile
                    565                 570                 575

Phe Ile Ile Ser Met Tyr Lys Asp Ser Gln Pro Arg Gly Met Ala Val
                580                 585                 590

Thr Ile Ser Val Lys Cys Glu Lys Ile Ser Thr Leu Ser Cys Glu Asn
            595                 600                 605

Lys Ile Ile Ser Phe Lys Glu Met Asn Pro Pro Asp Asn Ile Lys Asp
        610                 615                 620

Thr Lys Ser Asp Ile Ile Phe Phe Gln Arg Ser Val Pro Gly His Asp
625                 630                 635                 640
```

```
Asn Lys Met Gln Phe Glu Ser Ser Tyr Glu Gly Tyr Phe Leu Ala
                645                 650                 655

Cys Glu Lys Glu Arg Asp Leu Phe Lys Leu Ile Leu Lys Lys Glu Asp
            660                 665                 670

Glu Leu Gly Asp Arg Ser Ile Met Phe Thr Val Gln Asn Glu Asp Thr
        675                 680                 685

Thr Thr Pro Ala Pro Arg Pro Pro Thr Pro Ala Pro Thr Ile Ala Ser
    690                 695                 700

Gln Pro Leu Ser Leu Arg Pro Glu Ala Cys Arg Pro Ala Ala Gly Gly
705                 710                 715                 720

Ala Val His Thr Arg Gly Leu Asp Phe Ala Cys Asp Val Ala Ile Ser
                725                 730                 735

Thr Ser Thr Val Leu Leu Cys Gly Leu Ser Ala Val Ser Leu Leu Ala
            740                 745                 750

Cys Tyr

<210> SEQ ID NO 14
<211> LENGTH: 2273
<212> TYPE: DNA
<213> ORGANISM: Artificial Sequence
<220> FEATURE:
<223> OTHER INFORMATION: Synthetic Sequence

<400> SEQUENCE: 14
atggccttac cagtgaccgc cttgctcctg ccgctggcct tgctgctcca cgccgccagg     60
ccggacgtgg tgatgaccca gagccacagg ttcatgagca ccagcgtggg cgacagggtg    120
agcatcacct gcagggccag ccaggacgtg aacaccgccg tgagctggta ccagcagaag    180
cccggccaga gccccaagct gctgatcttc agcgccagct acaggtacac cggcgtgccc    240
gacaggttca ccggcagcgg cagcggcgcc gacttcaccc tgaccatcag cagcgtgcag    300
gccgaggacc tggccgtgta ctactgccag cagcactaca gcaccccctg gaccttcggc    360
ggcggcacca agctggacat caagggaggg ggggatccg ggggaggagg ctccggcgga    420
ggcggaagcc agatccagct ggtgcagagc ggccccgacc tgaagaagcc cggcgagacc    480
gtgaagctga gctgcaaggc cagcggctac accttcacca acttcggcat gaactgggtg    540
aagcaggccc ccggcaaggg cttcaagtgg atggcctgga tcaacaccta caccggcgag    600
agctacttcg ccgacgactt caagggcagg ttcgccttca gcgtggagac cagcgccacc    660
accgcctacc tgcagatcaa caacctgaag accgaggaca ccgccaccta cttctgcgcc    720
aggggcgaga tctactacgg ctacgacggc ggcttcgcct actggggcca gggcaccctg    780
gtgaccgtga gcgccaccac gacgccagcg ccgcgaccac caacaccggc gcccaccatc    840
gcgtcgcagc ccctgtccct gcgcccagag gcgtgccggc agcggcgggg ggcgcagtg    900 cacacgaggg ggctggactt cgcctgtgat atctacatct gggcgccctt ggccgggact    960 tgtgggtcc ttctcctgtc actggttatc acccttact gcaggagtaa gaggagcagg   1020
ctcctgcaca gtgactacat gaacatgact ccccgccgcc cgggcccac ccgcaagcat   1080 taccagccct atgccccacc acgcgacttc gcagcctatc gctccagagt gaagttcagc   1140
aggagcgcag acgccccgc gtaccagcag gccagaacc agctctataa cgagctcaat   1200
ctaggacgaa gagaggagta cgatgttttg gacaagagac gtggccggga ccctgagatg   1260 ggggaaagc cgcagagaag gaagaaccct caggaaggcc tgtacaatga actgcagaaa   1320
gataagatgg cggaggccta cagtgagatt gggatgaaag gcgagcgccg gaggggcaag   1380
```

```
gggcacgatg gcctttacca gggtctcagt acagccacca aggacaccta cgacgccctt    1440
cacatgcagg ccctgccccc tcgcggaagc ggagccacca acttcagcct gctgaagcag    1500
gccggcgacg tggaggagaa ccccggcccc atgtacagaa tgcagctgct gagctgcatc    1560
gccctgagcc tggccctggt gaccaacagc tacttcggca agctggagag caagctgagc    1620
gtgatcagga acctgaacga ccaggtgctg ttcatcgacc agggcaacag gcccctgttc    1680
gaggacatga ccgacagcga ctgcagggac aacgccccca ggaccatctt catcatcagc    1740
atgtacaagg acagccagcc caggggcatg gccgtgacca tcagcgtgaa gtgcgagaag    1800
atcagcaccc tgagctgcga gaacaagatc atcagcttca aggagatgaa ccccccccgac  1860 aacatcaagg acaccaagag cgacatcatc ttcttccaga ggagcgtgcc cggccacgac    1920
aacaagatgc agttcgagag cagcagctac gagggctact tcctggcctg cgagaaggag    1980
agggacctgt tcaagctgat cctgaagaag gaggacgagc tgggcgacag gagcatcatg    2040
ttcaccgtgc agaacgagga caccaccacc ccgccccca ggccccccac cccgcccccc     2100
accatcgcca gccagcccct gagcctgagg cccgaggcct gcaggcccgc cgccggcggc    2160
gccgtgcaca ccaggggcct ggacttcgcc tgcgacgtgg ctatctccac gtccactgtc    2220
ctgctgtgtg ggctgagcgc tgtgtctctc ctggcatgct actaagttta aac           2273
```

<210> SEQ ID NO 15
<211> LENGTH: 258
<212> TYPE: PRT
<213> ORGANISM: Artificial Sequence
<220> FEATURE:
<223> OTHER INFORMATION: Synthetic Sequence

<400> SEQUENCE: 15

```
Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205
```

```
Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 16
<211> LENGTH: 667
<212> TYPE: PRT
<213> ORGANISM: Artificial Sequence
<220> FEATURE:
<223> OTHER INFORMATION: Synthetic Sequence

<400> SEQUENCE: 16

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Ile Lys Pro Gly Ala Ser Val Lys Met Ser Cys Lys Ala Ser Gly Tyr
            35                  40                  45

Thr Phe Thr Ser Tyr Val Met His Trp Val Lys Gln Lys Pro Gly Gln
        50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255

Pro Phe Thr Phe Gly Ala Gly Thr Lys Leu Glu Leu Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300
```

```
Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
            325                 330                 335

Leu Tyr Cys Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Gln Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Ser Gly
                485                 490                 495

Glu Gly Arg Gly Ser Leu Leu Thr Cys Gly Asp Val Glu Glu Asn Pro
            500                 505                 510

Gly Pro Met Tyr Arg Met Gln Leu Leu Ser Cys Ile Ala Leu Ser Leu
        515                 520                 525

Ala Leu Val Thr Asn Ser Gln Gly Gln Asp Arg His Met Ile Arg Met
530                 535                 540

Arg Gln Leu Ile Asp Ile Val Asp Gln Leu Lys Asn Tyr Val Asn Asp
545                 550                 555                 560

Leu Val Pro Glu Phe Leu Pro Ala Pro Glu Asp Val Glu Thr Asn Cys
                565                 570                 575

Glu Trp Ser Ala Phe Ser Cys Phe Gln Lys Ala Gln Leu Lys Ser Ala
            580                 585                 590

Asn Thr Gly Asn Asn Glu Arg Ile Ile Asn Val Ser Ile Lys Lys Leu
        595                 600                 605

Lys Arg Lys Pro Pro Ser Thr Asn Ala Gly Arg Arg Gln Lys His Arg
610                 615                 620

Leu Thr Cys Pro Ser Cys Asp Ser Tyr Glu Lys Lys Pro Pro Lys Glu
625                 630                 635                 640

Phe Leu Glu Arg Phe Lys Ser Leu Leu Gln Lys Met Ile His Gln His
                645                 650                 655

Leu Ser Ser Arg Thr His Gly Ser Glu Asp Ser
            660                 665

<210> SEQ ID NO 17
<211> LENGTH: 2012
<212> TYPE: DNA
<213> ORGANISM: Artificial Sequence
<220> FEATURE:
<223> OTHER INFORMATION: Synthetic Sequence

<400> SEQUENCE: 17
```

| | |
|---|---|
| atggccttac cagtgaccgc cttgctcctg ccgctggcct tgctgctcca cgccgccagg | 60 |
| ccggaggtcc agctgcagca gtctggacct gagctgataa agcctggggc ttcagtgaag | 120 |
| atgtcctgca aggcttctgg atacacattc actagctatg ttatgcactg ggtgaagcag | 180 |
| aagcctgggc agggccttga gtggattgga tatattaatc cttacaatga tggtactaag | 240 |
| tacaatgaga agttcaaagg caaggccaca ctgacttcag acaaatcctc cagcacagcc | 300 |
| tacatggagc tcagcagcct gacctctgag gactctgcgg tctattactg tgcaagaggg | 360 |
| acttattact acggtagtag ggtatttgac tactggggcc aaggcaccac tctcacagtc | 420 |
| tcctcaggtg gaggggctc aggcggaggt ggctctgggg gtggaggctc ggacattgtg | 480 |
| atgactcagg ctgcaccctc tatacctgtc actcctggag agtcagtatc catctcctgc | 540 |
| aggtctagta agagtctcct gaatagtaat ggcaacactt acttgtattg gttcctgcag | 600 |
| aggccaggcc agtctcctca gctcctgata tatcggatgt ccaaccttgc ctcaggagtc | 660 |
| ccagacaggt tcagtggcag tgggtcagga actgctttca cactgagaat cagtagagtg | 720 |
| gaggctgagg atgtgggtgt ttattactgt atgcaacatc tagaatatcc gttcacgttc | 780 |
| ggtgctggga ccaagctgga gctgaaacgg accacgacgc cagcgccgcg accaccaaca | 840 |
| ccggcgccca ccatcgcgtc gcagcccctg tccctgcgcc cagaggcgtg ccggccagcg | 900 |
| gcggggggcg cagtgcacac gagggggctg gacttcgcct gtgatatcta catctgggcg | 960 |
| cccttggccg ggacttgtgg ggtccttctc ctgtcactgg ttatcaccct ttactgcagg | 1020 |
| agtaagagga gcaggctcct gcacagtgac tacatgaaca tgactccccg ccgccccggg | 1080 |
| cccacccgca agcattacca gccctatgcc ccaccacgcg acttcgcagc ctatcgctcc | 1140 |
| agagtgaagt tcagcaggag cgcagacgcc cccgcgtacc agcagggcca gaaccagctc | 1200 |
| tataacgagc tcaatctagg acgaagagag gagtacgatg ttttggacaa gagacgtggc | 1260 |
| cgggaccctg agatgggggg aaagccgcag agaaggaaga accctcagga aggcctgtac | 1320 |
| aatgaactgc agaaagataa gatggcggag gcctacagtg agattgggat gaaaggcgag | 1380 |
| cgccggaggg gcaaggggca cgatggcctt taccagggtc tcagtacagc caccaaggac | 1440 |
| acctacgacg cccttcacat gcaggccctg ccccctcgcg cagcggcga aggccgcggc | 1500 |
| agcctgctga cctgcggcga tgtggaagaa aacccgggcc ccatgtacag aatgcagctg | 1560 |
| ctgagctgca tcgccctgag cctggccctg gtgaccaaca gccagggcca ggacaggcac | 1620 |
| atgatcagga tgaggcagct gatcgacatc gtggaccagc tgaagaacta cgtgaacgac | 1680 |
| ctggtgcccg agttcctgcc cgcccccgag gacgtggaga ccaactgcga gtggagcgcc | 1740 |
| ttcagctgct tccagaaggc ccagctgaag agcgccaaca ccggcaacaa cgagaggatc | 1800 |
| atcaacgtga gcatcaagaa gctgaagagg aagccccca gcaccaacgc cggcaggagg | 1860 |
| cagaagcaca ggctgacctg ccccagctgc gacagctacg agaagaagcc ccccaaggag | 1920 |
| ttcctggaga ggttcaagag cctgctgcag aagatgatcc accagcacct gagcagcagg | 1980 |
| acccacggca gcgaggacag ctaagtttaa ac | 2012 |

<210> SEQ ID NO 18
<211> LENGTH: 1055
<212> TYPE: PRT
<213> ORGANISM: Artificial Sequence
<220> FEATURE:
<223> OTHER INFORMATION: Synthetic Sequence

<400> SEQUENCE: 18

Asp Arg Met Ala Leu Pro Val Thr Ala Leu Leu Leu Pro Leu Ala Leu

-continued

```
1               5                    10                    15
Leu Leu His Ala Ala Arg Pro Asp Ile Gln Met Thr Gln Ser Pro Ser
                20                  25                  30
Ser Leu Ser Ala Ser Val Gly Asp Arg Val Thr Ile Thr Cys Ser Ala
                35                  40                  45
Ser Ser Ser Val Ser Tyr Met Asn Trp Tyr Gln Gln Thr Pro Gly Lys
             50                  55                  60
Ala Pro Lys Arg Trp Ile Tyr Asp Thr Ser Lys Leu Ala Ser Gly Val
65                  70                  75                  80
Pro Ser Arg Phe Ser Gly Ser Gly Ser Gly Thr Asp Tyr Thr Phe Thr
                85                  90                  95
Ile Ser Ser Leu Gln Pro Glu Asp Ile Ala Thr Tyr Tyr Cys Gln Gln
                100                 105                 110
Trp Ser Ser Asn Pro Phe Thr Phe Gly Gln Gly Thr Lys Leu Gln Ile
                115                 120                 125
Gly Gly Gly Gly Ser Gly Gly Gly Ser Gly Gly Gly Gly Ser Gln
                130                 135                 140
Val Gln Leu Val Gln Ser Gly Gly Val Val Gln Pro Gly Arg Ser
145                 150                 155                 160
Leu Arg Leu Ser Cys Lys Ala Ser Gly Tyr Thr Phe Thr Arg Tyr Thr
                165                 170                 175
Met His Trp Val Arg Gln Ala Pro Gly Lys Gly Leu Glu Trp Ile Gly
                180                 185                 190
Tyr Ile Asn Pro Ser Arg Gly Tyr Thr Asn Tyr Asn Gln Lys Val Lys
                195                 200                 205
Asp Arg Phe Thr Ile Ser Arg Asp Asn Ser Lys Asn Thr Ala Phe Leu
                210                 215                 220
Gln Met Asp Ser Leu Arg Pro Glu Asp Thr Gly Val Tyr Phe Cys Ala
225                 230                 235                 240
Arg Tyr Tyr Asp Asp His Tyr Cys Leu Asp Tyr Trp Gly Gln Gly Thr
                245                 250                 255
Pro Val Thr Val Ser Ser Thr Thr Pro Ala Pro Arg Pro Pro Thr
                260                 265                 270
Pro Ala Pro Thr Ile Ala Ser Gln Pro Leu Ser Leu Arg Pro Glu Ala
                275                 280                 285
Cys Arg Pro Ala Ala Gly Gly Ala Val His Thr Arg Gly Leu Asp Phe
                290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Arg Ser Lys Arg Ser
                325                 330                 335
Arg Leu Leu His Ser Asp Tyr Met Asn Met Thr Pro Arg Arg Pro Gly
                340                 345                 350
Pro Thr Arg Lys His Tyr Gln Pro Tyr Ala Pro Pro Arg Asp Phe Ala
                355                 360                 365
Ala Tyr Arg Ser Arg Val Lys Phe Ser Arg Ser Ala Asp Ala Pro Ala
                370                 375                 380
Tyr Gln Gln Gly Gln Asn Gln Leu Tyr Asn Glu Leu Asn Leu Gly Arg
385                 390                 395                 400
Arg Glu Glu Tyr Asp Val Leu Asp Lys Arg Gly Arg Asp Pro Glu
                405                 410                 415
Met Gly Gly Lys Pro Gln Arg Arg Lys Asn Pro Gln Glu Gly Leu Tyr
                420                 425                 430
```

Asn Glu Leu Gln Lys Asp Lys Met Ala Glu Ala Tyr Ser Glu Ile Gly
            435                 440                 445

Met Lys Gly Glu Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg Gly Ser Gly Gly Arg Gly Ser Leu Leu Thr
                485                 490                 495

Cys Gly Asp Val Glu Glu Asn Pro Gly Pro Met Glu Tyr Ala Ser Asp
                500                 505                 510

Ala Ser Leu Asp Pro Glu Ala Pro Trp Pro Pro Ala Pro Arg Ala Arg
            515                 520                 525

Ala Cys Arg Val Leu Pro Trp Ala Leu Val Ala Gly Leu Leu Leu Leu
            530                 535                 540

Leu Leu Leu Ala Ala Ala Cys Ala Val Phe Leu Ala Cys Pro Trp Ala
545                 550                 555                 560

Val Ser Gly Ala Arg Ala Ser Pro Gly Ser Ala Ala Ser Pro Arg Leu
                565                 570                 575

Arg Glu Gly Pro Glu Leu Ser Pro Asp Asp Pro Ala Gly Leu Leu Asp
                580                 585                 590

Leu Arg Gln Gly Met Phe Ala Gln Leu Val Ala Gln Asn Val Leu Leu
            595                 600                 605

Ile Asp Gly Pro Leu Ser Trp Tyr Ser Asp Pro Gly Leu Ala Gly Val
            610                 615                 620

Ser Leu Thr Gly Gly Leu Ser Tyr Lys Glu Asp Thr Lys Glu Leu Val
625                 630                 635                 640

Val Ala Lys Ala Gly Val Tyr Tyr Val Phe Phe Gln Leu Glu Leu Arg
                645                 650                 655

Arg Val Val Ala Gly Glu Gly Ser Gly Ser Val Ser Leu Ala Leu His
                660                 665                 670

Leu Gln Pro Leu Arg Ser Ala Ala Gly Ala Ala Ala Leu Ala Leu Thr
            675                 680                 685

Val Asp Leu Pro Pro Ala Ser Ser Glu Ala Arg Asn Ser Ala Phe Gly
            690                 695                 700

Phe Gln Gly Arg Leu Leu His Leu Ser Ala Gly Gln Arg Leu Gly Val
705                 710                 715                 720

His Leu His Thr Glu Ala Arg Ala Arg His Ala Trp Gln Leu Thr Gln
                725                 730                 735

Gly Ala Thr Val Leu Gly Leu Phe Arg Val Thr Pro Glu Ile Pro Ala
                740                 745                 750

Gly Leu Pro Ser Pro Arg Ser Glu Gly Ser Gly Ala Thr Asn Phe Ser
            755                 760                 765

Leu Leu Lys Gln Ala Gly Asp Val Glu Glu Asn Pro Gly Pro Met Tyr
            770                 775                 780

Arg Met Gln Leu Leu Ser Cys Ile Ala Leu Ser Leu Ala Leu Val Thr
785                 790                 795                 800

Asn Ser Gly Ile His Val Phe Ile Leu Gly Cys Phe Ser Ala Gly Leu
                805                 810                 815

Pro Lys Thr Glu Ala Asn Trp Val Asn Val Ile Ser Asp Leu Lys Lys
            820                 825                 830

Ile Glu Asp Leu Ile Gln Ser Met His Ile Asp Ala Thr Leu Tyr Thr
835                 840                 845

```
Glu Ser Asp Val His Pro Ser Cys Lys Val Thr Ala Met Lys Cys Phe
850                 855                 860

Leu Leu Glu Leu Gln Val Ile Ser Leu Glu Ser Gly Asp Ala Ser Ile
865                 870                 875                 880

His Asp Thr Val Glu Asn Leu Ile Ile Leu Ala Asn Asn Ser Leu Ser
                885                 890                 895

Ser Asn Gly Asn Val Thr Glu Ser Gly Cys Lys Glu Cys Glu Glu Leu
            900                 905                 910

Glu Glu Lys Asn Ile Lys Glu Phe Leu Gln Ser Phe Val His Ile Val
        915                 920                 925

Gln Met Phe Ile Asn Thr Ser Ser Gly Gly Ser Gly Gly Gly Gly
930                 935                 940

Ser Gly Gly Gly Ser Gly Gly Gly Ser Gly Gly Gly Ser Leu
945                 950                 955                 960

Gln Ala Pro Arg Arg Ala Arg Gly Cys Arg Thr Leu Gly Leu Pro Ala
                965                 970                 975

Leu Leu Leu Leu Leu Leu Leu Arg Pro Pro Ala Thr Arg Gly Ile Thr
                980                 985                 990

Cys Pro Pro Pro Met Ser Val Glu His Ala Asp Ile Trp Val Lys Ser
                995                1000                1005

Tyr Ser Leu Tyr Ser Arg Glu Arg Tyr Ile Cys Asn Ser Gly Phe
    1010                1015                1020

Lys Arg Lys Ala Gly Thr Ser Ser Leu Thr Glu Cys Val Leu Asn
    1025                1030                1035

Lys Ala Thr Asn Val Ala His Trp Thr Thr Pro Ser Leu Lys Cys
    1040                1045                1050

Ile Arg
    1055

<210> SEQ ID NO 19
<211> LENGTH: 3170
<212> TYPE: DNA
<213> ORGANISM: Artificial Sequence
<220> FEATURE:
<223> OTHER INFORMATION: Synthetic Sequence

<400> SEQUENCE: 19
atggccttac cagtgaccgc cttgctcctg ccgctggcct tgctgctcca cgccgccagg      60
ccggacatcc agatgaccca gagccccagc agcctgagcg ccagcgtggg cgacagagtg     120
accatcacct gcagcgccag cagcagcgtg agctacatga actggtacca gcagaccccc     180
ggcaaggccc ccaagagatg gatctacgac accagcaagc tggccagcgg cgtgcccagc     240
agattcagcg gcagcggcag cggcaccgac tacaccttca ccatcagcag cctgcagccc     300
gaggacatcg ccacctacta ctgccagcag tggagcagca cccccttcac cttcggccag     360
ggcaccaagc tgcagatcgg cggcggcggc agcggcggcg cggcagcgg cggcggcggc     420 agccaggtgc agctggtgca gagcggcggc ggcgtggtgc agcccggcag aagcctgaga     480
ctgagctgca aggccagcgg ctacaccttc accagataca ccatgcactg ggtgagacag     540 gccccggca agggcctgga gtggatcggc tacatcaacc ccagcagagg ctacaccaac     600
tacaaccaga aggtgaagga cagattcacc atcagcagag acaacagcaa gaacaccgcc     660
ttcctgcaga tggacagcct gagacccgag gacaccggcg tgtacttctg cgccagatac     720
tacgacgacc actactgcct ggactactgg ggccagggca cccccgtgac cgtgagcagc     780
accacgacgc cagcgccgcg accaccaaca ccggcgccca ccatcgcgtc gcagccctg      840
```

-continued

| | |
|---|---|
| tccctgcgcc cagaggcgtg ccggccagcg gcggggggcg cagtgcacac gagggggctg | 900 |
| gacttcgcct gtgatatcta catctgggcg cccttggccg ggacttgtgg ggtccttctc | 960 |
| ctgtcactgg ttatcaccct ttactgcagg agtaagagga gcaggctcct gcacagtgac | 1020 |
| tacatgaaca tgactccccg ccgcccgggg cccacccgca agcattacca gccctatgcc | 1080 |
| ccaccacgcg acttcgcagc ctatcgctcc agagtgaagt tcagcaggag cgcagacgcc | 1140 |
| cccgcgtacc agcagggcca gaaccagctc tataacgagc tcaatctagg acgaagagag | 1200 |
| gagtacgatg ttttggacaa gagacgtggc cgggaccctg agatgggggg aaagccgcag | 1260 |
| agaaggaaga accctcagga aggcctgtac aatgaactgc agaaagataa gatggcggag | 1320 |
| gcctacagtg agattgggat gaaaggcgag cgccggaggg gcaaggggca cgatggcctt | 1380 |
| taccagggtc tcagtacagc caccaaggac acctacgacg cccttcacat gcaggccctg | 1440 |
| cccccctcgcg gcagcggcga aggccgcggc agcctgctga cctgcggcga tgtggaagaa | 1500 |
| aacccgggcc ccatggaata cgcctctgac gcttcactgg accccgaagc cccgtggcct | 1560 |
| cccgcgcccc gcgctcgcgc ctgccgcgta ctgccttggg ccctggtcgc ggggctgctg | 1620 |
| ctgctgctgc tgctcgctgc cgcctgcgcc gtcttcctcg cctgcccctg gccgtgtcc | 1680 |
| ggggctcgcg cctcgcccgg ctccgcggcc agcccgagac tccgcgaggg tcccgagctt | 1740 |
| tcgcccgacg atcccgccgg cctcttggac ctgcggcagg gcatgtttgc gcagctggtg | 1800 |
| gcccaaaatg ttctgctgat cgatgggccc ctgagctggt acagtgaccc aggcctggca | 1860 |
| ggcgtgtccc tgacgggggg cctgagctac aaagaggaca cgaaggagct ggtggtggcc | 1920 |
| aaggctggag tctactatgt cttctttcaa ctagagctgc ggcgcgtggt ggccggcgag | 1980 |
| ggctcaggct ccgtttcact tgcgctgcac ctgcagccac tgcgctctgc tgctggggcc | 2040 |
| gccgccctgg ctttgaccgt ggacctgcca cccgcctcct ccgaggctcg gaactcggcc | 2100 |
| ttcggtttcc agggccgctt gctgcacctg agtgccggcc agcgcctggg cgtccatctt | 2160 |
| cacactgagg ccagggcacg ccatgcctgg cagcttaccc agggcgccac agtcttggga | 2220 |
| ctcttccggg tgaccccga atcccagccg ggactccctt caccgaggtc ggaaggaagc | 2280 |
| ggagctacta acttcagcct gctgaagcag gctggagacg tggaggagaa ccctggacct | 2340 |
| atgtacagaa tgcagctgct gagctgcatc gccctgagcc tggccctggt gaccaacagc | 2400 |
| ggcatccacg tgttcatcct gggctgcttc agcgccggcc tgcccaagac cgaggccaac | 2460 |
| tgggtgaacg tgatcagcga cctgaagaag atcgaggacc tgatccagag catgcacatc | 2520 |
| gacgccaccc tgtacaccga gagcgacgtg caccccagct gcaaggtgac cgccatgaag | 2580 |
| tgcttcctgc tggagctgca ggtgatcagc ctggagagcg gcgacgccag catccacgac | 2640 |
| accgtggaga acctgatcat cctggccaac aacagcctga gcagcaacgg caacgtgacc | 2700 |
| gagagcggct gcaaggagtg cgaggagctg gaggagaaga catcaaggga gttcctgcag | 2760 |
| agcttcgtgc acatcgtgca gatgttcatc aacaccagct ccggcggcgg ctccggcggc | 2820 |
| ggcggctccg gcggcggcgg ctccggcggc ggcggctccg gcggcggctc cctgcaggcc | 2880 |
| cccagaagag ccagaggctg cagaaccctg ggcctgcccg ccctgctgct gctgctgctg | 2940 |
| ctgagacccc ccgccaccag aggcatcacc tgccccccc ccatgagcgt ggagcacgcc | 3000 |
| gacatctggg tgaagagcta cagcctgtac agcagagaga gatacatctg caacagcggc | 3060 |
| ttcaagagaa aggccggcac cagcagcctg accgagtgcg tgctgaacaa ggccaccaac | 3120 |
| gtggcccact ggaccacccc cagcctgaag tgcatcagat aagtttaaac | 3170 |

```
<210> SEQ ID NO 20
<211> LENGTH: 1066
<212> TYPE: PRT
<213> ORGANISM: Artificial Sequence
<220> FEATURE:
<223> OTHER INFORMATION: Synthetic Sequence

<400> SEQUENCE: 20

Asp Arg Thr Met Ala Leu Pro Val Thr Ala Leu Leu Leu Pro Leu Ala
1               5                   10                  15

Leu Leu Leu His Ala Ala Arg Pro Asp Ile Val Met Thr Gln Ser Pro
            20                  25                  30

Asp Ser Leu Ala Val Ser Leu Gly Glu Arg Val Thr Met Asn Cys Lys
        35                  40                  45

Ser Ser Gln Ser Leu Leu Tyr Ser Thr Asn Gln Lys Asn Tyr Leu Ala
    50                  55                  60

Trp Tyr Gln Gln Lys Pro Gly Gln Ser Pro Lys Leu Leu Ile Tyr Trp
65                  70                  75                  80

Ala Ser Thr Arg Glu Ser Gly Val Pro Asp Arg Phe Ser Gly Ser Gly
                85                  90                  95

Ser Gly Thr Asp Phe Thr Leu Thr Ile Ser Ser Val Gln Ala Glu Asp
            100                 105                 110

Val Ala Val Tyr Tyr Cys Gln Gln Tyr Ser Tyr Arg Thr Phe Gly
        115                 120                 125

Gly Gly Thr Lys Leu Glu Ile Lys Gly Gly Gly Ser Gly Gly Gly
    130                 135                 140

Gly Ser Gly Gly Gly Ser Gln Val Gln Leu Gln Gln Ser Gly Pro
145                 150                 155                 160

Glu Val Val Lys Pro Gly Ala Ser Val Lys Met Ser Cys Lys Ala Ser
                165                 170                 175

Gly Tyr Thr Phe Thr Ser Tyr Val Ile His Trp Val Arg Gln Lys Pro
            180                 185                 190

Gly Gln Gly Leu Asp Trp Ile Gly Tyr Ile Asn Pro Tyr Asn Asp Gly
        195                 200                 205

Thr Asp Tyr Asp Glu Lys Phe Lys Gly Lys Ala Thr Leu Thr Ser Asp
    210                 215                 220

Thr Ser Thr Ser Thr Ala Tyr Met Glu Leu Ser Ser Leu Arg Ser Glu
225                 230                 235                 240

Asp Thr Ala Val Tyr Tyr Cys Ala Arg Glu Lys Asp Asn Tyr Ala Thr
                245                 250                 255

Gly Ala Trp Phe Ala Tyr Trp Gly Gln Gly Thr Leu Val Thr Val Ser
            260                 265                 270

Ser Thr Thr Thr Pro Ala Pro Arg Pro Pro Thr Pro Ala Pro Thr Ile
    275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Arg Ser Lys Arg Ser Arg Leu Leu His Ser
            340                 345                 350

Asp Tyr Met Asn Met Thr Pro Arg Arg Pro Gly Pro Thr Arg Lys His
        355                 360                 365
```

```
Tyr Gln Pro Tyr Ala Pro Pro Arg Asp Phe Ala Ala Tyr Arg Ser Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Gly Arg Asp Pro Glu Met Gly Gly Lys Pro
                420                 425                 430

Gln Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
        450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

Gly Ser Gly Glu Gly Arg Gly Ser Leu Leu Thr Cys Gly Asp Val Glu
                500                 505                 510

Glu Asn Pro Gly Pro Met Glu Tyr Ala Ser Asp Ala Ser Leu Asp Pro
            515                 520                 525

Glu Ala Pro Trp Pro Pro Ala Pro Arg Ala Arg Ala Cys Arg Val Leu
        530                 535                 540

Pro Trp Ala Leu Val Ala Gly Leu Leu Leu Leu Leu Leu Leu Ala Ala
545                 550                 555                 560

Ala Cys Ala Val Phe Leu Ala Cys Pro Trp Ala Val Ser Gly Ala Arg
                565                 570                 575

Ala Ser Pro Gly Ser Ala Ala Ser Pro Arg Leu Arg Glu Gly Pro Glu
                580                 585                 590

Leu Ser Pro Asp Asp Pro Ala Gly Leu Leu Asp Leu Arg Gln Gly Met
            595                 600                 605

Phe Ala Gln Leu Val Ala Gln Asn Val Leu Leu Ile Asp Gly Pro Leu
        610                 615                 620

Ser Trp Tyr Ser Asp Pro Gly Leu Ala Gly Val Ser Leu Thr Gly Gly
625                 630                 635                 640

Leu Ser Tyr Lys Glu Asp Thr Lys Glu Leu Val Val Ala Lys Ala Gly
                645                 650                 655

Val Tyr Tyr Val Phe Phe Gln Leu Glu Leu Arg Arg Val Val Ala Gly
                660                 665                 670

Glu Gly Ser Gly Ser Val Ser Leu Ala Leu His Leu Gln Pro Leu Arg
            675                 680                 685

Ser Ala Ala Gly Ala Ala Leu Ala Leu Thr Val Asp Leu Pro Pro
        690                 695                 700

Ala Ser Ser Glu Ala Arg Asn Ser Ala Phe Gly Phe Gln Gly Arg Leu
705                 710                 715                 720

Leu His Leu Ser Ala Gly Gln Arg Leu Gly Val His Leu His Thr Glu
                725                 730                 735

Ala Arg Ala Arg His Ala Trp Gln Leu Thr Gln Gly Ala Thr Val Leu
                740                 745                 750

Gly Leu Phe Arg Val Thr Pro Glu Ile Pro Ala Gly Leu Pro Ser Pro
            755                 760                 765

Arg Ser Glu Gly Ser Gly Ala Thr Asn Phe Ser Leu Leu Lys Gln Ala
        770                 775                 780

Gly Asp Val Glu Glu Asn Pro Gly Pro Met Tyr Arg Met Gln Leu Leu
```

| | | | | | | | | | | |
|---|---|---|---|---|---|---|---|---|---|---|
|785| |790| |795| |800| | | | |
|Ser|Cys|Ile|Ala|Leu|Ser|Leu|Ala|Leu|Val|Thr|Asn|Ser|Gly|Ile|His|
| | | |805| | | |810| | | |815| | | | |

Ser Cys Ile Ala Leu Ser Leu Ala Leu Val Thr Asn Ser Gly Ile His
              805                 810                 815

Val Phe Ile Leu Gly Cys Phe Ser Ala Gly Leu Pro Lys Thr Glu Ala
              820                 825                 830

Asn Trp Val Asn Val Ile Ser Asp Leu Lys Lys Ile Glu Asp Leu Ile
              835                 840                 845

Gln Ser Met His Ile Asp Ala Thr Leu Tyr Thr Glu Ser Asp Val His
850                 855                 860

Pro Ser Cys Lys Val Thr Ala Met Lys Cys Phe Leu Leu Glu Leu Gln
865                 870                 875                 880

Val Ile Ser Leu Glu Ser Gly Asp Ala Ser Ile His Asp Thr Val Glu
              885                 890                 895

Asn Leu Ile Ile Leu Ala Asn Asn Ser Leu Ser Ser Asn Gly Asn Val
              900                 905                 910

Thr Glu Ser Gly Cys Lys Glu Cys Glu Glu Leu Glu Glu Lys Asn Ile
              915                 920                 925

Lys Glu Phe Leu Gln Ser Phe Val His Ile Val Gln Met Phe Ile Asn
930                 935                 940

Thr Ser Ser Gly Gly Gly Ser Gly Gly Gly Ser Gly Gly Gly Gly
945                 950                 955                 960

Ser Gly Gly Gly Ser Gly Gly Ser Leu Gln Ala Pro Arg Arg
              965                 970                 975

Ala Arg Gly Cys Arg Thr Leu Gly Leu Pro Ala Leu Leu Leu Leu
              980                 985                 990

Leu Leu Arg Pro Pro Ala Thr Arg Gly Ile Thr Cys Pro Pro Pro Met
        995                 1000                1005

Ser Val Glu His Ala Asp Ile Trp Val Lys Ser Tyr Ser Leu Tyr
        1010                1015                1020

Ser Arg Glu Arg Tyr Ile Cys Asn Ser Gly Phe Lys Arg Lys Ala
        1025                1030                1035

Gly Thr Ser Ser Leu Thr Glu Cys Val Leu Asn Lys Ala Thr Asn
        1040                1045                1050

Val Ala His Trp Thr Thr Pro Ser Leu Lys Cys Ile Arg
        1055                1060                1065

<210> SEQ ID NO 21
<211> LENGTH: 3200
<212> TYPE: DNA
<213> ORGANISM: Artificial Sequence
<220> FEATURE:
<223> OTHER INFORMATION: Synthetic Sequence

<400> SEQUENCE: 21

```
atggccctgc cgtgaccgc cctgctgctg cccctggccc tgctgctgca cgccgccagg      60
cccgacatcg tgatgaccca agcccccgac agcctggccg tgagcctggg cgagagggtg    120
accatgaact gcaaaagcag ccagtccctg ctgtactcca ccaaccagaa gaactacctg    180
gcttggtatc aacagaagcc cggacagagc cccaagctgc tgatctattg ggccagcact    240
agggaaagcg gcgtgcccga taggttcagc ggcagcggga gcggcacaga cttcactctg    300
accattagca gcgtgcaggc tgaggatgtg gccgtctact actgccagca gtactacagc    360
tacaggacct ttgggggcgg aactaagctg gagatcaagg gaggggggg atccggggga    420 ggaggctccg gcggaggcgg aagccaagtg caactgcagc agagcggccc agaggtggtc    480
```

| | |
|---|---|
| aaacctgggg caagcgtgaa gatgagctgc aaggctagcg gctataccttt caccagctat | 540 |
| gtgatccact gggtgaggca gaaaccagga cagggcctgg actggatcgg ctacatcaac | 600 |
| ccctacaatg acggcaccga ttatgacgaa aaattcaagg ggaaggccac cctgaccagc | 660 |
| gacaccagca caagcaccgc ctacatggag ctgtccagcc tgaggtccga ggacaccgcc | 720 |
| gtgtattact gtgccaggga aaggacaat tacgccaccg gcgcttggtt cgcctactgg | 780 |
| ggccagggca cactggtgac agtgagcagc accacgacgc cagcgccgcg accaccaaca | 840 |
| ccggcgccca ccatcgcgtc gcagccctg tccctgcgcc cagaggcgtg ccggccagcg | 900 |
| gcgggggggcg cagtgcacac gagggggctg gacttcgcct gtgatatcta catctgggcc | 960 |
| cccctggccg gcacctgcgg cgtgctgctg ctgagcctgg tgatcaccct gtactgcagg | 1020 |
| agtaagagga gcaggctcct gcacagtgac tacatgaaca tgactccccg ccgcccggg | 1080 |
| cccacccgca agcattacca gccctatgcc ccaccacgcg acttcgcagc ctatcgctcc | 1140 |
| agagtgaagt tcagcaggag cgcagacgcc ccgcgtacc agcagggcca gaaccagctc | 1200 |
| tataacgagc tcaatctagg acgaagagag gagtacgatg ttttggacaa gagacgtggc | 1260 |
| cgggacctg agatgggggg aaagccgcag agaaggaaga accctcagga aggcctgtac | 1320 |
| aatgaactgc agaaagataa gatggcgag gcctacagtg agattgggat gaaaggcgag | 1380 |
| cgccggaggg gcaaggggca cgatggcctt taccagggtc tcagtacagc caccaaggac | 1440 |
| acctacgacg cccttcacat gcaggccctg cccctcgcg gcagcggcga aggccgcggc | 1500 |
| agcctgctga cctgcggcga tgtggaagaa aacccgggcc ccatggaata cgcctctgac | 1560 |
| gcttcactgg accccgaagc cccgtggcct ccgcgcccc gcgctcgcgc ctgccgcgta | 1620 |
| ctgccttggg ccctggtcgc ggggctgctg ctgctgctgc tgctcgctgc cgcctgcgcc | 1680 |
| gtcttcctcg cctgccccctg gccgtgtcc ggggctcgcg cctcgcccgg ctccgcggcc | 1740 |
| agcccgagac tccgcgaggg tcccgagctt tcgcccgacg atcccgccgg cctcttggac | 1800 |
| ctgcggcagg gcatgtttgc gcagctggtg gcccaaaatg ttctgctgat cgatgggccc | 1860 |
| ctgagctggt acagtgaccc aggcctggca ggcgtgtccc tgacgggggg cctgagctac | 1920 |
| aaagaggaca cgaaggagct ggtggtggcc aaggctggag tctactatgt cttcttcaa | 1980 |
| ctagagctgc ggcgcgtggt ggccggcgag ggctcaggct ccgtttcact tgcgctgcac | 2040 |
| ctgcagccac tgcgctctgc tgctggggcc gccgccctgg cttttgaccgt ggacctgcca | 2100 |
| cccgcctcct ccgaggctcg gaactcggcc ttcggtttcc agggccgctt gctgcacctg | 2160 |
| agtgccggcc agcgcctggg cgtccatctt cacactgagg ccaggggcacg ccatgcctgg | 2220 |
| cagcttaccc agggcgccac agtcttggga ctcttccggg tgaccccga atcccagcc | 2280 |
| ggactcccttt caccgaggtc ggaaggaagc ggagctacta acttcagcct gctgaagcag | 2340 |
| gctggagacg tggaggagaa ccctggacct atgtacagaa tgcagctgct gagctgcatc | 2400 |
| gccctgagcc tggccctggt gaccaacagc ggcatccacg tgttcatcct gggctgcttc | 2460 |
| agcgccggcc tgcccaagac cgaggccaac tgggtgaacg tgatcagcga cctgaagaag | 2520 |
| atcgaggacc tgatccagag catgcacatc gacgccaccc tgtacaccga gagcgacgtg | 2580 |
| caccccagct gcaaggtgac cgccatgaag tgcttcctgc tggagctgca ggtgatcagc | 2640 |
| ctggagagcg gcgacgccag catccacgac accgtggaga acctgatcat cctggccaac | 2700 |
| aacagcctga gcagcaacgg caacgtgacc gagagcggct gcaaggagtg cgaggagctg | 2760 |
| gaggagaaga acatcaagga gttcctgcag agcttcgtgc acatcgtgca gatgttcatc | 2820 |
| aacaccagct ccggcggcgg ctccggcggc ggcggctccg gcggcggcgg ctccggcggc | 2880 |

```
ggcggctccg gcggcggctc cctgcaggcc cccagaagag ccagaggctg cagaaccctg    2940
ggcctgcccg ccctgctgct gctgctgctg ctgagacccc ccgccaccag aggcatcacc    3000
tgcccccccc ccatgagcgt ggagcacgcc gacatctggg tgaagagcta cagcctgtac    3060
agcagagaga gatacatctg caacagcggc ttcaagagaa aggccggcac cagcagcctg    3120
accgagtgcg tgctgaacaa ggccaccaac gtggcccact ggaccacccc cagcctgaag    3180
tgcatcagat aagtttaaac                                                 3200
```

<210> SEQ ID NO 22
<211> LENGTH: 832
<212> TYPE: PRT
<213> ORGANISM: Artificial Sequence
<220> FEATURE:
<223> OTHER INFORMATION: Synthetic Sequence

<400> SEQUENCE: 22

```
Asp Arg Met Ala Leu Pro Val Thr Ala Leu Leu Leu Pro Leu Ala Leu
1               5                   10                  15

Leu Leu His Ala Ala Arg Pro Asp Ile Val Met Thr Gln Ser Pro Asp
            20                  25                  30

Ser Leu Ala Val Ser Leu Gly Glu Arg Val Thr Met Asn Cys Lys Ser
        35                  40                  45

Ser Gln Ser Leu Leu Tyr Ser Thr Asn Gln Lys Asn Tyr Leu Ala Trp
    50                  55                  60

Tyr Gln Gln Lys Pro Gly Gln Ser Pro Lys Leu Leu Ile Tyr Trp Ala
65                  70                  75                  80

Ser Thr Arg Glu Ser Gly Val Pro Asp Arg Phe Ser Gly Ser Gly Ser
                85                  90                  95

Gly Thr Asp Phe Thr Leu Thr Ile Ser Ser Val Gln Ala Glu Asp Val
            100                 105                 110

Ala Val Tyr Tyr Cys Gln Gln Tyr Tyr Ser Tyr Arg Thr Phe Gly Gly
        115                 120                 125

Gly Thr Lys Leu Glu Ile Lys Gly Gly Gly Gly Ser Gly Gly Gly Gly
    130                 135                 140

Ser Gly Gly Gly Gly Ser Gln Val Gln Leu Gln Gln Ser Gly Pro Glu
145                 150                 155                 160

Val Val Lys Pro Gly Ala Ser Val Lys Met Ser Cys Lys Ala Ser Gly
                165                 170                 175

Tyr Thr Phe Thr Ser Tyr Val Ile His Trp Val Arg Gln Lys Pro Gly
            180                 185                 190

Gln Gly Leu Asp Trp Ile Gly Tyr Ile Asn Pro Tyr Asn Asp Gly Thr
        195                 200                 205

Asp Tyr Asp Glu Lys Phe Lys Gly Lys Ala Thr Leu Thr Ser Asp Thr
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Glu Lys Asp Asn Tyr Ala Thr Gly
                245                 250                 255

Ala Trp Phe Ala Tyr Trp Gly Gln Gly Thr Leu Val Thr Val Ser Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300
```

```
Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Lys Arg
    370                 375                 380

Gly Arg Lys Lys Leu Leu Tyr Ile Phe Lys Gln Pro Phe Met Arg Pro
385                 390                 395                 400

Val Gln Thr Thr Gln Glu Glu Asp Gly Cys Ser Cys Arg Phe Pro Glu
                405                 410                 415

Glu Glu Glu Gly Gly Cys Glu Leu Arg Val Lys Phe Ser Arg Ser Ala
            420                 425                 430

Asp Ala Pro Ala Tyr Gln Gln Gly Gln Asn Gln Leu Tyr Asn Glu Leu
        435                 440                 445

Asn Leu Gly Arg Arg Glu Glu Tyr Asp Val Leu Asp Lys Arg Arg Gly
450                 455                 460

Arg Asp Pro Glu Met Gly Gly Lys Pro Gln Arg Arg Lys Asn Pro Gln
465                 470                 475                 480

Glu Gly Leu Tyr Asn Glu Leu Gln Lys Asp Lys Met Ala Glu Ala Tyr
                485                 490                 495

Ser Glu Ile Gly Met Lys Gly Glu Arg Arg Arg Gly Lys Gly His Asp
            500                 505                 510

Gly Leu Tyr Gln Gly Leu Ser Thr Ala Thr Lys Asp Thr Tyr Asp Ala
        515                 520                 525

Leu His Met Gln Ala Leu Pro Pro Arg Gly Ser Gly Ala Thr Asn Phe
    530                 535                 540

Ser Leu Leu Lys Gln Ala Gly Asp Val Glu Glu Asn Pro Gly Pro Met
545                 550                 555                 560

Tyr Arg Met Gln Leu Leu Ser Cys Ile Ala Leu Ser Leu Ala Leu Val
                565                 570                 575

Thr Asn Ser Gly Ile His Val Phe Ile Leu Gly Cys Phe Ser Ala Gly
            580                 585                 590

Leu Pro Lys Thr Glu Ala Asn Trp Val Asn Val Ile Ser Asp Leu Lys
        595                 600                 605

Lys Ile Glu Asp Leu Ile Gln Ser Met His Ile Asp Ala Thr Leu Tyr
    610                 615                 620

Thr Glu Ser Asp Val His Pro Ser Cys Lys Val Thr Ala Met Lys Cys
625                 630                 635                 640

Phe Leu Leu Glu Leu Gln Val Ile Ser Leu Glu Ser Gly Asp Ala Ser
                645                 650                 655

Ile His Asp Thr Val Glu Asn Leu Ile Ile Leu Ala Asn Asn Ser Leu
            660                 665                 670

Ser Ser Asn Gly Asn Val Thr Glu Ser Gly Cys Lys Glu Cys Glu Glu
        675                 680                 685

Leu Glu Glu Lys Asn Ile Lys Glu Phe Leu Gln Ser Phe Val His Ile
    690                 695                 700

Val Gln Met Phe Ile Asn Thr Ser Ser Gly Gly Ser Gly Gly Gly Gly
705                 710                 715                 720
```

```
Gly Ser Gly Gly Gly Ser Gly Gly Gly Ser Gly Gly Gly Ser
            725                 730                 735

Leu Gln Ala Pro Arg Arg Ala Arg Gly Cys Arg Thr Leu Gly Leu Pro
        740                 745                 750

Ala Leu Leu Leu Leu Leu Leu Leu Arg Pro Pro Ala Thr Arg Gly Ile
        755                 760                 765

Thr Cys Pro Pro Pro Met Ser Val Glu His Ala Asp Ile Trp Val Lys
        770                 775                 780

Ser Tyr Ser Leu Tyr Ser Arg Glu Arg Tyr Ile Cys Asn Ser Gly Phe
785                 790                 795                 800

Lys Arg Lys Ala Gly Thr Ser Ser Leu Thr Glu Cys Val Leu Asn Lys
                805                 810                 815

Ala Thr Asn Val Ala His Trp Thr Thr Pro Ser Leu Lys Cys Ile Arg
        820                 825                 830

<210> SEQ ID NO 23
<211> LENGTH: 2501
<212> TYPE: DNA
<213> ORGANISM: Artificial Sequence
<220> FEATURE:
<223> OTHER INFORMATION: Synthetic Sequence

<400> SEQUENCE: 23
atggccttac cagtgaccgc cttgctcctg ccgctggcct tgctgctcca cgccgccagg      60
ccggacatcg tgatgaccca agcccccgac agcctggccg tgagcctggg cgagagggtg     120
accatgaact gcaaaagcag ccagtccctg ctgtactcca ccaaccagaa gaactacctg     180
gcttggtatc aacagaagcc cggacagagc cccaagctgc tgatctattg ggccagcact     240
agggaaagcg gcgtgcccga taggttcagc ggcagcggga gcggcacaga cttcactctg     300
accattagca gcgtgcaggc tgaggatgtg gccgtctact actgccagca gtactacagc     360
tacaggacct ttggggggcg gaactaagct gagatcaagg gagggggggg atccggggga     420
ggaggctccg gcggaggcgg aagccaagtg caactgcagc agagcggccc agaggtggtc     480
aaacctgggg caagcgtgaa gatgagctgc aaggctagcg gctataccct caccagctat     540
gtgatccact gggtgaggca gaaaccagga cagggcctgg actggatcgg ctacatcaac     600
ccctacaatg acggcaccga ttatgacgaa aaattcaagg gaaaggccac cctgaccagc     660
gacaccagca aagcaccgc ctacatggag ctgtccagcc tgaggtccga ggacaccgcc     720
gtgtattact gtgccaggga aaggacaat tacgccaccg gcgcttggtt cgcctactgg     780
ggccagggca cactggtgac agtgagcagc accacgacgc cagcgccgcg accaccaaca     840
ccggcgccca ccatcgcgtc gcagcccctg tccctgcgcc cagaggcgtg ccggccagcg     900 gcgggggggcg cagtgcacac gagggggctg gacttcgcct gtgatatcta catctgggcg     960
cccttggccg ggacttgtgg ggtccttctc ctgtcactgg ttatcaccct ttactgcagg    1020
agtaagagga gcaggctcct gcacagtgac tacatgaaca tgactccccg ccgccccggg    1080
cccacccgca agcattacca gccctatgcc ccaccacgcg acttcgcagc ctatcgctcc    1140
aaacggggca gaagaaact cctgtatata ttcaaacaac catttatgag accagtacaa    1200
actactcaag aggaagatgg ctgtagctgc cgatttccag aagaagaaga aggaggatgt    1260
gaactgagag tgaagttcag caggagcgca gacgcccccg cgtaccagca gggccagaac    1320
cagctctata cgagctcaa tctaggacga agagaggagt acgatgttt ggacaagaga    1380 cgtggccggg accctgagat gggggggaag ccgcagagaa ggaagaaccc tcaggaaggc    1440
```

```
ctgtacaatg aactgcagaa agataagatg gcggaggcct acagtgagat tgggatgaaa    1500
ggcgagcgcc ggaggggcaa ggggcacgat ggcctttacc agggtctcag tacagccacc    1560
aaggacacct acgacgccct tcacatgcag gccctgcccc ctcgcggaag cggagccacc    1620
aacttcagcc tgctgaagca ggccggcgac gtggaggaga accccggccc catgtacaga    1680
atgcagctgc tgagctgcat cgccctgagc ctggccctgg tgaccaacag cggcatccac    1740
gtgttcatcc tgggctgctt cagcgccggc ctgcccaaga ccgaggccaa ctgggtgaac    1800
gtgatcagcg acctgaagaa gatcgaggac ctgatccaga gcatgcacat cgacgccacc    1860
ctgtacaccg agagcgacgt gcaccccagc tgcaaggtga ccgccatgaa gtgcttcctg    1920
ctggagctgc aggtgatcag cctggagagc ggcgacgcca gcatccacga caccgtggag    1980
aacctgatca tcctggccaa caacagcctg agcagcaacg gcaacgtgac cgagagcggc    2040
tgcaaggagt gcgaggagct ggaggagaag aacatcaagg agttcctgca gagcttcgtg    2100
cacatcgtgc agatgttcat caacaccagc tccggcggcg gctccggcgg cggcggctcc    2160
ggcggcggcg gctccggcgg cggcggctcc ggcggcggct ccctgcaggc cccagaagaa    2220
gccagaggct gcagaaccct gggcctgccc gccctgctgc tgctgctgct gctgagaccc    2280
cccgccacca gaggcatcac ctgccccccc cccatgagcg tggagcacgc cgacatctgg    2340
gtgaagagct acagcctgta cagcagagag agatacatct gcaacagcgg cttcaagaga    2400
aaggccggca ccagcagcct gaccgagtgc gtgctgaaca aggccaccaa cgtggcccac    2460
tggaccaccc ccagcctgaa gtgcatcaga taagtttaaa c                        2501

<210> SEQ ID NO 24
<211> LENGTH: 789
<212> TYPE: PRT
<213> ORGANISM: Artificial Sequence
<220> FEATURE:
<223> OTHER INFORMATION: Synthetic Sequence

<400> SEQUENCE: 24

Asp Arg Met Ala Leu Pro Val Thr Ala Leu Leu Leu Pro Leu Ala Leu
1               5                   10                  15

Leu Leu His Ala Ala Arg Pro Glu Val Gln Leu Gln Gln Ser Gly Pro
            20                  25                  30

Glu Leu Ile Lys Pro Gly Ala Ser Val Lys Met Ser Cys Lys Ala Ser
        35                  40                  45

Gly Tyr Thr Phe Thr Ser Tyr Val Met His Val Lys Gln Lys Pro
    50                  55                  60

Gly Gln Gly Leu Glu Trp Ile Gly Tyr Ile Asn Pro Tyr Asn Asp Gly
65                  70                  75                  80

Thr Lys Tyr Asn Glu Lys Phe Lys Gly Lys Ala Thr Leu Thr Ser Asp
                85                  90                  95

Lys Ser Ser Ser Thr Ala Tyr Met Glu Leu Ser Ser Leu Thr Ser Glu
            100                 105                 110

Asp Ser Ala Val Tyr Tyr Cys Ala Arg Gly Thr Tyr Tyr Tyr Gly Ser
        115                 120                 125

Arg Val Phe Asp Tyr Trp Gly Gln Gly Thr Thr Leu Thr Val Ser Ser
    130                 135                 140

Gly Gly Gly Gly Ser Gly Gly Gly Ser Gly Gly Gly Gly Ser Asp
145                 150                 155                 160

Ile Val Met Thr Gln Ala Ala Pro Ser Ile Pro Val Thr Pro Gly Glu
                165                 170                 175
```

-continued

```
Ser Val Ser Ile Ser Cys Arg Ser Ser Lys Ser Leu Leu Asn Ser Asn
                180                 185                 190

Gly Asn Thr Tyr Leu Tyr Trp Phe Leu Gln Arg Pro Gly Gln Ser Pro
            195                 200                 205

Gln Leu Leu Ile Tyr Arg Met Ser Asn Leu Ala Ser Gly Val Pro Asp
        210                 215                 220

Arg Phe Ser Gly Ser Gly Ser Gly Thr Ala Phe Thr Leu Arg Ile Ser
225                 230                 235                 240

Arg Val Glu Ala Glu Asp Val Gly Val Tyr Tyr Cys Met Gln His Leu
                245                 250                 255

Glu Tyr Pro Phe Thr Phe Gly Ala Gly Thr Lys Leu Glu Leu Lys Arg
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Gln
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
                485                 490                 495

Ser Gly Glu Gly Arg Gly Ser Leu Leu Thr Cys Gly Asp Val Glu Glu
            500                 505                 510

Asn Pro Gly Pro Met Tyr Arg Met Gln Leu Leu Ser Cys Ile Ala Leu
        515                 520                 525

Ser Leu Ala Leu Val Thr Asn Ser Gly Ile His Val Phe Ile Leu Gly
530                 535                 540

Cys Phe Ser Ala Gly Leu Pro Lys Thr Glu Ala Asn Trp Val Asn Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asp Val His Pro Ser Cys Lys Val
            580                 585                 590

Thr Ala Met Lys Cys Phe Leu Leu Glu Leu Gln Val Ile Ser Leu Glu
```

```
              595                 600                 605
Ser Gly Asp Ala Ser Ile His Asp Thr Val Glu Asn Leu Ile Ile Leu
        610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Met Phe Ile Asn Thr Ser Ser Gly Gly
                660                 665                 670

Gly Ser Gly Gly Gly Ser Gly Gly Gly Ser Gly Gly Gly
        675                 680                 685

Ser Gly Gly Ser Leu Gln Ala Pro Arg Arg Ala Arg Gly Cys Arg
        690                 695                 700

Thr Leu Gly Leu Pro Ala Leu Leu Leu Leu Leu Leu Arg Pro Pro
705                 710                 715                 720

Ala Thr Arg Gly Ile Thr Cys Pro Pro Pro Met Ser Val Glu His Ala
                725                 730                 735

Asp Ile Trp Val Lys Ser Tyr Ser Leu Tyr Ser Arg Glu Arg Tyr Ile
                740                 745                 750

Cys Asn Ser Gly Phe Lys Arg Lys Ala Gly Thr Ser Ser Leu Thr Glu
                755                 760                 765

Cys Val Leu Asn Lys Ala Thr Asn Val Ala His Trp Thr Thr Pro Ser
770                 775                 780

Leu Lys Cys Ile Arg
785

<210> SEQ ID NO 25
<211> LENGTH: 2372
<212> TYPE: DNA
<213> ORGANISM: Artificial Sequence
<220> FEATURE:
<223> OTHER INFORMATION: Synthetic Sequence

<400> SEQUENCE: 25
atggccttac cagtgaccgc cttgctcctg ccgctggcct tgctgctcca cgccgccagg      60
ccggaggtcc agctgcagca gtctggacct gagctgataa agcctggggc ttcagtgaag     120
atgtcctgca aggcttctgg atacacattc actagctatg ttatgcactg ggtgaagcag     180
aagcctgggc agggccttga gtggattgga tatattaatc cttacaatga tggtactaag     240
tacaatgaga agttcaaagg caaggccaca ctgacttcag acaaatcctc cagcacagcc     300
tacatggagc tcagcagcct gacctctgag gactctgcgg tctattactg tgcaagaggg     360
acttattact acggtagtag ggtatttgac tactggggcc aaggcaccac tctcacagtc     420
tcctcaggtg agggggctc aggcggaggt ggctctgggg gtggaggctc ggacattgtg     480
atgactcagg ctgcaccctc tatacctgtc actcctggag agtcagtatc catctcctgc     540
aggtctagta gagtctcct gaatagtaat ggcaacactt acttgtattg gttcctgcag     600
aggccaggcc agtctcctca gctcctgata tatcggatgt ccaaccttgc ctcaggagtc     660
ccagacaggt tcagtggcag tgggtcagga actgctttca cactgagaat cagtagagtg     720
gaggctgagg atgtgggtgt ttattactgt atgcaacatc tagaatatcc gttcacgttc     780
ggtgctggga ccaagctgga gctgaaacgg accacgacgc cagcgccgcg accaccaaca     840
ccggcgccca ccatcgcgtc gcagcccctg tcctgcgcc agaggcgtg ccggccagcg     900 gcggggggcg cagtgcacac gagggggctg gacttcgcct gtgatatcta catctgggcg     960
```

```
cccttggccg ggacttgtgg ggtccttctc ctgtcactgg ttatcaccct ttactgcagg    1020
agtaagagga gcaggctcct gcacagtgac tacatgaaca tgactccccg ccgcccgg     1080 cccacccgca agcattacca gccctatgcc ccaccacgcg acttcgcagc ctatcgctcc    1140
agagtgaagt tcagcaggag cgcagacgcc ccgcgtacc agcagggcca gaaccagctc    1200
tataacgagc tcaatctagg acgaagagag gagtacgatg ttttggacaa gagacgtggc    1260
cgggaccctg agatgggggg aaagccgcag agaaggaaga accctcagga aggcctgtac    1320
aatgaactgc agaaagataa gatggcggag gcctacagtg agattgggat gaaaggcgag    1380
cgccggaggg gcaaggggca cgatggcctt taccagggtc tcagtacagc caccaaggac    1440
acctacgacg ccttcacat gcaggccctg ccccctcgcg gcagcggcga aggccgcggc    1500
agcctgctga cctgcggcga tgtggaagaa aacccgggcc ccatgtacag aatgcagctg    1560
ctgagctgca tcgccctgag cctggccctg gtgaccaaca gcggcatcca cgtgttcatc    1620
ctgggctgct tcagcgccgg cctgcccaag accgaggcca actgggtgaa cgtgatcagc    1680
gacctgaaga gatcgagga cctgatccag agcatgcaca tcgacgccac cctgtacacc    1740
gagagcgacg tgcaccccag ctgcaaggtg accgccatga agtgcttcct gctggagctg    1800
caggtgatca gcctggagag cggcgacgcc agcatccacg acaccgtgga gaacctgatc    1860
atcctggcca caacagcct gagcagcaac ggcaacgtga ccgagagcgg ctgcaaggag    1920
tgcgaggagc tggaggagaa gaacatcaag gagttcctgc agagcttcgt gcacatcgtg    1980
cagatgttca tcaacaccag ctccggcggc ggctccggcg gcggcggctc cggcggcggc    2040
ggctccggcg gcggcggctc cggcggcggc tccctgcagg cccccagaag agccagaggc    2100
tgcagaaccc tgggcctgcc cgccctgctg ctgctgctgc tgctgagacc ccgccacc     2160 agaggcatca cctgccccc ccccatgagc gtggagcacc ccgacatctg ggtgaagagc    2220
tacagcctgt acagcagaga gagatacatc tgcaacagcg gcttcaagag aaaggccggc    2280
accagcagcc tgaccgagtg cgtgctgaac aaggccacca cgtggcccca ctggaccacc    2340
cccagcctga agtgcatcag ataagtttaa ac                                  2372
```

<210> SEQ ID NO 26  
<211> LENGTH: 1066  
<212> TYPE: PRT  
<213> ORGANISM: Artificial Sequence  
<220> FEATURE:  
<223> OTHER INFORMATION: Synthetic Sequence

<400> SEQUENCE: 26

```
Asp Arg Thr Met Ala Leu Pro Val Thr Ala Leu Leu Leu Pro Leu Ala
1               5                   10                  15

Leu Leu Leu His Ala Ala Arg Pro Glu Val Gln Leu Gln Gln Ser Gly
                20                  25                  30

Pro Glu Leu Ile Lys Pro Gly Ala Ser Val Lys Met Ser Cys Lys Ala
            35                  40                  45

Ser Gly Tyr Thr Phe Thr Ser Tyr Val Met His Trp Val Lys Gln Lys
        50                  55                  60

Pro Gly Gln Gly Leu Glu Trp Ile Gly Tyr Ile Asn Pro Tyr Asn Asp
65                  70                  75                  80

Gly Thr Lys Tyr Asn Glu Lys Phe Lys Gly Lys Ala Thr Leu Thr Ser
                85                  90                  95

Asp Lys Ser Ser Ser Thr Ala Tyr Met Glu Leu Ser Ser Leu Thr Ser
                100                 105                 110
```

```
Glu Asp Ser Ala Val Tyr Tyr Cys Ala Arg Gly Thr Tyr Tyr Gly
        115                 120                 125

Ser Arg Val Phe Asp Tyr Trp Gly Gln Gly Thr Thr Leu Thr Val Ser
    130                 135                 140

Ser Gly Gly Gly Ser Gly Gly Gly Ser Gly Gly Gly Ser
145                 150                 155                 160

Asp Ile Val Met Thr Gln Ala Ala Pro Ser Ile Pro Val Thr Pro Gly
                165                 170                 175

Glu Ser Val Ser Ile Ser Cys Arg Ser Ser Lys Ser Leu Leu Asn Ser
        180                 185                 190

Asn Gly Asn Thr Tyr Leu Tyr Trp Phe Leu Gln Arg Pro Gly Gln Ser
        195                 200                 205

Pro Gln Leu Leu Ile Tyr Arg Met Ser Asn Leu Ala Ser Gly Val Pro
        210                 215                 220

Asp Arg Phe Ser Gly Ser Gly Ser Gly Thr Ala Phe Thr Leu Arg Ile
225                 230                 235                 240

Ser Arg Val Glu Ala Glu Asp Val Gly Val Tyr Tyr Cys Met Gln His
                245                 250                 255

Leu Glu Tyr Pro Phe Thr Phe Gly Ala Gly Thr Lys Leu Glu Leu Lys
            260                 265                 270

Arg Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Arg Ser Lys Arg Ser Arg Leu Leu His Ser
            340                 345                 350

Asp Tyr Met Asn Met Thr Pro Arg Arg Pro Gly Pro Thr Arg Lys His
        355                 360                 365

Tyr Gln Pro Tyr Ala Pro Pro Arg Asp Phe Ala Ala Tyr Arg Ser Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Gln Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

Gly Ser Gly Glu Gly Arg Gly Ser Leu Leu Thr Cys Gly Asp Val Glu
            500                 505                 510

Glu Asn Pro Gly Pro Met Glu Tyr Ala Ser Asp Ala Ser Leu Asp Pro
        515                 520                 525
```

```
Glu Ala Pro Trp Pro Pro Ala Pro Arg Ala Arg Ala Cys Arg Val Leu
    530                 535                 540
Pro Trp Ala Leu Val Ala Gly Leu Leu Leu Leu Leu Leu Ala Ala
545                 550                 555                 560
Ala Cys Ala Val Phe Leu Ala Cys Pro Trp Ala Val Ser Gly Ala Arg
                565                 570                 575
Ala Ser Pro Gly Ser Ala Ala Ser Pro Arg Leu Arg Glu Gly Pro Glu
            580                 585                 590
Leu Ser Pro Asp Asp Pro Ala Gly Leu Leu Asp Leu Arg Gln Gly Met
        595                 600                 605
Phe Ala Gln Leu Val Ala Gln Asn Val Leu Leu Ile Asp Gly Pro Leu
    610                 615                 620
Ser Trp Tyr Ser Asp Pro Gly Leu Ala Gly Val Ser Leu Thr Gly Gly
625                 630                 635                 640
Leu Ser Tyr Lys Glu Asp Thr Lys Glu Leu Val Val Ala Lys Ala Gly
                645                 650                 655
Val Tyr Tyr Val Phe Phe Gln Leu Glu Leu Arg Arg Val Val Ala Gly
            660                 665                 670
Glu Gly Ser Gly Ser Val Ser Leu Ala Leu His Leu Gln Pro Leu Arg
        675                 680                 685
Ser Ala Ala Gly Ala Ala Ala Leu Ala Leu Thr Val Asp Leu Pro Pro
    690                 695                 700
Ala Ser Ser Glu Ala Arg Asn Ser Ala Phe Gly Phe Gln Gly Arg Leu
705                 710                 715                 720
Leu His Leu Ser Ala Gly Gln Arg Leu Gly Val His Leu His Thr Glu
                725                 730                 735
Ala Arg Ala Arg His Ala Trp Gln Leu Thr Gln Gly Ala Thr Val Leu
            740                 745                 750
Gly Leu Phe Arg Val Thr Pro Glu Ile Pro Ala Gly Leu Pro Ser Pro
        755                 760                 765
Arg Ser Glu Gly Ser Gly Ala Thr Asn Phe Ser Leu Leu Lys Gln Ala
    770                 775                 780
Gly Asp Val Glu Glu Asn Pro Gly Pro Met Tyr Arg Met Gln Leu Leu
785                 790                 795                 800
Ser Cys Ile Ala Leu Ser Leu Ala Leu Val Thr Asn Ser Gly Ile His
                805                 810                 815
Val Phe Ile Leu Gly Cys Phe Ser Ala Gly Leu Pro Lys Thr Glu Ala
            820                 825                 830
Asn Trp Val Asn Val Ile Ser Asp Leu Lys Lys Ile Glu Asp Leu Ile
        835                 840                 845
Gln Ser Met His Ile Asp Ala Thr Leu Tyr Thr Glu Ser Asp Val His
    850                 855                 860
Pro Ser Cys Lys Val Thr Ala Met Lys Cys Phe Leu Leu Glu Leu Gln
865                 870                 875                 880
Val Ile Ser Leu Glu Ser Gly Asp Ala Ser Ile His Asp Thr Val Glu
                885                 890                 895
Asn Leu Ile Ile Leu Ala Asn Asn Ser Leu Ser Ser Asn Gly Asn Val
            900                 905                 910
Thr Glu Ser Gly Cys Lys Glu Cys Glu Glu Leu Glu Glu Lys Asn Ile
        915                 920                 925
Lys Glu Phe Leu Gln Ser Phe Val His Ile Val Gln Met Phe Ile Asn
    930                 935                 940
Thr Ser Ser Gly Gly Gly Ser Gly Gly Gly Gly Ser Gly Gly Gly Gly
```

```
              945           950           955           960
Ser Gly Gly Gly Ser Gly Gly Gly Ser Leu Gln Ala Pro Arg Arg
                    965           970           975

Ala Arg Gly Cys Arg Thr Leu Gly Leu Pro Ala Leu Leu Leu Leu
              980           985           990

Leu Leu Arg Pro Pro Ala Thr Arg Gly Ile Thr Cys Pro Pro Met
              995          1000          1005

Ser Val Glu His Ala Asp Ile Trp Val Lys Ser Tyr Ser Leu Tyr
        1010          1015          1020

Ser Arg Glu Arg Tyr Ile Cys Asn Ser Gly Phe Lys Arg Lys Ala
        1025          1030          1035

Gly Thr Ser Ser Leu Thr Glu Cys Val Leu Asn Lys Ala Thr Asn
        1040          1045          1050

Val Ala His Trp Thr Thr Pro Ser Leu Lys Cys Ile Arg
        1055          1060          1065

<210> SEQ ID NO 27
<211> LENGTH: 3200
<212> TYPE: DNA
<213> ORGANISM: Artificial Sequence
<220> FEATURE:
<223> OTHER INFORMATION: Synthetic Sequence

<400> SEQUENCE: 27
atggccttac cagtgaccgc cttgctcctg ccgctggcct tgctgctcca cgccgccagg      60
ccggaggtcc agctgcagca gtctggacct gagctgataa agcctggggc ttcagtgaag     120
atgtcctgca aggcttctgg atacacattc actagctatg ttatgcactg ggtgaagcag     180
aagcctgggc agggccttga gtggattgga tatattaatc cttacaatga tggtactaag     240
tacaatgaga agttcaaagg caaggccaca ctgacttcag acaaatcctc cagcacagcc     300
tacatggagc tcagcagcct gacctctgag gactctgcgg tctattactg tgcaagaggg     360
acttattact acggtagtag ggtatttgac tactggggcc aaggcaccac tctcacagtc     420
tcctcaggtg agggggctc aggcggaggt ggctctgggg gtggaggctc ggacattgtg     480
atgactcagg ctgcacctc tatacctgtc actcctggag agtcagtatc catctcctgc     540
aggtctagta agagtctcct gaatagtaat ggcaacactt acttgtattg gttcctgcag     600
aggccaggcc agtctcctca gctcctgata tatcggatgt ccaaccttgc ctcaggagtc     660
ccagacaggt tcagtggcag tgggtcagga actgctttca cactgagaat cagtagagtg     720
gaggctgagg atgtgggtgt ttattactgt atgcaacatc tagaatatcc gttcacgttc     780
ggtgctggga ccaagctgga gctgaaacgg accacgacgc cagcgccgcg accaccaaca     840
ccggcgccca ccatcgcgtc gcagcccctg tccctgcgcc cagaggcgtg ccggccagcg     900
gcgggggccg cagtgcacac gaggggggctg gacttcgcct gtgatatcta catctgggcg     960
cccttggccg ggacttgtgg ggtccttctc ctgtcactgg ttatcaccct ttactgcagg    1020
agtaagagga gcaggctcct gcacagtgac tacatgaaca tgactccccg ccgccccggg    1080
cccacccgca agcattacca gccctatgcc ccaccgcgcg acttcgcagc ctatcgctcc    1140
agagtgaagt tcagcaggag cgcagacgcc cccgcgtacc agcagggcca gaaccagctc    1200
tataacgagc tcaatctagg acgaagagag gagtacgatg ttttggacaa gagacgtggc    1260
cgggaccctg agatgggggg aaagccgcag agaaggaaga accctcagga aggcctgtac    1320
aatgaactgc agaaagataa gatggcggag gcctacagtg agattgggat gaaaggcgag    1380
```

```
cgccggaggg gcaaggggca cgatggcctt taccagggtc tcagtacagc caccaaggac    1440
acctacgacg cccttcacat gcaggccctg ccccctcgcg gcagcggcga aggccgcggc    1500
agcctgctga cctgcggcga tgtggaagaa aacccgggcc ccatggaata cgcctctgac    1560
gcttcactgg accccgaagc cccgtggcct ccgcgcgccc cgctcgcgc ctgccgcgta    1620 ctgccttggg ccctggtcgc ggggctgctg ctgctgctgc tgctcgctgc cgcctgcgcc    1680
gtcttcctcg cctgccctg gccgtgtcc ggggctcgcg cctcgcccgg ctccgcggcc    1740
agcccgagac tccgcgaggg tcccgagctt tcgcccgacg atcccgccgg cctcttggac    1800
ctgcggcagg gcatgtttgc gcagctggtg gcccaaaatg ttctgctgat cgatgggccc    1860
ctgagctggt acagtgaccc aggcctggca ggcgtgtccc tgacgggggg cctgagctac    1920
aaagaggaca cgaaggagct ggtggtggcc aaggctggag tctactatgt cttctttcaa    1980
ctagagctgc ggcgcgtggt ggccggcgag ggctcaggct ccgtttcact tgcgctgcac    2040
ctgcagccac tgcgctctgc tgctggggcc gccgccctgg ctttgaccgt ggacctgcca    2100
cccgcctcct ccgaggctcg gaactcggcc ttcggtttcc agggccgctt gctgcacctg    2160
agtgccggcc agcgcctggg cgtccatctt cacactgagg ccagggcacg ccatgcctgg    2220
cagcttaccc agggcgccac agtcttggga ctcttccggg tgaccccga atcccagcc    2280 ggactcccctt caccgaggtc ggaaggaagc ggagctacta acttcagcct gctgaagcag    2340
gctggagacg tggaggagaa ccctggacct atgtacagaa tgcagctgct gagctgcatc    2400
gccctgagcc tggccctggt gaccaacagc ggcatccacg tgttcatcct gggctgcttc    2460
agcgccggcc tgcccaagac cgaggccaac tgggtgaacg tgatcagcga cctgaagaag    2520
atcgaggacc tgatccagag catgcacatc gacgccaccc tgtacaccga gagcgacgtg    2580 cacccccagct gcaaggtgac cgccatgaag tgcttcctgc tggagctgca ggtgatcagc    2640
ctggagagcg gcgacgccag catccacgac accgtggaga acctgatcat cctggccaac    2700
aacagcctga gcagcaacgg caacgtgacc gagagcggct gcaaggagtg cgaggagctg    2760
gaggagaaga acatcaagga gttcctgcag agcttcgtgc acatcgtgca gatgttcatc    2820
aacaccagct ccggcggcgg ctccggcggc ggcggctccg gcggcggcgg ctccggcggc    2880
ggcggctccg gcggcggctc cctgcaggcc cccagaagag ccagaggctg cagaaccctg    2940
ggcctgcccg ccctgctgct gctgctgctg ctgagacccc ccgccaccag aggcatcacc    3000 tgccccccccc ccatgagcgt ggagcacgcc gacatctggg tgaagagcta cagcctgtac    3060
agcagagaga gatacatctg caacagcggc ttcaagagaa aggccggcac cagcagcctg    3120
accgagtgcg tgctgaacaa ggccaccaac gtggcccact ggaccacccc cagcctgaag    3180
tgcatcagat aagtttaaac                                               3200
```

<210> SEQ ID NO 28
<211> LENGTH: 1300
<212> TYPE: PRT
<213> ORGANISM: Artificial Sequence
<220> FEATURE:
<223> OTHER INFORMATION: Synthetic Sequence

<400> SEQUENCE: 28

```
Asp Arg Thr Met Ala Leu Pro Val Thr Ala Leu Leu Leu Pro Leu Ala
1               5                   10                  15

Leu Leu Leu His Ala Ala Arg Pro Asp Ile Gln Leu Thr Gln Ser Pro
            20                  25                  30

Ser Ser Leu Ser Ala Ser Val Gly Asp Arg Val Thr Met Thr Cys Arg
```

```
                    35                  40                  45
Ala Ser Ser Ser Val Ser Tyr Ile His Trp Phe Gln Gln Lys Pro Gly
 50                  55                  60

Lys Ala Pro Lys Pro Trp Ile Tyr Ala Thr Ser Asn Leu Ala Ser Gly
 65                  70                  75                  80

Val Pro Val Arg Phe Ser Gly Ser Gly Ser Gly Thr Asp Tyr Thr Phe
                 85                  90                  95

Thr Ile Ser Ser Leu Gln Pro Glu Asp Ile Ala Thr Tyr Tyr Cys Gln
                100                 105                 110

Gln Trp Thr Ser Asn Pro Pro Thr Phe Gly Gly Gly Thr Lys Leu Glu
                115                 120                 125

Ile Lys Arg Gly Gly Gly Gly Ser Gly Gly Gly Gly Ser Gly Gly Gly
            130                 135                 140

Gly Ser Gln Val Gln Leu Gln Gln Ser Gly Ala Glu Val Lys Lys Pro
145                 150                 155                 160

Gly Ser Ser Val Lys Val Ser Cys Lys Ala Ser Gly Tyr Thr Phe Ser
                165                 170                 175

Ser Tyr Asn Met His Trp Val Arg Gln Ala Pro Gly Gln Gly Leu Glu
                180                 185                 190

Trp Met Gly Ala Ile Tyr Pro Gly Asn Gly Asp Thr Ser Tyr Asn Gln
            195                 200                 205

Lys Phe Lys Gly Arg Ala Thr Ile Thr Ala Asp Glu Ser Thr Asn Thr
210                 215                 220

Ala Tyr Met Glu Leu Ser Ser Leu Arg Ser Glu Asp Thr Ala Phe Tyr
225                 230                 235                 240

Phe Cys Ala Arg Ser Thr Tyr Tyr Gly Gly Asp Trp Tyr Phe Asp Val
                245                 250                 255

Trp Gly Gln Gly Thr Thr Val Thr Val Ser Ser Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Arg Ser Lys Arg Ser Arg Leu Leu His Ser Asp Tyr Met Asn Met Thr
                340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Gln Arg Arg Lys Asn Pro
                420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460
```

```
Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Gly Ser Gly Ala Thr Asn
            485                 490                 495

Phe Ser Leu Leu Lys Gln Ala Gly Asp Val Glu Glu Asn Pro Gly Pro
        500                 505                 510

Met Ala Leu Pro Val Thr Ala Leu Leu Leu Pro Leu Ala Leu Leu Leu
            515                 520                 525

His Ala Ala Arg Pro Glu Val Gln Leu Gln Gln Ser Gly Pro Glu Leu
530                 535                 540

Ile Lys Pro Gly Ala Ser Val Lys Met Ser Cys Lys Ala Ser Gly Tyr
545                 550                 555                 560

Thr Phe Thr Ser Tyr Val Met His Trp Val Lys Gln Lys Pro Gly Gln
                565                 570                 575

Gly Leu Glu Trp Ile Gly Tyr Ile Asn Pro Tyr Asn Asp Gly Thr Lys
            580                 585                 590

Tyr Asn Glu Lys Phe Lys Gly Lys Ala Thr Leu Thr Ser Asp Lys Ser
        595                 600                 605

Ser Ser Thr Ala Tyr Met Glu Leu Ser Ser Leu Thr Ser Glu Asp Ser
610                 615                 620

Ala Val Tyr Tyr Cys Ala Arg Gly Thr Tyr Tyr Gly Ser Arg Val
625                 630                 635                 640

Phe Asp Tyr Trp Gly Gln Gly Thr Thr Leu Thr Val Ser Ser Gly Gly
                645                 650                 655

Gly Gly Ser Gly Gly Gly Gly Ser Gly Gly Gly Gly Ser Asp Ile Val
            660                 665                 670

Met Thr Gln Ala Ala Pro Ser Ile Pro Val Thr Pro Gly Glu Ser Val
        675                 680                 685

Ser Ile Ser Cys Arg Ser Ser Lys Ser Leu Leu Asn Ser Asn Gly Asn
690                 695                 700

Thr Tyr Leu Tyr Trp Phe Leu Gln Arg Pro Gly Gln Ser Pro Gln Leu
705                 710                 715                 720

Leu Ile Tyr Arg Met Ser Asn Leu Ala Ser Gly Val Pro Asp Arg Phe
                725                 730                 735

Ser Gly Ser Gly Ser Gly Thr Ala Phe Thr Leu Arg Ile Ser Arg Val
            740                 745                 750

Glu Ala Glu Asp Val Gly Val Tyr Tyr Cys Met Gln His Leu Glu Tyr
        755                 760                 765

Pro Phe Thr Phe Gly Ala Gly Thr Lys Leu Glu Leu Lys Arg Thr Thr
770                 775                 780

Thr Pro Ala Pro Arg Pro Pro Thr Pro Ala Pro Thr Ile Ala Ser Gln
785                 790                 795                 800

Pro Leu Ser Leu Arg Pro Glu Ala Cys Arg Pro Ala Ala Gly Gly Ala
                805                 810                 815

Val His Thr Arg Gly Leu Asp Phe Ala Cys Asp Ile Tyr Ile Trp Ala
            820                 825                 830

Pro Leu Ala Gly Thr Cys Gly Val Leu Leu Leu Ser Leu Val Ile Thr
        835                 840                 845

Leu Tyr Cys Lys Arg Gly Arg Lys Lys Leu Leu Tyr Ile Phe Lys Gln
850                 855                 860

Pro Phe Met Arg Pro Val Gln Thr Thr Gln Glu Glu Asp Gly Cys Ser
865                 870                 875                 880
```

```
Cys Arg Phe Pro Glu Glu Glu Gly Gly Cys Glu Leu Arg Val Lys
            885                 890                 895

Phe Ser Arg Ser Ala Asp Ala Pro Ala Tyr Gln Gln Gly Gln Asn Gln
            900                 905                 910

Leu Tyr Asn Glu Leu Asn Leu Gly Arg Arg Glu Glu Tyr Asp Val Leu
            915                 920                 925

Asp Lys Arg Arg Gly Arg Asp Pro Glu Met Gly Gly Lys Pro Gln Arg
930                 935                 940

Arg Lys Asn Pro Gln Glu Gly Leu Tyr Asn Glu Leu Gln Lys Asp Lys
945                 950                 955                 960

Met Ala Glu Ala Tyr Ser Glu Ile Gly Met Lys Gly Glu Arg Arg Arg
            965                 970                 975

Gly Lys Gly His Asp Gly Leu Tyr Gln Gly Leu Ser Thr Ala Thr Lys
            980                 985                 990

Asp Thr Tyr Asp Ala Leu His Met Gln Ala Leu Pro Pro Arg Gly Ser
            995                 1000                1005

Gly Glu Gly Arg Gly Ser Leu Leu Thr Cys Gly Asp Val Glu Glu
        1010                1015                1020

Asn Pro Gly Pro Met Tyr Arg Met Gln Leu Leu Ser Cys Ile Ala
        1025                1030                1035

Leu Ser Leu Ala Leu Val Thr Asn Ser Gly Ile His Val Phe Ile
        1040                1045                1050

Leu Gly Cys Phe Ser Ala Gly Leu Pro Lys Thr Glu Ala Asn Trp
        1055                1060                1065

Val Asn Val Ile Ser Asp Leu Lys Lys Ile Glu Asp Leu Ile Gln
        1070                1075                1080

Ser Met His Ile Asp Ala Thr Leu Tyr Thr Glu Ser Asp Val His
        1085                1090                1095

Pro Ser Cys Lys Val Thr Ala Met Lys Cys Phe Leu Leu Glu Leu
        1100                1105                1110

Gln Val Ile Ser Leu Glu Ser Gly Asp Ala Ser Ile His Asp Thr
        1115                1120                1125

Val Glu Asn Leu Ile Ile Leu Ala Asn Asn Ser Leu Ser Ser Asn
        1130                1135                1140

Gly Asn Val Thr Glu Ser Gly Cys Lys Glu Cys Glu Glu Leu Glu
        1145                1150                1155

Glu Lys Asn Ile Lys Glu Phe Leu Gln Ser Phe Val His Ile Val
        1160                1165                1170

Gln Met Phe Ile Asn Thr Ser Ser Gly Gly Ser Gly Gly Gly
        1175                1180                1185

Gly Ser Gly Gly Gly Gly Ser Gly Gly Gly Gly Ser Gly Gly Gly
        1190                1195                1200

Ser Leu Gln Ala Pro Arg Arg Ala Arg Gly Cys Arg Thr Leu Gly
        1205                1210                1215

Leu Pro Ala Leu Leu Leu Leu Leu Leu Leu Arg Pro Pro Ala Thr
        1220                1225                1230

Arg Gly Ile Thr Cys Pro Pro Pro Met Ser Val Glu His Ala Asp
        1235                1240                1245

Ile Trp Val Lys Ser Tyr Ser Leu Tyr Ser Arg Glu Arg Tyr Ile
        1250                1255                1260

Cys Asn Ser Gly Phe Lys Arg Lys Ala Gly Thr Ser Ser Leu Thr
        1265                1270                1275

Glu Cys Val Leu Asn Lys Ala Thr Asn Val Ala His Trp Thr Thr
```

```
                    1280             1285                1290
Pro Ser  Leu Lys Cys Ile Arg
    1295                1300

<210> SEQ ID NO 29
<211> LENGTH: 3902
<212> TYPE: DNA
<213> ORGANISM: Artificial Sequence
<220> FEATURE:
<223> OTHER INFORMATION: Synthetic Sequence

<400> SEQUENCE: 29
atggccttac cagtgaccgc cttgctcctg ccgctggcct tgctgctcca cgccgccagg    60
ccggacatcc agctgaccca gagccccagc agcctgagcg ccagcgtggg cgacagggtg   120
accatgacct gcagggccag cagcagcgtg agctacatcc actggttcca gcagaagccc   180
ggcaaggccc ccaagccctg gatctacgcc accagcaacc tggccagcgg cgtgcccgtg   240
aggttcagcg gcagcggcag cggcaccgac tacaccttca ccatcagcag cctgcagccc   300
gaggacatcg ccacctacta ctgccagcag tggaccagca cccccccac cttcggcggc   360 ggcaccaagc tggagatcaa gggggcggg ggcggcagcg gcggcggcgg cagcggcggc   420
ggcggcagcc aggtgcagct gcagcagagc ggcgccgagg tgaagaagcc cggcagcagc   480
gtgaaggtga gctgcaaggc cagcggctac accttcagca gctacaacat gcactgggtg   540
aggcaggccc ccggccaggg cctggagtgg atgggcgcca tctaccccgg caacggcgac   600
accagctaca accagaagtt caagggcagg gccaccatca ccgccgacga gagcaccaac   660
accgcctaca tggagctgag cagcctgagg agcgaggaca ccgccttcta cttctgcgcc   720
aggagcaccc tactacggcgg cgactggtac ttcgacgtgt ggggccaggg caccaccgtg   780
accgtgagca gcaccacgac gccagcgccg cgaccaccaa caccggcgcc caccatcgcg   840
tcgcagcccc tgtccctgcg cccagaggcg tgccggccag cggcgggggg cgcagtgcac   900 acgaggggc tggacttcgc ctgtgatatc tacatctggg cgcccttggc cgggacttgt   960
ggggtccttc tcctgtcact ggttatcacc ctttactgca ggagtaagag gagcaggctc  1020
ctgcacagtg actacatgaa catgactccc cgccgccccg ggcccacccg caagcattac  1080
cagccctatg ccccaccacg cgacttcgca gcctatcgct ccagagtgaa gttcagcagg  1140
agcgcagacg cccccgcgta ccagcagggc cagaaccagc tctataacga gctcaatcta  1200
ggacgaagag aggagtacga tgttttggac aagagacgtg gccgggaccc tgagatgggg  1260
ggaaagccgc agagaaggaa gaaccctcag gaaggcctgt acaatgaact gcagaaagat  1320
aagatggcgg aggcctacag tgagattggg atgaaaggcg agcgccggag gggcaagggg  1380
cacgatggcc tttaccaggg tctcagtaca gccaccaagg acacctacga cgcccttcac  1440
atgcaggccc tgccccctcg cggaagcgga gccaccaact tcagcctgct gaagcaggcc  1500
ggcgacgtgg aggagaaccc cggccccatg gccctgcccg tgaccgccct gctgctgccc  1560
ctggccctgc tgctgcacgc cgccaggccc gaggtccagc tgcagcagtc tggacctgag  1620
ctgataaagc ctgggcttc agtgaagatg tcctgcaagg cttctggata cacattcact  1680
agctatgtta tgcactgggt gaagcagaag cctgggcagg ccttgagtg gattggatat  1740 attaatcctt acaatgatgg tactaagtac aatgagaagt tcaaaggcaa ggccacactg  1800
acttcagaca atcctccag cacagcctac atggagctca gcagcctgac ctctgaggac  1860
tctgcggtct attactgtgc aagagggact tattactacg gtagtagggt atttgactac  1920
```

| | | | |
|---|---|---|---|
| tggggccaag gcaccactct cacagtctcc tcaggtggag ggggctcagg cggaggtggc | 1980 |
| tctgggggtg gaggctcgga cattgtgatg actcaggctg caccctctat acctgtcact | 2040 |
| cctggagagt cagtatccat ctcctgcagg tctagtaaga gtctcctgaa tagtaatggc | 2100 |
| aacacttact tgtattggtt cctgcagagg ccaggccagt ctcctcagct cctgatatat | 2160 |
| cggatgtcca accttgcctc aggagtccca gacaggttca gtggcagtgg gtcaggaact | 2220 |
| gctttcacac tgagaatcag tagagtggag gctgaggatg tgggtgttta ttactgtatg | 2280 |
| caacatctag aatatccgtt cacgttcggt gctgggacca agctggagct gaaacggacc | 2340 |
| accaccccg cccccaggcc cccacccccc gcccccacca cgccagcca gccctgagc | 2400 |
| ctgaggcccg aggcctgcag gcccgccgcc ggcggcgccg tgcacaccag gggcctggac | 2460 |
| ttcgcctgcg acatctacat ctgggccccc ctggccggca cctgcggcgt gctgctgctg | 2520 |
| agcctggtga tcaccctgta ctgcaaacgg ggcagaaaga aactcctgta tatattcaaa | 2580 |
| caaccattta tgagaccagt acaaactact caagaggaag atggctgtag ctgccgattt | 2640 |
| ccagaagaag aagaaggagg atgtgaactg agggtgaagt tcagcaggag cgccgacgcc | 2700 |
| cccgcctacc agcagggcca gaaccagctg tacaacgagc tgaacctggg caggagggag | 2760 |
| gagtacgacg tgctggacaa gaggaggggc agggaccccg agatgggcgg caagccccag | 2820 |
| aggaggaaga ccccccagga gggcctgtac aacgagctgc agaaggacaa gatggccgag | 2880 |
| gcctacagcg agatcggcat gaagggcgag aggaggaggg gcaagggcca cgacggcctg | 2940 |
| taccagggcc tgagcaccgc caccaaggac acctacgacg ccctgcacat gcaggccctg | 3000 |
| cccccaggg gcagcggcga aggccgcggc agcctgctga cctgcggcga tgtggaagaa | 3060 |
| aacccgggcc ccatgtacag aatgcagctg ctgagctgca tcgccctgag cctggccctg | 3120 |
| gtgaccaaca cgcatcca cgtgttcatc ctgggctgct tcagcgccgg cctgcccaag | 3180 |
| accgaggcca actgggtgaa cgtgatcagc gacctgaaga gatcgagga cctgatccag | 3240 |
| agcatgcaca tcgacgccac cctgtacacc gagagcgacg tgcaccccag ctgcaaggtg | 3300 |
| accgccatga agtgcttcct gctggagctg caggtgatca gcctggagag cggcgacgcc | 3360 |
| agcatccacg acaccgtgga gaacctgatc atcctggcca caacagcct gagcagcaac | 3420 |
| ggcaacgtga ccgagagcgg ctgcaaggag tgcgaggagc tggaggagaa gaacatcaag | 3480 |
| gagttcctgc agagcttcgt gcacatcgtg cagatgttca tcaacaccag ctccggcggc | 3540 |
| ggctccggcg gcggcggctc cggcggcggc ggctccggcg gcggcggctc cggcggcggc | 3600 |
| tccctgcagg cccccagaag agccagaggc tgcagaaccc tgggcctgcc cgccctgctg | 3660 |
| ctgctgctgc tgctgagacc cccgccacc agaggcatca cctgccccc ccccatgagc | 3720 |
| gtggagcacg ccgacatctg ggtgaagagc tacagcctgt acagcagaga gagatacatc | 3780 |
| tgcaacagcg gcttcaagag aaaggccggc accagcagcc tgaccgagtg cgtgctgaac | 3840 |
| aaggccacca cgtgcccca ctggaccacc cccagcctga agtgcatcag ataagtttaa | 3900 |
| ac | 3902 |

<210> SEQ ID NO 30
<211> LENGTH: 1069
<212> TYPE: PRT
<213> ORGANISM: Artificial Sequence
<220> FEATURE:
<223> OTHER INFORMATION: Synthetic Sequence

<400> SEQUENCE: 30

Asp Arg Thr Met Ala Leu Pro Val Thr Ala Leu Leu Leu Pro Leu Ala

-continued

```
1               5                   10                  15
Leu Leu Leu His Ala Arg Pro Met Ala Asp Tyr Lys Asp Ile Val
            20                  25                  30

Met Thr Gln Ser His Lys Phe Leu Leu Val Ser Val Gly Asp Arg Val
            35                  40                  45

Ser Ile Thr Cys Lys Ala Ser Gln Asp Val Ser Thr Ala Val Ala Trp
            50                  55                  60

Tyr Gln Gln Lys Pro Gly Gln Ser Pro Lys Leu Leu Ile Tyr Ser Ala
65                  70                  75                  80

Ser Tyr Arg Tyr Thr Gly Val Pro Asp Arg Phe Ile Gly Ser Gly Ser
            85                  90                  95

Gly Thr Asp Phe Thr Leu Thr Ile Ser Ser Val Gln Ala Glu Asp Leu
            100                 105                 110

Ala Asp Tyr Phe Cys Gln Gln His Tyr Ser Thr Pro Leu Thr Phe Gly
            115                 120                 125

Ala Gly Thr Lys Leu Glu Ile Lys Arg Gly Gly Gly Gly Ser Gly Gly
            130                 135                 140

Gly Gly Ser Gly Gly Gly Ser Ser Gly Gly Gly Ser Glu Val Gln
145                 150                 155                 160

Leu Lys Glu Ser Gly Pro Gly Leu Val Ala Pro Ser Gln Ser Leu Ser
            165                 170                 175

Ile Thr Cys Thr Val Ser Gly Phe Pro Leu Thr Ser Tyr Gly Val Ser
            180                 185                 190

Trp Val Arg Gln Pro Pro Gly Lys Gly Leu Glu Trp Leu Gly Val Ile
            195                 200                 205

Trp Gly Asp Gly Ser Thr Asn Tyr His Ser Ala Leu Ile Ser Arg Leu
            210                 215                 220

Ser Ile Ser Lys Asp Asn Ser Lys Ser Gln Val Phe Leu Lys Leu Asn
225                 230                 235                 240

Asn Leu Gln Thr Asp Asp Thr Ala Thr Tyr Tyr Cys Ala Arg Asp Thr
            245                 250                 255

Tyr Tyr Pro Tyr Tyr Ala Met Asp Tyr Trp Gly Gln Gly Thr Ser Val
            260                 265                 270

Thr Val Ser Ser Thr Thr Thr Pro Ala Pro Arg Pro Pro Thr Pro Ala
            275                 280                 285

Pro Thr Ile Ala Ser Gln Pro Leu Ser Leu Arg Pro Glu Ala Cys Arg
            290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
            325                 330                 335

Leu Ser Leu Val Ile Thr Leu Tyr Cys Arg Ser Lys Arg Ser Arg Leu
            340                 345                 350

Leu His Ser Asp Tyr Met Asn Met Thr Pro Arg Arg Pro Gly Pro Thr
            355                 360                 365

Arg Lys His Tyr Gln Pro Tyr Ala Pro Pro Arg Asp Phe Ala Ala Tyr
            370                 375                 380

Arg Ser Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
            405                 410                 415

Glu Tyr Asp Val Leu Asp Lys Arg Arg Gly Arg Asp Pro Glu Met Gly
            420                 425                 430
```

```
Gly Lys Pro Gln Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Glu Gly Arg Gly Ser Leu Leu Thr Cys Gly
            500                 505                 510

Asp Val Glu Glu Asn Pro Gly Pro Met Glu Tyr Ala Ser Asp Ala Ser
        515                 520                 525

Leu Asp Pro Glu Ala Pro Trp Pro Pro Ala Pro Arg Ala Arg Ala Cys
    530                 535                 540

Arg Val Leu Pro Trp Ala Leu Val Ala Gly Leu Leu Leu Leu Leu Leu
545                 550                 555                 560

Leu Ala Ala Ala Cys Ala Val Phe Leu Ala Cys Pro Trp Ala Val Ser
                565                 570                 575

Gly Ala Arg Ala Ser Pro Gly Ser Ala Ala Ser Pro Arg Leu Arg Glu
            580                 585                 590

Gly Pro Glu Leu Ser Pro Asp Asp Pro Ala Gly Leu Leu Asp Leu Arg
        595                 600                 605

Gln Gly Met Phe Ala Gln Leu Val Ala Gln Asn Val Leu Leu Ile Asp
    610                 615                 620

Gly Pro Leu Ser Trp Tyr Ser Asp Pro Gly Leu Ala Gly Val Ser Leu
625                 630                 635                 640

Thr Gly Gly Leu Ser Tyr Lys Glu Asp Thr Lys Glu Leu Val Val Ala
                645                 650                 655

Lys Ala Gly Val Tyr Tyr Val Phe Phe Gln Leu Glu Leu Arg Arg Val
            660                 665                 670

Val Ala Gly Glu Gly Ser Gly Ser Val Ser Leu Ala Leu His Leu Gln
        675                 680                 685

Pro Leu Arg Ser Ala Ala Gly Ala Ala Ala Leu Ala Leu Thr Val Asp
    690                 695                 700

Leu Pro Pro Ala Ser Ser Glu Ala Arg Asn Ser Ala Phe Gly Phe Gln
705                 710                 715                 720

Gly Arg Leu Leu His Leu Ser Ala Gly Gln Arg Leu Gly Val His Leu
                725                 730                 735

His Thr Glu Ala Arg Ala Arg His Ala Trp Gln Leu Thr Gln Gly Ala
            740                 745                 750

Thr Val Leu Gly Leu Phe Arg Val Thr Pro Glu Ile Pro Ala Gly Leu
        755                 760                 765

Pro Ser Pro Arg Ser Glu Gly Ser Gly Ala Thr Asn Phe Ser Leu Leu
    770                 775                 780

Lys Gln Ala Gly Asp Val Glu Glu Asn Pro Gly Pro Met Tyr Arg Met
785                 790                 795                 800

Gln Leu Leu Ser Cys Ile Ala Leu Ser Leu Ala Leu Val Thr Asn Ser
                805                 810                 815

Gly Ile His Val Phe Ile Leu Gly Cys Phe Ser Ala Gly Leu Pro Lys
            820                 825                 830

Thr Glu Ala Asn Trp Val Asn Val Ile Ser Asp Leu Lys Lys Ile Glu
        835                 840                 845
```

```
Asp Leu Ile Gln Ser Met His Ile Asp Ala Thr Leu Tyr Thr Glu Ser
    850                 855                 860

Asp Val His Pro Ser Cys Lys Val Thr Ala Met Lys Cys Phe Leu Leu
865                 870                 875                 880

Glu Leu Gln Val Ile Ser Leu Glu Ser Gly Asp Ala Ser Ile His Asp
        885                 890                 895

Thr Val Glu Asn Leu Ile Ile Leu Ala Asn Asn Ser Leu Ser Ser Asn
            900                 905                 910

Gly Asn Val Thr Glu Ser Gly Cys Lys Glu Cys Glu Glu Leu Glu Glu
                915                 920                 925

Lys Asn Ile Lys Glu Phe Leu Gln Ser Phe Val His Ile Val Gln Met
    930                 935                 940

Phe Ile Asn Thr Ser Ser Gly Gly Ser Gly Gly Gly Gly Ser Gly
945                 950                 955                 960

Gly Gly Gly Ser Gly Gly Gly Ser Gly Gly Gly Ser Leu Gln Ala
                965                 970                 975

Pro Arg Arg Ala Arg Gly Cys Arg Thr Leu Gly Leu Pro Ala Leu Leu
            980                 985                 990

Leu Leu Leu Leu Leu Arg Pro Pro  Ala Thr Arg Gly Ile  Thr Cys Pro
                995                 1000                1005

Pro Pro Met Ser Val Glu His  Ala Asp Ile Trp Val  Lys Ser Tyr
    1010                1015                1020

Ser Leu Tyr Ser Arg Glu Arg  Tyr Ile Cys Asn Ser  Gly Phe Lys
    1025                1030                1035

Arg Lys Ala Gly Thr Ser Ser  Leu Thr Glu Cys Val  Leu Asn Lys
    1040                1045                1050

Ala Thr Asn Val Ala His Trp  Thr Thr Pro Ser Leu  Lys Cys Ile
    1055                1060                1065

Arg

<210> SEQ ID NO 31
<211> LENGTH: 3209
<212> TYPE: DNA
<213> ORGANISM: Artificial Sequence
<220> FEATURE:
<223> OTHER INFORMATION: Synthetic Sequence

<400> SEQUENCE: 31
atggccctgc cgtgaccgc cctgctgctg cccctggccc tgctgctgca cgccgccagg      60
cccatggccg actacaagga catcgtgatg acccagagcc acaagttcct gctggtgagc    120
gtgggcgaca gggtgagcat cacctgcaag gccagccagg acgtgagcac cgccgtggcc    180
tggtaccagc agaagcccgg ccagagcccc aagctgctga tctacagcgc cagctacagg    240
tacaccggcg tgcccgacag gttcatcggc agcggcagcg gcaccgactt caccctgacc    300
atcagcagcg tgcaggccga ggacctggcc gactacttct gccagcagca ctacagcacc    360
cccctgacct tcggcgccgg caccaagctg gagatcaaga ggggcggcgg cggcagcggc    420
ggcggcggca gcggcggcgg cggcagcagc ggcggcggca gcgaggtgca gctgaaggag    480
agcggccccg gctggtggc cccagccag agcctgagca tcacctgcac cgtgagcggc    540
ttccccctga ccagctacgg cgtgagctgg gtgaggcagc ccccggcaa gggcctggag    600 tggctgggcg tgatctgggg cgacggcagc accaactacc acagcgccct gatcagcagg    660
ctgagcatca gcaaggacaa cagcaagagc caggtgttcc tgaagctgaa caacctgcag    720
accgacgaca ccgccaccta ctactgcgcc aggacacct actaccccta ctacgccatg    780
```

```
gactactggg gccagggcac cagcgtgacc gtgagcagca ccaccacccc cgcccccagg    840
cccccacccc ccgccccac catcgccagc cagcccctga gcctgaggcc cgaggcctgc    900
aggcccgccg ccggcggcgc cgtgcacacc aggggcctgg acttcgcctg cgacatctac    960
atctgggccc cctggccgg cacctgcggc gtgctgctgc tgagcctggt gatcaccctg   1020
tactgcagga gtaagaggag caggctcctg cacagtgact acatgaacat gactccccgc   1080
cgccccgggc ccaccgcaa gcattaccag ccctatgccc caccacgcga cttcgcagcc   1140
tatcgctcca gagtgaagtt cagcaggagc gcagacgccc ccgcgtacca gcagggccag   1200
aaccagctct ataacgagct caatctagga cgaagagagg agtacgatgt tttggacaag   1260
agacgtggcc gggaccctga gatggggga aagccgcaga gaaggaagaa ccctcaggaa   1320
ggcctgtaca atgaactgca gaaagataag atggcggagg cctacagtga gattgggatg   1380
aaaggcgagc gccggagggg caaggggcac gatggccttt accagggtct cagtacagcc   1440
accaaggaca cctacgacgc ccttcacatg caggccctgc ccctcgcgg cagcggcgaa   1500
ggccgcggca gcctgctgac ctgcggcgat gtggaagaaa cccgggccc catggaatac   1560
gcctctgacg cttcactgga ccccgaagcc ccgtggcctc ccgcgccccg cgctcgcgcc   1620
tgccgcgtac tgccttgggc cctggtcgcg gggctgctgc tgctgctgct gctcgctgcc   1680
gcctgcgccg tcttcctcgc ctgccccctgg gccgtgtccg gggctcgcgc ctcgccggc   1740
tccgcggcca gcccgagact ccgcgagggt cccgagcttt cgcccgacga tcccgccggc   1800
ctcttggacc tgcggcaggg catgtttgcg cagctggtgg cccaaaatgt tctgctgatc   1860
gatgggcccc tgagctggta cagtgaccca ggcctggcag gcgtgtccct gacgggggc   1920
ctgagctaca agaggacac gaaggagctg gtggtggcca aggctggagt ctactatgtc   1980
ttcttcaac tagagctgcg gcgcgtggtg gccggcgagg gctcaggctc cgtttcactt   2040
gcgctgcacc tgcagccact gcgctctgct gctggggccg ccgccctggc tttgaccgtg   2100
gacctgccac ccgcctcctc cgaggctcgg aactcggcct tcggtttcca gggccgcttg   2160
ctgcacctga gtgccggcca gcgcctgggc gtccatcttc acactgaggc cagggcacgc   2220
catgcctggc agcttaccca gggcgccaca gtcttggac tcttccgggt gacccccgaa   2280
atcccagccg gactcccttc accgaggtcg gaaggaagcg gagctactaa cttcagcctg   2340
ctgaagcagg ctggagacgt ggaggagaac cctggaccta tgtacagaat gcagctgctg   2400
agctgcatcg ccctgagcct ggccctggtg accaacagcg gcatccacgt gttcatcctg   2460
ggctgcttca gcgccggcct gcccaagacc gaggccaact gggtgaacgt gatcagcgac   2520
ctgaagaaga tcgaggacct gatccagagc atgcacatcg acgccaccct gtacaccgag   2580
agcgacgtgc accccagctg caaggtgacc gccatgaagt gcttcctgct ggagctgcag   2640
gtgatcagcc tggagagcgg cgacgccagc atccacgaca ccgtggagaa cctgatcatc   2700
ctggccaaca cagcctgag cagcaacggc aacgtgaccg agagcggctg caaggagtgc   2760
gaggagctgg aggagaagaa catcaaggag ttcctgcaga gcttcgtgca catcgtgcag   2820
atgttcatca acaccagctc cggcggcggc tccggcggcg cggctccgg cggcggcggc   2880
tccggcggcg cggctccgg cggcggctcc ctgcaggccc cagaagagc cagaggctgc   2940
agaaccctgg gcctgcccgc cctgctgctg ctgctgctgc tgagacccc cgccaccaga   3000
ggcatcacct gccccccccc catgagcgtg agcacgccg acatctgggt gaagagctac   3060
agcctgtaca gcagagagag atacatctgc aacagcggct tcaagagaaa ggccggcacc   3120
```

```
agcagcctga ccgagtgcgt gctgaacaag gccaccaacg tggcccactg gaccaccccc    3180
agcctgaagt gcatcagata agtttaaac                                      3209
```

<210> SEQ ID NO 32
<211> LENGTH: 1081
<212> TYPE: PRT
<213> ORGANISM: Artificial Sequence
<220> FEATURE:
<223> OTHER INFORMATION: Synthetic Sequence

<400> SEQUENCE: 32

```
Asp Arg Thr Met Ala Leu Pro Val Thr Ala Leu Leu Leu Pro Leu Ala
1               5                   10                  15

Leu Leu Leu His Ala Ala Arg Pro Met Ala Asp Tyr Lys Asp Ile Val
            20                  25                  30

Met Thr Gln Ser His Lys Phe Met Ser Thr Ser Val Gly Asp Arg Val
        35                  40                  45

Asn Ile Thr Cys Lys Ala Ser Gln Asn Val Asp Ser Ala Val Ala Trp
    50                  55                  60

Tyr Gln Gln Lys Pro Gly Gln Ser Pro Lys Ala Leu Ile Tyr Ser Ala
65                  70                  75                  80

Ser Tyr Arg Tyr Ser Gly Val Pro Asp Arg Phe Thr Gly Arg Gly Ser
                85                  90                  95

Gly Thr Asp Phe Thr Leu Thr Ile Ser Ser Val Gln Ala Glu Asp Leu
            100                 105                 110

Ala Val Tyr Tyr Cys Gln Gln Tyr Tyr Ser Thr Pro Trp Thr Phe Gly
        115                 120                 125

Gly Gly Thr Lys Leu Glu Ile Lys Arg Gly Gly Gly Gly Ser Gly Gly
    130                 135                 140

Gly Gly Ser Gly Gly Gly Gly Ser Gly Gly Gly Gly Ser Glu Val Lys
145                 150                 155                 160

Leu Val Glu Ser Gly Gly Gly Leu Val Gln Pro Gly Gly Ser Leu Ser
                165                 170                 175

Leu Ser Cys Ala Ala Ser Gly Phe Thr Phe Thr Asp Tyr Tyr Met Ser
            180                 185                 190

Trp Val Arg Gln Pro Pro Gly Lys Ala Leu Glu Trp Leu Ala Leu Ile
        195                 200                 205

Arg Ser Lys Ala Asp Gly Tyr Thr Thr Glu Tyr Ser Ala Ser Val Lys
    210                 215                 220

Gly Arg Phe Thr Leu Ser Arg Asp Asp Ser Gln Ser Ile Leu Tyr Leu
225                 230                 235                 240

Gln Met Asn Ala Leu Arg Pro Glu Asp Ser Ala Thr Tyr Tyr Cys Ala
                245                 250                 255

Arg Asp Ala Ala Tyr Tyr Ser Tyr Ser Pro Glu Gly Ala Met Asp
            260                 265                 270

Tyr Trp Gly Gln Gly Thr Ser Val Thr Val Ser Ser Ala Ser Gly Ala
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350
```

```
Ile Thr Leu Tyr Cys Arg Ser Lys Arg Ser Arg Leu Leu His Ser Asp
            355                 360                 365

Tyr Met Asn Met Thr Pro Arg Pro Gly Pro Thr Arg Lys His Tyr
    370                 375                 380

Gln Pro Tyr Ala Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Gln
            435                 440                 445

Arg Arg Lys Asn Pro Gln Glu Gly Leu Tyr Asn Glu Leu Gln Lys Asp
            450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg Gly
            500                 505                 510

Ser Gly Glu Gly Arg Gly Ser Leu Leu Thr Cys Gly Asp Val Glu Glu
            515                 520                 525

Asn Pro Gly Pro Met Glu Tyr Ala Ser Asp Ala Ser Leu Asp Pro Glu
            530                 535                 540

Ala Pro Trp Pro Pro Ala Pro Arg Ala Arg Ala Cys Arg Val Leu Pro
545                 550                 555                 560

Trp Ala Leu Val Ala Gly Leu Leu Leu Leu Leu Leu Ala Ala Ala
                565                 570                 575

Cys Ala Val Phe Leu Ala Cys Pro Trp Ala Val Ser Gly Ala Arg Ala
                580                 585                 590

Ser Pro Gly Ser Ala Ala Ser Pro Arg Leu Arg Glu Gly Pro Glu Leu
            595                 600                 605

Ser Pro Asp Asp Pro Ala Gly Leu Leu Asp Leu Arg Gln Gly Met Phe
            610                 615                 620

Ala Gln Leu Val Ala Gln Asn Val Leu Leu Ile Asp Gly Pro Leu Ser
625                 630                 635                 640

Trp Tyr Ser Asp Pro Gly Leu Ala Gly Val Ser Leu Thr Gly Gly Leu
                645                 650                 655

Ser Tyr Lys Glu Asp Thr Lys Glu Leu Val Val Ala Lys Ala Gly Val
                660                 665                 670

Tyr Tyr Val Phe Phe Gln Leu Glu Leu Arg Arg Val Val Ala Gly Glu
                675                 680                 685

Gly Ser Gly Ser Val Ser Leu Ala Leu His Leu Gln Pro Leu Arg Ser
            690                 695                 700

Ala Ala Gly Ala Ala Ala Leu Ala Leu Thr Val Asp Leu Pro Pro Ala
705                 710                 715                 720

Ser Ser Glu Ala Arg Asn Ser Ala Phe Gly Phe Gln Gly Arg Leu Leu
                725                 730                 735

His Leu Ser Ala Gly Gln Arg Leu Gly Val His Leu His Thr Glu Ala
                740                 745                 750

Arg Ala Arg His Ala Trp Gln Leu Thr Gln Gly Ala Thr Val Leu Gly
                755                 760                 765
```

```
Leu Phe Arg Val Thr Pro Glu Ile Pro Ala Gly Leu Pro Ser Pro Arg
        770                 775                 780

Ser Glu Gly Ser Gly Ala Thr Asn Phe Ser Leu Leu Lys Gln Ala Gly
785                 790                 795                 800

Asp Val Glu Glu Asn Pro Gly Pro Met Tyr Arg Met Gln Leu Leu Ser
                805                 810                 815

Cys Ile Ala Leu Ser Leu Ala Leu Val Thr Asn Ser Gly Ile His Val
                820                 825                 830

Phe Ile Leu Gly Cys Phe Ser Ala Gly Leu Pro Lys Thr Glu Ala Asn
                835                 840                 845

Trp Val Asn Val Ile Ser Asp Leu Lys Lys Ile Glu Asp Leu Ile Gln
850                 855                 860

Ser Met His Ile Asp Ala Thr Leu Tyr Thr Glu Ser Asp Val His Pro
865                 870                 875                 880

Ser Cys Lys Val Thr Ala Met Lys Cys Phe Leu Leu Glu Leu Gln Val
                885                 890                 895

Ile Ser Leu Glu Ser Gly Asp Ala Ser Ile His Asp Thr Val Glu Asn
                900                 905                 910

Leu Ile Ile Leu Ala Asn Asn Ser Leu Ser Ser Asn Gly Asn Val Thr
                915                 920                 925

Glu Ser Gly Cys Lys Glu Cys Glu Glu Leu Glu Glu Lys Asn Ile Lys
930                 935                 940

Glu Phe Leu Gln Ser Phe Val His Ile Val Gln Met Phe Ile Asn Thr
945                 950                 955                 960

Ser Ser Gly Gly Gly Ser Gly Gly Gly Ser Gly Gly Gly Gly Ser
                965                 970                 975

Gly Gly Gly Gly Ser Gly Gly Gly Ser Leu Gln Ala Pro Arg Arg Ala
                980                 985                 990

Arg Gly Cys Arg Thr Leu Gly Leu Pro Ala Leu Leu Leu Leu Leu Leu
                995                 1000                1005

Leu Arg Pro Pro Ala Thr Arg Gly Ile Thr Cys Pro Pro Pro Met
        1010                1015                1020

Ser Val Glu His Ala Asp Ile Trp Val Lys Ser Tyr Ser Leu Tyr
        1025                1030                1035

Ser Arg Glu Arg Tyr Ile Cys Asn Ser Gly Phe Lys Arg Lys Ala
        1040                1045                1050

Gly Thr Ser Ser Leu Thr Glu Cys Val Leu Asn Lys Ala Thr Asn
        1055                1060                1065

Val Ala His Trp Thr Thr Pro Ser Leu Lys Cys Ile Arg
        1070                1075                1080

<210> SEQ ID NO 33
<211> LENGTH: 3245
<212> TYPE: DNA
<213> ORGANISM: Artificial Sequence
<220> FEATURE:
<223> OTHER INFORMATION: Synthetic Sequence

<400> SEQUENCE: 33
atggccttac cagtgaccgc cttgctcctg ccgctggcct tgctgctcca cgccgccagg      60
ccgatggccg actacaagga catcgtgatg acccagagcc acaagttcat gagcaccagc     120
gtgggcgaca gggtgaacat cacctgcaag gccagccaga acgtggacag cgccgtggcc     180
tggtaccagc agaagcccgg ccagagcccc aaggccctga tctacagcgc cagctacagg     240
tacagcggcg tgcccgacag gttcaccggc agggcagcg gcaccgactt caccctgacc     300
```

```
atcagcagcg tgcaggccga ggacctggcc gtgtactact gccagcagta ctacagcacc    360
cccctggacct tcggcggcgg caccaagctg gagatcaaga ggggcggcgg cggcagcggc    420
ggcggcggca gcggcggcgg cggcagcggc ggcggcggca gcgaggtgaa gctggtggag    480
agcggcggcg gcctggtgca gcccggcggc agcctgagcc tgagctgcgc cgccagcggc    540
ttcaccttca ccgactacta catgagctgg gtgaggcagc cccccggcaa ggccctggag    600
tggctggccc tgatcaggag caaggccgac ggctacacca ccgagtacag cgccagcgtg    660
aagggcaggt tcaccctgag cagggacgac agccagagca tcctgtacct gcagatgaac    720
gccctgaggc ccgaggacag cgccacctac tactgcgcca gggacgccgc ctactacagc    780
tactacagcc ccgagggcgc catggactac tggggccagg gcaccagcgt gaccgtgagc    840
agcgccagcg cgccaccac gacgccagcc ccgcgaccac caacaccggc gcccaccatc    900
gcgtcgcagc ccctgtccct gcgcccagag gcgtgccggc cagcggcggg gggcgcagtg    960
cacacgaggg ggctggactt cgcctgtgat atctacatct gggcgccctt ggccgggact    1020
tgtggggtcc ttctcctgtc actggttatc acccctttact gcaggagtaa gaggagcagg    1080
ctcctgcaca gtgactacat gaacatgact ccccgccgcc ccgggcccac ccgcaagcat    1140
taccagccct atgccccacc acgcgacttc gcagcctatc gctccagagt gaagttcagc    1200
aggagcgcag acgcccccgc gtaccagcag ggccagaacc agctctataa cgagctcaat    1260
ctaggacgaa gagaggagta cgatgttttg gacaagagac gtggccggga ccctgagatg    1320
gggggaaagc cgcagagaag gaagaacccc caggaaggcc tgtacaatga actgcagaaa    1380
gataagatgg cggaggccta cagtgagatt gggatgaaag cgagcgccg gaggggcaag    1440
gggcacgatg gcctttacca gggtctcagt acagccacca aggacaccta cgacgccctt    1500
cacatgcagg ccctgccccc tcgcggcagc ggcgaaggcc cggcagcct gctgacctgc    1560
ggcgatgtgg aagaaaaccc gggccccatg aatacgcct ctgacgcttc actggacccc    1620
gaagccccgt ggcctcccgc gccccgcgct cgcgcctgcc gcgtactgcc ttgggccctg    1680
gtcgcgggc tgctgctgct gctgctgctc gctgccgcct gcgccgtctt cctcgcctgc    1740
ccctgggccg tgtccggggc tcgcgcctcg cccggctccg cggccagccc gagactccgc    1800
gagggtcccg agctttcgcc cgacgatccc gccggcctct tggacctgcg cagggcatg    1860
tttgcgcagc tggtggccca aaatgttctg ctgatcgatg ggcccctgag ctggtacagt    1920
gacccaggcc tggcaggcgt gtccctgacg gggggcctga gctacaaaga ggacacgaag    1980
gagctggtgg tggccaaggc tggagtctac tatgtcttct ttcaactaga gctgcggcgc    2040
gtggtggccg gcgagggctc aggctccgtt tcacttgcgc tgcacctgca gccactgcgc    2100
tctgctgctg ggccgccgc cctggctttg accgtggacc tgccaccgc ctcctccgag    2160
gctcggaact cggccttcgg tttccagggc cgcttgctgc acctgagtgc cggccagcgc    2220
ctgggcgtcc atcttcacac tgaggccagg gcacgccatg cctggcagct acccagggc    2280
gccacagtct tgggactctt ccgggtgacc cccgaaatcc cagccggact cccttcaccg    2340
aggtcggaag gaagcggagc tactaacttc agcctgctga gcaggctgg agacgtggag    2400
gagaaccctg gacctatgta cagaatgcag ctgctgagct gcatcgccct gagcctggcc    2460
ctggtgacca acagcggcat ccacgtgttc atcctgggct gcttcagcgc cggcctgccc    2520
aagaccgagg ccaactgggt gaacgtgatc agcgacctga agaagatcga ggacctgatc    2580
cagagcatgc acatcgacgc caccctgtac accgagagcg acgtgcaccc cagctgcaag    2640
```

```
gtgaccgcca tgaagtgctt cctgctggag ctgcaggtga tcagcctgga gagcggcgac    2700
gccagcatcc acgacaccgt ggagaacctg atcatcctgg ccaacaacag cctgagcagc    2760
aacggcaacg tgaccgagag cggctgcaag gagtgcgagg agctggagga agaacatc     2820 aaggagttcc tgcagagctt cgtgcacatc gtgcagatgt tcatcaacac cagctccggc    2880
ggcggctccg gcggcggcgg ctccggcggc ggcggctccg gcggcggcgg ctccggcggc    2940 ggctcctgc aggcccccag aagagccaga ggctgcagaa ccctgggcct gcccgccctg    3000
ctgctgctgc tgctgctgag acccccgcc accagaggca tcacctgccc cccccccatg    3060
agcgtggagc acgccgacat ctgggtgaag agctacagcc tgtacagcag agagagatac    3120
atctgcaaca gcggcttcaa gagaaaggcc ggcaccagca gcctgaccga gtgcgtgctg    3180
aacaaggcca ccaacgtggc ccactggacc accccccagcc tgaagtgcat cagataagtt    3240
taaac                                                              3245
```

<210> SEQ ID NO 34
<211> LENGTH: 1324
<212> TYPE: PRT
<213> ORGANISM: Artificial Sequence
<220> FEATURE:
<223> OTHER INFORMATION: Synthetic Sequence

<400> SEQUENCE: 34

```
Asp Arg Thr Met Ala Leu Pro Val Thr Ala Leu Leu Leu Pro Leu Ala
1               5                   10                  15

Leu Leu Leu His Ala Ala Arg Pro Met Ala Asp Tyr Lys Asp Ile Val
            20                  25                  30

Met Thr Gln Ser His Lys Phe Met Ser Thr Ser Val Gly Asp Arg Val
        35                  40                  45

Asn Ile Thr Cys Lys Ala Ser Gln Asn Val Asp Ser Ala Val Ala Trp
    50                  55                  60

Tyr Gln Gln Lys Pro Gly Gln Ser Pro Lys Ala Leu Ile Tyr Ser Ala
65                  70                  75                  80

Ser Tyr Arg Tyr Ser Gly Val Pro Asp Arg Phe Thr Gly Arg Gly Ser
                85                  90                  95

Gly Thr Asp Phe Thr Leu Thr Ile Ser Ser Val Gln Ala Glu Asp Leu
            100                 105                 110

Ala Val Tyr Tyr Cys Gln Gln Tyr Tyr Ser Thr Pro Trp Thr Phe Gly
        115                 120                 125

Gly Gly Thr Lys Leu Glu Ile Lys Arg Gly Gly Gly Ser Gly Gly
    130                 135                 140

Gly Gly Ser Gly Gly Gly Ser Gly Gly Gly Ser Glu Val Lys
145                 150                 155                 160

Leu Val Glu Ser Gly Gly Leu Val Gln Pro Gly Gly Ser Leu Ser
                165                 170                 175

Leu Ser Cys Ala Ala Ser Gly Phe Thr Phe Thr Asp Tyr Tyr Met Ser
            180                 185                 190

Trp Val Arg Gln Pro Pro Gly Lys Ala Leu Glu Trp Leu Ala Leu Ile
        195                 200                 205

Arg Ser Lys Ala Asp Gly Tyr Thr Thr Glu Tyr Ser Ala Ser Val Lys
    210                 215                 220

Gly Arg Phe Thr Leu Ser Arg Asp Asp Ser Gln Ser Ile Leu Tyr Leu
225                 230                 235                 240

Gln Met Asn Ala Leu Arg Pro Glu Asp Ser Ala Thr Tyr Tyr Cys Ala
                245                 250                 255
```

Arg Asp Ala Ala Tyr Tyr Ser Tyr Tyr Ser Pro Glu Gly Ala Met Asp
            260                 265                 270

Tyr Trp Gly Gln Gly Thr Ser Val Thr Val Ser Ser Ala Ser Gly Ala
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Arg Ser Lys Arg Ser Arg Leu Leu His Ser Asp
        355                 360                 365

Tyr Met Asn Met Thr Pro Arg Arg Pro Gly Pro Thr Arg Lys His Tyr
    370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg Gly
            500                 505                 510

Ser Gly Ala Thr Asn Phe Ser Leu Leu Lys Gln Ala Gly Asp Val Glu
        515                 520                 525

Glu Asn Pro Gly Pro Met Ala Leu Pro Val Thr Ala Leu Leu Leu Pro
    530                 535                 540

Leu Ala Leu Leu Leu His Ala Ala Arg Pro Met Ala Asp Tyr Lys Asp
545                 550                 555                 560

Ile Val Met Thr Gln Ser His Lys Phe Leu Val Ser Val Gly Asp
                565                 570                 575

Arg Val Ser Ile Thr Cys Lys Ala Ser Gln Asp Val Ser Thr Ala Val
        580                 585                 590

Ala Trp Tyr Gln Gln Lys Pro Gly Gln Ser Pro Lys Leu Leu Ile Tyr
    595                 600                 605

Ser Ala Ser Tyr Arg Tyr Thr Gly Val Pro Asp Arg Phe Ile Gly Ser
    610                 615                 620

Gly Ser Gly Thr Asp Phe Thr Leu Thr Ile Ser Ser Val Gln Ala Glu
625                 630                 635                 640

Asp Leu Ala Asp Tyr Phe Cys Gln Gln His Tyr Ser Thr Pro Leu Thr
                645                 650                 655

Phe Gly Ala Gly Thr Lys Leu Glu Ile Lys Arg Gly Gly Gly Gly Ser
            660                 665                 670

Gly Gly Gly Gly Ser Gly Gly Gly Ser Ser Gly Gly Ser Glu
              675                 680             685

Val Gln Leu Lys Glu Ser Gly Pro Gly Leu Val Ala Pro Ser Gln Ser
    690                 695                 700

Leu Ser Ile Thr Cys Thr Val Ser Gly Phe Pro Leu Thr Ser Tyr Gly
705                 710                 715                 720

Val Ser Trp Val Arg Gln Pro Pro Gly Lys Gly Leu Glu Trp Leu Gly
                725                 730                 735

Val Ile Trp Gly Asp Gly Ser Thr Asn Tyr His Ser Ala Leu Ile Ser
            740                 745                 750

Arg Leu Ser Ile Ser Lys Asp Asn Ser Lys Ser Gln Val Phe Leu Lys
        755                 760                 765

Leu Asn Asn Leu Gln Thr Asp Asp Thr Ala Thr Tyr Tyr Cys Ala Arg
    770                 775                 780

Asp Thr Tyr Tyr Pro Tyr Tyr Ala Met Asp Tyr Trp Gly Gln Gly Thr
785                 790                 795                 800

Ser Val Thr Val Ser Ser Thr Thr Thr Pro Ala Pro Arg Pro Pro Thr
                805                 810                 815

Pro Ala Pro Thr Ile Ala Ser Gln Pro Leu Ser Leu Arg Pro Glu Ala
            820                 825                 830

Cys Arg Pro Ala Ala Gly Gly Ala Val His Thr Arg Gly Leu Asp Phe
        835                 840                 845

Ala Cys Asp Ile Tyr Ile Trp Ala Pro Leu Ala Gly Thr Cys Gly Val
    850                 855                 860

Leu Leu Leu Ser Leu Val Ile Thr Leu Tyr Cys Lys Arg Gly Arg Lys
865                 870                 875                 880

Lys Leu Leu Tyr Ile Phe Lys Gln Pro Phe Met Arg Pro Val Gln Thr
                885                 890                 895

Thr Gln Glu Glu Asp Gly Cys Ser Cys Arg Phe Pro Glu Glu Glu Glu
            900                 905                 910

Gly Gly Cys Glu Leu Arg Val Lys Phe Ser Arg Ser Ala Asp Ala Pro
        915                 920                 925

Ala Tyr Gln Gln Gly Gln Asn Gln Leu Tyr Asn Glu Leu Asn Leu Gly
    930                 935                 940

Arg Arg Glu Glu Tyr Asp Val Leu Asp Lys Arg Arg Gly Arg Asp Pro
945                 950                 955                 960

Glu Met Gly Gly Lys Pro Gln Arg Arg Lys Asn Pro Gln Glu Gly Leu
                965                 970                 975

Tyr Asn Glu Leu Gln Lys Asp Lys Met Ala Glu Ala Tyr Ser Glu Ile
            980                 985                 990

Gly Met Lys Gly Glu Arg Arg Arg Gly Lys Gly His Asp Gly Leu Tyr
        995                 1000                1005

Gln Gly Leu Ser Thr Ala Thr Lys Asp Thr Tyr Asp Ala Leu His
    1010                1015                1020

Met Gln Ala Leu Pro Pro Arg Gly Ser Gly Glu Gly Arg Gly Ser
    1025                1030                1035

Leu Leu Thr Cys Gly Asp Val Glu Glu Asn Pro Gly Pro Met Tyr
    1040                1045                1050

Arg Met Gln Leu Leu Ser Cys Ile Ala Leu Ser Leu Ala Leu Val
    1055                1060                1065

Thr Asn Ser Gly Ile His Val Phe Ile Leu Gly Cys Phe Ser Ala
    1070                1075                1080

Gly Leu Pro Lys Thr Glu Ala Asn Trp Val Asn Val Ile Ser Asp

| | | | | | | | | | | |
|---|---|---|---|---|---|---|---|---|---|---|
| | | 1085 | | | 1090 | | | | 1095 | |
| Leu | Lys | Lys | Ile | Glu | Asp | Leu | Ile | Gln | Ser | Met | His | Ile | Asp | Ala |
| | | 1100 | | | | 1105 | | | | 1110 | |
| Thr | Leu | Tyr | Thr | Glu | Ser | Asp | Val | His | Pro | Ser | Cys | Lys | Val | Thr |
| | | 1115 | | | | 1120 | | | | 1125 | |
| Ala | Met | Lys | Cys | Phe | Leu | Leu | Glu | Leu | Gln | Val | Ile | Ser | Leu | Glu |
| | | 1130 | | | | 1135 | | | | 1140 | |
| Ser | Gly | Asp | Ala | Ser | Ile | His | Asp | Thr | Val | Glu | Asn | Leu | Ile | Ile |
| | | 1145 | | | | 1150 | | | | 1155 | |
| Leu | Ala | Asn | Asn | Ser | Leu | Ser | Ser | Asn | Gly | Asn | Val | Thr | Glu | Ser |
| | | 1160 | | | | 1165 | | | | 1170 | |
| Gly | Cys | Lys | Glu | Cys | Glu | Glu | Leu | Glu | Glu | Lys | Asn | Ile | Lys | Glu |
| | | 1175 | | | | 1180 | | | | 1185 | |
| Phe | Leu | Gln | Ser | Phe | Val | His | Ile | Val | Gln | Met | Phe | Ile | Asn | Thr |
| | | 1190 | | | | 1195 | | | | 1200 | |
| Ser | Ser | Gly | Gly | Gly | Ser | Gly | Gly | Gly | Ser | Gly | Gly | Gly | Gly | |
| | | 1205 | | | | 1210 | | | | 1215 | |
| Ser | Gly | Gly | Gly | Gly | Ser | Gly | Gly | Gly | Ser | Leu | Gln | Ala | Pro | Arg |
| | | 1220 | | | | 1225 | | | | 1230 | |
| Arg | Ala | Arg | Gly | Cys | Arg | Thr | Leu | Gly | Leu | Pro | Ala | Leu | Leu | Leu |
| | | 1235 | | | | 1240 | | | | 1245 | |
| Leu | Leu | Leu | Leu | Arg | Pro | Pro | Ala | Thr | Arg | Gly | Ile | Thr | Cys | Pro |
| | | 1250 | | | | 1255 | | | | 1260 | |
| Pro | Pro | Met | Ser | Val | Glu | His | Ala | Asp | Ile | Trp | Val | Lys | Ser | Tyr |
| | | 1265 | | | | 1270 | | | | 1275 | |
| Ser | Leu | Tyr | Ser | Arg | Glu | Arg | Tyr | Ile | Cys | Asn | Ser | Gly | Phe | Lys |
| | | 1280 | | | | 1285 | | | | 1290 | |
| Arg | Lys | Ala | Gly | Thr | Ser | Ser | Leu | Thr | Glu | Cys | Val | Leu | Asn | Lys |
| | | 1295 | | | | 1300 | | | | 1305 | |
| Ala | Thr | Asn | Val | Ala | His | Trp | Thr | Thr | Pro | Ser | Leu | Lys | Cys | Ile |
| | | 1310 | | | | 1315 | | | | 1320 | |
| Arg | | | | | | | | | | | | | | |

<210> SEQ ID NO 35
<211> LENGTH: 3985
<212> TYPE: DNA
<213> ORGANISM: Artificial Sequence
<220> FEATURE:
<223> OTHER INFORMATION: Synthetic Sequence

<400> SEQUENCE: 35

```
gcgatcgcac catggcctta ccagtgaccg ccttgctcct gccgctggcc ttgctgctcc      60
acgccgccag gccgatggcc gactacaagg acatcgtgat gacccagagc cacaagttca     120
tgagcaccag cgtgggcgac agggtgaaca tcacctgcaa ggccagccag aacgtggaca     180
gcgccgtggc ctggtaccag cagaagcccg gccagagccc caaggccctg atctacagcg     240
ccagctacag gtacagcggc gtgcccgaca ggttcaccgg cagggggcagc ggcaccgact     300
tcaccctgac catcagcagc gtgcaggccg aggacctggc cgtgtactac tgccagcagt     360
actacagcac ccccctggac cttcggcggcg gcaccaagct ggagatcaag aggggcggcg     420
gcggcagcgg cggcggcggc agcggcggcg gcggcagcgg cggcggcggc agcgaggtga     480
agctggtgga gagcggcggc ggcctggtgc agcccggcgg cagcctgagc ctgagctgcg     540
ccgccagcgg cttcaccttc accgactact acatgagctg ggtgaggcag ccccccggca     600
```

```
aggccctgga gtggctggcc ctgatcagga gcaaggccga cggctacacc accgagtaca    660
gcgccagcgt gaagggcagg ttcaccctga cagggacga cagccagagc atcctgtacc    720
tgcagatgaa cgccctgagg cccgaggaca cgccaccta ctactgcgcc agggacgccg    780
cctactacag ctactacagc cccgagggcg ccatggacta ctggggccag ggcaccagcg    840
tgaccgtgag cagcgccagc ggcgccacca cgacgccagc gccgcgacca ccaacaccgg    900
cgcccaccat cgcgtcgcag cccctgtccc tgcgcccaga ggcgtgccgg ccagcggcgg    960
ggggcgcagt gcacacgagg gggctggact tcgcctgtga tatctacatc tgggcgccct   1020
tggccgggac ttgtgggggtc cttctcctgt cactggttat caccctttac tgcaggagta   1080
agaggagcag gctcctgcac agtgactaca tgaacatgac tccccgccgc cccgggccca   1140
cccgcaagca ttaccagccc tatgccccac cacgcgactt cgcagcctat cgctccagag   1200
tgaagttcag caggagcgca gacgcccccg cgtaccagca gggccagaac cagctctata   1260
acgagctcaa tctaggacga agagaggagt acgatgtttt ggacaagaga cgtggccggg   1320
accctgagat gggggggaaag ccgcagagaa ggaagaaccc tcaggaaggc ctgtacaatg   1380
aactgcagaa agataagatg gcggaggcct acagtgagat tgggatgaaa ggcgagcgcc   1440
ggaggggcaa ggggcacgat ggcctttacc agggtctcag tacagccacc aaggacacct   1500
acgacgccct tcacatgcag gccctgcccc ctcgcggaag cggagccacc aacttcagcc   1560
tgctgaagca ggccggcgac gtggaggaga ccccggccc catggccctg cccgtgaccg   1620
ccctgctgct gccccctggcc ctgctgctgc acgccgccag gcccatggcc gactacaagg   1680
acatcgtgat gacccagagc cacaagttcc tgctggtgag cgtgggcgac agggtgagca   1740
tcacctgcaa ggccagccag gacgtgagca ccgccgtggc ctggtaccag cagaagcccg   1800
gccagagccc caagctgctg atctacacgcg ccagctacag gtacaccggc gtgcccgaca   1860
ggttcatcgg cagcggcagc ggcaccgact tcaccctgac catcagcagc gtgcaggccg   1920
aggacctggc cgactacttc tgccagcagc actacagcac ccccctgacc ttcggcgccg   1980
gcaccaagct ggagatcaag aggggcggcg gcggcagcgg cggcggcggc agcggcggcg   2040
gcggcagcag cggcggcggc agcgaggtgc agctgaagga gagcggcccc ggcctggtgg   2100
ccccccagcca gagcctgagc atcacctgca ccgtgagcgg cttcccctg accagctacg   2160
gcgtgagctg ggtgaggcag ccccccggca agggcctgga gtggctgggc gtgatctggg   2220
gcgacggcag caccaactac cacagcgccc tgatcagcag gctgagcatc agcaaggaca   2280
acagcaagag ccaggtgttc ctgaagctga acaacctgca gaccgacgac accgccacct   2340
actactgcgc cagggacacc tactacccct actacgccat ggactactgg ggccagggca   2400
ccagcgtgac cgtgagcagc accaccaccc ccgcccccag ccccccaccc ccgccccca   2460
ccatcgccag ccagcccctg agcctgaggc ccgaggcctg caggcccgcc gccggcggcg   2520
ccgtgcacac caggggcctg gacttcgcct gcgacatcta catctgggcc ccctggccg   2580
gcacctgcgg cgtgctgctg ctgagcctgg tgatcaccct gtactgcaaa cggggcagaa   2640
agaaactcct gtatatattc aaacaaccat ttatgagacc agtacaaact actcaagagg   2700
aagatggctg tagctgccga tttccagaag aagaagaagg aggatgtgaa ctgagggtga   2760
agttcagcag gagcgccgac gcccccgcct accagcaggg ccagaaccag ctgtacaacg   2820
agctgaacct gggcaggagg gaggagtacg acgtgctgga caagaggagg ggcagggacc   2880
ccgagatggg cggcaagccc cagaggagga gaaccccca ggagggcctg tacaacgagc   2940
tgcagaagga caagatggcc gaggcctaca gcgagatcgg catgaagggc gagaggagga   3000
```

-continued

```
ggggcaaggg ccacgacggc ctgtaccagg gcctgagcac cgccaccaag gacacctacg    3060
acgccctgca catgcaggcc ctgccccccca ggggcagcgg cgaaggccgc ggcagcctgc   3120
tgacctgcgg cgatgtggaa gaaaacccgg gccccatgta cagaatgcag ctgctgagct    3180
gcatcgccct gagcctggcc ctggtgacca acagcggcat ccacgtgttc atcctgggct    3240
gcttcagcgc cggcctgccc aagaccgagg ccaactgggt gaacgtgatc agcgacctga    3300
agaagatcga ggacctgatc cagagcatgc acatcgacgc caccctgtac accgagagcg    3360
acgtgcaccc cagctgcaag gtgaccgcca tgaagtgctt cctgctggag ctgcaggtga    3420
tcagcctgga gagcggcgac gccagcatcc acgacaccgt ggagaacctg atcatcctgg    3480
ccaacaacag cctgagcagc aacggcaacg tgaccgagag cggctgcaag gagtgcgagg    3540
agctggagga agaagaacatc aaggagttcc tgcagagctt cgtgcacatc gtgcagatgt   3600
tcatcaacac cagctccggc ggcggctccg gcggcggcgg ctccggcggc ggcggctccg    3660
gcggcggcgc ctccggcggc ggctccctgc aggcccccag aagagccaga ggctgcagaa    3720
ccctgggcct gcccgccctg ctgctgctgc tgctgctgag acccccccgcc accagaggca   3780 tcacctgccc ccccccccatg agcgtggagc acgccgacat ctgggtgaag agctacagcc   3840
tgtacagcag agagagatac atctgcaaca gcggcttcaa gagaaaggcc ggcaccagca    3900
gcctgaccga gtgcgtgctg aacaaggcca ccaacgtggc ccactggacc acccccagcc    3960
tgaagtgcat cagataagtt taaac                                         3985
```

<210> SEQ ID NO 36
<211> LENGTH: 1313
<212> TYPE: PRT
<213> ORGANISM: Artificial Sequence
<220> FEATURE:
<223> OTHER INFORMATION: Synthetic Sequence

<400> SEQUENCE: 36

```
Asp Arg Thr Met Ala Leu Pro Val Thr Ala Leu Leu Leu Pro Leu Ala
1               5                   10                  15

Leu Leu Leu His Ala Ala Arg Pro Met Ala Asp Tyr Lys Asp Ile Val
            20                  25                  30

Met Thr Gln Ser His Lys Phe Met Ser Thr Ser Val Gly Asp Arg Val
        35                  40                  45

Asn Ile Thr Cys Lys Ala Ser Gln Asn Val Asp Ser Ala Val Ala Trp
    50                  55                  60

Tyr Gln Gln Lys Pro Gly Gln Ser Pro Lys Ala Leu Ile Tyr Ser Ala
65                  70                  75                  80

Ser Tyr Arg Tyr Ser Gly Val Pro Asp Arg Phe Thr Gly Arg Gly Ser
                85                  90                  95

Gly Thr Asp Phe Thr Leu Thr Ile Ser Ser Val Gln Ala Glu Asp Leu
            100                 105                 110

Ala Val Tyr Tyr Cys Gln Gln Tyr Tyr Ser Thr Pro Trp Thr Phe Gly
        115                 120                 125

Gly Gly Thr Lys Leu Glu Ile Lys Arg Gly Gly Gly Ser Gly Gly
    130                 135                 140

Gly Gly Ser Gly Gly Gly Gly Ser Gly Gly Gly Ser Glu Val Lys
145                 150                 155                 160

Leu Val Glu Ser Gly Gly Gly Leu Val Gln Pro Gly Gly Ser Leu Ser
                165                 170                 175

Leu Ser Cys Ala Ala Ser Gly Phe Thr Phe Thr Asp Tyr Tyr Met Ser
```

```
            180                 185                 190
Trp Val Arg Gln Pro Pro Gly Lys Ala Leu Glu Trp Leu Ala Leu Ile
            195                 200                 205

Arg Ser Lys Ala Asp Gly Tyr Thr Thr Glu Tyr Ser Ala Ser Val Lys
        210                 215                 220

Gly Arg Phe Thr Leu Ser Arg Asp Asp Ser Gln Ser Ile Leu Tyr Leu
225                 230                 235                 240

Gln Met Asn Ala Leu Arg Pro Glu Asp Ser Ala Thr Tyr Tyr Cys Ala
                245                 250                 255

Arg Asp Ala Ala Tyr Tyr Ser Tyr Tyr Ser Pro Glu Gly Ala Met Asp
            260                 265                 270

Tyr Trp Gly Gln Gly Thr Ser Val Thr Val Ser Ser Ala Ser Gly Ala
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Arg Ser Lys Arg Ser Arg Leu Leu His Ser Asp
        355                 360                 365

Tyr Met Asn Met Thr Pro Arg Arg Pro Gly Pro Thr Arg Lys His Tyr
    370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg Gly
            500                 505                 510

Ser Gly Ala Thr Asn Phe Ser Leu Leu Lys Gln Ala Gly Asp Val Glu
        515                 520                 525

Glu Asn Pro Gly Pro Met Ala Leu Pro Val Thr Ala Leu Leu Leu Pro
    530                 535                 540

Leu Ala Leu Leu Leu His Ala Ala Arg Pro Asp Ile Gln Met Thr Gln
545                 550                 555                 560

Ser His Lys Phe Met Ser Thr Ser Val Gly Asp Arg Val Ser Ile Thr
                565                 570                 575

Cys Lys Ala Ser Gln Asp Val Ser Thr Ala Val Ala Trp Phe Gln Gln
            580                 585                 590

Lys Pro Gly Gln Ser Pro Lys Leu Leu Ile Tyr Ser Pro Ser Tyr Arg
        595                 600                 605
```

Tyr Thr Gly Val Pro Asp Arg Phe Thr Gly Ser Gly Ser Gly Thr Asp
    610             615                 620

Phe Thr Phe Thr Ile Ser Ser Val Gln Ala Glu Asp Leu Ala Val Tyr
625             630                 635                 640

Tyr Cys Gln Gln Leu Tyr Ser Thr Pro Tyr Thr Phe Gly Gly Gly Thr
            645                 650                 655

Lys Leu Glu Ile Lys Gly Gly Gly Ser Gly Gly Gly Gly Ser Gly
            660                 665                 670

Gly Gly Gly Ser Glu Val Gln Leu Gln Gln Ser Gly Pro Glu Leu Val
        675                 680                 685

Lys Pro Gly Ala Ser Val Lys Met Ser Cys Lys Ala Ser Gly Tyr Thr
690                 695                 700

Phe Thr Asp Tyr Tyr Leu Asp Trp Val Lys Gln Ser His Gly Glu Ser
705                 710                 715                 720

Phe Glu Trp Ile Gly Arg Val Asn Pro Tyr Asn Gly Gly Thr Ile Tyr
                725                 730                 735

Asn Gln Lys Phe Lys Gly Lys Ala Thr Leu Thr Val Asp Lys Ser Ser
            740                 745                 750

Ser Thr Ala Tyr Met Asp Leu Asn Ser Leu Thr Ser Glu Asp Ser Ala
        755                 760                 765

Val Tyr Tyr Cys Ala Arg Asp His Tyr Arg Tyr Asp Pro Leu Leu Asp
770                 775                 780

Tyr Trp Gly Gln Gly Thr Thr Leu Thr Val Ser Ser Thr Thr Thr Pro
785                 790                 795                 800

Ala Pro Arg Pro Pro Thr Pro Ala Pro Thr Ile Ala Ser Gln Pro Leu
                805                 810                 815

Ser Leu Arg Pro Glu Ala Cys Arg Pro Ala Ala Gly Gly Ala Val His
            820                 825                 830

Thr Arg Gly Leu Asp Phe Ala Cys Asp Ile Tyr Ile Trp Ala Pro Leu
        835                 840                 845

Ala Gly Thr Cys Gly Val Leu Leu Leu Ser Leu Val Ile Thr Leu Tyr
850                 855                 860

Cys Arg Ser Lys Arg Ser Arg Leu Leu His Ser Asp Tyr Met Asn Met
865                 870                 875                 880

Thr Pro Arg Arg Pro Gly Pro Thr Arg Lys His Tyr Gln Pro Tyr Ala
                885                 890                 895

Pro Pro Arg Asp Phe Ala Ala Tyr Arg Ser Arg Val Lys Phe Ser Arg
            900                 905                 910

Ser Ala Asp Ala Pro Ala Tyr Gln Gln Gly Gln Asn Gln Leu Tyr Asn
        915                 920                 925

Glu Leu Asn Leu Gly Arg Arg Glu Glu Tyr Asp Val Leu Asp Lys Arg
930                 935                 940

Arg Gly Arg Asp Pro Glu Met Gly Gly Lys Pro Gln Arg Arg Lys Asn
945                 950                 955                 960

Pro Gln Glu Gly Leu Tyr Asn Glu Leu Gln Lys Asp Lys Met Ala Glu
                965                 970                 975

Ala Tyr Ser Glu Ile Gly Met Lys Gly Glu Arg Arg Arg Gly Lys Gly
            980                 985                 990

His Asp Gly Leu Tyr Gln Gly Leu Ser Thr Ala Thr Lys Asp Thr Tyr
        995                 1000                1005

Asp Ala Leu His Met Gln Ala Leu Pro Pro Arg Gly Ser Gly Glu
    1010                1015                1020

| | | | | | | | | | | |
|---|---|---|---|---|---|---|---|---|---|---|
|Gly|Arg|Gly|Ser|Leu|Leu|Thr|Cys|Gly|Asp|Val|Glu|Glu|Asn|Pro|
| |1025| | | |1030| | | |1035| |

Gly Pro Met Tyr Arg Met Gln Leu Leu Ser Cys Ile Ala Leu Ser
    1040                1045                1050

Leu Ala Leu Val Thr Asn Ser Gly Ile His Val Phe Ile Leu Gly
    1055                1060                1065

Cys Phe Ser Ala Gly Leu Pro Lys Thr Glu Ala Asn Trp Val Asn
    1070                1075                1080

Val Ile Ser Asp Leu Lys Lys Ile Glu Asp Leu Ile Gln Ser Met
    1085                1090                1095

His Ile Asp Ala Thr Leu Tyr Thr Glu Ser Asp Val His Pro Ser
    1100                1105                1110

Cys Lys Val Thr Ala Met Lys Cys Phe Leu Leu Glu Leu Gln Val
    1115                1120                1125

Ile Ser Leu Glu Ser Gly Asp Ala Ser Ile His Asp Thr Val Glu
    1130                1135                1140

Asn Leu Ile Ile Leu Ala Asn Asn Ser Leu Ser Ser Asn Gly Asn
    1145                1150                1155

Val Thr Glu Ser Gly Cys Lys Glu Cys Glu Glu Leu Glu Glu Lys
    1160                1165                1170

Asn Ile Lys Glu Phe Leu Gln Ser Phe Val His Ile Val Gln Met
    1175                1180                1185

Phe Ile Asn Thr Ser Ser Gly Gly Ser Gly Gly Gly Gly Ser
    1190                1195                1200

Gly Gly Gly Ser Gly Gly Gly Ser Gly Gly Ser Leu
    1205                1210                1215

Gln Ala Pro Arg Arg Ala Arg Gly Cys Arg Thr Leu Gly Leu Pro
    1220                1225                1230

Ala Leu Leu Leu Leu Leu Leu Arg Pro Pro Ala Thr Arg Gly
    1235                1240                1245

Ile Thr Cys Pro Pro Pro Met Ser Val Glu His Ala Asp Ile Trp
    1250                1255                1260

Val Lys Ser Tyr Ser Leu Tyr Ser Arg Glu Arg Tyr Ile Cys Asn
    1265                1270                1275

Ser Gly Phe Lys Arg Lys Ala Gly Thr Ser Ser Leu Thr Glu Cys
    1280                1285                1290

Val Leu Asn Lys Ala Thr Asn Val Ala His Trp Thr Thr Pro Ser
    1295                1300                1305

Leu Lys Cys Ile Arg
    1310

<210> SEQ ID NO 37
<211> LENGTH: 3941
<212> TYPE: DNA
<213> ORGANISM: Artificial Sequence
<220> FEATURE:
<223> OTHER INFORMATION: Synthetic Sequence

<400> SEQUENCE: 37
atggccttac cagtgaccgc cttgctcctg ccgctggcct tgctgctcca cgccgccagg    60
ccgatggccg actacaagga catcgtgatg acccagagcc acaagttcat gagcaccagc   120
gtgggcgaca gggtgaacat cacctgcaag gccagccaga acgtggacag cgccgtggcc   180
tggtaccaga gaagcccgg ccagagcccc aaggccctga tctacagcgc cagctacagg   240
tacagcggcg tgcccgacag gttcaccggc agggggcagcg gcaccgactt caccctgacc   300

```
atcagcagcg tgcaggccga ggacctggcc gtgtactact gccagcagta ctacagcacc    360
ccctggacct tcggcggcgg caccaagctg gagatcaaga ggggcggcgg cggcagcggc    420
ggcggcggca gcggcggcgg cggcagcggc ggcggcggca gcgaggtgaa gctggtggag    480
agcggcggcg gcctggtgca gcccggcggc agcctgagcc tgagctgcgc cgccagcggc    540
ttcaccttca ccgactacta catgagctgg gtgaggcagc ccccggcaa ggccctggag     600
tggctggccc tgatcaggag caaggccgac ggctacacca ccgagtacag cgccagcgtg    660
aagggcaggt tcaccctgag cagggacgac agccagagca tcctgtacct gcagatgaac    720
gccctgaggc ccgaggacag cgccacctac tactgcgcca gggacgccgc ctactacagc    780
tactacagcc ccgagggcgc catggactac tggggccagg gcaccagcgt gaccgtgagc    840
agcgccagcg cgccaccac gacgccagcc ccgcgaccac caacaccggc gcccaccatc    900
gcgtcgcagc ccctgtccct gcgcccagag gcgtgccggc cagcggcggg gggcgcagtg    960
cacacgaggg ggctggactt cgcctgtgat atctacatct gggcgccctt ggccgggact   1020
tgtgggtcc ttctcctgtc actggttatc accctttact gcaggagtaa gaggagcagg    1080
ctcctgcaca gtgactacat gaacatgact ccccgccgcc ccgggcccac ccgcaagcat   1140
taccagccct atgccccacc acgcgacttc gcagcctatc gctccagagt gaagttcagc   1200
aggagcgcag acgcccccgc gtaccagcag ggccagaacc agctctataa cgagctcaat   1260
ctaggacgaa gagaggagta cgatgttttg gacaagagac gtggccggga ccctgagatg   1320
gggggaaagc cgcagagaag gaagaaccct caggaaggcc tgtacaatga actgcagaaa   1380
gataagatgg cggaggccta cagtgagatt gggatgaaag cgagcgccg gaggggcaag    1440
gggcacgatg gcctttacca gggtctcagt acagccacca aggacaccta cgacgccctt   1500
cacatgcagg ccctgccccc tcgcggaagc ggagccacca acttcagcct gctgaagcag   1560
gccggcgacg tggaggagaa ccccggcccc atgggccctg ccgtgaccgc cctgctgctg   1620
cccctggccc tgctgctgca cgccgccagg cccgacatcc agatgaccca gagccacaag   1680
ttcatgagca ccagcgtggg cgacagggtg agcatcacct gcaaggccag ccaggacgtg   1740
agcaccgccg tggcctggtt ccagcagaag cccggccaga gccccaagct gctgatctac   1800
agccccagct acaggtacac cggcgtgccc gacaggttca ccggcagcgg cagcggcacc   1860
gacttcacct tcaccatcag cagcgtgcag gccgaggacc tggccgtgta ctactgccag   1920
cagctgtaca gcacccccta caccttcggc ggcggcacca gctggagat caagggaggg   1980
gggggatccg ggggaggagg ctccggcgga ggcggaagcg aggtgcagct gcagcagagc   2040
ggccccgagc tggtgaagcc cggcgccagc gtgaagatga gctgcaaggc cagcggctac   2100
accttcaccg actactacct ggactgggtg aagcagagcc acggcgagag cttcgagtgg   2160
atcggcaggg tgaaccccta caacggcggc accatctaca accagaagtt caagggcaag   2220
gccaccctga ccgtggacaa gagcagcagc accgcctaca tggacctgaa cagcctgacc   2280
agcgaggaca gcgccgtgta ctactgcgcc agggaccact acaggtacga ccccctgctg   2340
gactactggg gccagggcac cacccctgacc gtgagcagca ccaccacccc cgcccccagg   2400
ccccccaccc ccgcccccac catcgccagc cagcccctga gctgaggcc cgaggcctgc   2460
aggcccgccg ccggcggcgc cgtgcacacc aggggcctgg acttcgcctg cgacatctac   2520
atctgggccc ccctggccgg cacctgcggc gtgctgctgc tgagcctggt gatcaccctg   2580
tactgcagga gtaagaggag caggctcctg cacagtgact acatgaacat gactcccgc    2640
```

| | |
|---|---|
| cgccccgggc ccaccgcaa gcattaccag ccctatgccc caccacgcga cttcgcagcc | 2700 |
| tatcgctcca gggtgaagtt cagcaggagc gccgacgccc ccgcctacca gcagggccag | 2760 |
| aaccagctgt acaacgagct gaacctgggc aggagggagg agtacgacgt gctggacaag | 2820 |
| aggaggggca gggaccccga gatgggcggc aagccccaga ggaggaagaa ccccaggag | 2880 |
| ggcctgtaca cgagctgca aaggacaag atggccgagg cctacagcga gatcggcatg | 2940 |
| aagggcgaga ggaggagggg caagggccac gacggcctgt accagggcct gagcaccgcc | 3000 |
| accaaggaca cctacgacgc cctgcacatg caggccctgc ccccagggg cagcggcgaa | 3060 |
| ggccgcggca gcctgctgac ctgcggcgat gtggaagaaa acccgggccc catgtacaga | 3120 |
| atgcagctgc tgagctgcat cgccctgagc ctggccctgg tgaccaacag cggcatccac | 3180 |
| gtgttcatcc tgggctgctt cagcgccggc ctgcccaaga ccgaggccaa ctgggtgaac | 3240 |
| gtgatcagcg acctgaagaa gatcgaggac ctgatccaga gcatgcacat cgacgccacc | 3300 |
| ctgtacaccg agagcgacgt gcaccccagc tgcaaggtga ccgccatgaa gtgcttcctg | 3360 |
| ctggagctgc aggtgatcag cctggagagc ggcgacgcca gcatccacga caccgtggag | 3420 |
| aacctgatca tcctggccaa caacagcctg agcagcaacg gcaacgtgac cgagagcggc | 3480 |
| tgcaaggagt gcgaggagct ggaggagaag aacatcaagg agttcctgca gagcttcgtg | 3540 |
| cacatcgtgc agatgttcat caacaccagc tccggcggcg gctccggcgg cggcggctcc | 3600 |
| ggcggcggcg gctccggcgg cggcggctcc ggcggcggct ccctgcaggc ccccagaaga | 3660 |
| gccagaggct gcagaaccct gggcctgccc gccctgctgc tgctgctgct gctgagaccc | 3720 |
| cccgccacca gaggcatcac ctgccccccc cccatgagcg tggagcacgc cgacatctgg | 3780 |
| gtgaagagct acagcctgta cagcagagag agatacatct gcaacagcgg cttcaagaga | 3840 |
| aaggccggca ccagcagcct gaccgagtgc gtgctgaaca aggccaccaa cgtggcccac | 3900 |
| tggaccaccc ccagcctgaa gtgcatcaga taagtttaaa c | 3941 |

<210> SEQ ID NO 38
<211> LENGTH: 1061
<212> TYPE: PRT
<213> ORGANISM: Artificial Sequence
<220> FEATURE:
<223> OTHER INFORMATION: Synthetic Sequence

<400> SEQUENCE: 38

```
Asp Arg Thr Met Ala Leu Pro Val Thr Ala Leu Leu Leu Pro Leu Ala
1               5                   10                  15

Leu Leu Leu His Ala Ala Arg Pro Asp Val Val Met Thr Gln Ser His
            20                  25                  30

Arg Phe Met Ser Thr Ser Val Gly Asp Arg Val Ser Ile Thr Cys Arg
        35                  40                  45

Ala Ser Gln Asp Val Asn Thr Ala Val Ser Trp Tyr Gln Gln Lys Pro
    50                  55                  60

Gly Gln Ser Pro Lys Leu Leu Ile Phe Ser Ala Ser Tyr Arg Tyr Thr
65                  70                  75                  80

Gly Val Pro Asp Arg Phe Thr Gly Ser Gly Ser Gly Ala Asp Phe Thr
                85                  90                  95

Leu Thr Ile Ser Ser Val Gln Ala Glu Asp Leu Ala Val Tyr Tyr Cys
            100                 105                 110

Gln Gln His Tyr Ser Thr Pro Trp Thr Phe Gly Gly Gly Thr Lys Leu
        115                 120                 125

Asp Ile Lys Gly Gly Gly Gly Ser Gly Gly Gly Gly Ser Gly Gly Gly
```

```
            130                 135                 140
Gly Ser Gln Ile Gln Leu Val Gln Ser Gly Pro Asp Leu Lys Lys Pro
145                 150                 155                 160

Gly Glu Thr Val Lys Leu Ser Cys Lys Ala Ser Gly Tyr Thr Phe Thr
                165                 170                 175

Asn Phe Gly Met Asn Trp Val Lys Gln Ala Pro Gly Lys Gly Phe Lys
                180                 185                 190

Trp Met Ala Trp Ile Asn Thr Tyr Thr Gly Glu Ser Tyr Phe Ala Asp
            195                 200                 205

Asp Phe Lys Gly Arg Phe Ala Phe Ser Val Glu Thr Ser Ala Thr Thr
210                 215                 220

Ala Tyr Leu Gln Ile Asn Asn Leu Lys Thr Glu Asp Thr Ala Thr Tyr
225                 230                 235                 240

Phe Cys Ala Arg Gly Glu Ile Tyr Tyr Gly Tyr Asp Gly Gly Phe Ala
                245                 250                 255

Tyr Trp Gly Gln Gly Thr Leu Val Thr Val Ser Ala Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Arg Ser Lys Arg Ser Arg Leu Leu His Ser Asp Tyr Met Asn Met
                340                 345                 350

Thr Pro Arg Arg Pro Gly Pro Thr Arg Lys His Tyr Gln Pro Tyr Ala
                355                 360                 365

Pro Pro Arg Asp Phe Ala Ala Tyr Arg Ser Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Gln Arg Arg Lys Asn
                420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Glu Gly
                485                 490                 495

Arg Gly Ser Leu Leu Thr Cys Gly Asp Val Glu Glu Asn Pro Gly Pro
            500                 505                 510

Met Glu Tyr Ala Ser Asp Ala Ser Leu Asp Pro Glu Ala Pro Trp Pro
            515                 520                 525

Pro Ala Pro Arg Ala Arg Ala Cys Arg Val Leu Pro Trp Ala Leu Val
            530                 535                 540

Ala Gly Leu Leu Leu Leu Leu Leu Leu Ala Ala Ala Cys Ala Val Phe
545                 550                 555                 560
```

```
Leu Ala Cys Pro Trp Ala Val Ser Gly Ala Arg Ala Ser Pro Gly Ser
                565                 570                 575

Ala Ala Ser Pro Arg Leu Arg Glu Gly Pro Glu Leu Ser Pro Asp Asp
            580                 585                 590

Pro Ala Gly Leu Leu Asp Leu Arg Gln Gly Met Phe Ala Gln Leu Val
        595                 600                 605

Ala Gln Asn Val Leu Leu Ile Asp Gly Pro Leu Ser Trp Tyr Ser Asp
    610                 615                 620

Pro Gly Leu Ala Gly Val Ser Leu Thr Gly Gly Leu Ser Tyr Lys Glu
625                 630                 635                 640

Asp Thr Lys Glu Leu Val Ala Lys Ala Gly Val Tyr Tyr Val Phe
                645                 650                 655

Phe Gln Leu Glu Leu Arg Arg Val Val Ala Gly Glu Gly Ser Gly Ser
                660                 665                 670

Val Ser Leu Ala Leu His Leu Gln Pro Leu Arg Ser Ala Ala Gly Ala
            675                 680                 685

Ala Ala Leu Ala Leu Thr Val Asp Leu Pro Pro Ala Ser Ser Glu Ala
        690                 695                 700

Arg Asn Ser Ala Phe Gly Phe Gln Gly Arg Leu Leu His Leu Ser Ala
705                 710                 715                 720

Gly Gln Arg Leu Gly Val His Leu His Thr Glu Ala Arg Ala Arg His
                725                 730                 735

Ala Trp Gln Leu Thr Gln Gly Ala Thr Val Leu Gly Leu Phe Arg Val
                740                 745                 750

Thr Pro Glu Ile Pro Ala Gly Leu Pro Ser Pro Arg Ser Glu Gly Ser
            755                 760                 765

Gly Ala Thr Asn Phe Ser Leu Leu Lys Gln Ala Gly Asp Val Glu Glu
770                 775                 780

Asn Pro Gly Pro Met Tyr Arg Met Gln Leu Leu Ser Cys Ile Ala Leu
785                 790                 795                 800

Ser Leu Ala Leu Val Thr Asn Ser Gly Ile His Val Phe Ile Leu Gly
            805                 810                 815

Cys Phe Ser Ala Gly Leu Pro Lys Thr Glu Ala Asn Trp Val Asn Val
            820                 825                 830

Ile Ser Asp Leu Lys Lys Ile Glu Asp Leu Ile Gln Ser Met His Ile
            835                 840                 845

Asp Ala Thr Leu Tyr Thr Glu Ser Asp Val His Pro Ser Cys Lys Val
        850                 855                 860

Thr Ala Met Lys Cys Phe Leu Leu Glu Leu Gln Val Ile Ser Leu Glu
865                 870                 875                 880

Ser Gly Asp Ala Ser Ile His Asp Thr Val Glu Asn Leu Ile Ile Leu
                885                 890                 895

Ala Asn Asn Ser Leu Ser Ser Asn Gly Asn Val Thr Glu Ser Gly Cys
            900                 905                 910

Lys Glu Cys Glu Glu Leu Glu Glu Lys Asn Ile Lys Glu Phe Leu Gln
                915                 920                 925

Ser Phe Val His Ile Val Gln Met Phe Ile Asn Thr Ser Ser Gly Gly
        930                 935                 940

Gly Ser Gly Gly Gly Ser Gly Gly Gly Ser Gly Gly Gly
945                 950                 955                 960

Ser Gly Gly Gly Ser Leu Gln Ala Pro Arg Arg Ala Arg Gly Cys Arg
                965                 970                 975
```

```
Thr Leu Gly Leu Pro Ala Leu Leu Leu Leu Leu Leu Arg Pro Pro
            980             985             990

Ala Thr Arg Gly Ile Thr Cys Pro Pro Met Ser Val Glu His Ala
        995                 1000            1005

Asp Ile Trp Val Lys Ser Tyr Ser Leu Tyr Ser Arg Glu Arg Tyr
    1010            1015            1020

Ile Cys Asn Ser Gly Phe Lys Arg Lys Ala Gly Thr Ser Ser Leu
    1025            1030            1035

Thr Glu Cys Val Leu Asn Lys Ala Thr Asn Val Ala His Trp Thr
    1040            1045            1050

Thr Pro Ser Leu Lys Cys Ile Arg
    1055            1060
```

<210> SEQ ID NO 39
<211> LENGTH: 3185
<212> TYPE: DNA
<213> ORGANISM: Artificial Sequence
<220> FEATURE:
<223> OTHER INFORMATION: Synthetic Sequence

<400> SEQUENCE: 39

```
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcacccctg gaccttcggc      360
ggcggcacca agctggacat caaggggagg ggggatccg ggggaggagg ctccggcgga      420
ggcggaagcc agatccagct ggtgcagagc ggccccgacc tgaagaagcc cggcgagacc     480
gtgaagctga gctgcaaggc cagcggctac accttcacca cttcggcat gaactgggtg      540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
accgcctacc tgcagatcaa caacctgaag accgaggaca ccgccaccta cttctgcgcc     720
aggggcgaga tctactacgg ctacgacggc ggcttcgcct actggggcca gggcaccctg     780
gtgaccgtga gcgccaccac gacgccagcg ccgcgaccac caacaccggc gcccaccatc     840
gcgtcgcagc cctgtccct cgcccagag cgtgccggc cagcggcggg gggcgcagtg        900
cacacgaggg ggctggactt cgcctgtgat atctacatct gggcgccctt ggccgggact     960
tgtgggtcc ttctcctgtc actggttatc ccctttact gcaggagtaa ggagcagg        1020
ctcctgcaca gtgactacat gaacatgact ccccgccgcc cgggcccac ccgcaagcat     1080
taccagccct atgccccacc acgcgacttc gcagcctatc gctccagagt gaagttcagc     1140
aggagcgcag acgcccccgc gtaccagcag gccagaacc agctctataa cgagctcaat     1200
ctaggacgaa gagaggagta cgatgttttg gacaagagac gtggccggga ccctgagatg     1260
ggggaaagc gcagagaag gaagaaccct caggaaggcc tgtacaatga actgcagaaa      1320
gataagatgg cggaggccta cagtgagatt gggatgaaag cgagcgccg gagggggcaag    1380
ggcacgatg cctttaccca gggtctcagt acagccacca aggacaccta cgacgccctt    1440
cacatgcagg ccctgccccc tcgcggcagc ggcgaaggcc gcggcagcct gctgacctgc    1500
ggcgatgtgg aagaaaaccc gggccccatg gaatacgcct ctgacgcttc actggaccc    1560
```

```
gaagccccgt ggcctcccgc gccccgcgct cgcgcctgcc gcgtactgcc ttgggccctg    1620
gtcgcggggc tgctgctgct gctgctgctc gctgccgcct gcgccgtctt cctcgcctgc    1680
ccctgggccg tgtccggggc tcgcgcctcg cccggctccg cggccagccc gagactccgc    1740
gagggtcccg agctttcgcc cgacgatccc gccggcctct ggacctgcg gcagggcatg     1800 tttgcgcagc tggtggccca aaatgttctg ctgatcgatg ggcccctgag ctggtacagt    1860
gacccaggcc tggcaggcgt gtccctgacg ggggcctga gctacaaaga ggacacgaag     1920
gagctggtgg tggccaaggc tggagtctac tatgtcttct ttcaactaga gctgcggcgc    1980
gtggtggccg gcgagggctc aggctccgtt tcacttgcgc tgcacctgca gccactgcgc    2040
tctgctgctg gggccgccgc cctggctttg accgtggacc tgccacccgc ctcctccgag    2100
gctcggaact cggccttcgg tttccagggc gcttgctgc acctgagtgc cggccagcgc     2160
ctgggcgtcc atcttcacac tgaggccagg gcacgccatg cctggcagct acccagggc     2220 gccacagtct tgggactctt ccgggtgacc cccgaaatcc cagccggact cccttcaccg    2280
aggtcggaag gaagcggagc tactaacttc agcctgctga gcaggctgg agacgtggag     2340 gagaaccctg gacctatgta cagaatgcag ctgctgagct gcatcgccct gagcctggcc    2400
ctggtgacca acagcggcat ccacgtgttc atcctgggct gcttcagcgc cggcctgccc    2460
aagaccgagg ccaactgggt gaacgtgatc agcgacctga agaagatcga ggacctgatc    2520
cagagcatgc acatcgacgc caccctgtac accgagagcg acgtgcaccc cagctgcaag    2580
gtgaccgcca tgaagtgctt cctgctggag ctgcaggtga tcagcctgga gagcggcgac    2640
gccagcatcc acgacaccgt ggagaacctg atcatcctgg ccaacaacag cctgagcagc    2700
aacggcaacg tgaccgagag cggctgcaag gagtgcgagg agctggagga gaagaacatc    2760
aaggagttcc tgcagagctt cgtgcacatc gtgcagatgt tcatcaacac cagctccggc    2820
ggcggctccg gcggcggcgg ctccggcggc ggcggctccg gcggcggcgg ctccggcggc    2880
ggctccctgc aggcccccag aagagccaga ggctgcagaa ccctgggcct gcccgccctg    2940
ctgctgctgc tgctgctgag accccccgcc accagaggca tcacctgccc ccccccatg     3000 agcgtggagc acgccgacat ctgggtgaag agctacagcc tgtacagcag agagagatac    3060
atctgcaaca gcggcttcaa gagaaaggcc ggcaccagca gcctgaccga gtgcgtgctg    3120
aacaaggcca ccaacgtggc ccactggacc accccagcc tgaagtgcat cagataagtt    3180
taaac                                                               3185
```

<210> SEQ ID NO 40
<211> LENGTH: 1301
<212> TYPE: PRT
<213> ORGANISM: Artificial Sequence
<220> FEATURE:
<223> OTHER INFORMATION: Synthetic Sequence

<400> SEQUENCE: 40

Asp Arg Thr Met Ala Leu Pro Val Thr Ala Leu Leu Leu Pro Leu Ala
1               5                   10                  15

Leu Leu Leu His Ala Ala Arg Pro Asp Val Val Met Thr Gln Ser His
            20                  25                  30

Arg Phe Met Ser Thr Ser Val Gly Asp Arg Val Ser Ile Thr Cys Arg
        35                  40                  45

Ala Ser Gln Asp Val Asn Thr Ala Val Ser Trp Tyr Gln Gln Lys Pro
    50                  55                  60

```
Gly Gln Ser Pro Lys Leu Leu Ile Phe Ser Ala Ser Tyr Arg Tyr Thr
 65                  70                  75                  80

Gly Val Pro Asp Arg Phe Thr Gly Ser Gly Ser Gly Ala Asp Phe Thr
                 85                  90                  95

Leu Thr Ile Ser Ser Val Gln Ala Glu Asp Leu Ala Val Tyr Tyr Cys
            100                 105                 110

Gln Gln His Tyr Ser Thr Pro Trp Thr Phe Gly Gly Gly Thr Lys Leu
            115                 120                 125

Asp Ile Lys Gly Gly Gly Ser Gly Gly Gly Ser Gly Gly Gly
            130                 135                 140

Gly Ser Gln Ile Gln Leu Val Gln Ser Gly Pro Asp Leu Lys Lys Pro
145                 150                 155                 160

Gly Glu Thr Val Lys Leu Ser Cys Lys Ala Ser Gly Tyr Thr Phe Thr
                165                 170                 175

Asn Phe Gly Met Asn Trp Val Lys Gln Ala Pro Gly Lys Gly Phe Lys
            180                 185                 190

Trp Met Ala Trp Ile Asn Thr Tyr Thr Gly Glu Ser Tyr Phe Ala Asp
            195                 200                 205

Asp Phe Lys Gly Arg Phe Ala Phe Ser Val Glu Thr Ser Ala Thr Thr
210                 215                 220

Ala Tyr Leu Gln Ile Asn Asn Leu Lys Thr Glu Asp Thr Ala Thr Tyr
225                 230                 235                 240

Phe Cys Ala Arg Gly Glu Ile Tyr Tyr Gly Tyr Asp Gly Gly Phe Ala
                245                 250                 255

Tyr Trp Gly Gln Gly Thr Leu Val Thr Val Ser Ala Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Arg Ser Lys Arg Ser Arg Leu Leu His Ser Asp Tyr Met Asn Met
            340                 345                 350

Thr Pro Arg Arg Pro Gly Pro Thr Arg Lys His Tyr Gln Pro Tyr Ala
            355                 360                 365

Pro Pro Arg Asp Phe Ala Ala Tyr Arg Ser Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Tyr Asp Val Leu Asp Lys Arg
                405                 410                 415

Arg Gly Arg Asp Pro Glu Met Gly Gly Lys Pro Gln Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Ala Thr
```

```
            485                 490                 495
Asn Phe Ser Leu Leu Lys Gln Ala Gly Asp Val Glu Glu Asn Pro Gly
                500                 505                 510

Pro Met Ala Leu Pro Val Thr Ala Leu Leu Pro Leu Ala Leu Leu
        515                 520                 525

Leu His Ala Ala Arg Pro Asp Ile Glu Leu Thr Gln Ser Pro Ser Ser
    530                 535                 540

Phe Ser Val Ser Leu Gly Asp Arg Val Thr Ile Thr Cys Lys Ala Ser
545                 550                 555                 560

Glu Asp Ile Tyr Asn Arg Leu Ala Trp Tyr Gln Gln Lys Pro Gly Asn
                565                 570                 575

Ala Pro Arg Leu Leu Ile Ser Gly Ala Thr Ser Leu Glu Thr Gly Val
            580                 585                 590

Pro Ser Arg Phe Ser Gly Ser Gly Ser Gly Lys Asp Tyr Thr Leu Ser
            595                 600                 605

Ile Thr Ser Leu Gln Thr Glu Asp Val Ala Thr Tyr Tyr Cys Gln Gln
        610                 615                 620

Tyr Trp Ser Thr Pro Thr Phe Gly Gly Gly Thr Lys Leu Glu Ile Lys
625                 630                 635                 640

Arg Ala Ala Gly Gly Gly Gly Ser Gly Gly Gly Gly Ser Gly Gly Gly
                645                 650                 655

Gly Ser Ala Gln Pro Ala Met Ala Lys Val Gln Leu Gln Glu Ser Gly
                660                 665                 670

Pro Ser Leu Val Gln Pro Ser Gln Arg Leu Ser Ile Thr Cys Thr Val
            675                 680                 685

Ser Gly Phe Ser Leu Ile Ser Tyr Gly Val His Trp Val Arg Gln Ser
        690                 695                 700

Pro Gly Lys Gly Leu Glu Trp Leu Gly Val Ile Trp Arg Gly Gly Ser
705                 710                 715                 720

Thr Asp Tyr Asn Ala Ala Phe Met Ser Arg Leu Ser Ile Thr Lys Asp
                725                 730                 735

Asn Ser Lys Ser Gln Val Phe Phe Lys Met Asn Ser Leu Gln Ala Asp
            740                 745                 750

Asp Thr Ala Ile Tyr Phe Cys Ala Lys Thr Leu Ile Thr Thr Gly Tyr
            755                 760                 765

Ala Met Asp Tyr Trp Gly Gln Gly Thr Thr Val Thr Val Ser Ser Thr
        770                 775                 780

Thr Thr Pro Ala Pro Arg Pro Pro Thr Pro Ala Pro Thr Ile Ala Ser
785                 790                 795                 800

Gln Pro Leu Ser Leu Arg Pro Glu Ala Cys Arg Pro Ala Ala Gly Gly
                805                 810                 815

Ala Val His Thr Arg Gly Leu Asp Phe Ala Cys Asp Ile Tyr Ile Trp
            820                 825                 830

Ala Pro Leu Ala Gly Thr Cys Gly Val Leu Leu Leu Ser Leu Val Ile
            835                 840                 845

Thr Leu Tyr Cys Lys Arg Gly Arg Lys Lys Leu Leu Tyr Ile Phe Lys
        850                 855                 860

Gln Pro Phe Met Arg Pro Val Gln Thr Thr Gln Glu Glu Asp Gly Cys
865                 870                 875                 880

Ser Cys Arg Phe Pro Glu Glu Glu Glu Gly Gly Cys Glu Leu Arg Val
                885                 890                 895

Lys Phe Ser Arg Ser Ala Asp Ala Pro Ala Tyr Gln Gln Gly Gln Asn
            900                 905                 910
```

```
Gln Leu Tyr Asn Glu Leu Asn Leu Gly Arg Arg Glu Tyr Asp Val
        915                 920                 925

Leu Asp Lys Arg Arg Gly Arg Asp Pro Glu Met Gly Gly Lys Pro Gln
930                 935                 940

Arg Arg Lys Asn Pro Gln Glu Gly Leu Tyr Asn Glu Leu Gln Lys Asp
945                 950                 955                 960

Lys Met Ala Glu Ala Tyr Ser Glu Ile Gly Met Lys Gly Glu Arg Arg
                965                 970                 975

Arg Gly Lys Gly His Asp Gly Leu Tyr Gln Gly Leu Ser Thr Ala Thr
                980                 985                 990

Lys Asp Thr Tyr Asp Ala Leu His Met Gln Ala Leu Pro Pro Arg Gly
            995                 1000                1005

Ser Gly Glu Gly Arg Gly Ser Leu Leu Thr Cys Gly Asp Val Glu
    1010                1015                1020

Glu Asn Pro Gly Pro Met Tyr Arg Met Gln Leu Leu Ser Cys Ile
    1025                1030                1035

Ala Leu Ser Leu Ala Leu Val Thr Asn Ser Gly Ile His Val Phe
    1040                1045                1050

Ile Leu Gly Cys Phe Ser Ala Gly Leu Pro Lys Thr Glu Ala Asn
    1055                1060                1065

Trp Val Asn Val Ile Ser Asp Leu Lys Lys Ile Glu Asp Leu Ile
    1070                1075                1080

Gln Ser Met His Ile Asp Ala Thr Leu Tyr Thr Glu Ser Asp Val
    1085                1090                1095

His Pro Ser Cys Lys Val Thr Ala Met Lys Cys Phe Leu Leu Glu
    1100                1105                1110

Leu Gln Val Ile Ser Leu Glu Ser Gly Asp Ala Ser Ile His Asp
    1115                1120                1125

Thr Val Glu Asn Leu Ile Ile Leu Ala Asn Asn Ser Leu Ser Ser
    1130                1135                1140

Asn Gly Asn Val Thr Glu Ser Gly Cys Lys Glu Cys Glu Glu Leu
    1145                1150                1155

Glu Glu Lys Asn Ile Lys Glu Phe Leu Gln Ser Phe Val His Ile
    1160                1165                1170

Val Gln Met Phe Ile Asn Thr Ser Ser Gly Gly Ser Gly Gly
    1175                1180                1185

Gly Gly Ser Gly Gly Gly Ser Gly Gly Gly Ser Gly Gly
    1190                1195                1200

Gly Ser Leu Gln Ala Pro Arg Arg Ala Arg Gly Cys Arg Thr Leu
    1205                1210                1215

Gly Leu Pro Ala Leu Leu Leu Leu Leu Leu Leu Arg Pro Pro Ala
    1220                1225                1230

Thr Arg Gly Ile Thr Cys Pro Pro Pro Met Ser Val Glu His Ala
    1235                1240                1245

Asp Ile Trp Val Lys Ser Tyr Ser Leu Tyr Ser Arg Glu Arg Tyr
    1250                1255                1260

Ile Cys Asn Ser Gly Phe Lys Arg Lys Ala Gly Thr Ser Ser Leu
    1265                1270                1275

Thr Glu Cys Val Leu Asn Lys Ala Thr Asn Val Ala His Trp Thr
    1280                1285                1290

Thr Pro Ser Leu Lys Cys Ile Arg
    1295                1300
```

<210> SEQ ID NO 41
<211> LENGTH: 3905
<212> TYPE: DNA
<213> ORGANISM: Artificial Sequence
<220> FEATURE:
<223> OTHER INFORMATION: Synthetic Sequence

<400> SEQUENCE: 41

```
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcacccctg gaccttcggc      360
ggcggcacca gctggacat caaggggaggg ggggatccg ggggaggagg ctccggcgga     420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
accgcctacc tgcagatcaa caacctgaag accgaggaca ccgccaccta cttctgcgcc     720
aggggcgaga tctactacgg ctacgacggc ggcttcgcct actggggcca gggcaccctg     780
gtgaccgtga cgccaccac gacgccagcg ccgcgaccac caacaccggc gccaccatc      840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtgggggtcc ttctcctgtc actggttatc acccttact gcaggagtaa gaggagcagg    1020
ctcctgcaca gtgactacat gaacatgact ccccgccgcc ccgggcccac ccgcaagcat    1080
taccagccct atgccccacc acgcgacttc gcagcctatc gctccagagt gaagttcagc    1140
aggagcgcag acgccccgc gtaccagcag ggccagaacc agctctataa cgagctcaat    1200
ctaggacgaa gagaggagta cgatgttttg gacaagagac gtggccggga ccctgagatg    1260
gggggaaagc cgcagagaag gaagaaccct caggaaggcc tgtacaatga actgcagaaa    1320
gataagatgg cggaggccta cagtgagatt gggatgaaag cgagcgccg gaggggcaag     1380
gggcacgatg gcctttacca gggtctcagt acagccacca aggacaccta cgacgccctt    1440
cacatgcagg ccctgccccc tcgcggaagc ggagccacca acttcagcct gctgaagcag    1500
gccggcgacg tggaggagaa ccccggcccc atggccctgc ccgtgaccgc cctgctgctg    1560
cccctggccc tgctgctgca cgccgccagg cccgacatcg agctgaccca gagccccagc    1620
agcttcagcg tgagcctggg cgacagggtg accatcacct gcaaggccag cgaggacatc    1680
tacaacaggc tggcctggta ccagcagaag cccggcaacg ccccaggct gctgatcagc    1740
ggcgccacca gcctggagac cggcgtgccc agcaggttca gcggcagcgg cagcggcaag    1800
gactacaccc tgagcatcac cagcctgcag accgaggacg tggccaccta ctactgccag    1860
cagtactgga gcacccccac cttcggcggc ggcaccaagc tggagatcaa gagggccgcc    1920
ggcggcggcg gcagcggcgg cggcggcagc ggcggcggcg gcagcgccca gcccgccatg    1980
gccaaggtgc agctgcagga gagcggcccc agcctggtgc agcccagcca gaggctgagc    2040
atcacctgca ccgtgagcgg cttcagcctg atcagctacg gcgtgcactg ggtgaggcag    2100
```

```
agccccggca agggcctgga gtggctgggc gtgatctgga ggggcggcag caccgactac    2160
aacgccgcct tcatgagcag gctgagcatc accaaggaca cagcaagag ccaggtgttc    2220 ttcaagatga acagcctgca ggccgacgac accgccatct acttctgcgc caagaccctg    2280
atcaccaccg gctacgccat ggactactgg ggccagggca ccaccgtgac cgtgagcagc    2340
accaccaccc ccgcccccag gccccccacc cccgccccca ccatcgccag ccagcccctg    2400
agcctgaggc ccgaggcctg caggcccgcc gccggcggcg ccgtgcacac caggggcctg    2460
gacttcgcct gcgacatcta catctgggcc cccctggccg gcacctgcgg cgtgctgctg    2520
ctgagcctgg tgatcaccct gtactgcaaa cggggcagaa agaaactcct gtatatattc    2580
aaacaaccat ttatgagacc agtacaaact actcaagagg aagatggctg tagctgccga    2640
tttccagaag aagaagaagg aggatgtgaa ctgagggtga agttcagcag gagcgccgac    2700
gcccccgcct accagcaggg ccagaaccag ctgtacaacg agctgaacct gggcaggagg    2760
gaggagtacg acgtgctgga caagaggagg ggcagggacc ccgagatggg cggcaagccc    2820
cagaggagga agaaccccca ggagggcctg tacaacgagc tgcagaagga caagatggcc    2880
gaggcctaca gcgagatcgg catgaagggc gagaggagga ggggcaaggg ccacgacggc    2940
ctgtaccagg gcctgagcac cgccaccaag gacacctacg acgccctgca catgcaggcc    3000
ctgcccccca ggggcagcgg cgaaggccgc ggcagcctgc tgacctgcgg cgatgtggaa    3060
gaaaacccgg gccccatgta cagaatgcag ctgctgagct gcatcgccct gagcctggcc    3120
ctggtgacca cagcggcat ccacgtgttc atcctgggct gcttcagcgc cggcctgccc    3180
aagaccgagg ccaactgggt gaacgtgatc agcgacctga agaagatcga ggacctgatc    3240
cagagcatgc acatcgacgc caccctgtac accgagagcg acgtgcaccc cagctgcaag    3300
gtgaccgcca tgaagtgctt cctgctggag ctgcaggtga tcagcctgga gagcggcgac    3360
gccagcatcc acgacaccgt ggagaacctg atcatcctgg ccaacaacag cctgagcagc    3420
aacggcaacg tgaccgagag cggctgcaag gagtgcgagg agctggagga agaacatc     3480 aaggagttcc tgcagagctt cgtgcacatc gtgcagatgt tcatcaacac cagctccggc    3540
ggcggctccg gcggcggcgg ctccggcggc ggcggctccg gcggcggcgg ctccggcggc    3600
ggctccctgc aggcccccag aagagccaga ggctgcagaa ccctgggcct gcccgccctg    3660
ctgctgctgc tgctgctgag accccccgcc accagaggca tcacctgccc cccccccatg    3720
agcgtggagc acgccgacat ctgggtgaag agctacagcc tgtacagcag agagagatac    3780
atctgcaaca gcggcttcaa gagaaaggcc ggcaccagca gcctgaccga gtgcgtgctg    3840
aacaaggcca ccaacgtggc ccactggacc accccagcc tgaagtgcat cagataagtt    3900
taaac                                                               3905
```

<210> SEQ ID NO 42
<211> LENGTH: 1291
<212> TYPE: PRT
<213> ORGANISM: Artificial Sequence
<220> FEATURE:
<223> OTHER INFORMATION: Synthetic Sequence

<400> SEQUENCE: 42

Asp Arg Thr Met Ala Leu Pro Val Thr Ala Leu Leu Leu Pro Leu Ala
1               5                   10                  15

Leu Leu Leu His Ala Ala Arg Pro Asp Val Val Met Thr Gln Ser His
            20                  25                  30

-continued

```
Arg Phe Met Ser Thr Ser Val Gly Asp Arg Val Ser Ile Thr Cys Arg
            35                  40                  45

Ala Ser Gln Asp Val Asn Thr Ala Val Ser Trp Tyr Gln Gln Lys Pro
 50                  55                  60

Gly Gln Ser Pro Lys Leu Leu Ile Phe Ser Ala Ser Tyr Arg Tyr Thr
 65                  70                  75                  80

Gly Val Pro Asp Arg Phe Thr Gly Ser Gly Ser Gly Ala Asp Phe Thr
                 85                  90                  95

Leu Thr Ile Ser Ser Val Gln Ala Glu Asp Leu Ala Val Tyr Tyr Cys
             100                 105                 110

Gln Gln His Tyr Ser Thr Pro Trp Thr Phe Gly Gly Gly Thr Lys Leu
             115                 120                 125

Asp Ile Lys Gly Gly Gly Gly Ser Gly Gly Gly Gly Ser Gly Gly Gly
         130                 135                 140

Gly Ser Gln Ile Gln Leu Val Gln Ser Gly Pro Asp Leu Lys Lys Pro
145                 150                 155                 160

Gly Glu Thr Val Lys Leu Ser Cys Lys Ala Ser Gly Tyr Thr Phe Thr
                 165                 170                 175

Asn Phe Gly Met Asn Trp Val Lys Gln Ala Pro Gly Lys Gly Phe Lys
             180                 185                 190

Trp Met Ala Trp Ile Asn Thr Tyr Thr Gly Glu Ser Tyr Phe Ala Asp
         195                 200                 205

Asp Phe Lys Gly Arg Phe Ala Phe Ser Val Glu Thr Ser Ala Thr Thr
     210                 215                 220

Ala Tyr Leu Gln Ile Asn Asn Leu Lys Thr Glu Asp Thr Ala Thr Tyr
225                 230                 235                 240

Phe Cys Ala Arg Gly Glu Ile Tyr Tyr Gly Tyr Asp Gly Gly Phe Ala
                 245                 250                 255

Tyr Trp Gly Gln Gly Thr Leu Val Thr Val Ser Ala Thr Thr Thr Pro
             260                 265                 270

Ala Pro Arg Pro Pro Thr Pro Ala Pro Thr Ile Ala Ser Gln Pro Leu
         275                 280                 285

Ser Leu Arg Pro Glu Ala Cys Arg Pro Ala Ala Gly Gly Ala Val His
     290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                 325                 330                 335

Cys Arg Ser Lys Arg Ser Arg Leu Leu His Ser Asp Tyr Met Asn Met
             340                 345                 350

Thr Pro Arg Arg Pro Gly Pro Thr Arg Lys His Tyr Gln Pro Tyr Ala
         355                 360                 365

Pro Pro Arg Asp Phe Ala Ala Tyr Arg Ser Arg Val Lys Phe Ser Arg
     370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                 405                 410                 415

Arg Gly Arg Asp Pro Glu Met Gly Gly Lys Pro Gln Arg Arg Lys Asn
             420                 425                 430

Pro Gln Glu Gly Leu Tyr Asn Glu Leu Gln Lys Asp Lys Met Ala Glu
         435                 440                 445

Ala Tyr Ser Glu Ile Gly Met Lys Gly Glu Arg Arg Arg Gly Lys Gly
```

```
              450                 455                 460
His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Ala Thr
                485                 490                 495

Asn Phe Ser Leu Leu Lys Gln Ala Gly Asp Val Glu Glu Asn Pro Gly
                500                 505                 510

Pro Met Ala Leu Pro Val Thr Ala Leu Leu Leu Pro Leu Ala Leu Leu
                515                 520                 525

Leu His Ala Ala Arg Pro Asp Ile Gln Met Thr Gln Ser Pro Ser Ser
    530                 535                 540

Leu Ser Ala Ser Val Gly Asp Arg Val Thr Ile Thr Cys Lys Ala Ser
545                 550                 555                 560

Gln Asp Val Gly Ile Ala Val Ala Trp Tyr Gln Gln Lys Pro Gly Lys
                565                 570                 575

Val Pro Lys Leu Leu Ile Tyr Trp Ala Ser Thr Arg His Thr Gly Val
                580                 585                 590

Pro Asp Arg Phe Ser Gly Ser Gly Ser Gly Thr Asp Phe Thr Leu Thr
                595                 600                 605

Ile Ser Ser Leu Gln Pro Glu Asp Val Ala Thr Tyr Tyr Cys Gln Gln
    610                 615                 620

Tyr Ser Ser Tyr Pro Tyr Thr Phe Gly Gln Gly Thr Lys Val Glu Ile
625                 630                 635                 640

Lys Gly Gly Gly Gly Ser Gly Gly Gly Gly Ser Gly Gly Gly Gly Ser
                645                 650                 655

Glu Val Gln Leu Val Glu Ser Gly Gly Gly Leu Val Gln Pro Gly Gly
                660                 665                 670

Ser Leu Arg Leu Ser Cys Ala Ala Ser Gly Phe Phe Ser Arg Tyr Trp
                675                 680                 685

Met Ser Trp Val Arg Gln Ala Pro Gly Lys Gly Leu Glu Trp Ile Gly
    690                 695                 700

Glu Ile Asn Pro Asp Ser Ser Thr Ile Asn Tyr Ala Pro Ser Leu Lys
705                 710                 715                 720

Asp Lys Phe Ile Ile Ser Arg Asp Asn Ala Lys Asn Ser Leu Tyr Leu
                725                 730                 735

Gln Met Asn Ser Leu Arg Ala Glu Asp Thr Ala Val Tyr Tyr Cys Ala
                740                 745                 750

Arg Pro Asp Gly Asn Tyr Trp Tyr Phe Asp Val Trp Gly Gln Gly Thr
                755                 760                 765

Leu Val Thr Val Ser Ser Thr Thr Pro Ala Pro Arg Pro Pro Thr
    770                 775                 780

Pro Ala Pro Thr Ile Ala Ser Gln Pro Leu Ser Leu Arg Pro Glu Ala
785                 790                 795                 800

Cys Arg Pro Ala Ala Gly Gly Ala Val His Thr Arg Gly Leu Asp Phe
                805                 810                 815

Ala Cys Asp Ile Tyr Ile Trp Ala Pro Leu Ala Gly Thr Cys Gly Val
                820                 825                 830

Leu Leu Leu Ser Leu Val Ile Thr Leu Tyr Cys Arg Ser Lys Arg Ser
                835                 840                 845

Arg Leu Leu His Ser Asp Tyr Met Asn Met Thr Pro Arg Arg Pro Gly
    850                 855                 860

Pro Thr Arg Lys His Tyr Gln Pro Tyr Ala Pro Pro Arg Asp Phe Ala
865                 870                 875                 880
```

-continued

```
Ala Tyr Arg Ser Arg Val Lys Phe Ser Arg Ser Ala Asp Ala Pro Ala
            885                 890                 895

Tyr Gln Gln Gly Gln Asn Gln Leu Tyr Asn Glu Leu Asn Leu Gly Arg
        900                 905                 910

Arg Glu Glu Tyr Asp Val Leu Asp Lys Arg Arg Gly Arg Asp Pro Glu
    915                 920                 925

Met Gly Gly Lys Pro Gln Arg Arg Lys Asn Pro Gln Glu Gly Leu Tyr
930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
                965                 970                 975

Gly Leu Ser Thr Ala Thr Lys Asp Thr Tyr Asp Ala Leu His Met Gln
            980                 985                 990

Ala Leu Pro Pro Arg Gly Ser Gly  Glu Gly Arg Gly Ser  Leu Leu Thr
        995                 1000                1005

Cys Gly Asp Val Glu Glu Asn  Pro Gly Pro Met Tyr  Arg Met Gln
    1010                1015                1020

Leu Leu Ser Cys Ile Ala Leu  Ser Leu Ala Leu Val  Thr Asn Ser
    1025                1030                1035

Gly Ile His Val Phe Ile Leu  Gly Cys Phe Ser Ala  Gly Leu Pro
    1040                1045                1050

Lys Thr Glu Ala Asn Trp Val  Asn Val Ile Ser Asp  Leu Lys Lys
    1055                1060                1065

Ile Glu Asp Leu Ile Gln Ser  Met His Ile Asp Ala  Thr Leu Tyr
    1070                1075                1080

Thr Glu Ser Asp Val His Pro  Ser Cys Lys Val Thr  Ala Met Lys
    1085                1090                1095

Cys Phe Leu Leu Glu Leu Gln  Val Ile Ser Leu Glu  Ser Gly Asp
    1100                1105                1110

Ala Ser Ile His Asp Thr Val  Glu Asn Leu Ile Ile  Leu Ala Asn
    1115                1120                1125

Asn Ser Leu Ser Ser Asn Gly  Asn Val Thr Glu Ser  Gly Cys Lys
    1130                1135                1140

Glu Cys Glu Glu Leu Glu Glu  Lys Asn Ile Lys Glu  Phe Leu Gln
    1145                1150                1155

Ser Phe Val His Ile Val Gln  Met Phe Ile Asn Thr  Ser Ser Gly
    1160                1165                1170

Gly Gly Ser Gly Gly Gly  Ser Gly Gly Gly Gly  Ser Gly Gly
    1175                1180                1185

Gly Gly Ser Gly Gly Gly Ser  Leu Gln Ala Pro Arg  Arg Ala Arg
    1190                1195                1200

Gly Cys Arg Thr Leu Gly Leu  Pro Ala Leu Leu Leu  Leu Leu Leu
    1205                1210                1215

Leu Arg Pro Pro Ala Thr Arg  Gly Ile Thr Cys Pro  Pro Pro Met
    1220                1225                1230

Ser Val Glu His Ala Asp Ile  Trp Val Lys Ser Tyr  Ser Leu Tyr
    1235                1240                1245

Ser Arg Glu Arg Tyr Ile Cys  Asn Ser Gly Phe Lys  Arg Lys Ala
    1250                1255                1260

Gly Thr Ser Ser Leu Thr Glu  Cys Val Leu Asn Lys  Ala Thr Asn
    1265                1270                1275
```

| Val | Ala | His | Trp | Thr | Thr | Pro | Ser | Leu | Lys | Cys | Ile | Arg |
|---|---|---|---|---|---|---|---|---|---|---|---|---|
| | 1280 | | | | 1285 | | | | | 1290 | | |

<210> SEQ ID NO 43
<211> LENGTH: 3875
<212> TYPE: DNA
<213> ORGANISM: Artificial Sequence
<220> FEATURE:
<223> OTHER INFORMATION: Synthetic Sequence

<400> SEQUENCE: 43

```
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcaccccctg gaccttcggc     360
ggcggcacca agctggacat caagggaggg gggggatccg ggggaggagg ctccggcgga     420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
accgcctacc tgcagatcaa caacctgaag accgaggaca ccgccaccta cttctgcgcc     720
aggggcgaga tctactacgg ctacgacggc ggcttcgcct actggggcca gggcaccctg     780
gtgaccgtga gcgccaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtgggggtcc ttctcctgtc actggttatc acccttaact gcaggagtaa gaggagcagg    1020
ctcctgcaca gtgactacat gaacatgact ccccgccgcc ccgggcccac ccgcaagcat    1080
taccagccct atgccccacc acgcgacttc gcagcctatc gctccagagt gaagttcagc    1140
aggagcgcag acgccccgc gtaccagcag ggccagaacc agctctataa cgagctcaat    1200
ctaggacgaa gagaggagta cgatgttttg gacaagagac gtggccggga ccctgagatg    1260
gggggaaagc cgcagagaag gaagaaccct caggaaggcc tgtacaatga actgcagaaa    1320
gataagatgg cggaggccta cagtgagatt gggatgaaag cgagcgccg gaggggcaag    1380
ggcacgatg cctttaccag ggtctcagt acagccacca aggacaccta cgacgccctt    1440
cacatgcagg ccctgccccc tcgcggaagc ggagccacca acttcagcct gctgaagcag    1500
gccggcgacg tggaggagaa ccccggcccc atggccttac cagtgaccgc cttgctcctg    1560
ccgctggcct tgctgctcca cgccgccagg ccggacatcc agatgaccca gagccccagc    1620
agcctgagcg ccagcgtggg cgacagggtg accatcacct gcaaggccag ccaggacgtg    1680
ggcatcgccg tggcctggta ccagcagaag cccggcaagg tgcccaagct gctgatctac    1740
tgggccagca ccaggcacac cggcgtgccc gacaggttca gcggcagcgg cagcggcacc    1800
gacttcaccc tgaccatcag cagcctgcag cccgaggacg tggccaccta ctactgccag    1860
cagtacagca gctaccccta caccttcggc cagggcacca aggtggagat caagggaggg    1920
gggggatccg ggggaggagg ctccggcgga ggcggaagcg aggtgcagct ggtggagagc    1980
```

```
ggcggcggcc tggtgcagcc cggcggcagc ctgaggctga gctgcgccgc cagcggcttc    2040
ttcagcaggt actggatgag ctgggtgagg caggcccccg gcaagggcct ggagtggatc    2100
ggcgagatca accccgacag cagcaccatc aactacgccc ccagcctgaa ggacaagttc    2160
atcatcagca gggacaacgc caagaacagc ctgtacctgc agatgaacag cctgagggcc    2220
gaggacaccg ccgtgtacta ctgcgccagg cccgacggca ctactggta cttcgacgtg    2280 tggggccagg gcaccctggt gaccgtgagc agcaccacga cgccagcgcc gcgaccacca    2340
acaccggcgc ccaccatcgc gtcgcagccc ctgtccctgc gcccagaggc gtgccggcca    2400
gcggcggggg gcgcagtgca cacgaggggg ctggacttcg cctgtgatat ctacatctgg    2460
gcgcccttgg ccgggacttg tggggtcctt ctcctgtcac tggttatcac cctttactgc    2520
aggagtaaga ggagcaggct cctgcacagt gactacatga acatgactcc ccgccgcccc    2580
gggcccaccc gcaagcatta ccagccctat gccccaccac gcgacttcgc agcctatcgc    2640
tccagagtga agttcagcag gagcgcagac gcccccgcgt accagcaggg ccagaaccag    2700
ctctataacg agctcaatct aggacgaaga gaggagtacg atgttttgga caagagacgt    2760
ggccgggacc ctgagatggg gggaaagccg cagagaagga gaacccctca ggaaggcctg    2820
tacaatgaac tgcagaaaga taagatggcg gaggcctaca gtgagattgg gatgaaaggc    2880
gagcgccgga ggggcaaggg gcacgatggc ctttaccagg gtctcagtac agccaccaag    2940
gacacctacg acgcccttca catgcaggcc ctgccccctc gcggcagcgg cgaaggccgc    3000
ggcagcctgc tgacctgcgg cgatgtggaa gaaaacccgg gccccatgta cagaatgcag    3060
ctgctgagct gcatcgccct gagcctggcc ctggtgacca cagcggcat ccacgtgttc    3120 atcctgggct gcttcagcgc cggcctgccc aagaccgagg ccaactgggt gaacgtgatc    3180
agcgacctga agaagatcga ggacctgatc cagagcatgc acatcgacgc caccctgtac    3240
accgagagcg acgtgcaccc cagctgcaag gtgaccgcca tgaagtgctt cctgctggag    3300
ctgcaggtga tcagcctgga gagcggcgac gccagcatcc acgacaccgt ggagaacctg    3360
atcatcctgg ccaacaacag cctgagcagc aacggcaacg tgaccgagag cggctgcaag    3420
gagtgcgagg agctggagga gaagaacatc aaggagttcc tgcagagctt cgtgcacatc    3480
gtgcagatgt tcatcaacac cagctccggc ggcggctccg gcggcggcgg ctccggcggc    3540
ggcggctccg gcggcggcgg ctccggcggc ggctccctgc aggcccccag aagagccaga    3600
ggctgcagaa ccctgggcct gccgcccctg ctgctgctgc tgctgctgag acccccgcc    3660 accagaggca tcacctgccc ccccccatg agcgtggagc acgccgacat ctgggtgaag    3720
agctacagcc tgtacagcag agagagatac atctgcaaca cggcttcaa gagaaaggcc    3780 ggcaccagca gcctgaccga gtgcgtgctg aacaaggcca ccaacgtggc ccactggacc    3840 accccccagcc tgaagtgcat cagataagtt taaac                              3875
```

<210> SEQ ID NO 44
<211> LENGTH: 1059
<212> TYPE: PRT
<213> ORGANISM: Artificial Sequence
<220> FEATURE:
<223> OTHER INFORMATION: Synthetic Sequence

<400> SEQUENCE: 44

Asp Arg Thr Met Ala Leu Pro Val Thr Ala Leu Leu Leu Pro Leu Ala
1               5                   10                  15

Leu Leu Leu His Ala Ala Arg Pro Asp Ile Gln Met Thr Gln Ser His
            20                  25                  30

```
Lys Phe Met Ser Thr Ser Val Gly Asp Arg Val Ser Ile Thr Cys Lys
        35                  40                  45

Ala Ser Gln Asp Val Ser Thr Ala Val Ala Trp Phe Gln Gln Lys Pro
 50                  55                  60

Gly Gln Ser Pro Lys Leu Leu Ile Tyr Ser Pro Ser Tyr Arg Tyr Thr
 65              70                  75                  80

Gly Val Pro Asp Arg Phe Thr Gly Ser Gly Ser Gly Thr Asp Phe Thr
                 85                  90                  95

Phe Thr Ile Ser Ser Val Gln Ala Glu Asp Leu Ala Val Tyr Tyr Cys
            100                 105                 110

Gln Gln Leu Tyr Ser Thr Pro Tyr Thr Phe Gly Gly Gly Thr Lys Leu
        115                 120                 125

Glu Ile Lys Gly Gly Gly Gly Ser Gly Gly Gly Gly Ser Gly Gly Gly
    130                 135                 140

Gly Ser Glu Val Gln Leu Gln Gln Ser Gly Pro Glu Leu Val Lys Pro
145                 150                 155                 160

Gly Ala Ser Val Lys Met Ser Cys Lys Ala Ser Gly Tyr Thr Phe Thr
                165                 170                 175

Asp Tyr Tyr Leu Asp Trp Val Lys Gln Ser His Gly Glu Ser Phe Glu
        180                 185                 190

Trp Ile Gly Arg Val Asn Pro Tyr Asn Gly Gly Thr Ile Tyr Asn Gln
    195                 200                 205

Lys Phe Lys Gly Lys Ala Thr Leu Thr Val Asp Lys Ser Ser Ser Thr
210                 215                 220

Ala Tyr Met Asp Leu Asn Ser Leu Thr Ser Glu Asp Ser Ala Val Tyr
225                 230                 235                 240

Tyr Cys Ala Arg Asp His Tyr Arg Tyr Asp Pro Leu Leu Asp Tyr Trp
                245                 250                 255

Gly Gln Gly Thr Thr Leu Thr Val Ser Ser Thr Thr Thr Pro Ala Pro
                260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Ser Lys Arg Ser Arg Leu Leu His Ser Asp Tyr Met Asn Met Thr Pro
                340                 345                 350

Arg Arg Pro Gly Pro Thr Arg Lys His Tyr Gln Pro Tyr Ala Pro Pro
                355                 360                 365

Arg Asp Phe Ala Ala Tyr Arg Ser Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Gln Arg Arg Lys Asn Pro Gln
                420                 425                 430

Glu Gly Leu Tyr Asn Glu Leu Gln Lys Asp Lys Met Ala Glu Ala Tyr
                435                 440                 445
```

-continued

```
Ser Glu Ile Gly Met Lys Gly Glu Arg Arg Gly Lys Gly His Asp
    450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg Gly Ser Gly Glu Gly Arg Gly
                    485                 490                 495
Ser Leu Leu Thr Cys Gly Asp Val Glu Glu Asn Pro Gly Pro Met Glu
                500                 505                 510
Tyr Ala Ser Asp Ala Ser Leu Asp Pro Glu Ala Pro Trp Pro Pro Ala
                515                 520                 525
Pro Arg Ala Arg Ala Cys Arg Val Leu Pro Trp Ala Leu Val Ala Gly
530                 535                 540
Leu Leu Leu Leu Leu Leu Leu Ala Ala Ala Cys Ala Val Phe Leu Ala
545                 550                 555                 560
Cys Pro Trp Ala Val Ser Gly Ala Arg Ala Ser Pro Gly Ser Ala Ala
                565                 570                 575
Ser Pro Arg Leu Arg Glu Gly Pro Glu Leu Ser Pro Asp Asp Pro Ala
                580                 585                 590
Gly Leu Leu Asp Leu Arg Gln Gly Met Phe Ala Gln Leu Val Ala Gln
                595                 600                 605
Asn Val Leu Leu Ile Asp Gly Pro Leu Ser Trp Tyr Ser Asp Pro Gly
610                 615                 620
Leu Ala Gly Val Ser Leu Thr Gly Gly Leu Ser Tyr Lys Glu Asp Thr
625                 630                 635                 640
Lys Glu Leu Val Val Ala Lys Ala Gly Val Tyr Tyr Val Phe Phe Gln
                645                 650                 655
Leu Glu Leu Arg Arg Val Val Ala Gly Glu Gly Ser Gly Ser Val Ser
                660                 665                 670
Leu Ala Leu His Leu Gln Pro Leu Arg Ser Ala Ala Gly Ala Ala Ala
                675                 680                 685
Leu Ala Leu Thr Val Asp Leu Pro Pro Ala Ser Ser Glu Ala Arg Asn
690                 695                 700
Ser Ala Phe Gly Phe Gln Gly Arg Leu Leu His Leu Ser Ala Gly Gln
705                 710                 715                 720
Arg Leu Gly Val His Leu His Thr Glu Ala Arg Ala Arg His Ala Trp
                725                 730                 735
Gln Leu Thr Gln Gly Ala Thr Val Leu Gly Leu Phe Arg Val Thr Pro
                740                 745                 750
Glu Ile Pro Ala Gly Leu Pro Ser Pro Arg Ser Glu Gly Ser Gly Ala
                755                 760                 765
Thr Asn Phe Ser Leu Leu Lys Gln Ala Gly Asp Val Glu Glu Asn Pro
770                 775                 780
Gly Pro Met Tyr Arg Met Gln Leu Leu Ser Cys Ile Ala Leu Ser Leu
785                 790                 795                 800
Ala Leu Val Thr Asn Ser Gly Ile His Val Phe Ile Leu Gly Cys Phe
                805                 810                 815
Ser Ala Gly Leu Pro Lys Thr Glu Ala Asn Trp Val Asn Val Ile Ser
                820                 825                 830
Asp Leu Lys Lys Ile Glu Asp Leu Ile Gln Ser Met His Ile Asp Ala
                835                 840                 845
Thr Leu Tyr Thr Glu Ser Asp Val His Pro Ser Cys Lys Val Thr Ala
850                 855                 860
Met Lys Cys Phe Leu Leu Glu Leu Gln Val Ile Ser Leu Glu Ser Gly
```

```
                            865                 870                 875                 880
Asp Ala Ser Ile His Asp Thr Val Glu Asn Leu Ile Ile Leu Ala Asn
                    885                 890                 895

Asn Ser Leu Ser Ser Asn Gly Asn Val Thr Glu Ser Gly Cys Lys Glu
                900                 905                 910

Cys Glu Glu Leu Glu Glu Lys Asn Ile Lys Glu Phe Leu Gln Ser Phe
            915                 920                 925

Val His Ile Val Gln Met Phe Ile Asn Thr Ser Gly Gly Gly Ser
        930                 935                 940

Gly Gly Gly Gly Ser Gly Gly Gly Ser Gly Gly Gly Ser Gly
945                 950                 955                 960

Gly Gly Ser Leu Gln Ala Pro Arg Arg Ala Arg Gly Cys Arg Thr Leu
                965                 970                 975

Gly Leu Pro Ala Leu Leu Leu Leu Leu Leu Arg Pro Pro Ala Thr
                980                 985                 990

Arg Gly Ile Thr Cys Pro Pro Pro Met Ser Val Glu His Ala Asp Ile
            995                 1000                1005

Trp Val Lys Ser Tyr Ser Leu Tyr Ser Arg Glu Arg Tyr Ile Cys
    1010                1015                1020

Asn Ser Gly Phe Lys Arg Lys Ala Gly Thr Ser Ser Leu Thr Glu
    1025                1030                1035

Cys Val Leu Asn Lys Ala Thr Asn Val Ala His Trp Thr Thr Pro
    1040                1045                1050

Ser Leu Lys Cys Ile Arg
    1055

<210> SEQ ID NO 45
<211> LENGTH: 3190
<212> TYPE: DNA
<213> ORGANISM: Artificial Sequence
<220> FEATURE:
<223> OTHER INFORMATION: Synthetic Sequence

<400> SEQUENCE: 45
gcgatcgcac catggccctg cccgtgaccg ccctgctgct gcccctggcc ctgctgctgc      60
acgccgccag gcccgacatc cagatgaccc agagccacaa gttcatgagc accagcgtgg     120
gcgacagggt gagcatcacc tgcaaggcca gcagacgt gagcaccgcc gtggcctggt      180
tccagcagaa gcccggccag agccccaagc tgctgatcta cagccccagc tacaggtaca     240
ccggcgtgcc cgacaggttc accggcagcg gcagcggcac cgacttcacc ttcaccatca     300
gcagcgtgca ggccgaggac ctggccgtgt actactgcca gcagctgtac agcaccccct     360
acaccttcgg cggcggcacc aagctggaga tcaaggagg gggggatcc ggggaggag       420 gctccggcgg aggcggaagc gaggtgcagc tgcagcagag cggccccgag ctggtgaagc     480
ccggcgccag cgtgaagatg agctgcaagg ccagcggcta caccttcacc gactactacc     540
tggactgggt gaagcagagc cacggcgaga gcttcgagtg gatcggcagg gtgaaccct      600 acaacggcgg caccatctac aaccagaagt tcaagggcaa ggccaccctg accgtggaca     660
agagcagcag caccgcctac atggacctga cagcctgac cagcgaggac agcgccgtgt     720
actactgcgc cagggaccac tacaggtacg accccctgct ggactactgg ggccagggca     780
ccaccctgac cgtgagcagc accaccaccc ccgcccccag gccccccacc ccgccccca     840 ccatcgccag ccagccctg agcctgaggc ccgaggcctg caggcccgcc gcggcggcg      900 ccgtgcacac caggggcctg gacttcgcct gcgacatcta catctgggcc ccctggccg     960
```

```
gcacctgcgg cgtgctgctg ctgagcctgg tgatcaccct gtactgcagg agtaagagga    1020
gcaggctcct gcacagtgac tacatgaaca tgactccccg ccgccccggg cccacccgca    1080
agcattacca gccctatgcc ccaccacgcg acttcgcagc ctatcgctcc agggtgaagt    1140
tcagcaggag cgccgacgcc cccgcctacc agcagggcca gaaccagctg tacaacgagc    1200
tgaacctggg caggagggag gagtacgacg tgctggacaa gaggaggggc agggaccccg    1260
agatgggcgg caagccccag aggaggaaga accccccagga gggcctgtac aacgagctgc    1320
agaaggacaa gatggccgag gcctacagcg agatcggcat gaagggcgag aggaggaggg    1380
gcaagggcca cgacggcctg taccagggcc tgagcaccgc caccaaggac acctacgacg    1440
ccctgcacat gcaggccctg cccccaggg gcagcggcga aggccgcggc agcctgctga    1500
cctgcggcga tgtggaagaa acccggggcc catggaata cgcctctgac gcttcactgg    1560
accccgaagc cccgtggcct cccgcgcccc gcgctcgcgc ctgccgcgta ctgccttggg    1620
ccctggtcgc ggggctgctg ctgctgctgc tgctcgctgc cgcctgcgcc gtcttcctcg    1680
cctgcccctg ggccgtgtcc ggggctcgcg cctcgcccgg ctccgcggcc agcccgagac    1740
tccgcgaggg tcccgagctt tcgcccgacg atcccgccgg cctcttggac ctgcggcagg    1800
gcatgtttgc gcagctggtg gcccaaaatg ttctgctgat cgatgggccc ctgagctggt    1860
acagtgaccc aggcctggca ggcgtgtccc tgacgggggg cctgagctac aaagaggaca    1920
cgaaggagct ggtggtggcc aaggctggag tctactatgt cttctttcaa ctagagctgc    1980
ggcgcgtggt ggccggcgag ggctcaggct ccgtttcact tgcgctgcac ctgcagccac    2040
tgcgctctgc tgctggggcc gccgccctgg cttttgaccgt ggacctgcca cccgcctcct    2100
ccgaggctcg gaactcggcc ttcggttttcc agggccgctt gctgcacctg agtgccggcc    2160
agcgcctggg cgtccatctt cacactgagg ccagggcacg ccatgcctgg cagcttaccc    2220
agggcgccac agtcttggga ctcttccggg tgacccccga atcccagccc ggactccctt    2280
caccgaggtc ggaaggaagc ggagctacta acttcagcct gctgaagcag gctggagacg    2340
tggaggagaa ccctggacct atgtacagaa tgcagctgct gagctgcatc gccctgagcc    2400
tggccctggt gaccaacagc ggcatccacg tgttcatcct gggctgcttc agcgccggcc    2460
tgcccaagac cgaggccaac tgggtgaacg tgatcagcga cctgaagaag atcgaggacc    2520
tgatccagag catgcacatc gacgccaccc tgtacaccga gagcgacgtg caccccagct    2580
gcaaggtgac cgccatgaag tgcttcctgc tggagctgca ggtgatcagc ctggagagcg    2640
gcgacgccca catccacgac accgtggaga acctgatcat cctggccaac aacagcctga    2700
gcagcaacgg caacgtgacc gagagcggct gcaaggagtg cgaggagctg gaggagaaga    2760
acatcaagga gttcctgcag agcttcgtgc acatcgtgca gatgttcatc aacaccagct    2820
ccggcggcgg ctccggcggc ggcggctccg gcggcggcgg ctccggcggc ggcggctccg    2880
gcggcggctc cctgcaggcc cccagaagag ccagaggctg cagaaccctg gcctgcccg    2940
ccctgctgct gctgctgctg ctgagacccc ccgccaccag aggcatcacc tgcccccccc    3000
ccatgagcgt ggagcacgcc gacatctggg tgaagagcta cagcctgtac agcagagaga    3060
gatacatctg caacagcggc ttcaagagaa aggccggcac cagcagcctg accgagtgcg    3120
tgctgaacaa ggccaccaac gtggcccact ggaccacccc cagcctgaag tgcatcagat    3180
aagtttaaac                                                          3190
```

<210> SEQ ID NO 46

```
<211> LENGTH: 1060
<212> TYPE: PRT
<213> ORGANISM: Artificial Sequence
<220> FEATURE:
<223> OTHER INFORMATION: Synthetic Sequence

<400> SEQUENCE: 46

Asp Arg Thr Met Ala Leu Pro Val Thr Ala Leu Leu Leu Pro Leu Ala
1               5                   10                  15

Leu Leu Leu His Ala Ala Arg Pro Glu Ile Val Met Thr Gln Ser Pro
            20                  25                  30

Ala Thr Leu Ser Val Ser Pro Gly Glu Arg Ala Thr Leu Ser Cys Arg
        35                  40                  45

Ser Ser Gln Ser Leu Val His Arg Asn Gly Asn Thr Tyr Leu His Trp
    50                  55                  60

Tyr Leu Gln Lys Pro Gly Gln Ser Pro Lys Leu Leu Ile His Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Pro Leu Thr Phe
        115                 120                 125

Gly Ala Gly Thr Lys Leu Glu Leu Lys Arg Gly Gly Gly Gly Ser Gly
    130                 135                 140

Gly Gly Gly Ser Gly Gly Gly Ser Glu Val Gln Leu Leu Gln Ser
145                 150                 155                 160

Gly Pro Glu Leu Glu Lys Pro Gly Ala Ser Val Met Ile Ser Cys Lys
                165                 170                 175

Ala Ser Gly Ser Ser Phe Thr Gly Tyr Asn Met Asn Trp Val Arg Gln
            180                 185                 190

Asn Ile Gly Lys Ser Leu Glu Trp Ile Gly Ala Ile Asp Pro Tyr Tyr
        195                 200                 205

Gly Gly Thr Ser Tyr Asn Gln Lys Phe Lys Gly Arg Ala Thr Leu Thr
    210                 215                 220

Val Asp Lys Ser Ser Ser Thr Ala Tyr Met His Leu Lys Ser Leu Thr
225                 230                 235                 240

Ser Glu Asp Ser Ala Val Tyr Tyr Cys Val Ser Gly Met Glu Tyr Trp
                245                 250                 255

Gly Gln Gly Thr Ser Val Thr Val Ser Ser Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Arg Val Lys Phe Ser Arg Ser Ala
    370                 375                 380
```

```
Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Ser Gly Glu Gly Arg Gly
            485                 490                 495

Ser Leu Leu Thr Cys Gly Asp Val Glu Glu Asn Pro Gly Pro Met Glu
            500                 505                 510

Tyr Ala Ser Asp Ala Ser Leu Asp Pro Glu Ala Pro Trp Pro Pro Ala
            515                 520                 525

Pro Arg Ala Arg Ala Cys Arg Val Leu Pro Trp Ala Leu Val Ala Gly
530                 535                 540

Leu Leu Leu Leu Leu Leu Leu Ala Ala Ala Cys Ala Val Phe Leu Ala
545                 550                 555                 560

Cys Pro Trp Ala Val Ser Gly Ala Arg Ala Ser Pro Gly Ser Ala Ala
            565                 570                 575

Ser Pro Arg Leu Arg Glu Gly Pro Glu Leu Ser Pro Asp Asp Pro Ala
            580                 585                 590

Gly Leu Leu Asp Leu Arg Gln Gly Met Phe Ala Gln Leu Val Ala Gln
            595                 600                 605

Asn Val Leu Leu Ile Asp Gly Pro Leu Ser Trp Tyr Ser Asp Pro Gly
            610                 615                 620

Leu Ala Gly Val Ser Leu Thr Gly Gly Leu Ser Tyr Lys Glu Asp Thr
625                 630                 635                 640

Lys Glu Leu Val Val Ala Lys Ala Gly Val Tyr Tyr Val Phe Phe Gln
            645                 650                 655

Leu Glu Leu Arg Arg Val Val Ala Gly Glu Gly Ser Gly Ser Val Ser
            660                 665                 670

Leu Ala Leu His Leu Gln Pro Leu Arg Ser Ala Ala Gly Ala Ala Ala
            675                 680                 685

Leu Ala Leu Thr Val Asp Leu Pro Pro Ala Ser Ser Glu Ala Arg Asn
            690                 695                 700

Ser Ala Phe Gly Phe Gln Gly Arg Leu Leu His Leu Ser Ala Gly Gln
705                 710                 715                 720

Arg Leu Gly Val His Leu His Thr Glu Ala Arg Ala Arg His Ala Trp
            725                 730                 735

Gln Leu Thr Gln Gly Ala Thr Val Leu Gly Leu Phe Arg Val Thr Pro
            740                 745                 750

Glu Ile Pro Ala Gly Leu Pro Ser Pro Arg Ser Glu Gly Ser Gly Ala
            755                 760                 765

Thr Asn Phe Leu Ser Leu Leu Lys Gln Ala Gly Asp Val Glu Glu Asn
            770                 775                 780

Pro Gly Pro Met Tyr Arg Met Gln Leu Leu Ser Cys Ile Ala Leu Ser
785                 790                 795                 800
```

```
Leu Ala Leu Val Thr Asn Ser Gly Ile His Val Phe Ile Leu Gly Cys
            805                 810                 815

Phe Ser Ala Gly Leu Pro Lys Thr Glu Ala Asn Trp Val Asn Val Ile
        820                 825                 830

Ser Asp Leu Lys Lys Ile Glu Asp Leu Ile Gln Ser Met His Ile Asp
        835                 840                 845

Ala Thr Leu Tyr Thr Glu Ser Asp Val His Pro Ser Cys Lys Val Thr
    850                 855                 860

Ala Met Lys Cys Phe Leu Leu Glu Leu Gln Val Ile Ser Leu Glu Ser
865                 870                 875                 880

Gly Asp Ala Ser Ile His Asp Thr Val Glu Asn Leu Ile Ile Leu Ala
                885                 890                 895

Asn Asn Ser Leu Ser Ser Asn Gly Asn Val Thr Glu Ser Gly Cys Lys
            900                 905                 910

Glu Cys Glu Glu Leu Glu Glu Lys Asn Ile Lys Glu Phe Leu Gln Ser
        915                 920                 925

Phe Val His Ile Val Gln Met Phe Ile Asn Thr Ser Ser Gly Gly Gly
    930                 935                 940

Ser Gly Gly Gly Ser Gly Gly Gly Ser Gly Gly Gly Ser
945                 950                 955                 960

Gly Gly Gly Ser Leu Gln Ala Pro Arg Arg Ala Arg Gly Cys Arg Thr
                965                 970                 975

Leu Gly Leu Pro Ala Leu Leu Leu Leu Leu Leu Arg Pro Pro Ala
            980                 985                 990

Thr Arg Gly Ile Thr Cys Pro Pro  Pro Met Ser Val Glu  His Ala Asp
        995                 1000                 1005

Ile Trp Val Lys Ser Tyr Ser  Leu Tyr Ser Arg Glu  Arg Tyr Ile
    1010                 1015                 1020

Cys Asn  Ser Gly Phe Lys Arg  Lys Ala Gly Thr Ser  Ser Leu Thr
    1025                 1030                 1035

Glu Cys  Val Leu Asn Lys Ala  Thr Asn Val Ala His  Trp Thr Thr
    1040                 1045                 1050

Pro Ser  Leu Lys Cys Ile Arg
    1055                 1060

<210> SEQ ID NO 47
<211> LENGTH: 3182
<212> TYPE: DNA
<213> ORGANISM: Artificial Sequence
<220> FEATURE:
<223> OTHER INFORMATION: Synthetic Sequence

<400> SEQUENCE: 47
atggccttac cagtgaccgc cttgctcctg ccgctggcct tgctgctcca cgccgccagg      60
ccggagatcg tgatgaccca gagccccgcc accctgagcg tgagccccgg cgagagggcc     120
accctgagct gcaggagcag ccagagcctg gtgcacagga acggcaacac ctacctgcac     180
tggtacctgc agaagcccgg ccagagcccc aagctgctga tccacaaggt gagcaacagg     240
ttcagcggcg tgcccgacag gttcagcggc agcggcagcg gcaccgactt caccctgaag     300
atcagcaggg tggaggccga ggacctgggc gtgtacttct gcagccagag cacccacgtg     360
ccccccctga ccttcggcgc cggcaccaag ctggagctga gaggggcgg cggcggcagc     420 ggcggcggcg gcagcggcgg cggcggcagc gaggtgcagc tgctgcagag cggccccgag     480
ctggagaagc ccggcgccag cgtgatgatc agctgcaagg ccagcggcag cagcttcacc     540
```

| | |
|---|---|
| ggctacaaca tgaactgggt gaggcagaac atcggcaaga gcctggagtg gatcggcgcc | 600 |
| atcgacccct actacggcgg caccagctac aaccagaagt tcaagggcag ggccaccctg | 660 |
| accgtggaca agagcagcag caccgcctac atgcacctga gagcctgac cagcgaggac | 720 |
| agcgccgtgt actactgcgt gagcggcatg gagtactggg gccagggcac cagcgtgacc | 780 |
| gtgagcagca ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| agggggctgg acttcgcctg tgatatctac atctgggcgc ccttggccgg gacttgtggg | 960 |
| gtccttctcc tgtcactggt tatcacccct tactgcagga gtaagaggag caggctcctg | 1020 |
| cacagtgact acatgaacat gactccccgc cgccccgggc ccacccgcaa gcattaccag | 1080 |
| ccctatgccc caccacgcga cttcgcagcc tatcgctcca gagtgaagtt cagcaggagc | 1140 |
| gcagacgccc ccgcgtacca gcagggccag aaccagctct ataacgagct caatctagga | 1200 |
| cgaagagagg agtacgatgt tttggacaag agacgtggcc gggaccctga tgggggga | 1260 |
| aagccgcaga gaaggaagaa ccctcaggaa ggcctgtaca tgaactgca gaaagataag | 1320 |
| atggcgagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc ccctcgcgg cagcggcgaa ggccgcggca gcctgctgac ctgcggcgat | 1500 |
| gtggaagaaa acccgggccc catggaatac gcctctgacg cttcactgga ccccgaagcc | 1560 |
| ccgtggcctc ccgcgccccg cgctcgcgcc tgccgcgtac tgccttgggc cctggtcgcg | 1620 |
| gggctgctgc tgctgctgct gctcgctgcc gcctgcgccg tcttcctcgc ctgcccctgg | 1680 |
| gccgtgtccg gggctcgcgc ctcgcccggc tccgcggcca gcccgagact ccgcgagggt | 1740 |
| cccgagcttt cgcccgacga tcccgccggc ctcttggacc tgcggcaggg catgtttgcg | 1800 |
| cagctggtgg cccaaaatgt tctgctgatc gatgggcccc tgagctggta cagtgaccca | 1860 |
| ggcctggcag gcgtgtccct gacgggggc ctgagctaca agaggacac gaaggagctg | 1920 |
| gtggtggcca aggctggagt ctactatgtc ttctttcaac tagagctgcg gcgcgtggtg | 1980 |
| gccggcgagg gctcaggctc cgtttcactt gcgctgcacc tgcagccact gcgctctgct | 2040 |
| gctgggccg ccgccctggc tttgaccgtg gacctgccac ccgcctcctc cgaggctcgg | 2100 |
| aactcggcct tcggttttcca gggccgcttg ctgcacctga gtgccggcca gcgcctgggc | 2160 |
| gtccatcttc acactgaggc cagggcacgc catgcctggc agcttaccca gggcgccaca | 2220 |
| gtcttgggac tcttccgggt gacccccgaa atcccagccg gactccttc accgaggtcg | 2280 |
| gaaggaagcg gagctactaa cttcttgagc ctgctgaagc aggctggaga cgtggaggag | 2340 |
| aaccctggac ctatgtacag aatgcagctg ctgagctgca tcgccctgag cctggccctg | 2400 |
| gtgaccaaca gcggcatcca cgtgttcatc ctgggctgct cagcgccgg cctgcccaag | 2460 |
| accgaggcca actgggtgaa cgtgatcagc gacctgaaga gatcgagga cctgatccag | 2520 |
| agcatgcaca tcgacgccac cctgtacacc gagagcgacg tgcaccccag ctgcaaggtg | 2580 |
| accgccatga agtgcttcct gctggagctg caggtgatca gcctggagag cggcgacgcc | 2640 |
| agcatccacg acaccgtgga gaacctgatc atcctggcca caacagcct gagcagcaac | 2700 |
| ggcaacgtga ccgagagcgg ctgcaaggag tgcgaggagc tggaggagaa gaacatcaag | 2760 |
| gagttcctgc agagcttcgt gcacatcgtg cagatgttca tcaacaccag ctccggcggc | 2820 |
| ggctccggcg gcggcggctc cggcggcggc ggctccggcg gcggcggctc cggcggcggc | 2880 |
| tccctgcagg cccccagaag agccagaggc tgcagaaccc tgggcctgcc cgccctgctg | 2940 |

```
ctgctgctgc tgctgagacc ccccgccacc agaggcatca cctgccccc ccccatgagc    3000 gtggagcacg ccgacatctg ggtgaagagc tacagcctgt acagcagaga gagatacatc    3060
tgcaacagcg gcttcaagag aaaggccggc accagcagcc tgaccgagtg cgtgctgaac    3120
aaggccacca acgtggccca ctggaccacc cccagcctga agtgcatcag ataagtttaa    3180
ac                                                                  3182
```

<210> SEQ ID NO 48
<211> LENGTH: 880
<212> TYPE: PRT
<213> ORGANISM: Artificial Sequence
<220> FEATURE:
<223> OTHER INFORMATION: Synthetic Sequence

<400> SEQUENCE: 48

```
Arg Ser Leu Thr Ser Arg Met Tyr Leu Trp Leu Lys Leu Leu Ala Phe
1               5                   10                  15

Gly Phe Ala Phe Leu Asp Thr Glu Val Phe Val Thr Gly Asp Ile Gln
            20                  25                  30

Val Thr Gln Ser Pro Ser Ser Leu Ser Ala Ser Leu Gly Glu Arg Ile
        35                  40                  45

Ser Leu Thr Cys Arg Thr Ser Gln Asp Ile Ser Asn Tyr Leu Asn Trp
    50                  55                  60

Phe Gln Gln Lys Pro Asp Gly Thr Phe Lys Arg Leu Ile Tyr Ala Thr
65                  70                  75                  80

Ser Ser Leu Asp Ser Gly Val Pro Lys Arg Phe Ser Gly Ser Gly Ser
                85                  90                  95

Gly Ser Asp Tyr Ser Leu Thr Ile Ser Ser Leu Glu Ser Glu Asp Phe
            100                 105                 110

Ala Asp Tyr Tyr Cys Leu Gln Tyr Ala Ser Tyr Pro Phe Thr Phe Gly
        115                 120                 125

Ser Gly Thr Lys Leu Glu Ile Lys Gly Gly Gly Ser Gly Gly Gly
    130                 135                 140

Gly Ser Gly Gly Gly Gly Ser Glu Val Gln Leu Gln Glu Ser Gly Pro
145                 150                 155                 160

Gly Leu Val Lys Pro Ser Gln Thr Leu Ser Leu Thr Cys Ser Val Thr
                165                 170                 175

Gly Tyr Ser Ile Thr Ser Gly Tyr Tyr Trp His Trp Ile Arg Gln Phe
            180                 185                 190

Pro Gly Asn Lys Leu Gln Trp Met Gly Tyr Ile Ser Tyr Ser Gly Phe
        195                 200                 205

Thr Asn Tyr Lys Thr Ser Leu Ile Asn Arg Ile Ser Ile Thr His Asp
    210                 215                 220

Thr Ser Glu Asn Gln Phe Phe Leu Asn Leu Asn Ser Val Thr Thr Glu
225                 230                 235                 240

Asp Thr Ala Thr Tyr Tyr Cys Ala Gly Asp Arg Thr Gly Ser Trp Phe
                245                 250                 255

Ala Tyr Trp Gly Gln Gly Thr Leu Val Thr Val Ser Ala Thr Thr Thr
            260                 265                 270

Pro Ala Pro Arg Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
```

```
                305                 310                 315                 320
        Leu Ala Gly Thr Cys Gly Val Leu Leu Leu Ser Leu Val Ile Thr Leu
                        325                 330                 335

Tyr Cys Arg Ser Lys Arg Ser Arg Leu Leu His Ser Asp Tyr Met Asn
                        340                 345                 350

Met Thr Pro Arg Arg Pro Gly Pro Thr Arg Lys His Tyr Gln Pro Tyr
                        355                 360                 365

Ala Pro Pro Arg Asp Phe Ala Ala Tyr Arg Ser Arg Val Lys Phe Ser
            370                 375                 380

Arg Ser Ala Asp Ala Pro Ala Tyr Gln Gln Gly Gln Asn Gln Leu Tyr
        385                 390                 395                 400

Asn Glu Leu Asn Leu Gly Arg Arg Glu Glu Tyr Asp Val Leu Asp Lys
                        405                 410                 415

Arg Arg Gly Arg Asp Pro Glu Met Gly Gly Lys Pro Arg Arg Lys
                        420                 425                 430

Asn Pro Gln Glu Gly Leu Tyr Asn Glu Leu Gln Lys Asp Lys Met Ala
                        435                 440                 445

Glu Ala Tyr Ser Glu Ile Gly Met Lys Gly Glu Arg Arg Arg Gly Lys
                        450                 455                 460

Gly His Asp Gly Leu Tyr Gln Gly Leu Ser Thr Ala Thr Lys Asp Thr
        465                 470                 475                 480

Tyr Asp Ala Leu His Met Gln Ala Leu Pro Pro Arg Gly Ser Gly Glu
                        485                 490                 495

Gly Arg Gly Ser Leu Leu Thr Cys Gly Asp Val Glu Glu Asn Pro Gly
                        500                 505                 510

Pro Met Tyr Leu Trp Leu Lys Leu Leu Ala Phe Gly Phe Ala Phe Leu
                        515                 520                 525

Asp Thr Glu Val Phe Val Thr Gly Gly Gln Asn Asp Thr Ser Gln Thr
                        530                 535                 540

Ser Ser Pro Ser Ser Pro Leu Phe Pro Gly Pro Ser Lys Pro Phe Trp
        545                 550                 555                 560

Val Leu Val Val Val Gly Gly Val Leu Ala Cys Tyr Ser Leu Leu Val
                        565                 570                 575

Thr Val Ala Phe Ile Ile Phe Trp Val Gly Ser Gly Ala Thr Asn Phe
                        580                 585                 590

Ser Leu Leu Lys Gln Ala Gly Asp Val Glu Glu Asn Pro Gly Pro Met
                        595                 600                 605

Tyr Arg Met Gln Leu Leu Ser Cys Ile Ala Leu Ser Leu Ala Leu Val
                        610                 615                 620

Thr Asn Ser Gly Ile His Val Phe Ile Leu Gly Cys Phe Ser Ala Gly
        625                 630                 635                 640

Leu Pro Lys Thr Glu Ala Asn Trp Val Asn Val Ile Ser Asp Leu Lys
                        645                 650                 655

Lys Ile Glu Asp Leu Ile Gln Ser Met His Ile Asp Ala Thr Leu Tyr
                        660                 665                 670

Thr Glu Ser Asp Val His Pro Ser Cys Lys Val Thr Ala Met Lys Cys
                        675                 680                 685

Phe Leu Leu Glu Leu Gln Val Ile Ser Leu Glu Ser Gly Asp Ala Ser
                        690                 695                 700

Ile His Asp Thr Val Glu Asn Leu Ile Ile Leu Ala Asn Asn Ser Leu
        705                 710                 715                 720

Ser Ser Asn Gly Asn Val Thr Glu Ser Gly Cys Lys Glu Cys Glu Glu
                        725                 730                 735
```

Leu Glu Glu Lys Asn Ile Lys Glu Phe Leu Gln Ser Phe Val His Ile
            740                 745                 750

Val Gln Met Phe Ile Asn Thr Ser Gly Gly Ser Gly Gly
            755                 760                 765

Gly Ser Gly Gly Gly Ser Gly Gly Gly Ser Gly Gly Ser
        770                 775                 780

Leu Gln Ala Pro Arg Arg Ala Arg Gly Cys Arg Thr Leu Gly Leu Pro
785                 790                 795                 800

Ala Leu Leu Leu Leu Leu Leu Arg Pro Pro Ala Thr Arg Gly Ile
            805                 810                 815

Thr Cys Pro Pro Pro Met Ser Val Glu His Ala Asp Ile Trp Val Lys
            820                 825                 830

Ser Tyr Ser Leu Tyr Ser Arg Glu Arg Tyr Ile Cys Asn Ser Gly Phe
            835                 840                 845

Lys Arg Lys Ala Gly Thr Ser Ser Leu Thr Glu Cys Val Leu Asn Lys
    850                 855                 860

Ala Thr Asn Val Ala His Trp Thr Thr Pro Ser Leu Lys Cys Ile Arg
865                 870                 875                 880

<210> SEQ ID NO 49
<211> LENGTH: 2633
<212> TYPE: DNA
<213> ORGANISM: Artificial Sequence
<220> FEATURE:
<223> OTHER INFORMATION: Synthetic Sequence

<400> SEQUENCE: 49
atgtatttgt ggcttaaact cttggcattt ggctttgcct ttctggacac agaagtattt      60
gtgacagggg acatccaggt gacccagagc cccagcagcc tgagcgccag cctgggcgag     120
agaatcagcc tgacctgcag aaccagccag gacatcagca actacctgaa ctggttccag     180
cagaagcccg acggcacctt caagagactg atctacgcca ccagcagcct ggacagcggc     240
gtgcccaaga gattcagcgg cagcggcagc ggcagcgact acagcctgac catcagcagc     300
ctggagagcg aggacttcgc cgactactac tgcctgcagt acgccagcta ccccttcacc     360
ttcggcagcg gcaccaagct ggagatcaag ggaggggggg gatccggggg aggaggctcc     420
ggcggaggcg gaagcgaggt gcagctgcag gagagcggcc ccggcctggt gaagcccagc     480
cagaccctga gcctgacctg cagcgtgacc ggctacagca tcaccagcgg ctactactgg     540
cactggatca acagttccc cggcaacaag ctgcagtgga tgggctacat cagctacagc     600
ggcttcacca actacaagac cagcctgatc aacagaatca gcatcaccca cgacaccagc     660
gagaaccagt tcttcctgaa cctgaacagc gtgaccaccg aggacaccgc cacctactac     720
tgcgccggcg acagaaccgg cagctggttc gcctactggg gccagggcac cctggtgacc     780
gtgagcgcca ccacgacgcc agcgccgcga ccaccaacac cggcgcccac catcgcgtcg     840
cagcccctgt ccctgcgccc agaggcgtgc cggcagcgg cggggggcgc agtgcacacg     900
agggggctgg acttcgcctg tgatatctac atctgggcgc ccttggccgg gacttgtggg     960
gtccttctcc tgtcactggt tatcacccctt tactgcagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tggggggga    1260

```
aagccgcaga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg cagcggcgaa ggccgcggca gctgctgac ctgcggcgat     1500 gtggaagaaa acccgggccc catgtacctg tggctgaagc tgctggcctt cggcttcgcc    1560
ttcctggaca ccgaggtgtt cgtgaccggc ggccagaacg acaccagcca gaccagcagc    1620
cccagcagcc cgctgtttcc gggcccgagc aaaccgtttt gggtgctggt ggtggtgggc    1680
ggcgtgctgg cgtgctatag cctgctggtg accgtggcgt ttattatttt ttgggtggga    1740
agcggagcta ctaacttcag cctgctgaag caggctggag acgtggagga aaccctgga     1800 cctatgtaca aatgcagct gctgagctgc atcgccctga gctggccct ggtgaccaac      1860 agcggcatcc acgtgttcat cctgggctgc ttcagcgccg gcctgcccaa gaccgaggcc    1920
aactgggtga acgtgatcag cgacctgaag aagatcgagg acctgatcca gagcatgcac    1980
atcgacgcca ccctgtacac cgagagcgac gtgcacccca gctgcaaggt gaccgccatg    2040
aagtgcttcc tgctggagct gcaggtgatc agcctggaga cggcgacgc cagcatccac     2100 gacaccgtgg agaacctgat catcctggcc aacaacagcc tgagcagcaa cggcaacgtg    2160
accgagagcg gctgcaagga gtgcgaggag ctggaggaga gaacatcaa ggagttcctg     2220 cagagcttcg tgcacatcgt gcagatgttc atcaacacca gctccggcgg cggctccggc    2280
ggcggcggct ccggcggcgg cggctccggc ggcggcggct ccggcggcgg ctccctgcag    2340
gcccccagaa gagccagagg ctgcagaacc ctgggcctgc ccgccctgct gctgctgctg    2400
ctgctgagac cccccgccac cagaggcatc acctgccccc ccccatgag cgtggagcac     2460 gccgacatct gggtgaagag ctacagcctg tacagcagag agagatacat ctgcaacagc    2520
ggcttcaaga aaaggccgg caccagcagc ctgaccgagt gcgtgctgaa caaggccacc     2580
aacgtggccc actggaccac ccccagcctg aagtgcatca gataagttta aac           2633
```

<210> SEQ ID NO 50
<211> LENGTH: 1099
<212> TYPE: PRT
<213> ORGANISM: Artificial Sequence
<220> FEATURE:
<223> OTHER INFORMATION: Synthetic Sequence

<400> SEQUENCE: 50

```
Asp Arg Thr Met Ala Leu Pro Val Thr Ala Leu Leu Leu Pro Leu Ala
1               5                   10                  15

Leu Leu Leu His Ala Ala Arg Pro Asp Val Val Met Thr Gln Ser His
            20                  25                  30

Arg Phe Met Ser Thr Ser Val Gly Asp Arg Val Ser Ile Thr Cys Arg
        35                  40                  45

Ala Ser Gln Asp Val Asn Thr Ala Val Ser Trp Tyr Gln Gln Lys Pro
    50                  55                  60

Gly Gln Ser Pro Lys Leu Leu Ile Phe Ser Ala Ser Tyr Arg Tyr Thr
65                  70                  75                  80

Gly Val Pro Asp Arg Phe Thr Gly Ser Gly Ser Gly Ala Asp Phe Thr
                85                  90                  95

Leu Thr Ile Ser Ser Val Gln Ala Glu Asp Leu Ala Val Tyr Tyr Cys
            100                 105                 110

Gln Gln His Tyr Ser Thr Pro Trp Thr Phe Gly Gly Gly Thr Lys Leu
```

```
            115                 120                 125
Asp Ile Lys Gly Gly Gly Ser Gly Gly Gly Ser Gly Gly
    130                 135                 140
Gly Ser Gln Ile Gln Leu Val Gln Ser Gly Pro Asp Leu Lys Lys Pro
145                 150                 155                 160
Gly Glu Thr Val Lys Leu Ser Cys Lys Ala Ser Gly Tyr Thr Phe Thr
                165                 170                 175
Asn Phe Gly Met Asn Trp Val Lys Gln Ala Pro Gly Lys Gly Phe Lys
            180                 185                 190
Trp Met Ala Trp Ile Asn Thr Tyr Thr Gly Glu Ser Tyr Phe Ala Asp
        195                 200                 205
Asp Phe Lys Gly Arg Phe Ala Phe Ser Val Glu Thr Ser Ala Thr Thr
    210                 215                 220
Ala Tyr Leu Gln Ile Asn Asn Leu Lys Thr Glu Asp Thr Ala Thr Tyr
225                 230                 235                 240
Phe Cys Ala Arg Gly Glu Ile Tyr Tyr Gly Tyr Asp Gly Gly Phe Ala
                245                 250                 255
Tyr Trp Gly Gln Gly Thr Leu Val Thr Val Ser Ala Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Arg Ser Lys Arg Ser Arg Leu Leu His Ser Asp Tyr Met Asn Met
            340                 345                 350
Thr Pro Arg Arg Pro Gly Pro Thr Arg Lys His Tyr Gln Pro Tyr Ala
        355                 360                 365
Pro Pro Arg Asp Phe Ala Ala Tyr Arg Ser Arg Val Lys Phe Ser Arg
    370                 375                 380
Ser Ala Asp Ala Pro Ala Tyr Gln Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Gln Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
    450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg Gly Ser Gly Ala Thr
                485                 490                 495
Asn Phe Ser Leu Leu Lys Gln Ala Gly Asp Val Glu Glu Asn Pro Gly
            500                 505                 510
Pro Met Glu Tyr Ala Ser Asp Ala Ser Leu Asp Pro Glu Ala Pro Trp
        515                 520                 525
Pro Pro Ala Pro Arg Ala Arg Ala Cys Arg Val Leu Pro Trp Ala Leu
    530                 535                 540
```

```
Val Ala Gly Leu Leu Leu Leu Leu Leu Ala Ala Cys Ala Val
545                 550                 555                 560

Phe Leu Ala Cys Pro Trp Ala Val Ser Gly Ala Arg Ala Ser Pro Gly
                565                 570                 575

Ser Ala Ala Ser Pro Arg Leu Arg Glu Gly Pro Glu Leu Ser Pro Asp
                580                 585                 590

Asp Pro Ala Gly Leu Leu Asp Leu Arg Gln Gly Met Phe Ala Gln Leu
                595                 600                 605

Val Ala Gln Asn Val Leu Leu Ile Asp Gly Pro Leu Ser Trp Tyr Ser
610                 615                 620

Asp Pro Gly Leu Ala Gly Val Ser Leu Thr Gly Gly Leu Ser Tyr Lys
625                 630                 635                 640

Glu Asp Thr Lys Glu Leu Val Val Ala Lys Ala Gly Val Tyr Tyr Val
                645                 650                 655

Phe Phe Gln Leu Glu Leu Arg Arg Val Val Ala Gly Glu Gly Ser Gly
                660                 665                 670

Ser Val Ser Leu Ala Leu His Leu Gln Pro Leu Arg Ser Ala Ala Gly
                675                 680                 685

Ala Ala Ala Leu Ala Leu Thr Val Asp Leu Pro Pro Ala Ser Ser Glu
690                 695                 700

Ala Arg Asn Ser Ala Phe Gly Phe Gln Gly Arg Leu Leu His Leu Ser
705                 710                 715                 720

Ala Gly Gln Arg Leu Gly Val His Leu His Thr Glu Ala Arg Ala Arg
                725                 730                 735

His Ala Trp Gln Leu Thr Gln Gly Ala Thr Val Leu Gly Leu Phe Arg
                740                 745                 750

Val Thr Pro Glu Ile Pro Ala Gly Leu Pro Ser Pro Arg Ser Glu Gly
                755                 760                 765

Ser Gly Glu Gly Arg Gly Ser Leu Leu Thr Cys Gly Asp Val Glu Glu
                770                 775                 780

Asn Pro Gly Pro Met Tyr Arg Met Gln Leu Leu Ser Cys Ile Ala Leu
785                 790                 795                 800

Ser Leu Ala Leu Val Thr Asn Ser Gly Ile His Val Phe Ile Leu Gly
                805                 810                 815

Cys Phe Ser Ala Gly Leu Pro Lys Thr Glu Ala Asn Trp Val Asn Val
                820                 825                 830

Ile Ser Asp Leu Lys Lys Ile Glu Asp Leu Ile Gln Ser Met His Ile
                835                 840                 845

Asp Ala Thr Leu Tyr Thr Glu Ser Asp Val His Pro Ser Cys Lys Val
                850                 855                 860

Thr Ala Met Lys Cys Phe Leu Leu Glu Leu Gln Val Ile Ser Leu Glu
865                 870                 875                 880

Ser Gly Asp Ala Ser Ile His Asp Thr Val Glu Asn Leu Ile Ile Leu
                885                 890                 895

Ala Asn Asn Ser Leu Ser Ser Asn Gly Asn Val Thr Glu Ser Gly Cys
                900                 905                 910

Lys Glu Cys Glu Glu Leu Glu Glu Lys Asn Ile Lys Glu Phe Leu Gln
                915                 920                 925

Ser Phe Val His Ile Val Gln Met Phe Ile Asn Thr Ser Ser Gly Gly
                930                 935                 940

Gly Ser Gly Gly Gly Gly Ser Gly Gly Gly Gly Ser Gly Gly Gly Gly
945                 950                 955                 960
```

Ser Gly Gly Gly Ser Leu Gln Ile Thr Cys Pro Pro Pro Met Ser Val
            965                 970                 975

Glu His Ala Asp Ile Trp Val Lys Ser Tyr Ser Leu Tyr Ser Arg Glu
        980                 985                 990

Arg Tyr Ile Cys Asn Ser Gly Phe Lys Arg Lys Ala Gly Thr Ser Ser
        995                 1000                1005

Leu Thr Glu Cys Val Leu Asn Lys Ala Thr Asn Val Ala His Trp
    1010                1015                1020

Thr Thr Pro Ser Leu Lys Cys Ile Arg Thr Thr Pro Ala Pro
    1025                1030                1035

Arg Pro Pro Thr Pro Ala Pro Thr Ile Ala Ser Gln Pro Leu Ser
    1040                1045                1050

Leu Arg Pro Glu Ala Cys Arg Pro Ala Ala Gly Gly Ala Val His
    1055                1060                1065

Thr Arg Gly Leu Asp Phe Ala Cys Asp Val Ala Ile Ser Thr Ser
    1070                1075                1080

Thr Val Leu Leu Cys Gly Leu Ser Ala Val Ser Leu Leu Ala Cys
    1085                1090                1095

Tyr

<210> SEQ ID NO 51
<211> LENGTH: 3299
<212> TYPE: DNA
<213> ORGANISM: Artificial Sequence
<220> FEATURE:
<223> OTHER INFORMATION: Synthetic Sequence

<400> SEQUENCE: 51

```
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcaccccctg gaccttcggc     360
ggcggcacca agctggacat caagggaggg ggggatccg ggggaggagg ctccggcgga     420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
accgcctacc tgcagatcaa caacctgaag accgaggaca ccgccaccta cttctgcgcc     720
aggggcgaga tctactacgg ctacgacggc ggcttcgcct actggggcca gggcaccctg     780
gtgaccgtga gcgccaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtgggtcc ttctcctgtc actggttatc acccttact gcaggagtaa gaggagcagg    1020
ctcctgcaca gtgactacat gaacatgact cccgccgcc cgggcccac cgcaagcat    1080
taccagccct atgccccacc acgcgacttc gcagcctatc gctccagagt gaagttcagc    1140
aggagcgcag acgccccgc gtaccagcag ggccagaacc agctctataa cgagctcaat    1200
```

| | |
|---|---|
| ctaggacgaa gagaggagta cgatgttttg acaagagac gtggccggga ccctgagatg | 1260 |
| ggggaaagc cgcagagaag gaagaaccct caggaaggcc tgtacaatga actgcagaaa | 1320 |
| gataagatgg cggaggccta cagtgagatt gggatgaaag gcgagcgccg gaggggcaag | 1380 |
| gggcacgatg gcctttacca gggtctcagt acagccacca aggacaccta cgacgccctt | 1440 |
| cacatgcagg ccctgccccc tcgcggaagc ggagccacca acttcagcct gctgaagcag | 1500 |
| gccggcgacg tggaggagaa ccccggcccc atggaatacg cctctgacgc ttcactggac | 1560 |
| cccgaagccc cgtggcctcc cgcgccccgc gctcgcgcct gccgcgtact gccttgggcc | 1620 |
| ctggtcgcgg ggctgctgct gctgctgctg ctcgctgccg cctgcgccgt cttcctcgcc | 1680 |
| tgcccctggg ccgtgtccgg ggctcgcgcc tcgcccggct ccgcggccag cccgagactc | 1740 |
| cgcgagggtc ccgagctttc gcccgacgat cccgccggcc tcttggacct gcggcagggc | 1800 |
| atgtttgcgc agctggtggc ccaaaatgtt ctgctgatcg atgggcccct gagctggtac | 1860 |
| agtgacccag gcctgcaggc cgtgtccctg acgggggggcc tgagctacaa agaggacacg | 1920 |
| aaggagctgg tggtggccaa ggctggagtc tactatgtct tctttcaact agagctgcgg | 1980 |
| cgcgtggtgg ccggcgaggg ctcaggctcc gtttcacttg cgctgcacct gcagccactg | 2040 |
| cgctctgctg ctggggccgc cgccctggct ttgaccgtgg acctgccacc cgcctcctcc | 2100 |
| gaggctcgga actcggcctt cggtttccag ggccgcttgc tgcacctgag tgccggccag | 2160 |
| cgcctgggcg tccatcttca cactgaggcc agggcacgcc atgcctggca gcttacccag | 2220 |
| ggcgccacag tcttgggact cttccggggtg accccgaaa tcccagccgg actcccttca | 2280 |
| ccgaggtcgg aaggcagcgg cgaaggccgc ggcagcctgc tgacctgcgg cgatgtggaa | 2340 |
| gaaaacccgg gccccatgta cagaatgcag ctgctgagct gcatcgccct gagcctggcc | 2400 |
| ctggtgacca cagcggcat ccacgtgttc atcctgggct gcttcagcgc cggcctgccc | 2460 |
| aagaccgagg ccaactgggt gaacgtgatc agcgacctga agaagatcga ggacctgatc | 2520 |
| cagagcatgc acatcgacgc caccctgtac accgagagcg acgtgcaccc cagctgcaag | 2580 |
| gtgaccgcca tgaagtgctt cctgctggag ctgcaggtga tcagcctgga gagcggcgac | 2640 |
| gccagcatcc acgacaccgt ggagaacctg atcatcctgg ccaacaacag cctgagcagc | 2700 |
| aacggcaacg tgaccgagag cggctgcaag gagtgcgagg agctggagga agaacatc | 2760 |
| aaggagttcc tgcagagctt cgtgcacatc gtgcagatgt tcatcaacac cagctccggc | 2820 |
| ggcggctccg gcggcggcgg ctccggcggc ggcggctccg gcggcggcgg ctccggcggc | 2880 |
| ggctccctgc agatcacctg ccccccccc atgagcgtgg agcacgccga catctgggtg | 2940 |
| aagagctaca gcctgtacag cagagagaga tacatctgca acagcggctt caagagaaag | 3000 |
| gccggcacca gcagcctgac cgagtgcgtg ctgaacaagg ccaccaacgt ggcccactgg | 3060 |
| accaccccca gcctgaagtg catcagaacc accaccccg ccccaggcc cccaccccc | 3120 |
| gccccacca tcgccagcca gcccctgagc ctgaggcccg aggcctgcag gcccgccgcc | 3180 |
| ggcggcgccg tgcacaccag gggcctggac ttcgcctgcg acgtggctat ctccacgtcc | 3240 |
| actgtcctgc tgtgtgggct gagcgctgtg tctctcctgg catgctacta agtttaaac | 3299 |

<210> SEQ ID NO 52
<211> LENGTH: 1006
<212> TYPE: PRT
<213> ORGANISM: Artificial Sequence
<220> FEATURE:
<223> OTHER INFORMATION: Synthetic Sequence

<400> SEQUENCE: 52

```
Asp Arg Thr Met Ala Leu Pro Val Thr Ala Leu Leu Pro Leu Ala
1               5                   10                  15

Leu Leu Leu His Ala Ala Arg Pro Asp Ile Gln Leu Thr Gln Ser Pro
                20                  25                  30

Ser Ser Leu Ser Ala Ser Val Gly Asp Arg Val Thr Met Thr Cys Arg
            35                  40                  45

Ala Ser Ser Ser Val Ser Tyr Ile His Trp Phe Gln Gln Lys Pro Gly
        50                  55                  60

Lys Ala Pro Lys Pro Trp Ile Tyr Ala Thr Ser Asn Leu Ala Ser Gly
65                  70                  75                  80

Val Pro Val Arg Phe Ser Gly Ser Gly Ser Gly Thr Asp Tyr Thr Phe
                85                  90                  95

Thr Ile Ser Ser Leu Gln Pro Glu Asp Ile Ala Thr Tyr Tyr Cys Gln
            100                 105                 110

Gln Trp Thr Ser Asn Pro Pro Thr Phe Gly Gly Gly Thr Lys Leu Glu
            115                 120                 125

Ile Lys Arg Gly Gly Gly Gly Ser Gly Gly Gly Gly Ser Gly Gly Gly
130                 135                 140

Gly Ser Gln Val Gln Leu Gln Gln Ser Gly Ala Glu Val Lys Lys Pro
145                 150                 155                 160

Gly Ser Ser Val Lys Val Ser Cys Lys Ala Ser Gly Tyr Thr Phe Ser
                165                 170                 175

Ser Tyr Asn Met His Trp Val Arg Gln Ala Pro Gly Gln Gly Leu Glu
            180                 185                 190

Trp Met Gly Ala Ile Tyr Pro Gly Asn Gly Asp Thr Ser Tyr Asn Gln
            195                 200                 205

Lys Phe Lys Gly Arg Ala Thr Ile Thr Ala Asp Glu Ser Thr Asn Thr
210                 215                 220

Ala Tyr Met Glu Leu Ser Ser Leu Arg Ser Glu Asp Thr Ala Phe Tyr
225                 230                 235                 240

Phe Cys Ala Arg Ser Thr Tyr Tyr Gly Gly Asp Trp Tyr Phe Asp Val
                245                 250                 255

Trp Gly Gln Gly Thr Thr Val Thr Val Ser Ser Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415
```

```
Gly Arg Asp Pro Glu Met Gly Gly Lys Pro Gln Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Gly Ser Gly Ala Thr Asn
                485                 490                 495

Phe Ser Leu Leu Lys Gln Ala Gly Asp Val Glu Glu Asn Pro Gly Pro
            500                 505                 510

Met Ala Leu Pro Val Thr Ala Leu Leu Leu Pro Leu Ala Leu Leu Leu
            515                 520                 525

His Ala Ala Arg Pro Glu Val Gln Leu Gln Gln Ser Gly Pro Glu Leu
        530                 535                 540

Ile Lys Pro Gly Ala Ser Val Lys Met Ser Cys Lys Ala Ser Gly Tyr
545                 550                 555                 560

Thr Phe Thr Ser Tyr Val Met His Trp Val Lys Gln Lys Pro Gly Gln
                565                 570                 575

Gly Leu Glu Trp Ile Gly Tyr Ile Asn Pro Tyr Asn Asp Gly Thr Lys
            580                 585                 590

Tyr Asn Glu Lys Phe Lys Gly Lys Ala Thr Leu Thr Ser Asp Lys Ser
        595                 600                 605

Ser Ser Thr Ala Tyr Met Glu Leu Ser Ser Leu Thr Ser Glu Asp Ser
    610                 615                 620

Ala Val Tyr Tyr Cys Ala Arg Gly Thr Tyr Tyr Tyr Gly Ser Arg Val
625                 630                 635                 640

Phe Asp Tyr Trp Gly Gln Gly Thr Thr Leu Thr Val Ser Ser Gly Gly
                645                 650                 655

Gly Gly Ser Gly Gly Gly Gly Ser Gly Gly Gly Gly Ser Asp Ile Val
            660                 665                 670

Met Thr Gln Ala Ala Pro Ser Ile Pro Val Thr Pro Gly Glu Ser Val
        675                 680                 685

Ser Ile Ser Cys Arg Ser Ser Lys Ser Leu Leu Asn Ser Asn Gly Asn
    690                 695                 700

Thr Tyr Leu Tyr Trp Phe Leu Gln Arg Pro Gly Gln Ser Pro Gln Leu
705                 710                 715                 720

Leu Ile Tyr Arg Met Ser Asn Leu Ala Ser Gly Val Pro Asp Arg Phe
                725                 730                 735

Ser Gly Ser Gly Ser Gly Thr Ala Phe Thr Leu Arg Ile Ser Arg Val
            740                 745                 750

Glu Ala Glu Asp Val Gly Val Tyr Tyr Cys Met Gln His Leu Glu Tyr
        755                 760                 765

Pro Phe Thr Phe Gly Ala Gly Thr Lys Leu Glu Leu Lys Arg Thr Thr
    770                 775                 780

Thr Pro Ala Pro Arg Pro Pro Thr Pro Ala Pro Thr Ile Ala Ser Gln
785                 790                 795                 800

Pro Leu Ser Leu Arg Pro Glu Ala Cys Arg Pro Ala Ala Gly Gly Ala
                805                 810                 815

Val His Thr Arg Gly Leu Asp Phe Ala Cys Asp Ile Tyr Ile Trp Ala
            820                 825                 830

Pro Leu Ala Gly Thr Cys Gly Val Leu Leu Leu Ser Leu Val Ile Thr
```

```
Leu Tyr Cys Lys Arg Gly Arg Lys Lys Leu Tyr Ile Phe Lys Gln
        850                 855                 860
Pro Phe Met Arg Pro Val Gln Thr Thr Gln Glu Glu Asp Gly Cys Ser
865                 870                 875                 880
Cys Arg Phe Pro Glu Glu Glu Gly Gly Cys Glu Leu Arg Val Lys
            885                 890                 895
Phe Ser Arg Ser Ala Asp Ala Pro Ala Tyr Gln Gln Gly Gln Asn Gln
                900                 905                 910
Leu Tyr Asn Glu Leu Asn Leu Gly Arg Arg Glu Glu Tyr Asp Val Leu
            915                 920                 925
Asp Lys Arg Arg Gly Arg Asp Pro Glu Met Gly Gly Lys Pro Gln Arg
        930                 935                 940
Arg Lys Asn Pro Gln Glu Gly Leu Tyr Asn Glu Leu Gln Lys Asp Lys
945                 950                 955                 960
Met Ala Glu Ala Tyr Ser Glu Ile Gly Met Lys Gly Glu Arg Arg Arg
            965                 970                 975
Gly Lys Gly His Asp Gly Leu Tyr Gln Gly Leu Ser Thr Ala Thr Lys
        980                 985                 990
Asp Thr Tyr Asp Ala Leu His Met  Gln Ala Leu Pro Pro Arg
        995                 1000                1005
```

<210> SEQ ID NO 53
<211> LENGTH: 3020
<212> TYPE: DNA
<213> ORGANISM: Artificial Sequence
<220> FEATURE:
<223> OTHER INFORMATION: Synthetic Sequence

<400> SEQUENCE: 53

```
atggccttac cagtgaccgc cttgctcctg ccgctggcct tgctgctcca cgccgccagg     60
ccggacatcc agctgaccca gagccccagc agcctgagcg ccagcgtggg cgacagggtg    120
accatgacct gcagggccag cagcagcgtg agctacatcc actggttcca gcagaagccc    180
ggcaaggccc ccaagccctg gatctacgcc accagcaacc tggccagcgg cgtgcccgtg    240
aggttcagcg gcagcggcag cggcaccgac tacaccttca ccatcagcag cctgcagccc    300
gaggacatcg ccacctacta ctgccagcag tggaccagca ccccccccac cttcggcggc    360
ggcaccaagc tggagatcaa gaggggcggc ggcggcagcg gcggcggcgg cagcggcggc    420
ggcggcagcc aggtgcagct gcagcagagc ggcgccgagg tgaagaagcc cggcagcagc    480
gtgaaggtga gctgcaaggc cagcggctac accttcagca gctacaacat gcactgggtg    540
aggcaggccc ccggccaggg cctggagtgg atgggcgcca tctacccggg caacggcgac    600
accagctaca ccagaagttt caagggcagg gccaccatca ccgccgacga gagcaccaac    660
accgcctaca tggagctgag cagcctgagg agcgaggaca ccgccttcta cttctgcgcc    720
aggagcacct actacggcgg cgactggtac ttcgacgtgt ggggccaggg caccaccgtg    780
accgtgagca gcaccacgac gccagcgccg cgaccaccaa caccggcgcc accatcgcg    840
tcgcagcccc tgtccctgcg cccagaggcg tgccggccag cggcgggggg cgcagtgcac    900
acgagggggc tggacttcgc ctgtgatatc tacatctggg cgcccttggc cgggacttgt    960
ggggtccttc tcctgtcact ggttatcacc ctttactgca ggagtaagag gagcaggctc   1020
ctgcacagtg actacatgaa catgactccc cgccgccccg ggcccacccg caagcattac   1080
cagccctatg ccccaccacg cgacttcgca gcctatcgct ccagagtgaa gttcagcagg   1140
```

```
agcgcagacg ccccgcgta ccagcagggc cagaaccagc tctataacga gctcaatcta   1200
ggacgaagag aggagtacga tgttttggac aagagacgtg gccggaccc tgagatgggg   1260 ggaaagccgc agagaaggaa gaaccctcag gaaggcctgt acaatgaact gcagaaagat   1320
aagatggcgc aggcctacag tgagattggg atgaaaggcg agcgccggag gggcaagggg   1380
cacgatggcc tttaccaggg tctcagtaca gccaccaagg acacctacga cgcccttcac   1440
atgcaggccc tgcccctcg cggaagcgga gccaccaact tcagcctgct gaagcaggcc   1500
ggcgacgtgg aggagaaccc cggccccatg gccctgcccg tgaccgccct gctgctgccc   1560
ctggccctgc tgctgcacgc cgccaggccc gaggtccagc tgcagcagtc tggacctgag   1620
ctgataaagc ctggggcttc agtgaagatg tcctgcaagg cttctggata cacattcact   1680
agctatgtta tgcactgggt gaagcagaag cctgggcagg gccttgagtg gattggatat   1740
attaatcctt acaatgatgg tactaagtac aatgagaagt tcaaaggcaa ggccacactg   1800
acttcagaca aatcctccag cacagcctac atggagctca gcagcctgac ctctgaggac   1860
tctgcggtct attactgtgc aagagggact tattactacg gtagtagggt atttgactac   1920
tggggccaag gcaccactct cacagtctcc tcaggtggag ggggctcagg cggaggtggc   1980 tctggggtg gaggctcgga cattgtgatg actcaggctg cacctctat acctgtcact   2040 cctggagagt cagtatccat ctcctgcagg tctagtaaga gtctcctgaa tagtaatggc   2100
aacacttact tgtattggtt cctgcagagg ccaggccagt ctcctcagct cctgatatat   2160
cggatgtcca accttgcctc aggagtccca gacaggttca gtggcagtgg gtcaggaact   2220
gctttcacac tgagaatcag tagagtggag gctgaggatg tgggtgttta ttactgtatg   2280
caacatctag aatatccgtt cacgttcggg gctgggacca agctggagct gaaacgacc    2340 accacccccg ccccaggcc ccccaccccc gccccacca tcgccagcca gcccctgagc   2400
ctgaggcccg aggcctgcag gcccgccgcc ggcggcgccg tgcacaccag gggcctggac   2460
ttcgcctgcg acatctacat ctgggccccc ctggccggca cctgcggcgt gctgctgctg   2520
agcctggtga tcacccctgta ctgcaaacgg ggcagaaaga aactcctgta tatattcaaa   2580
caaccattta tgagaccagt acaaactact caagaggaag atggctgtag ctgccgattt   2640
ccagaagaag aagaaggagg atgtgaactg agggtgaagt tcagcaggag cgccgacgcc   2700
cccgcctacc agcagggcca gaaccagctg tacaacgagc tgaacctggg caggagggag   2760
gagtacgacg tgctggacaa gaggaggggc agggaccccg agatgggcgg caagccccag   2820
aggaggaaga ccccccagga gggcctgtac aacgagctgc agaaggacaa gatggccgag   2880
gcctacagcg agatcggcat gaagggcgag aggaggaggg gcaagggcca cgacggcctg   2940
taccagggcc tgagcaccgc caccaaggac acctacgacg ccctgcacat gcaggccctg   3000
ccccccaggt aagtttaaac                                              3020
```

<210> SEQ ID NO 54
<211> LENGTH: 784
<212> TYPE: PRT
<213> ORGANISM: Artificial Sequence
<220> FEATURE:
<223> OTHER INFORMATION: Synthetic Sequence

<400> SEQUENCE: 54

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu

-continued

```
                20                  25                  30
Ala Val Ser Leu Gly Gln Arg Ala Thr Ile Ser Cys Arg Ala Ser Lys
            35                  40                  45
Ser Val Ser Thr Ser Gly Tyr Ser Tyr Leu His Trp Tyr Gln Gln Lys
        50                  55                  60
Pro Gly Gln Pro Pro Lys Leu Leu Ile Tyr Leu Ala Ser Asn Leu Glu
65                  70                  75                  80
Ser Gly Val Pro Ala Arg Phe Ser Gly Ser Gly Ser Gly Thr Asp Phe
                85                  90                  95
Thr Leu Asn Ile His Pro Val Glu Glu Asp Ala Ala Thr Tyr Tyr
            100                 105                 110
Cys Gln His Ser Arg Glu Leu Pro Phe Thr Phe Gly Ser Gly Thr Lys
            115                 120                 125
Leu Glu Ile Lys Gly Gly Gly Gly Ser Gly Gly Gly Ser Gly Gly
            130                 135                 140
Gly Gly Ser Gln Val Gln Leu Val Glu Ser Gly Gly Gly Leu Val Gln
145                 150                 155                 160
Pro Gly Gly Ser Leu Lys Leu Ser Cys Ala Ala Ser Gly Phe Asp Phe
                165                 170                 175
Ser Arg Tyr Trp Met Ser Trp Val Arg Gln Ala Pro Gly Lys Gly Leu
            180                 185                 190
Glu Trp Ile Gly Glu Ile Asn Pro Thr Ser Ser Thr Ile Asn Phe Thr
            195                 200                 205
Pro Ser Leu Lys Asp Lys Val Phe Ile Ser Arg Asp Asn Ala Lys Asn
            210                 215                 220
Thr Leu Tyr Leu Gln Met Ser Lys Val Arg Ser Glu Asp Thr Ala Leu
225                 230                 235                 240
Tyr Tyr Cys Ala Arg Gly Asn Tyr Tyr Arg Tyr Gly Asp Ala Met Asp
                245                 250                 255
Tyr Trp Gly Gln Gly Thr Ser Val Thr Val Ser Thr Thr Thr Pro Ala
            260                 265                 270
Pro Arg Pro Pro Thr Pro Ala Pro Thr Ile Ala Ser Gln Pro Leu Ser
            275                 280                 285
Leu Arg Pro Glu Ala Cys Arg Pro Ala Ala Gly Gly Ala Val His Thr
            290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Arg Ser Lys Arg Ser Arg Leu Leu His Ser Asp Tyr Met Asn Met Thr
            340                 345                 350
Pro Arg Arg Pro Gly Pro Thr Arg Lys His Tyr Gln Pro Tyr Ala Pro
            355                 360                 365
Pro Arg Asp Phe Ala Ala Tyr Arg Ser Arg Val Lys Phe Ser Arg Ser
            370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Gln Arg Arg Lys Asn Pro
            420                 425                 430
Gln Glu Gly Leu Tyr Asn Glu Leu Gln Lys Asp Lys Met Ala Glu Ala
            435                 440                 445
```

| | | | | | | | | | | |
|---|---|---|---|---|---|---|---|---|---|---|
Tyr Ser Glu Ile Gly Met Lys Gly Glu Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg Gly Ser Gly Glu Gly Arg
485 490 495

Gly Ser Leu Leu Thr Cys Gly Asp Val Glu Glu Asn Pro Gly Pro Met
500 505 510

Tyr Arg Met Gln Leu Leu Ser Cys Ile Ala Leu Ser Leu Ala Leu Val
515 520 525

Thr Asn Ser Gly Ile His Val Phe Ile Leu Gly Cys Phe Ser Ala Gly
530 535 540

Leu Pro Lys Thr Glu Ala Asn Trp Val Asn Val Ile Ser Asp Leu Lys
545 550 555 560

Lys Ile Glu Asp Leu Ile Gln Ser Met His Ile Asp Ala Thr Leu Tyr
565 570 575

Thr Glu Ser Asp Val His Pro Ser Cys Lys Val Thr Ala Met Lys Cys
580 585 590

Phe Leu Leu Glu Leu Gln Val Ile Ser Leu Glu Ser Gly Asp Ala Ser
595 600 605

Ile His Asp Thr Val Glu Asn Leu Ile Ile Leu Ala Asn Asn Ser Leu
610 615 620

Ser Ser Asn Gly Asn Val Thr Glu Ser Gly Cys Lys Glu Cys Glu Glu
625 630 635 640

Leu Glu Glu Lys Asn Ile Lys Glu Phe Leu Gln Ser Phe Val His Ile
645 650 655

Val Gln Met Phe Ile Asn Thr Ser Ser Gly Gly Gly Ser Gly Gly Gly
660 665 670

Gly Ser Gly Gly Gly Ser Gly Gly Gly Ser Gly Gly Gly Ser
675 680 685

Leu Gln Ala Pro Arg Arg Ala Arg Gly Cys Arg Thr Leu Gly Leu Pro
690 695 700

Ala Leu Leu Leu Leu Leu Leu Leu Arg Pro Pro Ala Thr Arg Gly Ile
705 710 715 720

Thr Cys Pro Pro Pro Met Ser Val Glu His Ala Asp Ile Trp Val Lys
725 730 735

Ser Tyr Ser Leu Tyr Ser Arg Glu Arg Tyr Ile Cys Asn Ser Gly Phe
740 745 750

Lys Arg Lys Ala Gly Thr Ser Ser Leu Thr Glu Cys Val Leu Asn Lys
755 760 765

Ala Thr Asn Val Ala His Trp Thr Thr Pro Ser Leu Lys Cys Ile Arg
770 775 780

<210> SEQ ID NO 55
<211> LENGTH: 2363
<212> TYPE: DNA
<213> ORGANISM: Artificial Sequence
<220> FEATURE:
<223> OTHER INFORMATION: Synthetic Sequence

<400> SEQUENCE: 55
atggccttac cagtgaccgc cttgctcctg ccgctggcct tgctgctcca cgccgccagg    60
ccggacatcg tgctgaccca gagccccgcc agcctggccg tgagcctggg ccagagggcc   120
accatcagct gcagggccag caagagcgtg agcaccagcg gctacagcta cctgcactgg   180

```
taccagcaga agcccggcca gccccccaag ctgctgatct acctggccag caacctggag    240
agcggcgtgc ccgccaggtt cagcggcagc ggcagcggca ccgacttcac cctgaacatc    300
caccccgtgg aggaggagga cgccgccacc tactactgcc agcacagcag ggagctgccc    360
ttcaccttcg gcagcggcac caagctggag atcaagggag gggggggatc cgggggagga    420
ggctccggcg gaggcggaag ccaggtgcag ctggtggaga gcggcggcgg cctggtgcag    480
cccggcggca gcctgaagct gagctgcgcc gccagcggct tcgacttcag caggtactgg    540
atgagctggg tgaggcaggc ccccggcaag ggcctggagt ggatcggcga gatcaacccc    600
accagcagca ccatcaactt cacccccagc ctgaaggaca aggtgttcat cagcagggac    660
aacgccaaga cacccctgta cctgcagatg agcaaggtga ggagcgagga caccgccctg    720
tactactgcg ccaggggcaa ctactacagg tacggcgacg ccatggacta ctggggccag    780
ggcaccagcg tgaccgtgag caccacgacg ccagcgccgc gaccaccaac accggcgccc    840
accatcgcgt cgcagcccct gtccctgcgc ccagaggcgt gccggccagc ggcgggggc    900
gcagtgcaca cgagggggct ggacttcgcc tgtgatatct acatctgggc gcccttggcc    960
gggacttgtg gggtccttct cctgtcactg gttatcaccc tttactgcag gagtaagagg   1020
agcaggctcc tgcacagtga ctacatgaac atgactcccc gccgccccgg gcccacccgc   1080
aagcattacc agcccctatgc cccaccacgc gacttcgcag cctatcgctc cagagtgaag   1140
ttcagcagga gcgcagacgc ccccgcgtac cagcagggcc agaaccagct ctataacgag   1200
ctcaatctag gacgaagaga ggagtacgat gttttggaca agagacgtgg ccgggacccct   1260
gagatggggg gaaagccgca gagaaggaag aaccctcagg aaggcctgta caatgaactg   1320
cagaaagata gatggcgga ggcctacagt gagattggga tgaaaggcga gcgccggagg   1380
ggcaagggc acgatggcct ttaccaggt ctcagtacag ccaccaagga cacctacgac   1440
gcccttcaca tgcaggcct gcccctcgc ggcagcggcg aaggccgcgg cagcctgctg   1500
acctgcggcg atgtggaaga aaacccgggc cccatgtaca gaatgcagct gctgagctgc   1560
atcgccctga gcctggccct ggtgaccaac agcggcatcc acgtgttcat cctgggctgc   1620
ttcagcgccg gcctgcccaa gaccgaggcc aactgggtga acgtgatcag cgacctgaag   1680
aagatcgagg acctgatcca gagcatgcac atcgacgcca ccctgtacac cgagagcgac   1740
gtgcacccca gctgcaaggt gaccgccatg aagtgcttcc tgctggagct gcaggtgatc   1800
agcctggaga gcggcgacgc cagcatccac gacaccgtgg agaacctgat catcctggcc   1860
aacaacagcc tgagcagcaa cggcaacgtg accgagagcg gctgcaagga gtgcgaggag   1920
ctggaggaga gaacatcaa ggagttcctg cagagcttcg tgcacatcgt gcagatgttc   1980
atcaacacca gctccggcgg cggctccggc ggcggcggct ccggcggcgg cggctccggc   2040
ggcggcggct ccggcggcgg ctccctgcag gcccccagaa gagccagagg ctgcagaacc   2100
ctgggcctgc ccgccctgct gctgctgctg ctgctgagac cccccgccac cagaggcatc   2160
acctgccccc cccccatgag cgtggagcac gccgacatct gggtgaagag ctacagcctg   2220
tacagcagag agagatacat ctgcaacagc ggcttcaaga gaaaggccgg caccagcagc   2280
ctgaccgagt gcgtgctgaa caaggccacc aacgtggccc actggaccac ccccagcctg   2340
aagtgcatca gataagttta aac                                           2363
```

<210> SEQ ID NO 56
<211> LENGTH: 489
<212> TYPE: PRT

<213> ORGANISM: Artificial Sequence
<220> FEATURE:
<223> OTHER INFORMATION: Synthetic Sequence

<400> SEQUENCE: 56

```
Asp Arg Thr Met Ala Leu Pro Val Thr Ala Leu Leu Leu Pro Leu Ala
1               5                   10                  15

Leu Leu Leu His Ala Ala Arg Pro Glu Ile Val Met Thr Gln Ser Pro
                20                  25                  30

Ala Thr Leu Ser Val Ser Pro Gly Glu Arg Ala Thr Leu Ser Cys Arg
            35                  40                  45

Ser Ser Gln Ser Leu Val His Arg Asn Gly Asn Thr Tyr Leu His Trp
        50                  55                  60

Tyr Leu Gln Lys Pro Gly Gln Ser Pro Lys Leu Leu Ile His Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Pro Leu Thr Phe
        115                 120                 125

Gly Ala Gly Thr Lys Leu Glu Leu Lys Arg Gly Gly Gly Gly Ser Gly
    130                 135                 140

Gly Gly Gly Ser Gly Gly Gly Gly Ser Glu Val Gln Leu Leu Gln Ser
145                 150                 155                 160

Gly Pro Glu Leu Glu Lys Pro Gly Ala Ser Val Met Ile Ser Cys Lys
                165                 170                 175

Ala Ser Gly Ser Ser Phe Thr Gly Tyr Asn Met Asn Trp Val Arg Gln
            180                 185                 190

Asn Ile Gly Lys Ser Leu Glu Trp Ile Gly Ala Ile Asp Pro Tyr Tyr
        195                 200                 205

Gly Gly Thr Ser Tyr Asn Gln Lys Phe Lys Gly Arg Ala Thr Leu Thr
    210                 215                 220

Val Asp Lys Ser Ser Ser Thr Ala Tyr Met His Leu Lys Ser Leu Thr
225                 230                 235                 240

Ser Glu Asp Ser Ala Val Tyr Tyr Cys Val Ser Gly Met Glu Tyr Trp
                245                 250                 255

Gly Gln Gly Thr Ser Val Thr Val Ser Ser Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Arg Val Lys Phe Ser Arg Ser Ala
    370                 375                 380

Asp Ala Pro Ala Tyr Gln Gln Gly Gln Asn Gln Leu Tyr Asn Glu Leu
```

```
              385                 390                 395                 400
Asn Leu Gly Arg Arg Glu Glu Tyr Asp Val Leu Asp Lys Arg Gly
                405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 57
<211> LENGTH: 1480
<212> TYPE: DNA
<213> ORGANISM: Artificial Sequence
<220> FEATURE:
<223> OTHER INFORMATION: Synthetic Sequence

<400> SEQUENCE: 57
gcgatcgcac catggcctta ccagtgaccg ccttgctcct gccgctggcc ttgctgctcc      60
acgccgccag gccggagatc gtgatgaccc agagccccgc caccctgagc gtgagccccg     120
gcgagagggc caccctgagc tgcaggagca gccagagcct ggtgcacagg aacggcaaca     180
cctacctgca ctggtacctg cagaagcccg gccagagccc caagctgctg atccacaagg     240
tgagcaacag gttcagcggc gtgcccgaca ggttcagcgg cagcggcagc ggcaccgact     300
tcaccctgaa gatcagcagg gtggaggccg aggacctggg cgtgtacttc tgcagccaga     360
gcacccacgt gcccccctg accttcggcg ccggcaccaa gctggagctg aagaggggcg     420
gcggcggcag cggcggcggc ggcagcggcg gcggcggcag cgaggtgcag ctgctgcaga     480
gcggccccga gctggagaag cccggcgcca gcgtgatgat cagctgcaag gccagcggca     540
gcagcttcac cggctacaac atgaactggg tgaggcagaa catcggcaag agcctggagt     600
ggatcggcgc catcgacccc tactacggcg gcaccagcta caaccagaag ttcaagggca     660
gggccaccct gaccgtggac aagagcagca gcaccgccta catgcacctg aagagcctga     720
ccagcgagga cagcgccgtg tactactgcg tgagcggcat ggagtactgg ggccagggca     780
ccagcgtgac cgtgagcagc accacgacgc agcgccgcg accaccaaca ccggcgccca     840
ccatcgcgtc gcagcccctg tccctgcgcc cagaggcgtg ccggccagcg gcggggggcg     900
cagtgcacac gagggggctg gacttcgcct gtgatatcta catctgggcg cccttggccg     960
ggacttgtgg ggtccttctc ctgtcactgg ttatcaccct ttactgcagg agtaagagga    1020
gcaggctcct gcacagtgac tacatgaaca tgactcccg ccgccccggg cccacccgca    1080
agcattacca gccctatgcc ccaccacgcg acttcgcagc ctatcgctcc agagtgaagt    1140
tcagcaggag cgcagacgcc cccgcgtacc agcagggcca gaaccagctc tataacgagc    1200
tcaatctagg acgaagagag gagtacgatg ttttggacaa gagacgtggc cgggaccctg    1260
agatgggggg aaagccgcag agaaggaaga accctcagga aggcctgtac aatgaactgc    1320
agaaagataa gatggcggag gcctacagtg agattgggat gaaaggcgag cgccggaggg    1380 gcaagggca cgatggcctt taccagggtc tcagtacagc caccaaggac acctacgacg    1440
cccttcacat gcaggccctg ccccctcgct aagtttaaac                         1480
```

<210> SEQ ID NO 58
<211> LENGTH: 764
<212> TYPE: PRT
<213> ORGANISM: Artificial Sequence
<220> FEATURE:
<223> OTHER INFORMATION: Synthetic Sequence

<400> SEQUENCE: 58

```
Asp Arg Thr Met Ala Leu Pro Val Thr Ala Leu Leu Leu Pro Leu Ala
1               5                   10                  15

Leu Leu Leu His Ala Ala Arg Pro Glu Ile Val Met Thr Gln Ser Pro
            20                  25                  30

Ala Thr Leu Ser Val Ser Pro Gly Glu Arg Ala Thr Leu Ser Cys Arg
        35                  40                  45

Ser Ser Gln Ser Leu Val His Arg Asn Gly Asn Thr Tyr Leu His Trp
    50                  55                  60

Tyr Leu Gln Lys Pro Gly Gln Ser Pro Lys Leu Leu Ile His Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Pro Leu Thr Phe
        115                 120                 125

Gly Ala Gly Thr Lys Leu Glu Leu Lys Arg Gly Gly Gly Gly Ser Gly
    130                 135                 140

Gly Gly Gly Ser Gly Gly Gly Ser Glu Val Gln Leu Leu Gln Ser
145                 150                 155                 160

Gly Pro Glu Leu Glu Lys Pro Gly Ala Ser Val Met Ile Ser Cys Lys
                165                 170                 175

Ala Ser Gly Ser Ser Phe Thr Gly Tyr Asn Met Asn Trp Val Arg Gln
            180                 185                 190

Asn Ile Gly Lys Ser Leu Glu Trp Ile Gly Ala Ile Asp Pro Tyr Tyr
        195                 200                 205

Gly Gly Thr Ser Tyr Asn Gln Lys Phe Lys Gly Arg Ala Thr Leu Thr
    210                 215                 220

Val Asp Lys Ser Ser Ser Thr Ala Tyr Met His Leu Lys Ser Leu Thr
225                 230                 235                 240

Ser Glu Asp Ser Ala Val Tyr Tyr Cys Val Ser Gly Met Glu Tyr Trp
                245                 250                 255

Gly Gln Gly Thr Ser Val Thr Val Ser Ser Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365
```

Arg Asp Phe Ala Ala Tyr Arg Ser Arg Val Lys Phe Ser Arg Ser Ala
        370             375                 380

Asp Ala Pro Ala Tyr Gln Gln Gly Gln Asn Gln Leu Tyr Asn Glu Leu
385             390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Gln Arg Arg Lys Asn Pro Gln
        420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Ser Gly Glu Gly Arg Gly
            485                 490                 495

Ser Leu Leu Thr Cys Gly Asp Val Glu Glu Asn Pro Gly Pro Met Glu
                500                 505                 510

Tyr Ala Ser Asp Ala Ser Leu Asp Pro Glu Ala Pro Trp Pro Pro Ala
            515                 520                 525

Pro Arg Ala Arg Ala Cys Arg Val Leu Pro Trp Ala Leu Val Ala Gly
    530                 535                 540

Leu Leu Leu Leu Leu Leu Leu Ala Ala Ala Cys Ala Val Phe Leu Ala
545                 550                 555                 560

Cys Pro Trp Ala Val Ser Gly Ala Arg Ala Ser Pro Gly Ser Ala Ala
                565                 570                 575

Ser Pro Arg Leu Arg Glu Gly Pro Glu Leu Ser Pro Asp Asp Pro Ala
            580                 585                 590

Gly Leu Leu Asp Leu Arg Gln Gly Met Phe Ala Gln Leu Val Ala Gln
            595                 600                 605

Asn Val Leu Leu Ile Asp Gly Pro Leu Ser Trp Tyr Ser Asp Pro Gly
    610                 615                 620

Leu Ala Gly Val Ser Leu Thr Gly Gly Leu Ser Tyr Lys Glu Asp Thr
625                 630                 635                 640

Lys Glu Leu Val Val Ala Lys Ala Gly Val Tyr Tyr Val Phe Phe Gln
                645                 650                 655

Leu Glu Leu Arg Arg Val Val Ala Gly Glu Gly Ser Gly Ser Val Ser
            660                 665                 670

Leu Ala Leu His Leu Gln Pro Leu Arg Ser Ala Ala Gly Ala Ala Ala
    675                 680                 685

Leu Ala Leu Thr Val Asp Leu Pro Pro Ala Ser Ser Glu Ala Arg Asn
690                 695                 700

Ser Ala Phe Gly Phe Gln Gly Arg Leu Leu His Leu Ser Ala Gly Gln
705                 710                 715                 720

Arg Leu Gly Val His Leu His Thr Glu Ala Arg Ala Arg His Ala Trp
            725                 730                 735

Gln Leu Thr Gln Gly Ala Thr Val Leu Gly Leu Phe Arg Val Thr Pro
            740                 745                 750

Glu Ile Pro Ala Gly Leu Pro Ser Pro Arg Ser Glu
        755                 760

<210> SEQ ID NO 59
<211> LENGTH: 2294

```
<212> TYPE: DNA
<213> ORGANISM: Artificial Sequence
<220> FEATURE:
<223> OTHER INFORMATION: Synthetic Sequence

<400> SEQUENCE: 59
```

| | | | | | |
|---|---|---|---|---|---|
| atggccttac | cagtgaccgc | cttgctcctg | ccgctggcct | tgctgctcca | cgccgccagg | 60 |
| ccggagatcg | tgatgaccca | gagccccgcc | accctgagcg | tgagcccgg | cgagagggcc | 120 |
| accctgagct | gcaggagcag | ccagagcctg | gtgcacagga | acggcaacac | ctacctgcac | 180 |
| tggtacctgc | agaagcccgg | ccagagcccc | aagctgctga | tccacaaggt | gagcaacagg | 240 |
| ttcagcggcg | tgcccgacag | gttcagcggc | agcggcagcg | gcaccgactt | caccctgaag | 300 |
| atcagcaggg | tggaggccga | ggacctgggc | gtgtacttct | gcagccagag | cacccacgtg | 360 |
| cccccctga | ccttcggcgc | cggcaccaag | ctggagctga | agaggggcgg | cggcggcagc | 420 |
| ggcggcggcg | gcagcggcgg | cggcggcagc | gaggtgcagc | tgctgcagag | cggccccgag | 480 |
| ctggagaagc | ccgcgccag | cgtgatgatc | agctgcaagg | ccagcggcag | cagcttcacc | 540 |
| ggctacaaca | tgaactgggt | gaggcagaac | atcggcaaga | gcctggagtg | gatcggcgcc | 600 |
| atcgaccct | actacggcgg | caccagctac | aaccagaagt | tcaagggcag | ggccaccctg | 660 |
| accgtggaca | gagcagcag | caccgcctac | atgcacctga | gagcctgac | cagcgaggac | 720 |
| agcgccgtgt | actactgcgt | gagcggcatg | gagtactggg | gccagggcac | cagcgtgacc | 780 |
| gtgagcagca | ccacgacgcc | agcgccgcga | ccaccaacac | cggcgcccac | catcgcgtcg | 840 |
| cagcccctgt | ccctgcgccc | agaggcgtgc | cggccagcgg | cggggggcgc | agtgcacacg | 900 |
| aggggctgg | acttcgcctg | tgatatctac | atctgggcgc | ccttggccgg | gacttgtggg | 960 |
| gtccttctcc | tgtcactggt | tatcacccttt | tactgcagga | gtaagaggag | caggctcctg | 1020 |
| cacagtgact | acatgaacat | gactccccgc | cgccccgggc | ccacccgcaa | gcattaccag | 1080 |
| ccctatgccc | caccacgcga | cttcgcagcc | tatcgctcca | gagtgaagtt | cagcaggagc | 1140 |
| gcagacgccc | ccgcgtacca | gcagggccag | aaccagctct | ataacgagct | caatctagga | 1200 |
| cgaagagagg | agtacgatgt | tttggacaag | agacgtggcc | gggaccctga | gatggggga | 1260 |
| aagccgcaga | gaaggaagaa | ccctcaggaa | ggcctgtaca | atgaactgca | gaaagataag | 1320 |
| atggcgagg | cctacagtga | gattgggatg | aaaggcgagc | gccggagggg | caaggggcac | 1380 |
| gatggccttt | accagggtct | cagtacagcc | accaaggaca | cctacgacgc | ccttcacatg | 1440 |
| caggccctgc | ccctcgcgg | cagcggcgaa | ggccgcggca | gcctgctgac | ctgcggcgat | 1500 |
| gtggaagaaa | acccgggccc | catgaatac | gcctctgacg | cttcactgga | ccccgaagcc | 1560 |
| ccgtggcctc | ccgcgccccg | cgctcgcgcc | tgccgcgtac | tgccttgggc | cctggtcgcg | 1620 |
| gggctgctgc | tgctgctgct | gctcgctgcc | gcctgcgccg | tcttcctcgc | ctgccccctgg | 1680 |
| gccgtgtccg | gggctcgcgc | ctcgcccggc | tccgcggcca | gcccgagact | ccgcgagggt | 1740 |
| cccgagcttt | cgcccgacga | tcccgccggc | ctcttggacc | tgcggcaggg | catgtttgcg | 1800 |
| cagctggtgg | cccaaaatgt | tctgctgatc | gatgggcccc | tgagctggta | cagtgaccca | 1860 |
| ggcctggcag | gcgtgtccct | gacgggggc | ctgagctaca | agaggacac | gaaggagctg | 1920 |
| gtggtggcca | aggctggagt | ctactatgtc | ttctttcaac | tagagctgcg | gcgcgtggtg | 1980 |
| gccggcgagg | gctcaggctc | cgtttcactt | gcgctgcacc | tgcagccact | gcgctctgct | 2040 |
| gctggggccg | ccgccctggc | tttgaccgtg | gacctgccac | ccgcctcctc | cgaggctcgg | 2100 |
| aactcggcct | tcggtttcca | gggccgcttg | ctgcacctga | gtgccggcca | gcgcctgggc | 2160 |

-continued

```
gtccatcttc acactgaggc cagggcacgc catgcctggc agcttaccca gggcgccaca    2220
gtcttgggac tcttccgggt gacccccgaa atcccagccg gactcccttc accgaggtcg    2280
gaataagttt aaac                                                      2294
```

<210> SEQ ID NO 60
<211> LENGTH: 1302
<212> TYPE: PRT
<213> ORGANISM: Artificial Sequence
<220> FEATURE:
<223> OTHER INFORMATION: Synthetic Sequence

<400> SEQUENCE: 60

```
Asp Arg Thr Met Ala Leu Pro Val Thr Ala Leu Leu Leu Pro Leu Ala
1               5                   10                  15

Leu Leu Leu His Ala Ala Arg Pro Asp Ile Gln Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Ala Val Ala Trp Phe Gln Gln Lys Pro
    50                  55                  60

Gly Gln Ser Pro Lys Leu Leu Ile Tyr Ser Pro Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln Leu Tyr Ser Thr Pro Tyr Thr Phe Gly Gly Gly Thr Lys Leu
        115                 120                 125

Glu Ile Lys Gly Gly Gly Gly Ser Gly Gly Gly Gly Ser Gly Gly Gly
    130                 135                 140

Gly Ser Glu Val Gln Leu Gln Gln Ser Gly Pro Glu Leu Val Lys Pro
145                 150                 155                 160

Gly Ala Ser Val Lys Met Ser Cys Lys Ala Ser Gly Tyr Thr Phe Thr
                165                 170                 175

Asp Tyr Tyr Leu Asp Trp Val Lys Gln Ser His Gly Glu Ser Phe Glu
            180                 185                 190

Trp Ile Gly Arg Val Asn Pro Tyr Asn Gly Gly Thr Ile Tyr Asn Gln
        195                 200                 205

Lys Phe Lys Gly Lys Ala Thr Leu Thr Val Asp Lys Ser Ser Ser Thr
    210                 215                 220

Ala Tyr Met Asp Leu Asn Ser Leu Thr Ser Glu Asp Ser Ala Val Tyr
225                 230                 235                 240

Tyr Cys Ala Arg Asp His Tyr Arg Tyr Asp Pro Leu Leu Asp Tyr Trp
                245                 250                 255

Gly Gln Gly Thr Thr Leu Thr Val Ser Ser Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335
```

```
Ser Lys Arg Ser Arg Leu Leu His Ser Asp Tyr Met Asn Met Thr Pro
                340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Ser Gly Ala Thr Asn Phe
                485                 490                 495

Ser Leu Leu Lys Gln Ala Gly Asp Val Glu Glu Asn Pro Gly Pro Met
            500                 505                 510

Ala Leu Pro Val Thr Ala Leu Leu Leu Pro Leu Ala Leu Leu Leu His
        515                 520                 525

Ala Ala Arg Pro Met Ala Asp Tyr Lys Asp Ile Val Met Thr Gln Ser
530                 535                 540

His Lys Phe Leu Leu Val Ser Val Gly Asp Arg Val Ser Ile Thr Cys
545                 550                 555                 560

Lys Ala Ser Gln Asp Val Ser Thr Ala Val Ala Trp Tyr Gln Gln Lys
                565                 570                 575

Pro Gly Gln Ser Pro Lys Leu Leu Ile Tyr Ser Ala Ser Tyr Arg Tyr
            580                 585                 590

Thr Gly Val Pro Asp Arg Phe Ile Gly Ser Gly Ser Gly Thr Asp Phe
        595                 600                 605

Thr Leu Thr Ile Ser Ser Val Gln Ala Glu Asp Leu Ala Asp Tyr Phe
    610                 615                 620

Cys Gln Gln His Tyr Ser Thr Pro Leu Thr Phe Gly Ala Gly Thr Lys
625                 630                 635                 640

Leu Glu Ile Lys Arg Gly Gly Gly Gly Ser Gly Gly Gly Gly Ser Gly
                645                 650                 655

Gly Gly Gly Ser Ser Gly Gly Gly Ser Glu Val Gln Leu Lys Glu Ser
            660                 665                 670

Gly Pro Gly Leu Val Ala Pro Ser Gln Ser Leu Ser Ile Thr Cys Thr
        675                 680                 685

Val Ser Gly Phe Pro Leu Thr Ser Tyr Gly Val Ser Trp Val Arg Gln
    690                 695                 700

Pro Pro Gly Lys Gly Leu Glu Trp Leu Gly Val Ile Trp Gly Asp Gly
705                 710                 715                 720

Ser Thr Asn Tyr His Ser Ala Leu Ile Ser Arg Leu Ser Ile Ser Lys
                725                 730                 735

Asp Asn Ser Lys Ser Gln Val Phe Leu Lys Leu Asn Asn Leu Gln Thr
            740                 745                 750

Asp Asp Thr Ala Thr Tyr Tyr Cys Ala Arg Asp Thr Tyr Tyr Pro Tyr
```

```
              755                 760                 765
Tyr Ala Met Asp Tyr Trp Gly Gln Gly Thr Ser Val Thr Val Ser Ser
770                 775                 780

Thr Thr Thr Pro Ala Pro Arg Pro Pro Thr Pro Ala Pro Thr Ile Ala
785                 790                 795                 800

Ser Gln Pro Leu Ser Leu Arg Pro Glu Ala Cys Arg Pro Ala Ala Gly
                    805                 810                 815

Gly Ala Val His Thr Arg Gly Leu Asp Phe Ala Cys Asp Ile Tyr Ile
                820                 825                 830

Trp Ala Pro Leu Ala Gly Thr Cys Gly Val Leu Leu Leu Ser Leu Val
                835                 840                 845

Ile Thr Leu Tyr Cys Lys Arg Gly Arg Lys Lys Leu Leu Tyr Ile Phe
850                 855                 860

Lys Gln Pro Phe Met Arg Pro Val Gln Thr Thr Gln Glu Glu Asp Gly
865                 870                 875                 880

Cys Ser Cys Arg Phe Pro Glu Glu Glu Glu Gly Gly Cys Glu Leu Arg
                    885                 890                 895

Val Lys Phe Ser Arg Ser Ala Asp Ala Pro Ala Tyr Gln Gln Gly Gln
                900                 905                 910

Asn Gln Leu Tyr Asn Glu Leu Asn Leu Gly Arg Arg Glu Glu Tyr Asp
                915                 920                 925

Val Leu Asp Lys Arg Arg Gly Arg Asp Pro Glu Met Gly Gly Lys Pro
930                 935                 940

Gln Arg Arg Lys Asn Pro Gln Glu Gly Leu Tyr Asn Glu Leu Gln Lys
945                 950                 955                 960

Asp Lys Met Ala Glu Ala Tyr Ser Glu Ile Gly Met Lys Gly Glu Arg
                965                 970                 975

Arg Arg Gly Lys Gly His Asp Gly Leu Tyr Gln Gly Leu Ser Thr Ala
                980                 985                 990

Thr Lys Asp Thr Tyr Asp Ala Leu His Met Gln Ala Leu Pro Pro Arg
                995                 1000                1005

Gly Ser Gly Glu Gly Arg Gly Ser Leu Leu Thr Cys Gly Asp Val
    1010                1015                1020

Glu Glu Asn Pro Gly Pro Met Tyr Arg Met Gln Leu Leu Ser Cys
    1025                1030                1035

Ile Ala Leu Ser Leu Ala Leu Val Thr Asn Ser Gly Ile His Val
    1040                1045                1050

Phe Ile Leu Gly Cys Phe Ser Ala Gly Leu Pro Lys Thr Glu Ala
    1055                1060                1065

Asn Trp Val Asn Val Ile Ser Asp Leu Lys Lys Ile Glu Asp Leu
    1070                1075                1080

Ile Gln Ser Met His Ile Asp Ala Thr Leu Tyr Thr Glu Ser Asp
    1085                1090                1095

Val His Pro Ser Cys Lys Val Thr Ala Met Lys Cys Phe Leu Leu
    1100                1105                1110

Glu Leu Gln Val Ile Ser Leu Glu Ser Gly Asp Ala Ser Ile His
    1115                1120                1125

Asp Thr Val Glu Asn Leu Ile Ile Leu Ala Asn Asn Ser Leu Ser
    1130                1135                1140

Ser Asn Gly Asn Val Thr Glu Ser Gly Cys Lys Glu Cys Glu Glu
    1145                1150                1155

Leu Glu Glu Lys Asn Ile Lys Glu Phe Leu Gln Ser Phe Val His
    1160                1165                1170
```

```
Ile Val Gln Met Phe Ile Asn Thr Ser Ser Gly Gly Gly Ser Gly
    1175                1180                1185

Gly Gly Gly Ser Gly Gly Gly Ser Gly Gly Gly Ser Gly
    1190                1195                1200

Gly Gly Ser Leu Gln Ala Pro Arg Arg Ala Arg Gly Cys Arg Thr
    1205                1210                1215

Leu Gly Leu Pro Ala Leu Leu Leu Leu Leu Leu Arg Pro Pro
    1220                1225                1230

Ala Thr Arg Gly Ile Thr Cys Pro Pro Pro Met Ser Val Glu His
    1235                1240                1245

Ala Asp Ile Trp Val Lys Ser Tyr Ser Leu Tyr Ser Arg Glu Arg
    1250                1255                1260

Tyr Ile Cys Asn Ser Gly Phe Lys Arg Lys Ala Gly Thr Ser Ser
    1265                1270                1275

Leu Thr Glu Cys Val Leu Asn Lys Ala Thr Asn Val Ala His Trp
    1280                1285                1290

Thr Thr Pro Ser Leu Lys Cys Ile Arg
    1295                1300
```

<210> SEQ ID NO 61
<211> LENGTH: 3919
<212> TYPE: DNA
<213> ORGANISM: Artificial Sequence
<220> FEATURE:
<223> OTHER INFORMATION: Synthetic Sequence

<400> SEQUENCE: 61

```
gcgatcgcac catggccctg cccgtgaccg ccctgctgct gcccctggcc ctgctgctgc      60
acgccgccag gccgacatc cagatgaccc agagccacaa gttcatgagc accagcgtgg     120
gcgacagggt gagcatcacc tgcaaggcca gcaggacgt gagcaccgcc gtggcctggt     180
tccagcagaa gccggccag agccccaagc tgctgatcta cagccccagc tacaggtaca     240
ccggcgtgcc cgacaggttc accggcagcg gcagcggcac cgacttcacc ttcaccatca     300
gcagcgtgca ggccgaggac ctggccgtgt actactgcca gcagctgtac agcaccccct     360
acaccttcgg cggcggcacc aagctggaga tcaagggagg ggggggatcc ggggaggag     420
gctccggcgg aggcggaagc gaggtgcagc tgcagcagag cggccccgag ctggtgaagc     480
ccggcgccag cgtgaagatg agctgcaagg ccagcggcta caccttcacc gactactacc     540
tggactgggt gaagcagagc cacggcgaga gcttcgagtg gatcggcagg gtgaaccccct     600
acaacggcgg caccatctac aaccagaagt tcaagggcaa ggccaccctg accgtggaca     660
agagcagcag caccgcctac atggacctga cagcctgac cagcgaggac agcgccgtgt     720
actactgcgc cagggaccac tacaggtacg accccctgct ggactactgg ggccagggca     780
ccaccctgac cgtgagcagc accaccaccc ccgccccag ccccccacc ccgccccca     840
ccatcgccag ccagccctg agcctgaggc ccgaggcctg caggcccgcc gcggcggcg     900
ccgtgcacac caggggcctg gacttcgcct gcgacatcta catctgggcc ccctggccg     960
gcacctgcgg cgtgctgctg ctgagcctgg tgatcaccct gtactgcagg agtaaggaga    1020
gcaggctcct gcacagtgac tacatgaaca tgactccccg ccgcccggg cccacccgca    1080
agcattacca gccctatgcc ccaccacgcg acttcgcagc ctatcgctcc agggtgaagt    1140
tcagcaggag cgccgacgcc cccgcctacc agcagggcca gaaccagctg tacaacgagc    1200
tgaacctggg caggagggag gagtacgacg tgctggacaa gaggagggc agggaccccg    1260
```

```
agatgggcgg caagccccag aggaggaaga accccaggga gggcctgtac aacgagctgc   1320
agaaggacaa gatggccgag gcctacagcg agatcggcat gaagggcgag aggaggaggg   1380
gcaagggcca cgacggcctg taccagggcc tgagcaccgc caccaaggac acctacgacg   1440
ccctgcacat gcaggccctg ccccccaggg aagcggagc caccaacttc agcctgctga    1500
agcaggccgg cgacgtggag gagaaccccg ccccatggc cctgccgtg accgccctgc     1560 tgctgcccct ggccctgctg ctgcacgccg ccaggcccat ggccgactac aaggacatcg   1620
tgatgaccca gagccacaag ttcctgctgg tgagcgtggg cgacagggtg agcatcacct   1680
gcaaggccag ccaggacgtg agcaccgccg tggcctggta ccagcagaag cccggccaga   1740
gccccaagct gctgatctac agcgccagct acaggtacac cggcgtgccc gacaggttca   1800
tcggcagcgg cagcggcacc gacttcaccc tgaccatcag cagcgtgcag gccgaggacc   1860
tggccgacta cttctgccag cagcactaca gcaccccct gaccttcggc gccggcacca    1920
agctggagat caagaggggc ggcggcggca ggcggcgcgg cggcagcggc ggcggcggca   1980
gcagcggcgg cggcagcgag gtgcagctga aggagagcgg ccccggcctg gtggccccca   2040
gccagagcct gagcatcacc tgcaccgtga gcggcttccc cctgaccagc tacgcgtga    2100 gctgggtgag gcagccccc ggcaagggcc tggagtggct gggcgtgatc tggggcgacg    2160
gcagcaccaa ctaccacagc gccctgatca gcaggctgag catcagcaag gacaacagca   2220
agagccaggt gttcctgaag ctgaacaacc tgcagaccga cgacaccgcc acctactact   2280
gcgccaggga cacctactac ccctactacg ccatggacta ctggggccag ggcaccagcg   2340
tgaccgtgag cagcaccacc accccgccc ccaggccccc caccccgcc cccaccatcg     2400 ccagccagcc cctgagcctg aggccccgag gcctgcaggcc cgccgccggc ggcgccgtgc  2460
acaccagggg cctggacttc gcctgcgaca tctacatctg gccccctg gccggcacct     2520 gcggcgtgct gctgctgagc ctggtgatca ccctgtactg caaacggggc agaaagaaac   2580
tcctgtatat attcaaacaa ccatttatga gaccagtaca aactactcaa gaggaagatg   2640
gctgtagctg ccgatttcca gaagaagaag aaggaggatg tgaactgagg gtgaagttca   2700
gcaggagcgc cgacgccccc gcctaccagc agggccagaa ccagctgtac aacgagctga   2760
acctgggcag gagggaggag tacgacgtgc tggacaagag gaggggcagg gaccccgaga   2820
tgggcggcaa gccccagagg aggaagaacc cccaggaggg cctgtacaac gagctgcaga   2880
aggacaagat ggccgaggcc tacagcgaga tcggcatgaa gggcgagagg aggaggggca   2940
agggccacga cggcctgtac cagggcctga gcaccgccac caaggacacc tacgacgccc   3000
tgcacatgca ggccctgccc ccagggca gcggcgaagg ccgcggcagc ctgctgacct     3060
gcggcgatgt ggaagaaaac ccgggcccca tgtacagaat gcagctgctg agctgcatcg   3120
ccctgagcct ggccctggtg accaacagcg gcatccacgt gttcatcctg gctgcttca    3180 gcgccggcct gcccaagacc gaggccaact gggtgaacgt gatcagcgac ctgaagaaga   3240
tcgaggacct gatccagagc atgcacatcg acgccaccct gtacaccgag agcgacgtgc   3300
accccagctg caaggtgacc gccatgaagt gcttcctgct ggagctgcag gtgatcagcc   3360
tggagagcgg cgacgccagc atccacgaca ccgtggagaa cctgatcatc ctggccaaca   3420
acagcctgag cagcaacggc aacgtgaccg agagcggctg caaggagtgc gaggagctgg   3480
aggaagagaa catcaaggag ttcctgcaga gcttcgtgca catcgtgcag atgttcatca   3540
acaccagctc cggcggcggc tccggcggcg gcggctccgg cggcggcggc tccggcggcg   3600
```

```
gcggctccgg cggcggctcc ctgcaggccc ccagaagagc cagaggctgc agaaccctgg    3660
gcctgcccgc cctgctgctg ctgctgctgc tgagaccccc cgccaccaga ggcatcacct    3720 gcccccccc  catgagcgtg gagcacgccg acatctgggt gaagagctac agcctgtaca    3780
gcagagagag atacatctgc aacagcggct tcaagagaaa ggccggcacc agcagcctga    3840
ccgagtgcgt gctgaacaag gccaccaacg tggcccactg gaccaccccc agcctgaagt    3900
gcatcagata agtttaaac                                                 3919
```